US012454691B2

(12) United States Patent
Beigelman et al.

(10) Patent No.: US 12,454,691 B2
(45) Date of Patent: Oct. 28, 2025

(54) MODIFIED SHORT INTERFERING NUCLEIC ACID (SINA) MOLECULES AND USES THEREOF

(71) Applicant: Aligos Therapeutics, Inc., South San Francisco, CA (US)

(72) Inventors: Leonid Beigelman, San Mateo, CA (US); Vivek Kumar Rajwanshi, Cupertino, CA (US); Markus Hossbach, Kulmbach (DE); Rajendra K. Pandey, Foster City, CA (US); Jin Hong, Pacifica, CA (US); Laxman Eltepu, San Ramon, CA (US); Saul Martinez Montero, San Bruno, CA (US); N. Tilani S. De Costa, South San Francisco, CA (US)

(73) Assignee: Aligos Therapeutics, Inc., South San Francisco, CA (US)

( * ) Notice: Subject to any disclaimer, the term of this patent is extended or adjusted under 35 U.S.C. 154(b) by 256 days.

(21) Appl. No.: 17/939,896

(22) Filed: Sep. 7, 2022

(65) Prior Publication Data

US 2023/0159929 A1 May 25, 2023

Related U.S. Application Data

(60) Provisional application No. 63/241,935, filed on Sep. 8, 2021.

(51) Int. Cl.

| | |
|---|---|
| ***C12N 15/113*** | (2010.01) |
| ***A61P 31/20*** | (2006.01) |
| ***C07H 19/067*** | (2006.01) |
| ***C07H 19/167*** | (2006.01) |
| ***C07H 21/02*** | (2006.01) |

(52) U.S. Cl.

CPC ............ *C12N 15/113* (2013.01); *A61P 31/20* (2018.01); *C07H 19/067* (2013.01); *C07H 19/167* (2013.01); *C07H 21/02* (2013.01); *C12N 2310/11* (2013.01); *C12N 2310/14* (2013.01); *C12N 2310/314* (2013.01); *C12N 2310/315* (2013.01)

(58) Field of Classification Search

CPC ...................................................... C07H 21/02

See application file for complete search history.

(56) References Cited

U.S. PATENT DOCUMENTS

| | | | |
|---|---|---|---|
| 11,033,556 B2 | 6/2021 | Beigelman et al. | |
| 11,191,747 B2 | 12/2021 | Vendeville et al. | |
| 2011/0112168 A1* | 5/2011 | Feinstein ................ | A61P 13/12 536/24.5 |
| 2020/0361947 A1 | 11/2020 | Vendeville et al. | |
| 2021/0095283 A1* | 4/2021 | Geall .................... | C12N 15/111 |
| 2024/0352464 A1* | 10/2024 | Beigelman ..... | C12Y 101/01062 |

FOREIGN PATENT DOCUMENTS

| | | | |
|---|---|---|---|
| WO | WO-2011/095576 A1 | 8/2011 | |
| WO | WO-2011/139699 A2 | 11/2011 | |
| WO | WO-2014/209979 A1 | 12/2014 | |
| WO | WO-2018/013999 A1 | 1/2018 | |
| WO | WO-2018/045317 A1 | 3/2018 | |
| WO | WO-2019/217397 A2 | 11/2019 | |
| WO | WO-2020097342 A1 * | 5/2020 | ......... A61K 31/7115 |
| WO | WO-2020/167984 A1 | 8/2020 | |
| WO | WO-2020/205934 | 10/2020 | |
| WO | WO-2020/214728 A1 | 10/2020 | |

OTHER PUBLICATIONS

Miroshnichenko et al., "Mesyl phosphoramidate antisense oligonucleotides as an alternative to phosphorothioates with improved biochemical and biological properties" PNAS vol. 116 No. 4 pp. 1229-1234, DOI:10.1073/pnas.1813376116 (Year: 2019).*

Kataoka et al., "Synthesis of 3'-deoxyapionucleoside triphosphates and their incorporation into DNA by DNA polymerase" Nucleic Acids Symposium Series No. 52, pp. 281-282, doi:10.1093/nass/nrn142 (Year: 2008).*

Wall et al., "Small RNA: can RNA interference be exploited for therapy?" The Lancet vol. 362 pp. 1401-1403 (Year: 2003).*

Arbuthnot, Patrick, "Harnessing RNA Interference for the Treatment of Viral Infections," Drug News & Perspectives, 2010, 23(6):341-350.

Berke et al., "Capsid Assembly Modulators Have a Dual Mechanism of Action in Primary Human Hepatocytes Infected with Hepatitis B Virus," Antimicrobial Agents and Chemotherapy, Jun. 5, 2017, 61:e00560-17, 14 pages.

Boudreau et al., "RNAi Therapy for Neurodegenerative Diseases," Current Topics in Developmental Biology, 2006, 75:73-92.

Chalbatani et al., "Small interfering RNAs (siRNAs) in cancer therapy: a nano-based approach," International Journal of Nanomedicine, 2019, 14:3111-3128.

Chernikov et al., "Current Development of siRNA Bioconjugates: From Research to the Clinic," Frontiers in Pharmacology, Reviews, Apr. 26, 2019, 10(444):1-25.

Klumpp et al,. "Efficacy of NVR 3-778, Alone and In Combination with Pegylated Interferon, vs Entecavir in uPA/SCID Mice with Humanized Livers and HBV infection," Gastroenterology, 2018, 154:652-662.

Periguad et al., "Potential Antiviral Agents. Stereospecific Synthesis of Purines and Pyrimidines Substituted with Chiral Acyclic Chains by Sugar-Ring Opening of alpha-L-Arabinopyranosyl Nucleosides," J. Chem. Soc., Perkin Trans. 1, 1992, 1943-1952.

Rajkamal et al., "Partially Acetylated or Benzoylated Arabinose Derivatives as Structurally Simple Organogelators: Effect of the Ester Protecting Group on Gel Properties," Chemistry - A European Journal, 2017, 23(47):11323 - 11329.

(Continued)

*Primary Examiner* — Eric Olson
(74) *Attorney, Agent, or Firm* — Foley & Lardner LLP

(57) ABSTRACT

Described are short interfering nucleic acid (siNA) molecules comprising modified nucleotides, compositions, and methods and uses thereof.

29 Claims, 7 Drawing Sheets

Specification includes a Sequence Listing.

(56) References Cited

OTHER PUBLICATIONS

Rondinone, Christina M., "Therapeutic potential of RNAi in metabolic diseases," BioTechniques, Apr. 2006, 40:S31-S36.
Elkayam et al., "siRNA carrying an (E)-vinylphosphonate moiety at the 5' end of the guide strand augments gene silencing by enhanced binding to human Argonaute-2", Nucleic Acids Research, 2017 (Nov. 28, 2016), 45(6):3528-3536.
Hu et al., "Therapeutic siRNA: state of the art," Signal Transduction and Targeted Therapy, Dec. 1, 2020, 5(101):1-25.
Invitation to Pay Fees and partial International Search Report dated Apr. 12, 2023 in PCT/US2022/042808.

* cited by examiner

MODIFIED SHORT INTERFERING NUCLEIC ACID (SINA) MOLECULES AND USES THEREOF

CROSS-REFERENCE TO RELATED APPLICATION

This application claims priority to U.S. Provisional Application No. 63/241,935, filed Sep. 8, 2021, the disclosures of which are hereby incorporated by reference in their entireties.

The instant application contains a Sequence Listing which has been submitted in XML format via Patent Center and is hereby incorporated by reference in its entirety. Said XML copy, created on Nov. 18, 2022, is named 122400-0305.xml and is 471,010 bytes.

TECHNICAL FIELD

Described are short interfering nucleic acid (siNA) molecules comprising modified nucleotides, compositions, and methods and uses thereof.

BACKGROUND

RNA interference (RNAi) is a biological response to double-stranded RNA that mediates resistance to both endogenous parasitic and exogenous pathogenic nucleic acids, and regulates the expression of protein-coding genes. The short interfering nucleic acids (siNA), such as siRNA, have been developed for RNAi therapy to treat a variety of diseases. For instance, RNAi therapy has been proposed for the treatment of metabolic diseases, neurodegenerative diseases, cancer, and pathogenic infections (See e.g., Rondindone, *Biotechniques,* 2018, 40 (4S), doi.org/10.2144/000112163, Boudreau and Davidson, *Curr Top Dev Biol,* 2006, 75:73-92, Chalbatani et al., *Int J Nanomedicine,* 2019, 14:3111-3128, Arbuthnot, *Drug News Perspect,* 2010, 23(6):341-50, and Chernikov et. al., *Front. Pharmacol.,* 2019, doi.org/10.3389/fphar.2019.00444, each of which are incorporated by reference in their entirety). However, major limitations of RNAi therapy are the ability to effectively deliver siRNA to target cells and the degradation of the siRNA.

The present disclosure improves the delivery and stability of siNA molecules by providing siNA molecules comprising modified nucleobases. The siNA molecules of the present disclosure provide optimized combinations and numbers of modified nucleotides, nucleotide lengths, design (e.g., blunt ends or overhangs, internucleoside linkages, conjugates), and modification patterns for improving the delivery and stability of siNA molecules.

SUMMARY

Described herein are short interfering nucleic acid (siNA) molecules comprising novel modified nucleobase monomers, phosphate mimics, and/or other modifications. Also described herein are methods of using the disclosed siNA molecules for treating various diseases and conditions.

In a first aspect, the present disclosure provides a nucleotide comprising a structure of:

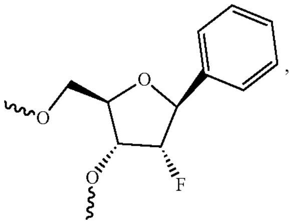
, (fB)

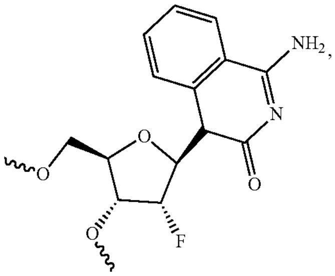
, or (f(4nh)Q)

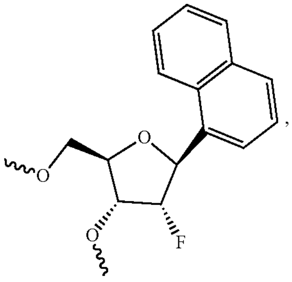
, (fN)

and nucleic acid sequences and siNA comprising any one of the foregoing nucleotides or a combination of nucleotides thereof.

In a second aspect, the present disclosure provides a nucleotide comprising a structure of:

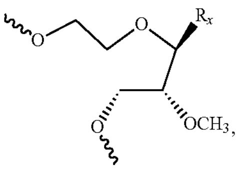

wherein Rx is a nucleobase, aryl, heteroaryl, or H. For example, the nucleotide may comprise a structure of:

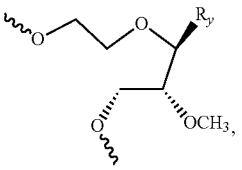

wherein $R_y$ is a nucleobase.

In a third aspect, the present disclosure provides a nucleotide comprising a structure of:

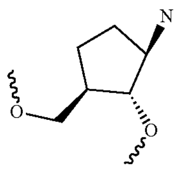

(apN)

wherein $R_y$ is a nucleobase, and nucleic acid sequences and siNA comprising the foregoing nucleotide. In some embodiments, the nucleotide may comprise a structure of:

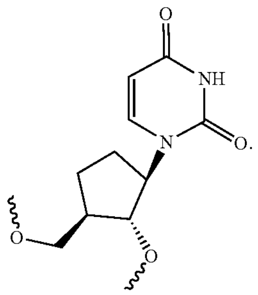

In a fourth aspect, the present disclosure provides a nucleotide phosphate mimic comprising a structure of:

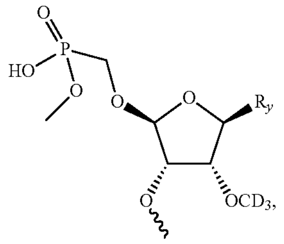

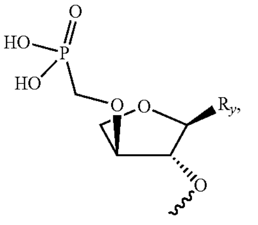

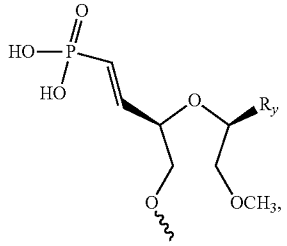

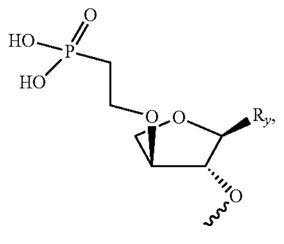

-continued

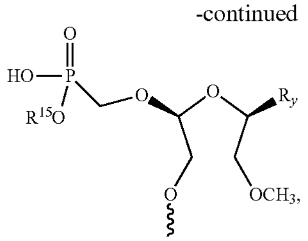

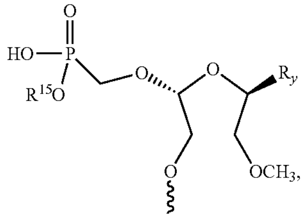

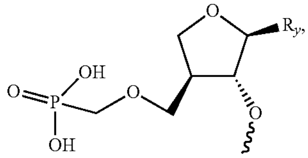

or

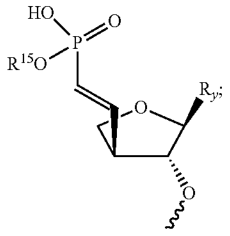

wherein $R_y$ is a nucleobase and $R^{15}$ is H or $CH_3$.

The present disclosure provides short interfering nucleic acid (siNA) molecules comprising at least one, at least two, at least 3, at least 4, or at least 5 nucleotide(s) according to the first, second, or third aspects, which optionally may be located in and/or capable of destabilizing a seed region of the siNA. In some embodiments, the antisense strand may comprise a 5'-stabilized end cap selected from:

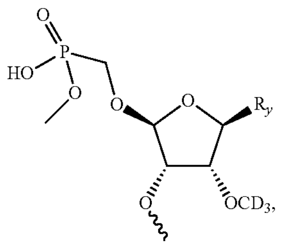

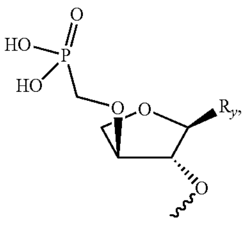

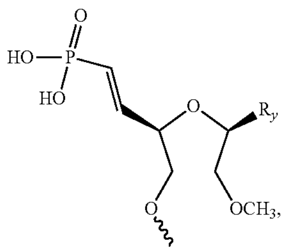

-continued

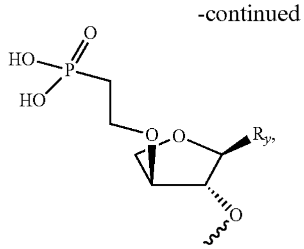

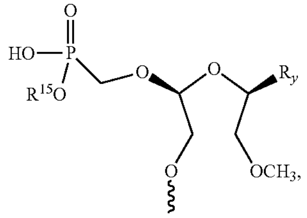

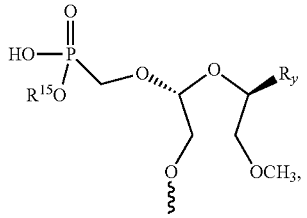

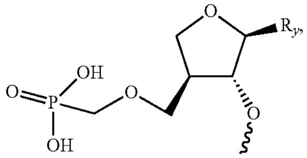

or

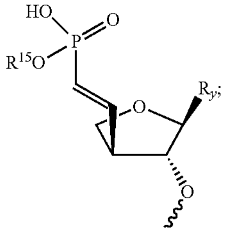

wherein $R_y$ is a nucleobase and $R^{15}$ is H or $CH_3$.

The present disclosure provides short interfering nucleic acid (siNA) molecules comprising a sense strand and an antisense strand, wherein the antisense comprises a nucleotide phosphate mimic according to the fourth aspect at its 5' end.

The present disclosure provides short interfering nucleic acid (siNA) molecules comprising:

(a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence:

is 15 to 30 nucleotides in length; and comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 3, 5, 7, 8, 9, 10, 11, 12, 14, 17, and/or 19 from the 5' end of the first nucleotide sequence is a 2'-fluoro nucleotide or wherein at least one modified nucleotide is a 2'-O-methyl nucleotide and at least one modified nucleotide is a 2'-fluoro nucleotide; and an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence:

is 15 to 30 nucleotides in length; and comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; or (b) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence:

(i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence:

(iii) is 15 to 30 nucleotides in length; and (iv) comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 2, 5, 6, 8, 10, 14, 16, 17, and/or 18 from the 5' end of the second nucleotide sequence is a 2'-fluoro nucleotide;

wherein the sense strand and/or the antisense strand comprise at least one, at least two, at least 3, at least 4, or at least 5 nucleotide(s) according to the first, second, or third aspects. In some embodiments, the antisense strand may comprise a 5'-stabilized end cap selected from:

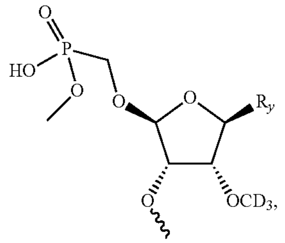

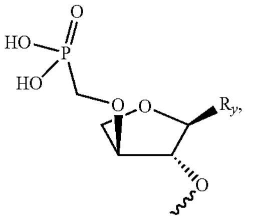

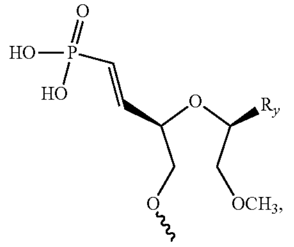

-continued

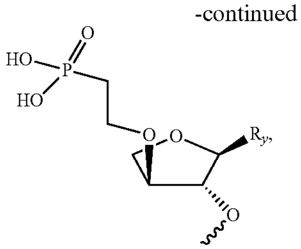

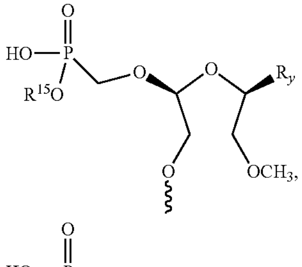

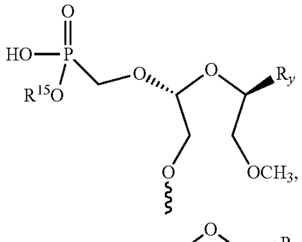

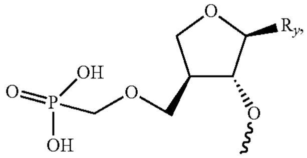

or

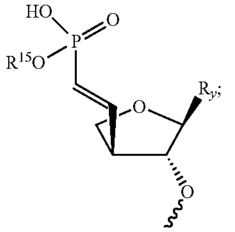

wherein $R_y$ is a nucleobase and $R^{15}$ is H or $CH_3$.

The present disclosure provides short interfering nucleic acid (siNA) molecules comprising:

(a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence:

is 15 to 30 nucleotides in length; and comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 3, 5, 7, 8, 9, 10, 11, 12, 14, 17, and/or 19 from the 5' end of the first nucleotide sequence is a 2'-fluoro nucleotide or wherein at least one modified nucleotide is a 2'-O-methyl nucleotide and at least one modified nucleotide is a 2'-fluoro nucleotide; and an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence:

is 15 to 30 nucleotides in length; and comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; or (b) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence:

(i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence:

(iii) is 15 to 30 nucleotides in length; and (iv) comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 2, 5, 6, 8, 10, 14, 16, 17, and/or 18 from the 5' end of the second nucleotide sequence is a 2'-fluoro nucleotide;

wherein the antisense strand comprises a nucleotide phosphate mimic according the fourth aspect at its 5' end.

In some embodiments of the disclosed siNA molecules, the sense strand and/or the antisense strand independently comprise 1 or more phosphorothioate internucleoside linkages.

In some embodiments of the disclosed siNA molecules, the sense strand and/or the antisense strand independently comprise 1 or more mesyl phosphoroamidate internucleoside linkages.

In some embodiments of the disclosed siNA molecules, the siNA further comprises a phosphorylation blocker, a galactosamine, and/or a 5'-stabilized end cap.

In some embodiments of the disclosed siNA molecules, the sense strand comprises at least 1, 2, 3, 4, 5, 6, 7, 8, 9, 10, 11, 12, 13, 14, 15 or more phosphorothioate internucleoside linkages. In some embodiments, (i) at least one phosphorothioate internucleoside linkage in the sense strand is between the nucleotides at positions 1 and 2 from the 5' end of the first nucleotide sequence; (ii) at least one phosphorothioate internucleoside linkage is between the nucleotides at positions 2 and 3 from the 5' end of the first nucleotide sequence.

In some embodiments of the disclosed siNA molecules, the antisense strand further comprises at least 1, 2, 3, 4, 5, 6, 7, 8, 9, 10, 11, 12, 13, 14, 15 or more phosphorothioate internucleoside linkages. In some embodiments, (i) at least one phosphorothioate internucleoside linkage in the antisense strand is between the nucleotides at positions 1 and 2 from the 5' end of the second nucleotide sequence; (ii) at least one phosphorothioate internucleoside linkage in the antisense strand is between the nucleotides at positions 2 and 3 from the 5' end of the second nucleotide sequence; (iii) at least one phosphorothioate internucleoside linkage in the antisense strand is between the nucleotides at positions 1 and 2 from the 3' end of the second nucleotide sequence; and/or (iv) at least one phosphorothioate internucleoside linkage is between the nucleotides at positions 2 and 3 from the 3' end of the second nucleotide sequence.

In some embodiments of the disclosed siNA molecules, the sense strand comprises at least 1, 2, 3, 4, 5, 6, 7, 8, 9, 10, 11, 12, 13, 14, 15 or more mesyl phosphoroamidate internucleoside linkages. In some embodiments, (i) at least one mesyl phosphoroamidate internucleoside linkage in the sense strand is between the nucleotides at positions 1 and 2 from the 5' end of the first nucleotide sequence; (ii) at least one mesyl phosphoroamidate internucleoside linkage is between the nucleotides at positions 2 and 3 from the 5' end of the first nucleotide sequence.

In some embodiments of the disclosed siNA molecules, the antisense strand further comprises at least 1, 2, 3, 4, 5, 6, 7, 8, 9, 10, 11, 12, 13, 14, 15 or more mesyl phosphoroamidate internucleoside linkages. In some embodiments, (i) at least one mesyl phosphoroamidate internucleoside linkage in the antisense strand is between the nucleotides at positions 1 and 2 from the 5' end of the second nucleotide sequence; (ii) at least one mesyl phosphoroamidate internucleoside linkage in the antisense strand is between the nucleotides at positions 2 and 3 from the 5' end of the second nucleotide sequence; (iii) at least one mesyl phosphoroamidate internucleoside linkage in the antisense strand is between the nucleotides at positions 1 and 2 from the 3' end of the second nucleotide sequence; and/or (iv) at least one mesyl phosphoroamidate internucleoside linkage is between the nucleotides at positions 2 and 3 from the 3' end of the second nucleotide sequence.

The present disclosure additionally provides short interfering nucleic acids (siNAs) comprising a sense strand and an antisense strand, wherein the sense strand and/or the antisense strand independently comprise at least 1, 2, 3, 4, 5, 6, 7, 8, 9, 10, 11, 12, 13, 14, 15 or more mesyl phosphoroamidate internucleoside linkages.

In some embodiments of the disclosed siNA molecules, the antisense strand comprises a 5'-stabilized end cap selected from the group consisting of Formula (1) to Formula (16), Formula (9X) to Formula (12X), Formula (16X), Formula (9Y) to Formula (12Y), Formula (16Y), Formula (21) to Formula (36), Formula 36X, Formula (41) to (56), Formula (49X) to (52X), Formula (49Y) to (52Y), Formula 56X, Formula 56Y, Formula (61), Formula (62), and Formula (63):

Formula (1)

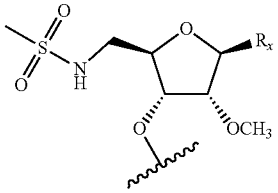

Formula (2)

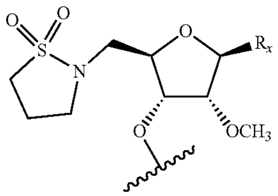

Formula (3)

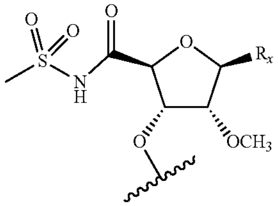

-continued

Formula (4)

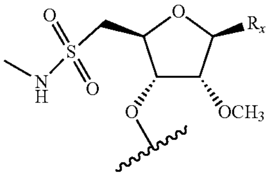

Formula (5)

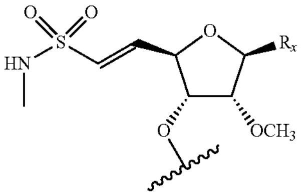

Formula (6)

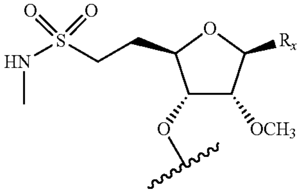

Formula (7)

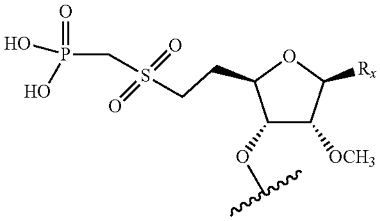

Formula (8)

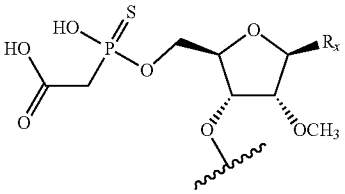

Formula (9)

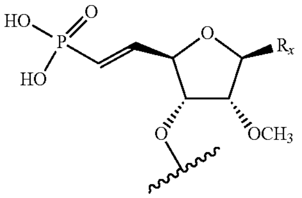

Formula (9X)

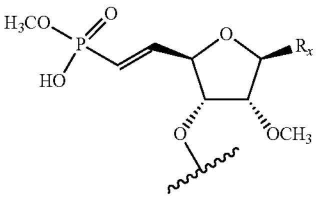

-continued
Formula (9Y)
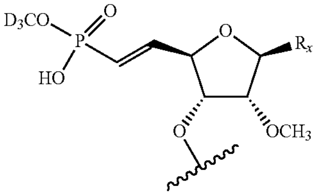
Formula (10)
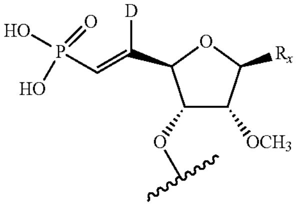
Formula (10X)
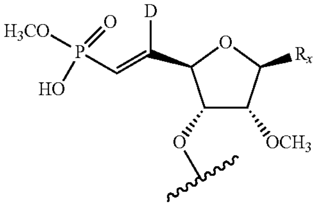
Formula (10Y)
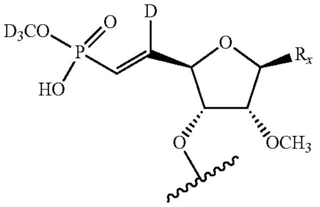
Formula (11)
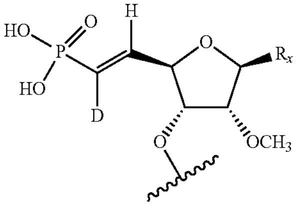
Formula (11X)
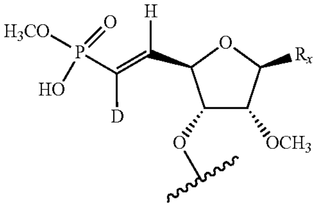
Formula (11Y)
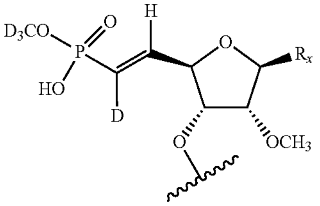
-continued
Formula (12)
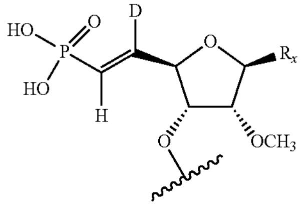
Formula (12X)
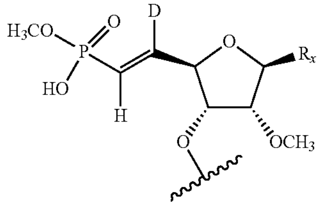
Formula (12Y)
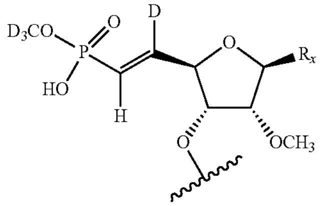
Formula (13)
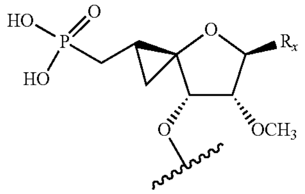
Formula (14)
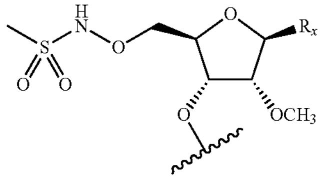
Formula (15)
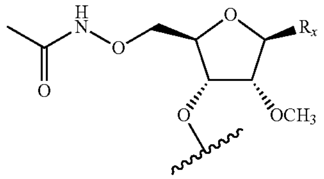
Formula (16)
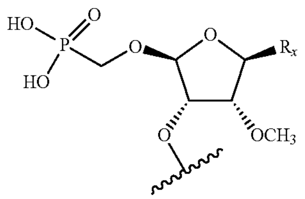

-continued
Formula (16X)
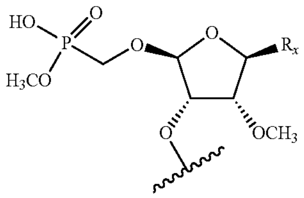
Formula (16Y)
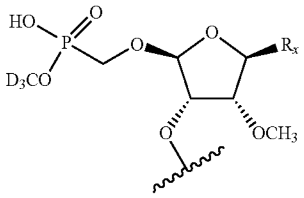
Formula (21)
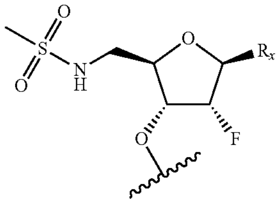
Formula (22)
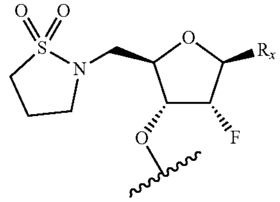
Formula (23)
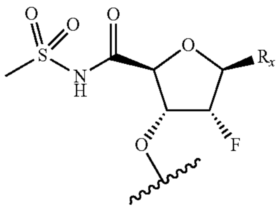
Formula (24)
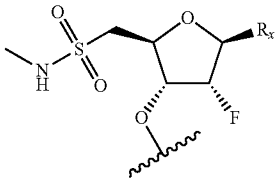
Formula (25)
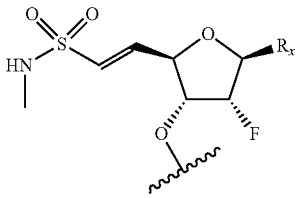
-continued
Formula (26)
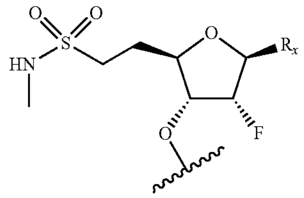
Formula (27)
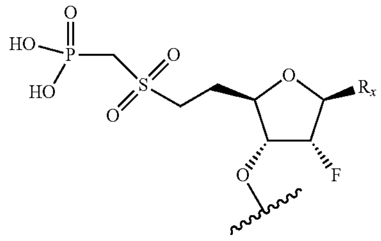
Formula (28)
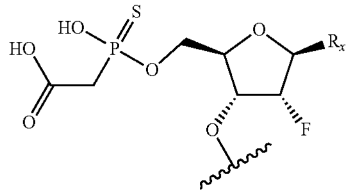
Formula (29)
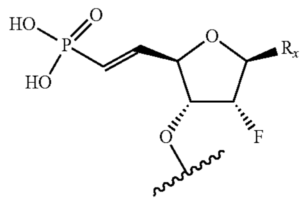
Formula (30)
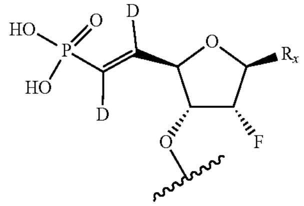
Formula (31)
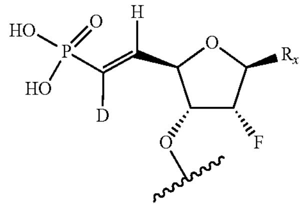
Formula (32)
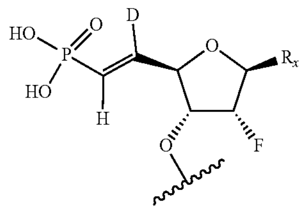

-continued
Formula (33)
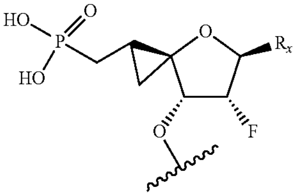
Formula (34)
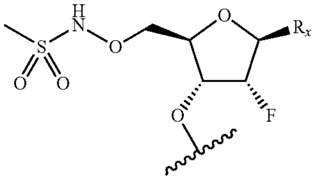
Formula (35)
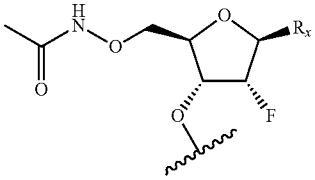
Formula (36)
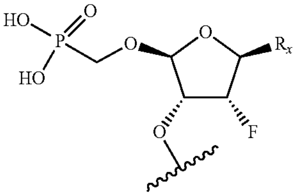
Formula (36X)
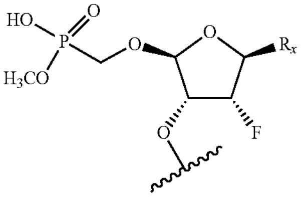
Formula (41)
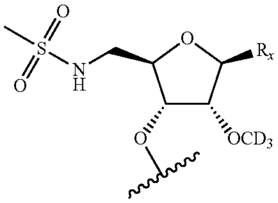
Formula (42)
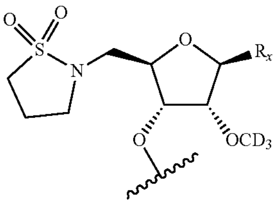
-continued
Formula (43)
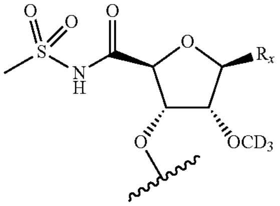
Formula (44)
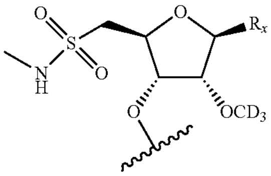
Formula (45)
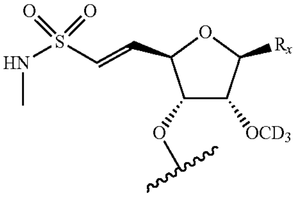
Formula (46)
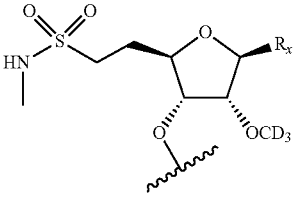
Formula (47)
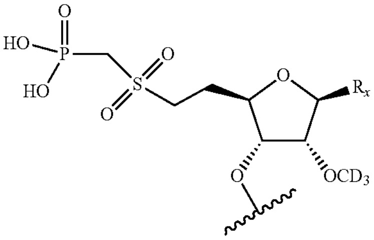
Formula (48)
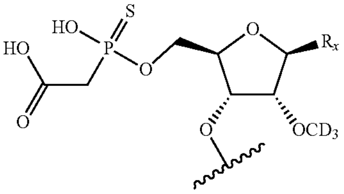
Formula (49)
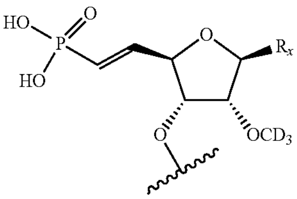

-continued
Formula (49X)
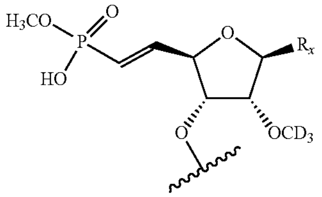
Formula (49Y)
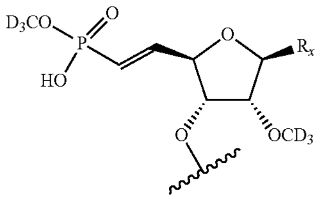
Formula (50)
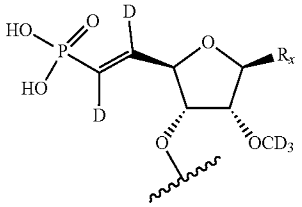
Formula (50X)
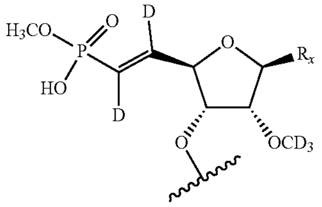
Formula (50Y)
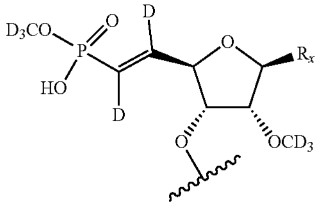
Formula (51)
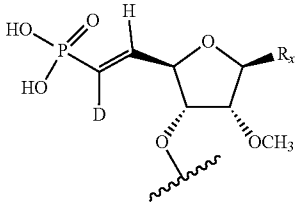
Formula (51X)
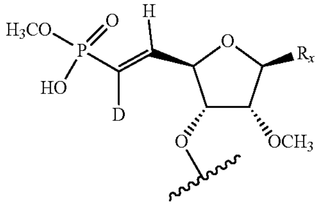
-continued
Formula (51Y)
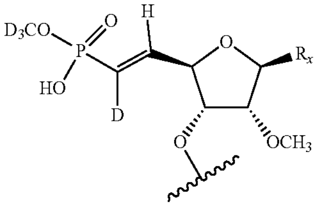
Formula (52)
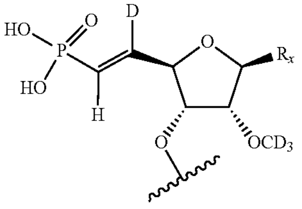
Formula (52X)
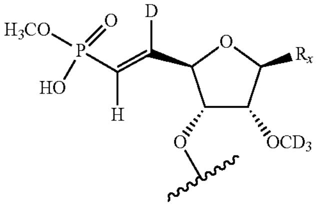
Formula (52Y)
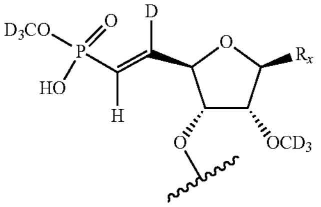
Formula (53)
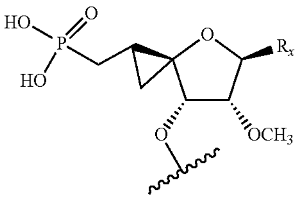
Formula (54)
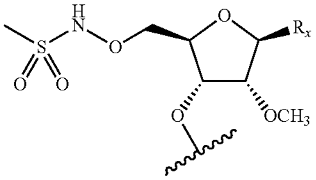
Formula (55)
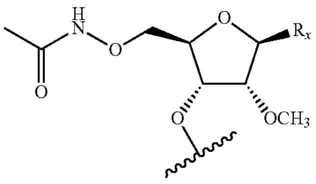

-continued

Formula (56)

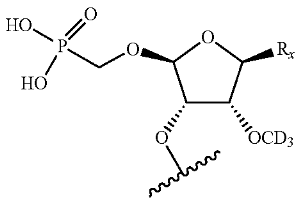

Formula (56X)

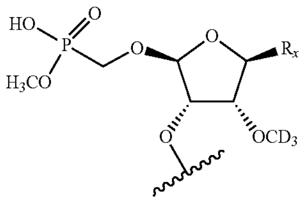

Formula (56Y)

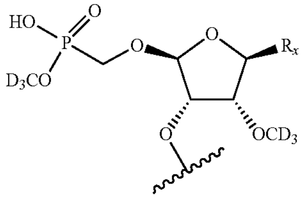

Formula (61)

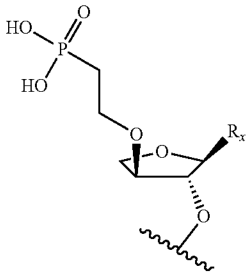

Formula (62)

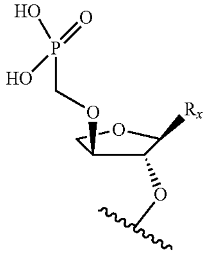

Formula (63)

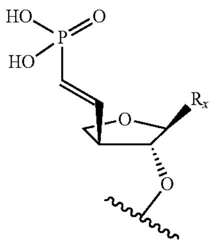

, wherein $R_x$ is a nucleobase, aryl, heteroaryl, or H.

In some embodiments of the disclosed siNA molecules, the antisense strand comprises a 5'-stabilized end cap selected from the group consisting of Formula (71) to Formula (86), Formula (79X) to Formula (82X), Formula (79Y) to (82Y), Formula 86X, Formula 86X', Formula 86Y, and Formula 86Y':

Formula (71)

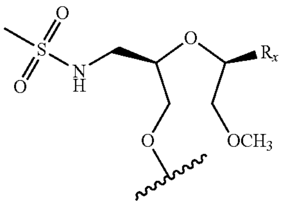

Formula (72)

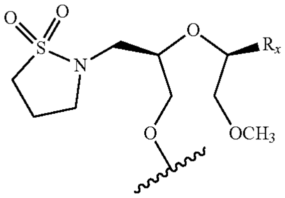

Formula (73)

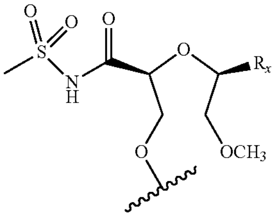

Formula (74)

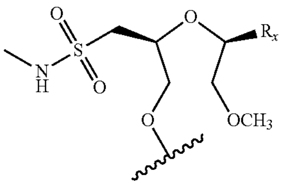

Formula (75)

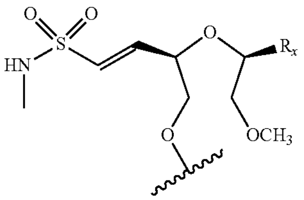

Formula (76)

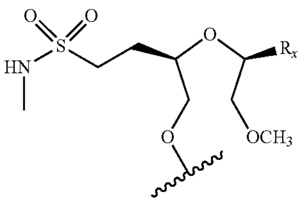

Formula (77)

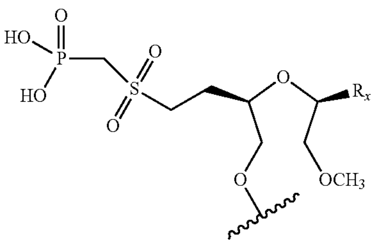

-continued
Formula (78)
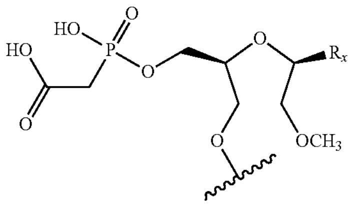
Formula (79)
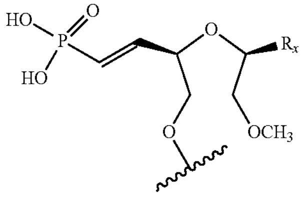
Formula (79X)
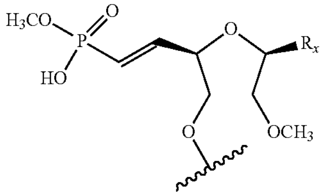
Formula (79Y)
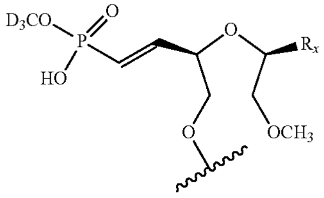
Formula (80)
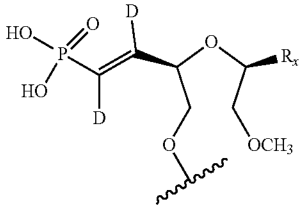
Formula (80X)
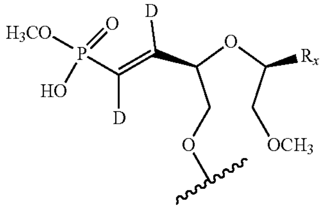
Formula (80Y)
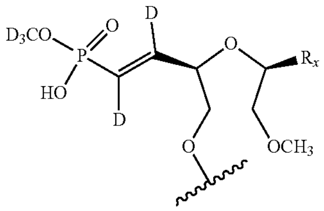
-continued
Formula (81)
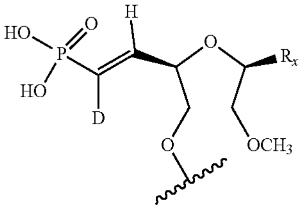
Formula (81X)
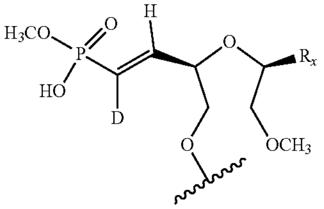
Formula (81Y)
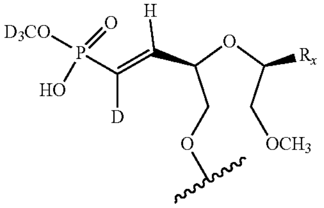
Formula (82)
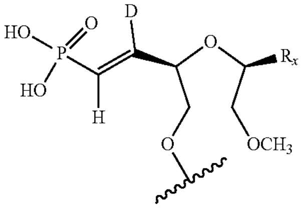
Formula (82X)
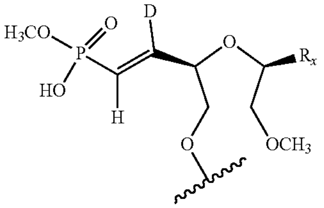
Formula (82Y)
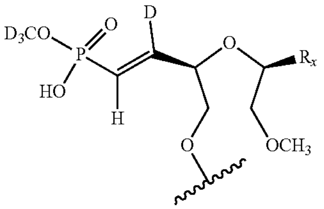
Formula (83)
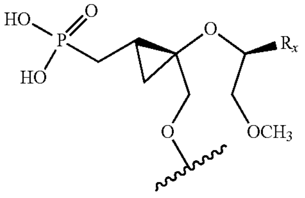

-continued

Formula (84)

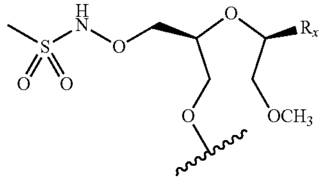

Formula (85)

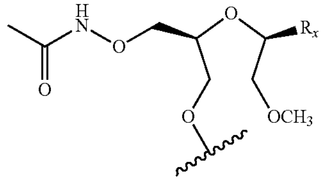

Formula (86)

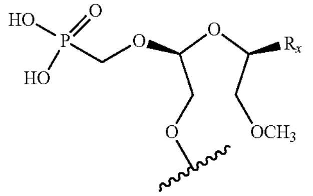

Formula (86X)

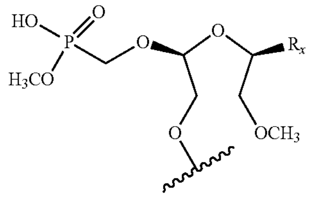

Formula (86X')

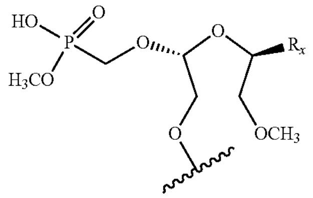

Formula (86Y)

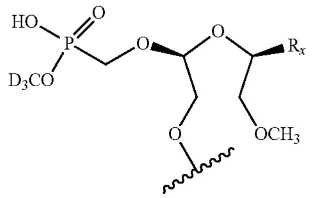

Formula (86Y')

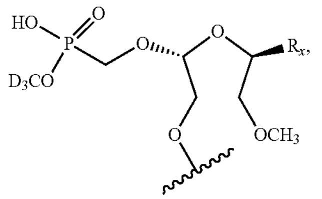

wherein $R_x$ is a nucleobase, aryl, heteroaryl, or H.

In some embodiments of the disclosed siNA molecules, the antisense strand comprises a 5'-stabilized end cap selected from the group consisting of Formulas (1A)-(15 A), Formulas (1A-1)-(7 A-1), Formulas (1A-2)-(7 A-2), Formulas (1A-3)-(7 A-3), Formulas (1A-4)-(7 A-4), Formulas (9B)-(12B), Formulas (9AX)-(12AX), Formulas (9AY)-(12AY), Formulas (9BX)-(12BX), and Formulas (9BY)-(12BY):

Formula (1A)

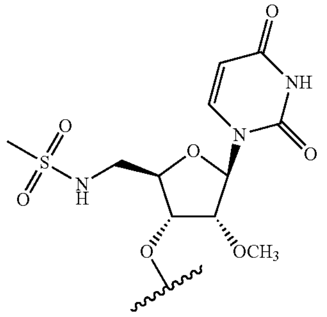

Formula (2A)

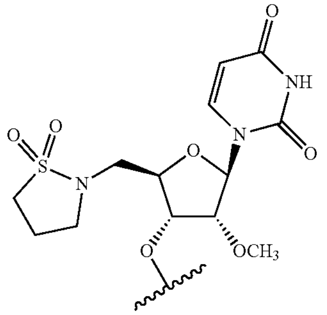

Formula (3A)

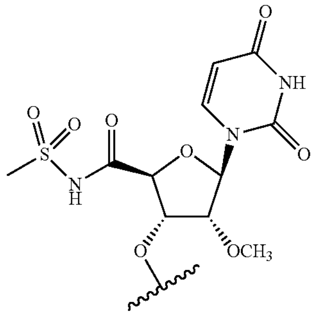

Formula (4A)

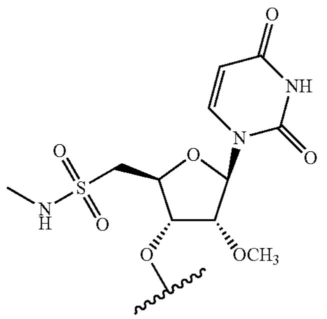

-continued
Formula (1A-1)
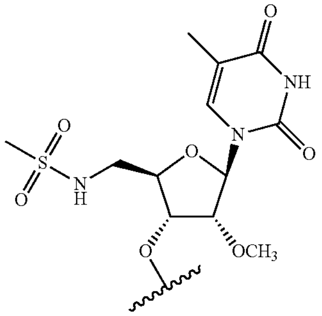
Formula (2A-1)
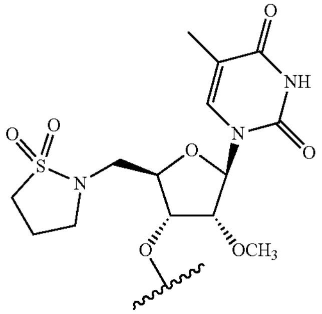
Formula (3A-1)
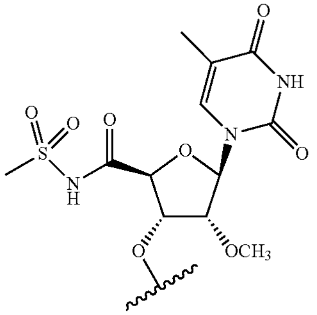
Formula (4A-1)
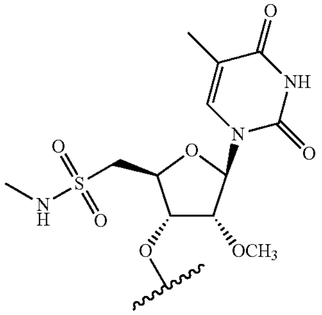
Formula (1A-2)
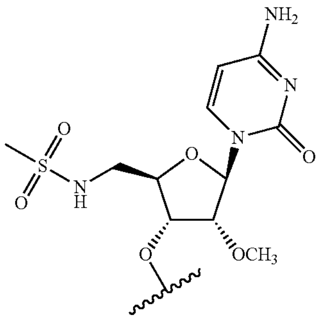
-continued
Formula (2A-2)
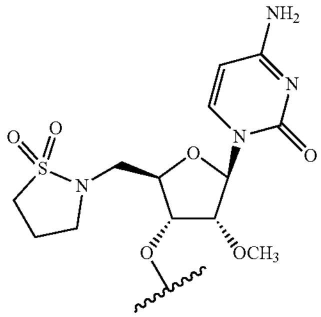
Formula (3A-2)
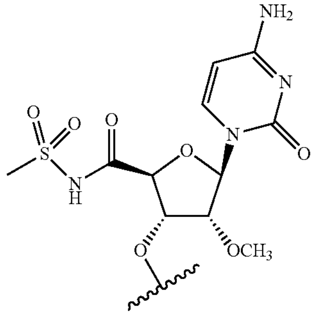
Formula (4A-2)
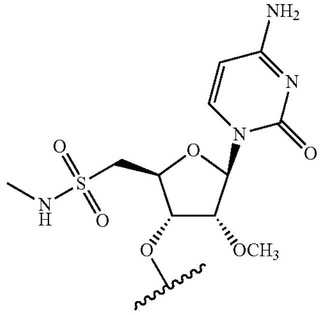
Formula (1A-3)
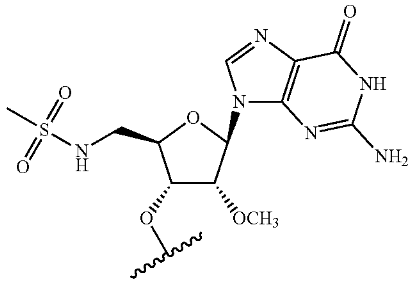
Formula (2A-3)
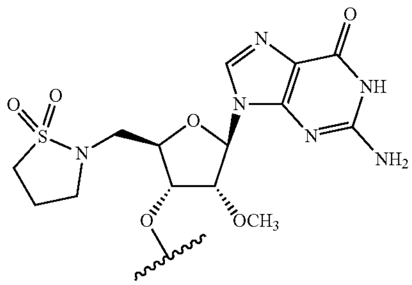

-continued
Formula (3A-3)
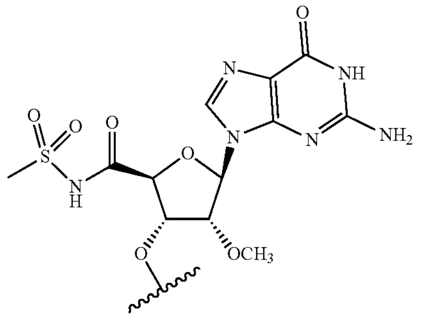
Formula (4A-3)
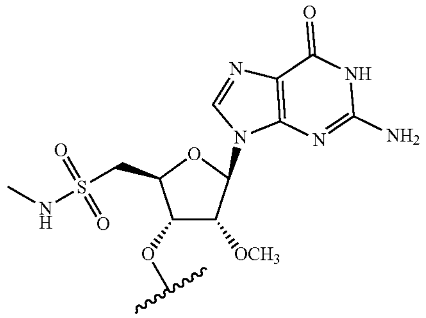
Formula (1A-4)
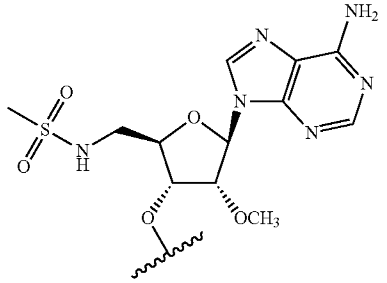
Formula (2A-4)
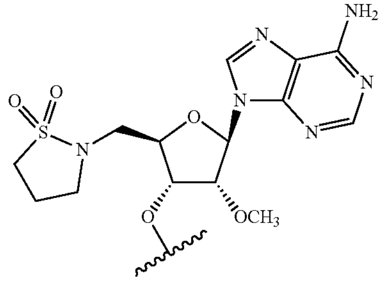
Formula (3A-4)
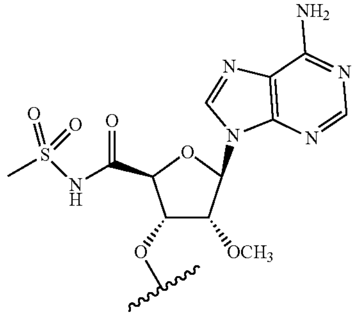
-continued
Formula (4A-4)
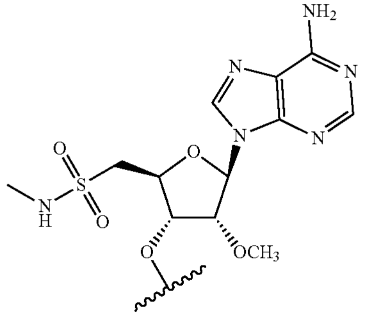
Formula (5A)
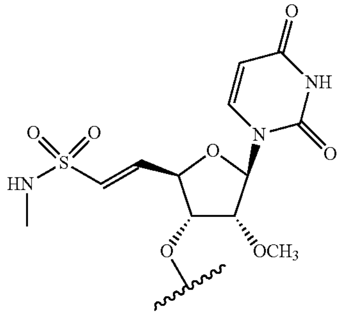
Formula (5A-1)
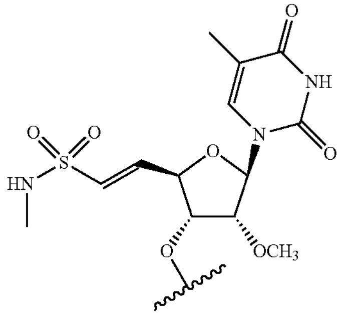
Formula (5A-2)
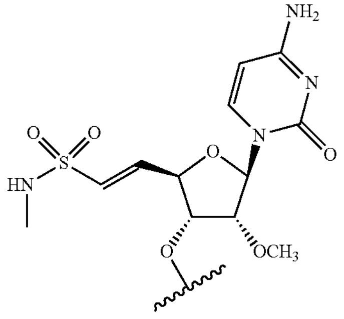
Formula (5A-3)
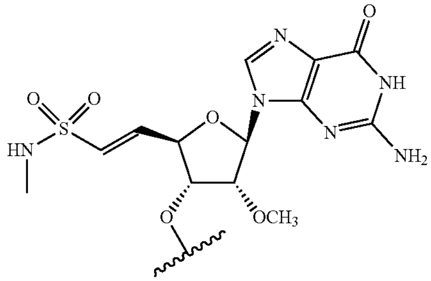

-continued
Formula (5A-4)
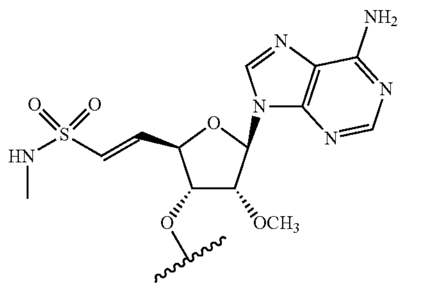
Formula (6A)
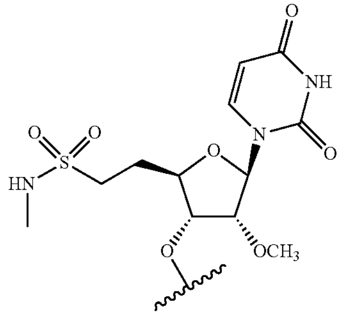
Formula (6A-1)
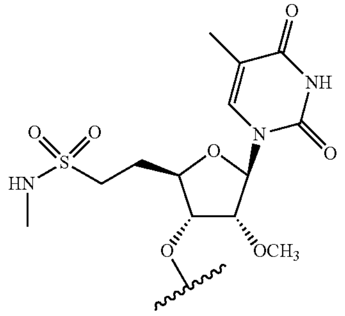
Formula (6A-2)
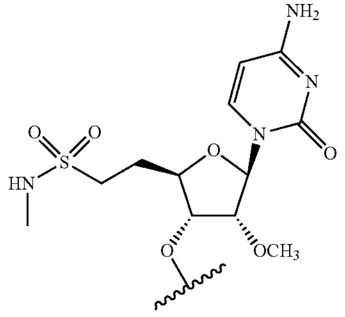
Formula (6A-3)
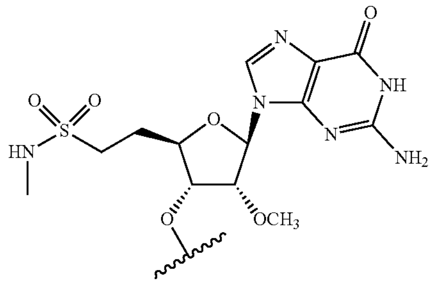
-continued
Formula (6A-4)
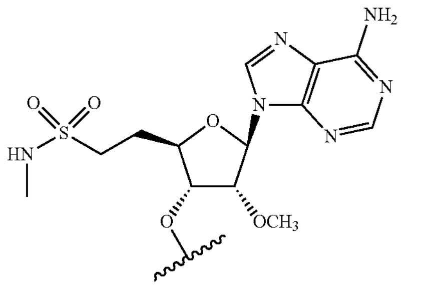
Formula (7A)
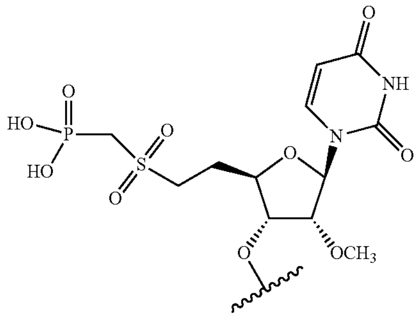
Formula (7A-1)
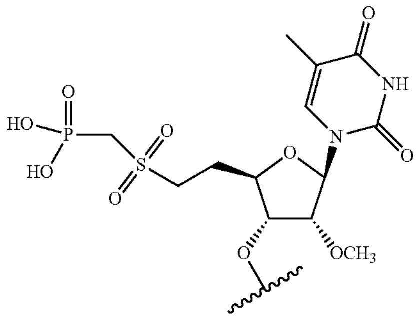
Formula (7A-2)
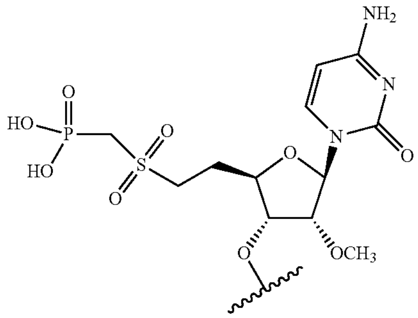
Formula (7A-3)
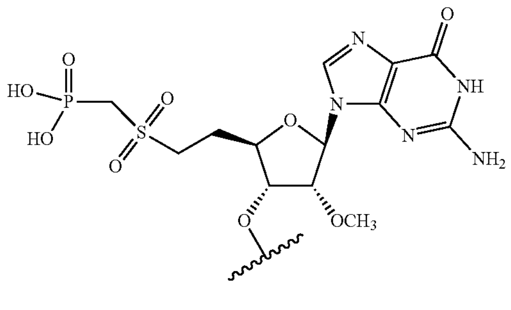

-continued
Formula (7A-4)
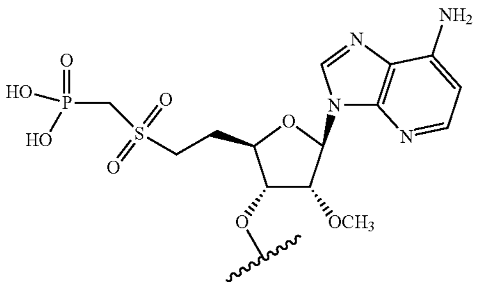
Formula (8A)
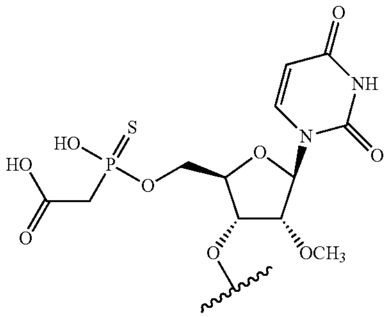
Formula (9A)
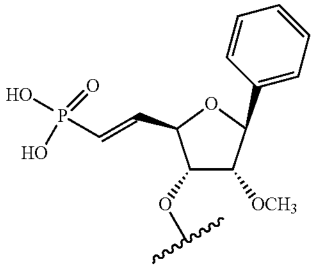
Formula (9AX)
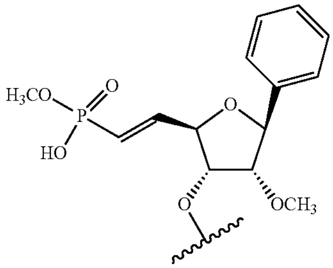
Formula (9AY)
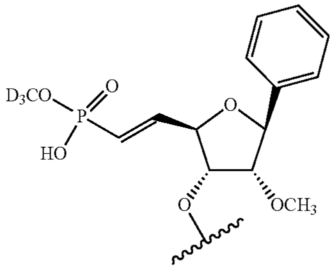
-continued
Formula (9B)
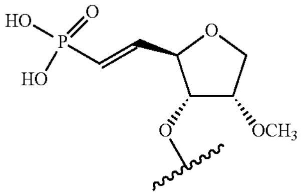
Formula (9BX)
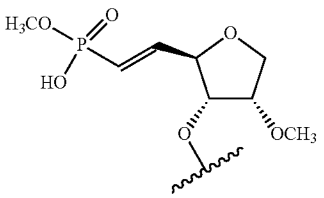
Formula (9BY)
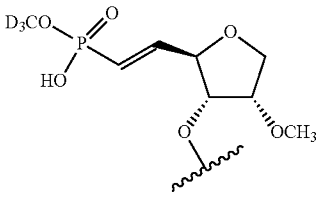
Formula (10A)
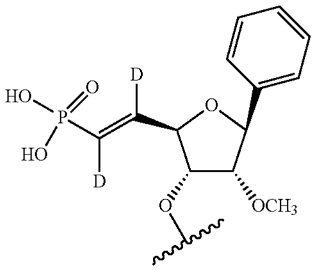
Formula (10AX)
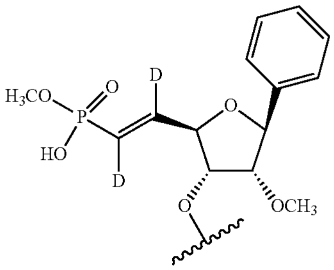
Formula (10AY)
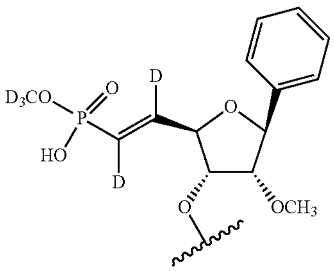

-continued
Formula (10B)
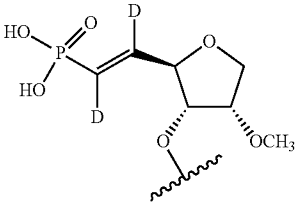
Formula (10BX)
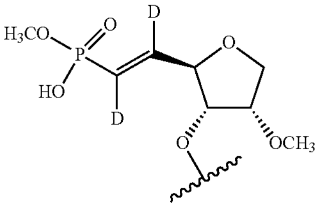
Formula (10BY)
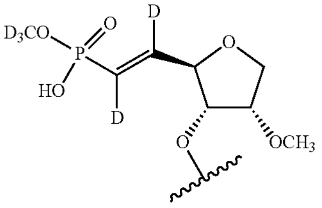
Formula (11A)
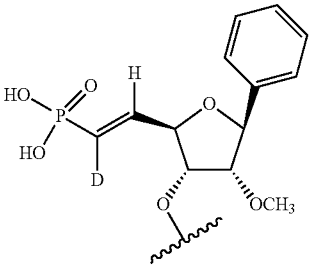
Formula (11AX)
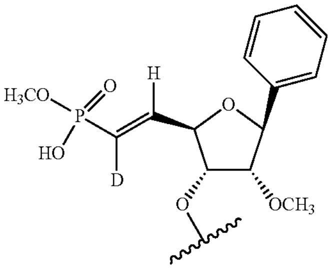
Formula (11AY)
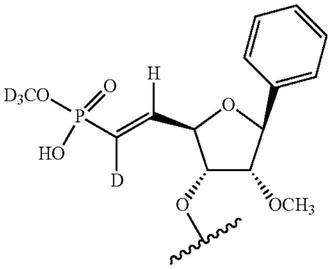
-continued
Formula (11B)
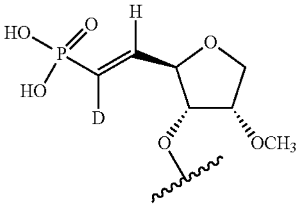
Formula (11BX)
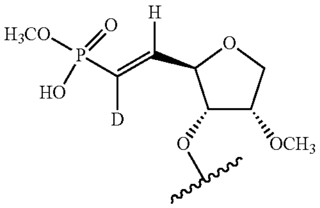
Formula (11BY)
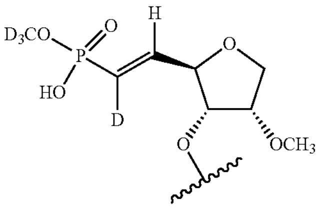
Formula (12A)
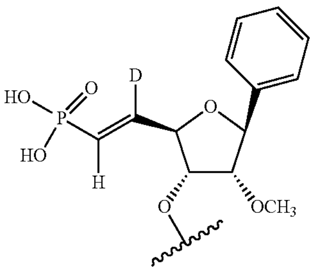
Formula (12AX)
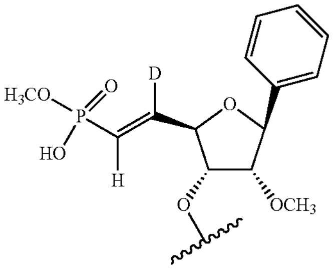
Formula (12AY)
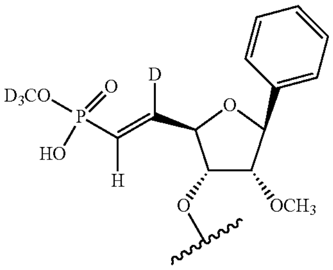

-continued
Formula (12B)
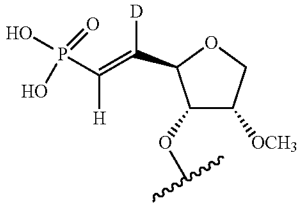
Formula (12BX)
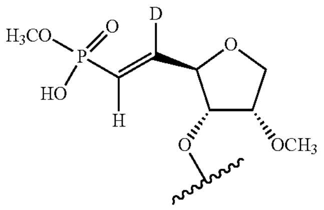
Formula (12BY)
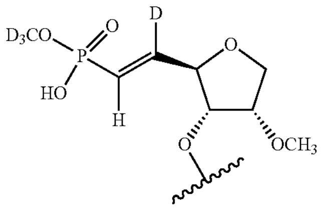
Formula (13A)
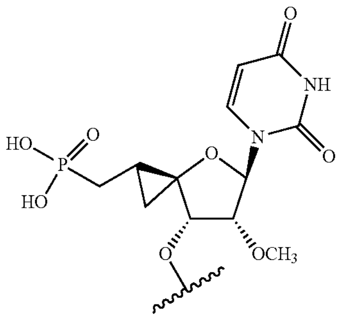
Formula (14A)
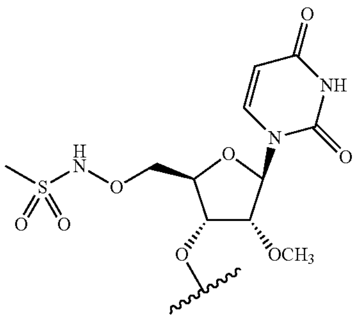
Formula (15A)
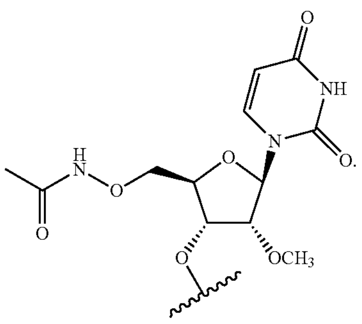
In some embodiments of the disclosed siNA molecules, the antisense strand comprises a 5'-stabilized end cap selected from the group consisting of Formulas (21A)-(35 A), Formulas (29B)-(32B), Formulas (29AX)-(32AX), Formulas (29AY)-(32AY), Formulas (29BX)-(32BX), and Formulas (29BY)-(32BY):
Formula (21A)
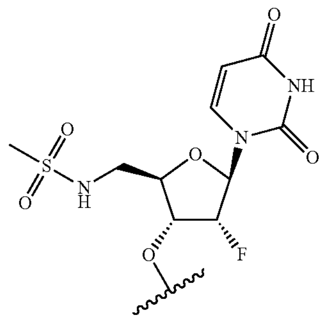
Formula (22A)
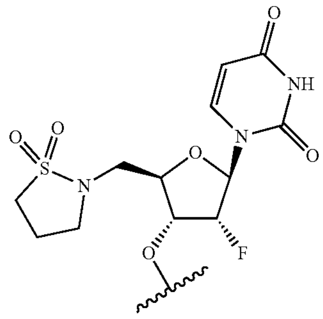
Formula (23A)
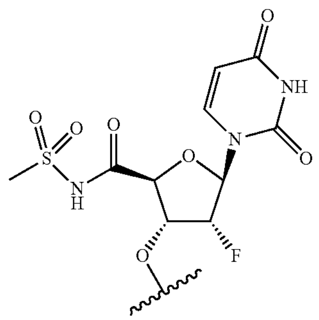
Formula (24A)
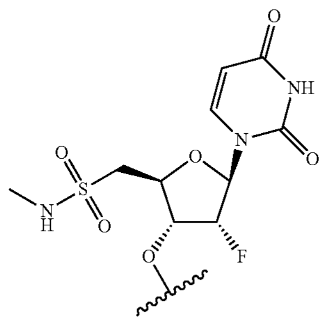

-continued
Formula (25A)
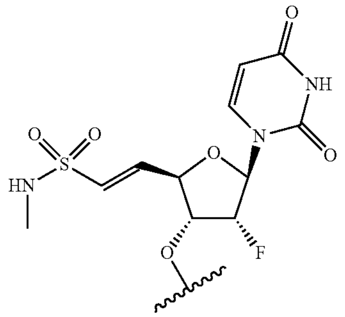
Formula (26A)
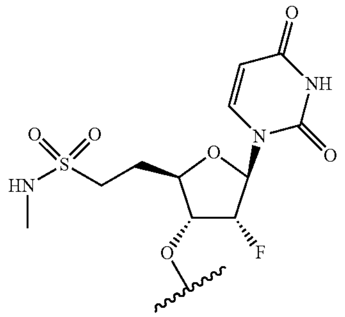
Formula (27A)
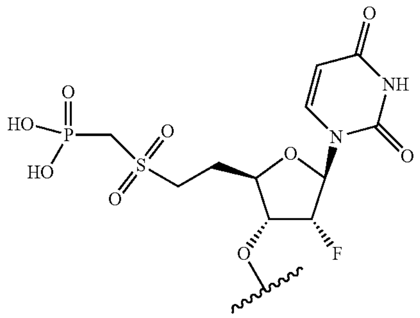
Formula (28A)
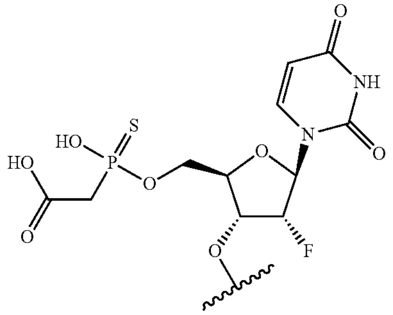
Formula (29A)
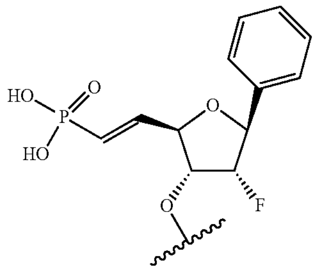
-continued
Formula (29AX)
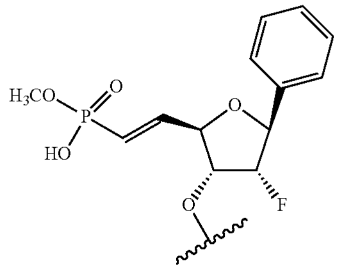
Formula (29AY)
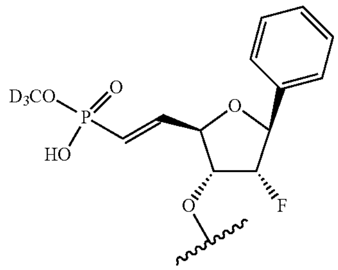
Formula (29B)
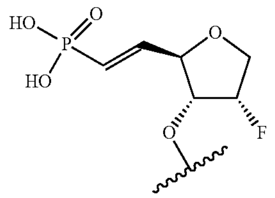
Formula (29BX)
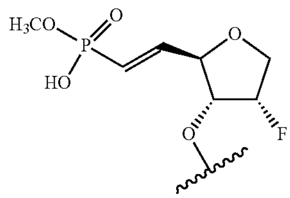
Formula (29BY)
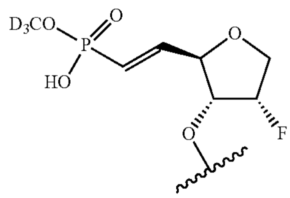
Formula (30A)
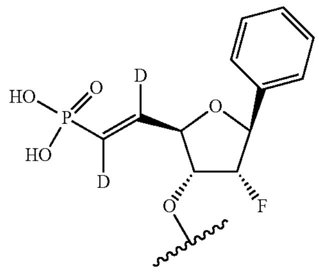

-continued
Formula (30AX)
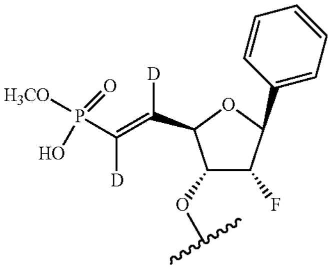
Formula (30AY)
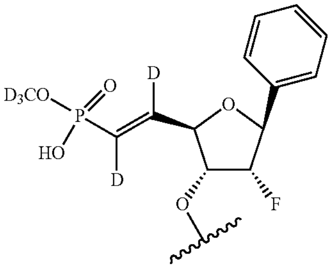
Formula (30B)
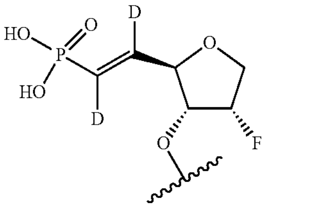
Formula (30BX)
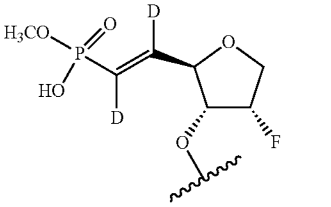
Formula (30BY)
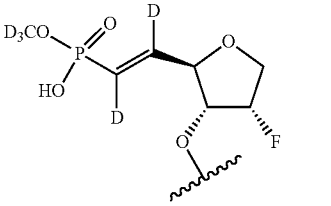
Formula (31A)
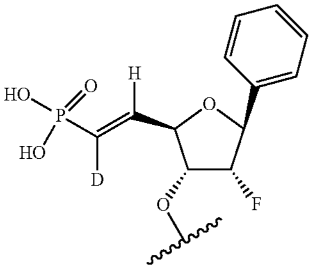
-continued
Formula (31AX)
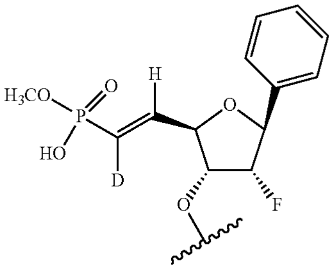
Formula (31AY)
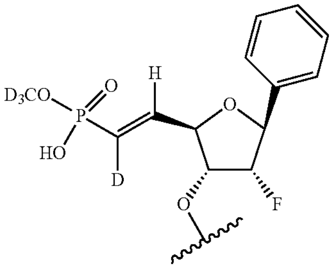
Formula (31B)
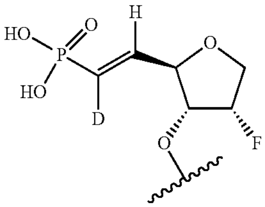
Formula (31BX)
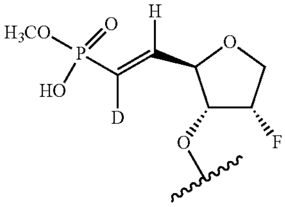
Formula (31BY)
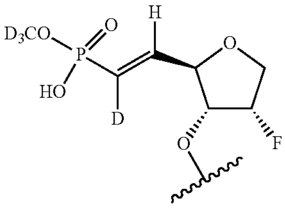
Formula (32A)
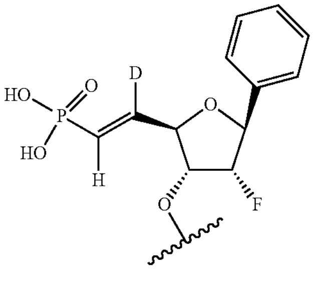

-continued
Formula (32AX)
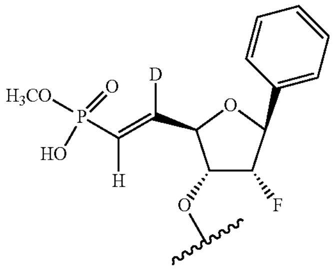
Formula (32AY)
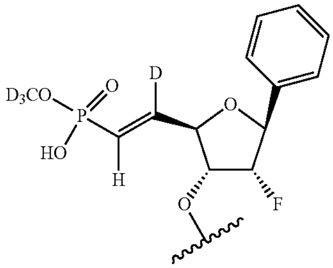
Formula (32B)
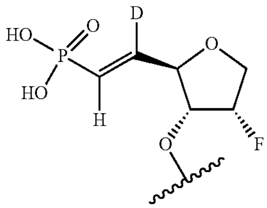
Formula (32BX)
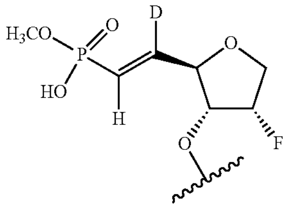
Formula (32BY)
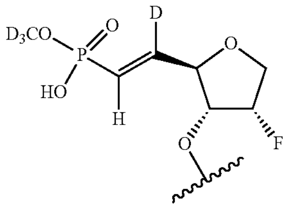
Formula (33A)
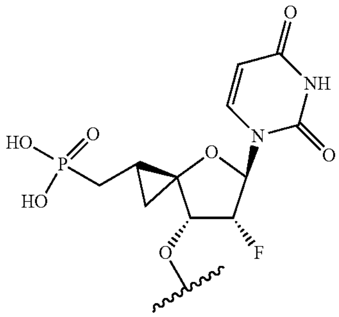
-continued
Formula (34A)
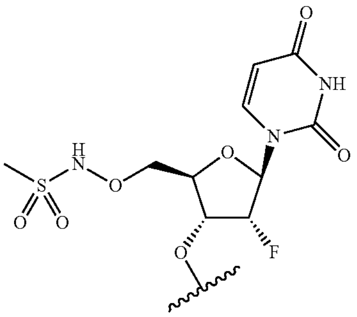
Formula (35A)
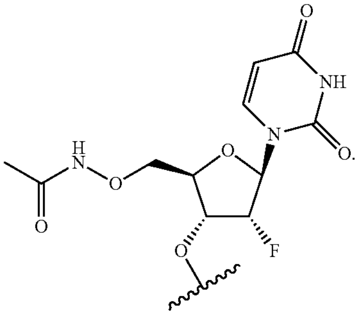
In some embodiments of the disclosed siNA molecules, the antisense strand comprises a 5'-stabilized end cap selected from the group consisting of Formulas (71A)-(86 A), Formulas (79XA)-(82XA), Formulas (79YA)-(82YA); Formula (86XA), Formula (86X'A), Formula (86Y), and Formula (86Y'):
Formula (71A)
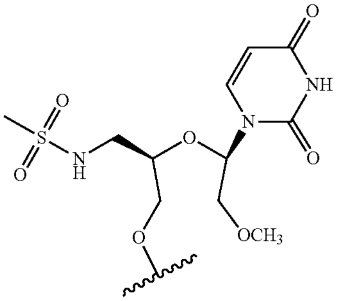
Formula (72A)
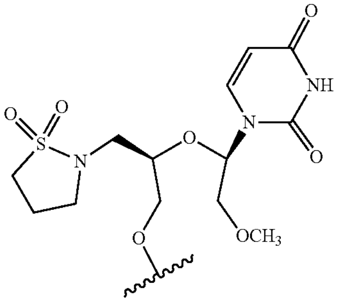

Formula (73A)
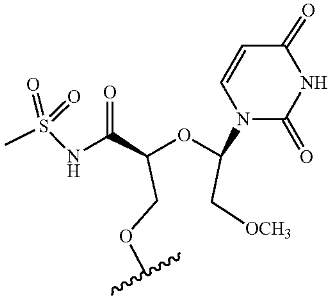
Formula (74A)
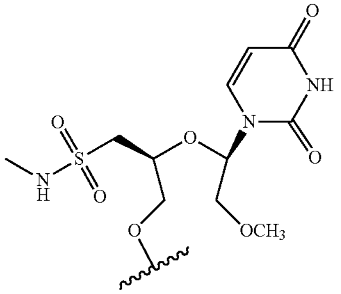
Formula (75A)
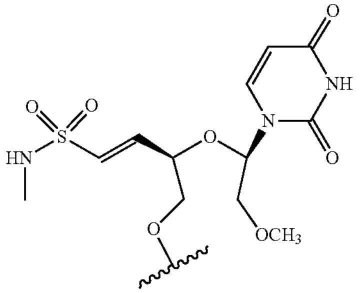
Formula (76A)
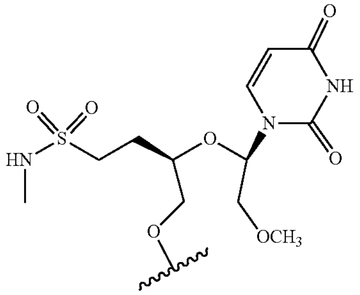
Formula (77A)
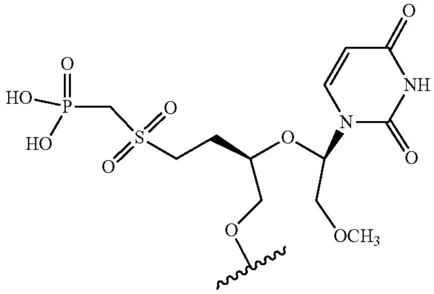
Formula (78A)
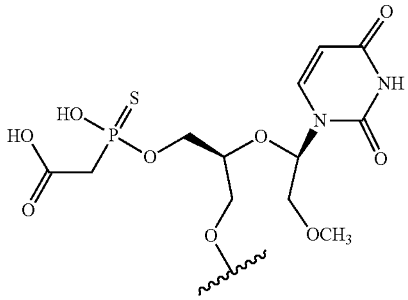
Formula (79A)
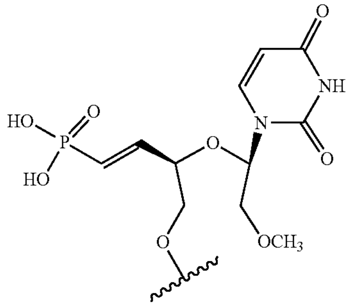
Formula (79XA)
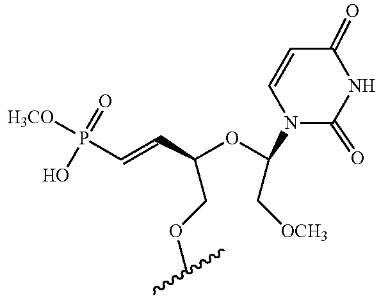
Formula (79YA)
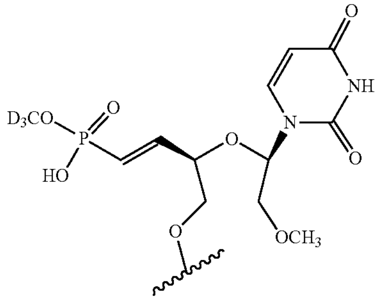
Formula (80A)
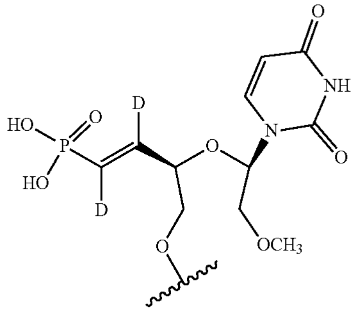

-continued
Formula (80XA)
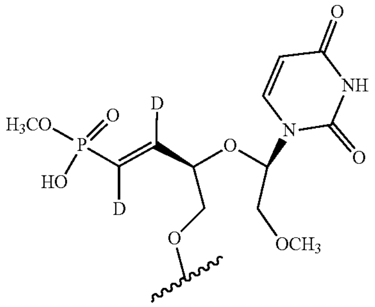
Formula (80YA)
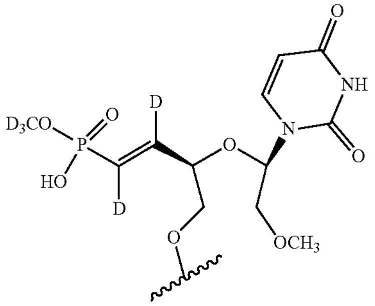
Formula (81A)
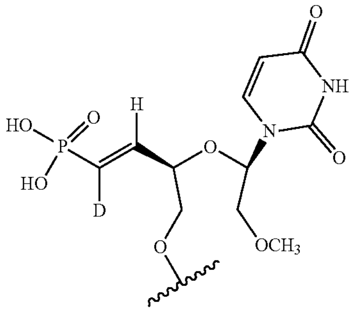
Formula (81XA)
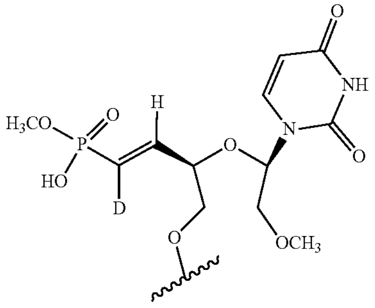
Formula (81YA)
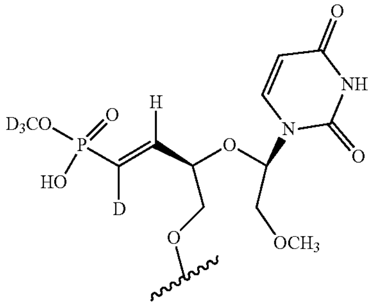
-continued
Formula (82A)
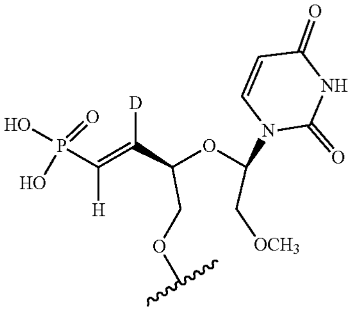
Formula (82XA)
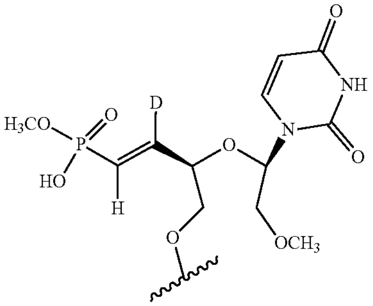
Formula (82YA)
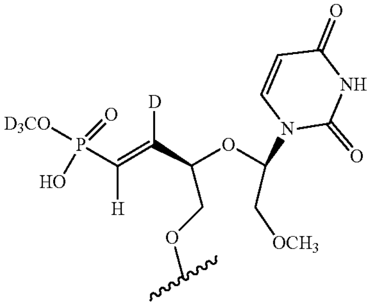
Formula (83A)
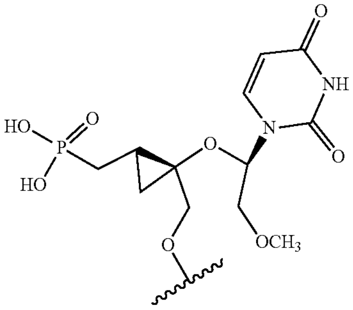
Formula (84A)
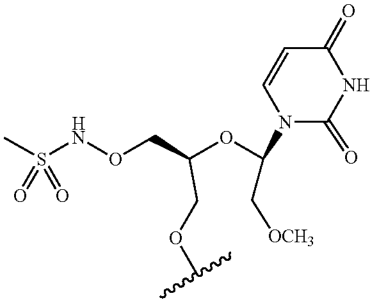

-continued
Formula (85A)
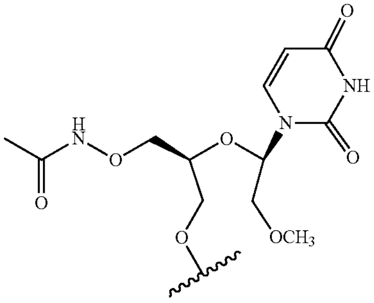
Formula (86A)
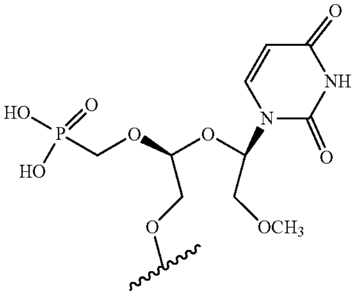
Formula (86XA)
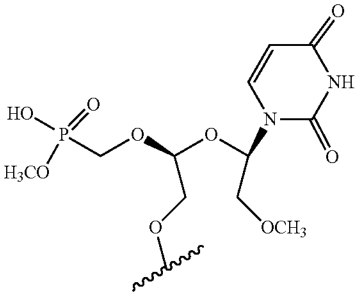
Formula (86X'A)
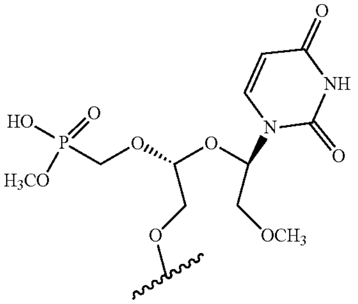
-continued
Formula (86Y)
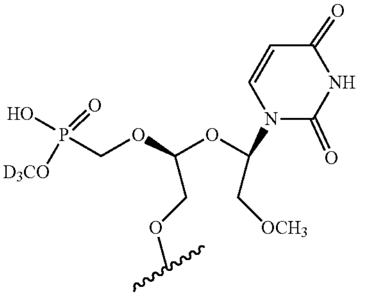
Formula (86Y')
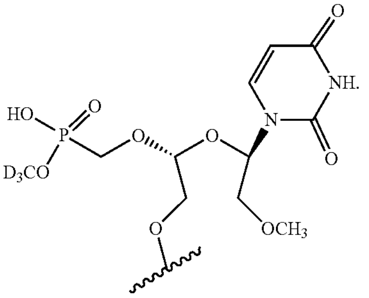
In some embodiments of the disclosed siNA molecules, the siNA further comprises a galactosamine. In some embodiments, the galactosamine is N-acetylgalactosamine (GalNAc) of Formula (VI):
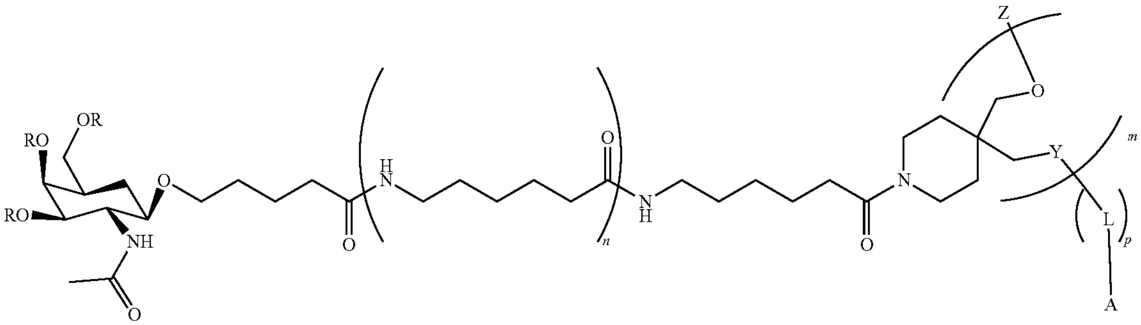
, wherein m is 1, 2, 3, 4, or 5;

each n is independently 1 or 2;

p is 0 or 1;

each R is independently H;

each Y is independently selected from —O—P(=O)(SH)—, —O—P(=O)(O)—, —O—P(=O)(OH)—, and —O—P(S)S—;

Z is H or a second protecting group;

either L is a linker or L and Y in combination are a linker; and

A is H, OH, a third protecting group, an activated group, or an oligonucleotide.

In some embodiments of the disclosed siNA molecules, the galactosamine is N-acetylgalactosamine (GalNAc) of Formula (VII):

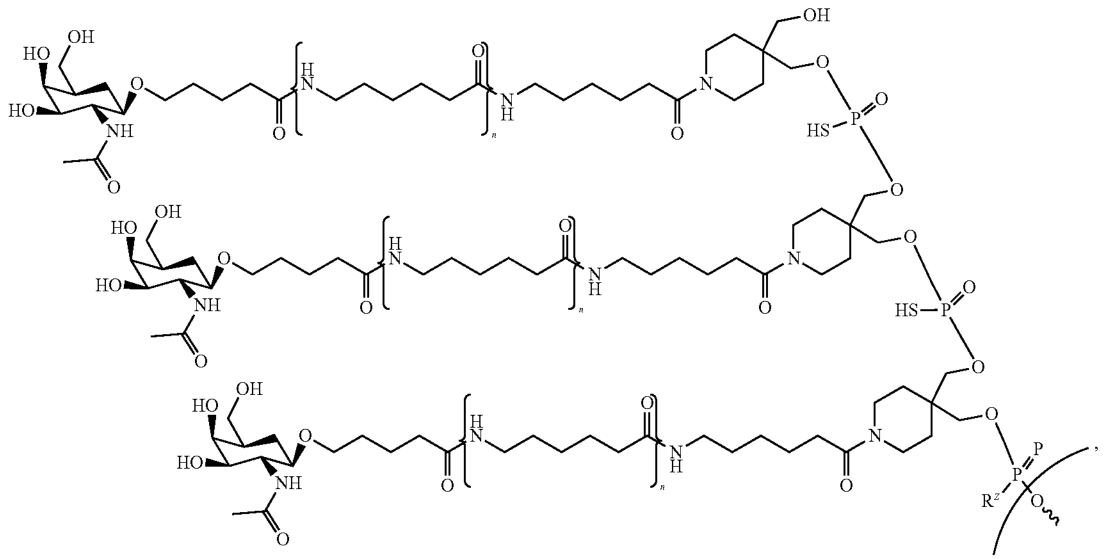

wherein $R^z$ is OH or SH; and each n is independently 1 or 2.

In some embodiments of the disclosed siNA molecules, (i) at least one end of the siNA is a blunt end; (ii) at least one end of the siNA comprises an overhang, wherein the overhang comprises at least one nucleotide; or (iii) both ends of the siNA comprise an overhang, wherein the overhang comprises at least one nucleotide.

In some embodiments of the disclosed siNA molecules, (i) the target gene is a viral gene; (ii) the target gene is a gene is from a DNA virus; (iii) the target gene is a gene from a double-stranded DNA (dsDNA) virus; (iv) the target gene is a gene from a hepadnavirus; (v) the target gene is a gene from a a hepatitis B virus (HBV); (vi) the target gene is a gene from a HBV of any one of genotypes A-J; or (vii) the target gene is selected from the S gene or X gene of a HBV The present disclosure provides siNA shown in Table 1, Table 2, Table 3, Table 4, and Table 5.

The present disclosure provides compositions comprising the siNA as disclosed herein; and a pharmaceutically acceptable excipient. In some embodiments, the compositions may further comprise 2, 3, 4, 5, 6, 7, 8, 9, 10 or more siNAs as disclosed herein. In some embodiments, the compositions may further comprise an additional treatment agent. For example, the additional treatment agent is selected from a nucleotide analog, nucleoside analog, a capsid assembly modulator (CAM), a recombinant interferon, an entry inhibitor, a small molecule immunomodulatory, and oligonucleotide therapy, such as an additional siNA, an antisense oligonucleotide (ASO), NAPs, or STOPS™.

The present disclosure provides methods of treating a disease in a subject in need thereof, comprising administering to the subject the siNA disclosed herein or a composition comprising the siNA disclosed herein. The present disclosure further provides uses of the disclosed siNA and compositions for treating a disease in a subject. The present disclosure further provides siNA and compositions for use in treating a disease in a subject.

In some embodiments of the disclosed methods and uses, the disease is a viral disease, which is optionally caused by a DNA virus or a a double stranded DNA (dsDNA) virus. In some embodiments, the dsDNA virus is a hepadnavirus. In some embodiments, the hepadnavirus is a hepatitis B virus (HBV), and optionally wherein the HBV is selected from HBV genotypes A-J. In some embodiments, the methods and uses may further comprise administering an additional HBV treatment agent. In some embodiments, the siNA or the composition and the additional HBV treatment agent are administered concurrently or administered sequentially. In some embodiments, the additional HBV treatment agent is selected from a nucleotide analog, nucleoside analog, a capsid assembly modulator (CAM), a recombinant interferon, an entry inhibitor, a small molecule immunomodulator and oligonucleotide therapy. In some embodiments, the viral disease is a disease caused by a coronavirus, and optionally wherein the coronavirus is SARS-CoV-2.

In some embodiments of the disclosed methods and uses, the disease is a liver disease. In some embodiments, the liver disease is a nonalcoholic fatty liver disease (NAFLD) or hepatocellular carcinoma (HCC). In some embodiments, the NAFLD is nonalcoholic steatohepatitis (NASH). Some embodiments may further comprise administering to the subject a liver disease treatment agent. In some embodiments, the liver disease treatment agent is selected from a peroxisome proliferator-activator receptor (PPAR) agonist, farnesoid X receptor (FXR) agonist, lipid-altering agent, and incretin-based therapy. In some embodiments, (i) the PPAR agonist is selected from a PPARα agonist, dual PPARα/δ agonist, PPARγ agonist, and dual PPARα/γ agonist; (ii) the lipid-altering agent is aramchol; or (iii) the incretin-based therapy is a glucagon-like peptide 1 (GLP-1) receptor agonist or dipeptidyl peptidase 4 (DPP-4) inhibitor. In some embodiments, the siNA or composition and the liver disease treatment agent are administered concurrently or administered sequentially.

In some embodiments of the disclosed methods and uses, the siNA or the composition is administered at a dose of at least 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg 14 mg/kg, or 15 mg/kg.

In some embodiments of the disclosed methods and uses, the siNA or the composition is administered at a dose of between 0.5 mg/kg to 50 mg/kg, 0.5 mg/kg to 40 mg/kg 0.5 mg/kg to 30 mg/kg, 1 mg/kg to 50 mg/kg, 1 mg/kg to 40 mg/kg, 1 mg/kg to 30 mg/kg, 1 mg/kg to 20 mg/kg, 3 mg/kg to 50 mg/kg, 3 mg/kg to 40 mg/kg, 3 mg/kg to 30 mg/kg, 3 mg/kg to 20 mg/kg, 3 mg/kg to 15 mg/kg, 3 mg/kg to 10 mg/kg, 4 mg/kg to 50 mg/kg, 4 mg/kg to 40 mg/kg, 4 mg/kg to 30 mg/kg, 4 mg/kg to 20 mg/kg, 4 mg/kg to 15 mg/kg, 4 mg/kg to 10 mg/kg, 5 mg/kg to 50 mg/kg, 5 mg/kg to 40 mg/kg, 5 mg/kg to 30 mg/kg, 5 mg/kg to 20 mg/kg, 5 mg/kg to 15 mg/kg, or 5 mg/kg to 10 mg/kg.

In some embodiments of the disclosed methods and uses, the siNA or the composition is administered at least 1, 2, 3, 4, 5, 6, 7, 8, 9, or 10 times.

In some embodiments of the disclosed methods and uses, the siNA or the composition is administered at least 1, 2, 3, 4, 5, 6, 7, 8, 9, or 10 times a day, at least 1, 2, 3, 4, 5, 6, 7, 8, 9, or 10 times a week, or at least 1, 2, 3, 4, 5, 6, 7, 8, 9, or 10 times a month.

In some embodiments of the disclosed methods and uses, the siNA or the composition is administered at least once every 1, 2, 3, 4, 5, 6, 7, 8, 9, 10, 11, 12, 13, 14, 15, 16, 17, 18, 19, 20, or 21 days.

In some embodiments of the disclosed methods and uses, the siNA or the composition is administered for a period of at least 1, 2, 3, 4, 5, 6, 7, 8, 9, 10, 11, 12, 13, 14, 15, 16, 17, 18, 19, 20, or 21 days, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 51, 52, 53, 54, or 55 weeks.

In some embodiments of the disclosed methods and uses, the siNA or the composition is administered at a single dose of 5 mg/kg or 10 mg/kg, at three doses of 10 mg/kg once a week, at three doses of 10 mg/kg once every three days, or at five doses of 10 mg/kg once every three days.

In some embodiments of the disclosed methods and uses, the siNA or the composition is administered at six doses of ranging from 1 mg/kg to 15 mg/kg, 1 mg/kg to 10 mg/kg, 2 mg/kg to 15 mg/kg, 2 mg/kg to 10 mg/kg, 3 mg/kg to 15 mg/kg, or 3 mg/kg to 10 mg/kg; wherein the first dose and second dose are optionally administered at least 3 days apart; wherein the second dose and third dose are optionally administered at least 4 days apart; and wherein the third dose and fourth dose, fourth dose and fifth dose, and or fifth dose and sixth dose are optionally administered at least 7 days apart.

In some embodiments of the disclosed methods and uses, the siNA or the composition are administered in a particle or viral vector, wherein the viral vector is optionally selected from a vector of adenovirus, adeno-associated virus (AAV), alphavirus, flavivirus, herpes simplex virus, lentivirus, measles virus, picornavirus, poxvirus, retrovirus, and rhabdovirus. In some embodiments, the viral vector is a recombinant viral vector. In some embodiments, the viral vector is selected from AAVrh.74, AAVrh.10, AAVrh.20, AAV-1, AAV-2, AAV-3, AAV-4, AAV-5, AAV-6, AAV-7, AAV-8, AAV-9, AAV-10, AAV-11, AAV-12 and AAV-13.

In some embodiments of the disclosed methods and uses, the siNA or the composition is administered systemically or administered locally.

In some embodiments of the disclosed methods and uses, the siNA or the composition is administered intravenously, subcutaneously, or intramuscularly.

The foregoing general description and following detailed description are exemplary and explanatory and are intended to provide further explanation of the disclosure as claimed. Other objects, advantages, and novel features will be readily apparent to those skilled in the art from the following brief description of the drawings and detailed description of the disclosure.

DETAILED DESCRIPTION

Figure 1:
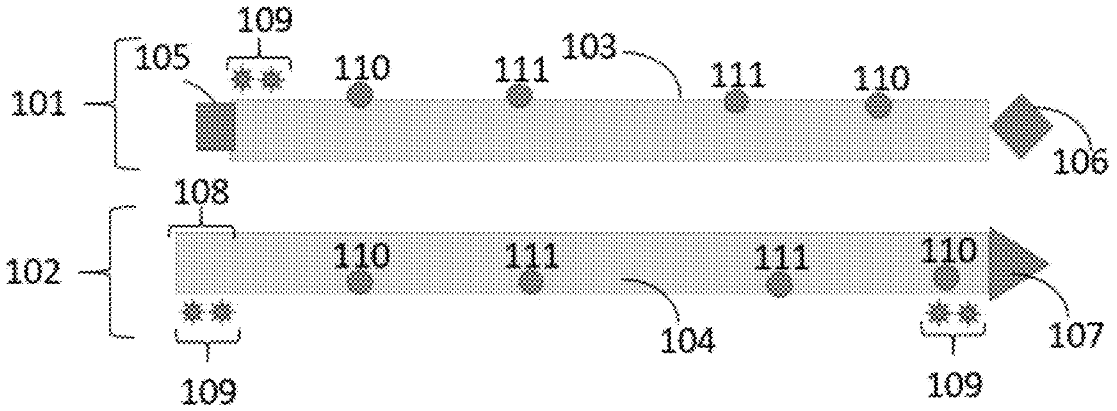
FIG. 1 illustrates an exemplary siNA molecule.

Disclosed herein are novel, modified nucelobase monomers that may comprise a unique chemical moiety in place of a base, lack a bond between the 3' and 4' carbons of the central furanose ring (i.e., an unlocked nucleotide), and/or possess a phosphate mimicking group (such nucleotides may henceforth be referred to as “nucleotide phosphate mimics”). Also disclosed herein are short interfering nucleic acid (siNA) molecules comprising modified nucleobases (i.e., nucleotides).

In general, the siNA molecules described herein may be double-stranded siNA (ds-siNA) molecules. The siNA molecules described herein may comprise modified nucleotides selected from 2'-O-methyl nucleotides and 2'-fluoro nucleotides. The siNA molecules described herein may comprise 1, 2, 3, 4, 5, 6, 7, 8, 9, or 10 or more phosphorothioate internucleoside linkages. The siNA molecules described herein may comprise 1, 2, 3, 4, 5, 6, 7, 8, 9, or 10 or more mesyl phosphoramidate internucleoside linkages. The siNA molecules described herein may comprise at least one phosphorylation blocker. The siNA molecules described herein may comprise a 5'-stabilized end cap (including but not limited to the disclosed nucleotide phosphate mimics). The siNA molecules described herein may comprise a galactosamine. The siNA molecules described herein may comprise one or more blunt ends. The siNA molecules described herein may comprise one or more overhangs.

For instance, the present disclosure provides modified nucleotides comprising a structure of:

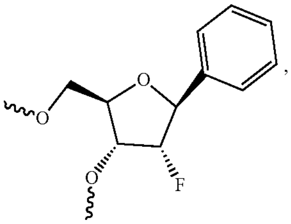

, (fB)

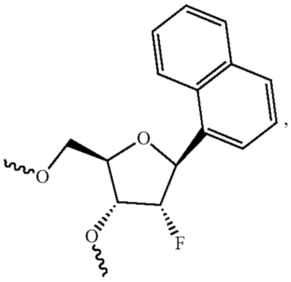

, (fN)

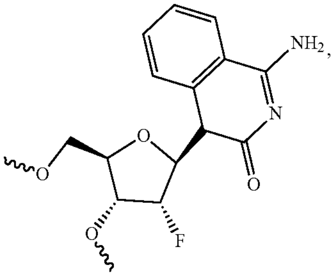

, or (f(4nh)Q)

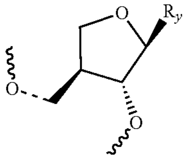

(apN)

wherein $R_y$ is a nucleobase, as well as modified nucleotides comprising a structure of:

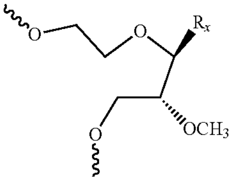

, wherein $R_x$ is a nucleobase, aryl, heteroaryl, or H. In some embodiments, the modified nucleotides may comprise a structure of:

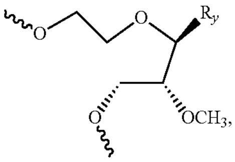

, wherein $R_y$ is a nucleobase. In some embodiments, the nucleobase is selected from thymine, cytosine, guanine, adenine, uracil, and an analogue or derivative thereof.

The present disclosure also provides nucleotide phosphate mimics that can serve as a stabilized end cap at the 5' end of the antisense strand of any of the disclosed siNA. The disclosed nucleotide phosphate mimics include, but are not limited to, the structures:

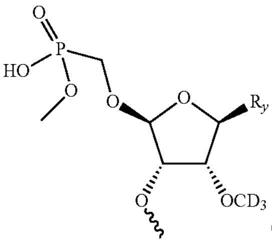

(omeco-d3 nucleotide),

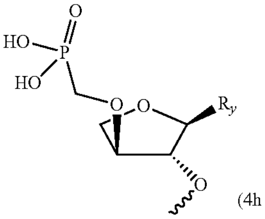

(4h nucleotide),

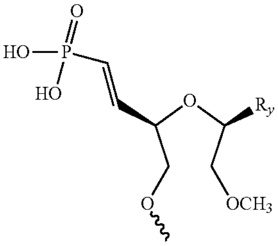

(v-mun nucleotide),

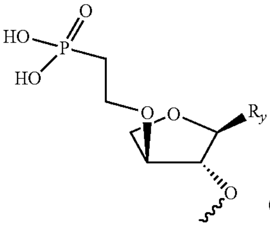

(c2o-4h nucleotide),

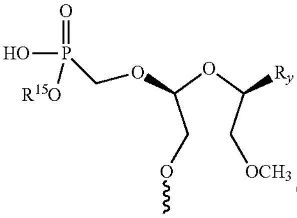

(omceo-mun*enamtiomer1),

-continued

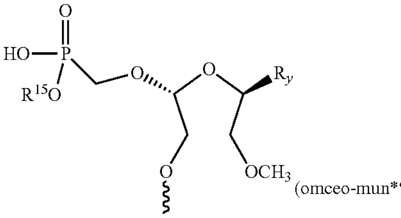

(omceo-mun*enamtiomer2),

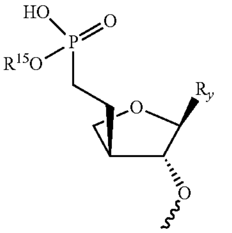

(4h-vp nucleotide), and

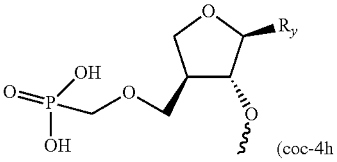

(coc-4h nucleotide);

wherein $R_y$ is a nucleobase and $R^{15}$ is H or $CH_3$. In some embodiments, the nucleobase is selected from thymine, cytosine, guanine, adenine, uracil, and an analogue or derivative thereof. In some embodiments, the disclosed nucleotide phosphate mimics include, but are not limited to, the structures:

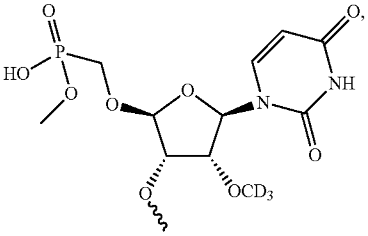

(omeco-d3U)

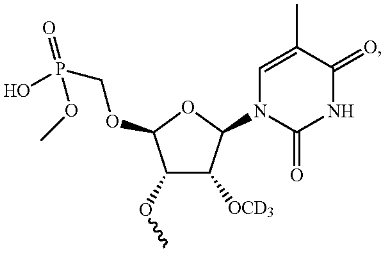

(omeco-d3T)

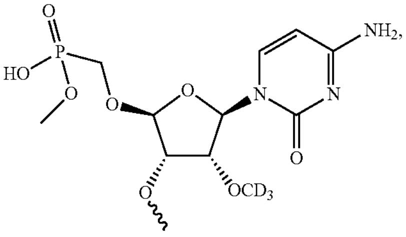

(omeco-d3C)

-continued

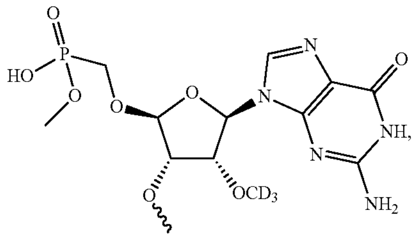

(omeco-d3G)

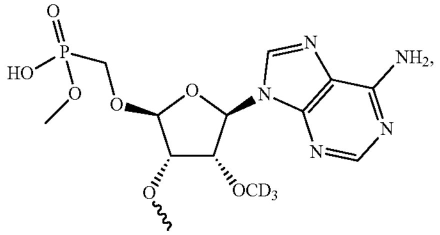

(omeco-d3A)

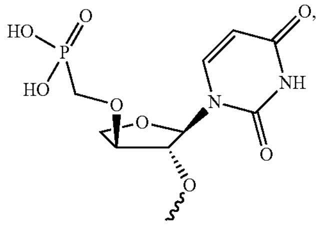

(4hU)

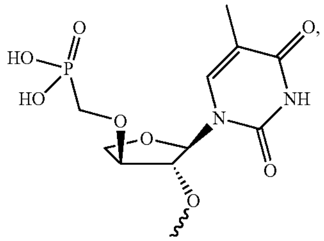

(4hT)

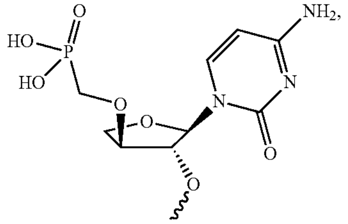

(4hC)

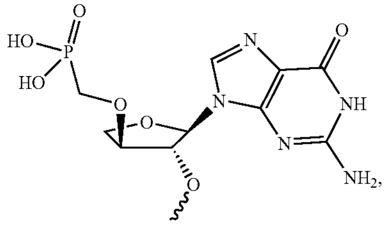

(4hG)

-continued
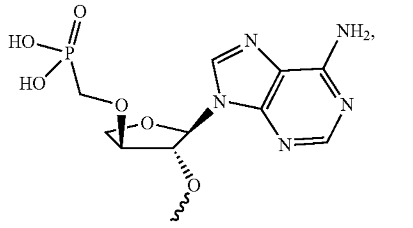
(4hA)
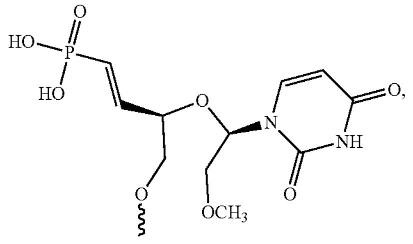
(v-munU)
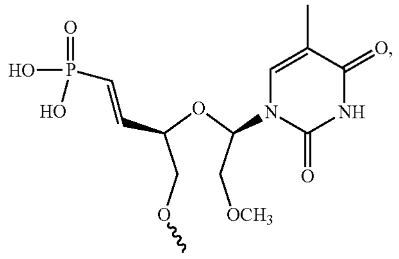
(v-munT)
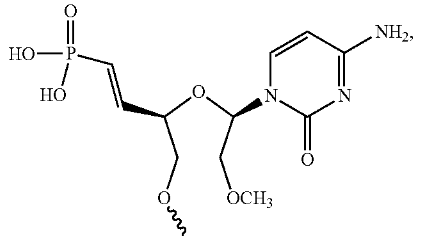
(v-munC)
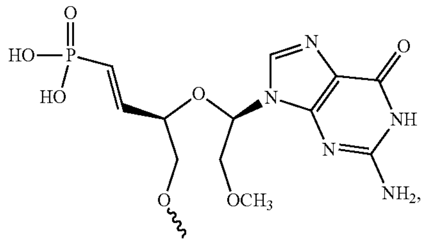
(v-munG)
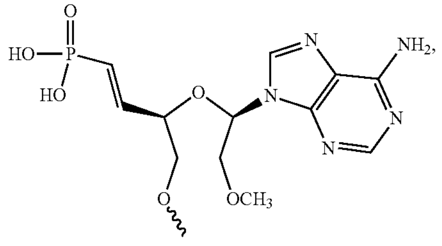
(v-munA)
-continued
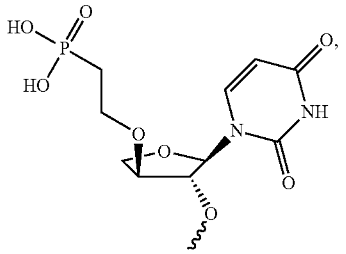
(c2o-4hU)
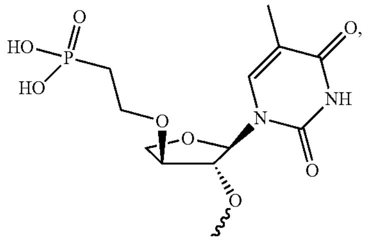
(c2o-4hT)
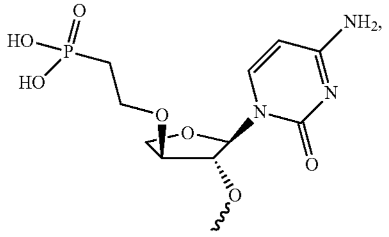
(c2o-4hC)
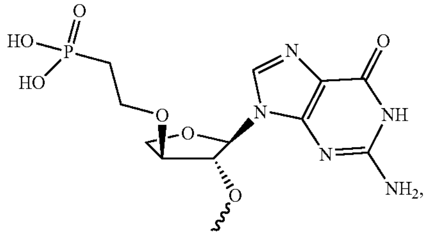
(c2o-4hG)
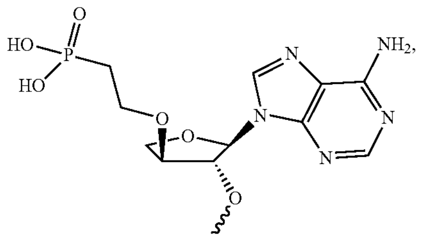
(c2o-4hA)
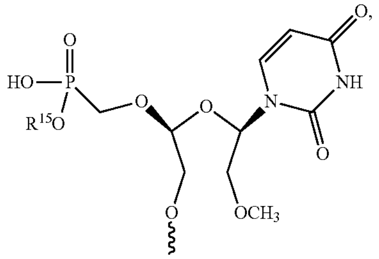
(omeco-munU)

-continued
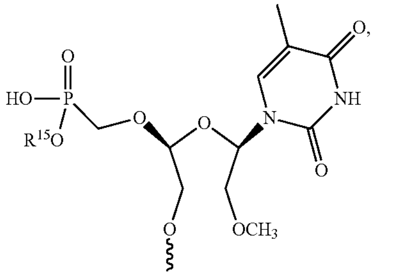
(omeco-munT)
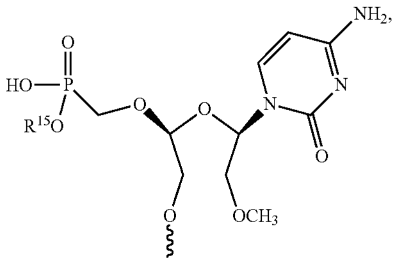
(omeco-munC)
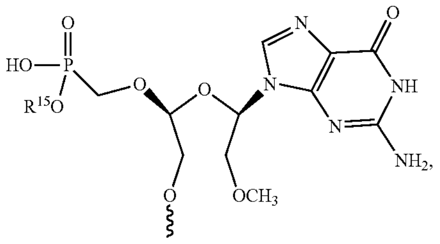
(omeco-munG)
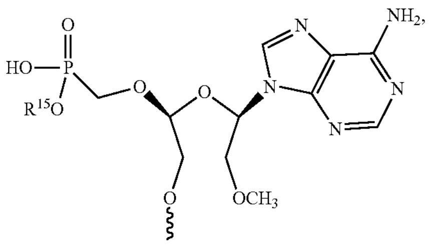
(omeco-munA)
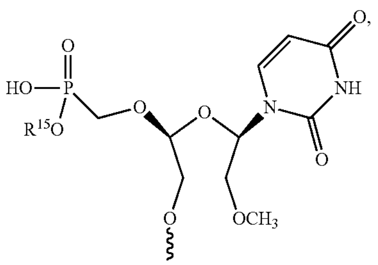
(omeco-munU)
-continued
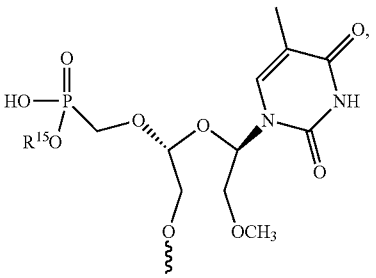
(omeco-munT)
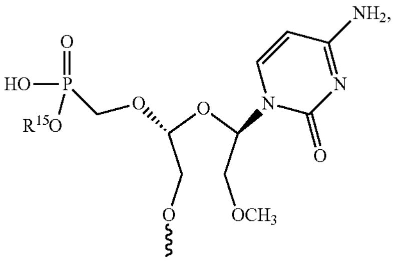
(omeco-munC)
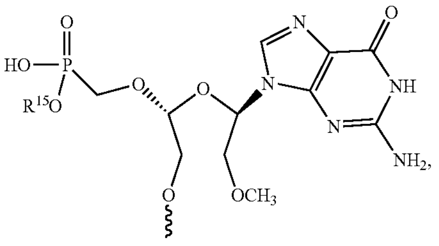
(omeco-munG)
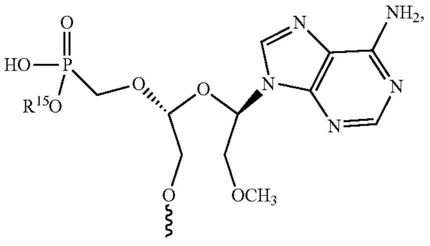
(omeco-munA)
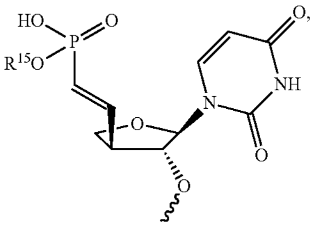
(4h-vp-U)
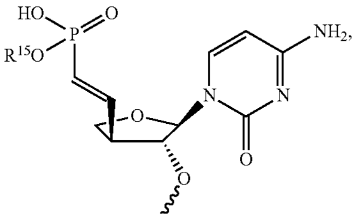
(4h-vp-C)

-continued

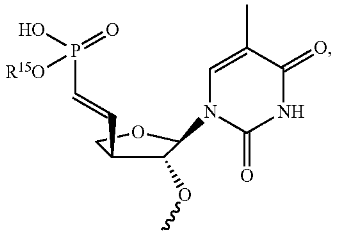

(4h-vp-T)

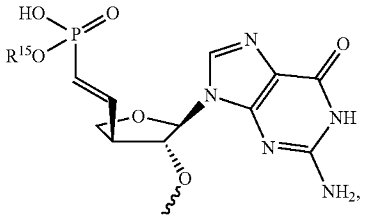

(4h-vp-G)

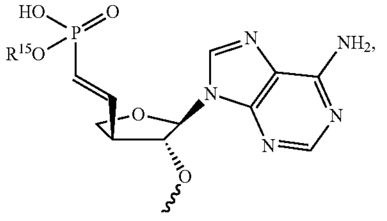

(4h-vp-A)

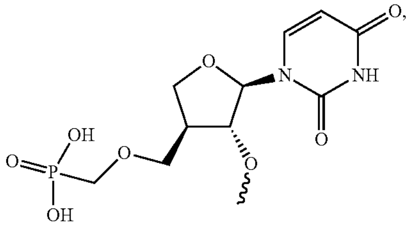

(coc-4hU)

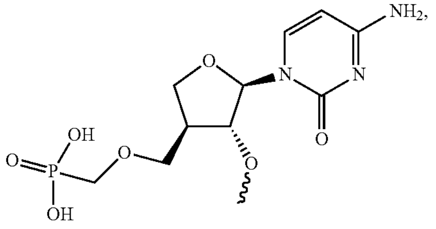

(coc-4hC)

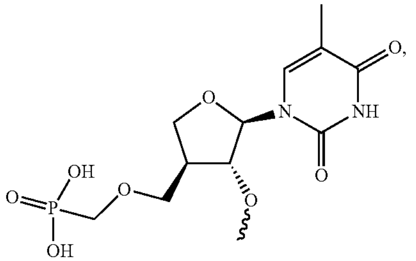

(coc-4hT)

-continued

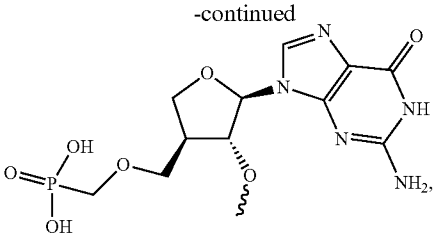

and (coc-4hG)

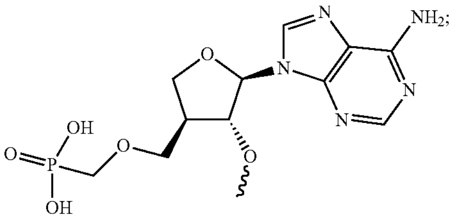

(coc-4hA)

wherein $R^{15}$ is H or $CH_3$.

The disclosed short interfering nucleic acid (siNA) molecules may comprise at least one, at least two, at least 3, at least 4, or at least 5 of the foregoing modified nucleotides and/or one of the foregoing nucleotide phosphate mimics at the 5' end of the antisense strand. Indeed, a short interfering nucleic acid (siNA) molecule of the present disclosure may comprise:

(a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence:
(i) is 15 to 30 nucleotides in length; and
(ii) comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 3, 5, 7, 8, 9, 10, 11, 12, 14, 17, and/or 19 from the 5' end of the first nucleotide sequence is a 2'-fluoro nucleotide or wherein at least one modified nucleotide is a 2'-O-methyl nucleotide and at least one modified nucleotide is a 2'-fluoro nucleotide; and an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence:
(iii) is 15 to 30 nucleotides in length; and
(iv) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; or (b) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence:
(i) is 15 to 30 nucleotides in length; and
(ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence:

(iii) is 15 to 30 nucleotides in length; and (iv) comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 2, 5, 6, 8, 10, 14, 16, 17, and/or 18 from the 5' end of the second nucleotide sequence is a 2'-fluoro nucleotide; or (c) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence:

(i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 3, 5, 7, 8, 9, 10, 11, 12, 14, 17, and/or 19 from the 5' end of the first nucleotide sequence is a 2'-fluoro nucleotide or wherein at least one modified nucleotide is a 2'-O-methyl nucleotide and at least one modified nucleotide is a 2'-fluoro nucleotide; and an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence:

(iii) is 15 to 30 nucleotides in length; and (iv) comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 2, 5, 6, 8, 10, 14, 16, 17, and/or 18 from the 5' end of the second nucleotide sequence is a 2'-fluoro nucleotide;

so long as the sense strand and/or the antisense strand comprise at least one, at least two, at least 3, at least 4, or at least 5 of the modified nucleotide(s) selected from

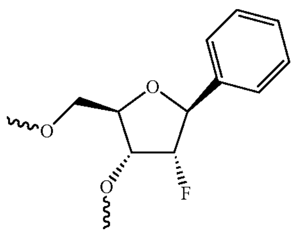

(fB)

and

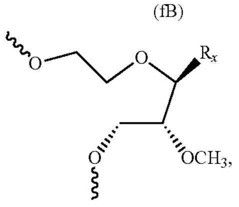

wherein Rx is a nucleobase, aryl, heteroaryl, or H; and/or so long as the antisense strand comprises a nucleotide phosphate mimic selected from:

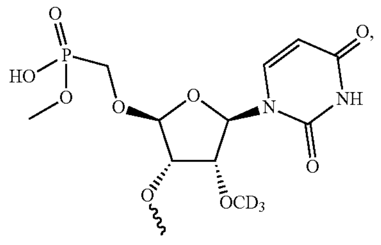

(omeco-d3U)

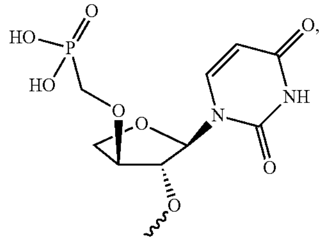

(4hU)

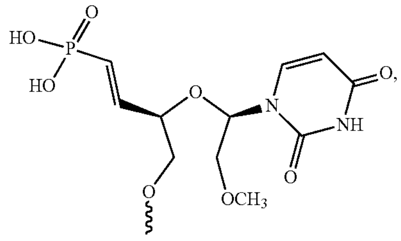

(v-mun)

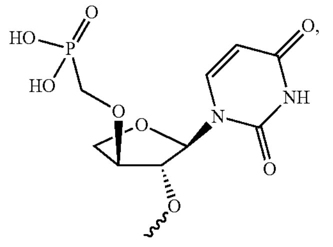

(c2o-4h)

and

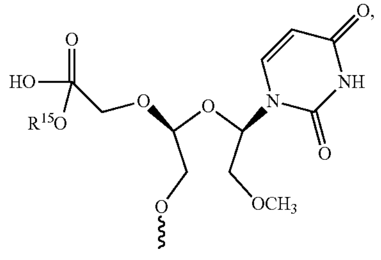

(omeco-munU)

when $R^{15}$ is $CH_3$); where $R^{15}$ is H or $CH_3$.

Further, the siNA of the present disclosure may comprise a sense strand and/or an antisense strand that each independently comprise 1 or more phosphorothioate internucleoside linkages, 1 or more mesyl phosphoramidate internucleoside linkages, or a combination thereof. The siNA may comprise a phosphorylation blocker, a galactosamine, and/or a 5'-stabilized end cap (other than those noted above). The siNA may be conjugated to a targeting moiety, such as a galactosamine.

Further disclosed herein are compositions comprising two or more of the siNA molecules described herein.

Further disclosed herein are compositions comprising any of the siNA molecule described and a pharmaceutically acceptable carrier or diluent. Such compositions may also include an additional therapeutic agent, or may be administered in conjunction with an additional therapeutic agent (either concurrently or sequentially).

Further disclosed herein are compositions comprising two or more of the siNA molecules described herein for use as a medicament.

Further disclosed herein are compositions comprising any of the siNA molecule described and a pharmaceutically acceptable carrier or diluent for use as a medicament. Such medicaments may also include an additional therapeutic agent, or may be administered in conjunction with an additional therapeutic agent (either concurrently or sequentially).

Further disclosed herein are methods of treating a disease in a subject in need thereof, the methods comprising administering to the subject any of the siNA molecules (or a combination thereof) or compositions/medicaments described herein.

Further disclosed herein are uses of any of the siNA molecules described herein (or a combination thereof) in the manufacture of a medicament for treating a disease.

Short Interfering Nucleic Acid (siNA) Molecules

As indicated above, the present disclosure provides siNA molecules comprising modified nucleotides. Any of the siNA molecules described herein may be double-stranded siNA (ds-siNA) molecules. The terms "siNA molecules" and "ds-siNA molecules" may be used interchangeably. In some embodiments, the ds-siNA molecules comprise a sense strand and an antisense strand.

For the purposes of the present disclosure, the siNA molecules disclosed herein may generally comprise (a) at least one phosphorylation blocker, conjugated moiety, and/or 5'-stabilized end cap; and (b) a short interfering nucleic acid (siNA). In some embodiments, the phosphorylation blocker is a phosphorylation blocker disclosed herein. In some embodiments, the conjugated moiety is a galactosamine disclosed herein. In some embodiments, the 5'-stabilized end cap is a 5'-stabilized end cap disclosed herein.

The siNA may comprise any of the first nucleotide, second nucleotide, sense strand, or antisense strand sequences disclosed herein. The siNA may comprise 5 to 100, 5 to 90, 10 to 100, 10 to 90, 10 to 80, 10 to 70, 10 to 60, 10 to 50, 10 to 30, 10 to 25, 15 to 100, 15 to 90, 15 to 80, 15 to 70, 15 to 60, 15 to 50, 15 to 30, or 15 to 25 nucleotides. The siNA may comprise at least 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. The siNA may comprise less than or equal to 50, 45, 40, 39, 38, 37, 36, 35, 34, 33, 32, 31, 30, 29, 28, 27, 26, 25, 24, 23, 22, 21, 20, or 19 nucleotides. The nucleotides may be modified nucleotides. The siNA may be single stranded (ss-siNA). The siNA may be double stranded (ds-siNA).

The ds-siNA may comprise (a) a sense strand comprising 15 to 30, 15 to 25, 15 to 24, 15 to 23, 15 to 22, 15 to 21, 17 to 30, 17 to 25, 17 to 24, 17 to 23, 17 to 22, 17 to 21, 18 to 30, 18 to 25, 18 to 24, 18 to 23, 18 to 22, 18 to 21, 19 to 30, 19 to 25, 19 to 24, 19 to 23, 19 to 22, 19 to 21, 20 to 25, 20 to 24, 20 to 23, 21 to 25, 21 to 24, or 21 to 23 nucleotides; and (b) an antisense strand comprising 15 to 30, 15 to 25, 15 to 24, 15 to 23, 15 to 22, 15 to 21, 17 to 30, 17 to 25, 17 to 24, 17 to 23, 17 to 22, 17 to 21, 18 to 30, 18 to 25, 18 to 24, 18 to 23, 18 to 22, 18 to 21, 19 to 30, 19 to 25, 19 to 24, 19 to 23, 19 to 22, 19 to 21, 20 to 25, 20 to 24, 20 to 23, 21 to 25, 21 to 24, or 21 to 23 nucleotides. The ds-siNA may comprise (a) a sense strand comprising about 15, 16, 17, 18, 19, 20, 21, 22, or 23 nucleotides; and (b) an antisense strand comprising about 15, 16, 17, 18, 19, 20, 21, 22, or 23 nucleotides. The ds-siNA may comprise (a) a sense strand comprising about 19 nucleotides; and (b) an antisense strand comprising about 21 nucleotides. The ds-siNA may comprise (a) a sense strand comprising about 21 nucleotides; and (b) an antisense strand comprising about 23 nucleotides.

Any of the siNA molecules disclosed herein may further comprise one or more linkers independently selected from a phosphodiester (PO) linker, phosphorothioate (PS) linker, phosphorodithioate linker, mesyl phosphoramidate (Ms), and PS-mimic linker. In some embodiments, the PS-mimic linker is a sulfur linker. In some embodiments, the linkers are internucleoside linkers. Alternatively or additionally, the linkers may connect a nucleotide of the siNA molecule to at least one phosphorylation blocker, conjugated moiety, or 5'-stabilized end cap. In some embodiments, the linkers connect a conjugated moiety to a phosphorylation blocker or 5'-stabilized end cap.

An exemplary siNA molecule of the present disclosure is shown in FIG. 1. As shown in FIG. 1, an exemplary siNA molecule comprises a sense strand (101) and an antisense strand (102). The sense strand (101) may comprise a first oligonucleotide sequence (103). The first oligonucleotide sequence (103) may comprise one or more phosphorothioate internucleoside linkages (109). The phosphorothioate internucleoside linkage (109) may be between the nucleotides at the 5' or 3' terminal end of the first oligonucleotide sequence (103). The phosphorothioate internucleoside linkage (109) may be between the first three nucleotides from the 5' end of the first oligonucleotide sequence (103). The first oligonucleotide sequence (103) may comprise one or more 2'-fluoro nucleotides (110). The first oligonucleotide sequence (103) may comprise one or more 2'-O-methyl nucleotides (111). The first oligonucleotide sequence (103) may comprise 15 or more modified nucleotides independently selected from 2'-fluoro nucleotides (110) and 2'-O-methyl nucleotides (111). The sense strand (101) may further comprise a phosphorylation blocker (105). The sense strand (101) may further comprise a galactosamine (106). The antisense strand (102) may comprise a second oligonucleotide sequence (104). The second oligonucleotide sequence (104) may comprise one or more phophorothioate internucleoside linkages (109). The phosphorothioate internucleoside linkage (109) may be between the nucleotides at the 5' or 3' terminal end of the second oligonucleotide sequence (104). The phosphorothioate internucleoside linkage (109) may be between the first three nucleotides from the 5' end of the second oligonucleotide sequence (104). The phosphorothioate internucleoside linkage (109) may be between the first three nucleotides from the 3' end of the second oligonucleotide sequence (104). The second oligonucleotide sequence (104) may comprise one or more 2'-fluoro nucleotides (110). The second oligonucleotide sequence (104) may comprise one or more 2'-O-methyl nucleotides (111). The second oligonucleotide sequence (104) may comprise 15 or more modified nucleotides independently selected from 2'-fluoro nucleotides (110) and 2'-O-methyl nucleotides (111). The antisense strand (102) may further comprise a 5'-stabilized end cap (107). The siNA may further comprise one or more blunt ends. Alternatively, or additionally, one end of the siNA may comprise an overhang (108). The overhang (108) may be part of the sense strand (101). The overhang (108) may be part of the antisense strand (102). The overhang (108) may be distinct from the first nucleotide sequence (103). The overhang (108)

may be distinct from the second nucleotide sequence (104). The overhang (108) may be part of the first nucleotide sequence (103). The overhang (108) may be part of the second nucleotide sequence (104). The overhang (108) may comprise 1 or more nucleotides. The overhang (108) may comprise 1 or more deoxyribonucleotides. The overhang (108) may comprise 1 or more modified nucleotides. The overhang (108) may comprise 1 or more modified ribonucleotides. The sense strand (101) may be shorter than the antisense strand (102). The sense strand (101) may be the same length as the antisense strand (102). The sense strand (101) may be longer than the antisense strand (102).

Figure 2:
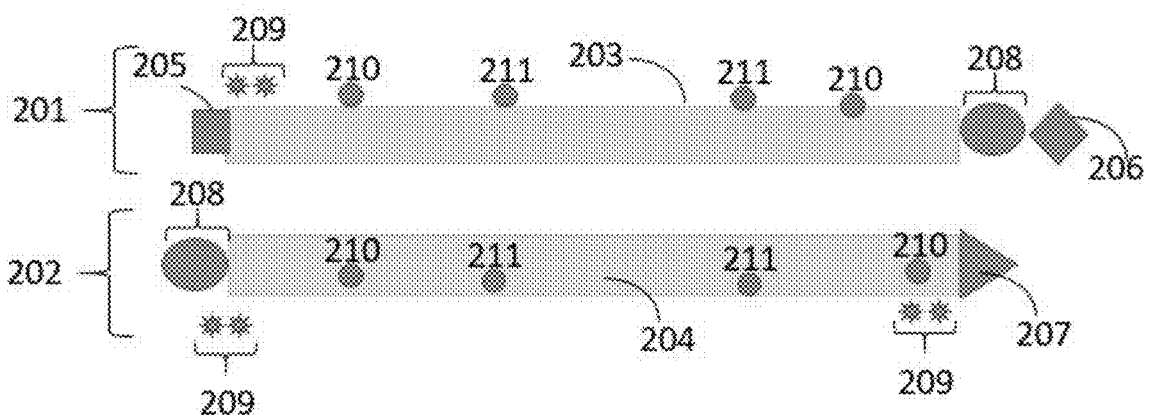
FIG. 2 illustrates an exemplary siNA molecule.

An exemplary siNA molecule of the present disclosure is shown in FIG. 2. As shown in FIG. 2, an exemplary siNA molecule comprises a sense strand (201) and an antisense strand (202). The sense strand (201) may comprise a first oligonucleotide sequence (203). The first oligonucleotide sequence (203) may comprise one or more phophorothioate internucleoside linkages (209). The phosphorothioate internucleoside linkage (209) may be between the nucleotides at the 5' or 3' terminal end of the first oligonucleotide sequence (203). The phosphorothioate internucleoside linkage (209) may be between the first three nucleotides from the 5' end of the first oligonucleotide sequence (203). The first oligonucleotide sequence (203) may comprise one or more 2'-fluoro nucleotides (210). The first oligonucleotide sequence (203) may comprise one or more 2'-O-methyl nucleotides (211). The first oligonucleotide sequence (203) may comprise 15 or more modified nucleotides independently selected from 2'-fluoro nucleotides (210) and 2'-O-methyl nucleotides (211). The sense strand (201) may further comprise a phosphorylation blocker (205). The sense strand (201) may further comprise a galactosamine (206). The antisense strand (202) may comprise a second oligonucleotide sequence (204). The second oligonucleotide sequence (204) may comprise one or more phophorothioate internucleoside linkages (209). The phosphorothioate internucleoside linkage (209) may be between the nucleotides at the 5' or 3' terminal end of the second oligonucleotide sequence (204). The phosphorothioate internucleoside linkage (209) may be between the first three nucleotides from the 5' end of the second oligonucleotide sequence (204). The phosphorothioate internucleoside linkage (209) may be between the first three nucleotides from the 3' end of the second oligonucleotide sequence (204). The second oligonucleotide sequence (204) may comprise one or more 2'-fluoro nucleotides (210). The second oligonucleotide sequence (204) may comprise one or more 2'-O-methyl nucleotides (211). The second oligonucleotide sequence (204) may comprise 15 or more modified nucleotides independently selected from 2'-fluoro nucleotides (210) and 2'-O-methyl nucleotides (211). The antisense strand (202) may further comprise a 5'-stabilized end cap (207). The siNA may further comprise one or more overhangs (208). The overhang (208) may be part of the sense strand (201). The overhang (208) may be part of the antisense strand. (202). The overhang (208) may be distinct from the first nucleotide sequence (203). The overhang (208) may be distinct from the second nucleotide sequence (204). The overhang (208) may be part of the first nucleotide sequence (203). The overhang (208) may be part of the second nucleotide sequence (204). The overhang (208) may be adjacent to the 3' end of the first nucleotide sequence (203). The overhang (208) may be adjacent to the 5' end of the first nucleotide sequence (203). The overhang (208) may be adjacent to the 3' end of the second nucleotide sequence (204). The overhang (208) may be adjacent to the 5' end of the second nucleotide sequence (204). The overhang (208) may comprise 1 or more nucleotides. The overhang (208) may comprise 1 or more deoxyribonucleotides. The overhang (208) may comprise a TT sequence. The overhang (208) may comprise 1 or more modified nucleotides. The overhang (208) may comprise 1 or more modified nucleotides disclosed herein (e.g., 2-fluoro nucleotide, 2'-O-methyl nucleotide, 2'-fluoro nucleotide mimic, 2'-O-methyl nucleotide mimic, or a nucleotide comprising a modified nucleobase). The overhang (208) may comprise 1 or more modified ribonucleotides. The sense strand (201) may be shorter than the antisense strand (202). The sense strand (201) may be the same length as the antisense strand (202). The sense strand (201) may be longer than the antisense strand (202).

FIGS. 3A-3H depict exemplary ds-siNA modification patterns. As shown in FIGS. 3A-3G, an exemplary ds-siNA molecule may have the following formula:

$$5'\text{-}A_n{}^1B_n{}^2A_n{}^3B_n{}^4A_n{}^5B_n{}^6A_n{}^7B_n{}^8A_n{}^9\text{-}3'$$

$$3'\text{-}C_q{}^1A_q{}^2B_q{}^3A_q{}^4B_q{}^5A_q{}^6B_q{}^7A_q{}^8B_q{}^9A_q{}^{10}B_q{}^{11}A_q{}^{12}\text{-}5'$$

wherein:

- the top strand is a sense strand comprising a first nucleotide sequence that is at least about 60%, 65%, 70%, 75%, 80%, 85%, 90%, 95%, or 100% identical to an RNA corresponding to a target gene, wherein the first nucleotide sequence comprises 15 to 30 nucleotides;
- the bottom strand is an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence comprises 15 to 30 nucleotides;
- each A is independently a 2'-O-methyl nucleotide or a nucleotide comprising a 5' stabilized end cap or phosphorylation blocker;
- B is a 2'-fluoro nucleotide;
- C represents overhanging nucleotides and is a 2'-O-methyl nucleotide, a deoxy nucleotide, or uracil;
- $n^1$=1-6 nucleotides in length;
- each $n^2$, $n^6$, $n^8$, $q^3$, $q^5$, $q^7$, $q^9$, $q^{11}$, and $q^{12}$ is independently 0-1 nucleotides in length; each $n^3$ and $n^4$ is independently 1-3 nucleotides in length;
- $n^5$ is 1-10 nucleotides in length;
- $n^7$ is 0-4 nucleotides in length;
- each $n^9$, $q^1$, and $q^2$ is independently 0-2 nucleotides in length;
- $q^4$ is 0-3 nucleotides in length;
- $q^6$ is 0-5 nucleotides in length;
- $q^8$ is 2-7 nucleotides in length; and
- $q^{10}$ is 2-11 nucleotides in length.

The ds-siNA may further comprise a conjugated moiety. The conjugated moiety may comprise any of the galactosamines disclosed herein. The ds-siNA may further comprise (i) phosphorothioate internucleoside linkages between the nucleotides at positions 1 and 2 and positions 2 and 3 from the 5' end of the sense strand; and (ii) phosphorothioate internucleoside linkages between the nucleotides at positions 1 and 2; positions 2 and 3; positions 19 and 20; and positions 20 and 21 from the 5' end of the antisense strand. The ds-siNA may further comprise a 5'-stabilizing end cap. The 5'-stabilizing end cap may be a vinyl phosphonate. The 5'-stabilizing end cap may be attached to the 5' end of the antisense strand. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker. An exemplary ds-siNA molecule may have the following formula:

$$5'\text{-}A_{2\text{-}4}B_1A_{1\text{-}3}B_{2\text{-}3}A_{2\text{-}10}B_{0\text{-}1}A_{0\text{-}4}B_{0\text{-}1}A_{0\text{-}2}\text{-}3'$$

$$3'\text{-}C_2A_{0\text{-}2}B_{0\text{-}1}A_{0\text{-}3}B_{0\text{-}1}A_{0\text{-}5}B_{0\text{-}1}A_{2\text{-}7}B_1A_{2\text{-}11}B_1A_1\text{-}5'$$

wherein:

the top strand is a sense strand comprising a first nucleotide sequence that is at least about 60%, 65%, 70%, 75%, 80%, 85%, 90%, 95%, or 100% identical to an RNA corresponding to a target gene, wherein the first nucleotide sequence comprises 15 to 30 nucleotides;

the bottom strand is an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence comprises 15 to 30 nucleotides;

each A is independently a 2'-O-methyl nucleotide or a nucleotide comprising a 5' stabilized end cap or phosphorylation blocker;

B is a 2'-fluoro nucleotide;

C represents overhanging nucleotides and is a 2'-O-methyl nucleotide, a deoxy nucleotide, or uracil.

The ds-siNA may further comprise a conjugated moiety. The conjugated moiety may comprise any of the galactosamines disclosed herein. The ds-siNA may further comprise (i) phosphorothioate internucleoside linkages between the nucleotides at positions 1 and 2 and positions 2 and 3 from the 5' end of the sense strand; and (ii) phosphorothioate internucleoside linkages between the nucleotides at positions 1 and 2; positions 2 and 3; positions 19 and 20; and positions 20 and 21 from the 5' end of the antisense strand. The ds-siNA may further comprise a 5'-stabilizing end cap. The 5'-stabilizing end cap may be a vinyl phosphonate. The vinyl phosphonate may be a deuterated vinyl phosphonate. The deuterated vinyl phosphonate may be a mono-deuterated vinyl phosphonate. The deuterated vinyl phosphonate may be a mono-di-deuterated vinyl phosphonate. The 5'-stabilizing end cap may be attached to the 5' end of the antisense strand. The 5'-stabilizing end cap may be attached to the 3' end of the antisense strand. The 5'-stabilizing end cap may be attached to the 5' end of the sense strand. The 5'-stabilizing end cap may be attached to the 3' end of the sense strand. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker.

The exemplary ds-siNA shown in FIGS. 3A-3H comprise (i) a sense strand comprising 19-21 nucleotides; and (ii) an antisense strand comprising 21-23 nucleotides. The ds-siNA may optionally further comprise (iii) a conjugated moiety, wherein the conjugated moiety (e.g., a GalNAc, noted as G3 in FIGS. 3A-3G) is attached to the 3' end or the 5' end of the sense strand or the antisense strand. The ds-siNA may comprise a 2 nucleotide overhang consisting of nucleotides at positions 20 and 21 from the 5' end of the antisense strand. The ds-siNA may comprise a 2 nucleotide overhang consisting of nucleotides at positions 22 and 23 from the 5' end of the antisense strand. The ds-siNA may further comprise 1, 2, 3, 4, 5, 6 or more phosphorothioate (ps) internucleoside linkages or mesyl phosphoramidate internucleoside linkage (Ms). At least one phosphorothioate internucleoside linkage or mesyl phosphoramidate internucleoside linkage (Ms) may be between the nucleotides at positions 1 and 2 or positions 2 and 3 from the 5' end of the sense strand. At least one phosphorothioate internucleoside linkage or mesyl phosphoramidate internucleoside linkage (Ms) may be between the nucleotides at positions 1 and 2 or positions 2 and 3 from the 5' end of the antisense strand. At least one phosphorothioate internucleoside linkage or mesyl phosphoramidate internucleoside linkage (Ms) may be between the nucleotides at positions 19 and 20, positions 20 and 21, positions 21 and 22, or positions 22 and 23 from the 5' end of the antisense strand. As shown in FIGS. 3A-3H, 4-6 nucleotides in the sense strand may be 2'-fluoro nucleotides. As shown in FIGS. 3A-3H, 2-5 nucleotides in the antisense strand may be 2'-fluoro nucleotides. As shown in FIGS. 3A-3H, 13-15 nucleotides in the sense strand may be 2'-O-methyl nucleotides. As shown in FIGS. 3A-3H, 14-19 nucleotides in the antisense strand may be 2'-O-methyl nucleotides. As shown in FIGS. 3A-3H, the ds-siNA does not contain a base pair between 2'-fluoro nucleotides on the sense and antisense strands. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker.

Figure 3A:
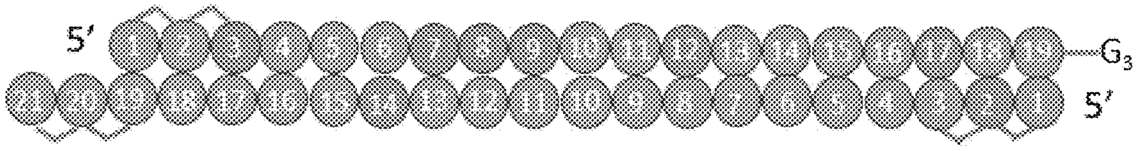
FIGS. 3A-3H illustrate exemplary double-stranded siNA molecules.

As shown in FIG. 3A, a ds-siNA may comprise (a) a sense strand consisting of 19 nucleotides, wherein 2'-fluoro nucleotides are at positions 3, 7-9, 12, and 17 from the 5' end of the sense strand, and wherein 2'-O-methyl nucleotides are at positions 1, 2, 4-6, 10, 11, 13-16, 18, and 19 from the 5' end of the sense strand; (b) an antisense strand consisting of 21 nucleotides, wherein nucleotides at positions 2 and 14 from the 5' end of the antisense strand are 2'-fluoro nucleotides; and wherein nucleotides at positions 1, 3-13, and 15-21 are 2'-O-methyl nucleotides. The ds-siNA may further comprise a conjugated moiety attached to the 3' end of the sense strand. The ds-siNA may further comprise (i) phosphorothioate internucleoside linkages between the nucleotides at positions 1 and 2 and positions 2 and 3 from the 5' end of the sense strand; and (ii) phosphorothioate internucleoside linkages between the nucleotides at positions 1 and 2; positions 2 and 3; positions 19 and 20; and positions 20 and 21 from the 5' end of the antisense strand. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker. In some embodiments, the 2'-O-methyl nucleotide at position 1 from the 5' end of the sense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 5' end of the antisense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 3' end of the sense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 3' end of the antisense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, at least 1, 2, 3, 4 or more 2'-fluoro nucleotides on the sense strand or antisense strand is a 2'-fluoro nucleotide mimic. In some embodiments, at least 1, 2, 3, 4 or more 2'-fluoro nucleotides on the sense strand or antisense strand is a fB, fN, f(4nh)Q, f4P, f2P, or fX nucleotide. In some embodiments, at least 1, 2, 3, 4 or more 2'-O-methyl nucleotide on the sense or antisense strand is a 2'-O-methyl nucleotide mimic. In some embodiments, one or more nucleotides in the sense strand and/or the antisense strand may be a 3',4' seco modified nucleotide in which the bond between the 3' and 4' positions of the furanose ring is broken (e.g., mun34).

Figure 3B:
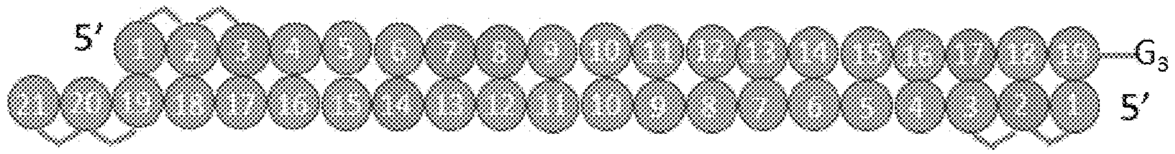

As shown in FIG. 3B, a ds-siNA may comprise (a) a sense strand consisting of 19 nucleotides, wherein 2'-fluoro nucleotides are at positions 3, 7, 8, and 17 from the 5' end of the sense strand, and wherein 2'-O-methyl nucleotides are at positions 1, 2, 4-6, 9-16, 18, and 19 from the 5' end of the sense strand; (b) an antisense strand consisting of 21 nucleotides, wherein nucleotides at positions 2 and 14 from the 5' end of the antisense strand are 2'-fluoro nucleotides; and wherein nucleotides at positions 1, 3-13, and 15-21 are 2'-O-methyl nucleotides. The ds-siNA may further comprise a conjugated moiety attached to the 3' end of the sense strand. The ds-siNA may further comprise (i) phosphorothioate internucleoside linkages between the nucleotides at positions 1 and 2 and positions 2 and 3 from the 5' end of the sense strand; and (ii) phosphorothioate internucleoside linkages between the nucleotides at positions 1 and 2; positions 2 and 3; positions 19 and 20; and positions 20 and 21 from the 5' end of the antisense strand. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker. In some embodiments, the 2'-O-methyl nucleotide at position 1 from the 5' end of the sense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 5' end of the antisense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 3' end of the sense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 3' end of the antisense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, at least 1, 2, 3, 4 or more 2'-fluoro nucleotides on the sense strand or antisense strand is a 2'-fluoro nucleotide mimic. In some embodiments, at least 1, 2, 3, 4 or more 2'-fluoro nucleotides on the sense strand or antisense strand is a fB, fN, f(4nh)Q, f4P, f2P, or fX nucleotide. In some embodiments, at least 1, 2, 3, 4 or more 2'-O-methyl nucleotide on the sense or antisense strand is a 2'-O-methyl nucleotide mimic. In some embodiments, one or more nucleotides in the sense strand and/or the antisense strand may be a 3',4' seco modified nucleotide in which the bond between the 3' and 4' positions of the furanose ring is broken (e.g., mun34).

Figure 3C:
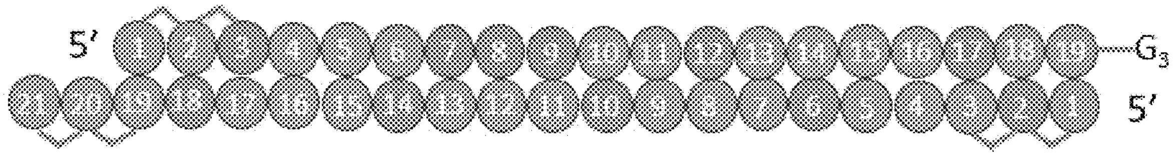

As shown in FIG. 3C, a ds-siNA may comprise (a) a sense strand consisting of 19 nucleotides, wherein 2'-fluoro nucleotides are at positions 3, 7-9, 12 and 17 from the 5' end of the sense strand, and wherein 2'-O-methyl nucleotides are at positions 1, 2, 4-6, 10, 11, 13-16, 18, and 19 from the 5' end of the sense strand; (b) an antisense strand consisting of 21 nucleotides, wherein the nucleotides in the antisense strand comprise an alternating 1:3 modification pattern, and wherein 1 nucleotide is a 2'-fluoro nucleotide and 3 nucleotides are 2'-O-methyl nucleotides. The ds-siNA may further comprise a conjugated moiety attached to the 3' end of the sense strand. The ds-siNA may further comprise (i) phosphorothioate internucleoside linkages between the nucleotides at positions 1 and 2 and positions 2 and 3 from the 5' end of the sense strand; and (ii) phosphorothioate internucleoside linkages between the nucleotides at positions 1 and 2; positions 2 and 3; positions 19 and 20; and positions 20 and 21 from the 5' end of the antisense strand. The ds-siNA may comprise 2-5 alternating 1:3 modification patterns on the antisense strand. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker. In some embodiments, the 2'-O-methyl nucleotide at position 1 from the 5' end of the sense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 5' end of the antisense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 3' end of the sense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 3' end of the antisense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, at least 1, 2, 3, 4 or more 2'-fluoro nucleotides on the sense strand or antisense strand is a 2'-fluoro nucleotide mimic. In some embodiments, at least 1, 2, 3, 4 or more 2'-fluoro nucleotides on the sense strand is a fB, fN, f(4nh)Q, f4P, f2P, or fX nucleotide. In some embodiments, at least 1, 2, 3, 4 or more 2'-fluoro nucleotides on the antisense strand is a fB, fN, f(4nh)Q, f4P, f2P, or fX nucleotide. In some embodiments, at least 1, 2, 3, 4 or more 2'-O-methyl nucleotide on the sense or antisense strand is a 2'-O-methyl nucleotide mimic. In some embodiments, one or more nucleotides in the sense strand and/or the antisense strand may be a 3',4' seco modified nucleotide in which the bond between the 3' and 4' positions of the furanose ring is broken (e.g., mun34).

Figure 3D:
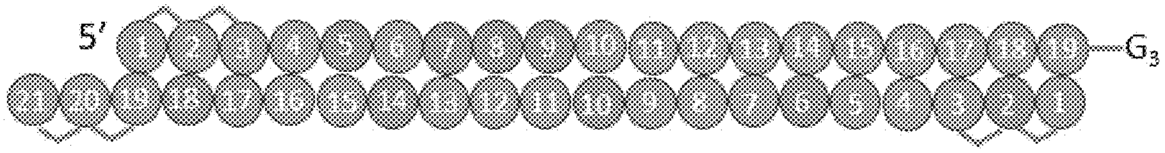
Figure 3D:
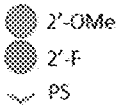

As shown in FIG. 3D, a ds-siNA may comprise (a) a sense strand consisting of 19 nucleotides, wherein 2'-fluoro nucleotides are at positions 5 and 7-9 from the 5' end of the sense strand, and wherein 2'-O-methyl nucleotides are at positions 1-4, 6, and 10-19 from the 5' end of the sense strand; (b) an antisense strand consisting of 21 nucleotides, wherein the nucleotides in the antisense strand comprise an alternating 1:3 modification pattern, and wherein 1 nucleotide is a 2'-fluoro nucleotide and 3 nucleotides are 2'-O-methyl nucleotides. The ds-siNA may further comprise a conjugated moiety attached to the 3' end of the sense strand. The ds-siNA may further comprise (i) phosphorothioate internucleoside linkages between the nucleotides at positions 1 and 2 and positions 2 and 3 from the 5' end of the sense strand; and (ii) phosphorothioate internucleoside linkages between the nucleotides at positions 1 and 2; positions 2 and 3; positions 19 and 20; and positions 20 and 21 from the 5' end of the antisense strand. The ds-siNA may comprise 2-5 alternating 1:3 modification patterns on the antisense strand. The alternating 1:3 modification pattern may start at the nucleotide at any of positions 2, 6, 10, 14, and/or 18 from the 5' end of the antisense strand. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker. In some embodiments, the 2'-O-methyl nucleotide at position 1 from the 5' end of the sense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 5' end of the antisense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 3' end of the sense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 3' end of the antisense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, at least 1, 2, 3, 4 or more 2'-fluoro nucleotides on the sense strand or antisense strand is a 2'-fluoro nucleotide mimic. In some embodiments, at least 1, 2, 3, 4 or more 2'-fluoro nucleotides on the sense strand is a fB, fN, f(4nh)Q, f4P, f2P, or fX nucleotide. In some embodiments, at least 1, 2, 3, 4 or more 2'-fluoro nucleotides on the antisense strand is a fB, fN, f(4nh)Q, f4P, f2P, or fX nucleotide. In some embodiments, at least 1, 2, 3, 4 or more 2'-O-methyl nucleotide on the sense or antisense strand is a 2'-O-methyl nucleotide mimic. In some embodiments, one or more nucleotides in the sense strand and/or the antisense strand may be a 3',4' seco modified nucleotide in which the bond between the 3' and 4' positions of the furanose ring is broken (e.g., mun34).

Figure 3E:
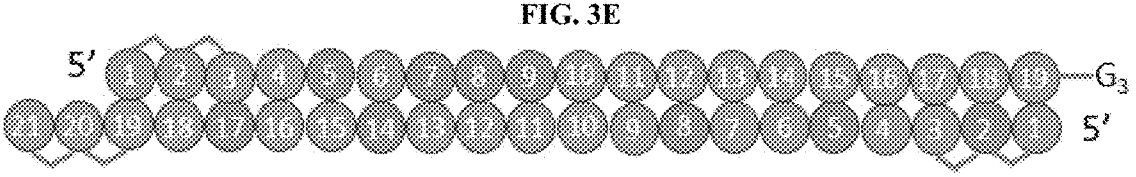

As shown in FIG. 3E, a ds-siNA may comprise (a) a sense strand consisting of 19 nucleotides, wherein 2'-fluoro nucleotides are at positions 5 and 7-9 from the 5' end of the sense strand, and wherein 2'-O-methyl nucleotides are at positions 1-4, 6, and 10-19 from the 5' end of the sense strand; (b) an antisense strand consisting of 21 nucleotides, wherein the nucleotides in the antisense strand comprise an alternating 1:2 modification pattern, and wherein 1 nucleotide is a 2'-fluoro nucleotide and 2 nucleotides are 2'-O-methyl nucleotides. The ds-siNA may further comprise a conjugated moiety attached to the 3' end of the sense strand. The ds-siNA may further comprise (i) phosphorothioate internucleoside linkages between the nucleotides at positions 1 and 2 and positions 2 and 3 from the 5' end of the sense strand; and (ii) phosphorothioate internucleoside linkages between the nucleotides at positions 1 and 2; positions 2 and 3; positions 19 and 20; and positions 20 and 21 from the 5' end of the antisense strand. The ds-siNA may comprise 2-5 alternating 1:2 modification patterns on the antisense strand. The alternating 1:2 modification pattern may start at the nucleotide at any of positions 2, 5, 8, 14, and/or 17 from the 5' end of the antisense strand. In some embodiments, the ds-siNA comprises (a) a sense strand consisting of 19 nucleotides, wherein 2'-fluoro nucleotides are at positions 5 and 7-9 from the 5' end of the sense strand, and wherein 2'-O-methyl nucleotides are at positions 1-4, 6, and 10-19 from the 5' end of the sense strand; (b) an antisense strand consisting of 21 nucleotides, wherein 2'-fluoro nucleotides are at positions 2, 5, 8, 14, and 17 from the 5' end of the antisense strand, and wherein 2'-O-methyl nucleotides are at positions 1, 3, 4, 6, 7, 9-13, 15, 16, and 18-21 from the 5' end of the sense strand. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker. In some embodiments, the 2'-O-methyl nucleotide at position 1 from the 5' end of the sense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 5' end of the antisense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 3' end of the sense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 3' end of the antisense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, at least 1, 2, 3, 4 or more 2'-fluoro nucleotides on the sense strand or antisense strand is a 2'-fluoro nucleotide mimic. In some embodiments, at least 1, 2, 3, 4 or more 2'-fluoro nucleotides on the sense strand is a fB, fN, f(4nh)Q, f4P, f2P, or fX nucleotide. In some embodiments, at least 1, 2, 3, 4 or more 2'-fluoro nucleotides on the antisense strand is a fB, fN, f(4nh)Q, f4P, f2P, or fX nucleotide. In some embodiments, at least 1, 2, 3, 4 or more 2'-O-methyl nucleotide on the sense or antisense strand is a 2'-O-methyl nucleotide mimic. In some embodiments, one or more nucleotides in the sense strand and/or the antisense strand may be a 3',4' seco modified nucleotide in which the bond between the 3' and 4' positions of the furanose ring is broken (e.g., mun34).

Figure 3F:
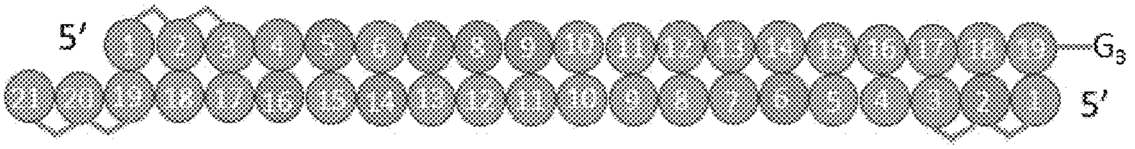

As shown in FIG. 3F, a ds-siNA may comprise (a) a sense strand consisting of 19 nucleotides, wherein 2'-fluoro nucleotides are at positions 5 and 7-9 from the 5' end of the sense strand, and wherein 2'-O-methyl nucleotides are at positions 1-4, 6, and 10-19 from the 5' end of the sense strand; (b) an antisense strand consisting of 21 nucleotides, wherein 2'-fluoro nucleotides are at positions 2, 6, 14, and 16 from the 5' end of the antisense strand, and wherein 2'-O-methyl nucleotides are at positions 1, 3-5, 7-13, 15, and 17-21 from the 5' end of the antisense strand. The ds-siNA may further comprise a conjugated moiety attached to the 3' end of the sense strand. The ds-siNA may further comprise (i) phosphorothioate internucleoside linkages between the nucleotides at positions 1 and 2 and positions 2 and 3 from the 5' end of the sense strand; and (ii) phosphorothioate internucleoside linkages between the nucleotides at positions 1 and 2; positions 2 and 3; positions 19 and 20; and positions 20 and 21 from the 5' end of the antisense strand. In some embodiments, at least 1, 2, 3, 4 or more 2'-fluoro nucleotides on the sense strand or antisense strand is a fB, fN, f(4nh)Q, f4P, f2P, or fX nucleotide. In some embodiments, at least 1, 2, 3, 4 or more 2'-fluoro nucleotides on the sense strand or antisense strand is a f4P nucleotide. In some embodiments, at least 1, 2, 3, or 4 of the 2'-fluoro-nucleotides at positions 2, 6, 14, and 16 from the 5' end of the antisense strand is a f4P nucleotide. In some embodiments, at least one of the 2'-fluoro-nucleotides at positions 2, 6, 14, and 16 from the 5' end of the antisense strand is a f4P nucleotide. In some embodiments, at least two of the 2'-fluoro-nucleotides at positions 2, 6, 14, and 16 from the 5' end of the antisense strand is a f4P nucleotide. In some embodiments, less than or equal to 3 of the 2'-fluoro-nucleotides at positions 2, 6, 14, and 16 from the 5' end of the antisense strand is a f4P nucleotide. In some embodiments, less than or equal to 2 of the 2'-fluoro-nucleotides at positions 2, 6, 14, and 16 from the 5' end of the antisense strand is a f4P nucleotide. In some embodiments, the 2'-fluoro-nucleotide at position 2 from the 5' end of the antisense strand is a f4P nucleotide. In some embodiments, the 2'-fluoro-nucleotide at position 6 from the 5' end of the antisense strand is a f4P nucleotide. In some embodiments, the 2'-fluoro-nucleotide at position 14 from the 5' end of the antisense strand is a f4P nucleotide. In some embodiments, the 2'-fluoro-nucleotide at position 16 from the 5' end of the antisense strand is a f4P nucleotide. In some embodiments, at least 1, 2, 3, 4 or more 2'-fluoro nucleotides on the sense strand or antisense strand is a f2P nucleotide. In some embodiments, at least 1, 2, 3, or 4 of the 2'-fluoro-nucleotides at positions 2, 6, 14, and 16 from the 5' end of the antisense strand is a f2P nucleotide. In some embodiments, at least one of the 2'-fluoro-nucleotides at positions 2, 6, 14, and 16 from the 5' end of the antisense strand is a f2P nucleotide. In some embodiments, at least two of the 2'-fluoro-nucleotides at positions 2, 6, 14, and 16 from the 5' end of the antisense strand is a f2P nucleotide. In some embodiments, less than or equal to 3 of the 2'-fluoro-nucleotides at positions 2, 6, 14, and 16 from the 5' end of the antisense strand is a f2P nucleotide. In some embodiments, less than or equal to 2 of the 2'-fluoro-nucleotides at positions 2, 6, 14, and 16 from the 5' end of the antisense strand is a f2P nucleotide. In some embodiments, the 2'-fluoro-nucleotide at position 2 from the 5' end of the antisense strand is a f2P nucleotide. In some embodiments, the 2'-fluoro-nucleotide at position 6 from the 5' end of the antisense strand is a f2P nucleotide. In some embodiments, the 2'-fluoro-nucleotide at position 14 from the 5' end of the antisense strand is a f2P nucleotide. In some embodiments, the 2'-fluoro-nucleotide at position 16 from the 5' end of the antisense strand is a f2P nucleotide. In some embodiments, at least 1, 2, 3, 4 or more 2'-fluoro nucleotides on the sense strand or antisense strand is a fX nucleotide. In some embodiments, at least 1, 2, 3, or 4 of the 2'-fluoro-nucleotides at positions 2, 6, 14, and 16 from the 5' end of the antisense strand is a fX nucleotide. In some embodiments, at least one of the 2'-fluoro-nucleotides at positions 2, 6, 14, and 16 from the 5' end of the antisense strand is a fX nucleotide. In some embodiments, at least two of the 2'-fluoro-nucleotides at positions 2, 6, 14, and 16 from the 5' end of the antisense strand is a fX nucleotide. In some embodiments, less than or equal to 3 of the 2'-fluoro-nucleotides at positions 2, 6, 14, and 16 from the 5' end of the antisense strand is a fX nucleotide. In some embodiments, less than or equal to 2 of the 2'-fluoro-nucleotides at positions 2, 6, 14, and 16 from the 5' end of the antisense strand is a fX nucleotide. In some embodiments, the 2'-fluoro-nucleotide at position 2 from the 5' end of the antisense strand is a fX nucleotide. In some embodiments, the 2'-fluoro-nucleotide at position 6 from the 5' end of the antisense strand is a fX nucleotide. In some embodiments, the 2'-fluoro-nucleotide at position 14 from the 5' end of the antisense strand is a fX nucleotide. In some embodiments, the 2'-fluoro-nucleotide at position 16 from the 5' end of the antisense strand is a fX nucleotide. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker. In some embodiments, the 2'-O-methyl nucleotide at position 1 from the 5' end of the sense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 5' end of the antisense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 3' end of the sense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 3' end of the antisense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, at least 1, 2, 3, 4 or more 2'-fluoro nucleotides on the sense strand or antisense strand is a 2'-fluoro nucleotide mimic. In some embodiments, at least 1, 2, 3, 4 or more 2'-fluoro nucleotides on the sense strand is a fB, fN, f(4nh)Q, f4P, f2P, or fX nucleotide. In some embodiments, at least 1, 2, 3, 4 or more 2'-fluoro nucleotides on the antisense strand is a fB, fN, f(4nh)Q, f4P, f2P, or fX nucleotide. In some embodiments, at least 1, 2, 3, 4 or more 2'-O-methyl nucleotide on the sense or antisense strand is a 2'-O-methyl nucleotide mimic. In some embodiments, one or more nucleotides in the sense strand and/or the antisense strand may be a 3',4' seco modified nucleotide in which the bond between the 3' and 4' positions of the furanose ring is broken (e.g., mun34).

Figure 3G:
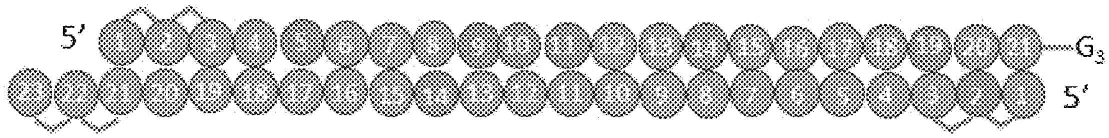

As shown in FIG. 3G, a ds-siNA may comprise (a) a sense strand consisting of 21 nucleotides, wherein 2'-fluoro nucleotides are at positions 5, 9-11, 14, and 19 from the 5' end of the sense strand, and wherein 2'-O-methyl nucleotides are at positions 1-4, 6-8, 12, 13, 15-18, 20, and 21 from the 5' end of the sense strand; and (b) an antisense strand consisting of 23 nucleotides, wherein 2'-flouro nucleodies are at positions 2 and 14 from the 5' end of the antisense strand, and wherein 2'-O-methyl nucleotides are at positions 1, 3-13, and 15-23 from the 5' end of the antisense strand. The ds-siNA may further comprise a conjugated moiety attached to the 3' end of the sense strand. The ds-siNA may further comprise (i) phosphorothioate internucleoside linkages between the nucleotides at positions 1 and 2 and positions 2 and 3 from the 5' end of the sense strand; and (ii) phosphorothioate internucleoside linkages between the nucleotides at positions 1 and 2; positions 2 and 3; positions 19 and 20; and positions 20 and 21 from the 5' end of the antisense strand. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker. In some embodiments, the 2'-O-methyl nucleotide at position 1 from the 5' end of the sense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 5' end of the antisense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 3' end of the sense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 3' end of the antisense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, at least 1, 2, 3, 4 or more 2'-fluoro nucleotides on the sense strand or antisense strand is a 2'-fluoro nucleotide mimic. In some embodiments, at least 1, 2, 3, 4 or more 2'-fluoro nucleotides on the sense strand is a fB, fN, f(4nh)Q, f4P, f2P, or fX nucleotide. In some embodiments, at least 1, 2, 3, 4 or more 2'-fluoro nucleotides on the antisense strand is a fB, fN, f(4nh)Q, f4P, f2P, or fX nucleotide. In some embodiments, at least 1, 2, 3, 4 or more 2'-O-methyl nucleotide on the sense or antisense strand is a 2'-O-methyl nucleotide mimic. In some embodiments, one or more nucleotides in the sense strand and/or the antisense strand may be a 3',4' seco modified nucleotide in which the bond between the 3' and 4' positions of the furanose ring is broken (e.g., mun34).

Figure 3H:
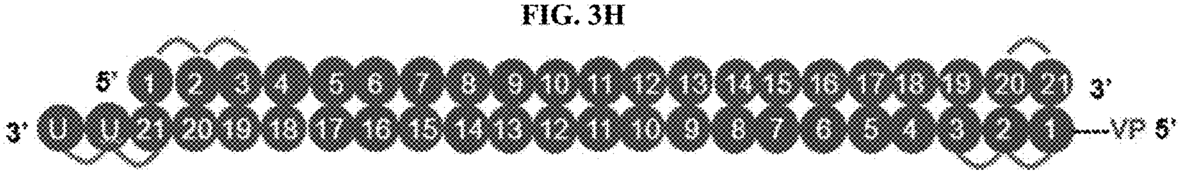
Figure 3H:
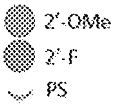

As shown in FIG. 3H, a ds-siNA may comprise (a) a sense strand consisting of 21 nucleotides, wherein 2'-fluoro nucleotides are at positions 7 and 9-11 from the 5' end of the sense strand, and wherein 2'-O-methyl nucleotides are at positions 1-6, 8, and 12-21 from the 5' end of the sense strand; and (b) an antisense strand consisting of 23 nucleotides, wherein 2'-flouro nucleodies are at positions 2, 6, 14, and 16 from the 5' end of the antisense strand, and wherein 2'-O-methyl nucleotides are at positions 1, 3-5, 7-13, 15, and 17-23 from the 5' end of the antisense strand. Optionally, the nucleotides at positions 22 and 23 of from the 5' end of the antisense strand may be unlocked nucleotides. Optionally, the ds-siNA may further comprise a conjugated moiety attached to the 3' end of the sense strand (not pictured). The ds-siNA may optionally comprise a vinyl phosphonate attached to the 5' end of the antisense strand (pictured), but in some embodiments, a 5' end cap disclosed herein may be suitable as well. The ds-siNA may further comprise (i) phosphorothioate internucleoside linkages between the nucleotides at positions 1 and 2, positions 2 and 3, and positions 20 and 21 from the 5' end of the sense strand; and (ii) phosphorothioate internucleoside linkages between the nucleotides at positions 1 and 2; positions 2 and 3; positions 21 and 22, and positions 22 and 23 from the 5' end of the antisense strand. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker. In some embodiments, the 2'-O-methyl nucleotide at position 1 from the 5' end of the sense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide, a d2vd3U nucleotide, an omeco-d3U nucleotide, a 4hU nucleotide, a v-mun nucleotide, a c2o-4h nucleotide, an omeco-mun nucleotide, or a d2vmA nucleotide. In some embodiments, the 2'-O-methyl nucleotide at position 1 from the 5' end of the antisense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 3' end of the sense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, the 2'-O-methyl nucleotide at position 1 from the 3' end of the antisense strand is a d2vd3 nucleotide, a d2vd3U nucleotide, an omeco-d3 nucleotide, an omeco-d3U nucleotide, a 4h nucleotide, a 4hU nucleotide, a v-mun nucleotide, a c2o-4h nucleotide, an omeco-mun nucleotide, a d2vm nucleotide, or a d2vmA nucleotide. In some embodiments, at least 1, 2, 3, 4 or more 2'-fluoro nucleotides on the sense strand or antisense strand is a 2'-fluoro nucleotide mimic. In some embodiments, at least 1, 2, 3, 4 or more 2'-fluoro nucleotides on the sense strand is a fB, fN, f(4nh)Q, f4P, f2P, or fX nucleotide. In some embodiments, at least 1, 2, 3, 4 or more 2'-fluoro nucleotides on the antisense strand is a fB, fN, f(4nh)Q, f4P, f2P, or fX nucleotide. In some embodiments, at least 1, 2, 3, 4 or more 2'-O-methyl nucleotide on the sense or antisense strand is a 2'-O-methyl nucleotide mimic. In some embodiments, one or more nucleotides in the sense strand and/or the antisense strand may be a 3',4' seco modified nucleotide in which the bond between the 3' and 4' positions of the furanose ring is broken (e.g., mun34).

siNA Sense Strand

Any of the siNA molecules described herein may comprise a sense strand. The sense strand may comprise a first nucleotide sequence. The first nucleotide sequence may be 15 to 30, 15 to 25, 15 to 23, 17 to 23, 19 to 23, or 19 to 21 nucleotides in length. In some embodiments, the first nucleotide sequence is 15, 16, 17, 18, 19, 20, 21, 22, 23, 24, 25, 26, 27, 28, 29, or 30 nucleotides in length. In some embodiments, the first nucleotide sequence is at least 19 nucleotides in length. In some embodiments, the first nucleotide sequence is at least 21 nucleotides in length.

In some embodiments, the sense strand is the same length as the first nucleotide sequence. In some embodiments, the sense strand is longer than the first nucleotide sequence. In some embodiments, the sense strand may further comprise 1, 2, 3, 4, or 5 or more nucleotides than the first nucleotide sequence. In some embodiments, the sense strand may further comprise a deoxyribonucleic acid (DNA). In some embodiments, the DNA is thymine (T). In some embodiments, the sense strand may further comprise a TT sequence. In some embodiments, the sense strand may further comprise one or more modified nucleotides that are adjacent to the first nucleotide sequence. In some embodiments, the one or more modified nucleotides are independently selected from any of the modified nucleotides disclosed herein (e.g., 2'-fluoro nucleotide, 2'-O-methyl nucleotide, 2'-fluoro nucleotide mimic, 2'-O-methyl nucleotide mimic, or a nucleotide comprising a modified nucleobase).

In some embodiments, the first nucleotide sequence comprises 15, 16, 17, 18, 19, 20, 21, 22, 23, or more modified nucleotides independently selected from a 2'-O-methyl nucleotide and a 2'-fluoro nucleotide. In some embodiments, 70%, 75%, 80%, 85%, 90%, 95% or 100% of the nucleotides in the first nucleotide sequence are modified nucleotides independently selected from a 2'-O-methyl nucleotide and a 2'-fluoro nucleotide. In some embodiments, 100% of the nucleotides in the first nucleotide sequence are modified nucleotides independently selected from a 2'-O-methyl nucleotide and a 2'-fluoro nucleotide. In some embodiments, the 2'-O-methyl nucleotide is a 2'-O-methyl nucleotide mimic. In some embodiments, the 2'-fluoro nucleotide is a 2'-fluoro nucleotide mimic.

In some embodiments, between about 15 to 30, 15 to 25, 15 to 24, 15 to 23, 15 to 22, 15 to 21, 17 to 30, 17 to 25, 17 to 24, 17 to 23, 17 to 22, 17 to 21, 18 to 30, 18 to 25, 18 to 24, 18 to 23, 18 to 22, 18 to 21, 19 to 30, 19 to 25, 19 to 24, 19 to 23, 19 to 22, 19 to 21, 20 to 25, 20 to 24, 20 to 23, 21 to 25, 21 to 24, or 21 to 23 modified nucleotides of the first nucleotide sequence are 2'-O-methyl nucleotides. In some embodiments, between about 2 to 20 modified nucleotides of the first nucleotide sequence are 2'-O-methyl nucleotides. In some embodiments, between about 5 to 25 modified nucleotides of the first nucleotide sequence are 2'-O-methyl nucleotides. In some embodiments, between about 10 to 25 modified nucleotides of the first nucleotide sequence are 2'-O-methyl nucleotides. In some embodiments, between about 12 to 25 modified nucleotides of the first nucleotide sequence are 2'-O-methyl nucleotides. In some embodiments, at least about 10, 11, 12, 13, 14, 15, 16, 17, 18, 19, 20, 21, or 22 modified nucleotides of the first nucleotide sequence are 2'-O-methyl nucleotides. In some embodiments, at least about 12 modified nucleotides of the first nucleotide sequence are 2'-O-methyl nucleotides. In some embodiments, at least about 13 modified nucleotides of the first nucleotide sequence are 2'-O-methyl nucleotides. In some embodiments, at least about 14 modified nucleotides of the first nucleotide sequence are 2'-O-methyl nucleotides. In some embodiments, at least about 15 modified nucleotides of the first nucleotide sequence are 2'-O-methyl nucleotides. In some embodiments, at least about 16 modified nucleotides of the first nucleotide sequence are 2'-O-methyl nucleotides. In some embodiments, at least about 17 modified nucleotides of the first nucleotide sequence are 2'-O-methyl nucleotides. In some embodiments, at least about 18 modified nucleotides of the first nucleotide sequence are 2'-O-methyl nucleotides. In some embodiments, at least about 19 modified nucleotides of the first nucleotide sequence are 2'-O-methyl nucleotides. In some embodiments, less than or equal to 25, 24, 23, 22, 21, 20, 19, 18, 17, 16, 15, 14, 13, 12, 11, 10, 9, 8, 7, 6, 5, 4, 3, or 2 modified nucleotides of the first nucleotide sequence are 2'-O-methyl nucleotides. In some embodiments, less than or equal to 21 modified nucleotides of the first nucleotide sequence are 2'-O-methyl nucleotides. In some embodiments, less than or equal to 20 modified nucleotides of the first nucleotide sequence are 2'-O-methyl nucleotides. In some embodiments, less than or equal to 19 modified nucleotides of the first nucleotide sequence are 2'-O-methyl nucleotides. In some embodiments, less than or equal to 18 modified nucleotides of the first nucleotide sequence are 2'-O-methyl nucleotides. In some embodiments, less than or equal to 17 modified nucleotides of the first nucleotide sequence are 2'-O-methyl nucleotides. In some embodiments, less than or equal to 16 modified nucleotides of the first nucleotide sequence are 2'-O-methyl nucleotides. In some embodiments, less than or equal to 15 modified nucleotides of the first nucleotide sequence are 2'-O-methyl nucleotides. In some embodiments, less than or equal to 14 modified nucleotides of the first nucleotide sequence are 2'-O-methyl nucleotides. In some embodiments, less than or equal to 13 modified nucleotides of the first nucleotide sequence are 2'-O-methyl nucleotides. In some embodiments, at least one modified nucleotide of the first nucleotide sequence is a 2'-O-methyl pyrimidine. In some embodiments, at least 5, 6, 7, 8, 9, or 10 modified nucleotides of the first nucleotide sequence are 2'-O-methyl pyrimidines. In some embodiments, at least one modified nucleotide of the first nucleotide sequence is a 2'-O-methyl purine. In some embodiments, at least 5, 6, 7, 8, 9, or 10 modified nucleotides of the first nucleotide sequence are 2'-O-methyl purines. In some embodiments, the 2'-O-methyl nucleotide is a 2'-O-methyl nucleotide mimic.

In some embodiments, between 2 to 15 modified nucleotides of the first nucleotide sequence are 2'-fluoro nucleotides. In some embodiments, between 2 to 10 modified nucleotides of the first nucleotide sequence are 2'-fluoro nucleotides. In some embodiments, between 2 to 6 modified nucleotides of the first nucleotide sequence are 2'-fluoro nucleotides. In some embodiments, 1 to 6, 1 to 5, 1 to 4, or 1 to 3 modified nucleotides of the first nucleotide sequence are 2'-fluoro nucleotides. In some embodiments, at least 1, 2, 3, 4, 5, or 6 modified nucleotides of the first nucleotide sequence are 2'-fluoro nucleotides. In some embodiments, at least 1 modified nucleotide of the first nucleotide sequence is a 2'-fluoro nucleotide. In some embodiments, at least 2 modified nucleotides of the first nucleotide sequence are 2'-fluoro nucleotides. In some embodiments, at least 3 modified nucleotides of the first nucleotide sequence are 2'-fluoro nucleotides. In some embodiments, at least 4 modified nucleotides of the first nucleotide sequence are 2'-fluoro nucleotides. In some embodiments, at least 5 modified nucleotides of the first nucleotide sequence are 2'-fluoro nucleotides. In some embodiments, at least 6 modified nucleotides of the first nucleotide sequence are 2'-fluoro nucleotides. In some embodiments, 10, 9, 8, 7, 6, 5, 4, 3 or fewer modified nucleotides of the first nucleotide sequence are 2'-fluoro nucleotides. In some embodiments, 10 or fewer modified nucleotides of the first nucleotide sequence are 2'-fluoro nucleotides. In some embodiments, 7 or fewer modified nucleotides of the first nucleotide sequence are 2'-fluoro nucleotides. In some embodiments, 6 or fewer modified nucleotides of the first nucleotide sequence are 2'-fluoro nucleotides. In some embodiments, 5 or fewer modified nucleotides of the first nucleotide sequence are 2'-fluoro nucleotides. In some embodiments, 4 or fewer modified nucleotides of the first nucleotide sequence are 2'-fluoro nucleotides. In some embodiments, 3 or fewer modified nucleotides of the first nucleotide sequence are 2'-fluoro nucleotides. In some embodiments, 2 or fewer modified nucleotides of the first nucleotide sequence are 2'-fluoro nucleotides. In some embodiments, at least one modified nucleotide of the first nucleotide sequence is a 2'-fluoro pyrimidine. In some embodiments, 1, 2, 3, 4, 5, or 6 modified nucleotides of the first nucleotide sequence are 2'-fluoro pyrimidines. In some embodiments, at least one modified nucleotide of the first nucleotide sequence is a 2'-fluoro purine. In some embodiments, 1, 2, 3, 4, 5, or 6 modified nucleotides of the first nucleotide sequence are 2'-fluoro purines. In some embodiments, the 2'-fluoro nucleotide is a 2'-fluoro nucleotide mimic.

In some embodiments, the nucleotide at position 3, 5, 7, 8, 9, 10, 11, 12, 14, 17, and/or 19 from the 5' end of the first nucleotide sequence is a 2'-fluoro nucleotide. In some embodiments, at least two nucleotides at positions 3, 5, 7, 8, 9, 10, 11, 12, 14, 17, and/or 19 from the 5' end of the first nucleotide sequence are 2'-fluoro nucleotides. In some embodiments, at least three nucleotides at positions 3, 5, 7, 8, 9, 10, 11, 12, 14, 17, and/or 19 from the 5' end of the first nucleotide sequence are 2'-fluoro nucleotides. In some embodiments, at least four nucleotides at positions 3, 5, 7, 8, 9, 10, 11, 12, 14, 17, and/or 19 from the 5' end of the first nucleotide sequence are 2'-fluoro nucleotides. In some embodiments, at least five nucleotides at positions 3, 5, 7, 8, 9, 10, 11, 12, 14, 17, and/or 19 from the 5' end of the first nucleotide sequence are 2'-fluoro nucleotides. In some embodiments, the nucleotides at positions 3, 5, 7, 8, 9, 10, 11, 12, 14, 17, and/or 19 from the 5' end of the first nucleotide sequence are 2'-fluoro nucleotides. In some embodiments, the nucleotide at position 3 from the 5' end of the first nucleotide sequence is a 2'-fluoro nucleotide. In some embodiments, the nucleotide at position 7 from the 5' end of the first nucleotide sequence is a 2'-fluoro nucleotide. In some embodiments, the nucleotide at position 8 from the 5' end of the first nucleotide sequence is a 2'-fluoro nucleotide. In some embodiments, the nucleotide at position 9 from the 5' end of the first nucleotide sequence is a 2'-fluoro nucleotide. In some embodiments, the nucleotide at position 12 from the 5' end of the first nucleotide sequence is a 2'-fluoro nucleotide. In some embodiments, the nucleotide at position 17 from the 5' end of the first nucleotide sequence is a 2'-fluoro nucleotide. In some embodiments, the 2'-fluoro nucleotide is a 2'-fluoro nucleotide mimic.

In some embodiments, at least 1, 2, 3, 4, 5, 6, or 7 nucleotides at position 3, 5, 7, 8, 9, 10, 11, 12, 14, 17, and/or 19 from the 5' end of the first nucleotide sequence is a 2'-fluoro nucleotide. In some embodiments, the nucleotide at positions 3, 5, 7, 8, 9, 10, 11, 12, 14, 17, and/or 19 from the 5' end of the first nucleotide sequence is a 2'-fluoro nucleotide. In some embodiments, at least two nucleotides at positions 3, 5, 7, 8, 9, 10, 11, 12, 14, 17, and/or 19 from the 5' end of the first nucleotide sequence are 2'-fluoro nucleotides. In some embodiments, at least three nucleotides at positions 3, 5, 7, 8, 9, 10, 11, 12, 14, 17, and/or 19 from the 5' end of the first nucleotide sequence are 2'-fluoro nucleotides. In some embodiments, the nucleotides at positions 3, 5, 7, 8, 9, 10, 11, 12, 14, 17, and/or 19 from the 5' end of the first nucleotide sequence are 2'-fluoro nucleotides. In some embodiments, the nucleotide at position 3 from the 5' end of the first nucleotide sequence is a 2'-fluoro nucleotide. In some embodiments, the nucleotide at position 5 from the 5' end of the first nucleotide sequence is a 2'-fluoro nucleotide. In some embodiments, the nucleotide at position 7 from the 5' end of the first nucleotide sequence is a 2'-fluoro nucleotide. In some embodiments, the nucleotide at position 8 from the 5' end of the first nucleotide sequence is a 2'-fluoro nucleotide. In some embodiments, the nucleotide at position 9 from the 5' end of the first nucleotide sequence is a 2'-fluoro nucleotide. In some embodiments, the nucleotide at position 10 from the 5' end of the first nucleotide sequence is a 2'-fluoro nucleotide. In some embodiments, the nucleotide at position 11 from the 5' end of the first nucleotide sequence is a 2'-fluoro nucleotide. In some embodiments, the nucleotide at position 12 from the 5' end of the first nucleotide sequence is a 2'-fluoro nucleotide. In some embodiments, the nucleotide at position 14 from the 5' end of the first nucleotide sequence is a 2'-fluoro nucleotide. In some embodiments, the nucleotide at position 17 from the 5' end of the first nucleotide sequence is a 2'-fluoro nucleotide. In some embodiments, the nucleotide at position 19 from the 5' end of the first nucleotide sequence is a 2'-fluoro nucleotide. In some embodiments, the nucleotide at position 3, 7, 8, 9, 12, and/or 17 from the 5' end of the first nucleotide sequence is a 2'-fluoro nucleotide. In some embodiments, the nucleotide at position 3, 7, 8, and/or 17 from the 5' end of the first nucleotide sequence is a 2'-fluoro nucleotide. In some embodiments, the nucleotide at position 3, 7, 8, 9, 12, and/or 17 from the 5' end of the first nucleotide sequence is a 2'-fluoro nucleotide. In some embodiments, the nucleotide at position 5, 7, 8, and/or 9 from the 5' end of the first nucleotide sequence is a 2'-fluoro nucleotide. In some embodiments, the nucleotide at position 5, 9, 10, 11, 12, and/or 19 from the 5' end of the first nucleotide sequence is a 2'-fluoro nucleotide. In some embodiments, the 2'-fluoro nucleotide is a 2'-fluoro nucleotide mimic.

In some embodiments, the 2'-fluoro or 2'-O-methyl nucleotide mimic is a nucleotide mimic of Formula (V):

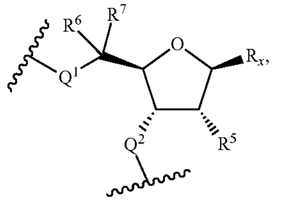

wherein $R_x$ is independently a nucleobase, aryl, heteroaryl, or H, $Q^1$ and $Q^2$ are independently S or O, $R^5$ is independently $-OCD_3$, $-F$, or $-OCH_3$, and $R^6$ and $R^7$ are independently H, D, or $CD_3$. In some embodiments, the nucleobase is selected from thymine, cytosine, guanine, adenine, uracil, and an analogue or derivative thereof.

In some embodiments, the 2'-fluoro or 2'-O-methyl nucleotide mimic is a nucleotide mimic of Formula (16)-Formula (20):

Formula (16)

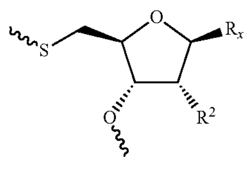

-continued

Formula (17)

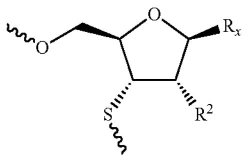

Formula (18)

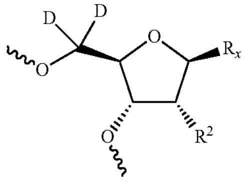

Formula (19)

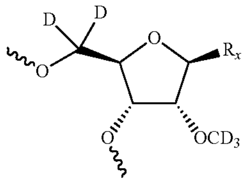

Formula (20)

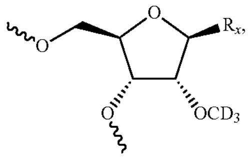

wherein $R_x$ is independently a nucleobase, aryl, heteroaryl, or H and $R^2$ is F or —$OCH_3$. In some embodiments, the nucleobase is selected from thymine, cytosine, guanine, adenine, uracil, and an analogue or derivative thereof.

In some embodiments, the sense strand, the antisense strand, or both may each independently comprise at least 1, at least 2, at least 3, at least 4, or at least 5 or more modified nucleotide(s) having the following chemical structure:

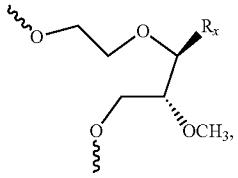

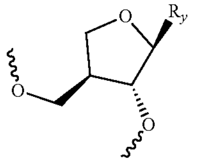

(apN)

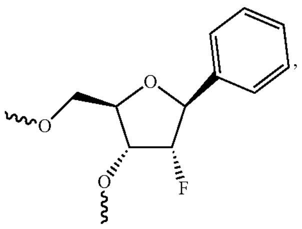

(fB)

-continued

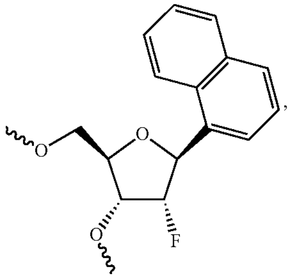

or (fN)

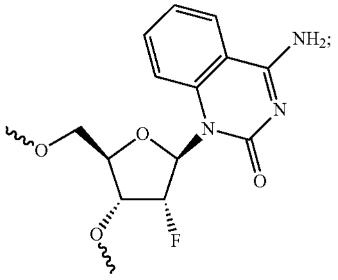

(f(4nh)Q)

wherein $R_y$ is a nucleobase and wherein $R_x$ is a nucleobase, aryl, heteroaryl, or H. In some embodiments, the nucleobase is selected from thymine, cytosine, guanine, adenine, uracil, and an analogue or derivative thereof.

In some embodiments, the sense strand, the antisense strand, or both may each independently comprise at least 1, at least 2, at least 3, at least 4, or at least 5 or more modified nucleotide(s) having the following chemical structure:

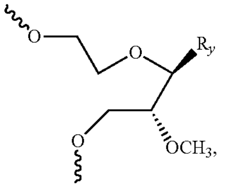

(mun34)

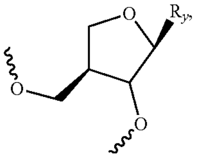

(apN)

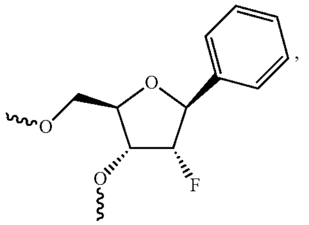

(fB)

-continued

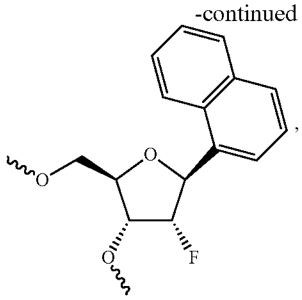

, or (fN)

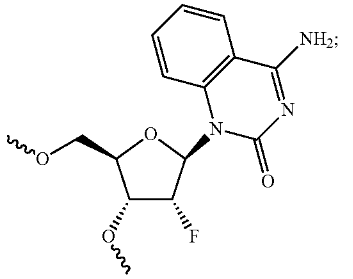

(f(4nh)Q)

wherein $R_y$ is a nucleobase. In some embodiments, the nucleobase is selected from thymine, cytosine, guanine, adenine, uracil, and an analogue or derivative thereof.

For the purposes of the present disclosure, the modified nucleotide may be in any position of the sense strand. In some embodiments, the modified nucleotide may be at position 1, 2, 3, 4, 5, 6, 7, 8, 9, 10, 11, 12, 13, 14, 15, 16, 17, 18, 19, 20, 21, 22, or 23 of the sense strand relative to the 5' end. For example, when the modified nucleotide is

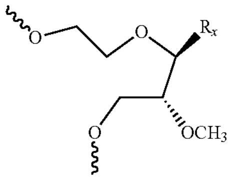

or

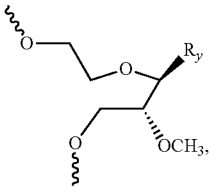

(mun34)

it may be located at position 1, 2, 3, 4, 5, 6, 7, 8, 9, 10, 11, 12, 13, 14, 15, 16, 17, 18, 19, 20, 21, 22, or 23 of the sense strand relative to the 5' end. In some embodiments, when the modified nucleotide is

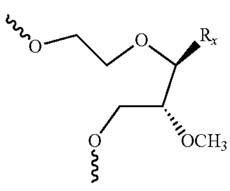

or

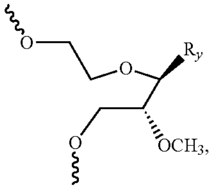

(mun34)

it may be located at position 3, 16, 17, or 18, relative to the 5' end of the sense strand.

In some embodiments, the first nucleotide sequence comprises, consists of, or consists essentially of ribonucleic acids (RNAs). In some embodiments, the first nucleotide sequence comprises, consists of, or consists essentially of modified RNAs. In some embodiments, the modified RNAs are selected from a 2'-O-methyl RNA and 2'-fluoro RNA. In some embodiments, 15, 16, 17, 18, 19, 20, 21, 22, or 23 modified nucleotides of the first nucleotide sequence are independently selected from 2'-O-methyl RNA and 2'-fluoro RNA.

In some embodiments, the sense strand may further comprise one or more internucleoside linkages independently selected from a phosphodiester (PO) internucleoside linkage, phosphorothioate (PS) internucleoside linkage, mesyl phosphoramidate internucleoside linkage (Ms), phosphorodithioate internucleoside linkage, and PS-mimic internucleoside linkage. In some embodiments, the PS-mimic internucleoside linkage is a sulfo internucleoside linkage.

In some embodiments, the sense strand may further comprise at least 1, 2, 3, 4, 5, 6, 7, 8, 9, 10, 11, 12, 13, 14, or 15 or more phosphorothioate internucleoside linkages. In some embodiments, the sense strand comprises 20, 19, 18, 17, 16, 15, 14, 13, 12, 11, 10, 9, 8, 7, 6, 5, 4, or 3 or fewer phosphorothioate internucleoside linkages. In some embodiments, the sense strand comprises 2 to 10, 2 to 8, 2 to 6, 1 to 5, 1 to 4, 1 to 3, or 1 to 2 phosphorothioate internucleoside linkages. In some embodiments, the sense strand comprises 1 to 2 phosphorothioate internucleoside linkages. In some embodiments, the sense strand comprises 2 to 4 phosphorothioate internucleoside linkages. In some embodiments, at least one phosphorothioate internucleoside linkage is between the nucleotides at positions 1 and 2 from the 5' end of the first nucleotide sequence. In some embodiments, at least one phosphorothioate internucleoside linkage is between the nucleotides at positions 2 and 3 from the 5' end of the first nucleotide sequence. In some embodiments, the sense strand comprises two phosphorothioate internucleoside linkages between the nucleotides at positions 1 to 3 from the 5' end of the first nucleotide sequence.

In some embodiments, the sense strand may further comprise at least 1, 2, 3, 4, 5, 6, 7, 8, 9, 10, 11, 12, 13, 14, or 15 or more mesyl phosphoramidate internucleoside linkages. In some embodiments, the sense strand comprises 20, 19, 18, 17, 16, 15, 14, 13, 12, 11, 10, 9, 8, 7, 6, 5, 4, or 3 or fewer mesyl phosphoramidate internucleoside linkages. In some embodiments, the sense strand comprises 2 to 10, 2 to 8, 2 to 6, 1 to 5, 1 to 4, 1 to 3, or 1 to 2 mesyl phosphoramidate internucleoside linkages. In some embodiments, the sense strand comprises 1 to 2 mesyl phosphoramidate internucleoside linkages. In some embodiments, the sense strand comprises 2 to 4 mesyl phosphoramidate internucleoside linkages.

In some embodiments, the sense strand may comprise any of the modified nucleotides disclosed in the sub-section titled "Modified Nucleotides" below. In some embodiments, the sense strand may comprise a 5'-stabilized end cap, and the 5'-stabilized end cap may be selected from those disclosed in the sub-section titled "5'-Stabilized End Cap" below.

siNA Antisense Strand

Any of the siNA molecules described herein may comprise an antisense strand. The antisense strand may comprise a second nucleotide sequence. The second nucleotide sequence may be 15 to 30, 15 to 25, 15 to 23, 17 to 23, 19 to 23, or 19 to 21 nucleotides in length. In some embodiments, the second nucleotide sequence is 15, 16, 17, 18, 19, 20, 21, 22, 23, 24, 25, 26, 27, 28, 29, or 30 nucleotides in length. In some embodiments, the second nucleotide sequence is at least 19 nucleotides in length. In some embodiments, the second nucleotide sequence is at least 21 nucleotides in length.

In some embodiments, the antisense strand is the same length as the second nucleotide sequence. In some embodiments, the antisense strand is longer than the second nucleotide sequence. In some embodiments, the antisense strand may further comprise 1, 2, 3, 4, or 5 or more nucleotides than the second nucleotide sequence. In some embodiments, the antisense strand is the same length as the sense strand. In some embodiments, the antisense strand is longer than the sense strand. In some embodiments, the antisense strand may further comprise 1, 2, 3, 4, or 5 or more nucleotides than the sense strand. In some embodiments, the antisense strand may further comprise a deoxyribonucleic acid (DNA). In some embodiments, the DNA is thymine (T). In some embodiments, the antisense strand may further comprise a TT sequence. In some embodiments, the antisense strand may further comprise one or more modified nucleotides that are adjacent to the second nucleotide sequence. In some embodiments, the one or more modified nucleotides are independently selected from any of the modified nucleotides disclosed herein (e.g., 2'-fluoro nucleotide, 2'-O-methyl nucleotide, 2'-fluoro nucleotide mimic, 2'-O-methyl nucleotide mimic, or a nucleotide comprising a modified nucleobase).

In some embodiments, the second nucleotide sequence comprises 15, 16, 17, 18, 19, 20, 21, 22, 23, or more modified nucleotides independently selected from a 2'-O-methyl nucleotide and a 2'-fluoro nucleotide. In some embodiments, 70%, 75%, 80%, 85%, 90%, 95% or 100% of the nucleotides in the second nucleotide sequence are modified nucleotides independently selected from a 2'-O-methyl nucleotide and a 2'-fluoro nucleotide. In some embodiments, 100% of the nucleotides in the second nucleotide sequence are modified nucleotides independently selected from a 2'-O-methyl nucleotide and a 2'-fluoro nucleotide.

In some embodiments, between about 15 to 30, 15 to 25, 15 to 24, 15 to 23, 15 to 22, 15 to 21, 17 to 30, 17 to 25, 17 to 24, 17 to 23, 17 to 22, 17 to 21, 18 to 30, 18 to 25, 18 to 24, 18 to 23, 18 to 22, 18 to 21, 19 to 30, 19 to 25, 19 to 24, 19 to 23, 19 to 22, 19 to 21, 20 to 25, 20 to 24, 20 to 23, 21 to 25, 21 to 24, or 21 to 23 modified nucleotides of the second nucleotide sequence are 2'-O-methyl nucleotides. In some embodiments, between about 2 to 20 modified nucleotides of the second nucleotide sequence are 2'-O-methyl nucleotides. In some embodiments, between about 5 to 25 modified nucleotides of the second nucleotide sequence are 2'-O-methyl nucleotides. In some embodiments, between about 10 to 25 modified nucleotides of the second nucleotide sequence are 2'-O-methyl nucleotides. In some embodiments, between about 12 to 25 modified nucleotides of the second nucleotide sequence are 2'-O-methyl nucleotides. In some embodiments, at least 10, 11, 12, 13, 14, 15, 16, 17, 18, 19, 20, 21, or 22 modified nucleotides of the second nucleotide sequence are 2'-O-methyl nucleotides. In some embodiments, at least about 12 modified nucleotides of the second nucleotide sequence are 2'-O-methyl nucleotides. In some embodiments, at least about 13 modified nucleotides of the second nucleotide sequence are 2'-O-methyl nucleotides. In some embodiments, at least about 14 modified nucleotides of the second nucleotide sequence are 2'-O-methyl nucleotides. In some embodiments, at least about 15 modified nucleotides of the second nucleotide sequence are 2'-O-methyl nucleotides. In some embodiments, at least about 16 modified nucleotides of the second nucleotide sequence are 2'-O-methyl nucleotides. In some embodiments, at least about 17 modified nucleotides of the second nucleotide sequence are 2'-O-methyl nucleotides. In some embodiments, at least about 18 modified nucleotides of the second nucleotide sequence are 2'-O-methyl nucleotides. In some embodiments, at least about 19 modified nucleotides of the second nucleotide sequence are 2'-O-methyl nucleotides. In some embodiments, less than or equal to 25, 24, 23, 22, 21, 20, 19, 18, 17, 16, 15, 14, 13, 12, 11, 10, 9, 8, 7, 6, 5, 4, 3, or 2 modified nucleotides of the second nucleotide sequence are 2'-O-methyl nucleotides. In some embodiments, less than or equal to 21 modified nucleotides of the second nucleotide sequence are 2'-O-methyl nucleotides. In some embodiments, less than or equal to 20 modified nucleotides of the second nucleotide sequence are 2'-O-methyl nucleotides. In some embodiments, less than or equal to 19 modified nucleotides of the second nucleotide sequence are 2'-O-methyl nucleotides. In some embodiments, less than or equal to 18 modified nucleotides of the second nucleotide sequence are 2'-O-methyl nucleotides. In some embodiments, less than or equal to 17 modified nucleotides of the second nucleotide sequence are 2'-O-methyl nucleotides. In some embodiments, less than or equal to 16 modified nucleotides of the second nucleotide sequence are 2'-O-methyl nucleotides. In some embodiments, less than or equal to 15 modified nucleotides of the second nucleotide sequence are 2'-O-methyl nucleotides. In some embodiments, less than or equal to 14 modified nucleotides of the second nucleotide sequence are 2'-O-methyl nucleotides. In some embodiments, less than or equal to 13 modified nucleotides of the second nucleotide sequence are 2'-O-methyl nucleotides. In some embodiments, at least one modified nucleotide of the second nucleotide sequence is a 2'-O-methyl pyrimidine. In some embodiments, at least 5, 6, 7, 8, 9, or 10 modified nucleotides of the second nucleotide sequence are 2'-O-methyl pyrimidines. In some embodiments, at least one modified nucleotide of the second nucleotide sequence is a 2'-O-methyl purine. In some embodiments, at least 5, 6, 7, 8, 9, or 10 modified nucleotides of the second nucleotide sequence are 2'-O-methyl purines. In some embodiments, the 2'-O-methyl nucleotide is a 2'-O-methyl nucleotide mimic.

In some embodiments, between 2 to 15 modified nucleotides of the second nucleotide sequence are 2'-fluoro nucleotides. In some embodiments, between 2 to 10 modified nucleotides of the second nucleotide sequence are 2'-fluoro nucleotides. In some embodiments, between 2 to 6 modified nucleotides of the second nucleotide sequence are 2'-fluoro nucleotides. In some embodiments, 1 to 6, 1 to 5, 1 to 4, or 1 to 3 modified nucleotides of the second nucleotide sequence are 2'-fluoro nucleotides. In some embodiments, at least 1, 2, 3, 4, 5, or 6 modified nucleotides of the second nucleotide sequence are 2'-fluoro nucleotides. In some embodiments, at least 1 modified nucleotide of the second nucleotide sequence is a 2'-fluoro nucleotide. In some embodiments, at least 2 modified nucleotides of the second nucleotide sequence are 2'-fluoro nucleotides. In some embodiments, at least 3 modified nucleotides of the second nucleotide sequence are 2'-fluoro nucleotides. In some embodiments, at least 4 modified nucleotides of the second nucleotide sequence are 2'-fluoro nucleotides. In some embodiments, at least 5 modified nucleotides of the second nucleotide sequence are 2'-fluoro nucleotides. In some embodiments, 10, 9, 8, 7, 6, 5, 4, 3 or fewer modified nucleotides of the second nucleotide sequence are 2'-fluoro nucleotides. In some embodiments, 10 or fewer modified nucleotides of the second nucleotide sequence are 2'-fluoro nucleotides. In some embodiments, 7 or fewer modified nucleotides of the second nucleotide sequence are 2'-fluoro nucleotides. In some embodiments, 6 or fewer modified nucleotides of the second nucleotide sequence are 2'-fluoro nucleotides. In some embodiments, 5 or fewer modified nucleotides of the second nucleotide sequence are 2'-fluoro nucleotides. In some embodiments, 4 or fewer modified nucleotides of the second nucleotide sequence are 2'-fluoro nucleotides. In some embodiments, 3 or fewer modified nucleotides of the second nucleotide sequence are 2'-fluoro nucleotides. In some embodiments, 2 or fewer modified nucleotides of the second nucleotide sequence are 2'-fluoro nucleotides. In some embodiments, at least one modified nucleotide of the second nucleotide sequence is a 2'-fluoro pyrimidine. In some embodiments, 1, 2, 3, 4, 5, or 6 modified nucleotides of the second nucleotide sequence are 2'-fluoro pyrimidines. In some embodiments, at least one modified nucleotide of the second nucleotide sequence is a 2'-fluoro purine. In some embodiments, 1, 2, 3, 4, 5, or 6 modified nucleotides of the second nucleotide sequence are 2'-fluoro purines. In some embodiments, the 2'-fluoro nucleotide is a 2'-fluoro nucleotide mimic.

In some embodiments, the 2'-fluoro nucleotide or 2'-O-methyl nucleotide is a 2'-fluoro or 2'-O-methyl nucleotide mimic. In some embodiments, the 2'-fluoro or 2'-O-methyl nucleotide mimic is a nucleotide mimic of Formula (V):

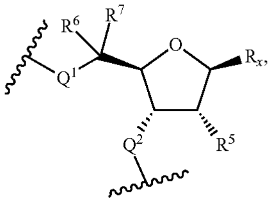

wherein $R_x$ is independently a nucleobase, aryl, heteroaryl, or H, $Q^1$ and $Q^2$ are independently S or O, $R^5$ is independently —$OCD_3$, —F, or —$OCH_3$, and $R^6$ and $R^7$ are independently H, D, or $CD_3$. In some embodiments, the nucleobase is selected from thymine, cytosine, guanine, adenine, uracil, and an analogue or derivative thereof.

In some embodiments, the 2'-fluoro or 2'-O-methyl nucleotide mimic is a nucleotide mimic of Formula (16)-Formula (20):

Formula (16)

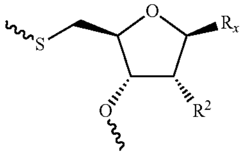

Formula (17)

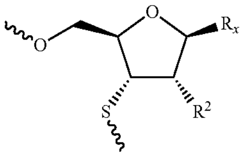

-continued

Formula (18)

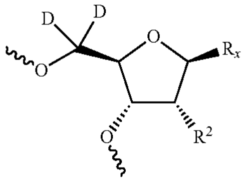

Formula (19)

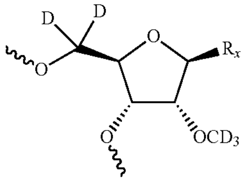

Formula (20)

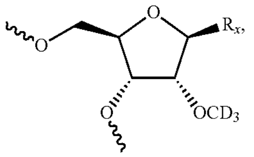

wherein $R_x$ is a nucleobase, aryl, heteroaryl, or H and $R^2$ is independently F or —$OCH_3$. In some embodiments, the nucleobase is selected from thymine, cytosine, guanine, adenine, uracil, and an analogue or derivative thereof.

In some embodiments, the antisense strand, sense strand, or both may each independently comprise at least 1, at least 2, at least 3, at least 4, or at least 5 or more modified nucleotide(s) having the following chemical structure:

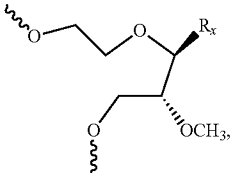

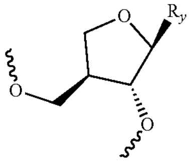

(apN)

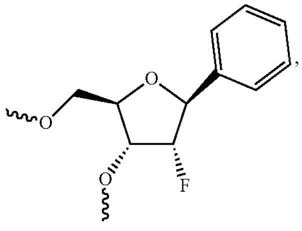

, (fB)

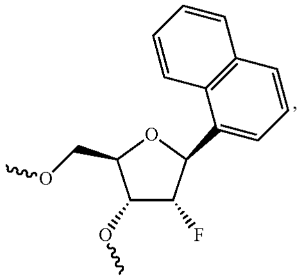

, or (fN)

-continued

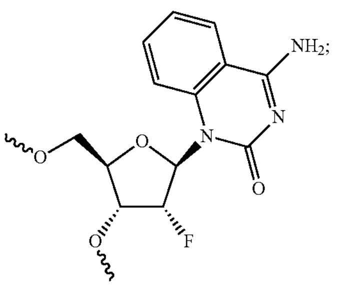

(f(4nh)Q)

-continued

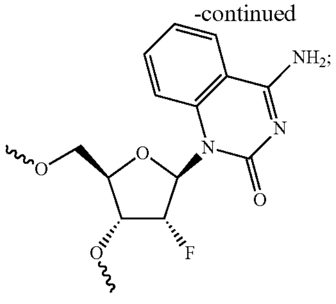

(F(4nh)Q)

wherein $R_y$ is a nucleobase and wherein Rx is a nucleobase, aryl, heteroaryl, or H. In some embodiments, the nucleobase is selected from thymine, cytosine, guanine, adenine, uracil, and an analogue or derivative thereof.

In some embodiments, the antisense strand, sense strand, or both may each independently comprise at least 1, at least 2, at least 3, at least 4, or at least 5 or more modified nucleotide(s) having the following chemical structure:

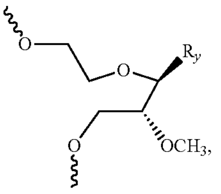

(mun34)

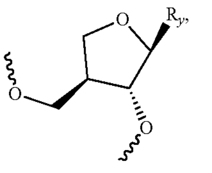

(apN)

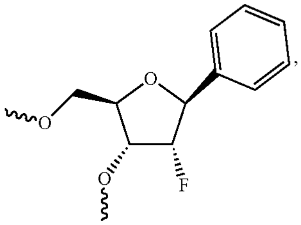

(fB)

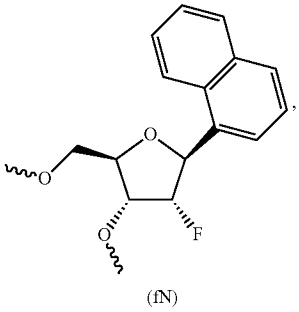

, or (fN)

wherein $R_y$ is a nucleobase. In some embodiments, the nucleobase is selected from thymine, cytosine, guanine, adenine, uracil, and an analogue or derivative thereof.

For the purposes of the present disclosure, the modified nucleotide may be in any position of the antisense strand. In some embodiments, the modified nucleotide may be at position 1, 2, 3, 4, 5, 6, 7, 8, 9, 10, 11, 12, 13, 14, 15, 16, 17, 18, 19, 20, 21, 22, or 23 of the antisense strand relative to the 5' end.

In some embodiments, at least 1, 2, 3, 4, 5, 6, 7, 8, or 9 nucleotides at position 2, 5, 6, 8, 10, 14, 16, 17, and/or 18 from the 5' end of the second nucleotide sequence is a 2'-fluoro nucleotide. In some embodiments, the nucleotide at position 2, 5, 6, 8, 10, 14, 16, 17, and/or 18 from the 5' end of the second nucleotide sequence is a 2'-fluoro nucleotide. In some embodiments, at least two nucleotides at positions 2, 5, 6, 8, 10, 14, 16, 17, and/or 18 from the 5' end of the second nucleotide sequence are 2'-fluoro nucleotides. In some embodiments, at least three nucleotides at positions 2, 5, 6, 8, 10, 14, 16, 17, and/or 18 from the 5' end of the second nucleotide sequence are 2'-fluoro nucleotides. In some embodiments, at least four nucleotides at positions 2, 5, 6, 8, 10, 14, 16, 17, and/or 18 from the 5' end of the second nucleotide sequence are 2'-fluoro nucleotides. In some embodiments, at least five nucleotides at positions 2, 5, 6, 8, 10, 14, 16, 17, and/or 18 from the 5' end of the second nucleotide sequence are 2'-fluoro nucleotides. In some embodiments, the nucleotides at positions 2 and/or 14 from the 5' end of the second nucleotide sequence are 2'-fluoro nucleotides. In some embodiments, the nucleotides at positions 2, 6, and/or 16 from the 5' end of the second nucleotide sequence are 2'-fluoro nucleotides. In some embodiments, the nucleotides at positions 2, 6, 14, and/or 16 from the 5' end of the second nucleotide sequence are 2'-fluoro nucleotides. In some embodiments, the nucleotides at positions 2, 6, 10, 14, and/or 18 from the 5' end of the second nucleotide sequence are 2'-fluoro nucleotides. In some embodiments, the nucleotides at positions 2, 5, 8, 14, and/or 17 from the 5' end of the second nucleotide sequence are 2'-fluoro nucleotides. In some embodiments, the nucleotide at position 2 from the 5' end of the second nucleotide sequence is a 2'-fluoro nucleotide. In some embodiments, the nucleotide at position 5 from the 5' end of the second nucleotide sequence is a 2'-fluoro nucleotide. In some embodiments, the nucleotide at position 6 from the 5' end of the second nucleotide sequence is a 2'-fluoro nucleotide. In some embodiments, the nucleotide at position 8 from the 5' end of the second nucleotide sequence is a 2'-fluoro nucleotide. In some embodiments, the nucleotide at position 10 from the 5' end of the second nucleotide sequence is a 2'-fluoro nucleotide. In some embodiments, the nucleotide at position 14 from the 5' end of the second nucleotide sequence is a 2'-fluoro nucleotide. In some embodiments, the nucleotide at position 16 from the 5' end of the second nucleotide sequence is a 2'-fluoro nucleotide. In some embodiments, the nucleotide at position 17 from the 5' end of the second nucleotide sequence is a 2'-fluoro nucleotide. In some embodiments, the nucleotide at position 18 from the 5' end of the second nucleotide sequence is a 2'-fluoro nucleotide. In some embodiments, the 2'-fluoro nucleotide is a 2'-fluoro nucleotide mimic.

In some embodiments, the nucleotides in the second nucleotide sequence are arranged in an alternating 1:3 modification pattern, wherein 1 nucleotide is a 2'-fluoro nucleotide and 3 nucleotides are 2'-O-methyl nucleotides, and wherein the alternating 1:3 modification pattern occurs at least 2 times. In some embodiments, the alternating 1:3 modification pattern occurs 2-5 times. In some embodiments, at least two of the alternating 1:3 modification pattern occur consecutively. In some embodiments, at least two of the alternating 1:3 modification pattern occurs nonconsecutively. In some embodiments, at least 1, 2, 3, 4, or 5 alternating 1:3 modification pattern begins at nucleotide position 2, 6, 10, 14, and/or 18 from the 5' end of the antisense strand. In some embodiments, at least one alternating 1:3 modification pattern begins at nucleotide position 2 from the 5' end of the antisense strand. In some embodiments, wherein at least one alternating 1:3 modification pattern begins at nucleotide position 6 from the 5' end of the antisense strand. In some embodiments, at least one alternating 1:3 modification pattern begins at nucleotide position 10 from the 5' end of the antisense strand. In some embodiments, at least one alternating 1:3 modification pattern begins at nucleotide position 14 from the 5' end of the antisense strand. In some embodiments, at least one alternating 1:3 modification pattern begins at nucleotide position 18 from the 5' end of the antisense strand. In some embodiments, the 2'-fluoro nucleotide is a 2'-fluoro nucleotide mimic.

In some embodiments, the nucleotides in the second nucleotide sequence are arranged in an alternating 1:2 modification pattern, wherein 1 nucleotide is a 2'-fluoro nucleotide and 2 nucleotides are 2'-O-methyl nucleotides, and wherein the alternating 1:2 modification pattern occurs at least 2 times. In some embodiments, the alternating 1:2 modification pattern occurs 2-5 times. In some embodiments, at least two of the alternating 1:2 modification pattern occurs consecutively. In some embodiments, at least two of the alternating 1:2 modification pattern occurs nonconsecutively. In some embodiments, at least 1, 2, 3, 4, or 5 alternating 1:2 modification pattern begins at nucleotide position 2, 5, 8, 14, and/or 17 from the 5' end of the antisense strand. In some embodiments, at least one alternating 1:2 modification pattern begins at nucleotide position 2 from the 5' end of the antisense strand. In some embodiments, at least one alternating 1:2 modification pattern begins at nucleotide position 5 from the 5' end of the antisense strand. In some embodiments, at least one alternating 1:2 modification pattern begins at nucleotide position 8 from the 5' end of the antisense strand. In some embodiments, at least one alternating 1:2 modification pattern begins at nucleotide position 14 from the 5' end of the antisense strand. In some embodiments, at least one alternating 1:2 modification pattern begins at nucleotide position 17 from the 5' end of the antisense strand. In some embodiments, the 2'-fluoro nucleotide is a 2'-fluoro nucleotide mimic.

In some embodiments, the second nucleotide sequence comprises, consists of, or consists essentially of ribonucleic acids (RNAs). In some embodiments, the second nucleotide sequence comprises, consists of, or consists essentially of modified RNAs. In some embodiments, the modified RNAs are selected from a 2'-O-methyl RNA and 2'-fluoro RNA. In some embodiments, 15, 16, 17, 18, 19, 20, 21, 22, or 23 modified nucleotides of the second nucleotide sequence are independently selected from 2'-O-methyl RNA and 2'-fluoro RNA. In some embodiments, the 2'-fluoro nucleotide is a 2'-fluoro nucleotide mimic.

In some embodiments, the sense strand may further comprise one or more internucleoside linkages independently selected from a phosphodiester (PO) internucleoside linkage, phosphorothioate (PS) internucleoside linkage, phosphorodithioate internucleoside linkage, and PS-mimic internucleoside linkage. In some embodiments, the PS-mimic internucleoside linkage is a sulfo internucleoside linkage.

In some embodiments, the antisense strand may further comprise at least 1, 2, 3, 4, 5, 6, 7, 8, 9, 10, 11, 12, 13, 14, or 15 or more phosphorothioate internucleoside linkages. In some embodiments, the antisense strand comprises 20, 19, 18, 17, 16, 15, 14, 13, 12, 11, 10, 9, 8, 7, 6, 5, 4, or 3 or fewer phosphorothioate internucleoside linkages. In some embodiments, the antisense strand comprises 2 to 10, 2 to 8, 2 to 6, 1 to 5, 1 to 4, 1 to 3, or 1 to 2 phosphorothioate internucleoside linkages. In some embodiments, the antisense strand comprises 2 to 10, 2 to 8, 2 to 6, 1 to 5, 1 to 4, 1 to 3, or 1 to 2 phosphorothioate internucleoside linkages. In some embodiments, the antisense strand comprises 2 to 8 phosphorothioate internucleoside linkages. In some embodiments, the antisense strand comprises 3 to 8 phosphorothioate internucleoside linkages. In some embodiments, the antisense strand comprises 4 to 8 phosphorothioate internucleoside linkages. In some embodiments, at least one phosphorothioate internucleoside linkage is between the nucleotides at positions 1 and 2 from the 5' end of the second nucleotide sequence. In some embodiments, at least one phosphorothioate internucleoside linkage is between the nucleotides at positions 2 and 3 from the 5' end of the second nucleotide sequence. In some embodiments, at least one phosphorothioate internucleoside linkage is between the nucleotides at positions 1 and 2 from the 3' end of the second nucleotide sequence. In some embodiments, at least one phosphorothioate internucleoside linkage is between the nucleotides at positions 2 and 3 from the 3' end of the second nucleotide sequence. In some embodiments, the antisense strand comprises two phosphorothioate internucleoside linkages between the nucleotides at positions 1 to 3 from the 5' end of the first nucleotide sequence. In some embodiments, the antisense strand comprises two phosphorothioate internucleoside linkages between the nucleotides at positions 1 to 3 from the 3' end of the first nucleotide sequence. In some embodiments, the antisense strand comprises (a) two phosphorothioate internucleoside linkages between the nucleotides at positions 1 to 3 from the 5' end of the first nucleotide sequence; and (b) two phosphorothioate internucleoside linkages between the nucleotides at positions 1 to 3 from the 3' end of the first nucleotide sequence.

In some embodiments, the antisense strand may further comprise at least 1, 2, 3, 4, 5, 6, 7, 8, 9, 10, 11, 12, 13, 14, or 15 or more mesyl phosphoramidate internucleoside linkages. In some embodiments, the antisense strand comprises 20, 19, 18, 17, 16, 15, 14, 13, 12, 11, 10, 9, 8, 7, 6, 5, 4, or 3 or fewer mesyl phosphoramidate internucleoside linkages. In some embodiments, the antisense strand comprises 2 to 10, 2 to 8, 2 to 6, 1 to 5, 1 to 4, 1 to 3, or 1 to 2 mesyl phosphoramidate internucleoside linkages. In some embodiments, the antisense strand comprises 2 to 10, 2 to 8, 2 to 6, 1 to 5, 1 to 4, 1 to 3, or 1 to 2 mesyl phosphoramidate internucleoside linkages. In some embodiments, the antisense strand comprises 2 to 8 mesyl phosphoramidate internucleoside linkages. In some embodiments, the antisense strand comprises 3 to 8 mesyl phosphoramidate internucleoside linkages. In some embodiments, the antisense strand comprises 4 to 8 mesyl phosphoramidate internucleoside linkages.

In some embodiments, at least one end of the ds-siNA is a blunt end. In some embodiments, at least one end of the ds-siNA comprises an overhang, wherein the overhang comprises at least one nucleotide. In some embodiments, both ends of the ds-siNA comprise an overhang, wherein the overhang comprises at least one nucleotide. In some embodiments, the overhang comprises 1 to 5 nucleotides, 1 to 4 nucleotides, 1 to 3 nucleotides, or 1 to 2 nucleotides. In some embodiments, the overhang consists of 1 to 2 nucleotides.

In some embodiments, the sense strand may comprise any of the modified nucleotides disclosed in the sub-section titled “Modified Nucleotides” below. In some embodiments, the sense strand may comprise a 5'-stabilized end cap, and the 5'-stabilized end cap may be selected from those disclosed in the sub-section titled “5'-Stabilized End Cap” below.

Modified Nucleotides

The siNA molecules disclosed herein comprise one or more modified nucleotides. In some embodiments, the sense strands disclosed herein comprise one or more modified nucleotides. In some embodiments, any of the first nucleotide sequences disclosed herein comprise one or more modified nucleotides. In some embodiments, the antisense strands disclosed herein comprise one or more modified nucleotides. In some embodiments, any of the second nucleotide sequences disclosed herein comprise one or more modified nucleotides. In some embodiments, the one or more modified nucleotides is adjacent to the first nucleotide sequence. In some embodiments, at least one modified nucleotide is adjacent to the 5' end of the first nucleotide sequence. In some embodiments, at least one modified nucleotide is adjacent to the 3' end of the first nucleotide sequence. In some embodiments, at least one modified nucleotide is adjacent to the 5' end of the first nucleotide sequence and at least one modified nucleotide is adjacent to the 3' end of the first nucleotide sequence. In some embodiments, the one or more modified nucleotides is adjacent to the second nucleotide sequence. In some embodiments, at least one modified nucleotide is adjacent to the 5' end of the second nucleotide sequence. In some embodiments, at least one modified nucleotide is adjacent to the 3' end of the second nucleotide sequence. In some embodiments, at least one modified nucleotide is adjacent to the 5' end of the second nucleotide sequence and at least one modified nucleotide is adjacent to the 3' end of the second nucleotide sequence. In some embodiments, a 2'-O-methyl nucleotide in any of sense strands or first nucleotide sequences disclosed herein is replaced with a modified nucleotide. In some embodiments, a 2'-O-methyl nucleotide in any of antisense strands or second nucleotide sequences disclosed herein is replaced with a modified nucleotide.

In some embodiments, any of the siNA molecules, siNAs, sense strands, first nucleotide sequences, antisense strands, and second nucleotide sequences disclosed herein comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more modified nucleotides. In some embodiments, 1%, 2%, 3%, 4%, 5%, 10%, 15%, 20%, 25%, 30%, 35%, 40%, 45%, 50%, 55%, 60%, 70%, 75%, 80%, 85%, 86%, 87%, 88%, 90%, 91%, 92%, 93%, 94%, 95%, 96%, 97%, 98%, 99% or 100% of the nucleotides in the siNA molecule, siNA, sense strand, first nucleotide sequence, antisense strand, or second nucleotide sequence are modified nucleotides.

In some embodiments, a modified nucleotide is selected from the group consisting of 2'-fluoro nucleotide, 2'-O-methyl nucleotide, 2'-fluoro nucleotide mimic, 2'-O-methyl nucleotide mimic, a locked nucleic acid, an unlocked nucleic acid, and a nucleotide comprising a modified nucleobase. In some embodiments, the unlocked nucleic acid is a 2',3'-unlocked nucleic acid. In some embodiments, the unlocked nucleic acid is a 3',4'-unlocked nucleic acid (e.g., mun34) in which the furanose ring lacks a bond between the 3' and 4; carbons.

In some aspects, the siNA of the present disclosure will comprise at least one modified nucleotide selected from:

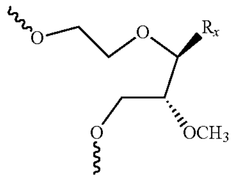

(wherein Rx is a nucleobase, aryl, heteroaryl, or H),

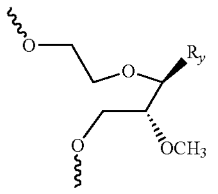

(mun34)

wherein $R_y$ is a nucleobase,

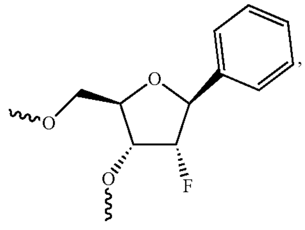, (fB)

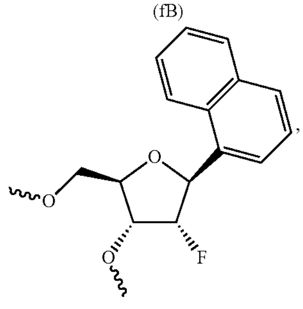, (fN)

-continued

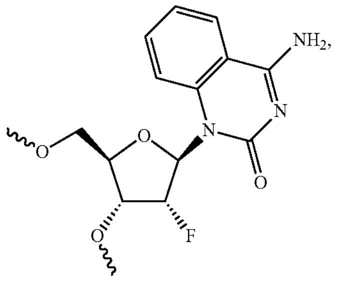

and (F(4nh)Q)

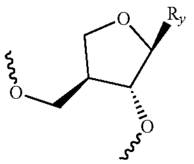

(apN)

wherein $R_y$ is a nucleobase, or combinations thereof. In some embodiments, the siNA may comprise at least 2, at least 3, at least 4, or at least 5 or more of these modified nucleotides. In some embodiments, the sense strand may comprise at least 1, at least 2, at least 3, at least 4, or at least 5 or more of

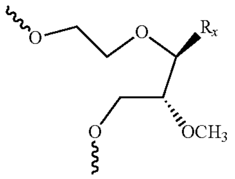

(wherein Rx is a nucleobase, aryl, heteroaryl, H),

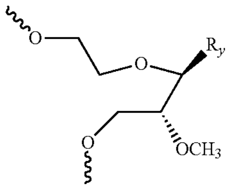

(mun34)

wherein $R_y$ is a nucleobase,

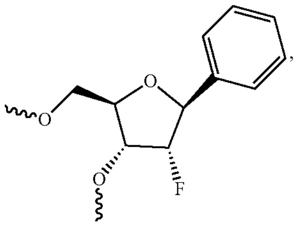

(fB)

-continued

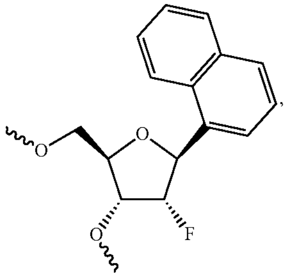

(fN)

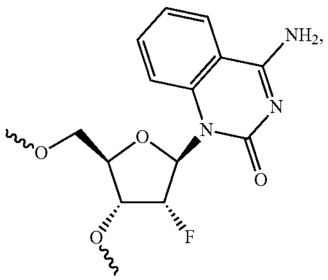

or (f(4nh)Q)

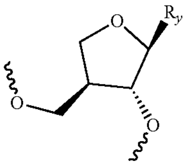

(apN)

wherein $R_y$ is a nucleobase, or combinations thereof. In some embodiments, the antisense strand may comprise at least 1, at least 2, at least 3, at least 4, or at least 5 or more of

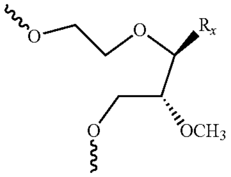

(wherein Rx is a nucleobase, aryl, heteroaryl, or H),

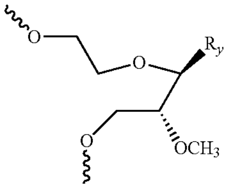

(mun34)

wherein $R_y$ is a nucleobase

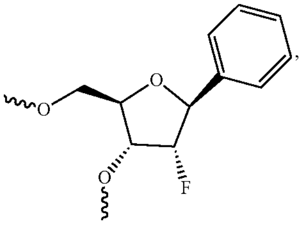

(fB)

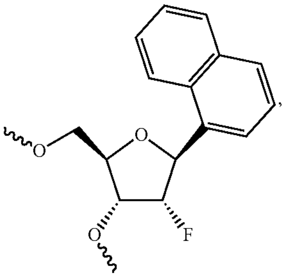

(fN)

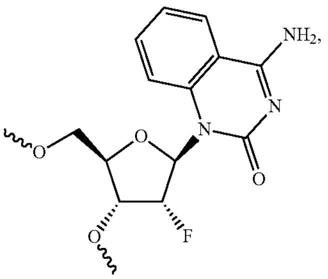 or (f(4nh)Q)

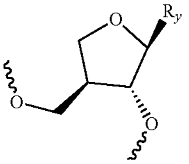

(apN)

wherein $R_y$ is a nucleobase, or combinations thereof. In some embodiments, both the sense strand and the antisense strand may each independently comprise at least 1, at least 2, at least 3, at least 4, or at least 5 or more of

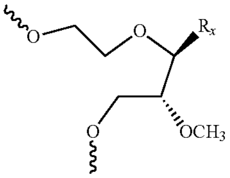

(wherein $R_x$ is a nucleobase, aryl, heteroaryl, or H)

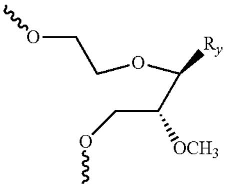

(mun34)

wherein $R_y$ is a nucleobase,

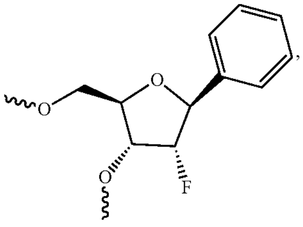

(fB)

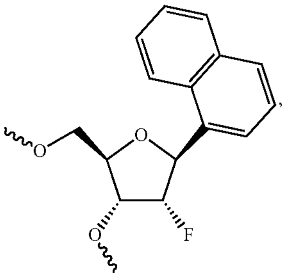

(fN)

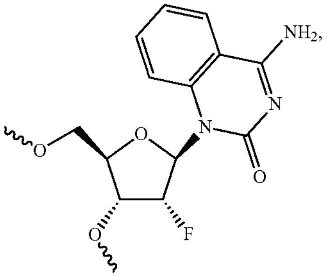 or (F(4nh)Q)

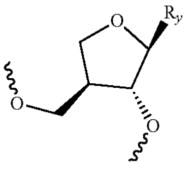

(apN)

wherein $R_y$ is a nucleobase, or combinations thereof. In some embodiments, the nucleobase is selected from thymine, cytosine, guanine, adenine, uracil, and an analogue or derivative thereof. For example, in some embodiments of

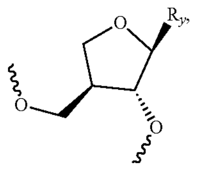

(apN)

the modified nucleotide may have a structure of

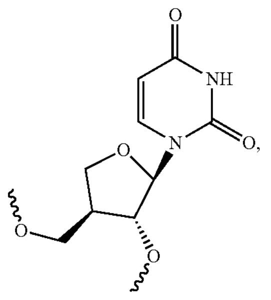

(apU)

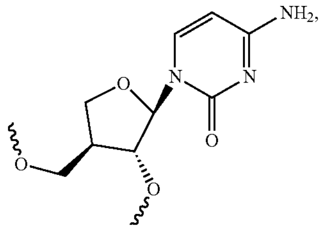

(apC)

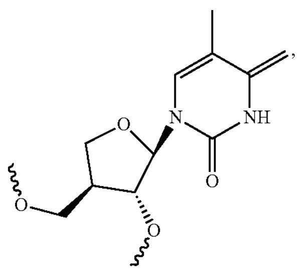

(apT)

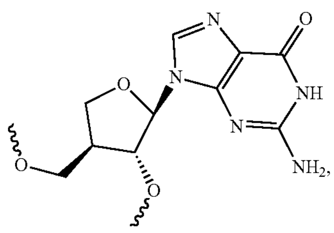

or (apG)

-continued

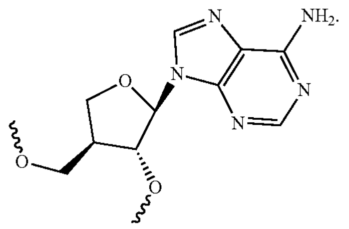

(apA)

In some embodiments, any of the siRNAs disclosed herein may additionally comprise other modified nucleotides, such as 2'-fluoro or 2'-O-methyl nucleotide mimics. For example, the disclosed siNA may comprise at least 1, 2, 3, 4, 5, 6, 7, 8, 9, or 10 or more 2'-fluoro or 2'-O-methyl nucleotide mimics. In some embodiments, any of the sense strands disclosed herein comprise at least 1, 2, 3, 4, 5, 6, 7, 8, 9, or 10 or more 2'-fluoro or 2'-O-methyl nucleotide mimics. In some embodiments, any of the first nucleotide sequences disclosed herein comprise at least 1, 2, 3, 4, 5, 6, 7, 8, 9, or 10 or more 2'-fluoro or 2'-O-methyl nucleotide mimics. In some embodiments, any of the antisense strand disclosed herein comprise at least 1, 2, 3, 4, 5, 6, 7, 8, 9, or 10 or more 2'-fluoro or 2'-O-methyl nucleotide mimics. In some embodiments, any of the second nucleotide sequences disclosed herein comprise at least 1, 2, 3, 4, 5, 6, 7, 8, 9, or 10 or more 2'-fluoro or 2'-O-methyl nucleotide mimics. In some embodiments, the 2'-fluoro or 2'-O-methyl nucleotide mimic is a nucleotide mimic of Formula (16)-Formula (20):

Formula (16)

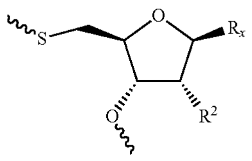

Formula (17)

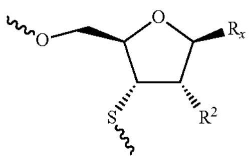

Formula (18)

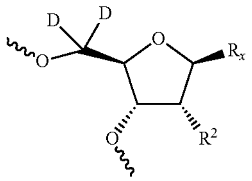

Formula (19)

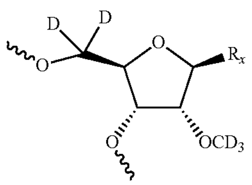

-continued

Formula (20)

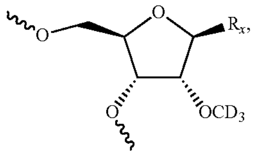

wherein $R_x$ is a nucleobase, aryl, heteroaryl, or H and $R^2$ is independently F or —$OCH_3$. In some embodiments, the nucleobase is selected from thymine, cytosine, guanine, adenine, uracil, and an analogue or derivative thereof.

In some embodiments, the siNA molecules disclosed herein comprise at least one 2'-fluoro nucleotide, at least one 2'-O-methyl nucleotide, and at least one 2'-fluoro or 2'-O-methyl nucleotide mimic. In some embodiments, the at least one 2'-fluoro or 2'-O-methyl nucleotide mimic is adjacent to the first nucleotide sequence. In some embodiments, the at least one 2'-fluoro or 2'-O-methyl nucleotide mimic is adjacent to the 5' end of first nucleotide sequence. In some embodiments, the at least one 2'-fluoro or 2'-O-methyl nucleotide mimic is adjacent to the 3' end of first nucleotide sequence. In some embodiments, the at least one 2'-fluoro or 2'-O-methyl nucleotide mimic is adjacent to the second nucleotide sequence. In some embodiments, the at least one 2'-fluoro or 2'-O-methyl nucleotide mimic is adjacent to the 5' end of second nucleotide sequence. In some embodiments, the at least one 2'-fluoro or 2'-O-methyl nucleotide mimic is adjacent to the 3' end of second nucleotide sequence. In some embodiments, the first nucleotide sequence does not comprise a 2'-fluoro nucleotide mimic. In some embodiments, the first nucleotide sequence does not comprise a 2'-O-methyl nucleotide mimic. In some embodiments, the second nucleotide sequence does not comprise a 2'-fluoro nucleotide mimic. In some embodiments, the second nucleotide sequence does not comprise a 2'-O-methyl nucleotide mimic.

In some embodiments, any of the siRNAs, sense strands, first nucleotide sequences, antisense strands, or second nucleotide sequences disclosed herein comprise at least one modified nucleotide that is

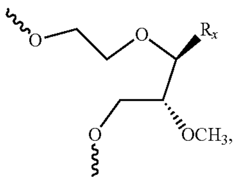

wherein Rx is a nucleobase, aryl, heteroaryl, or H; or

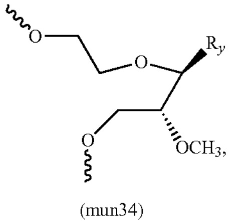

(mun34)

wherein $R_y$ is a nucleobase.

Phosphorylation Blocker

Further disclosed herein are siNA molecules comprising a phosphorylation blocker. In some embodiments, a 2'-O-methyl nucleotide in any of sense strands or first nucleotide sequences disclosed herein is replaced with a nucleotide containing a phosphorylation blocker. In some embodiments, a 2'-O-methyl nucleotide in any of antisense strands or second nucleotide sequences disclosed herein is replaced with a nucleotide containing a phosphorylation blocker. In some embodiments, a 2'-O-methyl nucleotide in any of sense strands or first nucleotide sequences disclosed herein is further modified to contain a phosphorylation blocker. In some embodiments, a 2'-O-methyl nucleotide in any of antisense strands or second nucleotide sequences disclosed herein is further modified to contain a phosphorylation blocker.

In some embodiments, any of the siNA molecules disclosed herein comprise a phosphorylation blocker of Formula (IV):

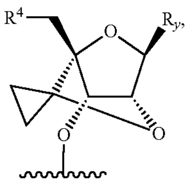

wherein $R_y$ is a nucleobase, $R^4$ is —O—$R^{30}$ or —$NR^{31}R^{32}$, $R^{30}$ is $C_1$-$C_8$ substituted or unsubstituted alkyl; and $R^{31}$ and $R^{32}$ together with the nitrogen to which they are attached form a substituted or unsubstituted heterocyclic ring. In some embodiments, the nucleobase is selected from thymine, cytosine, guanine, adenine, uracil, and an analogue or derivative thereof.

In some embodiments, any of the siNA molecules disclosed herein comprise a phosphorylation blocker of Formula (IV):

Formula (IV)

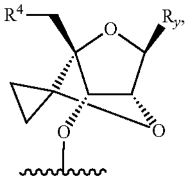

wherein $R_y$ is a nucleobase, and $R^4$ is —$OCH_3$ or —$N(CH_2CH_2)_2O$. In some embodiments, the nucleobase is selected from thymine, cytosine, guanine, adenine, uracil, and an analogue or derivative thereof.

In some embodiments, a siNA molecule comprises (a) a phosphorylation blocker of Formula (IV):

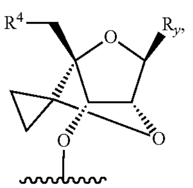

wherein $R_y$ is a nucleobase, $R^4$ is —O—$R^{30}$ or —$NR^{31}R^{32}$, $R^{30}$ is $C_1$-$C_8$ substituted or unsubstituted alkyl; and $R^{31}$ and $R^{32}$ together with the nitrogen to which they are attached form a substituted or unsubstituted heterocyclic ring; and (b) a short interfering nucleic acid (siNA), wherein the phosphorylation blocker is conjugated to the siNA. In some embodiments, the nucleobase is selected from thymine, cytosine, guanine, adenine, uracil, and an analogue or derivative thereof.

In some embodiments, a siNA molecule comprises (a) a phosphorylation blocker of Formula (IV):

Formula (IV)

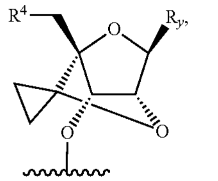

wherein $R_y$ is a nucleobase, and $R^4$ is —$OCH_3$ or —$N(CH_2CH_2)_2O$; and (b) a short interfering nucleic acid (siNA), wherein the phosphorylation blocker is conjugated to the siNA.

In some embodiments, the phosphorylation blocker is attached to the 3' end of the sense strand or first nucleotide sequence. In some embodiments, the phosphorylation blocker is attached to the 3' end of the sense strand or first nucleotide sequence via 1, 2, 3, 4, or 5 or more linkers. In some embodiments, the phosphorylation blocker is attached to the 5' end of the sense strand or first nucleotide sequence. In some embodiments, the phosphorylation blocker is attached to the 5' end of the sense strand or first nucleotide sequence via 1, 2, 3, 4, or 5 or more linkers. In some embodiments, the phosphorylation blocker is attached to the 3' end of the antisense strand or second nucleotide sequence. In some embodiments, the phosphorylation blocker is attached to the 3' end of the antisense strand or second nucleotide sequence via 1, 2, 3, 4, or 5 or more linkers. In some embodiments, the phosphorylation blocker is attached to the 5' end of the antisense strand or second nucleotide sequence. In some embodiments, the phosphorylation blocker is attached to the 5' end of the antisense strand or second nucleotide sequence via 1, 2, 3, 4, or 5 or more linkers. In some embodiments, the one or more linkers are independently selected from the group consisting of a phosphodiester linker, phosphorothioate linker, mesyl phosphoramidate linker and phosphorodithioate linker.

Conjugated Moiety

Further disclosed herein are siNA molecules comprising a conjugated moiety. In some embodiments, the conjugated moiety is selected from galactosamine, peptides, proteins, sterols, lipids, phospholipids, biotin, phenoxazines, active drug substance, cholesterols, phenanthridine, anthraquinone, acridine, fluoresceins, rhodamines, coumarins, and dyes. In some embodiments, the conjugated moiety is attached to the 3' end of the sense strand or first nucleotide sequence. In some embodiments, the conjugated moiety is attached to the 3' end of the sense strand or first nucleotide sequence via 1, 2, 3, 4, or 5 or more linkers. In some embodiments, the conjugated moiety is attached to the 5' end of the sense strand or first nucleotide sequence. In some embodiments, the conjugated moiety is attached to the 5' end of the sense strand or first nucleotide sequence via 1, 2, 3, 4, or 5 or more linkers. In some embodiments, the conjugated moiety is attached to the 3' end of the antisense strand or second nucleotide sequence. In some embodiments, the conjugated moiety is attached to the 3' end of the antisense strand or second nucleotide sequence via 1, 2, 3, 4, or 5 or more linkers. In some embodiments, the conjugated moiety is attached to the 5' end of the antisense strand or second nucleotide sequence. In some embodiments, the conjugated moiety is attached to the 5' end of the antisense strand or second nucleotide sequence via 1, 2, 3, 4, or 5 or more linkers. In some embodiments, the one or more linkers are independently selected from the group consisting of a phosphodiester linker, phosphorothioate linker, phosphorodithioate linker, and mesyl phosphoramidate linker.

In some embodiments, the conjugated moiety is galactosamine. In some embodiments, any of the siNAs disclosed herein are attached to a conjugated moiety that is galactosamine. In some embodiments, the galactosamine is N-acetylgalactosamine (GalNAc). In some embodiments, any of the siNA molecules disclosed herein comprise GalNAc. In some embodiments, the GalNAc is of Formula (VI):

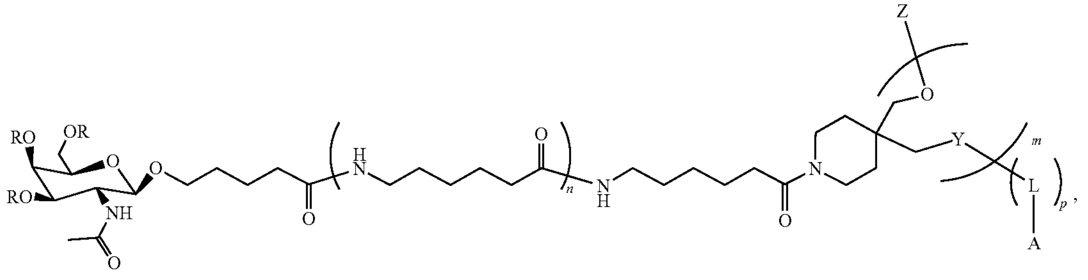

wherein m is 1, 2, 3, 4, or 5; each n is independently 1 or 2; p is 0 or 1; each R is independently H or a first protecting group; each Y is independently selected from —O—P(═O)(SH)—, —O—P(═O)(O)—, —O—P(═O)(OH)—, —O—P(S)S—, and —O—; Z is H or a second protecting group; either L is a linker or L and Y in combination are a linker; and A is H, OH, a third protecting group, an activated group, or an oligonucleotide. In some embodiments, the first protecting group is acetyl. In some embodiments, the second protecting group is trimethoxytrityl (TMT). In some embodiments, the activated group is a phosphoramidite group. In some embodiments, the phosphoramidite group is a cyanoethoxy N,N-diisopropylphosphoramidite group. In some embodiments, the linker is a C6-$NH_2$ group. In some embodiments, A is a short interfering nucleic acid (siNA) or siNA molecule. In some embodiments, m is 3. In some embodiments, R is H, Z is H, and n is 1. In some embodiments, R is H, Z is H, and n is 2.

In some embodiments, the GalNAc is Formula (VII):

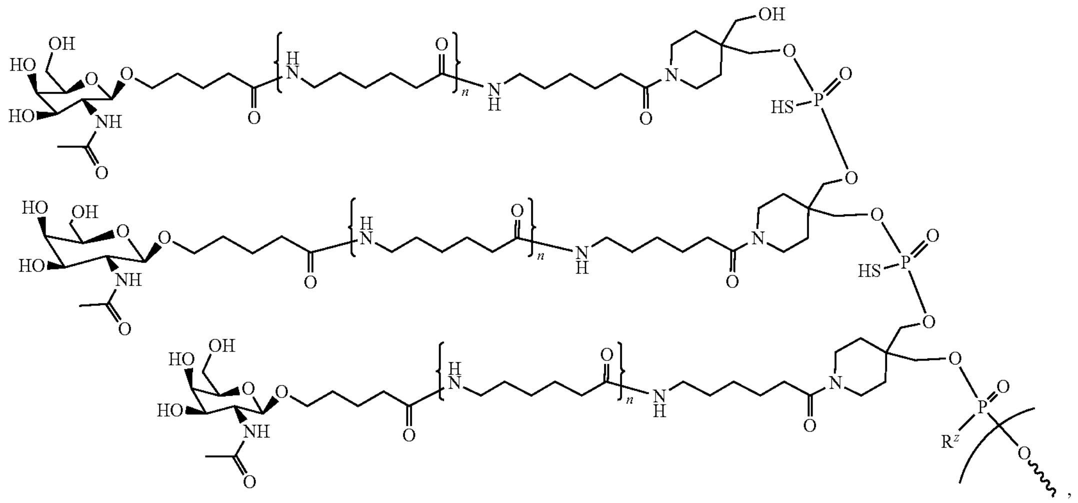

wherein $R^z$ is OH or SH; and each n is independently 1 or 2. In some embodiments, the targeting ligand may be a GalNAc targeting ligand may comprise 1, 2, 3, 4, 5 or 6 GalNAc units. In some embodiments, the targeting ligand may be a GalNAc selected from GalNAc2, GalNAc3, GalNAc4 (the GalNAc of Formula VII, wherein n=1 and $R^z$=OH), GalNAc5, and GalNAc6.

In some embodiments, the GalNAc may be GalNAc amidite (i.e., compound 40-9, see Example 22), GalNAc4 CPG (i.e., compound 40-8, see Example 22 and Example 23), GalNAc phophoramidite, or GalNAc4-ps-GalNAc4-ps-GalNAc4. These GalNAc moieties are shown below:

| GalNAc 4 moieties |
| --- |
| 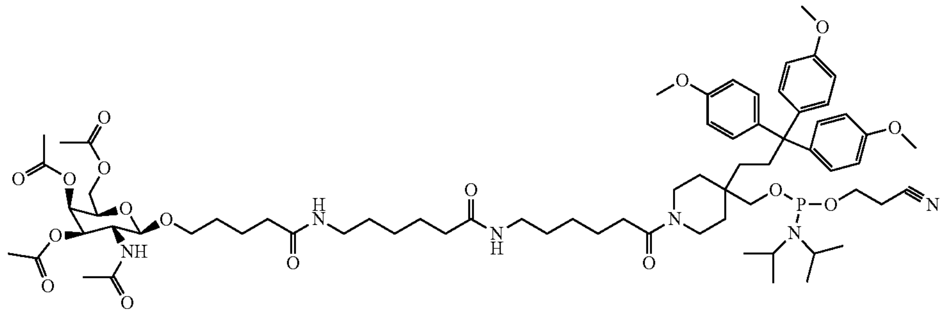 |
| GalNAc4 phosphoramidite |
| 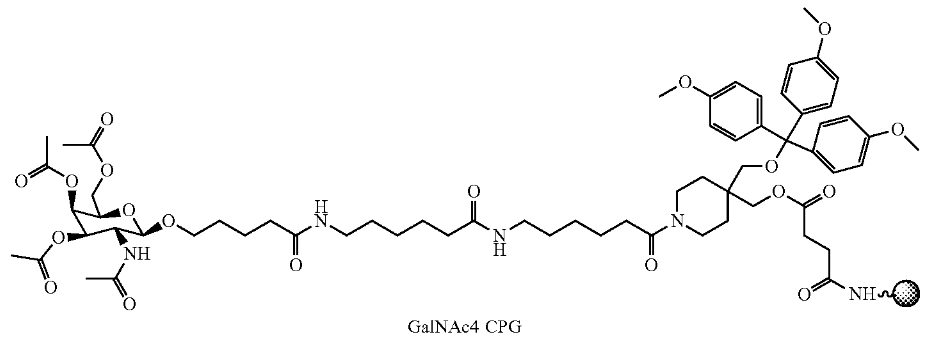 |
| GalNAc4 CPG |

GalNAc3, GalNAc4, GalNAc5 and GalNAc6 may be conjugated to an siNA disclosed herein during synthesis with 1 2, or 3 moieties. Further GalNAc moieties, such as GalNAc1 and GalNAc2, can be used to form 5' and 3'-GalNAc using post synthesis conjugation.

GalNAc Phosphoramidites

GalNAc building blocks

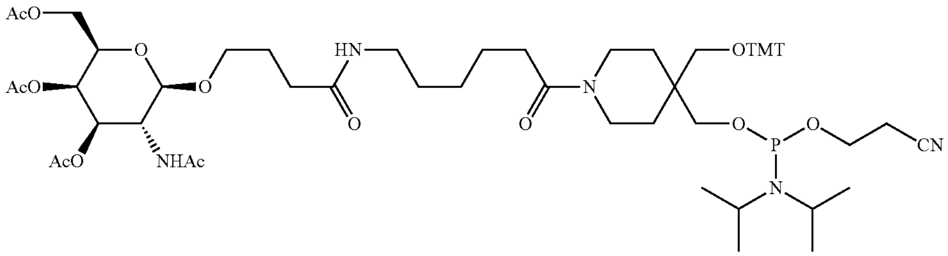

GalNAc-3 phosphoramidite

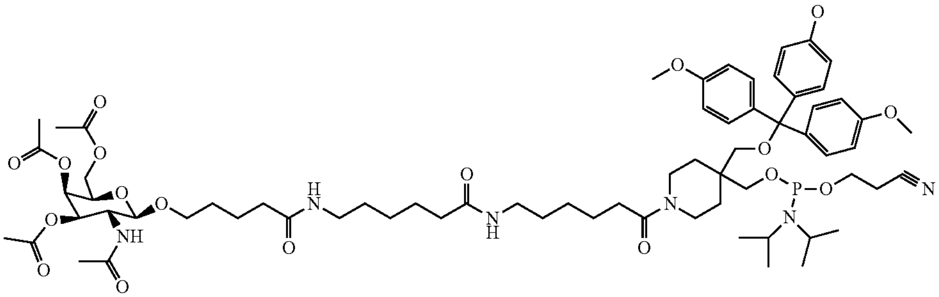

GalNAc-4 phosphoramidite

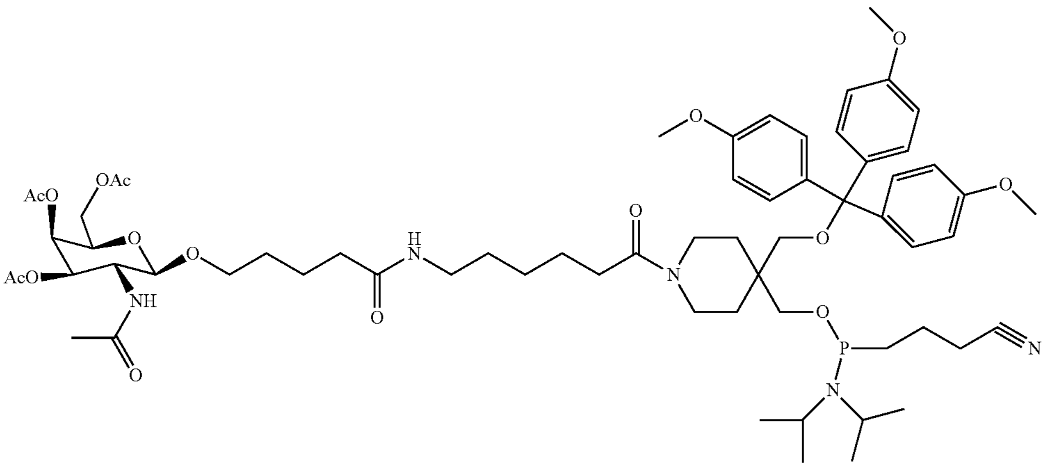

GalNAc-5 phosphoramidite

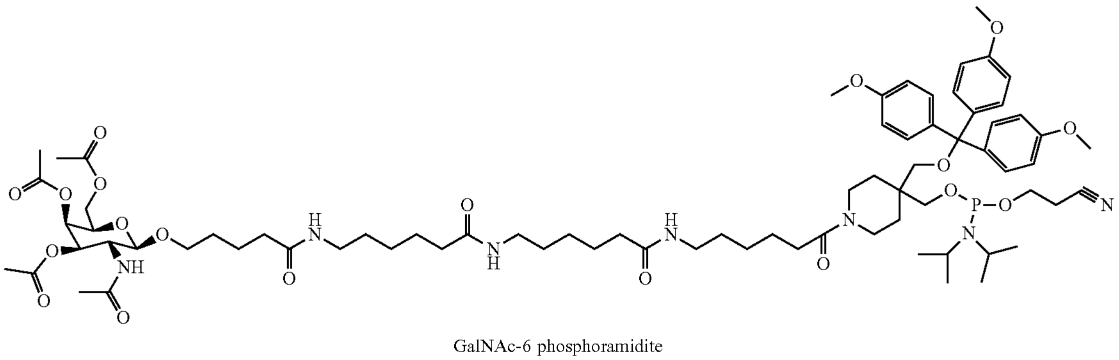

GalNAc-6 phosphoramidite

-continued
| After Attachment to Oligos (Nomenclature) |
| --- |
| 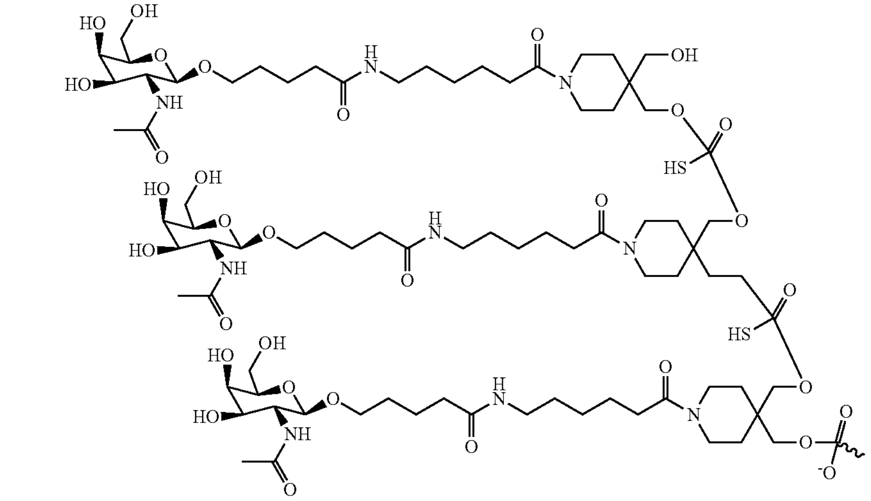 |
| (GalNAc3-(PS)2-p) |
| 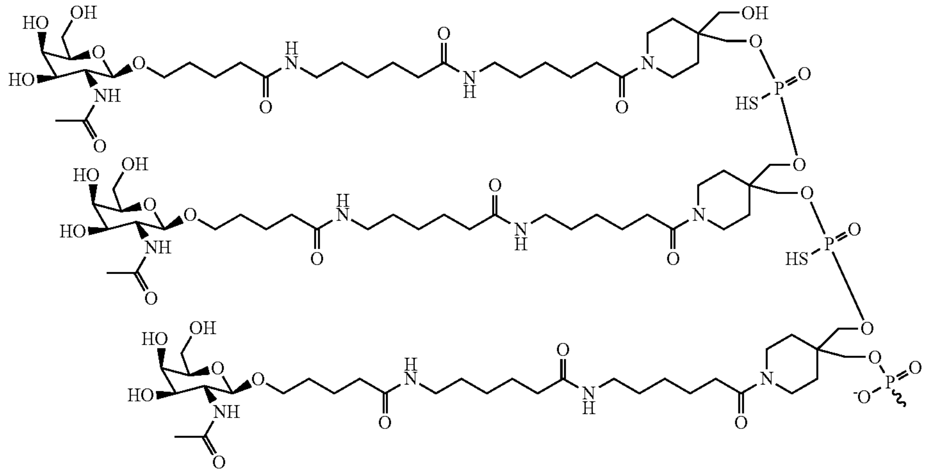 |
| (GalNAc4-(PS)2-p) |
| 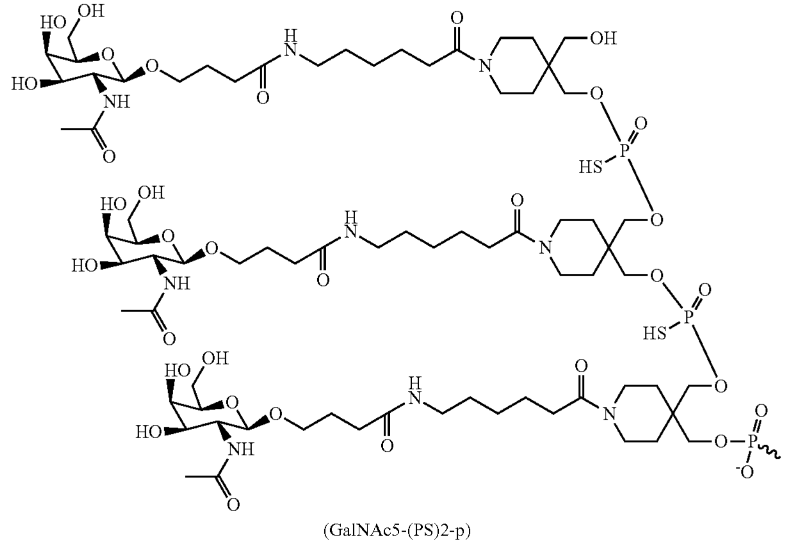 |
| (GalNAc5-(PS)2-p) |

-continued

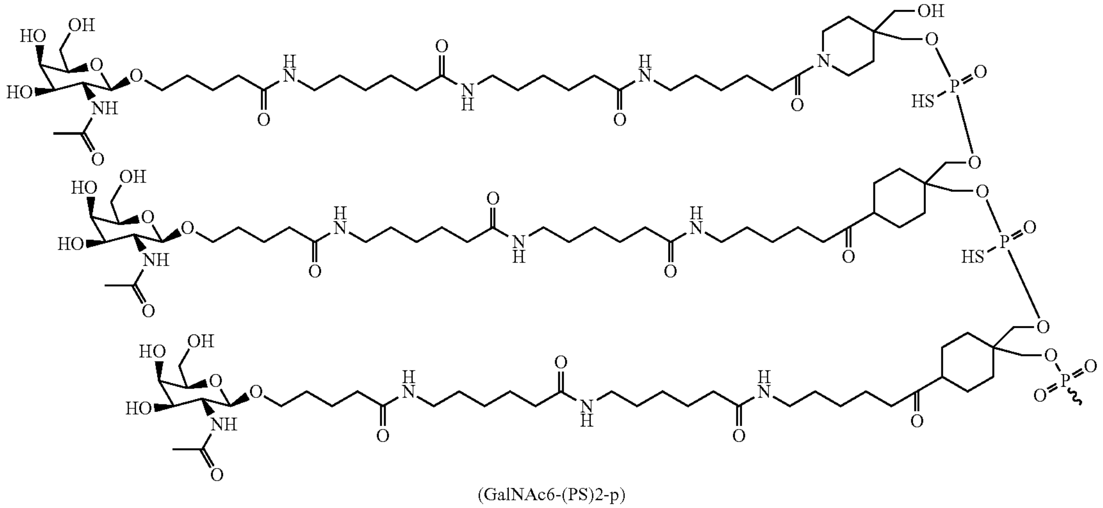

(GalNAc6-(PS)2-p)

In some embodiments, the galactosamine is attached to the 3' end of the sense strand or first nucleotide sequence. In some embodiments, the galactosamine is attached to the 3' end of the sense strand or first nucleotide sequence via 1, 2, 3, 4, or 5 or more linkers. In some embodiments, the galactosamine is attached to the 5' end of the sense strand or first nucleotide sequence. In some embodiments, the galactosamine is attached to the 5' end of the sense strand or first nucleotide sequence via 1, 2, 3, 4, or 5 or more linkers. In some embodiments, the galactosamine is attached to the 3' end of the antisense strand or second nucleotide sequence. In some embodiments, the galactosamine is attached to the 3' end of the antisense strand or second nucleotide sequence via 1, 2, 3, 4, or 5 or more linkers. In some embodiments, the galactosamine is attached to the 5' end of the antisense strand or second nucleotide sequence. In some embodiments, the galactosamine is attached to the 5' end of the antisense strand or second nucleotide sequence via 1, 2, 3, 4, or 5 or more linkers. In some embodiments, the one or more linkers are independently selected from the group consisting of a phosphodiester (p or po) linker, phosphorothioate (ps) linker, mesyl phosphoramidate linker (Ms), phosphoramidite (HEG) linker, triethylene glycol (TEG) linker, and/or phosphorodithioate linker. In some embodiments, the one or more linkers are independently selected from the group consisting of p-(PS)2, (PS)2-p-TEG-p, (PS)2-p-HEG-p, and (PS)2-p-(HEG-p)2.

In some embodiments, the conjugated moiety is a lipid moiety. In some embodiments, any of the siNAs disclosed herein are attached to a conjugated moiety that is a lipid moiety. Examples of lipid moieties include, but are not limited to, a cholesterol moiety, a thioether, e.g., hexyl-S-tritylthiol, a thiocholesterol, an aliphatic chain, e.g., dodecandiol or undecyl residues a phospholipid, e.g., di-hexadecyl-rac-glycerol or triethylammonium 1-di-O-hexadecyl-rac-glycero-S—H-phosphonate, a polyamine or a polyethylene glycol chain, adamantane acetic acid, a palmityl moiety, or an octadecylamine or hexylamino-carbonyl-oxycholesterol moiety.

In some embodiments, the conjugated moiety is an active drug substance. In some embodiments, any of the siNAs disclosed herein are attached to a conjugated moiety that is an active drug substance. Examples of active drug substances include, but are not limited to, aspirin, warfarin, phenylbutazone, ibuprofen, suprofen, fenbufen, ketoprofen, (5)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

5'-Stabilized End Cap

Further disclosed herein are siNA molecules comprising a 5'-stabilized end cap. As used herein the terms "5'-stabilized end cap" and "5' end cap" are used interchangeably. In some embodiments, a 2'-O-methyl nucleotide in any of sense strands or first nucleotide sequences disclosed herein is replaced with a nucleotide containing a 5'-stabilized end cap. In some embodiments, a 2'-O-methyl nucleotide in any of antisense strands or second nucleotide sequences disclosed herein is replaced with a nucleotide containing a 5'-stabilized end cap. In some embodiments, a 2'-O-methyl nucleotide in any of sense strands or first nucleotide sequences disclosed herein is further modified to contain a 5'-stabilized end cap. In some embodiments, a 2'-O-methyl nucleotide in any of antisense strands or second nucleotide sequences disclosed herein is further modified to contain a 5'-stabilized end cap.

In some embodiments, the 5'-stabilized end cap is a 5' phosphate mimic. In some embodiments, the 5'-stabilized end cap is a modified 5' phosphate mimic. In some embodiments, the modified 5' phosphate is a chemically modified 5' phosphate. In some embodiments, the 5'-stabilized end cap is a 5'-vinyl phosphonate. In some embodiments, the 5'-vinyl phosphonate is a 5'-(E)-vinyl phosphonate or 5'-(Z)-vinyl phosphonate. In some embodiments, the 5'-vinyl phosphonate is a deuterated vinyl phosphonate. In some embodiments, the deuterated vinyl phosphonate is a mono-deuterated vinyl phosphonate. In some embodiments, the deuterated vinyl phosphonate is a di-deuterated vinyl phosphonate. In some embodiments, the 5'-stabilized end cap is a phosphate mimic. Examples of phosphate mimics are disclosed in Parmar et al., *J Med Chem,* 201861(3):734-744, International Publication Nos. WO2018/045317 and WO2018/044350, and U.S. Pat. No. 10,087,210, each of which is incorporated by reference in its entirety.

In some aspects, the present disclosure provides siNA comprising a nucleotide phosphate mimic selected from:

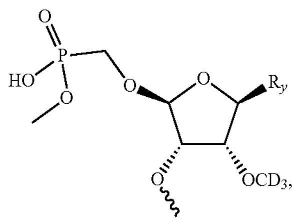

(omeco-d3 nucleotide)

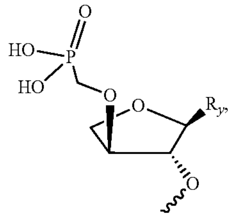

(4h nucleotide)

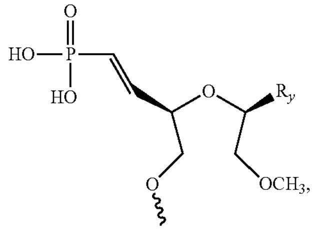

(v-mun nucleotide)

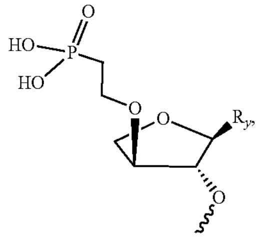

(c2o-4h nucleotide)

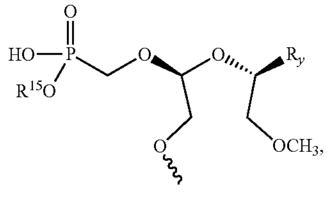

(omceo-mun*enantiomer1)

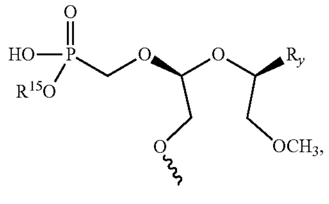

(omceo-mun*enantiomer2)

-continued

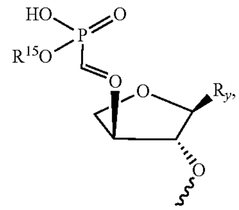

and (4h=vp nucleotide)

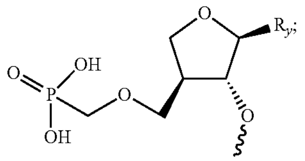

(coc-4h nucleotide)

wherein $R_y$ is a nucleobase and $R^{15}$ is H or $CH_3$. In some embodiments, the nucleobase is selected from thymine, cytosine, guanine, adenine, uracil, and an analogue or derivative thereof. In some embodiments, the disclosed nucleotide phosphate mimics include, but are not limited to, the structures:

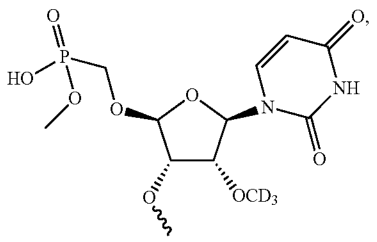

(omeco-d3U)

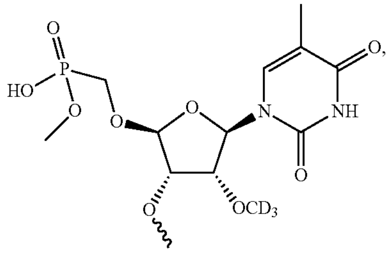

(omeco-d3T)

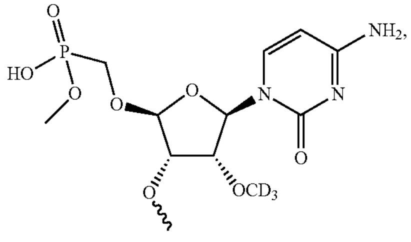

(omeco-d3C)

-continued
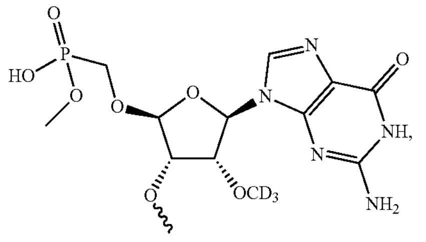
(omeco-d3G)
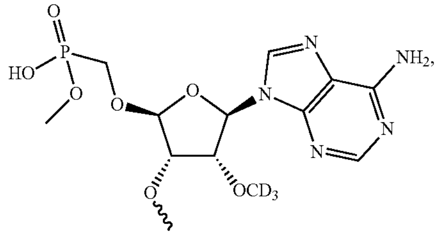
(omeco-d3A)
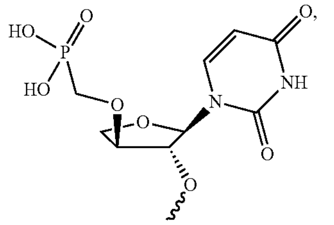
(4hU)
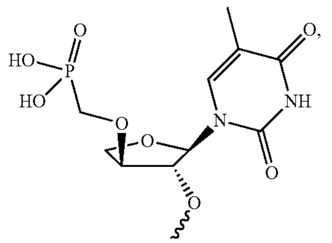
(4hT)
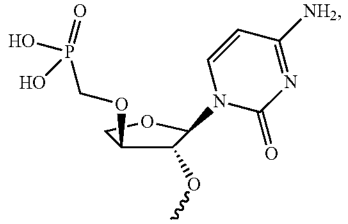
(4hC)
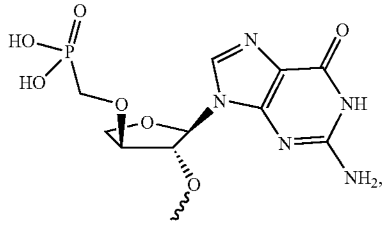
(4hG)
-continued
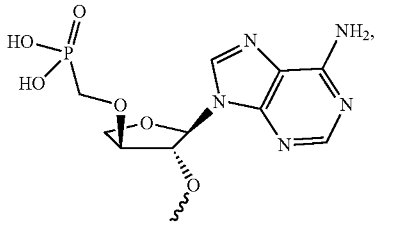
(4hA)
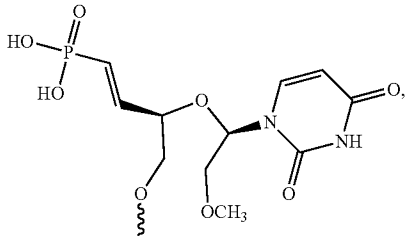
(v-munU)
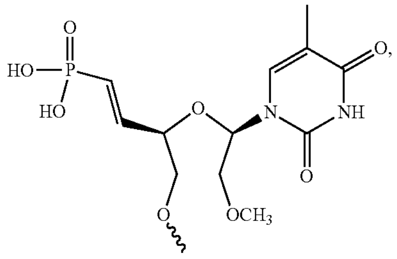
(v-munT)
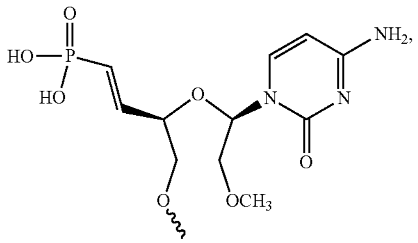
(v-munC)
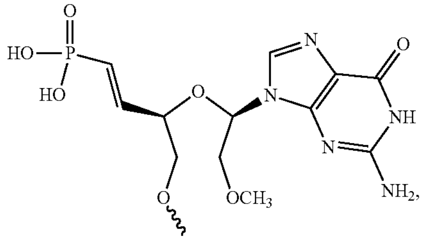
(v-munG)
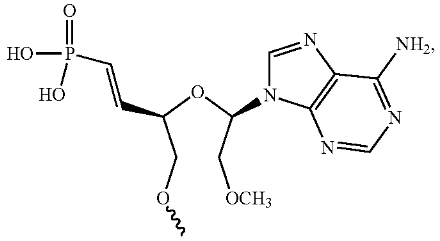
(v-munA)

-continued
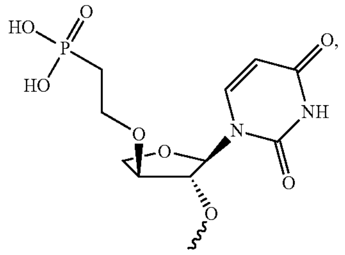
(c2o-4hU)
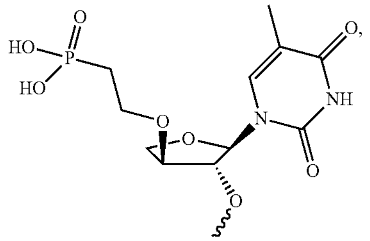
(c2o-4hT)
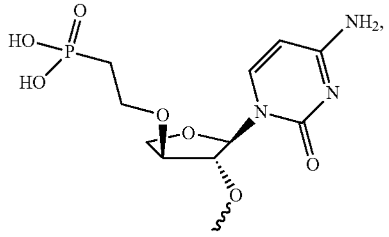
(c2o-4hC)
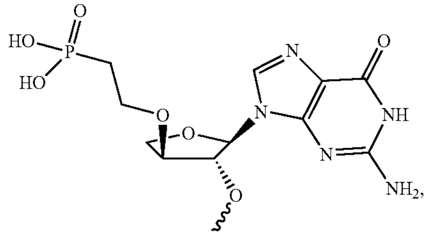
(c2o-4hG)
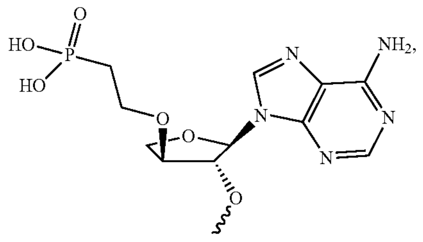
(c2o-4hA)
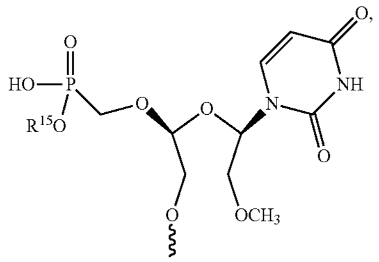
(omeco-munU)
-continued
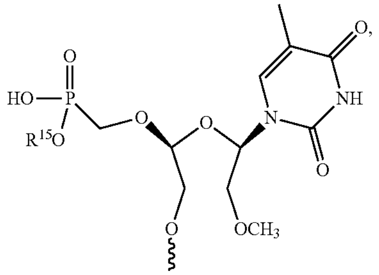
(omeco-munT)
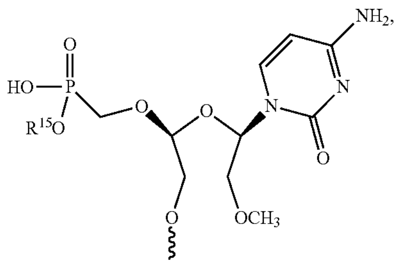
(omeco-munC)
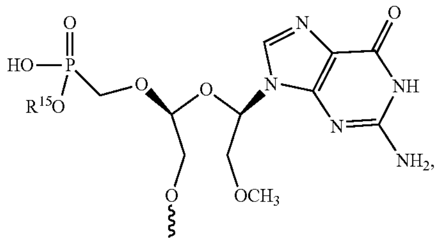
(omeco-munG)
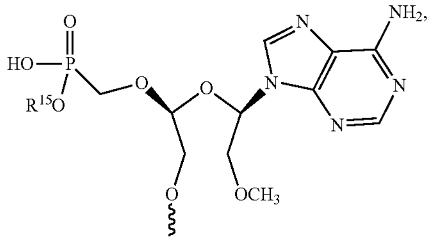
(omeco-munA)
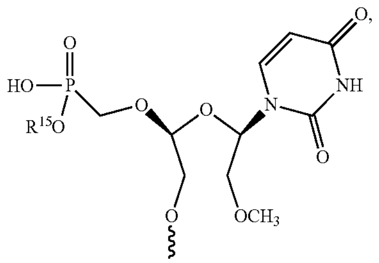
(omeco-munU)

-continued
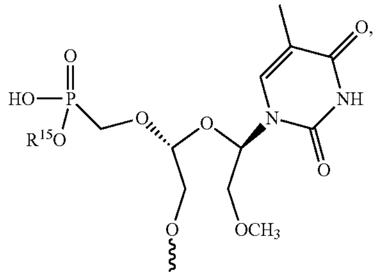
(omeco-munT)
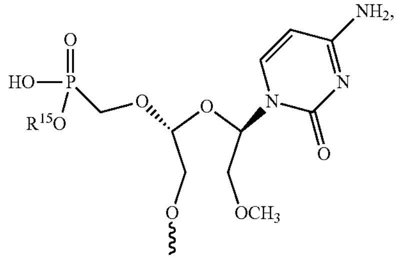
(omeco-munC)
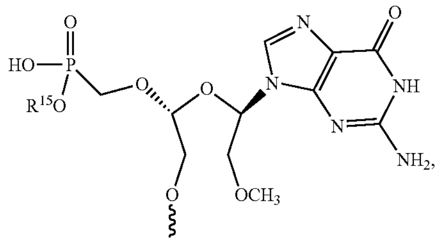
(omeco-munG)
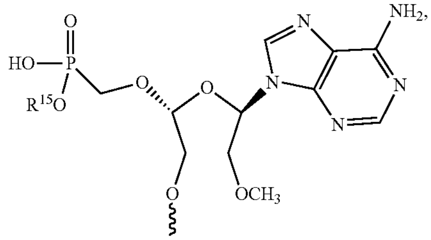
(omeco-munA)
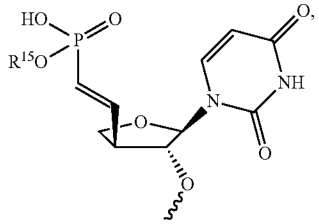
(4h-vp-U)
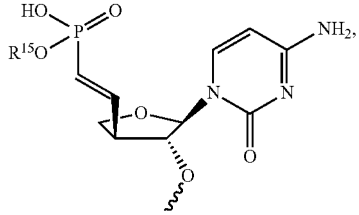
(4h-vp-C)
-continued
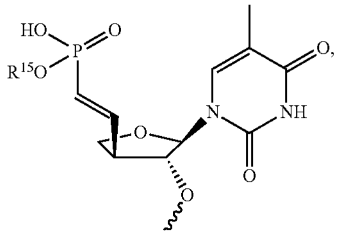
(4h-vp-T)
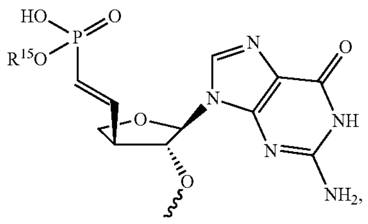
(4h-vp-G)
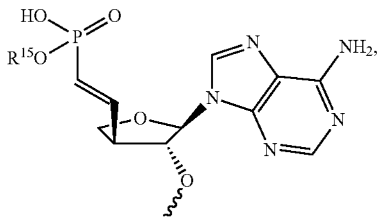
(4h-vp-A)
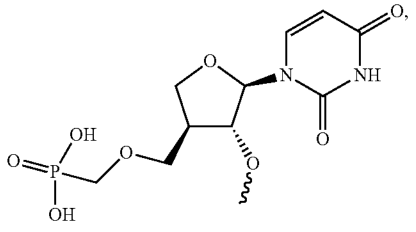
(coc-4hU)
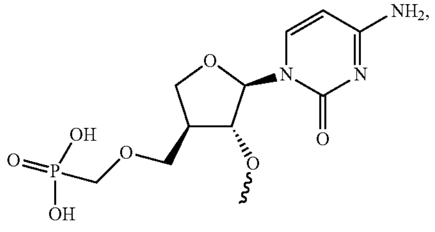
(coc-4hC)
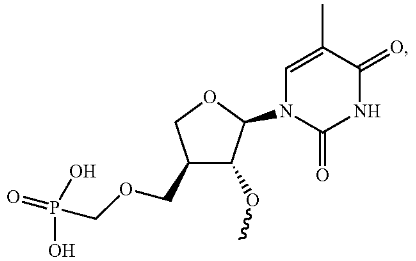
(coc-4hT)

-continued

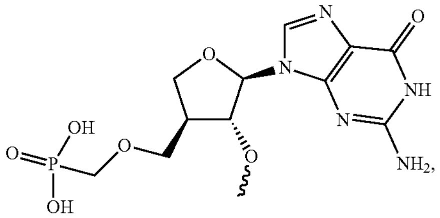

and (coc-4hG)

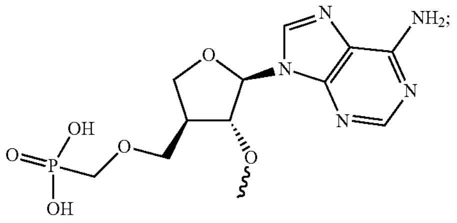

(coc-4hA)

wherein $R^{15}$ is H or $CH_3$.

In some aspects, the present disclosure provides siNA comprising a nucleotide phosphate mimic selected from:

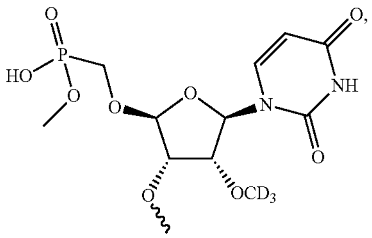

(omeco-d3U)

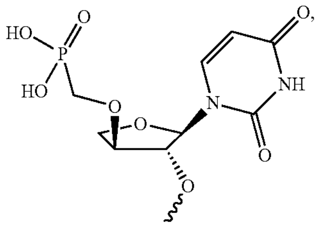

(4hU)

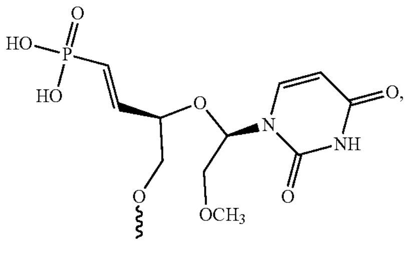

(v-mun)

-continued

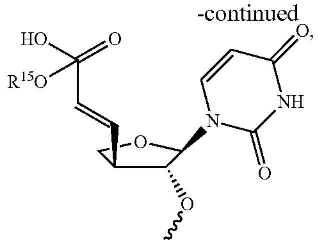

(4h-vp-U)

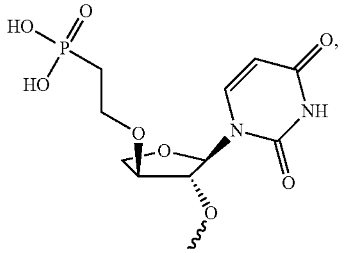

(c2o-4h)

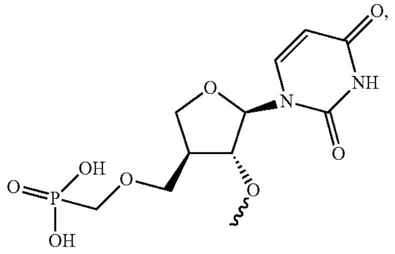

(coc-4hU)

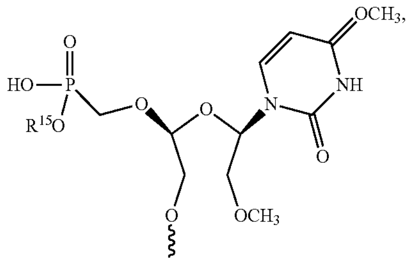

(omeco-munU and

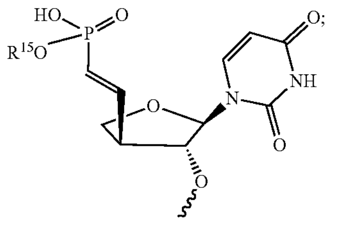

where $R^{15}$ is H or $CH_3$. In some embodiments, one of these novel nucleotide phosphate mimics (e.g., omeco-d3 nucleotide, 4h nucleotide, v-mun nucleotide, c2o-4h nucleotide, coc-4h nucleotide, omeco-mun nucleotide, 4h-vp nucleotide, or d2vm nucleotide) are located at the 5' end of the antisense strand; however, these novel nucleotide phosphate mimics may also be incorporated at the 5' end of the sense strand, the 3' end of the antisense strand, or the 3' end of the sense strand.

Additionally or alternatively, the siNA molecules disclosed herein may comprise in the sense strand, the antisense strand, or both a 5'-stabilized end cap of Formula (Ia):

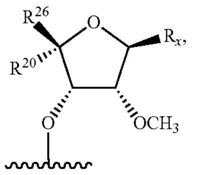

wherein $R_x$ is H, a nucleobase, aryl, or heteroaryl; $R^{26}$ is

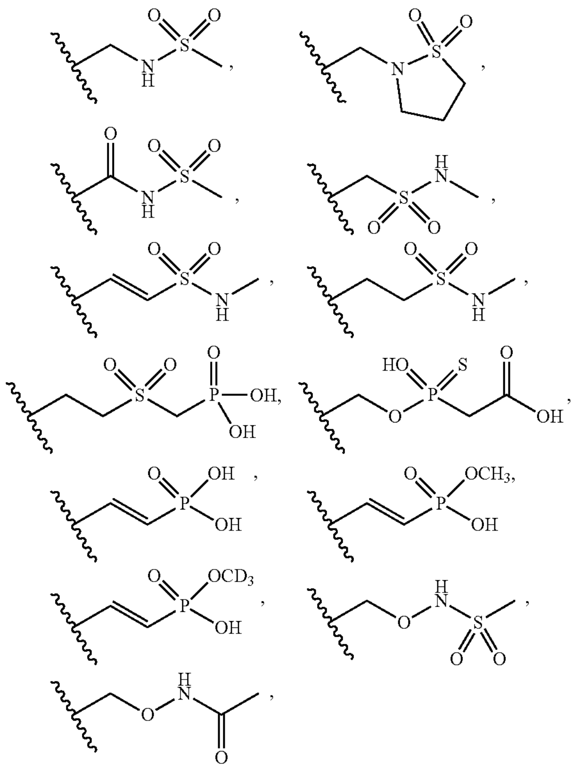

—CH═CD-Z, —CD═CH—Z, —CD═CD-Z, $-(CR^{21}R^{22})_n-Z$, or $-(C_2-C_6$ alkenylene)-Z and $R^{20}$ is H; or $R^{26}$ and $R^{20}$ together form a 3- to 7-membered carbocyclic ring substituted with $-(CR^{21}R^{22})_n-Z$ or $-(C_2-C_6$ alkenylene)-Z; n is 1, 2, 3, or 4; Z is $-ONR^{23}R^{24}$, $-OP(O)OH(CH_2)_mCO_2R^{23}$, $-OP(S)OH(CH_2)_mCO_2R^{23}$, $-P(O)(OH)_2$, $-P(O)(OH)(OCH_3)$, $-P(O)(OH)(OCD_3)$, $-SO_2(CH_2)_mP(O)(OH)_2$, $-SO_2NR^{23}R^{25}$, $-NR^{23}R^{24}$, $-NR^{23}SO_2R^{24}$; either $R^{21}$ and $R^{22}$ are independently hydrogen or $C_1$-$C_6$ alkyl, or $R^{21}$ and $R^{22}$ together form an oxo group; $R^{23}$ is hydrogen or $C_1$-$C_6$ alkyl; $R^{24}$ is $-SO_2R^{25}$ or $-C(O)R^{25}$; or $R^{23}$ and $R^{24}$ together with the nitrogen to which they are attached form a substituted or unsubstituted heterocyclic ring; $R^{25}$ is $C_1$-$C_6$ alkyl; and m is 1, 2, 3, or 4. In some embodiments, $R^1$ is an aryl. In some embodiments, the aryl is a phenyl.

Additionally or alternatively, the siNA molecules disclosed herein may comprise in the sense strand, the antisense strand, or both a 5'-stabilized end cap of Formula (Ib):

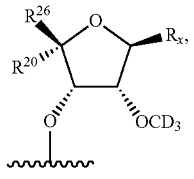

wherein $R_x$ is H, a nucleobase, aryl, or heteroaryl; $R^{26}$ is

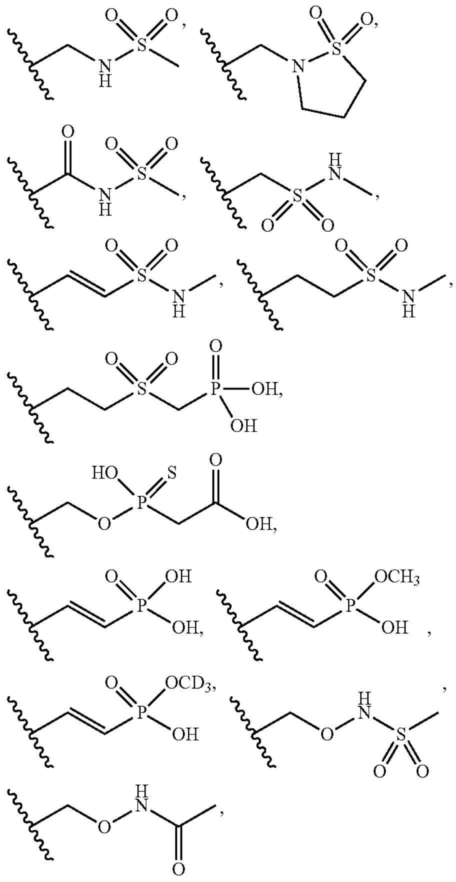

—CH═CD-Z, —CD═CH—Z, —CD═CD-Z, $-(CR^{21}R^{22})_n-Z$, or $-(C_2-C_6$ alkenylene)-Z and $R^{20}$ is H; or $R^{26}$ and $R^{20}$ together form a 3- to 7-membered carbocyclic ring substituted with $-(CR^{21}R^{22})_n-Z$ or $-(C_2-C_6$ alkenylene)-Z; n is 1, 2, 3, or 4; Z is $-ONR^{23}R^{24}$, $-OP(O)OH(CH_2)_mCO_2R^{23}$, $-OP(S)OH(CH_2)_mCO_2R^{23}$, $-P(O)(OH)_2$, $-P(O)(OH)(OCH_3)$, $-P(O)(OH)(OCD_3)$, $-SO_2(CH_2)_mP(O)(OH)_2$, $-SO_2NR^{23}R^{25}$, $-NR^{23}R^{24}$, $-NR^{23}SO_2R^{24}$; either $R^{21}$ and $R^{22}$ are independently hydrogen or $C_1$-$C_6$ alkyl, or $R^{21}$ and $R^{22}$ together form an oxo group; $R^{23}$ is hydrogen or $C_1$-$C_6$ alkyl; $R^{24}$ is $-SO_2R^{25}$ or $-C(O)R^{25}$; or $R^{23}$ and $R^{24}$ together with the nitrogen to which they are attached form a substituted or unsubstituted heterocyclic ring; $R^{25}$ is $C_1$-$C_6$ alkyl; and m is 1, 2, 3, or 4. In some embodiments, $R^1$ is an aryl. In some embodiments, the aryl is a phenyl.

Additionally or alternatively, the siNA molecules disclosed herein may comprise in the sense strand, the antisense strand, or both a 5'-stabilized end cap of Formula (Ic):

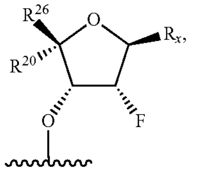

wherein $R_x$ is a nucleobase, aryl, heteroaryl, or H, $R^{26}$ is

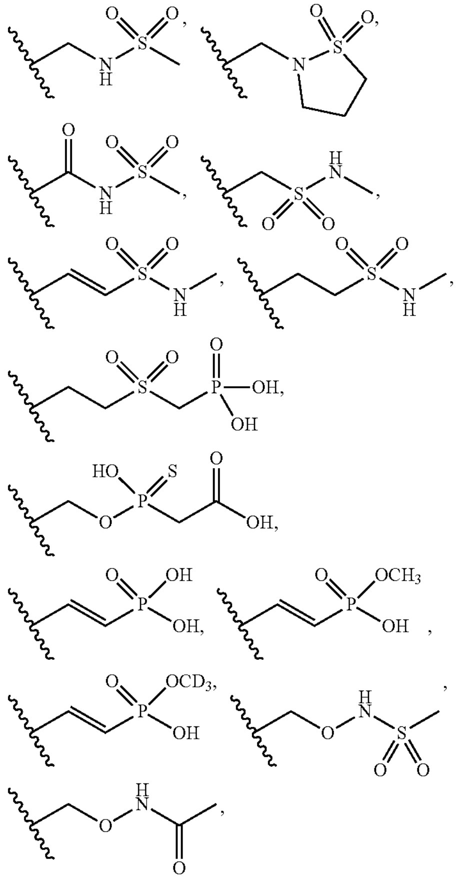

—CH═CD-Z, —CD═CH—Z, —CD═CD-Z, —$(CR^{21}R^{22})_n$—Z, or —($C_2$-$C_6$alkenylene)-Z and $R^{20}$ is hydrogen; or $R^{26}$ and $R^{20}$ together form a 3- to 7-membered carbocyclic ring substituted with —$(CR^{21}R^{22})_n$—Z or —($C_2$-$C_6$ alkenylene)-Z; n is 1, 2, 3, or 4; Z is —$ONR^{23}R^{24}$, —$OP(O)OH(CH_2)_mCO_2R^{23}$, —$OP(S)OH(CH_2)_mCO_2R^{23}$, —$P(O)(OH)_2$, —$P(O)(OH)(OCH_3)$, —$P(O)(OH)(OCD_3)$, —$SO_2(CH_2)_mP(O)(OH)_2$, —$SO_2NR^{23}R^{25}$, —$NR^{23}R^{24}$, or —$NR^{23}SO_2R^{24}$; $R^{21}$ and $R^{22}$ either are independently hydrogen or $C_1$-$C_6$ alkyl, or $R^{21}$ and $R^{22}$ together form an oxo group; $R^{23}$ is hydrogen or $C_1$-$C_6$ alkyl; $R^{24}$ is —$SO_2R^{25}$ or —$C(O)R^{25}$; or $R^{23}$ and $R^{24}$ together with the nitrogen to which they are attached form a substituted or unsubstituted heterocyclic ring; $R^{25}$ is $C_1$-$C_6$ alkyl; and m is 1, 2, 3, or 4. In some embodiments, $R^1$ is an aryl. In some embodiments, the aryl is a phenyl.

Additionally or alternatively, the siNA molecules disclosed herein may comprise in the sense strand, the antisense strand, or both a 5'-stabilized end cap of Formula (IIa):

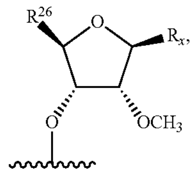

wherein $R_x$ is a nucleobase, aryl, heteroaryl, or H, $R^{26}$ is

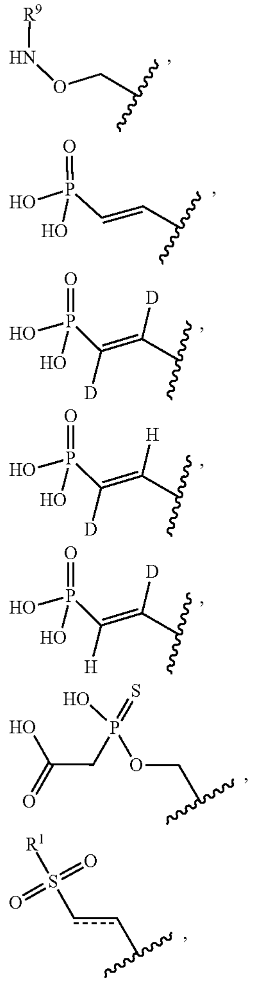

—$CH_2SO_2NHCH_3$, or

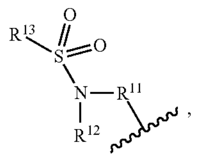

$R^9$ is —$SO_2CH_3$ or —$COCH_3$, ⎓ is a double or single bond, $R^{10}$═—$CH_2PO_3H$ or —$NHCH_3$, $R^{11}$ is —$CH_2$— or —CO—, and $R^{12}$ is H and $R^{13}$ is $CH_3$ or $R^{12}$ and $R^{13}$ together form —$CH_2CH_2CH_2$—. In some embodiments, $R^1$ is an aryl. In some embodiments, the aryl is a phenyl.

Additionally or alternatively, the siNA molecules disclosed herein may comprise in the sense strand, the antisense strand, or both a 5'-stabilized end cap of Formula (IIb):

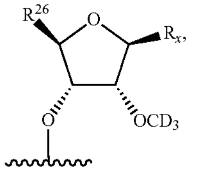

wherein $R_x$ is a nucleobase, aryl, heteroaryl, or H, $R^{26}$ is

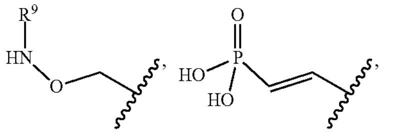

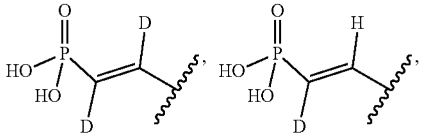

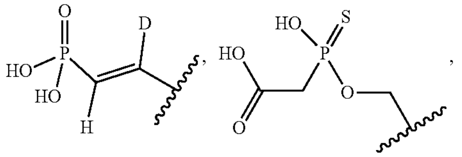

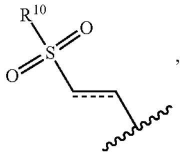

—$CH_2SO_2NHCH_3$, or

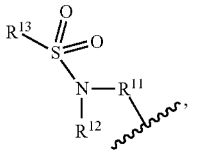

$R^9$ is —$SO_2CH_3$ or —$COCH_3$, $\overline{---}$ is a double or single bond, $R^{10}$=—$CH_2PO_3H$ or —$NHCH_3$, $R^{11}$ is —$CH_2$— or —CO—, and $R^{12}$ is H and $R^{13}$ is $CH_3$ or $R^{12}$ and $R^{13}$ together form —$CH_2CH_2CH_2$—. In some embodiments, $R^1$ is an aryl. In some embodiments, the aryl is a phenyl.

Additionally or alternatively, the siNA molecules disclosed herein may comprise in the sense strand, the antisense strand, or both a 5'-stabilized end cap of Formula (III):

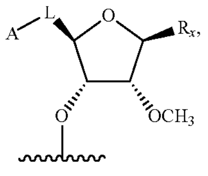

wherein $R_x$ is a nucleobase, aryl, heteroaryl, or H, L is —$CH_2$—, —CH═CH—, —CO—, or —$CH_2CH_2$—, and A is —$ONHCOCH_3$, —$ONHSO_2CH_3$, —$PO_3H$, —OP(SOH)$CH_2CO_2H$, —$SO_2CH_2PO_3H$, —$SO_2NHCH_3$, —$NHSO_2CH_3$, or —N($SO_2CH_2CH_2CH_2$). In some embodiments, $R^1$ is an aryl. In some embodiments, the aryl is a phenyl.

Additionally or alternatively, the siNA molecules disclosed herein may comprise a 5'-stabilized end cap selected from the group consisting of Formula (1) to Formula (16), Formula (9X) to Formula (12X), Formula (16X), Formula (9Y) to Formula (12Y), Formula (16Y), Formula (21) to Formula (36), Formula 36X, Formula (41) to (56), Formula (49X) to (52X), Formula (49Y) to (52Y), Formula 56X, Formula 56Y, Formula (61) and Formula (62):

Formula (1)

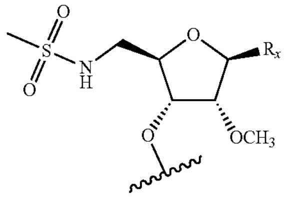

Formula (2)

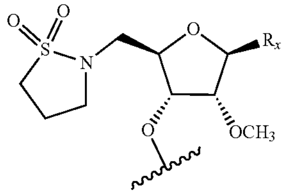

Formula (3)

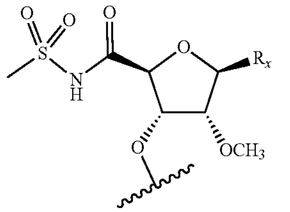

Formula (4)

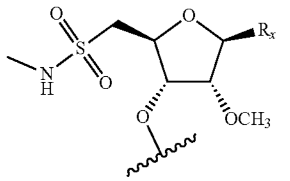

Formula (5)

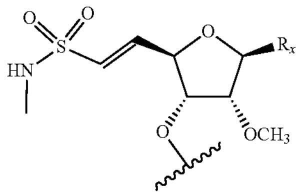

Formula (6)

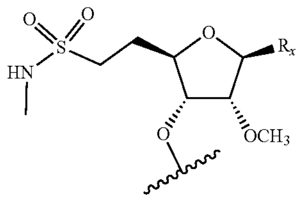

-continued
Formula (7)
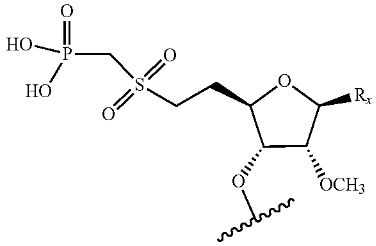
Formula (8)
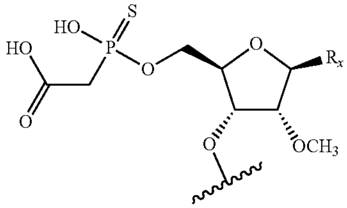
Formula (9)
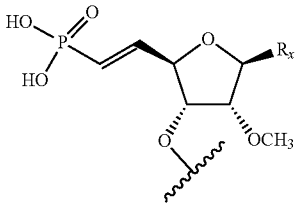
Formula (9X)
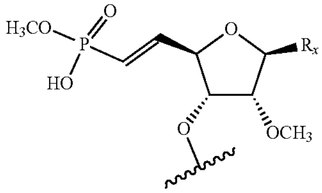
Formula (9Y)
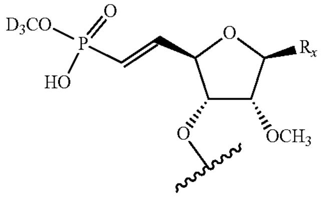
Formula (10)
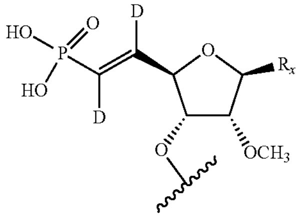
Formula (10X)
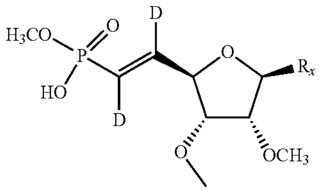
-continued
Formula (10Y)
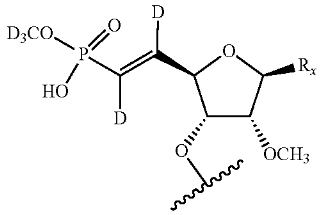
Formula (11)
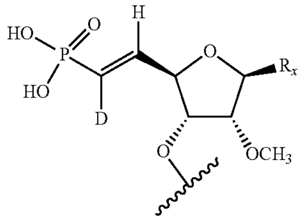
Formula (11X)
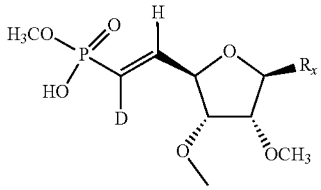
Formula (11Y)
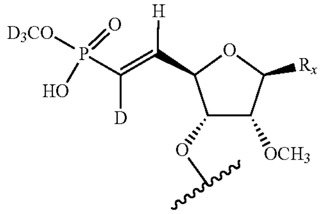
Formula (12)
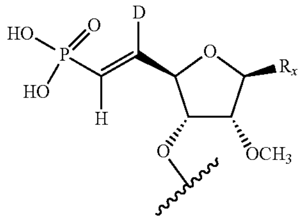
Formula (12X)
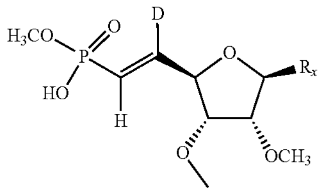
Formula (12Y)
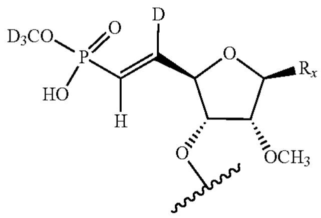

-continued
Formula (13)
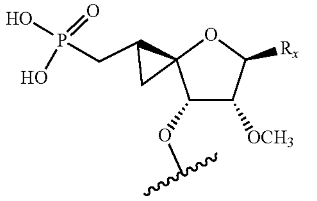
Formula (14)
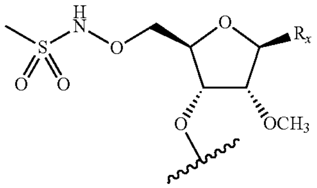
Formula (15)
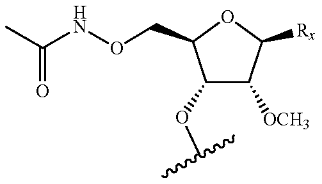
Formula (16)
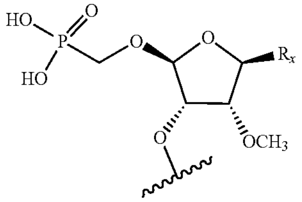
Formula (16X)
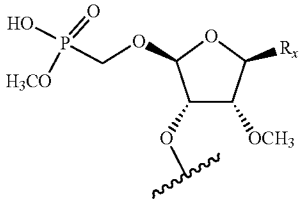
Formula (16Y)
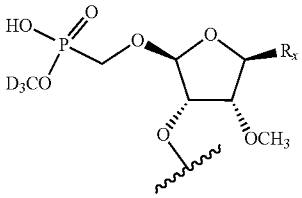
Formula (21)
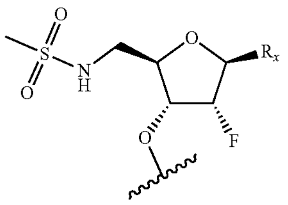
-continued
Formula (22)
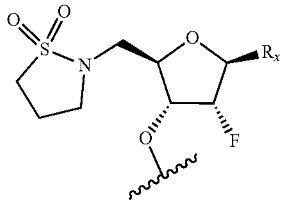
Formula (23)
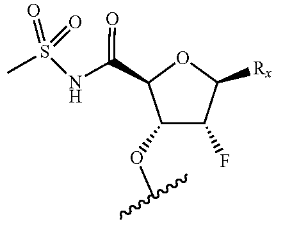
Formula (24)
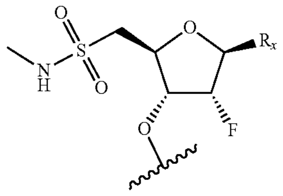
Formula (25)
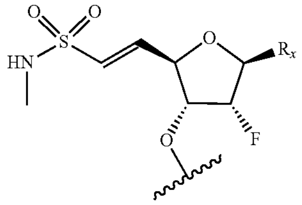
Formula (26)
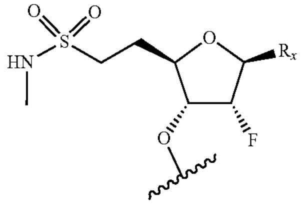
Formula (27)
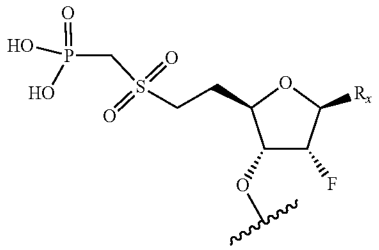
Formula (28)
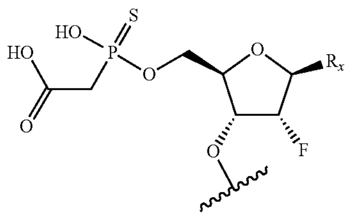

-continued
Formula (29)
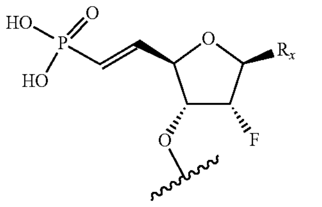
Formula (30)
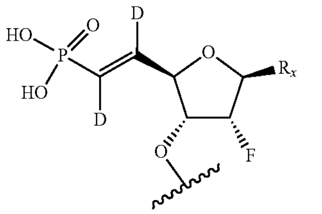
Formula (31)
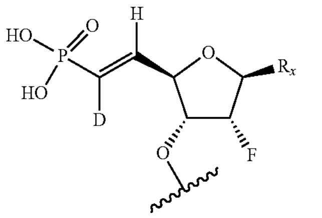
Formula (32)
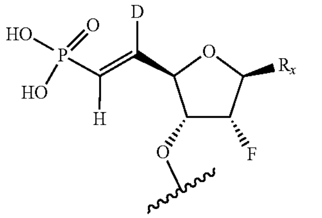
Formula (33)
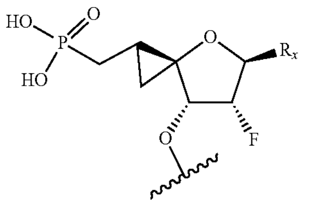
Formula (34)
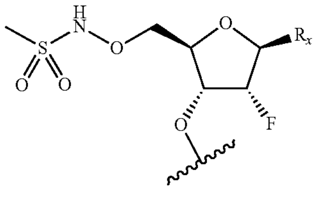
Formula (35)
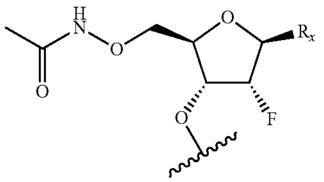
-continued
Formula (36)
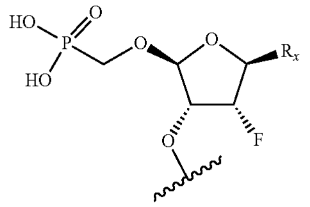
Formula (36X)
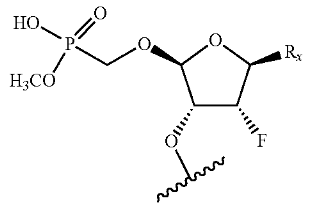
Formula (41)
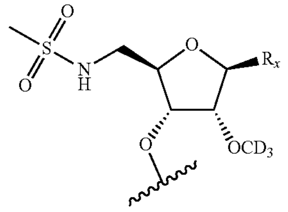
Formula (42)
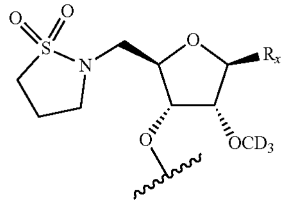
Formula (43)
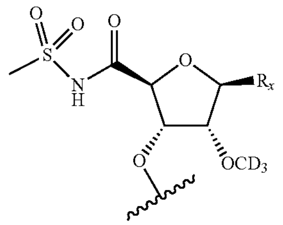
Formula (44)
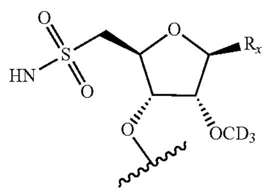
Formula (45)
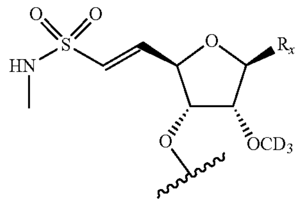

-continued
Formula (46)
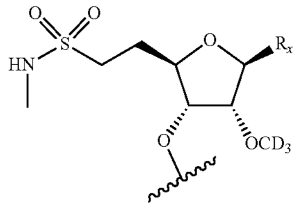
Formula (47)
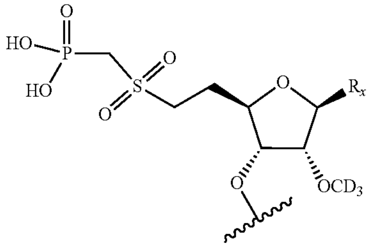
Formula (48)
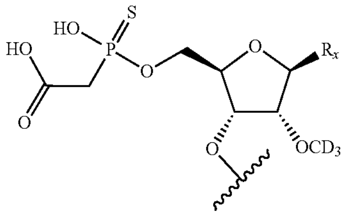
Formula (49)
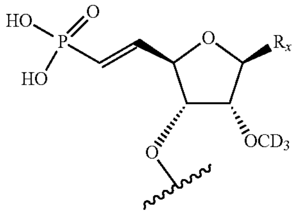
Formula (49X)
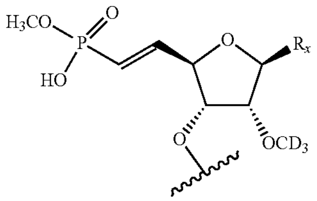
Formula (49Y)
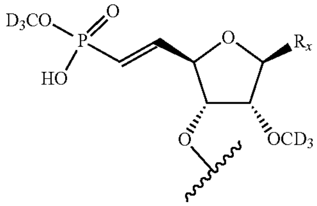
Formula (50)
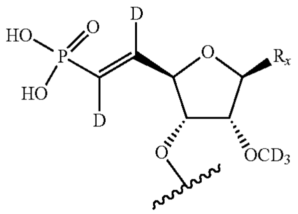
-continued
Formula (50X)
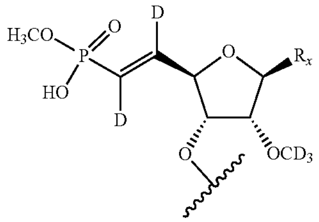
Formula (50Y)
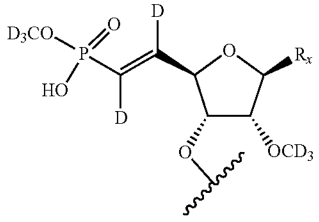
Formula (51)
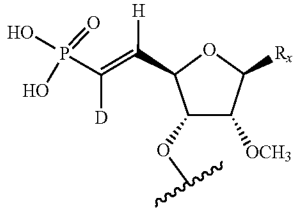
Formula (51X)
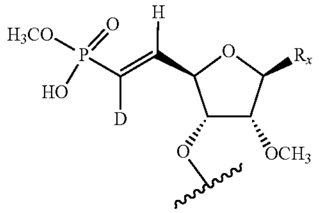
Formula (51Y)
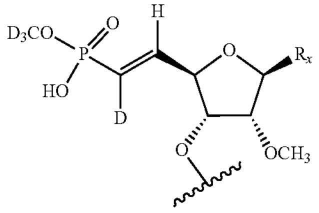
Formula (52)
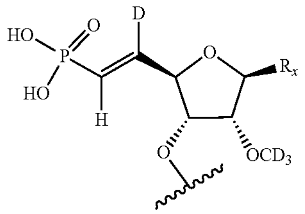
Formula (52X)
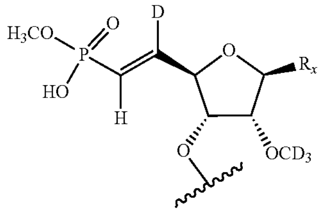

-continued

Formula (52Y)

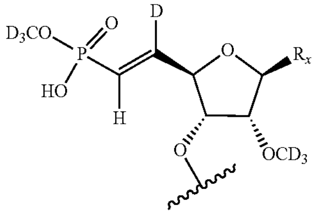

Formula (53)

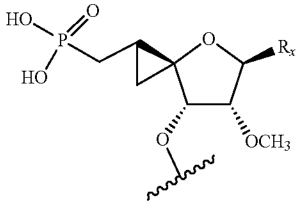

Formula (54)

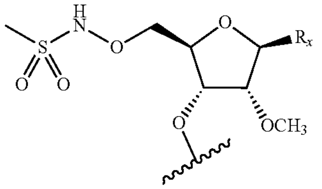

Formula (55)

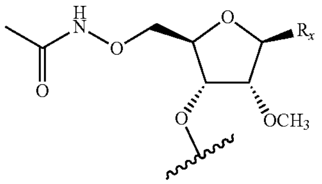

Formula (56)

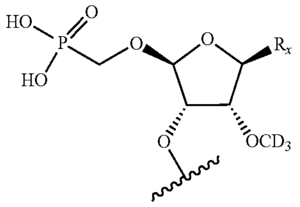

Formula (56X)

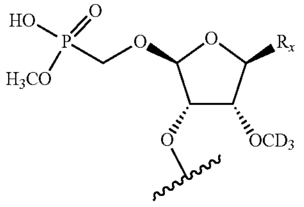

Formula (56Y)

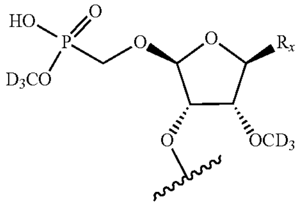

-continued

Formula (61)

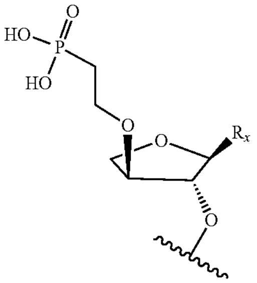

Formula (62)

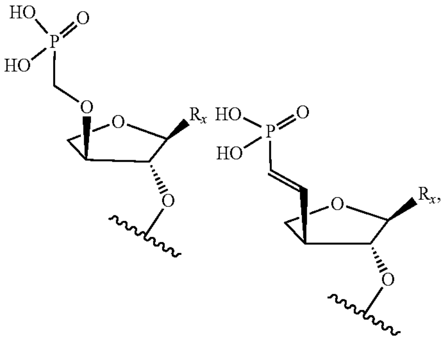

wherein $R_x$ is a nucleobase, aryl, heteroaryl, or H.

In some embodiments, any of the siNA molecules disclosed herein comprise a 5'-stabilized end cap selected from the group consisting of Formula (50), Formula (50X), Formula (50Y), Formula (56), Formula (56X), Formula (56Y), Formula (61), Formula (62), and Formula (63):

Formula (50)

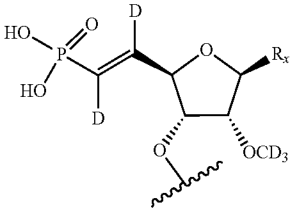

Formula (50X)

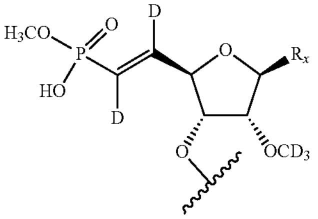

Formula (50Y)

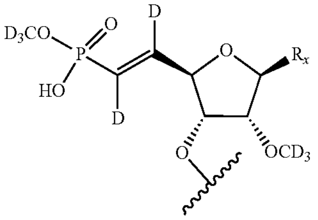

-continued

Formula (56)

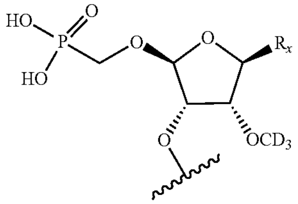

Formula (56X)

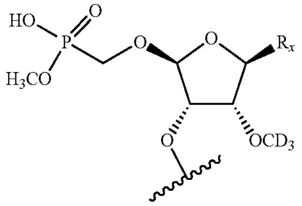

Formula (56Y)

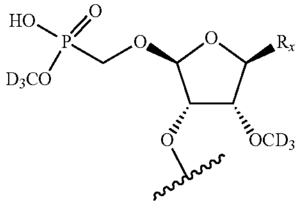

Formula (61)

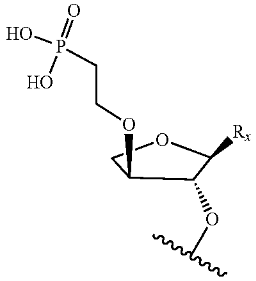

Formula (62)

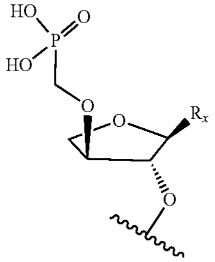

Formula (63)

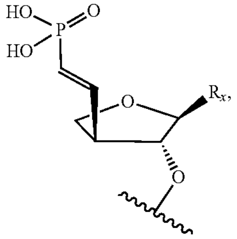

wherein $R_x$ is a nucleobase, aryl, heteroaryl, or H.

In some embodiments, any of the siNA molecules disclosed herein comprise a 5'-stabilized end cap selected from the group consisting of Formula (71) to Formula (86), Formula (79X) to Formula (82X), Formula (79Y) to (82Y), Formula 86X, Formula 86X', Formula 86Y, and Formula 86Y':

Formula (71)

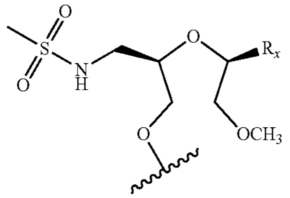

Formula (72)

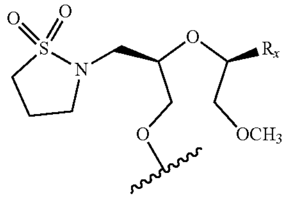

Formula (73)

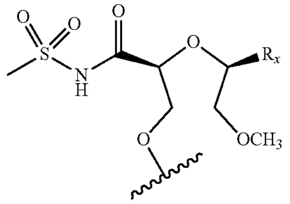

Formula (74)

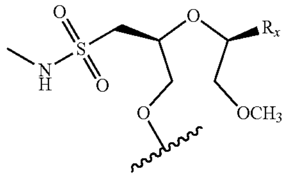

Formula (75)

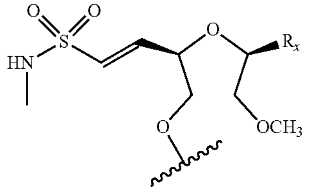

Formula (76)

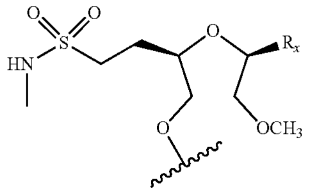

Formula (77)

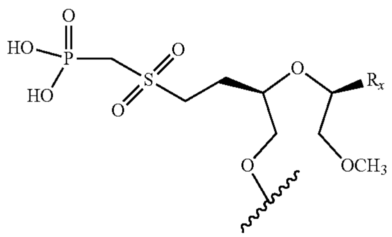

-continued
Formula (78)
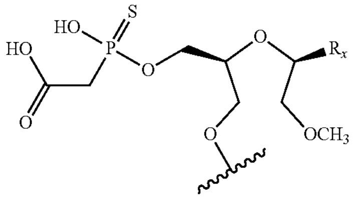
Formula (79)
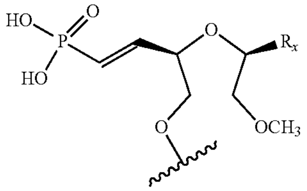
Formula (79X)
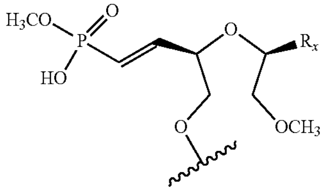
Formula (79Y)
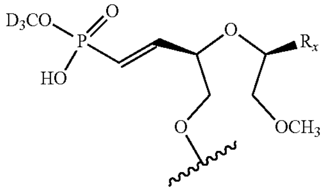
Formula (80)
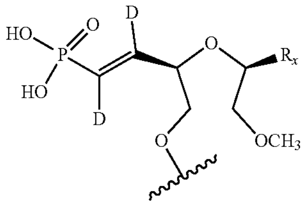
Formula (80X)
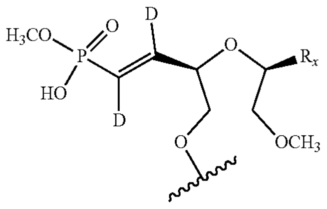
Formula (80Y)
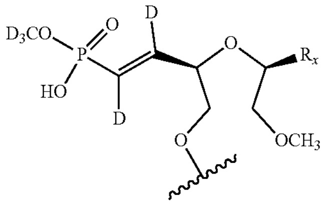
-continued
Formula (81)
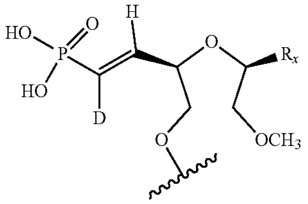
Formula (81X)
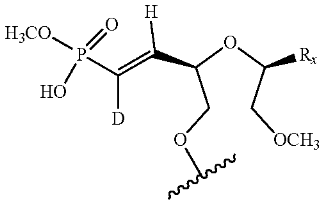
Formula (81Y)
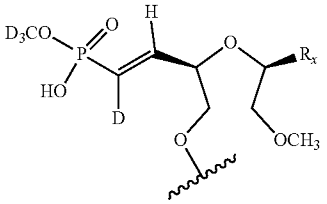
Formula (82)
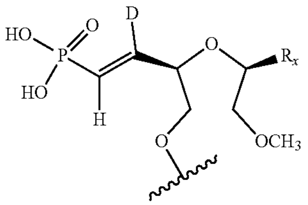
Formula (82X)
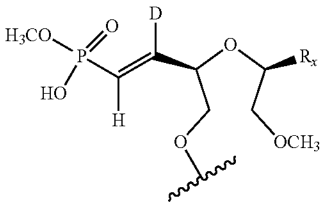
Formula (82Y)
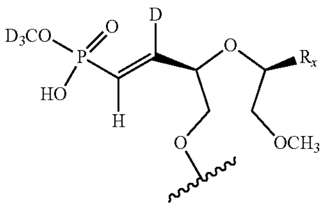
Formula (83)
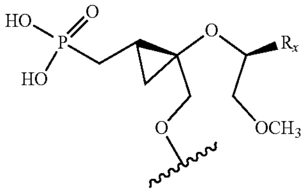

-continued

Formula (84)

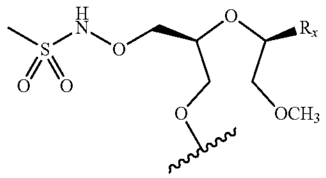

Formula (85)

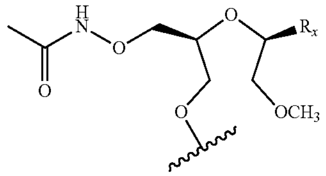

Formula (86)

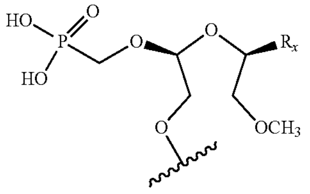

Formula (86X)

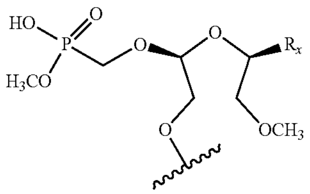

Formula (86X')

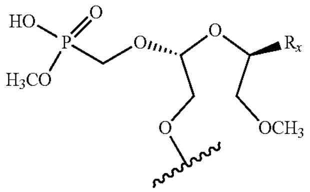

Formula (86Y)

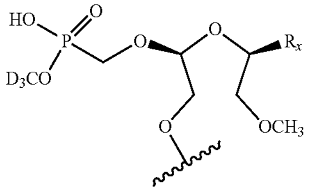

Formula (86Y')

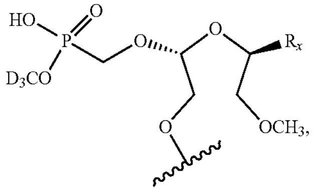

wherein $R_x$ is a nucleobase, aryl, heteroaryl, or H.

In some embodiments, any of the siNA molecules disclosed herein comprise a 5'-stabilized end cap selected from the group consisting of Formula (78), Formula (79), Formula (79X), Formula (79Y), Formula (86), Formula (86X), and Formula (86X'):

Formula (78)

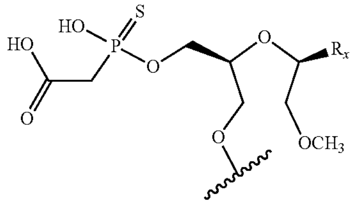

Formula (79)

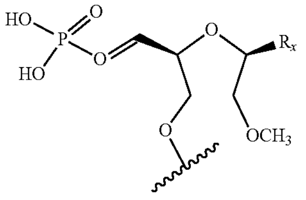

Formula (79X)

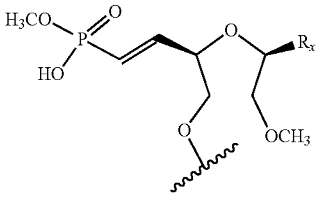

Formula (79Y)

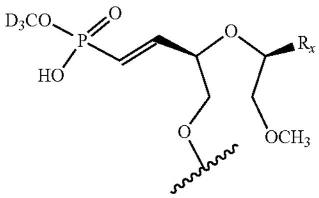

Formula (86)

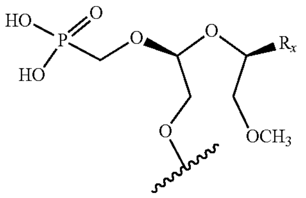

Formula (86X)

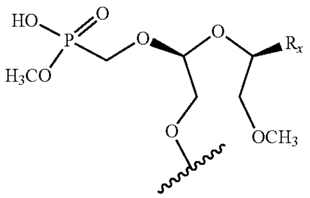

Formula (86X')

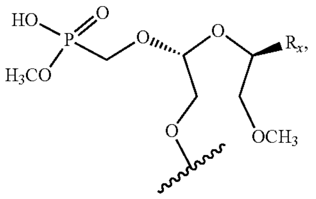

wherein $R_x$ is a nucleobase, aryl, heteroaryl, or H.

In some embodiments, any of the siNA molecules disclosed herein comprise a 5'-stabilized end cap selected from the group consisting of Formulas (1A)-(15 A), Formulas (1A-1)-(7 A-1), Formulas (1A-2)-(7 A-2), Formulas (1A-3)-(7 A-3), Formulas (1A-4)-(7 A-4), Formulas (9B)-(12B), Formulas (9AX)-(12AX), Formulas (9AY)-(12AY), Formulas (9BX)-(12BX), and Formulas (9BY)-(12BY):
Formula (1A)
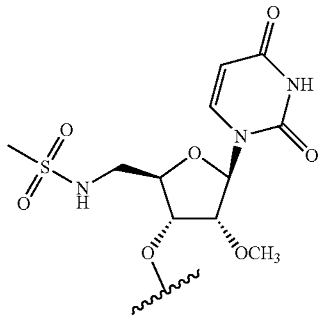
Formula (2A)
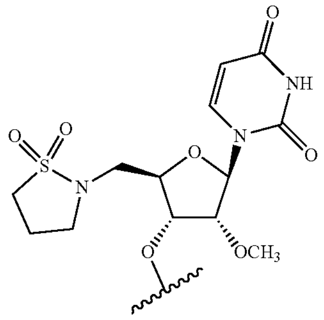
Formula (3A)
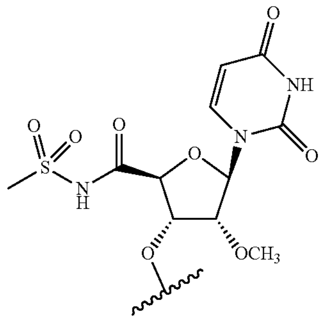
Formula (4A)
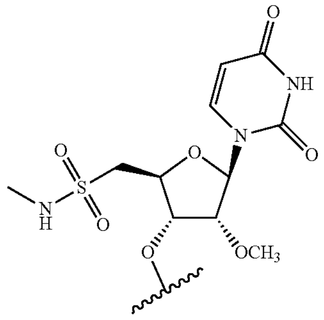
-continued
Formula (1A-1)
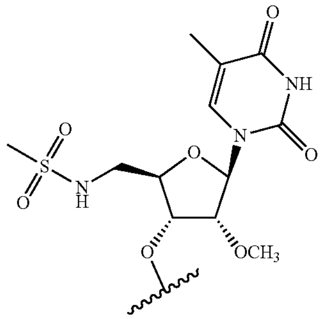
Formula (2A-1)
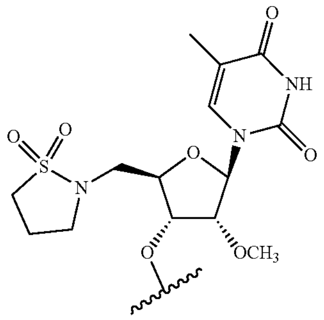
Formula (3A-1)
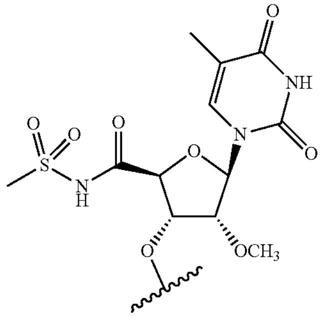
Formula (4A-1)
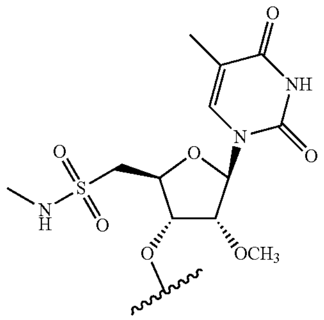
Formula (1A-2)
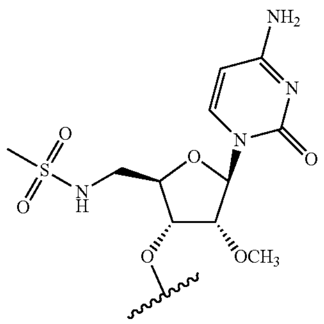

-continued
Formula (2A-2)
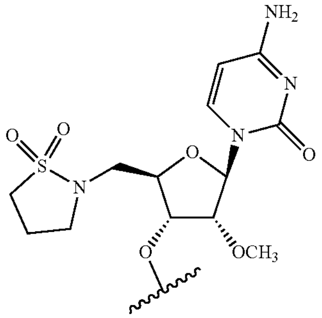
Formula (3A-2)
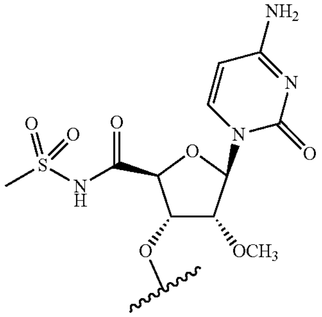
Formula (4A-2)
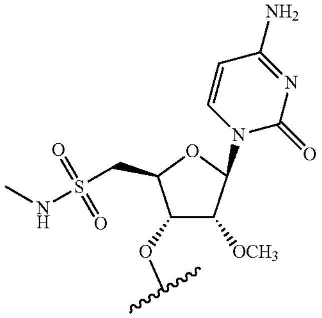
Formula (1A-3)
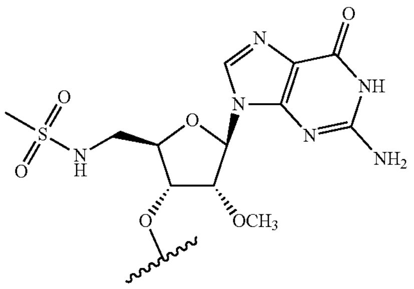
Formula (2A-3)
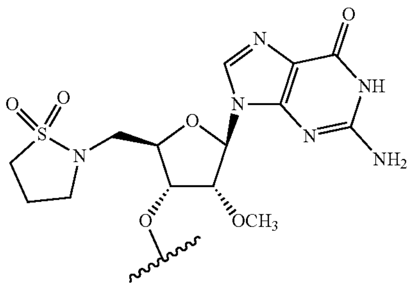
-continued
Formula (3A-3)
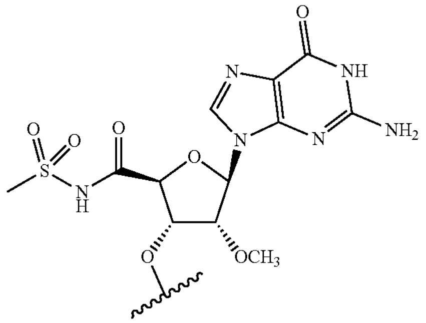
Formula (4A-3)
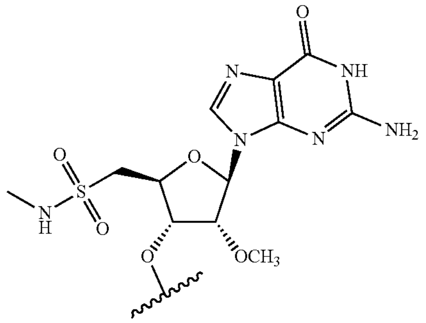
Formula (1A-4)
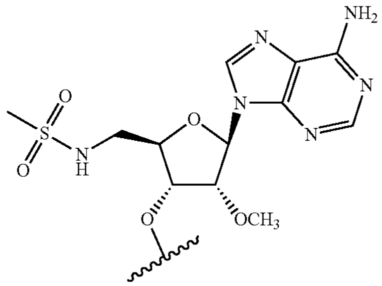
Formula (2A-4)
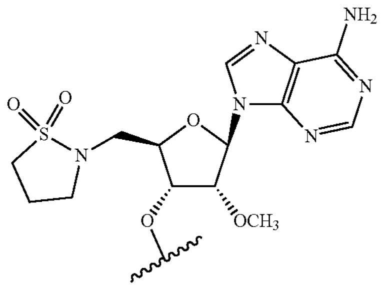
Formula (3A-4)
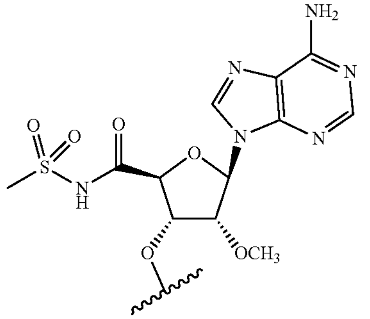

-continued
Formula (4A-4)
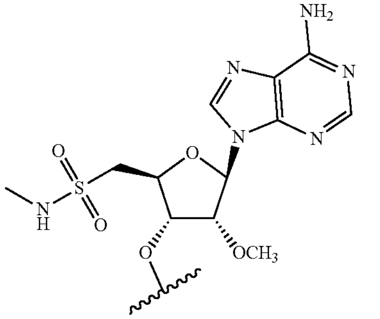
Formula (5A)
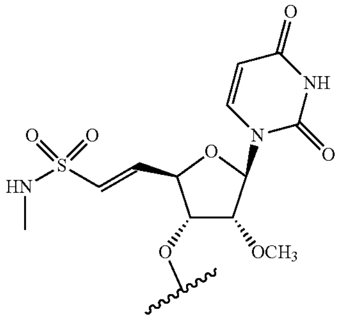
Formula (5A-1)
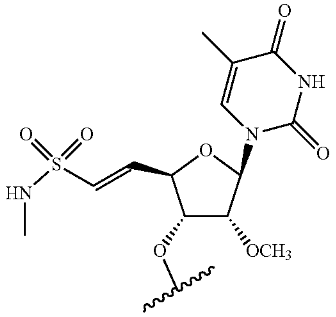
Formula (5A-2)
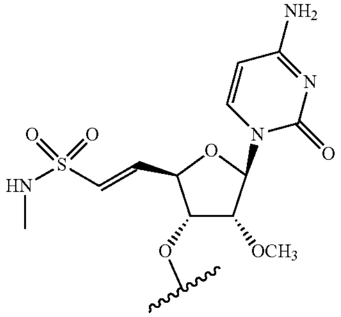
Formula (5A-3)
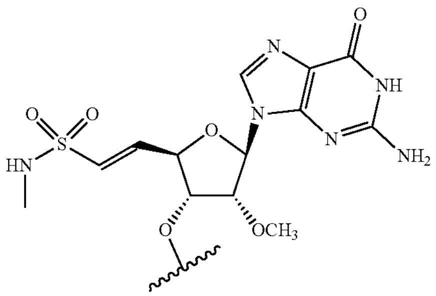
-continued
Formula (5A-4)
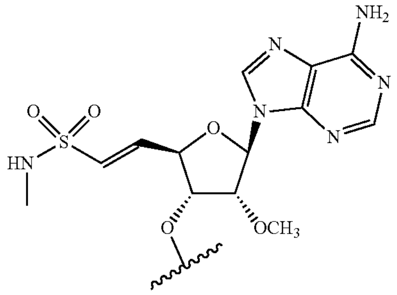
Formula (6A)
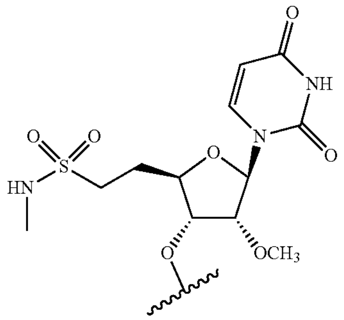
Formula (6A-1)
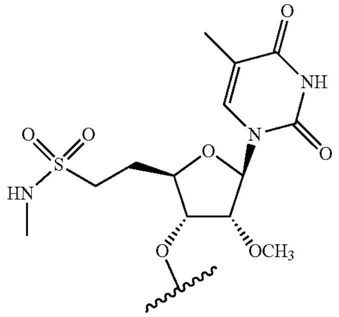
Formula (6A-2)
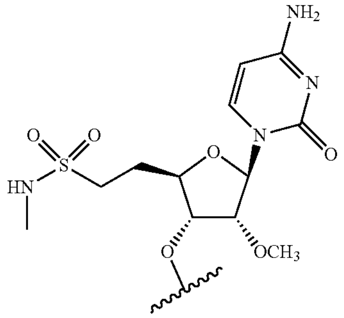
Formula (6A-3)
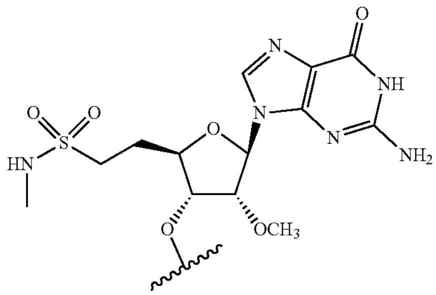

-continued
Formula (6A-4)
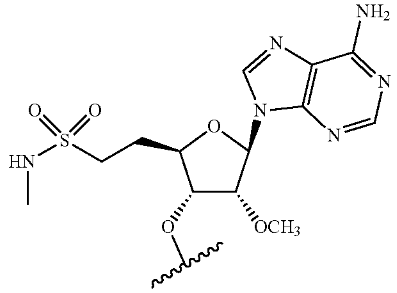
Formula (7A)
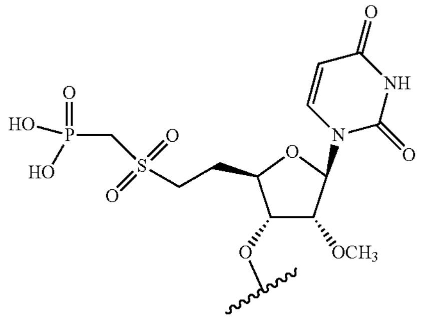
Formula (7A-1)
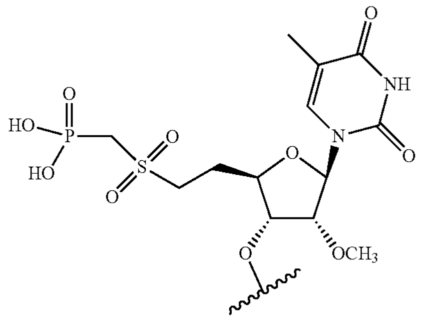
Formula (7A-2)
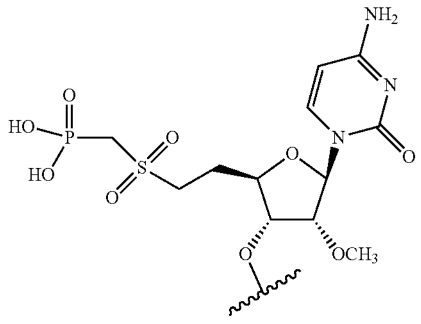
Formula (7A-3)
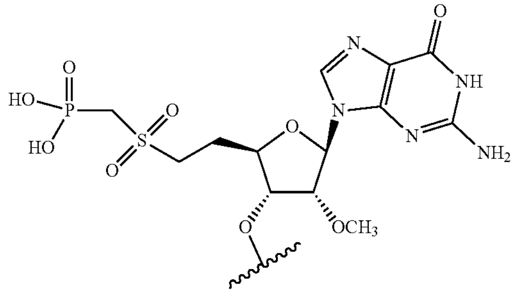
-continued
Formula (7A-4)
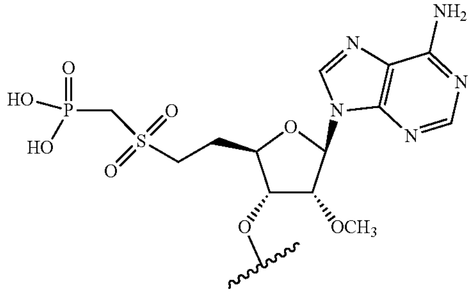
Formula (8A)
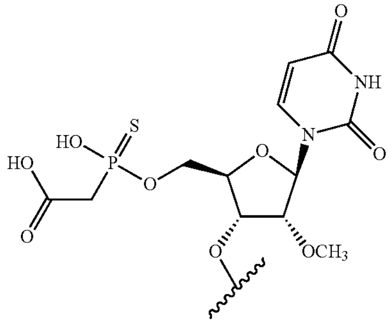
Formula (9A)
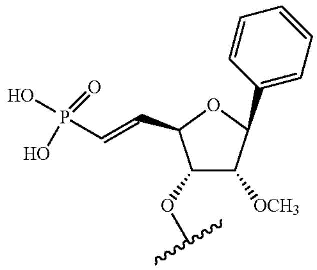
Formula (9AX)
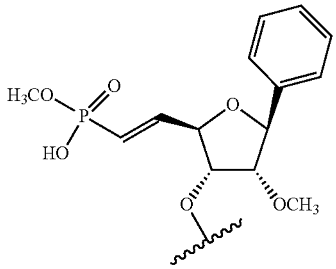
Formula (9AY)
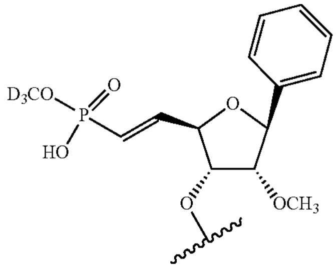

-continued
Formula (9B)
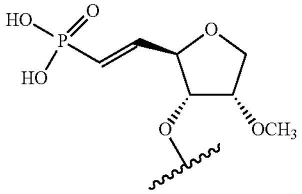
Formula (9BX)
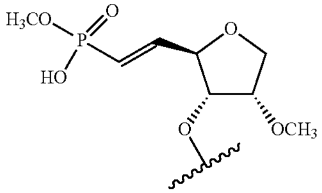
Formula (9BY)
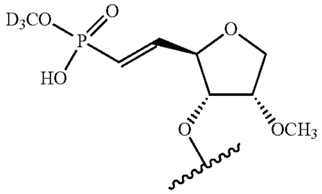
Formula (10A)
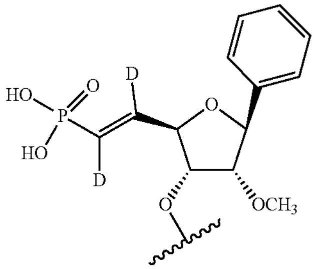
Formula (10AX)
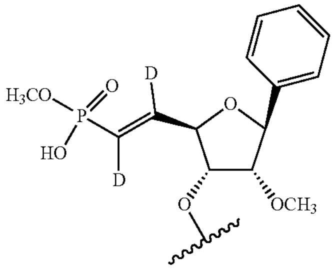
Formula (10AY)
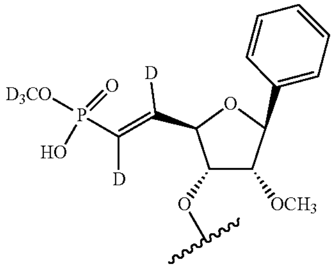
-continued
Formula (10B)
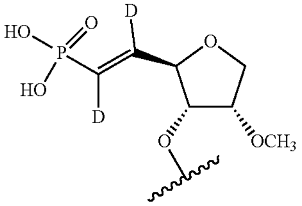
Formula (10BX)
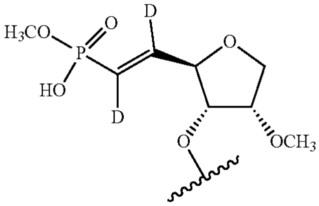
Formula (10BY)
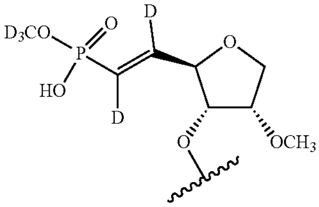
Formula (11A)
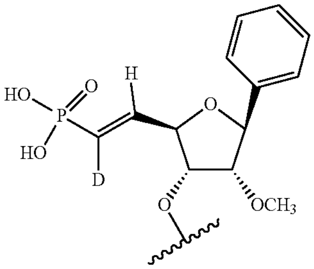
Formula (11AX)
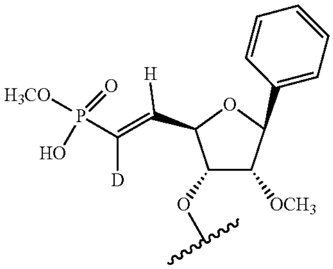
Formula (11AY)
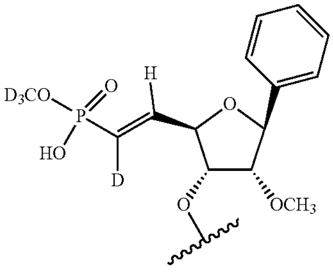

-continued
Formula (11B)
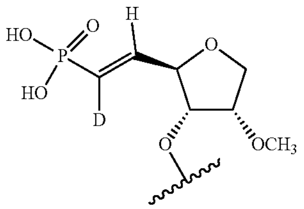
Formula (11BX)
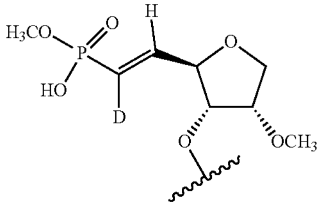
Formula (11BY)
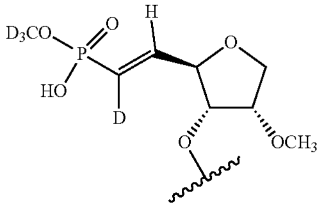
Formula (12A)
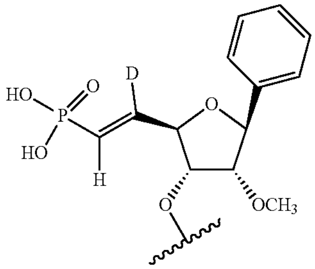
Formula (12AX)
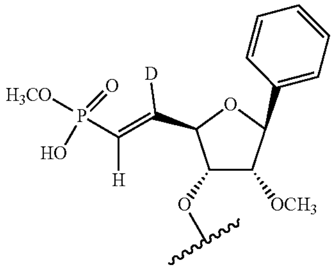
Formula (12AY)
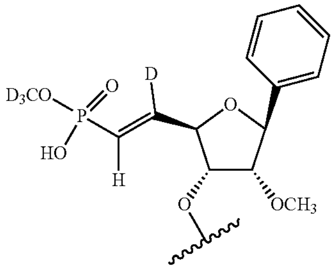
-continued
Formula (12B)
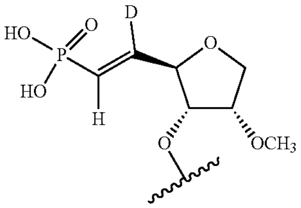
Formula (12BX)
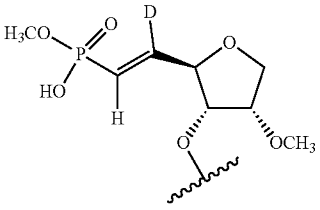
Formula (12BY)
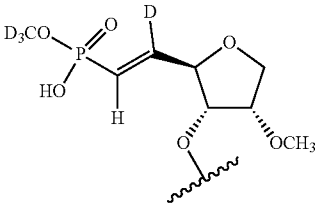
Formula (13A)
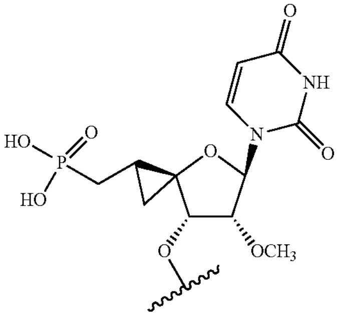
Formula (14A)
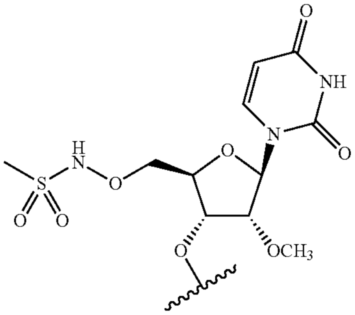
Formula (15A)
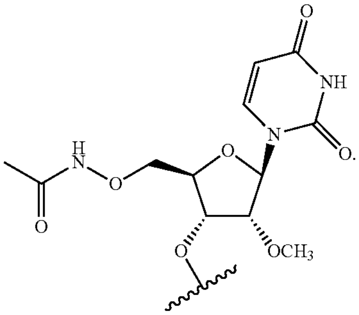

In some embodiments, any of the siNA molecules disclosed herein comprise a 5'-stabilized end cap selected from the group consisting of Formulas (21A)-(35 A), Formulas (29B)-(32B), Formulas (29AX)-(32AX), Formulas (29AY)-(32AY), Formulas (29BX)-(32BX), and Formulas (29BY)-(32BY):
Formula (21A)
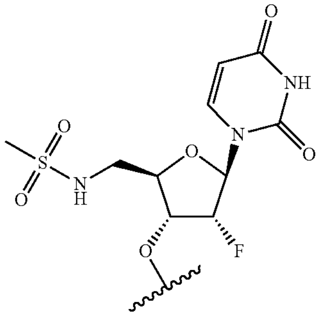
Formula (22A)
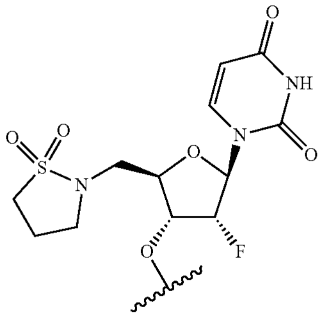
Formula (23A)
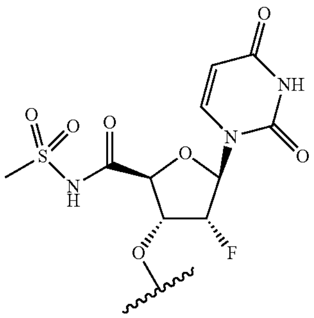
Formula (24A)
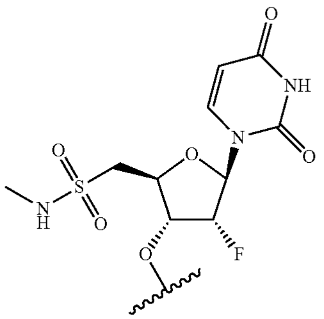
-continued
Formula (25A)
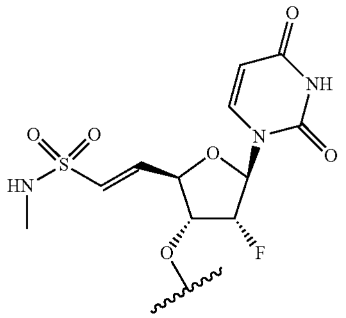
Formula (26A)
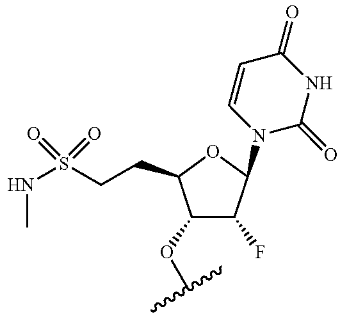
Formula (27A)
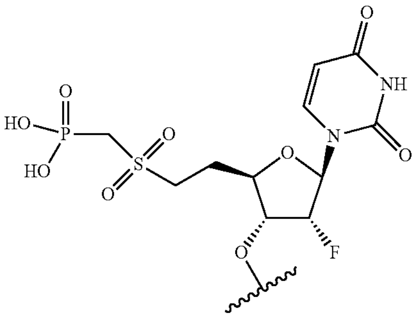
Formula (28A)
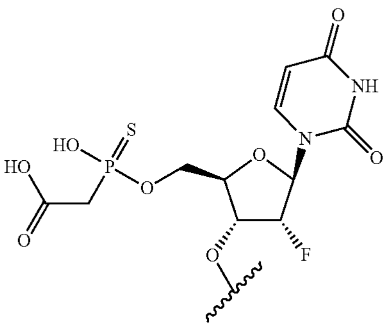
Formula (29A)
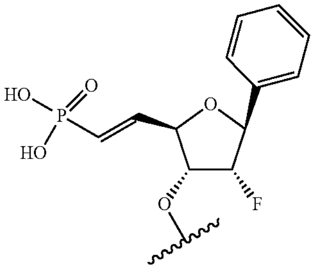

-continued
Formula (29AX)
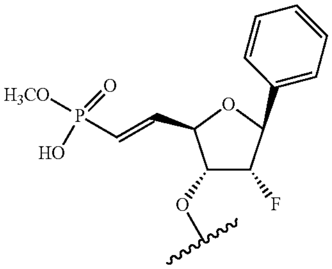
Formula (29AY)
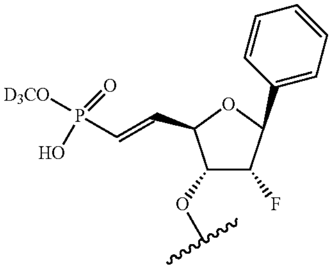
Formula (29B)
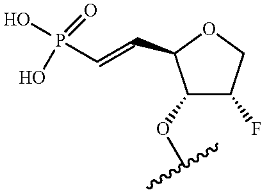
Formula (29BX)
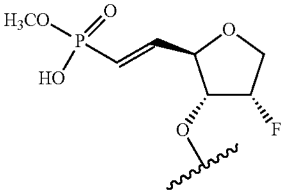
Formula (29BY)
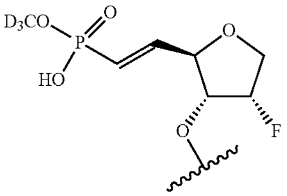
Formula (30A)
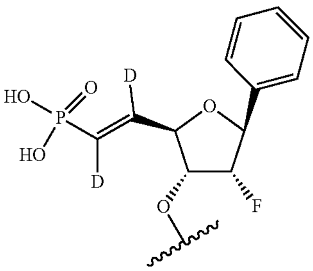
-continued
Formula (30AX)
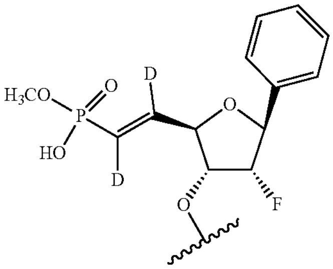
Formula (30AY)
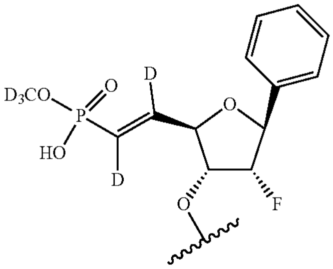
Formula (30B)
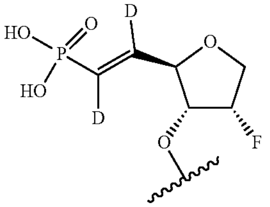
Formula (30BX)
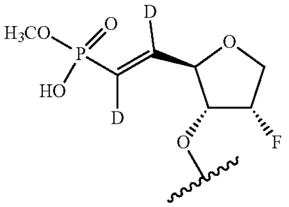
Formula (30BY)
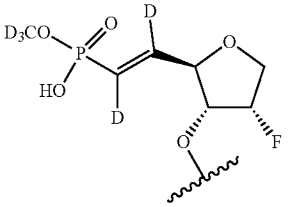
Formula (31A)
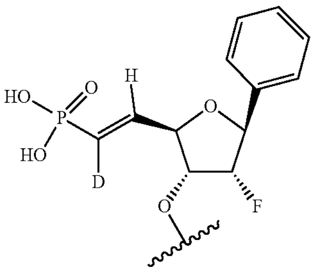

-continued
Formula (31AX)
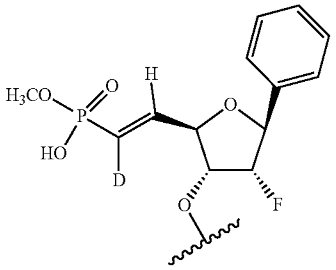
Formula (31AY)
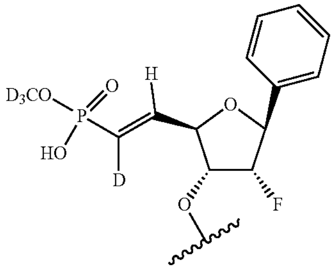
Formula (31B)
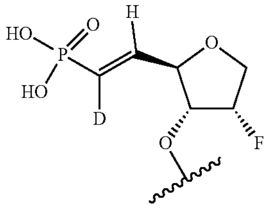
Formula (31BX)
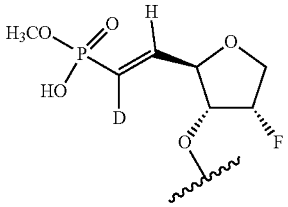
Formula (31BY)
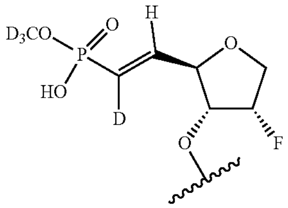
Formula (32A)
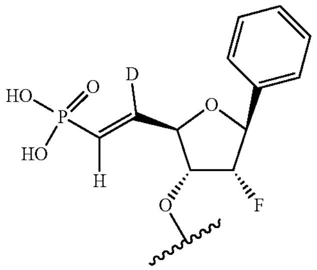
-continued
Formula (32AX)
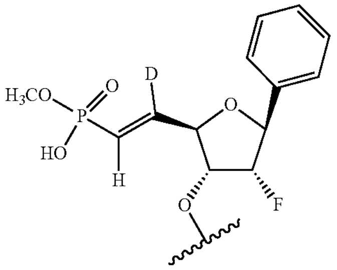
Formula (32AY)
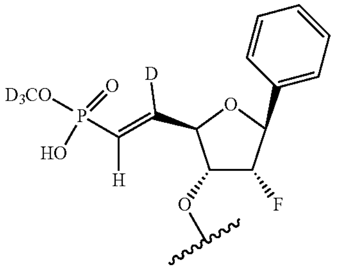
Formula (32B)
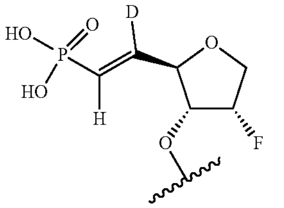
Formula (32BX)
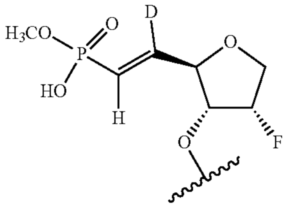
Formula (32BY)
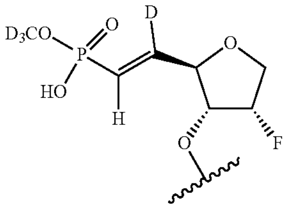
Formula (33A)
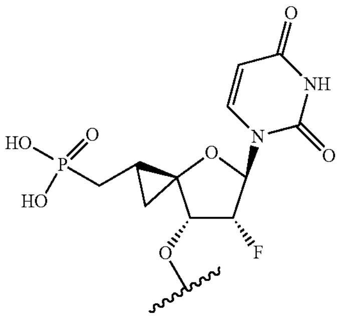

-continued
Formula (34A)
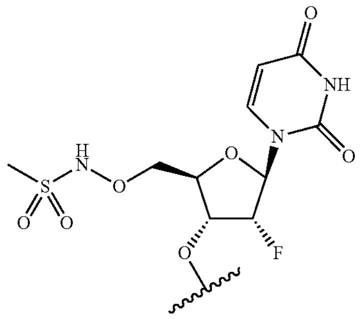
Formula (35A)
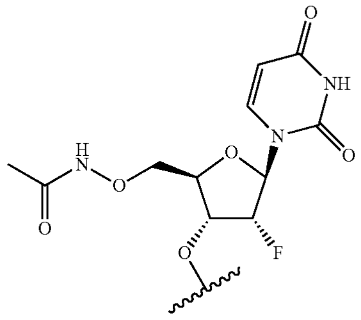
In some embodiments, any of the siNA molecules disclosed herein comprise a 5'-stabilized end cap selected from the group consisting of Formulas (71A)-(86 A), Formulas (79XA)-(82XA), Formulas (79YA)-(82YA); Formula (86XA), Formula (86X'A), Formula (86Y), and Formula (86Y'):
Formula (71A)
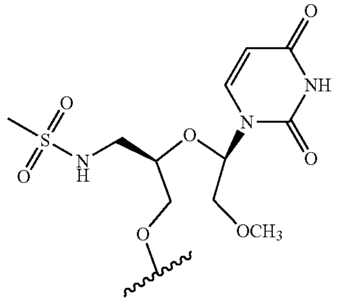
Formula (72A)
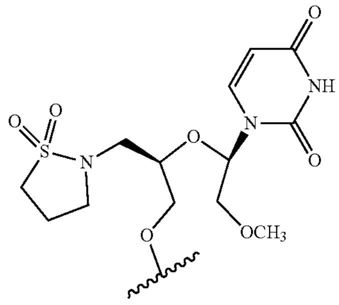
-continued
Formula (73A)
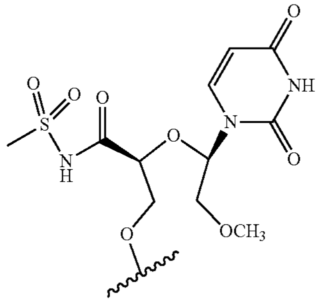
Formula (74A)
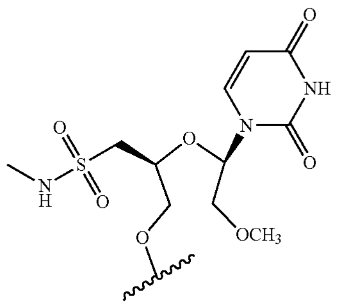
Formula (75A)
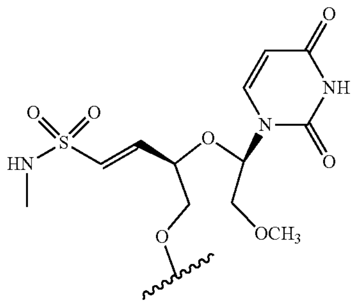
Formula (76A)
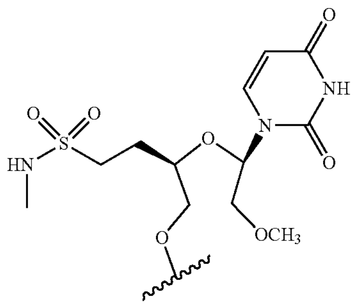
Formula (77A)
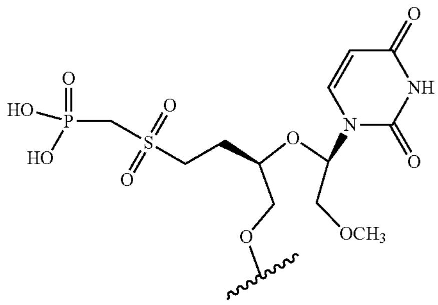

-continued
Formula (78A)
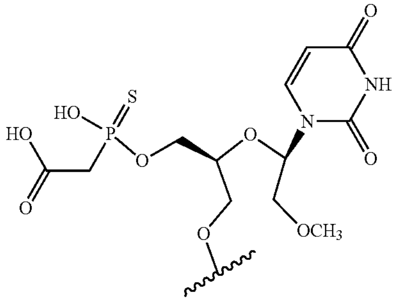
Formula (79A)
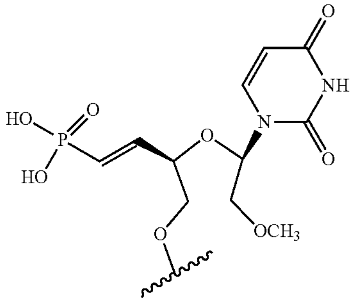
Formula (79XA)
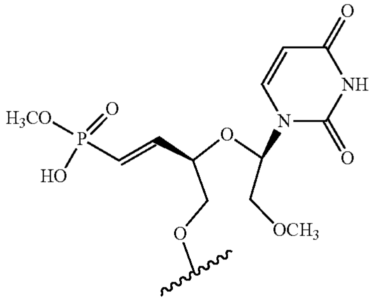
Formula (79YA)
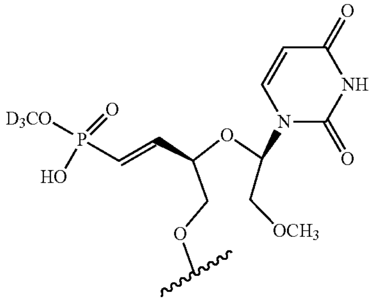
Formula (80A)
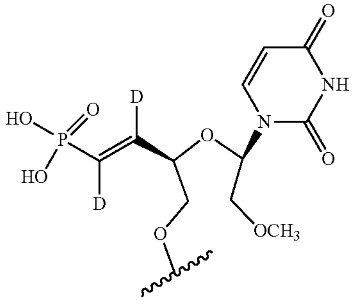
-continued
Formula (80XA)
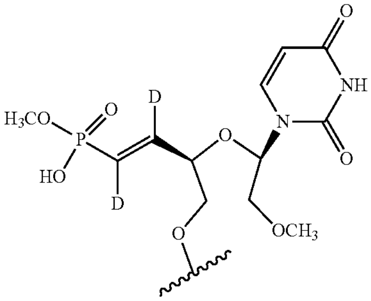
Formula (80YA)
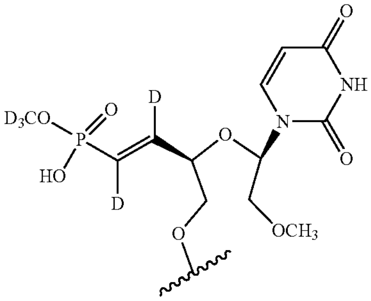
Formula (81A)
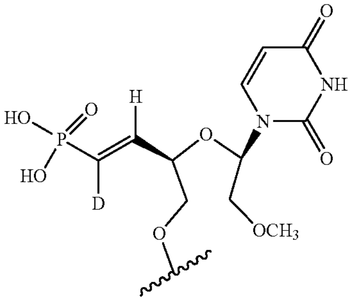
Formula (81XA)
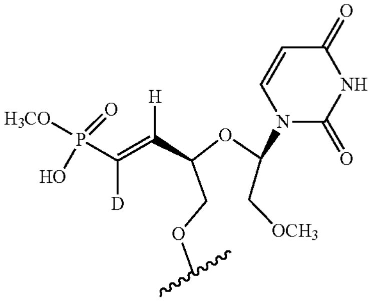
Formula (81YA)
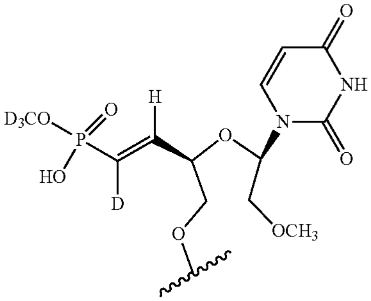

-continued
Formula (82A)
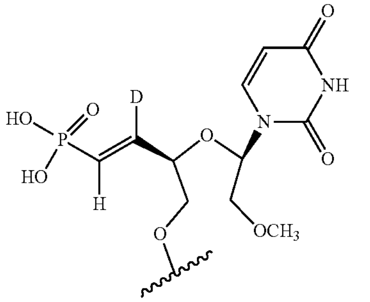
Formula (82XA)
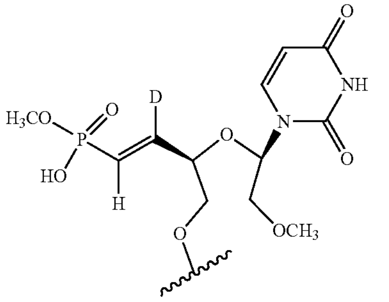
Formula (82YA)
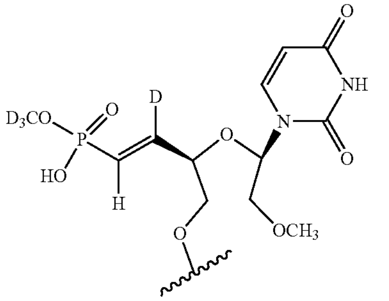
Formula (83A)
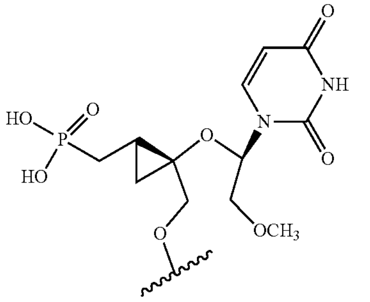
Formula (84A)
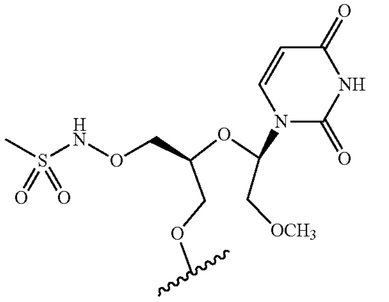
-continued
Formula (85A)
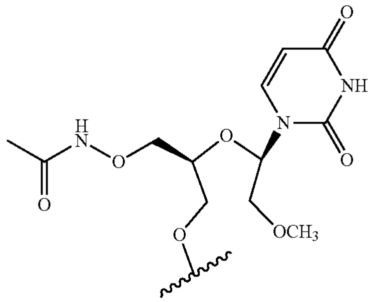
Formula (86A)
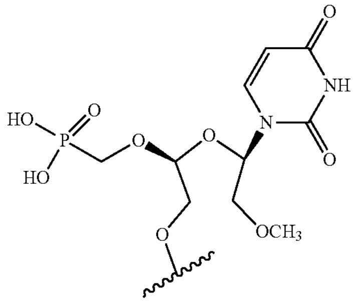
Formula (86XA)
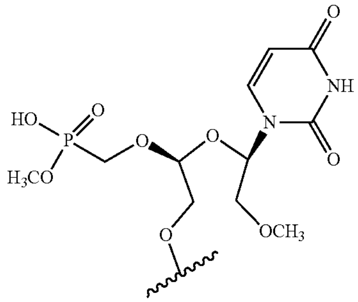
Formula (86X'A)
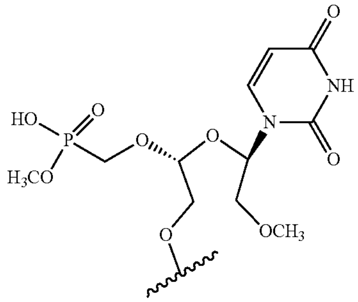
Formula (86Y)
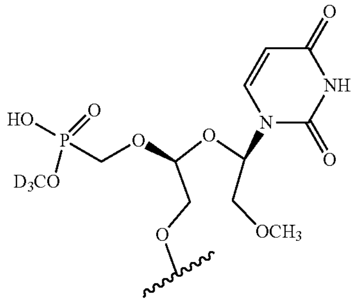

-continued

Formula (86Y')

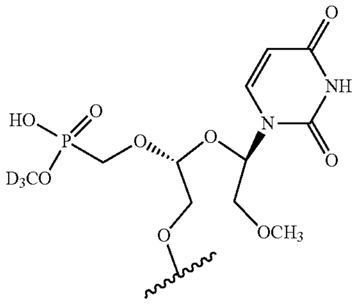

In some embodiments, any of the siNA molecules disclosed herein comprise a 5'-stabilized end cap selected from the group consisting of Formula (78A), Formula (79A), Formula (79XA), Formula (79YA), Formula (86A), Formula (86XA), and Formula (86X'A):

Formula (78A)

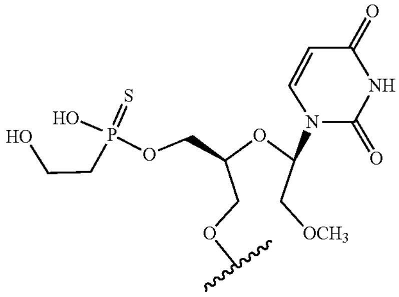

Formula (79A)

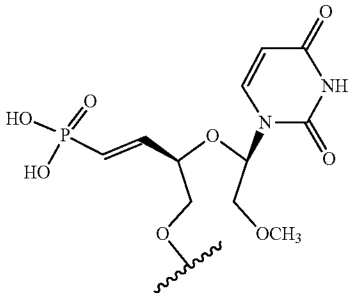

Formula (79xA)

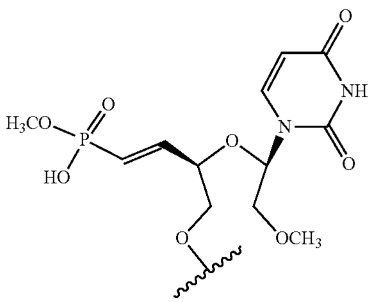

-continued

Formula (79YA)

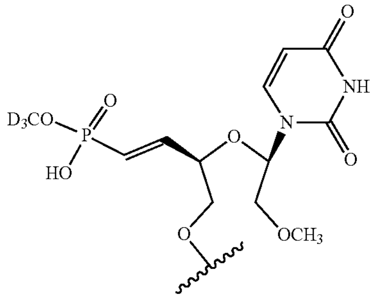

Formula (86A)

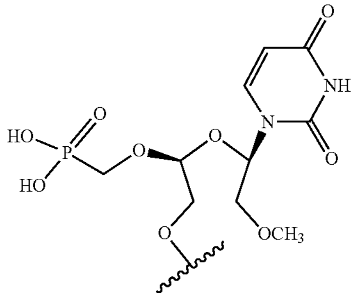

Formula (86XA)

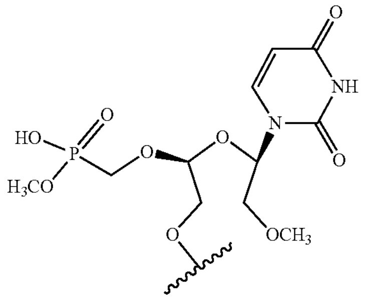

Formula (86X'A)

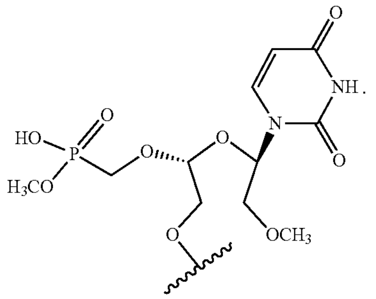

In some embodiments, the 5'-stabilized end cap is attached to the 5' end of the antisense strand. In some embodiments, the 5'-stabilized end cap is attached to the 5' end of the antisense strand via 1, 2, 3, 4, or 5 or more linkers. In some embodiments, the one or more linkers are independently selected from the group consisting of a phosphodiester (p or po) linker, phosphorothioate (ps) linker, mesyl phosphoramidate (Ms) linker, phosphoramidite (HEG) linker, triethylene glycol (TEG) linker, and/or phosphorodithioate linker. In some embodiments, the one or more linkers are independently selected from the group consisting of p-$(PS)_2$, $(PS)_2$-p-TEG-p, $(PS)_2$-p-IEG-p, and $(PS)_2$-p-(HEG-$p)_2$.

As indicated above, the present disclosure provides compositions comprising any of the siNA molecules, sense strands, antisense strands, first nucleotide sequences, or second nucleotide sequences described herein. The disclosed siNA and compositions thereof can be used in the treatment of various diseases and conditions (e.g., viral diseases, liver disease, etc.).

Linker

In some embodiments, any of the siRNAs, sense strands, first nucleotide sequences, antisense strands, and/or second nucleotide sequences disclosed herein comprise 1, 2, 3, 4, 5, 6, 7, 8, 9, 10, 11, 12, 13, 14, 15, 16, 17, 18, 19, 20, 21, 22, 23 or more internucleoside linkers. In some embodiments, 1, 2, 3, 4, 5, 6, 7, 8, 9, 10 or more internucleoside linkers are independently selected from the group consisting of a phosphodiester (p or po) linker, phosphorothioate (ps) linker, mesyl phosphoramidate (Ms) linker, or phosphorodithioate linker.

In some embodiments, any of the siRNAs, sense strands, first nucleotide sequences, antisense strands, and/or second nucleotide sequences disclosed herein further comprise 1, 2, 3, 4 or more linkers that attach a conjugated moiety, phosphorylation blocker, and/or 5' end cap to the siRNA, sense strand, first nucleotide sequence, antisense strand, and/or second nucleotide sequences. In some embodiments, the 1, 2, 3, 4 or more linkers are independently selected from the group consisting of a phosphodiester (p or po) linker, phosphorothioate (ps) linker, mesyl phosphoramidate (Ms), phosphoramidite (HEG) linker, triethylene glycol (TEG) linker, and/or phosphorodithioate linker. In some embodiments, the one or more linkers are independently selected from the group consisting of p-(PS)2, (PS)2-p-TEG-p, (PS)2-p-HEG-p, and (PS)2-p-(IEG-p)2.

Exemplary siNA

As noted above, the siNA disclosed herein may comprise a modified nucleotide, such as the 2'-fluoro nucleotide fB, fN, or 4 (4nh)Q. Other 2'-fluoro nucleotides, such as f2P, f4P, and fX may be incorporated into the disclosed siNA as well. A siNA comprising a disclosed 2'-fluoro nucleotide (e.g., fB, fN, or 4 (4nh)Q and bolded in the Table) may comprise one or more of the disclosed 2'-fluoro nucleotides and the one or more 2'-fluoro nucleotides may be present in the sense strand or the antisense strand or both. Table 1 shows exemplary siNA comprising these 2'-fluoro nucleotides.

TABLE 1 siNA Comprising 2'-Fluoro Nucleotides

| Name | SS/AS 5' to 3' |
|---|---|
| ds-siNA-001 | mGpsmUpsmGmGfUmGfGfAfCmUmUmCmUmCmUmCmAmAmU (SEQ ID NO: 1)<br>mAps**f2P**psmUmGmAfGmAmGmAmAmGmUmCfCmAfCmCmAmCpsmGpsmA (SEQ ID NO: 2) |
| ds-siNA-002 | mGpsmUpsmGmGfUmGfGfAfCmUmUmCmUmCmUmCmAmAmU (SEQ ID NO: 3)<br>mApsfUpsmUmGmAfGmAmGmAmAmGmUmC**f4P**mAfCmCmAmCpsmGpsmA (SEQ ID NO: 4) |
| ds-siNA-003 | mGpsmUpsmGmGfUmGfGfAfCmUmUmCmUmCmUmCmAmAmU (SEQ ID NO: 5)<br>mApsfUpsmUmGmAfGmAmGmAmAmGmUmCfCmA**f2P**mCmAmCpsmGpsmA (SEQ ID NO: 6) |
| ds-siNA-004 | mGpsmUpsmGmGfUmGfGfAfCmUmUmCmUmCmUmCmAmAmU (SEQ ID NO: 7)<br>mApsfUpsmUmGmAfGmAmGmAmAmGmUmC**f2P**mA**f2P**mCmAmCpsmGpsmA (SEQ ID NO: 8) |
| ds-siNA-005 | mGpsmUpsmGmGfUmGfGfAfCmUmUmCmUmCmUmCmAmAmU (SEQ ID NO: 9)<br>mAps**fB**psmUmGmAfGmAmGmAmAmGmUmCfCmAfCmCmAmCpsmGpsmA (SEQ ID NO: 10) |
| ds-siNA-006 | mGpsmUpsmGmGfUmGfGfAfCmUmUmCmUmCmUmCmAmAmU (SEQ ID NO: 11)<br>mApsfUpsmUmGmAfGmAmGmAmAmGmUmC**fB**mAfCmCmAmCpsmGpsmA (SEQ ID NO: 12) |
| ds-siNA-007 | mGpsmUpsmGmGfUmGfGfAfCmUmUmCmUmCmUmCmAmAmU (SEQ ID NO: 13)<br>mApsfUpsmUmGmAfGmAmGmAmAmGmUmC**fB**mA**fB**mCmAmCpsmGpsmA (SEQ ID NO: 14) |
| ds-siNA-008 | mGpsmUpsmGmGfUmGfGfAfCmUmUmCmUmCmUmCmAmAmU (SEQ ID NO: 15)<br>mApsfUpsmUmGmAfGmAmGmAmAmGmUmC**f2P**mAfCmCmAmCpsmGpsmA (SEQ ID NO: 16) |
| ds-siNA-O23 | 5'-mCpsmCpsmGmUfGmUfGf**(4nh)Q**fAmCmUmUmCmGmCmUmUmCmA-**p-(ps)2-GalNAc4** (SEQ ID NO: 63)<br>3'-mCpsmUpsmGmGfCmAmCfAmCmGmUmGmAfAmGmCfGmAmApsfGps**d2vd3U**-5' (SEQ ID NO: 64) |

TABLE 1-continued

| siNA Comprising 2'-Fluoro Nucleotides | |
|---|---|
| Name | SS/AS 5' to 3' |
| ds-siNA-O24 | 5 ' -mCpsmCpsmGmUfGmUfGfCfAmCmUmUmCmGmCmUmUmCm A-**p-(ps)2-GalNAc4** (SEQ ID NO: 65) 3'-mCpsmUpsmGmGfCmAmCfAmCmGmUmGmAfAmGf**(4nh)Q**fGmAmApsf Gpsd**2vd3U**-5' (SEQ ID NO: 66) |
| ds-siNA-O25 | 5 ' -mCpsmCpsmGmUfGmUfGfCfAmCmUmUmCmGmCmUmUmCm A-**p-(ps)2GalNAc4** (SEQ ID NO: 67) 3'-mCpsmUpsmGmGf**(4nh)Q**mAmCfAmCmGmUmGmAfAmGmCfGmAmApsf Gps**d2vd3U**-5' (SEQ ID NO: 68) |

mX = 2'-O-methyl nucleotide;

fX = 2'-fluoro nucleotide;

5dcd3X = nucleotide of Formula 17;

5dfX = nucleotide of Formula 16;

vX= 5' vinyl phosphonate nucleotide;

d2vX = deuterated 5' vinyl phosphonate nucleotide;

vmX = 5' vinyl phosphonate, 2'-O-methyl nucleotide;

;

f4P =

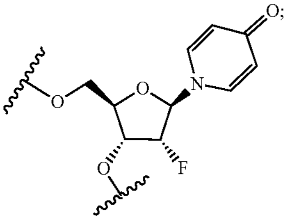 [SMILES: *OC[C@H]1O[C@@H](n2ccc(=O)cc2)[C@H](F)[C@@H]1O*]

f2P =

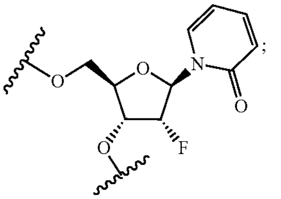 [SMILES: *OC[C@H]1O[C@@H](n2ccccc2=O)[C@H](F)[C@@H]1O*]

fB =

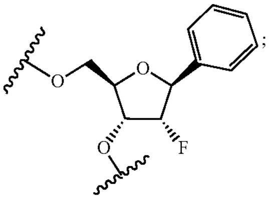 [SMILES: *OC[C@H]1O[C@@H](c2ccccc2)[C@H](F)[C@@H]1O*]

f(4nh)Q =

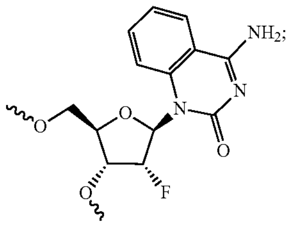

ps = phosphorothioate linkage;

X is a nucleobase (e.g. A, G, C, U or T)

Additionally or alternatively, the disclosed siNA may also incorporate a novel nucleotide phosphate mimic (e.g., omeco-d3U, 4hU, v-mun, c2o-4h, omeco-mun, d2vmA, coc-4h, 4H-VP nucleotide). Table 2 shows exemplary siNA comprising these nucleotide phosphate mimics. A siNA comprising a disclosed novel phosphate mimic (e.g., omeco-d3U, 4hU, v-mun, c2o-4h, omeco-mun, coc-4h, or d2vmA and bolded in the Table) may comprise one or more of the disclosed novel phosphate mimic and the one or more novel phosphate mimics may be present in the sense strand or the antisense strand or both.

TABLE 2 siNA Comprising Nucleotide Phosphate Mimics

| Name | SS/AS 5' to 3' |
|---|---|
| ds-siNA-009 | mCpsmCpsmGmUfGmUfGfCfAmCmUmUmCmGmCmUmUmCmAp-ps2-GalNAc4<br>(SEQ ID NO: 17)<br>**omeco-d3U**psfGpsmAmAfGmCmGfAmAmGmUmGmCfAmCmAfCmGmGpsmUpsmC<br>(SEQ ID NO: 18) |
| ds-siNA-010 | mCpsmCpsmGmUfGmUfGfCfAmCmUmUmCmGmCmUmUmCmAp-ps2-GalNAc4<br>(SEQ ID NO: 19)<br>**4hU**psfGpsmAmAfGmCmGfAmAmGmUmGmCfAmCmAfCmGmGpsmUpsmC<br>(SEQ ID NO: 20) |
| ds-siNA-011 | mCpsmCpsmGmUfGmUfGfCfAmCmUmUmCmGmCmUmUmCmAp-ps2-GalNAc4<br>(SEQ ID NO: 21)<br>**d2vd3U**psfGpsmAmAfGmCmGfAmAmGmUmGmCfAmCmAfCmGmGpsmUpsmC<br>(SEQ ID NO: 22) |
| ds-siNA-012 | mCpsmCpsmGmUfGmUfGfCfAmCmUmUmCmGmCmUmUmCmA-p-ps2-GalNAc4<br>(SEQ ID NO: 23)<br>V-**munU**psfGpsmAmAfGmCmGfAmAmGmUmGmCfAmCmAfCmGmGpsmUpsmC<br>(SEQ ID NO: 24) |
| ds-siNA-013 | mCpsmCpsmGmUfGmUfGfCfAmCmUmUmCmGmCmUmUmCmA-p-ps2-GalNAc4<br>(SEQ ID NO: 25)<br>**c2o-4hU**psfGpsmAmAfGmCmGfAmAmGmUmGmCfAmCmAfCmGmGpsmUpsmC<br>(SEQ ID NO: 26) |
| ds-siNA-014 | mCpsmCpsmGmUfGmUfGfCfAmCmUmUmCmGmCmUmUmCmA-p-ps2-GalNAc4<br>(SEQ ID NO: 27)<br>omeco-**munU**psfGpsmAmAfGmCmGfAmAmGmUmGmCfAmCmAfCmGmGpsmUpsmC<br>(SEQ ID NO: 28) |
| ds-siNA-015 | mCpsmCpsmGmUfGmUfGfCfAmCmUmUmCmGmCmUmUmCmA-p-ps2-GalNAc4<br>(SEQ ID NO: 29)<br>**omeco-munU**psfGpsmAmAfGmCmGfAmAmGmUmGmCfAmCmAfCmGmGpsmUpsmC<br>(SEQ ID NO: 30) |
| ds-siNA-016 | mGpsmUpsmGmGfUmGfGfAfCmUmUmCmUmCmUmCmAmAmU-p-ps2-GalNAc4<br>(SEQ ID NO: 33)<br>d2vmApsfUpsmUmGmAfGmAmGmAmAmGmUmCfCm**Af2P**mCmAmCpsmGpsmA<br>(SEQ ID NO: 34) |
| ds-siNA-050 | mCpsmCpsmGmUfGmUfGfCfAmCmUmUmCmGmCmUmUmCmA-p-(ps)2-GalNAc4<br>(SEQ ID NO: 111) |

TABLE 2-continued siNA Comprising Nucleotide Phosphate Mimics

| Name | SS/AS 5' to 3' |
|---|---|
| | **coc-4hU**psfGpsmAmAfGmCmGfAmAmGmUmGmCfAmCmAfCmGmGpsm UpsmC (SEQ ID NO: 112) |

mX = 2'-O-methyl nucleotide;
fX = 2'-fluoro nucleotide;
5dcd3X = nucleotide of Formula 17;
5dfX = nucleotide of Formula 16;
vX= 5' vinyl phosphonate nucleotide;
d2vX = deuterated 5' vinyl phosphonate nucleotide;
vmX = 5' vinyl phosphonate, 2'-O-methyl nucleotide;
omeco-d3U =

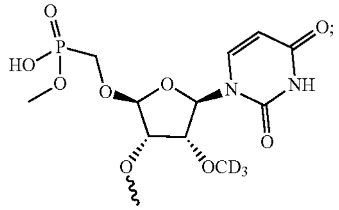

4hU =

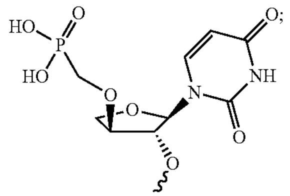

d2vd3U =

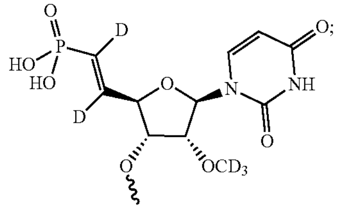

v-munU =

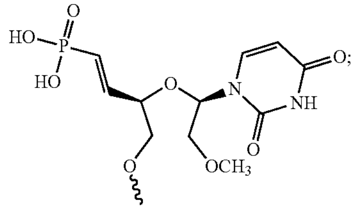

c2o-4hU =

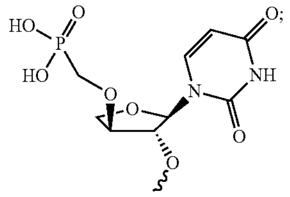

coc-4hU =

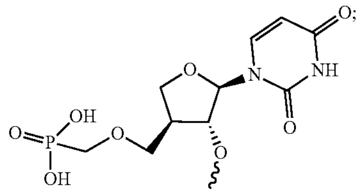

omeco-munU =

TABLE 2-continued

| siNA Comprising Nucleotide Phosphate Mimics | |
|---|---|
| Name | SS/AS 5' to 3' |

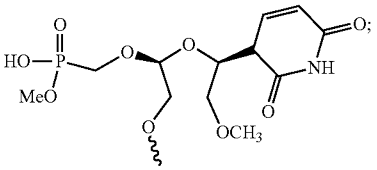

ps = phosphorothioate linkage;
X is a nucleobase (e.g. A, G, C, U or T)

Additionally or alternatively, the disclosed siNA may also incorporate a novel unlocked nucleotide monomers. These novel unlocked nucleotides may have of structure of

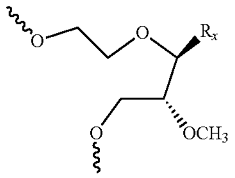

(wherein $R_x$ is a nucleobase, aryl, heteroaryl, or H) or, more specifically,

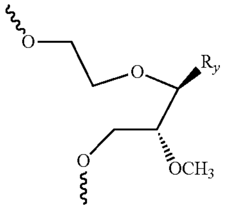

(mun34)

wherein $R_y$ is a nucleobase. These unlocked nucleotides are distinct from unlock nucleic acids (UNA) known in the art in which the 2' to 3' bond is missing (e.g., 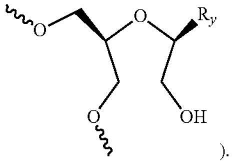 ).

Table 3 shows exemplary siNA comprising these unlocked nucleotides. A siNA comprising a 3',4' UNA (e.g., mun34) may comprise one or more of the disclosed 3', 4' UNAs and the one or more 3', 4' UNAs may be present in the sense strand or the antisense strand or both.

TABLE 3

| siNA Comprising Modified Unlocked Nucleotides | |
|---|---|
| Name | SS/AS (5' to 3') |
| ds-siNA-017 | mCpsmCpsmGmUfGmUfGfCfAmCmUmUmCmGmCmUmUmCmA (SEQ ID NO: 35) mUpsfGpsmAmAfG**mun34C**mGfAmAmGmUmGmCfAmCmAfCmGmGpsmUpsmC (SEQ ID NO: 36) |
| ds-siNA-018 | mCpsmCpsmGmUfGmUfGfCfAmCmUmUmCmGmCmUmUmCmA (SEQ ID NO: 37) mUpsfGpsmAmAfGmC**mun34G**fAmAmGmUmGmCfAmCmAfCmGmGpsmUpsmC (SEQ ID NO: 38) |
| ds-siNA-019 | mCpsmCpsmGmUfGmUfGfCfAmCmUmUmCmGmCmUmUmCmA-**p-ps2-GalNAc4** (SEQ ID NO: 39) **d2vd3U**psfGpsmAmAfGmC**mun34G**fAmAmGmUmGmCfAmCmAfCmGmGpsmUpsmC (SEQ ID NO: 40) |
| ds-siNA-034 | mCpsmCps**mun34G**mUfGmUfGfCfAmCmUmUmCmGmCmUmUmCmA (SEQ ID NO: 93) psmUpsfGmAmAfGmCmGfAmAmGmUmGmCfAmCmAfCmGpsmGpsmUmC (SEQ ID NO: 94) |
| ds-siNA-035 | mCpsmCpsmG**mun34U**fGmUfGfCfAmCmUmUmCmGmCmUmUmCmA (SEQ ID NO: 95) |

TABLE 3-continued siNA Comprising Modified Unlocked Nucleotides

| Name | SS/AS (5' to 3') |
|---|---|
| | psmUpsfGmAmAfGmCmGfAmAmGmUmGmCfAmCmAfCmGpsmGpsmUmC (SEQ ID NO: 94) |
| ds-siNA-036 | mCpsmCpsmGmUfG**mun34U**fGfCfAmCmUmUmCmGmCmUmUmCmA (SEQ ID NO: 96) psmUpsfGmAmAfGmCmGfAmAmGmUmGmCfAmCmAfCmGpsmGpsmUmC (SEQ ID NO: 94) |
| ds-siNA-037 | mCpsmCpsmGmUfGmUfGfCfA**mun34C**mUmUmCmGmCmUmUmCmA (SEQ ID NO: 97) psmUpsfGmAmAfGmCmGfAmAmGmUmGmCfAmCmAfCmGpsmGpsmUmC (SEQ ID NO: 94) |
| ds-siNA-038 | mCpsmCpsmGmUfGmUfGfCfAmC**mun34U**mUmCmGmCmUmUmCmA (SEQ ID NO: 98) psmUpsfGmAmAfGmCmGfAmAmGmUmGmCfAmCmAfCmGpsmGpsmUmC (SEQ ID NO: 94) |
| ds-siNA-039 | mCpsmCpsmGmUfGmUfGfCfAmCmU**mun34U**mCmGmCmUmUmCmA (SEQ ID NO: 99) psmUpsfGmAmAfGmCmGfAmAmGmUmGmCfAmCmAfCmGpsmGpsmUmC (SEQ ID NO: 94) |
| ds-siNA-040 | mCpsmCpsmGmUfGmUfGfCfAmCmUmU**mun34C**mGmCmUmUmCmA (SEQ ID NO: 100) psmUpsfGmAmAfGmCmGfAmAmGmUmGmCfAmCmAfCmGpsmGpsmUmC (SEQ ID NO: 94) |
| ds-siNA-041 | mCpsmCpsmGmUfGmUfGfCfAmCmUmUmC**mun34G**mCmUmUmCmA (SEQ ID NO: 101) psmUpsfGmAmAfGmCmGfAmAmGmUmGmCfAmCmAfCmGpsmGpsmUmC (SEQ ID NO: 94) |
| ds-siNA-042 | mCpsmCpsmGmUfGmUfGfCfAmCmUmUmCmG**mun34C**mUmUmCmA (SEQ ID NO: 102) psmUpsfGmAmAfGmCmGfAmAmGmUmGmCfAmCmAfCmGpsmGpsmUmC (SEQ ID NO: 94) |
| ds-siNA-043 | mCpsmCpsmGmUfGmUfGfCfAmCmUmUmCmGmC**mun34U**mUmCmA (SEQ ID NO: 103) psmUpsfGmAmAfGmCmGfAmAmGmUmGmCfAmCmAfCmGpsmGpsmUmC (SEQ ID NO: 94) |
| ds-siNA-044 | mCpsmCpsmGmUfGmUfGfCfAmCmUmUmCmGmCmU**mun34U**mCmA (SEQ ID NO: 104) psmUpsfGmAmAfGmCmGfAmAmGmUmGmCfAmCmAfCmGpsmGpsmUmC (SEQ ID NO: 94) |
| ds-siNA-045 | mCpsmCpsmGmUfGmUfGfCfAmCmUmUmCmGmCmUmU**mun34C**mA (SEQ ID NO: 105) psmUpsfGmAmAfGmCmGfAmAmGmUmGmCfAmCmAfCmGpsmGpsmUmC (SEQ ID NO: 94) |

mX = 2'-O-methyl nucleotide;
fX = 2'-fluoro nucleotide;
5dcd3X = nucleotide of Formula 17;
5dfX = nucleotide of Formula 16;
vX = 5' vinyl phosphonate nucleotide;
d2vX = deuterated 5' vinyl phosphonate nucleotide;
vmX = 5' vinyl phosphonate, 2'-O-methyl nucleotide;
d2vd3U =

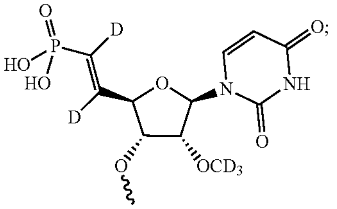

mun34C =

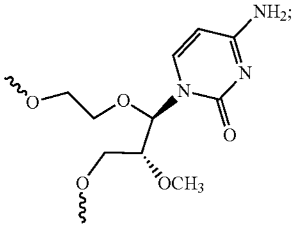

TABLE 3-continued

| siNA Comprising Modified Unlocked Nucleotides | |
|---|---|
| Name | SS/AS (5' to 3') |

mun34G =

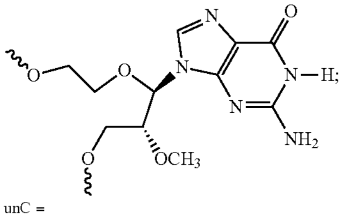

unC =

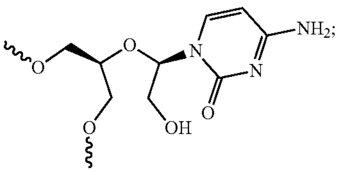

unG =

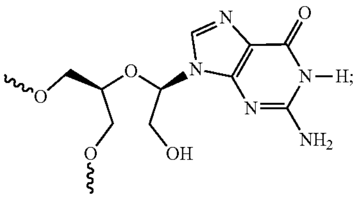

ps = phosphorothioate linkage;
X is a nucleobase (e.g. A, G, C, U or T)

Additionally or alternatively, the disclosed siNA may also incorporate 1 or more mesyl phosphoroamidate internucleoside linkages. The mesyl phosphoroamidate internucleoside linkage (also known as "yp") may have the structure of

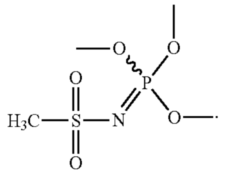

Table 4 shows exemplary siNA comprising these mesyl phosphoroamidate internucleoside linkages. A siNA comprising mesyl phosphoroamidate internucleoside linkage (denoted "yp" and bolded in the Table) may comprise one or more yp linkages and the one or more yp linkages may be present in the sense strand or the antisense strand or both.

TABLE 4

| siNA Comprising Mesyl Phosphoroamidate Internucleoside Linkages | |
|---|---|
| Name | SS/AS (5' to 3') |
| ds-siNA-020 | 5'-mGpsmUpsmGmGfUmGfGfAfCmUmUmCmUmCmUmCm Am AmU-**p-(ps)2-GalNAc4** (SEQ ID NO: 69) 3'-mApsmGpsmCmAmCfCmAfCmCmUmGmAmAmGmAfGmAmGmUypfUypm A-5' (SEQ ID NO: 70) |
| ds-siNA-021 | 5'-mGpsmUpsmGmGfUmGfGfAfCmUmUmCmUmCmUmCm Am AmU-**p-(ps)2-GalNAc4** (SEQ ID NO: 71) 3'- |

TABLE 4-continued

| siNA Comprising Mesyl Phosphoroamidate Internucleoside Linkages | |
|---|---|
| Name | SS/AS (5' to 3') |
| | mA**yp**mG**yp**mCmAmCfCmAfCmCmUmGmAmAmGmAfGmAmGmUpsfUpsm A-5' (SEQ ID NO: 72) |
| ds-siNA-022 | 5'-mGpsmUpsmGmGfUmGfGfAfCmUmUmCmUmCmUmCm Am AmU-**p-(ps)2-GalNAc4** (SEQ ID NO: 73) |
| | 3'-mA**yp**mG**yp**mCmAmCfCmAfCmCmUmGmAmAmGmAfGmAmGmU**yp**fU**yp** mA-5' (SEQ ID NO: 74) |

mX = 2'-O-methyl nucleotide;
fX = 2'-fluoro nucleotide;
ps = phosphorothioate linkage;
X is a nucleobase (e.g. A, G, C, U or T);
yp =

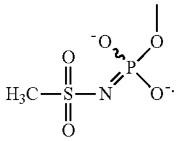

Additionally or alternatively, the disclosed siNA may also incorporate a novel monomer referred to herein as "apN," which has a structure of

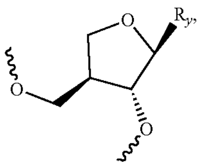

wherein Ry represents a nucleobase (e.g., U, A, G, T, C), and in some embodiments, the apN may be an "apU," which has a structure of

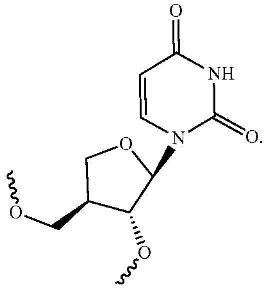

Table 5 shows exemplary siNA comprising these modified nucleotides. A siNA comprising an apU nucleotide (denoted "aU" and bolded in the Table) may comprise one or more apU nucleotides and the one or more apU nucleotides may be present in the sense strand or the antisense strand or both.

TABLE 5

| siNA Comprising Modified apU Nucleotides | |
|---|---|
| Name | SS/AS (5' to 3') |
| ds-siNA-026 | mCpsmCpsmGaUfGmUfGfCfAmCmUmUmCmGmCmUmUmCmA-**p-(ps)2-GalNAc4** (SEQ ID NO: 77) |
| | **d2vd3U**psfGpsmAmAfGmCmGfAmAmGmUmGmCfAmCmAfCmGmGpsmUp smC (SEQ ID NO: 78) |
| ds-siNA-027 | mCpsmCpsmGmUfG**aU**fGfCfAmCmUmUmCmGmCmUmUmCmA-**p-(ps)2-GalNAc4** (SEQ ID NO: 79) |
| | **d2vd3U**psfGpsmAmAfGmCmGfAmAmGmUmGmCfAmCmAfCmGmGpsmUp smC (SEQ ID NO: 80) |
| ds-siNA-028 | mCpsmCpsmGmUfGmUfGfCfAmCmUaUmCmGmCmUmUmCmA-**p-(ps)2-GalNAc4** (SEQ ID NO: 81) |
| | **d2vd3U**psfGpsmAmAfGmCmGfAmAmGmUmGmCfAmCmAfCmGmGpsmUp smC (SEQ ID NO: 82) |
| ds-siNA-O29 | mCpsmCpsmGmUfGmUfGfCfAmCmUmUmCmGmC**aU**mUmCmA-**p-(ps)2-GalNAc4** (SEQ ID NO: 83) |

TABLE 5-continued siNA Comprising Modified apU Nucleotides

| Name | SS/AS (5' to 3') |
|---|---|
| | **d2vd3U**psfGpsmAmAfGmCmGfAmAmGmUmGmCfAmCmAfCmGmGpsmUpsmC (SEQ ID NO: 84) |
| ds-siNA-030 | mCpsmCpsmGmUfGmUfGfCfAmCmUmUmCmGmCmU**aU**mCmA-**p-(ps)2-GalNAc4** (SEQ ID NO: 85) |
| | **d2vd3U**psfGpsmAmAfGmCmGfAmAmGmUmGmCfAmCmAfCmGmGpsmUpsmC (SEQ ID NO: 86) |
| ds-siNA-031 | mCpsmCpsmGmUfGmUfGfCfAmCmUmUmCmGmCmUmUmCmA-**p-(ps)2-GalNAc4** (SEQ ID NO: 87) |
| | **d2vd3U**psfGpsmAmAfGmCmGfAmAmG**aU**mGmCfAmCmAfCmGmGpsmUpsmC (SEQ ID NO: 88) |
| ds-siNA-032 | mCpsmCpsmGmUfGmUfGfCfAmCmUmUmCmGmCmUmUmCmA-**p-(ps)2-GalNAc4** (SEQ ID NO: 89) |
| | **d2vd3U**psfGpsmAmAfGmCmGfAmAmGmUmGmCfAmCmAfCmGmGps**aU**psmC (SEQ ID NO: 90) |
| ds-siNA-O33 | mCpsmCpsmGmUfGmUfGfCfAmCmUmUmCmGmCmUmUmCmA-p-(ps)2-GalNAc4 (SEQ ID NO: 91) |
| | **aU**psfGpsmAmAfGmCmGfAmAmGmUmGmCfAmCmAfCmGmGpsmUpsmC (SEQ ID NO: 92) |

mX = 2'-O-methyl nucleotide;
fX = 2'-fluoro nucleotide;
5dcd3X = nucleotide of Formula 17;
5dfX = nucleotide of Formula 16;
vX= 5' vinyl phosphonate nucleotide;
d2vX = deuterated 5' vinyl phosphonate nucleotide;
vmX = 5' vinyl phosphonate, 2'-O-methyl nucleotide;
d2vd3U =

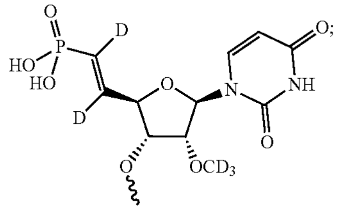

aU =

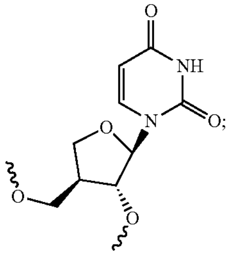

ps = phosphorothioate linkage;
X is a nucleobase (e.g. A, G, C, U or T)

Target Gene

Without wishing to be bound by theory, upon entry into a cell, any of the ds-siNA molecules disclosed herein may interact with proteins in the cell to form a RNA-Induced Silencing Complex (RISC). Once the ds-siNA is part of the RISC, the ds-siNA may be unwound to form a single-stranded siNA (ss-siNA). The ss-siNA may comprise the antisense strand of the ds-siNA. The antisense strand may bind to a complementary messenger RNA (mRNA), which results in silencing of the gene that encodes the mRNA.

The target gene may be any gene in a cell. In some embodiments, the target gene is a viral gene. In some embodiments, the viral gene is from a DNA virus. In some embodiments, the DNA virus is a double-stranded DNA (dsDNA) virus. In some embodiments, the dsDNA virus is a hepadnavirus. In some embodiments, the hepadnavirus is a hepatitis B virus (HBV). In some embodiments, the HBV is selected from HBV genotypes A-J. In some embodiments, the viral disease is caused by an RNA virus. In some embodiments, the RNA virus is a single-stranded RNA virus (ssRNA virus). In some embodiments, the ssRNA virus is a positive-sense single-stranded RNA virus ((+)ssRNA virus). In some embodiments, the (+)ssRNA virus is a coronavirus. In some embodiments, the coronavirus is a β-coronaviruses. In some embodiments, the β-coronaviruses is selected from the group consisting of severe acute respiratory syndrome coronavirus 2 (SARS-CoV-2) (also known by the provisional name 2019 novel coronavirus, or 2019-nCoV), human coronavirus OC43 (hCoV-OC43), Middle East respiratory syndrome-related coronavirus (MERS-CoV, also known by the provisional name 2012 novel coronavirus, or 2012-nCoV), and severe acute respiratory syndrome-related coronavirus (SARS-CoV, also known as SARS-CoV-1). In some embodiments, the β-coronaviruses is SARS-CoV-2, the causative agent of COVID-19. Some exemplary target genes are shown in Table 17 at the end of the specification.

In some embodiments, the target gene is selected from the S gene or X gene of the HBV. In some embodiments, the HBV has a genome sequence shown in the nucleotide sequence of SEQ ID NO: 55 which corresponds to the nucleotide sequence of GenBank Accession No. U95551.1, which is incorporated by reference in its entirety.

An exemplary HBV genome sequence is shown in SEQ ID NO: 60, corresponding to Genbank Accession No. KC315400.1, which is incorporated by reference in its entirety. Nucleotides 2307 . . . 3215, 1 . . . 1623 of SEQ ID NO: 60 correspond to the polymerase/RT gene sequence, which encodes for the polymerase protein. Nucleotides 2848 . . . 3215, 1 . . . 835 of SEQ ID NO: 60 correspond to the PreS1/S2/S gene sequence, which encodes for the large S protein. Nucleotides 3205 . . . 3215, 1 . . . 835 of SEQ ID NO: 60 correspond to the PreS2/S gene sequence, which encodes for the middle S protein. Nucleotides 155 . . . 835 of SEQ ID NO: 60 correspond to the S gene sequence, which encodes the small S protein. Nucleotides 1374 . . . 1838 of SEQ ID NO: 60 correspond to the X gene sequence, which encodes the X protein. Nucleotides 1814 . . . 2452 of SEQ ID NO: 60 correspond to the PreC/C gene sequence, which encodes the precore/core protein. Nucleotides 1901 . . . 2452 of SEQ ID NO: 60 correspond to the C gene sequence, which encodes the core protein. The HBV genome further comprises viral regulatory elements, such as viral promoters (preS2, preS1, Core, and X) and enhancer elements (ENH1 and ENH2). Nucleotides 1624 . . . 1771 of SEQ ID NO: 60 correspond to ENH2. Nucleotides 1742 . . . 1849 of SEQ ID NO: 60 correspond to the Core promoter. Nucleotides 1818 . . . 3215, 1 . . . 1930 of SEQ ID NO: 60 correspond to the pregenomic RNA (pgRNA), which encodes the core and polymerase proteins.

In some embodiments, the sense strand comprises a sequence that is at least about 60%, 65%, 70%, 75%, 80%, 85%, 90%, 95%, or 100% complementary or hybridizes to a viral target RNA sequence that begins in an X region of HBV or in an S region of HBV. The viral target may, e.g., begin at the 5'-end of target-site in acc. KC315400.1 (genotype B, "gt B"), or in any one of genotypes A, C, or D. The skilled person would understand the HBV position, e.g., as described in Wing-Kin Sung, et al., *Nature Genetics* 44:765 (2012). In some embodiments, the S region is defined as from the beginning of small S protein (in genotype B KC315400.1 isolate, position #155) to before beginning of X protein (in genotype B KC315400.1 isolate, position #1373). In some embodiments, the X region is defined as from the beginning X protein (in genotype B KC315400.1 isolate, position #1374) to end of DR2 site (in genotype B KC315400.1 isolate, position #1603).

In some embodiments, the second nucleotide sequence is at least about 60%, 65%, 70%, 75%, 80%, 85%, 90%, 95%, or 100% complementary to 15 to 30, 15 to 25, 15 to 23, 15 to 22, 15 to 21, 17 to 25, 17 to 23, 17 to 22, 17 to 21, or 19 to 21 nucleotides within positions 200-720 or 1100-1700 of SEQ ID NO: 55. In some embodiments, the second nucleotide sequence is at least about 60%, 65%, 70%, 75%, 80%, 85%, 90%, 95%, or 100% complementary to 15 to 30, 15 to 25, 15 to 23, 15 to 22, 15 to 21, 17 to 25, 17 to 23, 17 to 22, 17 to 21, or 19 to 21 nucleotides within positions 200-280, 300-445, 460-510, 650-720, 1170-1220, 1250-1300, or 1550-1630 of SEQ ID NO: 55. In some embodiments, the second nucleotide sequence is at least about 60%, 65%, 70%, 75%, 80%, 85%, 90%, 95%, or 100% complementary to 15 to 30, 15 to 25, 15 to 23, 15 to 22, 15 to 21, 17 to 25, 17 to 23, 17 to 22, 17 to 21, or 19 to 21 nucleotides within positions 200-230, 250-280, 300-330, 370-400, 405-445, 460-500, 670-700, 1180-1210, 1260-1295, 1520-1550, or 1570-1610 of SEQ ID NO: 55. In some embodiments, the second nucleotide sequence is at least about 60%, 65%, 70%, 75%, 80%, 85%, 90%, 95%, or 100% complementary to 15 to 30, 15 to 25, 15 to 23, 15 to 22, 15 to 21, 17 to 25, 17 to 23, 17 to 22, 17 to 21, or 19 to 21 nucleotides starting at position 203, 206, 254, 305, 375, 409, 412, 415, 416, 419, 462, 466, 467, 674, 676, 1182, 1262, 1263, 1268, 1526, 1577, 1578, 1580, 1581, 1583, or 1584 of SEQ ID NO: 55.

In some embodiments, the first nucleotide is at least about 60%, 65%, 70%, 75%, 80%, 85%, 90%, 95%, or 100% identical to a nucleotide region within SEQ ID NO: 55, with the exception that the thymines (Ts) in SEQ ID NO: 55 are replaced with uracil (U). In some embodiments, the first nucleotide sequence is at least about 60%, 65%, 70%, 75%, 80%, 85%, 90%, 95%, or 100% identical to 15 to 30, 15 to 25, 15 to 23, 15 to 22, 15 to 21, 17 to 25, 17 to 23, 17 to 22, 17 to 21, or 19 to 21 nucleotides within positions 200-720 or 1100-1700 of SEQ ID NO: 55. In some embodiments, the first nucleotide sequence is at least about 60%, 65%, 70%, 75%, 80%, 85%, 90%, 95%, or 100% identical to 15 to 30, 15 to 25, 15 to 23, 15 to 22, 15 to 21, 17 to 25, 17 to 23, 17 to 22, 17 to 21, or 19 to 21 nucleotides within positions 200-280, 300-445, 460-510, 650-720, 1170-1220, 1250-1300, or 1550-1630 of SEQ ID NO: 55. In some embodiments, the first nucleotide sequence is at least about 60%, 65%, 70%, 75%, 80%, 85%, 90%, 95%, or 100% identical to 15 to 30, 15 to 25, 15 to 23, 15 to 22, 15 to 21, 17 to 25, 17 to 23, 17 to 22, 17 to 21, or 19 to 21 nucleotides within positions 200-230, 250-280, 300-330, 370-400, 405-445, 460-500, 670-700, 1180-1210, 1260-1295, 1520-1550, or 1570-1610 of SEQ ID NO: 55. In some embodiments, the first nucleotide sequence is at least about 60%, 65%, 70%, 75%, 80%, 85%, 90%, 95%, or 100% identical to 15 to 30, 15 to 25, 15 to 23, 15 to 22, 15 to 21, 17 to 25, 17 to 23, 17 to 22, 17 to 21, or 19 to 21 nucleotides starting at position 203, 206, 254, 305, 375, 409, 412, 415, 416, 419, 462, 466, 467, 674, 676, 1182, 1262, 1263, 1268, 1526, 1577, 1578, 1580, 1581, 1583, or 1584 of SEQ ID NO: 55.

Several disease-causing coronaviruses share a high degree of homology in the regions of the genome encoding non-structural proteins (nsp), and more specifically, in the region encoding nsp8-nsp15. Indeed, there is roughly 65% identity across the roughly 7 kB sequence of β-coronaviruses from about nucleotide 12900 to about nucleotide 19900 of 2019-nCoV, and some subsections of the genomic span of nsp8 to nsp15 may comprise 95% or more identity. All of the genes in this region encode non-structural proteins associated with replication. Accordingly, this segment of the genome is suitable for targeting with an siNA that can provide a broad spectrum treatment for multiple different types of coronavirus, such as MERS-CoV, SARS-CoV-1, and SARS-CoV-2.

In some embodiments, the target gene is selected from genome of SARS-COV-2. In some embodiments, SARS-COV-2 has a genome sequence shown in the nucleotide sequence of (SEQ ID NO: 113), which corresponds to the nucleotide sequence of GenBank Accession No. NC 045512.2, which is incorporated by reference in its entirety. In some embodiments, the target gene a sequence 15 to 30, 15 to 25, 15 to 23, 17 to 23, 19 to 23, or 19 to 21 nucleotides in length, and preferably 19 or 21 nucleotides in length, within (SEQ ID NO: 113). In some embodiments, the antisense strand sequence is complementary to 15 to 30, 15 to 25, 15 to 23, 15 to 22, 15 to 21, 17 to 25, 17 to 23, 17 to 22, 17 to 21, or 19 to 21 nucleotides, and preferably 19 to 21 nucleotides, and more preferably 19 or 21 nucleotides, within positions 190-216, 233-279, 288-324, 455-477, 626-651, 704-723, 3352-3378, 5384-5403, 6406-6483, 7532-7551, 9588-9606, 10484-10509, 11609-11630, 11834-11853, 12023-12045, 12212-12234, 12401-12420, 12839-12867, 12885-12924, 12966-12990, 13151-13176, 13363-13386, 13388-13416, 13458-13416, 13458-13520, 13762-13790, 14290-14312, 14404-14429, 14500-14531, 14623-14642, 14650-14687, 14698-14717, 14722-14748, 14750-14777, 14821-14846, 14854-14873, 14875-14903, 14962-14990, 14992-15020, 15055-15140, 15172-15200, 15310-15332, 15346-15367, 15496-15518, 15622-15644, 15838-15869, 15886-15905, 15985-16010, 16057-16079, 16186-16205, 16430-16448, 16822-16865, 16954-16976, 17008-17042, 17080-17111, 17137-17156, 17269-17289, 17530-17549, 17563-17582, 17680-17699, 17746-17765, 17857-17876, 17956-17975, 18100-18122, 18196-18218, 19618-19639, 19783-19802, 19831-19850, 20107-20130, 20776-20795, 21502-21524, 24302-24325, 24446-24465, 24620-24651, 24662-24684, 25034-25057, 25104-25128, 25364-25387, 25502-25530, 26191-26227, 26232-26267, 26269-26330, 26332-26394, 26450-26481, 26574-26600, 27003-27064, 27093-27111, 27183-27212, 27382-27407, 27511-27533, 27771-27818, 28270-28296, 28397-28434, 28513-28546, 28673-28692, 28706-28726, 28744-28794, 28799-28827, 28946-28972, 28976-29034, 29144-29172, 29174-29196, 29228-29259, 29285-29305, 29342-29394, 29444-29463, 29543-29566, 29598-29630, 29652-29687, 29689-29731, 29733-29757, or 29770-29828 of (SEQ ID NO: 113). In some embodiments, the sense strand sequence is identical to 15 to 30, 15 to 25, 15 to 23, 15 to 22, 15 to 21, 17 to 25, 17 to 23, 17 to 22, 17 to 21, or 19 to 21 nucleotides, and preferably 19 to 21 nucleotides, and more preferably 19 or 21 nucleotides, within positions 190-216, 233-279, 288-324, 455-477, 626-651, 704-723, 3352-3378, 5384-5403, 6406-6483, 7532-7551, 9588-9606, 10484-10509, 11609-11630, 11834-11853, 12023-12045, 12212-12234, 12401-12420, 12839-12867, 12885-12924, 12966-12990, 13151-13176, 13363-13386, 13388-13416, 13458-13416, 13458-13520, 13762-13790, 14290-14312, 14404-14429, 14500-14531, 14623-14642, 14650-14687, 14698-14717, 14722-14748, 14750-14777, 14821-14846, 14854-14873, 14875-14903, 14962-14990, 14992-15020, 15055-15140, 15172-15200, 15310-15332, 15346-15367, 15496-15518, 15622-15644, 15838-15869, 15886-15905, 15985-16010, 16057-16079, 16186-16205, 16430-16448, 16822-16865, 16954-16976, 17008-17042, 17080-17111, 17137-17156, 17269-17289, 17530-17549, 17563-17582, 17680-17699, 17746-17765, 17857-17876, 17956-17975, 18100-18122, 18196-18218, 19618-19639, 19783-19802, 19831-19850, 20107-20130, 20776-20795, 21502-21524, 24302-24325, 24446-24465, 24620-24651, 24662-24684, 25034-25057, 25104-25128, 25364-25387, 25502-25530, 26191-26227, 26232-26267, 26269-26330, 26332-26394, 26450-26481, 26574-26600, 27003-27064, 27093-27111, 27183-27212, 27382-27407, 27511-27533, 27771-27818, 28270-28296, 28397-28434, 28513-28546, 28673-28692, 28706-28726, 28744-28794, 28799-28827, 28946-28972, 28976-29034, 29144-29172, 29174-29196, 29228-29259, 29285-29305, 29342-29394, 29444-29463, 29543-29566, 29598-29630, 29652-29687, 29689-29731, 29733-29757, or 29770-29828 of (SEQ ID NO: 113).

In some embodiments, the target gene is selected from genome of SARS-CoV. In some embodiments, SARS-CoV has a genome corresponding to the nucleotide sequence of GenBank Accession No. NC_004718.3, which is incorporated by reference in its entirety.

In some embodiments, the target gene is selected from the genome of MERS-CoV. In some embodiments, MERS-CoV has a genome corresponding to the nucleotide sequence of GenBank Accession No. NC_019843.3, which is incorporated by reference in its entirety.

In some embodiments, the target gene is selected from the genome of hCoV-OC43. In some embodiments, hCoV-OC43 has a genome corresponding to the nucleotide sequence of GenBank Accession No. NC_006213.1, which is incorporated by reference in its entirety.

In some embodiments, the target gene is involved in liver metabolism. In some embodiments, the target gene is an inhibitor of the electron transport chain. In some embodiments, the target gene encodes the MCJ protein (MCJ/DnaJC15 or Methylation-Controlled J protein). In some embodiments, the MCJ protein is encoded by the mRNA sequence of SEQ ID NO: 56, which corresponds to the nucleotide sequence of GenBank Accession No. NM_013238.3, which is incorporated by reference in its entirety.

In some embodiments, the target gene is TAZ. In some embodiments, TAZ comprises the nucleotide sequence of SEQ ID NO: 57, which corresponds to the nucleotide sequence of GenBank Accession No. NM_000116.5, which is incorporated by reference in its entirety.

In some embodiments, the target gene is angiopoietin like 3 (ANGPTL3). In some embodiments, ANGPTL3 comprises the nucleotide sequence of SEQ ID NO: 60, which corresponds to the nucleotide sequence of GenBank Accession No. NM_014495.4, which is incorporated by reference in its entirety.

In some embodiments, the target gene is diacylglycerol acyltransferase 2 (DGAT2). In some embodiments, DGAT2 comprises the nucleotide sequence of SEQ ID NO: 59, which corresponds to the nucleotide sequence of GenBank Accession No. NM_001253891.1, which is incorporated by reference in its entirety.

Compositions

As indicated above, the present disclosure provides compositions comprising any of the siNA molecules, sense strands, antisense strands, first nucleotide sequences, or second nucleotide sequences described herein. The compositions may comprise 1, 2, 3, 4, 5, 6, 7, 8, 9, 10, 11, 12 or more siNA molecules described herein. The compositions may comprise a first nucleotide sequence comprising a nucleotide sequence of any one SEQ ID NOs: 1 and 2. In some embodiments, the composition comprises a second nucleotide sequence comprising a nucleotide sequence of any one of SEQ ID NOs: 51-74. In some embodiments, the composition comprises a sense strand comprising a nucleotide sequence of any one of SEQ ID NOs: 1 and 2. In some embodiments, the composition comprises an antisense strand comprising a nucleotide sequence of any one of SEQ ID NOs: 51-74.

Alternatively, the compositions may comprise (a) a phosphorylation blocker; and (b) a short interfering nucleic acid (siNA). In some embodiments, the phosphorylation blocker is any of the phosphorylation blockers disclosed herein. In some embodiments, the siNA is any of the siNAs disclosed herein. In some embodiments, the siNA comprises any of the sense strands, antisense strands, first nucleotide sequences, or second nucleotide sequences described herein. In some embodiments, the siNA comprises any of the sense strands, antisense strands, first nucleotide sequences, or second nucleotide sequences described herein. In some embodiments, the siNA comprises one or more modified nucleotides. In some embodiments, the one or more modified nucleotides are independently selected from a 2'-fluoro nucleotide and a 2'-O-methyl nucleotide. In some embodiments, the 2'-fluoro nucleotide or the 2'-O-methyl nucleotide is independently selected from any of the 2'-fluoro or 2'-O-methyl nucleotide mimics disclosed herein. In some embodiments, the siNA comprises a nucleotide sequence comprising any of the modification patterns disclosed herein.

In some embodiments, the composition comprises (a) a conjugated moiety; and (b) a short interfering nucleic acid (siNA). In some embodiments, the conjugated moiety is any of the galactosamines disclosed herein. In some embodiments, the siNA is any of the siNAs disclosed herein. In some embodiments, the siNA comprises any of the sense strands, antisense strands, first nucleotide sequences, or second nucleotide sequences described herein. In some embodiments, the siNA comprises any of the sense strands, antisense strands, first nucleotide sequences, or second nucleotide sequences described herein. In some embodiments, the siNA comprises one or more modified nucleotides. In some embodiments, the one or more modified nucleotides are independently selected from a 2'-fluoro nucleotide and a 2'-O-methyl nucleotide. In some embodiments, the 2'-fluoro nucleotide or the 2'-O-methyl nucleotide is independently selected from any of the 2'-fluoro or 2'-O-methyl nucleotide mimics disclosed herein. In some embodiments, the siNA comprises a nucleotide sequence comprising any of the modification patterns disclosed herein.

In some embodiments, the composition comprises (a) a 5'-stabilized end cap; and (b) a short interfering nucleic acid (siNA). In some embodiments, the 5'-stabilized end cap is any of the 5-stabilized end caps disclosed herein. In some embodiments, the siNA is any of the siNAs disclosed herein. In some embodiments, the siNA comprises any of the sense strands, antisense strands, first nucleotide sequences, or second nucleotide sequences described herein. In some embodiments, the siNA comprises one or more modified nucleotides. In some embodiments, the one or more modified nucleotides are independently selected from a 2'-fluoro nucleotide and a 2'-O-methyl nucleotide. In some embodiments, the 2'-fluoro nucleotide or the 2'-O-methyl nucleotide is independently selected from any of the 2'-fluoro or 2'-O-methyl nucleotide mimics disclosed herein. In some embodiments, the siNA comprises a nucleotide sequence comprising any of the modification patterns disclosed herein.

In some embodiments, the composition comprises (a) at least one phosphorylation blocker, conjugated moiety, or 5'-stabilized end cap; and (b) a short interfering nucleic acid (siNA). In some embodiments, the phosphorylation blocker is any of the phosphorylation blockers disclosed herein. In some embodiments, the conjugated moiety is any of the galactosamines disclosed herein. In some embodiments, the 5'-stabilized end cap is any of the 5-stabilized end caps disclosed herein. In some embodiments, the siNA is any of the siNAs disclosed herein. In some embodiments, the siNA comprises any of the sense strands, antisense strands, first nucleotide sequences, or second nucleotide sequences described herein. In some embodiments, the siNA comprises one or more modified nucleotides. In some embodiments, the one or more modified nucleotides are independently selected from a 2'-fluoro nucleotide and a 2'-O-methyl nucleotide. In some embodiments, the 2'-fluoro nucleotide or the 2'-O-methyl nucleotide is independently selected from any of the 2'-fluoro or 2'-O-methyl nucleotide mimics disclosed herein. In some embodiments, the siNA comprises a nucleotide sequence comprising any of the modification patterns disclosed herein.

The composition may be a pharmaceutical composition. In some embodiments, the pharmaceutical composition comprises an amount of one or more of the siNA molecules described herein formulated with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a siNA of the present disclosure which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound (e.g., siNA molecule) which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present disclosure comprises an excipient selected from the group consisting of cyclodextrins, celluloses, liposomes, micelle forming agents, e.g., bile acids, and polymeric carriers, e.g., polyesters and polyanhydrides; and a compound (e.g., siNA molecule) of the present disclosure. In certain embodiments, an aforementioned formulation renders orally bioavailable a compound (e.g., siNA molecule) of the present disclosure.

Methods of preparing these formulations or compositions include the step of bringing into association a compound (e.g., siNA molecule) of the present disclosure with the carrier and, optionally, one or more accessory ingredients. In general, the formulations are prepared by uniformly and intimately bringing into association a compound (e.g., siNA molecule) of the present disclosure with liquid carriers, or finely divided solid carriers, or both, and then, if necessary, shaping the product.

Formulations of the disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound (e.g., siNA molecule) of the present disclosure as an active ingredient. A compound (e.g., siNA molecule) of the present disclosure may also be administered as a bolus, electuary or paste.

In solid dosage forms of the disclosure for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose.

In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried.

They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds (e.g., siNA molecules) of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (I particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds (e.g., siNA molecules), may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the disclosure for rectal or vaginal administration may be presented as a suppository, which may be prepared by mixing one or more compounds (e.g., siNA molecules) of the disclosure with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound (e.g., siNA molecule).

Formulations of the present disclosure which are suitable for vaginal administration also include pessaries, tampons, creams, gels, pastes, foams or spray formulations containing such carriers as are known in the art to be appropriate.

Dosage forms for the topical or transdermal administration of a compound (e.g., siNA molecule) of this disclosure include powders, sprays, ointments, pastes, creams, lotions, gels, solutions, patches and inhalants. The active compound (e.g., siNA molecule) may be mixed under sterile conditions with a pharmaceutically acceptable carrier, and with any preservatives, buffers, or propellants which may be required.

The ointments, pastes, creams and gels may contain, in addition to an active compound (e.g., siNA molecule) of this disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound (e.g., siNA molecule) of this disclosure, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound (e.g., siNA molecule) of the present disclosure to the body. Such dosage forms can be made by dissolving or dispersing the compound (e.g., siNA molecule) in the proper medium. Absorption enhancers can also be used to increase the flux of the compound (e.g., siNA molecule) across the skin. The rate of such flux can be controlled by either providing a rate controlling membrane or dispersing the compound (e.g., siNA molecule) in a polymer matrix or gel.

Ophthalmic formulations, eye ointments, powders, solutions and the like, are also contemplated as being within the scope of this disclosure.

Pharmaceutical compositions of this disclosure suitable for parenteral administration comprise one or more compounds (e.g., siNA molecules) of the disclosure in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds (e.g., siNA molecules) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds (e.g., siNA molecules) of the present disclosure are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Treatments and Administration

The siNA molecules of the present disclosure may be used to treat a disease in a subject in need thereof. In some embodiments, a method of treating a disease in a subject in need thereof comprises administering to the subject any of the siNA molecules disclosed herein. In some embodiments, a method of treating a disease in a subject in need thereof comprises administering to the subject any of the compositions disclosed herein.

The preparations (e.g., siNA molecules or compositions) of the present disclosure may be given orally, parenterally, topically, or rectally. They are of course given in forms suitable for each administration route. For example, they are administered in tablets or capsule form, administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds (e.g., siNA molecules) of the present disclosure, which may be used in a suitable hydrated form, and/or the pharmaceutical compositions of the present disclosure, are formulated into pharmaceutically-acceptable dosage forms by conventional methods known to those of skill in the art.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound (e.g., siNA molecule) of the present disclosure employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds (e.g., siNA molecules) of the disclosure employed in the pharmaceutical composition at levels lower than that required in order to achieve the desired therapeutic effect and gradually increase the dosage until the desired effect is achieved.

In general, a suitable daily dose of a compound (e.g., siNA molecule) of the disclosure is the amount of the compound that is the lowest dose effective to produce a therapeutic effect. Such an effective dose generally depends upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. In some embodiments, the compound is administered at a dose equal to or greater than 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.35, 0.40, 0.45, 0.50, 0.55, 0.60, 0.65, 0.7, 0.75, 0.8, 0.85, 0.9, 0.95, or 1 mg/kg. In some embodiments, the compound is administered at a dose equal to or less than 200, 190, 180, 170, 160, 150, 140, 130, 120, 110, 100, 95, 90, 85, 80, 75, 70, 65, 60, 55, 50, 45, 40, 35, 30, 25, 20, or 15 mg/kg. In some embodiments, the total daily dose of the compound is equal to or greater than 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 100 mg.

When the compounds (e.g., siNA molecules) described herein are co-administered with another, the effective amount may be less than when the compound is used alone.

If desired, the effective daily dose of the active compound (e.g., siNA molecule) may be administered as two, three, four, five, six or more sub-doses administered separately at appropriate intervals throughout the day, optionally, in unit dosage forms. Preferred dosing is one administration per day. In some embodiments, the compound is administered at least 1, 2, 3, 4, 5, 6, 7, 8, 9, 10, 11, 12, 13, 14, 15, 16, 17, 18, 19, 20, or 21 times a week. In some embodiments, the compound is administered at least 1, 2, 3, 4, 5, 6, 7, 8, 9, 10, 11, 12, 13, 14, 15, 16, 17, 18, 19, 20, or 21 times a month. In some embodiments, the compound is administered once every 1, 2, 3, 4, 5, 6, 7, 8, 9, 10, 11, 12, 13, 14, 15, 16, 17, 18, 19, 20, or 21 days. In some embodiments, the compound is administered once every 1, 2, 3, 4, 5, 6, 7, or 8 weeks.

Diseases

The siNA molecules and compositions described herein may be administered to a subject to treat a disease. Further disclosed herein are uses of any of the siNA molecules or compositions disclosed herein in the manufacture of a medicament for treating a disease.

In some embodiments, the disease is a viral disease. In some embodiments, the viral disease is caused by a DNA virus. In some embodiments, the DNA virus is a double stranded DNA (dsDNA virus). In some embodiments, the dsDNA virus is a hepadnavirus. In some embodiments, the hepadnavirus is a hepatitis B virus (HBV).

In some embodiments, the disease is a liver disease. In some embodiments, the liver disease is nonalcoholic fatty liver disease (NAFLD). In some embodiments, the NAFLD is nonalcoholic steatohepatitis (NASH). In some embodiments, the liver disease is hepatocellular carcinoma (HCC).

The siNA molecules of the present disclosure may be used to treat or prevent a disease in a subject in need thereof. In some embodiments, a method of treating or preventing a disease in a subject in need thereof comprises administering to the subject any of the siNA molecules disclosed herein. In some embodiments, a method of treating or preventing a disease in a subject in need thereof comprises administering to the subject any of the compositions disclosed herein.

In some embodiments of the disclosed methods and uses, the disease is a respiratory disease. In some embodiments, the respiratory disease is a viral infection. In some embodiments, the respiratory disease is viral pneumonia. In some embodiments, the respiratory disease is an acute respiratory infection. In some embodiments, the respiratory disease is a cold. In some embodiments, the respiratory disease is severe acute respiratory syndrome (SARS). In some embodiments, the respiratory disease is Middle East respiratory syndrome (MERS). In some embodiments, the disease is coronavirus disease 2019 (e.g., COVID-19). In some embodiments, the respiratory disease can include one or more symptoms selected from coughing, sore throat, runny nose, sneezing, headache, fever, shortness of breath, myalgia, abdominal pain, fatigue, difficulty breathing, persistent chest pain or pressure, difficulty waking, loss of smell and taste, muscle or joint pain, chills, nausea or vomiting, nasal congestion, diarrhea, haemoptysis, conjunctival congestion, sputum production, chest tightness, and palpitations. In some embodiments, the respiratory disease can include complications selected from sinusitis, otitis media, pneumonia, acute respiratory distress syndrome, disseminated intravascular coagulation, pericarditis, and kidney failure. In some embodiments, the respiratory disease is idiopathic.

In some embodiments, the present disclosure provides methods of treating or preventing a coronavirus infection, comprising administering to a subject in need thereof a therapeutically effective amount of one or more of the siNAs or a pharmaceutical composition as disclosed herein. In some embodiments, the coronavirus infection is selected from the group consisting of Middle East Respiratory Syndrome (MERS), Severe Acute Respiratory Syndrome (SARS), and COVID-19. In some embodiments, the subject has been treated with one or more additional coronavirus treatment agents. In some embodiments, the subject is concurrently treated with one or more additional coronavirus treatment agents.

Administration of siNA

Administration of any of the siNAs disclosed herein may be conducted by methods known in the art. In some embodiments, the siNA is administered by subcutaneous (SC) or intravenous (IV) delivery. The preparations (e.g., siNAs or compositions) of the present disclosure may be given orally, parenterally, topically, or rectally. They are of course given in forms suitable for each administration route. For example, they are administered in tablets or capsule form, administration by injection, infusion or inhalation; topical by lotion or ointment; and rectal by suppositories. In some embodiments, subcutaneous administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds (e.g., siNAs) of the present disclosure, which may be used in a suitable hydrated form, and/or the pharmaceutical compositions of the present disclosure, are formulated into pharmaceutically-acceptable dosage forms by conventional methods known to those of skill in the art.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound (e.g., siNA) of the present disclosure employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds (e.g., siNAs) of the disclosure employed in the pharmaceutical composition at levels lower than that required in order to achieve the desired therapeutic effect and gradually increase the dosage until the desired effect is achieved.

In general, a suitable daily dose of a compound (e.g., siNA) of the disclosure is the amount of the compound that is the lowest dose effective to produce a therapeutic effect. Such an effective dose generally depends upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. In some embodiments, the compound is administered at about 1 mg/kg to about 40 mg/kg, about 1 mg/kg to about 30 mg/kg, about 1 mg/kg to about 20 mg/kg, about 1 mg/kg to about 15 mg/kg, or 1 mg/kg to about 10 mg/kg. In some embodiments, the compound is administered at a dose equal to or greater than 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.35, 0.40, 0.45, 0.50, 0.55, 0.60, 0.65, 0.7, 0.75, 0.8, 0.85, 0.9, 0.95, or 1 mg/kg. In some embodiments, the compound is administered at a dose equal to or greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mg/kg. In some embodiments, the compound is administered at a dose equal to or less than 200, 190, 180, 170, 160, 150, 140, 130, 120, 110, 100, 95, 90, 85, 80, 75, 70, 65, 60, 55, 50, 45, 40, 35, 30, 25, 20, or 15 mg/kg. In some embodiments, the total daily dose of the compound is equal to or greater than 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 100 mg.

If desired, the effective daily dose of the active compound (e.g., siNA) may be administered as two, three, four, five, six, seven, eight, nine, ten or more doses or sub-doses administered separately at appropriate intervals throughout the day, optionally, in unit dosage forms. In some embodiments, the compound is administered at least 1, 2, 3, 4, 5, 6, 7, 8, 9, 10, 11, 12, 13, 14, or 15 times. Preferred dosing is one administration per day. In some embodiments, the compound is administered at least 1, 2, 3, 4, 5, 6, 7, 8, 9, 10, 11, 12, 13, 14, 15, 16, 17, 18, 19, 20, or 21 times a week. In some embodiments, the compound is administered at least 1, 2, 3, 4, 5, 6, 7, 8, 9, 10, 11, 12, 13, 14, 15, 16, 17, 18, 19, 20, or 21 times a month. In some embodiments, the compound is administered once every 1, 2, 3, 4, 5, 6, 7, 8, 9, 10, 11, 12, 13, 14, 15, 16, 17, 18, 19, 20, or 21 days. In some embodiments, the compound is administered every 3 days. In some embodiments, the compound is administered once every 1, 2, 3, 4, 5, 6, 7, 8, 9, 10, 11, 12, 13, 14, or 15 weeks. In some embodiments, the compound is administered every month. In some embodiments, the compound is administered once every 1, 2, 3, 4, 5, 6, 7, 8, 9, 10, 11, 12, 13, 14, or 15 months. In some embodiments, the compound is administered at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 times over a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 days. In some embodiments, the compound is administered at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 times over a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 weeks. In some embodiments, the compound is administered at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 times over a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 months. In some embodiments, the compound is administered at least once a week for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 weeks. In some embodiments, the compound is administered at least once a week for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 months. In some embodiments, the compound is administered at least twice a week for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 weeks. In some embodiments, the compound is administered at least twice a week for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 months. In some embodiments, the compound is administered at least once every two weeks for a period of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 weeks. In some embodiments, the compound is administered at least once every two weeks for a period of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 months. In some embodiments, the compound is administered at least once every four weeks for a period of at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 weeks. In some embodiments, the compound is administered at least once every four weeks for a period of at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 months.

In some embodiments, any one of the siNAs or compositions disclosed herein is administered in a particle or viral vector. In some embodiments, the viral vector is a vector of adenovirus, adeno-associated virus (AAV), alphavirus, flavivirus, herpes simplex virus, lentivirus, measles virus, picornavirus, poxvirus, retrovirus, or rhabdovirus. In some embodiments, the viral vector is a recombinant viral vector. In some embodiments, the viral vector is selected from AAVrh.74, AAVrh.10, AAVrh.20, AAV-1, AAV-2, AAV-3, AAV-4, AAV-5, AAV-6, AAV-7, AAV-8, AAV-9, AAV-10, AAV-11, AAV-12 and AAV-13.

The subject of the described methods may be a mammal, and it includes humans and non-human mammals. In some embodiments, the subject is a human, such as an adult human.

Some embodiments include a method for treating an HBV virus in a subject infected with the virus comprising administering a therapeutically effective amount of one or more siNA of the present disclosure or a composition of the present disclosure to the subject in need thereof thereby reducing the viral load of the virus in the subject and/or reducing a level of a virus antigen in the subject. The siNA may be complementary or hybridize to a portion of the target RNA in the virus, e.g., an X region and/or an S region of HBV.

Combination Therapies

Any of the methods disclosed herein may further comprise administering to the subject an additional HBV treatment agent. Any of the compositions disclosed herein may further comprise an additional HBV treatment agent. In some embodiments, the additional HBV treatment agent is selected from a nucleotide analog, nucleoside analog, a capsid assembly modulator (CAM), a recombinant interferon, an entry inhibitor, a small molecule immunomodulator and oligonucleotide therapy. In some embodiments, the additional HBV treatment agent is selected from HBV STOPS™ ALG-010133, HBV CAM ALG-000184, ASO 1 (SEQ ID NO: 61), ASO 2 (SEQ ID NO: 62) recombinant interferon alpha 2b, IFN-a, PEG-IFN-a-2a, lamivudine, telbivudine, adefovir dipivoxil, clevudine, entecavir, tenofovir alafenamide, tenofovir disoproxil, NVR3-778, BAY41-4109, JNJ-632, JNJ-3989 (ARO-HBV), RG6004, GSK3228836, REP-2139, REP-2165, AB-729, VIR-2218, RG6346 (DCR-HBVS), JNJ-6379, GLS4, ABI-HO731, JNJ-440, NZ-4, RG7907, EDP-514, AB-423, AB-506, ABI-H03733 and ABI-H2158. In some embodiments, the oligonucleotide therapy is selected from Nucleic Acid Polymers or S-Antigen Transport-inhibiting Oligonucleotide Polymers (NAPs or STOPS), siRNA, and ASO. In some embodiments, the oligonucleotide therapy is an additional siNA. In some embodiments, the additional siNA is selected from any of ds-siNA-001 to ds-siNA-025. In some embodiments, the oligonucleotide therapy is an antisense oligonucleotide (ASO). In some embodiments, the ASO is ASO 1 (SEQ ID NO: 61) or ASO 2 (SEQ ID NO: 62). In some embodiments, any of the siNAs disclosed herein are co-administered with STOPS. Exemplary STOPS are described in International Publication No. WO2020/097342 and U.S. Publication No. 2020/0147124, both of which are incorporated by reference in their entirety. In some embodiments, the STOPS is ALG-010133. In some embodiments, any of the siNAs disclosed herein are co-administered with tenofovir. In some embodiments, any of the siNAs disclosed herein are co-administered with a CAM. Exemplary CAMs are described in Berke et al., *Antimicrob Agents Chemother,* 2017, 61(8): e00560-17, Klumpp, et al., Gastroenterology, 2018, 154(3): 652-662.e8, International Application Nos. PCT/US2020/017974, PCT/US2020/026116, and PCT/US2020/028349 and U.S. application Ser. Nos. 16/789,298, 16/837,515, and 16/849,851, each which is incorporated by reference in its entirety. In some embodiments, the CAM is ALG-000184, ALG-001075, ALG-001024, JNJ-632, BAY41-4109, or NVR3-778. In some embodiments, the siNA and the HBV treatment agent are administered simultaneously. In some embodiments, the siNA and the HBV treatment agent are administered concurrently. In some embodiments, the siNA and the HBV treatment agent are administered sequentially. In some embodiments, the siNA is administered prior to administering the HBV treatment agent. In some embodiments, the siNA is administered after administering the HBV treatment agent. In some embodiments, the siNA and the HBV treatment agent are in separate containers. In some embodiments, the siNA and the HBV treatment agent are in the same container.

Any of the methods disclosed herein may further comprise administering to the subject a liver disease treatment agent. Any of the compositions disclosed herein may further comprise a liver disease treatment agent. In some embodiments, the liver disease treatment agent is selected from a peroxisome proliferator-activator receptor (PPAR) agonist, farnesoid X receptor (FXR) agonist, lipid-altering agent, and incretin-based therapy. In some embodiments, the PPAR agonist is selected from a PPARα agonist, dual PPARα/δ agonist, PPARγ agonist, and dual PPARα/γ agonist. In some embodiments, the dual PPARα agonist is a fibrate. In some embodiments, the PPARα/δ agonist is elafibranor. In some embodiments, the PPARγ agonist is a thiazolidinedione (TZD). In some embodiments, TZD is pioglitazone. In some embodiments, the dual PPARα/γ agonist is saroglitazar. In some embodiments, the FXR agonist is obeticholic acis (OCA). In some embodiments, the lipid-altering agent is aramchol. In some embodiments, the incretin-based therapy is a glucagon-like peptide 1 (GLP-1) receptor agonist or dipeptidyl peptidase 4 (DPP-4) inhibitor. In some embodiments, the GLP-1 receptor agonist is exenatide or liraglutide. In some embodiments, the DPP-4 inhibitor is sitagliptin or vildapliptin. In some embodiments, the siNA and the liver disease treatment agent are administered concurrently. In some embodiments, the siNA and the liver disease treatment agent are administered sequentially. In some embodiments, the siNA is administered prior to administering the liver disease treatment agent. In some embodiments, the siNA is administered after administering the liver disease treatment agent. In some embodiments, the siNA and the liver disease treatment agent are in separate containers. In some embodiments, the siNA and the liver disease treatment agent are in the same container.

Definitions

Unless defined otherwise, all technical and scientific terms used herein have the meaning commonly understood by a person skilled in the art to which this disclosure belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al., (eds.), Springer Verlag (1991); and Hale & Marham, The Harper Collins Dictionary of Biology (1991). As used herein, the following terms have the meanings ascribed to them below, unless specified otherwise. The terminology used herein is for the purpose of describing particular embodiments only and is not intended to be limiting of the disclosure.

The terms "a" and "an" as used herein mean "one or more" and include the plural unless the context is inappropriate.

As used herein, the terms "patient" and "subject" refer to organisms to be treated by the methods of the present disclosure. Such organisms are preferably mammals (e.g., marines, simians, equines, bovines, porcinis, canines, felines, and the like), and more preferably humans.

As used herein, the term "effective amount" refers to the amount of a compound (e.g., a siNA of the present disclosure) sufficient to effect beneficial or desired results. An effective amount can be administered in one or more administrations, applications, or dosages and is not intended to be limited to a particular formulation or administration route.

As used herein, the term "treating" includes any effect, e.g., lessening, reducing, modulating, ameliorating or eliminating, that results in the improvement of the condition, disease, disorder, and the like, or ameliorating a symptom thereof.

As used herein, the terms "alleviate" and "alleviating" refer to reducing the severity of the condition, such as reducing the severity by, for example, at least 10%, 20%, 30%, 40%, 50%, 60%, 70%, 80%, 90%, or 95%.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, for example, Martin, Remington's Pharmaceutical Sciences, 15th Ed., Mack Publ. Co., Easton, PA [1975].

The term "about" as used herein when referring to a measurable value (e.g., weight, time, and dose) is meant to encompass variations, such as ±10%, 5%, +1%, or ±0.1% of the specified value.

As used herein, the term "nucleobase" refers to a nitrogen-containing biological compound that forms a nucleoside. Examples of nucleobases include, but are not limited to, thymine, uracil, adenine, cytosine, guanine, and an analogue or derivative thereof.

Throughout the description, where compositions are described as having, including, or comprising specific components, or where processes and methods are described as having, including, or comprising specific steps, it is contemplated that, additionally, there are compositions of the present disclosure that consist essentially of, or consist of, the recited components, and that there are processes and methods according to the present disclosure that consist essentially of, or consist of, the recited processing steps.

As a general matter, compositions specifying a percentage are by weight unless otherwise specified. Further, if a variable is not accompanied by a definition, then the previous definition of the variable controls.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided may be different from the actual publication dates that may need to be independently confirmed.

EXAMPLES

Example 1: siNA Synthesis

This example describes an exemplary method for synthesizing ds-siNAs, such as the siNAs disclosed in Tables 1-5 (as identified by the ds-siNA ID).

The 2'-O-Me phosphoramidite 5'-O-DMT-deoxy Adenosine (NH-Bz), 3'-O-(2-cyanoethyl-N,N-diisopropyl phosphoramidite, 5'-O-DMT-deoxy Guanosine (NH-ibu), 3'-O-(2-cyanoethyl-N,N-diisopropyl phosphoramidite, 5'-O-DMT-deoxy Cytosine (NH-Bz), 3'-O-(2-cyanoethyl-N,N-diisopropyl phosphoramidite, 5'-O-DMT-Uridine 3'-O-(2-cyanoethyl-N,N-diisopropyl phosphoramidite and solid supports were purchased from Chemgenes Corp. MA.

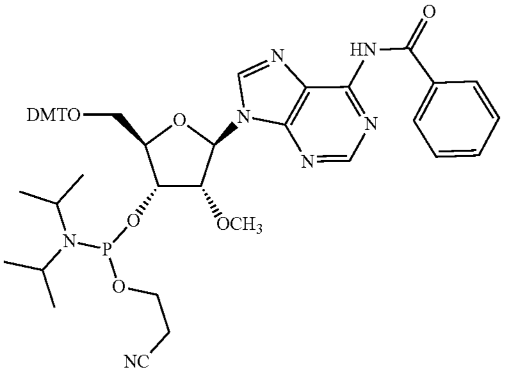

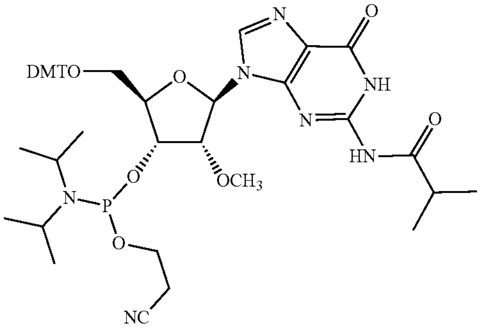

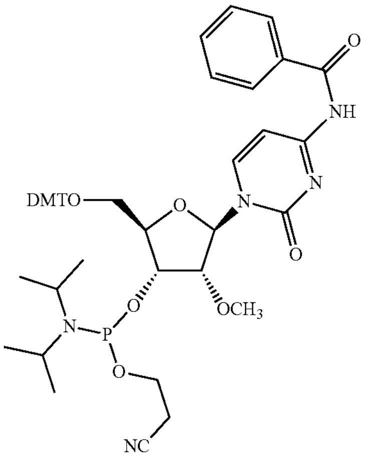

-continued

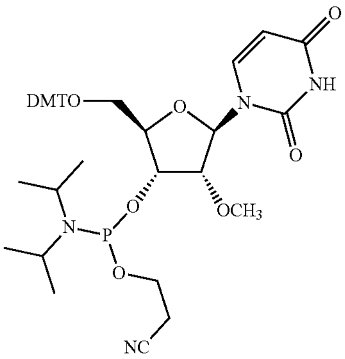

The 2'-F-5'-O-DMT-(NH-Bz) Adenosine-3'-O-(2-cyanoethyl-N,N-diisopropyl phosphoramidite, 2'-F-5'-O-DMT-(NH-ibu)-Guanosine, 3'-O-(2-cyanoethyl-N,N-diisopropyl phosphoramidite, 5'-O-DMT-(NH-Bz)-Cytosine, 2'-F-3'-O-(2-cyanoethyl-N,N-diisopropyl phosphoramidite, 5'-O-DMT-Uridine, 2'-F-3'-O-(2-cyanoethyl-N,N-diisopropyl phosphoramidite and solid supports were purchased from Thermo Fischer Milwaukee WI, USA.

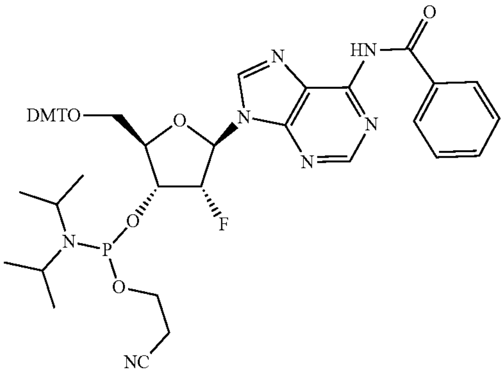

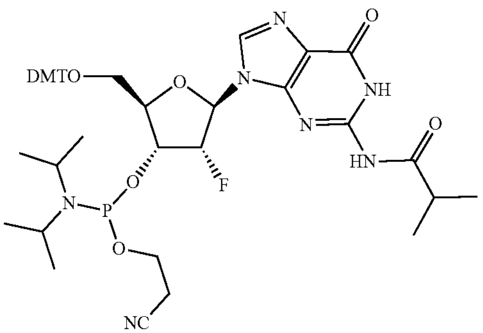

-continued

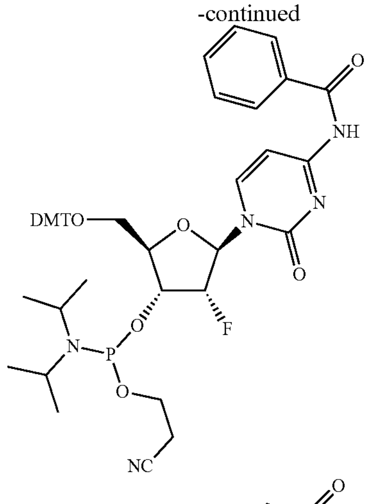

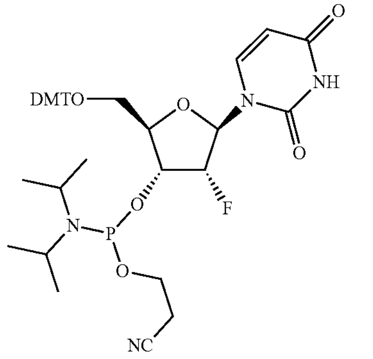

All the monomers were dried in vacuum desiccator with desiccants ($P_2O_5$, RT 24h). The solid supports (CPG) attached to the nucleosides and universal supports was obtained from LGC and Chemgenes. The chemicals and solvents for post synthesis workflow were purchased from commercially available sources like VWR/Sigma and used without any purification or treatment. Solvent (Acetonitrile) and solutions (amidite and activator) were stored over molecular sieves during synthesis.

The oligonucleotides were synthesized on a DNA/RNA Synthesizers (Expedite 8909 or ABI-394 or MM-48) using standard oligonucleotide phosphoramidite chemistry starting from the 3' residue of the oligonucleotide preloaded on CPG support. An extended coupling of 0.1M solution of phosphoramidite in $CH_3CN$ in the presence of 5-(ethylthio)-1H-tetrazole activator to a solid bound oligonucleotide followed by standard capping, oxidation and deprotection afforded modified oligonucleotides. The 0.1M 12, THF: Pyridine; Water-7:2:1 was used as oxidizing agent while DDTT ((dimethylamino-methylidene)amino)-3H-1,2,4-dithiazaoline-3-thione was used as the sulfur-transfer agent for the synthesis of oligoribonucleotide phosphorothioates. The stepwise coupling efficiency of all modified phosphoramidites was more than 98%.

| Reagents | Detailed Description |
|---|---|
| Deblock Solution | 3% Dichloroacetic acid (DCA) in Dichloromethane (DCM) |
| Amidite Concentration | 0.1M in Anhydrous Acetonitrile |
| Activator | 0.25M Ethyl-thio-Tetrazole (ETT) |
| Cap-A solution | Acetic anhydride in pyridine/THF |
| Cap-B Solution | 16% 1-Methylimidazole in THF |

-continued

| Reagents | Detailed Description |
|---|---|
| Oxidizing Solution | 0.02M $I_2$, THF:pyridine; water-7:2:1 |
| Sulfurizing Solution | 0.2M DDTT in pyridine/acetonitrile 1:1 |

Cleavage and Deprotection:

Deprotection and cleavage from the solid support was achieved with mixture of ammonia methylamine (1:1, AMA) for 15 min at 65° C. When the universal linker was used, the deprotection was left for 90 min at 65° C. or solid supports were heated with aqueous ammonia (28%) solution at 55° C. for 8-16 h to deprotect the base labile protecting groups.

Quantitation of Crude siNA or Raw Analysis

Samples were dissolved in deionized water (1.0 mL) and quantitated as follows: Blanking was first performed with water alone (2 ul) on Thermo Scientific™ Nanodrop UV spectrophotometer or BioTek™ Epoch™ plate reader then Oligo sample reading was obtained at 260 nm. The crude material is dried down and stored at −20° C.

Crude HPLC/LC-MS Analysis

The 0.1 OD of the crude samples were analyzed for crude HPLC and LC-MS analysis. After Confirming the crude LC-MS data then purification step was performed if needed based on the purity.

HPLC Purification

The unconjugated and GalNac modified oligonucleotides were purified by anion-exchange HPLC. The buffers were 20 mM sodium phosphate in 10% $CH_3CN$, pH 8.5 (buffer A) and 20 mM sodium phosphate in 10% $CH_3CN$, 1.0 M NaBr, pH 8.5 (buffer B). Fractions containing full-length oligonucleotides were pooled.

Desalting of Purified SiNA

The purified dry siNA was then desalted using Sephadex G-25 M (Amersham Biosciences). The cartridge was conditioned with 10 mL of deionized water thrice. Finally, the purified siNA dissolved thoroughly in 2.5 mL RNAse free water was applied to the cartridge with very slow drop wise elution. The salt free siNA was eluted with 3.5 ml deionized water directly into a screw cap vial. Alternatively, some unconjugated siNA was deslated using Pall AcroPrep™ 3K MWCO desalting plates.

IEX HPLC and Electrospray LC/MS Analysis

Approximately 0.10 OD of siNA is dissolved in water and then pipetted into HPLC autosampler vials for IEX-HPLC and LC/MS analysis. Analytical HPLC and ES LC-MS confirmed the identity and purity of the compounds.

Duplex Preparation:

Single strand oligonucleotides (Sense and Antisense strands) were annealed (1:1 by molar equivalents, heat at 90° C. for 2 min followed by gradual cooling at room temperature) to give the duplex ds-siNA. The final compounds were analyzed on size exclusion chromatography (SEC).

Example 2
Scheme-1
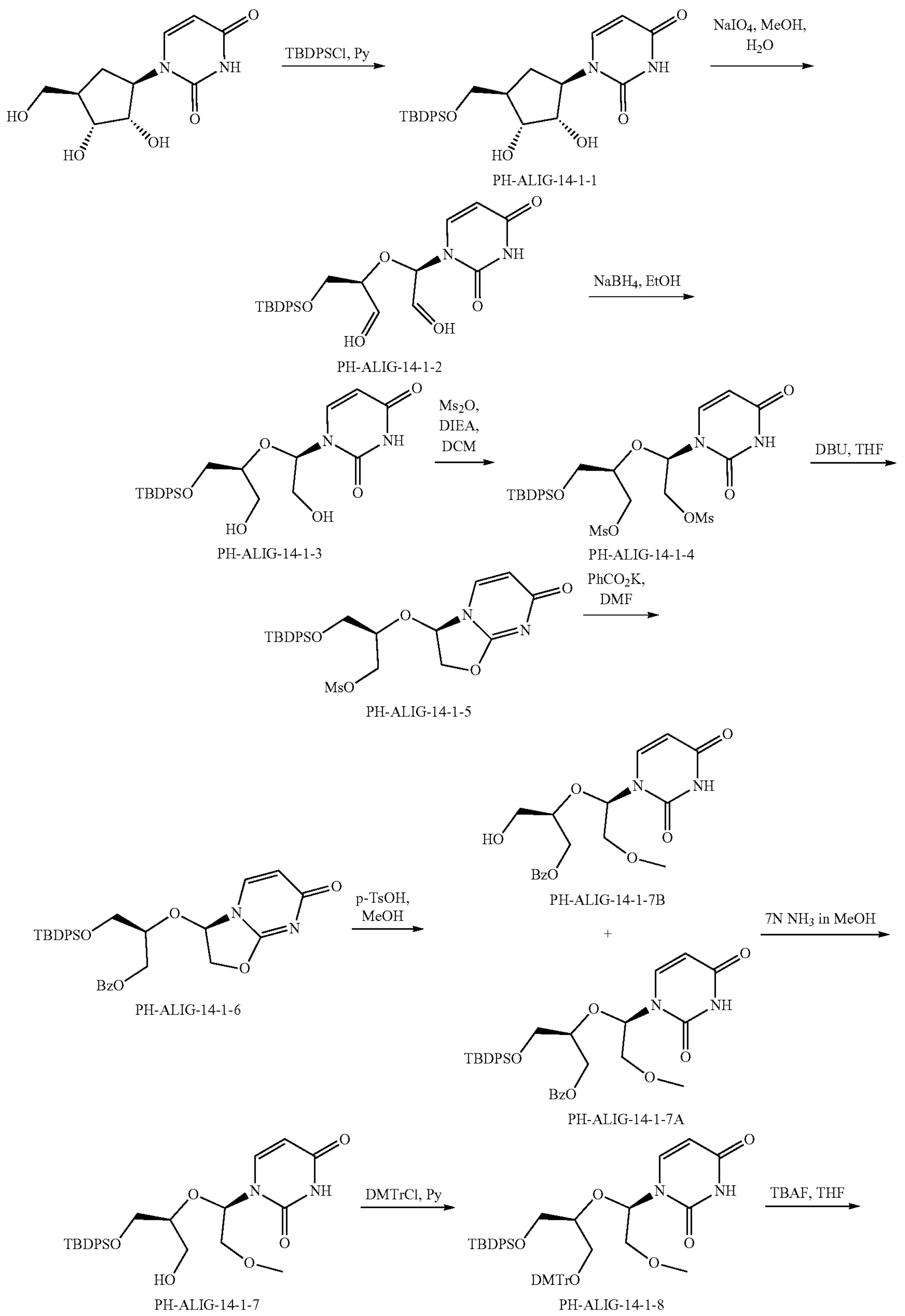

-continued

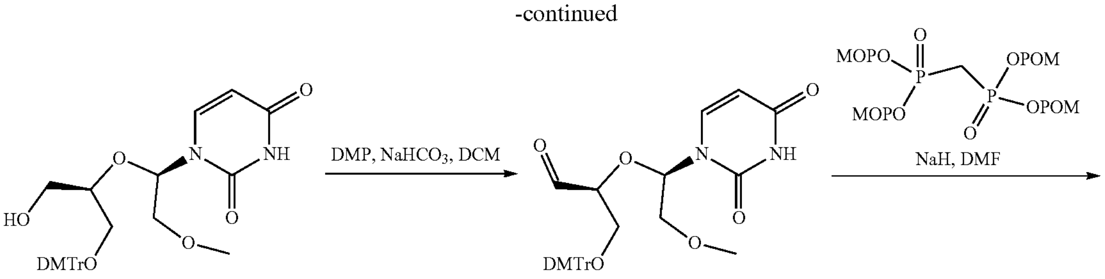

PH-ALIG-14-1-9 PH-ALIG-14-1-10

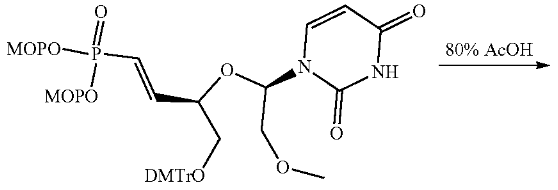

PH-ALIG-14-1-11

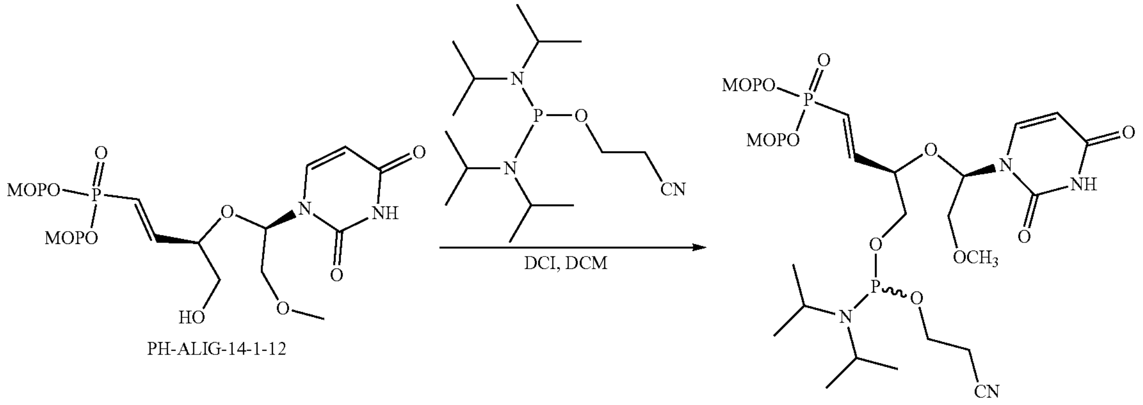

PH-ALIG-14-1-12 PH-ALIG-14-1-0

Preparation of PH-ALIG-14-1-1

Into a 5000-mL 3-necked round-bottom flask purged and maintained with an inert atmosphere of argon, was placed uridine (150.00 g, 614.24 mmol, 1.00 eq), pyridine (2.2 L), TBDPSCl (177.27 g, 644.95 mmol, 1.05 eq). The resulting solution was stirred overnight at room temperature. The resulting mixture was concentrated. The resulting solution was extracted with 3×1000 mL of dichloromethane and the organic layers combined. The resulting mixture was washed with 3×1 L of 0.5N HCl(aq.) and 2×500 mL of 0.5N $NaHCO_3$ (aq.). The resulting mixture was washed with 2×1 L of $H_2O$. The mixture was dried over anhydrous sodium sulfate. The solids were filtered out. The filtrate was concentrated. This resulted in 262 g (crude) PH-ALIG-14-1-1. LC-MS (m/z) 483.00 $[M+H]^+$; 1 H NMR (400 MHz, DMSO-$d_6$) δ 11.35 (d, J=2.2 Hz, 1H), 7.70 (d, J=8.1 Hz, 1H), 7.64 (m, 4H), 7.52-7.40 (m, 6H), 5.80 (d, J=4.1 Hz, 1H), 5.50 (d, J=5.1 Hz, 1H), 5.28 (dd, J=8.0, 2.2 Hz, 1H), 5.17 (d, J=5.3 Hz, 1H), 4.15-4.05 (m, 2H), 4.00-3.85 (m, 2H), 3.85-3.73 (m, 1H), 1.03 (s, 9H).

Preparation of PH-ALIG-14-1-2

Into a 10 L 3-necked round-bottom flask purged and maintained with an inert atmosphere of argon, was placed a solution of PH-ALIG-14-1-1 (260.00 g, 538.7 mmol, 1.0 eq.) in MeOH (5000 mL). This was followed by the addition of a solution of $NaIO_4$ (126.8 g, 592.6 mmol, 1.1 eq.) in $H_2O$ (1600 mL) in several batches at 0° C. The resulting solution was stirred for 1 hr at room temperature. The reaction was then quenched by the addition of 3 L of $Na_2S_2O_3$(sat.) at 0° C. The resulting solution was extracted with 3×1 L of dichloromethane and the organic layers combined and dried over anhydrous sodium sulfate. The solids were filtered out. The filtrate was concentrated. This resulted in 290 g (crude) of PH-ALIG-14-1-2 as a white solid.

Preparation of PH-ALIG-14-1-3

Into a 5 L 3-necked round-bottom flask purged and maintained with an inert atmosphere of argon, was placed PH-ALIG-14-1-2 (290 g, 603.4 mmol, 1.0 eq), EtOH (3 L). This was followed by the addition of $NaBH_4$ (22.8 g, 603.4 mmol, 1.0 eq), in portions at 0° C. The resulting solution was stirred for 1 hr at room temperature. The reaction was then quenched by the addition of 2000 mL of water/ice. The resulting solution was extracted with 3×1000 mL of dichloromethane and the organic layers combined and dried over anhydrous sodium sulfate. The solids were filtered out. The filtrate was concentrated. This resulted in 230 g (crude) of PH-ALIG-14-1-3 as a white solid. LC-MS: m/z 485.10 $[M+H]^+$. $^1H$ NMR (400 MHz, DMSO-$d_6$) δ 11.28 (d, J=2.2 Hz, 1H), 7.63-7.37 (m, 11H), 5.84 (dd, J=6.4, 4.9 Hz, 1H), 5.44 (dd, J=8.0, 2.2 Hz, 1H), 5.11 (t, J=6.0 Hz, 1H), 4.78 (t, J=5.2 Hz, 1H), 3.65 (dd, J=11.4, 5.7 Hz, 1H), 3.60-3.52 (m, 5H), 3.18 (d, J=5.2 Hz, 1H), 0.96 (s, 9H).

Preparation of PH-ALIG-14-1-4

Into a 5000-mL 3-necked round-bottom flask purged and maintained with an inert atmosphere of argon, was placed a solution of PH-ALG-14-1-3 (120 g, 1 eq) in DCM (1200 mL). This was followed by the addition of DIEA (95.03 g, 3 eq) at 0 degrees C. To this was added methanesulfonic anhydride (129 g, 3 eq), in portions at 0° C. The resulting solution was stirred for 1 hr at room temperature. The reaction was then quenched by the addition of 1000 mL of water/ice. The resulting solution was extracted with 3×500 mL of dichloromethane and the organic layers combined and dried over anhydrous magnesium sulfate. The solids were filtered out. The filtrate was concentrated. This resulted in 160 g (crude) of PH-ALG-14-1-4 as a yellow solid; LC-MS (m/z) 641.05$[M+H]^+$ Preparation of PH-ALIG-14-1-5

Into a 1 L round-bottom flask, was placed a solution of PH-ALG-14-1-4 (160.00 g, 1.00 equiv) in THF (1600 mL), DBU (108 g, 2.8 equiv). The resulting solution was stirred for 1 hr at 30° C. The reaction was then quenched by the addition of 3000 mL of water/ice. The resulting solution was extracted with 3×500 mL of dichloromethane and the organic layers combined and dried over anhydrous sodium sulfate. The solids were filtered out. The filtrate was concentrated. This resulted in 150 g (crude) of PH-ALG-14-1-5 as brown oil; LC-MS:(ES, m/z): 567.25$[M+H]^+$ $^1$HNMR (400 MHz, DMSO-$d_6$) δ 7.83 (d, J=7.4 Hz, 1H), 7.67-7.55 (m, 4H), 7.55-7.35 (m, 6H), 6.05 (dd, J=5.9, 1.7 Hz, 1H), 5.72 (d, J=7.4 Hz, 1H), 4.81 (dd, J=10.4, 5.8 Hz, 1H), 4.58-4.46 (m, 2H), 4.42 (p, J=5.2, 4.6 Hz, 1H), 4.33 (dd, J=10.6, 5.9 Hz, 1H), 3.79-3.70 (m, 2H), 3.23 (s, 3H), 0.98 (s, 9H).

Preparation of PH-ALIG-14-1-6

Into a 3000-mL round-bottom flask purged and maintained with an inert atmosphere of argon, was placed PH-ALIG-14-1-5 (150.00 g, 201.950 mmol, 1. eq), DMF (1300.00 mL), potassium benzoate (44.00 g, 1.0 eq). The resulting solution was stirred for 1.5 hr at 80° C. The reaction was then quenched by the addition of 500 mL of water/ice. The resulting solution was extracted with 3×500 mL of dichloromethane The resulting mixture was washed with 3×1000 ml of $H_2O$. The resulting mixture was concentrated. The residue was applied onto a silica gel column with EA/PE (99:1). The collected fractions were combined and concentrated. This resulted in 40 g of PH-ALIG-14-1-6 as yellow oil. LC-MS: m/z 571.20 $[M+H]^+$;

1HNMR: (400 MHz, DMSO-$d_6$) δ 7.97-7.91 (m, 2H), 7.89 (d, J=7.4 Hz, 1H), 7.74-7.51 (m, 7H), 7.51-7.31 (m, 6H), 6.16 (m, 1H), 5.76 (d, J=7.4 Hz, 1H), 4.78 (m, 1H), 4.61 (m, 1H), 4.55-4.46 (m, 2H), 4.38 (m, 1H), 3.82 (d, J=5.0 Hz, 2H), 0.97 (s, 9H)

Preparation of PH-ALIG-14-1-7 A

Into a 2-L round-bottom flask, was placed PH-ALIG-14-1-6 (30.00 g, 1 eq), MeOH (1.20 L), p-toluenesulfonic acid (4.50 g, 0.5 eq). The resulting solution was stirred for 2 hr at 70° C. The reaction was then quenched by the addition of 3 L of $NaHCO_3$(sat.). The pH value of the solution was adjusted to 7 with $NaHCO_3$(sat.). The resulting solution was extracted with 3×1 L of ethyl acetate and the organic layers combined and dried over anhydrous sodium sulfate. The solids were filtered out. The filtrate was concentrated under vacuum. The crude product was purified by Flash-Prep-HPLC with the following conditions (IntelFlash-1): Column, silica gel; mobile phase, PE/EA=50/50 increasing to PE/EA=25/75 within 30; Detector, 254. This resulted in 11.5 g (3.1% yield in seven steps) PH-ALIG-14-1-7 A as a white solid. LC-MS: m/z 625.15$[M+Na]^+$; $^1$HNMR: (400 MHz, DMSO-$d_6$) δ 11.37 (d, J=2.3 Hz, 1H), 7.99-7.93 (m, 2H), 7.74-7.65 (m, 1H), 7.63-7.50 (m, 7H), 7.50-7.33 (m, 6H), 6.08 (t, J=6.0 Hz, 1H), 5.49 (m, 1H), 4.60 (m, 1H), 4.43 (m, 1H), 4.03-3.96 (m, 1H), 3.70 (d, J=5.3 Hz, 2H), 3.62-3.49 (m, 2H), 3.21 (s, 3H), 0.97 (s, 9H).

Preparation of PH-ALIG-14-1-7

Into a 2-L round-bottom flask, was placed PH-ALIG-14-1-7 A (11.50 g). To the above 7M $NH_3$(g) in MeOH (690.00 mL) was introduced in at 30° C. The resulting solution was stirred overnight at 30 degrees C. The resulting mixture was concentrated under vacuum. The crude product was purified by Flash with the following conditions (IntelFlash-1): Column, silica gel; mobile phase, PE/EA=60/40 increasing to PE/EA=1/99 within 60; Detector, 254. This resulted in 8.1 g (97% yield) of PH-ALIG-14-1-7 as a white solid. LC-MS-: m/z 499.35 $[M+H]^+$; $^1$HNMR: (300 MHz, DMSO-$d_6$) δ 11.31 (s, 1H), 7.64-7.50 (m, 5H), 7.48-7.35 (m, 6H), 6.02 (t, J=5.8 Hz, 1H), 5.45 (d, J=8.0 Hz, 1H), 4.80 (t, J=5.1 Hz, 1H), 3.58 (m, 7H), 3.27 (s, 3H), 0.96 (s, 9H).

Preparation of PH-ALIG-14-1-8

Into a 250-mL round-bottom flask, was placed PH-ALIG-14-1-7 (8.10 g, 1 equiv), pyridine (80.0 mL), DMTr-Cl (7.10 g, 1.3 eq). The flask was evacuated and flushed three times with Argon. The resulting solution was stirred for 2 hr at room temperature. The reaction was then quenched by the addition of 500 mL of $NaHCO_3$(sat.). The resulting solution was extracted with 2×500 mL of ethyl acetate and the organic layers combined and dried over anhydrous sodium sulfate. The solids were filtered out. The filtrate was concentrated under vacuum. The crude product was purified by Flash with the following conditions (IntelFlash-1): Column, C18; mobile phase, ACN/$H_2O$=5/95 increasing to ACN/$H_2O$=95/5 within 30; Detector, 254. This resulted in 11.5 g (88% yield) of PH-ALIG-14-1-8 as a white solid; LC-MS: m/z 823.40 $[M+Na]^+$; 1HNMR: (300 MHz, DMSO-$d_6$) δ 11.37 (s, 1H), 7.55-7.18 (m, 20H), 6.92-6.83 (m, 4H), 6.14 (t, J=5.9 Hz, 1H), 5.48 (d, J=8.0 Hz, 1H), 3.74 (m, 7H), 3.57 (m, 4H), 3.25 (m, 5H), 0.84 (s, 9H).

Preparation of PH-ALIG-14-1-9

Into a 1000-mL round-bottom flask, was placed PH-ALIG-14-1-8 (11.5 g, 1.00 eq), THF (280.00 mL), TBAF (14.00 mL, 1.00 eq). The resulting solution was stirred for 3 hr at room temperature. The reaction was then quenched by the addition of 1 L of water. The resulting solution was extracted with 3×500 mL of ethyl acetate and the organic layers combined and dried over anhydrous sodium sulfate. The solids were filtered out. The filtrate was concentrated under vacuum. The crude product was purified by Flash with the following conditions (IntelFlash-1): Column, C18; mobile phase, ACN/$H_2O$=5/95 increasing to ACN/$H_2O$=95/5 within 30; Detector, 254. This resulted in 7.8 g (98% yield) of PH-ALIG-14-1-9 as a white solid. LC-MS: m/z 561.20 $[M-H]^-$; $^1$HNMR: (300 MHz, DMSO-$d_6$) δ 11.32 (s, 1H), 7.66 (d, J=8.1 Hz, 1H), 7.52-7.39 (m, 2H), 7.39-7.20 (m, 7H), 6.96-6.83 (m, 4H), 6.17 (t, J=5.9 Hz, 1H), 5.63 (d, J=8.0 Hz, 1H), 4.63 (t, J=5.6 Hz, 1H), 3.90-3.46 (m, 9H), 3.26 (s, 5H), 3.19-2.98 (m, 2H).

Preparation of PH-ALIG-14-1-10

Into a 3-L round-bottom flask, was placed PH-ALIG-14-1-9 (7.80 g, 1.00 eq), DCM (300.00 mL), $NaHCO_3$ (3.50 g, 3 eq). This was followed by the addition of Dess-Martin (7.06 g, 1.2 equiv) with stirring at 0° C., and the resulting solution was stirred for 20 min at 0° C. The resulting solution was stirred for 5 hr at room temperature. The reaction mixture was cooled to 0 degree C. with a water/ice bath. The reaction was then quenched by the addition of 500 mL of $NaHCO_3$:$Na_2S_2O_3$=1:1. The resulting solution was extracted with 3×500 mL of ethyl acetate and the organic layers combined and dried over anhydrous sodium sulfate. The solids were filtered out. The filtrate was concentrated under vacuum. The crude product was purified by Flash with the following conditions (IntelFlash-1): Column, C18; mobile phase, ACN/$H_2O$=5/95 increasing to ACN/$H_2O$=95/5 within 30; Detector, 254. This resulted in 5.8 g (75% yield) of PH-ALIG-14-1-10 as a white solid. LC-MS: m/z 558.80 $[M-H]^-$; $^1$HNMR-: (300 MHz, DMSO-$d_6$) δ 11.35-11.22 (m, 1H), 9.43 (s, 1H), 7.75 (d, J=8.1 Hz, 1H), 7.49-7.19 (m, 8H), 6.90 (m, 5H), 6.00 (t, J=5.9 Hz, 1H), 5.66 (m, 1H), 4.40 (m, 1H), 3.75 (s, 7H), 3.70-3.56 (m, 3H), 3.29 (d, J=3.7 Hz, 3H).

Preparation of PH-ALIG-14-1-11

Into a 250-mL 3-round-bottom flask, was placed THF (150.00 mL), NaH (1.07 g, 60% w, 3.00 equiv). The flask was evacuated and flushed three times with Argon, and the reaction mixture was cooled to −78° C. This was followed by the addition of [[(bis[[(2,2-dimethylpropanoyl)oxy]methoxy]phosphoryl)methyl([[(2,2-dimethylpropanoyl)oxy]methoxy)phosphoryl]oxy]methyl 2,2-dimethylpropanoate (14.60 g, 2.6 eq, in 60 m L THF) dropwise with stirring at −78° C. in 10 min, and the resulting solution was stirred for 30 min at −78° C. This was followed by the addition of PH-ALIG-14-1-10 (5.00 g, 1.00 eq, in 50 mL THF) dropwise with stirring at −78° C. in 10 min. The resulting solution was stirred for 4 hr at room temperature. The reaction was then quenched by the addition of 400 mL of $NH_4Cl$(sat.). The resulting solution was extracted with 3×400 mL of ethyl acetate and the organic layers combined and dried over anhydrous sodium sulfate. The solids were filtered out. The filtrate was concentrated under vacuum. The crude product was purified by Flash with the following conditions (IntelFlash-1): Column, C18; mobile phase, ACN/$H_2O$=5/95 increasing to ACN/$H_2O$=95/5 within 30; Detector, 254. This resulted in 7.2 g (crude) of PH-ALIG-14-1-11a solid. LC-MS: m/z: 865.10 $[M-H]^-$

Preparation of PH-ALIG-14-1-12

Into a 500-mL round-bottom flask, was placed PH-ALIG-14-1-11 (6.00 g), $H_2O$ (30.00 mL), AcOH (120.00 mL). The resulting solution was stirred for 1 hr at 50 degrees C. The reaction mixture was cooled to 0 degree C. with a water/ice bath. The reaction was then quenched by the addition of 2 L of $NaHCO_3$(sat.). The pH value of the solution was adjusted to 7 with $NaHCO_3$(sat.). The resulting solution was extracted with 3×500 mL of ethyl acetate and the organic layers combined and dried over anhydrous sodium sulfate. The solids were filtered out. The filtrate was concentrated under vacuum. The crude product was purified by Flash with the following conditions (IntelFlash-1): Column, C18; mobile phase, ACN/$H_2O$=5/95 increasing to ACN/$H_2O$=95/5 within 30; Detector, 254. This resulted in 2.6 g (44% yield in two steps) of PH-ALIG-14-1-12 as yellow oil. LC-MS: m/z 587.25 $[M+Na]^+$; $^1$HNMR: (300 MHz, DMSO-$d_6$) δ 11.31 (s, 1H), 7.73 (d, J=8.1 Hz, 1H), 6.63 (ddd, J=24.2, 17.2, 4.2 Hz, 1H), 6.14-5.96 (m, 2H), 5.65-5.48 (m, 5H), 5.09 (t, J=5.6 Hz, 1H), 4.17 (s, 1H), 3.65 (d, J=6.1 Hz, 2H), 3.52 (m, 2H), 3.27 (s, 3H), 1.15 (d, J=3.7 Hz, 18H); $^{31}$PNMR-: (162 MHz, DMSO-$d_6$) δ 17.96.

Preparation of PH-ALIG-14-1-0

Into a 250-mL 3-necked round-bottom flask, was placed DCM (60.00 mL), DCI (351.00 mg, 1.2 eq), 3-[[bis(diisopropylamino)phosphanyl]oxy]propanenitrile (971.00 mg, 1.3 eq), 4 A MS. The flask was evacuated and flushed three times with Argon, and the reaction mixture was cooled to 0° C. This was followed by the addition of PH-ALIG-14-1-12 (1.40 g, 1.00 eq, in 30 mL DCM) dropwise with stirring at 0° C. in 30 second. The resulting solution was stirred for 1 hr at room temperature. The reaction was then quenched by the addition of 50 mL of water. The resulting solution was extracted with 3×50 mL of ethyl acetate and the organic layers combined. The resulting mixture was washed with 3×50 ml of NaCl(sat.). The mixture was dried over anhydrous magnesium sulfate. The solids were filtered out. The filtrate was concentrated under vacuum. The crude product was purified by Prep-Archiral-SFC with the following conditions: Column: Ultimate Diol, 2*25 cm, 5|Im; Mobile Phase A: $CO_2$, Mobile Phase B: ACN (0.2% TEA); Flow rate: 50 mL/min; Gradient: isocratic 30% B; Column Temperature (20° C.): 35; Back Pressure (bar): 100; Wave Length: 254 nm; RT1 (min): 2.58; Sample Solvent: MeOH—HPLC; Injection Volume: 1 mL; Number Of Runs: 4. This resulted in 1.31 g (65% yield) PH-ALIG-14-1-0 as yellow oil. LC-MS: m/z 763.40 $[M-H]^-$; 1HNMR-: (300 MHz, Acetonitrile-$d_3$) δ 9.05 (s, 1H), 7.51 (d, J=8.1 Hz, 1H), 6.64 (dddd, J=23.8, 17.1, 4.8, 1.9 Hz, 1H), 6.23-5.92 (m, 2H), 5.70-5.51 (m, 5H), 4.38 (d, J=4.9 Hz, 1H), 3.96-3.56 (m, 8H), 3.35 (s, 3H), 2.70 (m, 2H), 1.33-1.14 (m, 30H); 31 PNMR-:(Acetonitrile-$d_3$) δ 148.75, 148.53, 16.68.

Example 3

Scheme-2

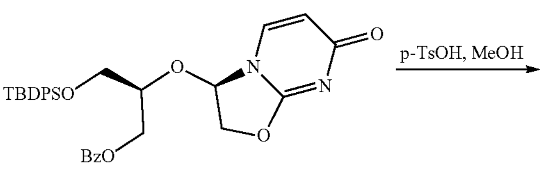

PH-ALIG-14-1-6

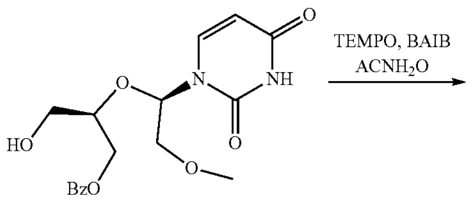

PH-ALIG-14-1-7B

-continued

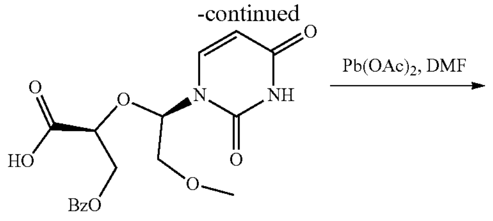

PH-ALIG-14-3-1

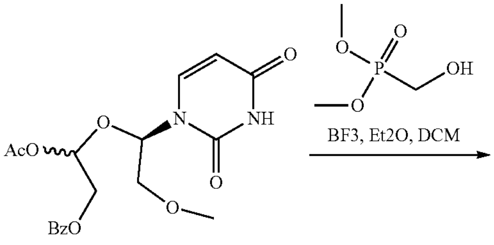

PH-ALIG-14-3-2

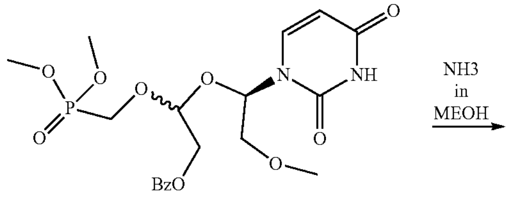

PH-ALIG-14-3-3

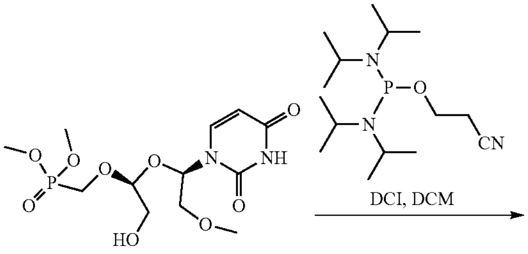

PH-ALIG-14-3-4

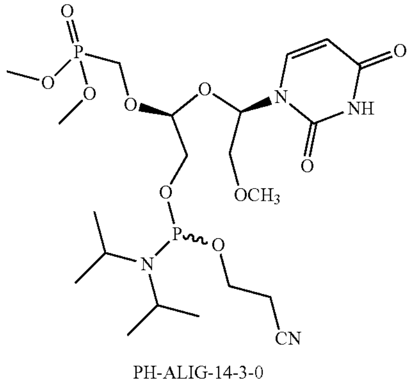 [SMILES: COC[C@@H](O[C@@H](COP(OCCC#N)N(C(C)C)C(C)C)OCP(=O)(OC)OC)n1ccc(=O)[nH]c1=O]

PH-ALIG-14-3-0

Preparation of PH-ALIG-14-1-7B

A solution of PH-ALIG-14-1-6 (23 g, 40.300 mmol, 1.00 equiv) and p-TsOH (9.02 g, 52.390 mmol, 1.3 equiv) in MeOH (1000 mL) was stirred for overnight at 40° C. under argon atmosphere. The reaction was quenched with sat. sodium bicarbonate (aq.) at 0 degrees C. The resulting mixture was extracted with EtOAc (2×500 mL). The combined organic layers were washed with water (2×500 mL), dried over anhydrous $MgSO_4$. After filtration, the filtrate was concentrated under reduced pressure. The residue was purified by reverse flash chromatography with the following conditions: column, C18 silica gel; mobile phase, ACN in water, 10% to 90% gradient in 30 min; detector, UV 254 nm. This resulted in PH-ALIG-14-1-7B (5.3 g, 36.%) as a colorless oil; LC-MS:(ES, m/z): 365 $[M+H]^+$; $^1H$-NMR: (300 MHz, DMSO-$d_6$) δ 11.20 (s, 1H), 8.09-7.78 (m, 2H), 7.63-7.50 (m, 2H), 7.51-7.35 (m, 2H), 5.95 (t, J=5.9 Hz, 1H), 5.51 (d, J=8.1 Hz, 1H), 4.73 (t, J=5.7 Hz, 1H), 4.41 (dd, J=11.9, 3.3 Hz, 1H), 4.17 (dd, J=11.9, 6.3 Hz, 1H), 3.69 (dq, J=10.1, 6.8, 6.3 Hz, 1H), 3.48-3.40 (m, 2H), 3.39-3.29 (m, 2H), 3.07 (s, 3H).

Preparation s of PH-ALIG-14-3-1

Into a 250-mL 3-necked round-bottom flask, was placed PH-ALIG-14-1-7B (7.00 g, 19.212 mmol, 1.00 equiv), ACN (60.00 mL), $H_2O$ (60.00 mL), TEMPO (0.72 g, 4.611 mmol, 0.24 equiv), BAIB (13.61 g, 42.267 mmol, 2.20 equiv). The resulting solution was stirred for 1 overnight at 30° C. The reaction was then quenched by the addition of 200 mL of water/ice. The resulting solution was extracted with 2×200 mL of ethyl acetate, The resulting mixture was washed with 2×200 ml of water. The mixture was dried over anhydrous sodium sulfate and concentrated. The crude product was purified by Flash-Prep-HPLC with the following conditions (IntelFlash-1): Column, C18 silica gel; mobile phase, ACN/$H_2O$=5/95 increasing to ACN/$H_2O$=95/5 within 30 min; Detector, UV 254 nm; product was obtained. This resulted in 5 g (68.8%) of PH-ALIG-14-3-1 as a solid. LC-MS:(ES, m/z): 379 $[M+H]^+$; $^1H$ NMR (300 MHz, DMSO-$d_6$) δ 13.24 (s, 1H), 11.31 (d, J=2.2 Hz, 1H), 8.18-7.83 (m, 2H), 7.81-7.63 (m, 2H), 7.61-7.42 (m, 2H), 6.01 (t, J=6.0 Hz, 1H), 5.61 (dd, J=8.0, 2.2 Hz, 1H), 4.72-4.40 (m, 3H), 3.73-3.55 (m, 2H), 3.22 (s, 3H).

Preparation of PH-ALIG-14-3-2

Into a 250-mL round-bottom flask, was placed PH-ALIG-14-3-1 (4.5 g, 11.894 mmol, 1.00 equiv), DMF (90.00 mL), $Pb(OAc)_4$ (15.82 g, 35.679 mmol, 3.00 equiv). The resulting solution was stirred overnight at 30° C. The reaction was then quenched by the addition of 200 mL of water/ice. The resulting solution was extracted with 2×200 mL of ethyl acetate The resulting mixture was washed with 2×200 ml of water. The mixture was dried over anhydrous sodium sulfate and concentrated. The crude product was purified by Flash with the following conditions (IntelFlash-1): Column, C18 silica gel; mobile phase, ACN/$H_2O$=5/95 increasing to ACN/$H_2O$=95/5 within 30 min; Detector, UV 254 nm; product was obtained. This resulted in 4 g PH-ALIG-14-3-2 as oil; LC-MS:(ES, m/z): 415 $[M+Na]^+$; $^1H$ NMR (300 MHz, DMSO-$d_6$) δ 11.39 (s, 1H), 7.93 (dd, J=24.2, 7.6 Hz, 2H), 7.75-7.46 (m, 4H), 6.35-6.03 (m, 2H), 5.71-5.47 (m, 1H), 4.60-4.14 (m, 2H), 3.88-3.54 (m, 2H), 3.26 (d, J=6.7 Hz, 3H), 2.03 (d, J=49.7 Hz, 3H).

Preparation of PH-ALIG-14-3-3

Into a 250-mL 3-necked round-bottom flask purged and maintained with an inert atmosphere of argon, was placed PH-ALIG-14-3-2 (4.00 g, 10.195 mmol, 1.00 eq), DCM (80.00 mL), dimethyl hydroxymethylphosphonate (22.85 g, 163.114 mmol, 16.00 eq), $BF_3$·$Et_2O$ (28.94 g, 203.91 mmol, 20 eq). The resulting solution was stirred overnight at room temperature. The reaction was then quenched by the addition of 500 mL of water/ice. The resulting solution was extracted with 2×500 mL of ethyl acetate The resulting mixture was washed with 2×500 ml of water. The mixture was dried over anhydrous sodium sulfate and concentrated. The residue was applied onto a silica gel column with dichloromethane/methanol (20/1). This resulted in 2 g (41.5%) of PH-ALIG-14-3-3 as a solid.

LC-MS:(ES, m/z): 490 $[M+H_2O]+$; 1H-NMR (300 MHz, DMSO-$d_6$) δ 11.39 (d, J=5.4 Hz, 1H), 7.96 (dt, J=11.5, 9.3 Hz, 2H), 7.81-7.40 (m, 4H), 6.29-5.98 (m, 1H), 5.56 (dd, J=12.2, 8.1 Hz, 1H), 5.28-4.99 (m, 1H), 4.29 (dp, J=25.1, 5.9 Hz, 2H), 4.16-3.84 (m, 2H), 3.75-3.53 (m, 7H), 3.28 (d, J=12.5 Hz, 2H).

Preparation of PH-ALIG-14-3-4

Into a 100-mL round-bottom flask, was placed PH-ALIG-14-3-3 (2.00 g, 4.234 mmol, 1.00 equiv), 7M $NH_3$ (g) in THF (20.00 mL) was added. The resulting solution was stirred overnight at 25° C. The resulting mixture was concentrated under vacuum. The crude product was purified by prep-sfc Column: Lux Sum i-Cellulose-5, 3*25 cm, 5 m; Mobile Phase A: $CO_2$, Mobile Phase B: MeOH (0.1% 2M $NH_3$-MEOH); Flow rate: 70 mL/min; Gradient: isocratic 50% B; Column Temperature (25° C.): 35; Back Pressure (bar): 100; Wave Length: 220 nm; RT1 (min): 3.75; RT2 (min): 4.92; Sample Solvent: MeOH:DCM=1:1; Injection Volume: 1 mL; Number Of Runs: 15, This resulted in 330 mg (21.2%) of PH-ALIG-14-3-4 as a solid. 1H-NMR-: (300 MHz, DMSO-$d_6$) δ 11.14 (s, 1H), 7.63 (d, J=8.1 Hz, 1H), 6.06 (t, J=5.9 Hz, 1H), 5.64 (d, J=8.0 Hz, 1H), 4.89 (s, 1H), 4.63 (t, J=5.3 Hz, 1H), 3.98 (d, J=9.8 Hz, 2H), 3.70 (dd, J=10.7, 1.2 Hz, 8H), 3.63 (dd, J=6.0, 3.2 Hz, 1H), 3.29 (s, 3H).

Preparation of PH-ALIG-14-3-0

To a stirred solution of 3-{[bis(diisopropylamino)phosphanyl]oxy}propanenitrile (324.10 mg, 1.075 mmol, 1.2 equiv) and 1H-imidazole-4,5-dicarbonitrile (126.99 mg, 1.075 mmol, 1.2 equiv) in DCM (10 mL) was added PH-ALIG-14-3-4 (330 mg, 0.9 mmol, 1.00 eq) dropwise at 25° C. under argon atmosphere. The resulting mixture was stirred for 30 min at 25 degrees C. The reaction was quenched with water/ice. The resulting mixture was extracted with EtOAc (2×10 mL). The combined organic layers were washed with water (2×10 mL), dried over anhydrous $MgSO_4$. After filtration, the filtrate was concentrated under reduced pressure. Column: Ultimate Diol, 2*25 cm, 5 m; Mobile Phase A: CO2, Mobile Phase B: ACN; Flow rate: 50 mL/min; Gradient: isocratic 30% B; Column Temperature (25° C.): 35; Back Pressure (bar): 100; Wave Length: 254 nm; RT1 (min): 3.95; Sample Solvent: ACN; Injection Volume: 1 mL; Number Of Runs: 10, This resulted in PH-ALIG-14-3-0 (349 mg, 68.4%) as a light yellow oil. LC-MS:(ES, m/z): 567.25 $[M+H]^+$; 1H-NMR: (300 MHz, DMSO-$d_6$) δ 11.38 (s, 1H), 7.64 (dd, J=8.0, 1.3 Hz, 1H), 6.09 (dt, J=5.8, 3.4 Hz, 1H), 5.65 (dd, J=8.0, 3.2 Hz, 1H), 4.83 (q, J=5.5 Hz, 1H), 4.03 (dt, J=9.7, 2.2 Hz, 2H), 3.83-3.40 (m, 14H), 3.30 (s, 3H), 2.77 (t, J=5.9 Hz, 2H), 1.12 (ddd, J=9.2, 6.7, 1.7 Hz, 12H); $^{31}P$ NMR (DMSO-$d_6$) δ 148.0, 147.6, 23.1

Example 4

Scheme-3

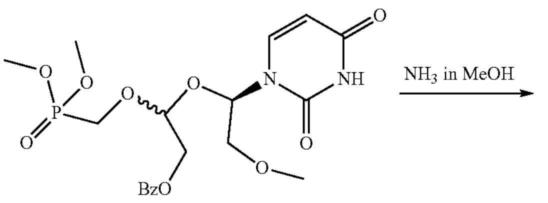

PH-ALIG-14-3-3

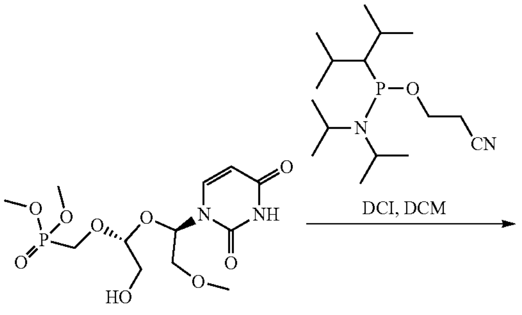

PH-ALIG-14-3-40

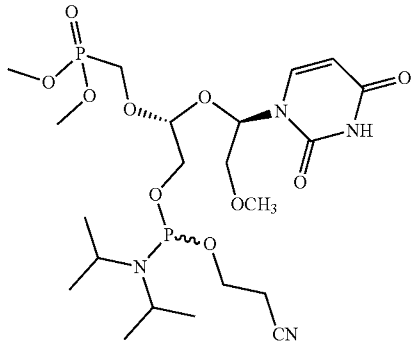

PH-ALIG-14-3-100

Preparation of PH-ALIG-14-3-40

Into a 100-mL round-bottom flask, was placed 2 PH-ALIG-14-3-3 (2.00 g, 4.234 mmol, 1.00 equiv), 7M $NH_3$ (g) in THF (20.00 mL) was added. The resulting solution was stirred overnight at 25° C. The resulting mixture was concentrated under vacuum. The crude product was purified by prep-sfc Column: Lux 5 um i-Cellulose-5, 3*25 cm, 5 m; Mobile Phase A: CO2, Mobile Phase B: MeOH (0.1% 2M $NH_3$-MeOH); Flow rate: 70 mL/min; Gradient: isocratic 50% B; Column Temperature (° C.): 35; Back Pressure (bar): 100; Wave Length: 220 nm; RT1 (min): 3.75; RT2 (min): 4.92; Sample Solvent: MeOH:DCM=1:1; Injection Volume: 1 mL; Number Of Runs: 15, This resulted in 320 mg (22.8%) of PH-ALIG-14-3-40 as a solid. 1H-NMR—-14-3-40: (300 MHz, DMSO-$d_6$) δ 11.11 (s, 1H), 7.70 (d, J=8.0 Hz, 1H), 6.03 (t, J=6.1 Hz, 1H), 5.64 (d, J=8.0 Hz, 1H), 4.97 (s, 1H), 4.76 (t, J=5.3 Hz, 1H), 4.07-3.85 (m, 1H), 3.79 (dd, J=13.9, 9.3 Hz, 1H), 3.73-3.55 (m, 9H), 3.41 (d, J=5.0 Hz, 2H), 3.28 (s, 3H).

Preparation of PH-ALIG-14-3-100

To a stirred solution/mixture of 3-{[bis(diisopropylamino)phosphanyl]oxy}propanenitrile (517.58 mg, 1.717 mmol, 1.2 equiv) and 1H-imidazole-4,5-dicarbonitrile (202.79 mg, 1.717 mmol, 1.2 equiv) in DCM was added PH-ALIG-14-3-40 (527 mg, 1.431 mmol, 1.00 eq.) dropwise at 25° C. under argon atmosphere. The resulting mixture was stirred for 30 min at 25° C. The reaction was quenched with Water/Ice. The resulting mixture was extracted with EtOAc (2×10 mL). The combined organic layers were washed with water (2×10 mL), dried over anhydrous $MgSO_4$. After filtration, the filtrate was concentrated under reduced pressure. Column: Ultimate Diol, 2*25 cm, 5 m; Mobile Phase A: $CO_2$, Mobile Phase B: ACN (0.1% DEA)—HPLC—merk; Flow rate: 50 mL/min; Gradient: isocratic 30% B; Column Temperature (° C.): 35; Back Pressure (bar): 100; Wave Length: 254 nm; RT1 (min): 4.57; Sample Solvent: ACN; Injection Volume: 1 mL; Number Of Runs: 10 to afford PH-ALIG-14-3-100 (264.8 mg, 31.7%) as a light yellow oil. LC-MS:(ES, m/z): 567.25 $[M-H]^-$: 1H NMR (300 MHz, DMSO-$d_6$) δ 13.24 (s, 1H), 11.31 (d, J=2.2 Hz, 1H), 8.18-7.83 (m, 2H), 7.81-7.63 (m, 2H), 7.61-7.42 (m, 2H), 6.01 (t, J=6.0 Hz, 1H), 5.61 (dd, J=8.0, 2.2 Hz, 1H), 4.72-4.40 (m, 3H), 3.73-3.55 (m, 2H), 3.22 (s, 3H); $^{31}P$ NMR (DMSO-$d_6$) δ 148.01, 147.67, 22.8

Example 5

Scheme-4

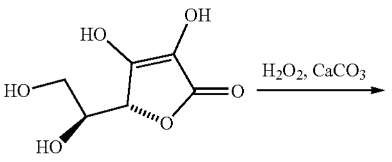

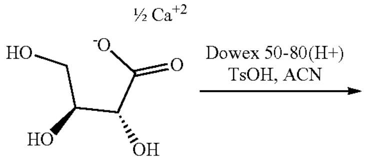

PH-ALIG-14-4-1

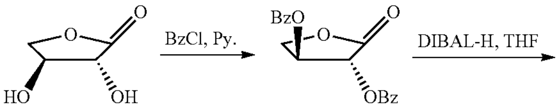

PH-ALIG-14-4-2 PH-ALIG-14-4-3

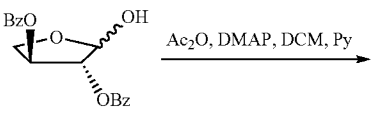

PH-ALIG-14-4-4

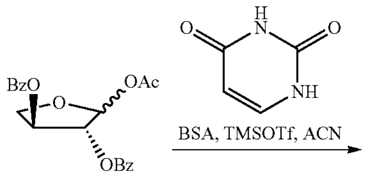

PH-ALIG-14-4-5

-continued

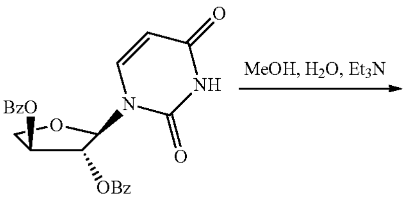

PH-ALIG-14-4-6

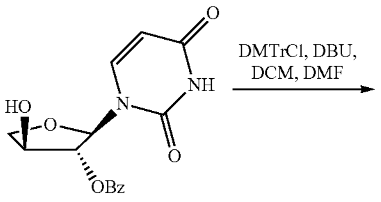

PH-ALIG-14-4-7

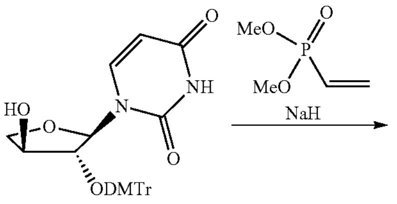

PH-ALIG-14-4-8

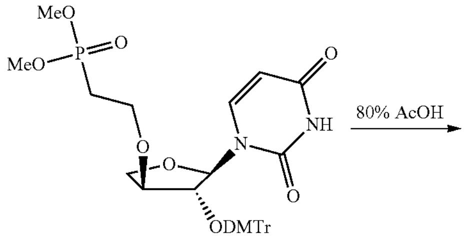

PH-ALIG-14-4-9A

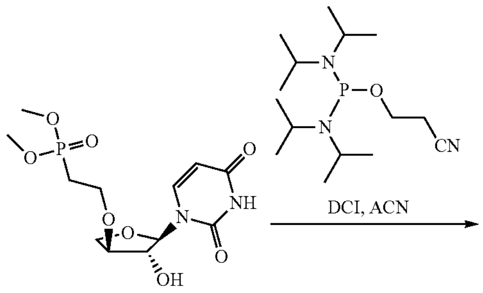

PH-ALIG-14-4-10A

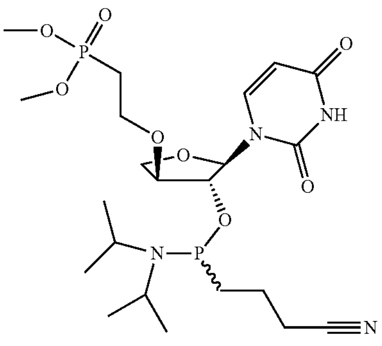

PH-ALIG-14-4-100

Preparation of PH-ALIG-14-4-1

To a stirred mixture of ascorbic acid (100.00 g, 567.78 mmol, 1.00 equiv) and $CaCO_3$(113.0 g, 1129.02 mmol, 2 equiv) in $H_2O$ (1.00 L) was added $H_2O_2$ (30%)(236.0 g, 6938.3 mmol, 12.22 equiv) dropwise at 0° C. The resulting mixture was stirred overnight at room temperature. The mixture was treat with charcoal and heat to 70 degrees until the no more peroxide was detected. The resulting mixture was filtered, the filter cake was washed with warm water (3×300 mL). The filtrate was concentrated under reduced pressure. The solid was diluted with MeOH (200 mL) and the mixture was stirred for 5 h. The resulting mixture was filtered, the filter cake was washed with MeOH (3×80 mL). The filtrate was concentrated under reduced pressure to afford L-threonate (86 g, 96.6%) as a white crude solid. 1H-NMR-: (300 MHz, Deuterium Oxide) δ 4.02 (dd, J=4.6, 2.4 Hz, 1H), 3.91 (ddt, J=7.6, 5.3, 2.2 Hz, 1H), 3.78-3.44 (m, 2H).

Preparation of PH-ALIG-14-4-2

Into a 5 L round-bottom flask were added L-threonate (70.00 g, 518.150 mmol, 1.00 equiv) and $H_2O$ (2 L) at room temperature. The residue was acidified to pH=1 with Dowex 50wX8, H (+) Form). The resulting mixture was stirred for 1 h at 70° C. The resulting mixture was filtered, the filter cake was washed with water (2×1 L). The filtrate was concentrated under reduced pressure. The solid was co-evaporated with (2×2 L). Then the solid was diluted with ACN (700.00 mL), and the TsOH (5.35 g, 31.089 mmol, 0.06 equiv) was added. The resulting mixture was stirred for 1 h at 80 degrees C. under air atmosphere. The resulting mixture was filtered, the filter cake was washed with ACN (2×500 mL). The filtrate was concentrated under reduced pressure to PH-ALIG-14-4-2 (70 g, crude) as a yellow oil.

Preparation of PH-ALIG-14-4-3

To a stirred solution of (PH-ALIG-14-4-2 (70.0 g crude, 593.2 mmol, 1.00 eq.) in pyridine (280.00 mL) was added benzoyl chloride (207.62 g, 1.483 mol, 2.5 equiv) dropwise at 0° C. under argon atmosphere. The resulting mixture was stirred for 1 h at room temperature under argon atmosphere. The reaction was quenched by the addition of sat. $NaHCO_3$ (aq.) (500 mL) at 0 degrees C. The resulting mixture was extracted with $CH_2Cl_2$ (3×500 mL). The combined organic layers were washed with brine (2×300 mL), dried over anhydrous $Na_2SO_4$. After filtration, the filtrate was concentrated under reduced pressure. The residue was purified by silica gel column chromatography, eluted with PE/EtOAc to afford (PH-ALIG-14-4-3 (80 g, 41.4%) as an off-white solid. LC-MS:(ES, m/z): 327 $[M+H]^+$; 1H-NMR: (300 MHz, $CDCl_3$) δ 8.18-8.04 (m, 4H), 7.68-7.61 (m, 2H), 7.50 (tt, J=7.1, 1.4 Hz, 4H), 5.96-5.57 (m, 2H), 5.11-5.00 (m, 1H), 4.45-4.35 (m, 1H).

Preparation of PH-ALIG-14-4-4

To a stirred solution of PH-ALIG-14-4-3 (125 g, 383.078 mmol, 1.00 eq) in THF (1.50 L) was added DIBAL-H (1M)(600 mL, 2 eq) dropwise at −78° C. under argon atmosphere. The resulting mixture was stirred for 1 h at −78 degrees C. under argon atmosphere. Desired product was detected by LCMS. The reaction was quenched with MeOH at 0° C. The resulting mixture was diluted with EtOAc (600 mL). Then the resulting mixture was filtered, the filter cake was washed with EtOAc (3×800 mL). The filtrate was concentrated under reduced pressure. This resulted in PH-ALIG-14-4-4 (73 g, crude) as a colorless solid. LC-MS: (ES, m/z): 392 [M+Na+ACN]+; 1H-NMR-: (400 MHz, Chloroform-d) δ 8.22-7.99 (m, 8H), 7.62 (dtd, J=7.4, 4.4, 2.2 Hz, 4H), 7.48 (td, J=7.8, 2.4 Hz, 8H), 5.87 (d, J=4.3 Hz, 1H), 5.77 (dt, J=6.6, 3.6 Hz, 1H), 5.56 (d, J=4.9 Hz, 2H), 5.50 (t, J=4.3 Hz, 1H), 4.73 (s, 1H), 4.63 (ddd, J=10.4, 7.9, 6.1 Hz, 2H), 4.28 (dd, J=10.3, 3.8 Hz, 1H), 3.99 (dd, J=10.6, 3.2 Hz, 1H).

Preparation of PH-ALIG-14-4-5

To a stirred solution of (PH-ALIG-14-4-4 (73.00 g, 222.344 mmol, 1.00 equiv) and DMAP (271.63 mg, 2.223 mmol, 0.01 equiv) and pyridine (365.00 mL) in DCM (365.00 mL) were added $Ac_2O$ (24.97 g, 244.6 mmol, 1.1 equiv) dropwise at 0 degrees C. under argon atmosphere. The resulting mixture was stirred for 1 h at room temperature under argon atmosphere. The reaction was quenched with sat. $NaHCO_3$ (aq.) at 0 degrees C. The resulting mixture was extracted with $CH_2Cl_2$ (3×500 mL). The combined organic layers were washed with sat. $CuSO_4$ (3×200 mL), dried over anhydrous $Na_2SO_4$. After filtration, the filtrate was concentrated under reduced pressure. The residue was purified by silica gel column chromatography, eluted with PE/EtOAc to afford PH-ALIG-14-4-5 (60 g, 73%) as a colorless oil. LC-MS:(ES, m/z): 434 $[M+Na+ACN]^+$; 1H-NMR: (400 MHz, Chloroform-d) δ 8.17-8.02 (m, 8H), 7.63 (tddd, J=7.9, 6.6, 3.2, 1.6 Hz, 4H), 7.57-7.44 (m, 8H), 6.66 (d, J=4.5 Hz, 1H), 6.40 (s, 1H), 5.83-5.53 (m, 4H), 4.67 (ddd, J=23.4, 10.5, 6.2 Hz, 2H), 4.24 (dd, J=10.5, 3.8 Hz, 1H), 4.19-4.01 (m, 1H), 2.18 (s, 3H), 2.06 (d, J=3.2 Hz, 3H).

Preparation of PH-ALIG-14-4-6

To a stirred mixture of PH-ALIG-14-4-5 (50.00 g, 135.005 mmol, 1.00 eq) and uracil (15.13 g, 135.005 mmol, 1 eq) in can (500.00 mL) was added BSA (54.81 g, 270.010 mmol, 2 eq) in portions at room temperature under air atmosphere. The resulting mixture was stirred for 1 h at 60° C. under argon atmosphere. After that, the TMSOTf (90.02 g, 405.0 mmol, 3 eq) was added dropwise at 0° C. The resulting mixture was stirred for 2 h at 60° C. under argon atmosphere. The mixture was neutralized to pH=7 with saturated $NaHCO_3$ (aq.) at 0° C. The resulting mixture was extracted with $CH_2C_2$ (3×400 mL). The combined organic layers were washed with brine (2×400 mL), dried over anhydrous $Na_2SO_4$. After filtration, the filtrate was concentrated under reduced pressure. The residue was purified by silica gel column chromatography, eluted with PE/EtOAc (1:1) to afford PH-ALIG-14-4-6 (43 g, 75.4%) as a white solid. LC-MS:(ES, m/z): $[M+H]^+$; 423 464 [M+H+ACN]+; 1H-NMR-: (300 MHz, Chloroform-d) δ 9.08-8.89 (m, 1H), 8.17-7.94 (m, 4H), 7.70-7.43 (m, 7H), 6.19 (d, J=1.9 Hz, 1H), 5.84-5.71 (m, 2H), 5.62 (td, J=3.3, 2.8, 1.4 Hz, 1H), 4.59-4.44 (m, 2H), 4.14 (q, J=7.2 Hz, 1H).

Preparation of PH-ALIG-14-4-7

A solution of PH-ALIG-14-4-6 (52.00 g, 123.108 mmol, 1 eq) was dissolved in 642 ml of MeOH/$H_2O$/TEA (5:1:1) at room temperature and heat to reflux until no more starting material was detected (2~3 h). The resulting mixture was concentrated under reduced pressure. The residue was dissolved in EtOAc (600 mL) and the organic layer was extracted with water (5×800 mL). The aqueous layer was concentrated under vacuum to afford PH-ALIG-14-4-7 (21 g, crude) as a off-white solid. The crude product was used in the next step directly without further purification. LC-MS-: (ES, m/z): 213 [M−H]$^-$; 1 H-NMR: (300 MHz, DMSO-$d_6$) δ 11.26 (s, 1H), 7.68 (d, J=8.1 Hz, 1H), 5.75 (s, 1H), 5.65 (d, J=1.2 Hz, 1H), 5.59 (d, J=8.1 Hz, 1H), 5.39 (s, 1H), 4.10-3.97 (m, 4H).

Preparation of PH-ALIG-14-4-8

To a stirred mixture of PH-ALIG-14-4-7 (16.00 g, 74.705 mmol, 1.00 equiv) and DBU (22.75 g, 149.409 mmol, 2 equiv) in DCM (80.00 mL) and DMF (200.00 mL) was added DMTr-Cl (7.88 g, 25.680 mmol, 1.1 equiv) dropwise at room temperature under argon atmosphere. The resulting mixture was stirred for 2 h at room temperature under argon atmosphere. The reaction was quenched by the addition of sat. $NaHCO_3$ (aq.) (100 mL) at 0 degrees C. The resulting mixture was extracted with EtOAc (3×60 mL). The combined organic layers were washed with brine (2×50 mL), dried over anhydrous $Na_2SO_4$. After filtration, the filtrate was concentrated under reduced pressure. The residue was purified by silica gel column chromatography, eluted with PE (0.5% TEA)/EtOAc (2:3) to afford PH-ALIG-14-4-8 (25 g, 64.8%) as a off-white solid; LC-MS:(ES, m/z): 515 [M−H]$^-$; $^1$H-NMR: (400 MHz, DMSO-$d_6$) δ 11.33 (s, 1H), 7.57 (d, J=8.1 Hz, 1H), 7.45-7.13 (m, 9H), 6.86 (t, J=8.5 Hz, 4H), 5.94 (d, J=1.7 Hz, 1H), 5.58 (d, J=8.1 Hz, 1H), 5.15 (d, J=2.6 Hz, 1H), 3.97-3.79 (m, 3H), 3.73 (d, J=2.3 Hz, 6H), 3.33 (d, J=2.5 Hz, 1H).

Preparation of PH-ALIG-14-4-9 A

To a stirred solution of PH-ALIG-14-4-8 (6.00 g, 11.616 mmol, 1.00 eq) in THF (240.00 mL) was added NaH (60%) (1.40 g, 35.003 mmol, 3 eq) dropwise at 0° C. under argon atmosphere. The resulting mixture was stirred for 30 min at 0 degrees C. under argon atmosphere. Then the dimethyl ethenylphosphonate (15.81 g, 116.2 mmol, 10.00 eq) was added and the resulting mixture was stirred overnight at room temperature under argon atmosphere. The reaction was quenched with sat. $NH_4Cl$ (aq.) at room temperature. The resulting mixture was extracted with EtOAc (3×100 mL). The combined organic layers were washed with brine (3×80 mL), dried over anhydrous $Na_2SO_4$. After filtration, the filtrate was concentrated under reduced pressure. The residue was purified by reverse flash chromatography with the following conditions: column, C18 mobile phase, ACN in water, 5% to 95% gradient in 30 min; detector, UV 254 nm to afford PH-ALIG-14-4-9 A (3.65 g, 48.15%) as a white solid.

LC-MS:(ES, m/z): 675 [M+Na]$^+$; 1 H-NMR-: (300 MHz, DMSO-$d_6$) δ 11.39 (s, 1H), 7.44-7.36 (m, 3H), 7.34-7.21 (m, 7H), 6.93-6.83 (m, 4H), 6.08 (d, J=2.0 Hz, 1H), 5.55 (d, J=8.1 Hz, 1H), 4.08 (d, J=11.0 Hz, 1H), 3.92 (d, J=2.0 Hz, 1H), 3.82-3.71 (m, 7H), 3.57 (dd, J=10.9, 3.6 Hz, 6H), 3.30-3.23 (m, 1H), 3.06-2.86 (m, 2H), 1.96 (dt, J=18.1, 7.1 Hz, 2H).

Preparation of PH-ALIG-14-4-10 A

A solution of PH-ALIG-14-4-9 A (2.80 g, 4.3 mmol, 1.00 equiv) in AcOH (12.00 mL) and $H_2O$ (3.00 mL) was stirred for overnight at room temperature under air atmosphere. The reaction was quenched with sat. $NaHCO_3$ (aq.) at 0 degrees C. The resulting mixture was washed with 3×20 mL of $CH_2Cl_2$. The product in the water layer. The water layer was concentrated under reduced pressure. The product was purified by Prep-SFC with the following conditions (Prep SFC80-2): Column, Green Sep Basic, 3*15 cm; mobile phase, $CO_2$ (70%) and IPA (0.5% 2M $NH_3$-MeOH)(30%); Detector, UV 254 nm; product was obtained. This resulted in 870 mg (57.89%) of PH-ALIG-14-4-10 A as a white solid. LC-MS:(ES, m/z): 351 [M+Na]+; 1H-NMR-: (300 MHz, DMSO-$d_6$) δ 11.28 (s, 1H), 7.56 (d, J=8.1 Hz, 1H), 5.86 (d, J=4.4 Hz, 1H), 5.65 (d, J=1.6 Hz, 1H), 5.56 (d, J=8.1 Hz, 1H), 4.17 (d, J=10.1 Hz, 1H), 4.10 (d, J=4.3 Hz, 1H), 4.00 (dd, J=10.1, 3.9 Hz, 1H), 3.87 (dt, J=4.1, 1.3 Hz, 1H), 3.72-3.49 (m, 8H), 2.08 (dd, J=7.1, 2.8 Hz, 1H), 2.05-1.96 (m, 1H).

Preparation of PH-ALIG-14-4-100

Into a 250 mL 3-necked round-bottom flask were added Molecularsieve and ACN (30.00 mL) at room temperature. The resulting mixture was stirred for 10 min at room temperature under argon atmosphere. Then to the stirred solution were added 3-[[bis(diisopropylamino)phosphanyl] oxy] propanenitrile (1058.46 mg, 3.512 mmol, 1.5 equiv) and DCI (359.12 mg, 3.043 mmol, 1.30 equiv). Then the dimethyl PH-ALIG-14-4-10 A (820.00 mg, 2.341 mmol, 1.00 equiv) in 30 mL ACN was added dropwise at room temperature under argon atmosphere. The resulting mixture was stirred for 1 h at room temperature under argon atmosphere. The resulting mixture was diluted with CH2Cl2 (60 mL). The combined organic layers were washed with water (3×40 mL) after filtration, dried over anhydrous MgSO4. After filtration, the filtrate was concentrated under reduced pressure. The residue was purified by Prep-TLC (0.5% TEA in PE/10% EtOH in EtOAc 1:9) to afford PH-ALIG-14-4-100 (800 mg, 62.1%) as a colorless oil. LC-MS:(ES, m z): 549 [M−H]$^-$; 1H-NMR: (300 MHz, DMSO-$d_6$) δ 11.34 (s, 1H), 7.61 (dd, J=8.1, 1.7 Hz, 1H), 5.80 (dd, J=15.0, 1.8 Hz, 1H), 5.60 (d, J=8.1 Hz, 1H), 4.48-4.23 (m, 2H), 4.17-3.98 (m, 2H), 3.88-3.73 (m, 2H), 3.72-3.51 (m, 10H), 2.79 (q, J=5.9 Hz, 2H), 2.07 (dtt, J=17.9, 7.1, 3.2 Hz, 2H), 1.15 (ddd, J=6.3, 3.8, 2.1 Hz, 12H); $^{31}$P NMR (DMSO-$d_6$) δ 149.71, 149.35, 30.85, 30.75

Example 6

Scheme-5

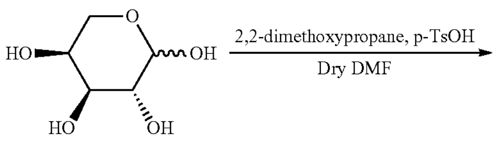

1

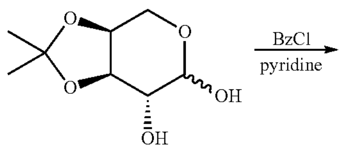

2

-continued

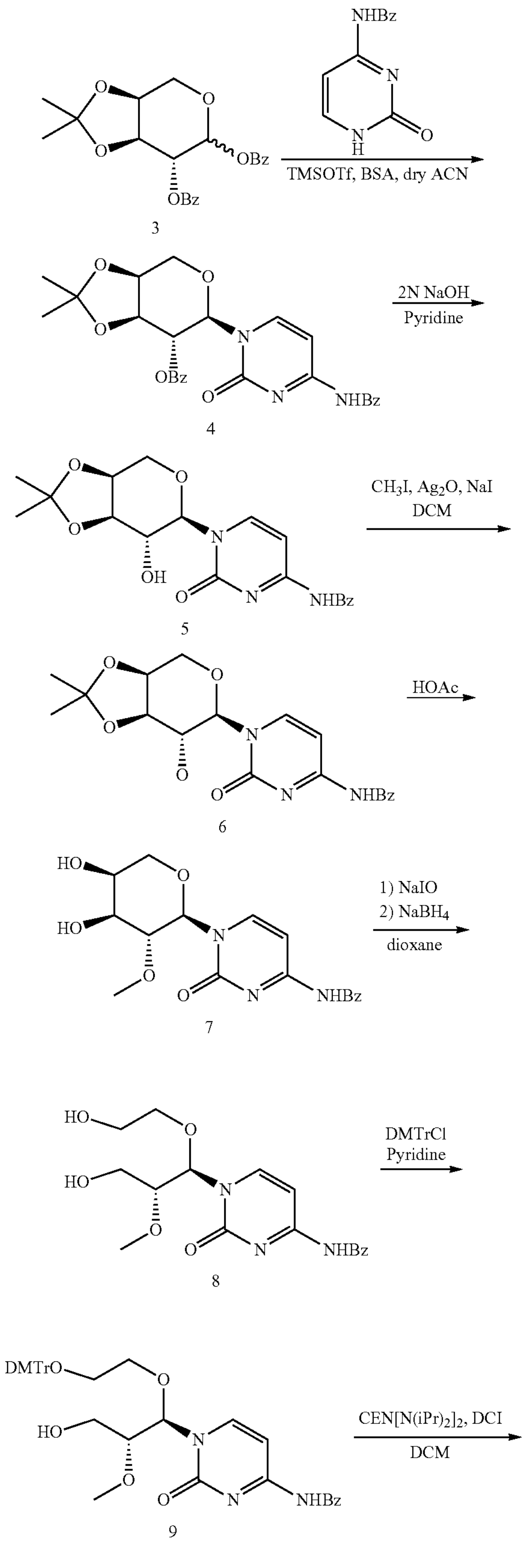

-continued

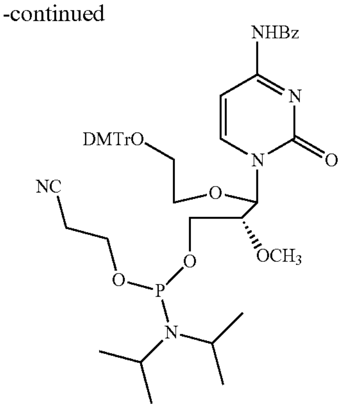

10

Preparation of 2: (*J. Chem. Soc., Perkin Trans.* 1, 1992, 1943-1952) To a solution of 1 (150.0 g, 1.0 mol) in DMF (2.0 L) was added 2, 2-dimethoxypropane (312.0 g, 3.0 mol) and p-TsOH (1.7 g, 10.0 mmol), then the reaction mixture was stirred at r.t. for 4 h, after the reaction, the solvent was concentrated to give the crude products which was used directly to next step.

Preparation of 3: (*J. Chem. Soc., Perkin Trans.* 1, 1992, 1943-1952) To a solution of 2 (190.0 g, 1.0 mol) in pyridine (2.0 L) was added BzCl (560.0 g, 4.0 mol) then the reaction mixture was stirred at r.t. for 2 h, after the reaction, the reaction mixture was poured into the ice water, EA was added for extraction, and the organic phase was washed with brine, dried over $Na_2SO_4$ and concentrated to give the crude product which was purified by silica gel column (EA: PE=1:5 to 1:1) to give 3 (350.0 g, 87.9% yield), ESI-LCMS: m/z=421.2 $[M+Na]^+$.

Preparation of 4: (J. Chem. Soc., Perkin Trans. 1, 1992, 1943-1952) to a solution of 3 (240.0 g, 815.5 mmol) in MeCN (3.0 L) was added N-(2-oxo-1H-pyrimidin-4-yl) benzamide (193.0 g, 897.0 mmol) and BSA (496.6 g, 2.4 mol). then the reaction mixture was stirred at 50° C. for 30 min, then the reaction mixture was cooled to 0° C., and the TMSOTf (271.5 g, 1.2 mol) was added into the mixture at 0° C., then the reaction mixture was stirred at 70° C. for 2 h, after the reaction, the solvent was concentrated to give an oil, then the oil was poured into the solution of $NaHCO_3$ maintaining the mixture was slightly alkaline, EA was added for extraction, and the organic phase was washed with brine, dried over $Na_2SO_4$ and concentrated to give the crude product which was purified by silica gel column (EA: PE=1:3 to 1:1) to give 4 (180.0 g, 44.9% yield). ESI-LCMS: m/z=491.2 $[M+H]^+$; $^1H$ NMR (400 MHz, DMSO-$d_6$) δ 11.19 (s, 1H), 8.20 (d, J=7.6 Hz, 1H), 8.01-7.84 (m, 4H), 7.73-7.57 (m, 2H), 7.50 (dt, J=10.4, 7.7 Hz, 4H), 7.40 (d, J=7.4 Hz, 1H), 6.03 (d, J=9.4 Hz, 1H), 5.33 (dd, J=9.4, 7.3 Hz, 1H), 4.66 (dd, J=7.3, 5.3 Hz, 1H), 4.45-4.35 (m, 2H), 4.22 (dd, J=13.7, 2.5 Hz, 1H), 1.58 (s, 3H), 1.34 (s, 3H).

Preparation of 5: To a solution of 4 (78.0 g, 158.7 mmol) in pyridine (800.0 mL) was added a solution of NaOH (6.3 g, 158.7 mmol) in a mixture solvent of $H_2O$ and MeOH (4:1, 2N), Then the reaction mixture was stirred at 0° C. for 20 min, LC-MS and TLC show that the raw material was disappeared, then the mixture was pour into a solution of $NH_4Cl$, EA was added for extraction, and the organic phase was washed with brine, dried over $Na_2SO_4$ and concentrated to give the crude product, which was purified by silica gel column (DCM:MeOH=30:1 to 10:1) to give 5 (56.0 g, 91.0% yield). ESI-LCMS: m/z=388.1 $[M+H]^+$; $^1H$ NMR (400 MHz, DMSO-$d_6$) δ 11.29 (s, 1H), 8.16 (d, J=7.6 Hz, 1H), 8.08-7.99 (m, 2H), 7.67-7.60 (m, 1H), 7.53 (t, J=7.6 Hz, 2H), 7.35 (d, J=7.6 Hz, 1H), 5.63 (d, J=6.1 Hz, 1H), 5.51 (d, J=9.5 Hz, 1H), 4.35-4.13 (m, 3H), 3.78 (dt, J=9.6, 6.5 Hz, 1H), 3.19 (d, J=5.1 Hz, 1H), 1.53 (s, 3H), 1.32 (s, 3H).

Preparation of 6: To a solution of 5 (15.0 g, 38.7 mmol) in DCM (200.0 mL) was added $Ag_2O$ (35.8 g, 154.8 mmol), $CH_3I$ (54.6 g, 387.2 mmol) and NaI (1.1 g, 7.7 mmol), then the reaction mixture was stirred at r.t. overnight, after the reaction, filtrate was obtained through filtration, and the filtrate concentrated the solvent to obtain the product 6 (13.0 g, 75.2% yield). ESI-LCMS: m/z=402.30 $[M+H]^+$; $^1H$ NMR (400 MHz, DMSO-$d_6$) δ 11.30 (s, 1H), 8.22 (s, 1H), 8.00 (d, J=7.6 Hz, 2H), 7.71-7.20 (m, 4H), 5.56 (d, J=9.3 Hz, 1H), 4.33 (t, J=6.1 Hz, 1H), 4.26 (dd, J=6.2, 2.1 Hz, 1H), 4.20 (d, J=13.5 Hz, 1H), 3.98 (dd, J=13.5, 2.5 Hz, 1H), 3.66 (dd, J=9.3, 6.6 Hz, 1H), 3.34 (s, 3H), 1.57 (s, 3H), 1.32 (s, 3H).

Preparation of 7: To a solution of 6 (12.0 g, 29.9 mmol) was added $CH_3COOH$ (120.0 mL), then the mixture was stirred at r.t. for 2 h, LC-MS and TLC showed that the raw material was disappeared, then the solvent was concentrated to get the crude product 7 (10.0 g, 83.3% yield). ESI-LCMS: m/z=362.1 $[M+H]^+$.

Preparation of 8: To a solution of 7 (10.0 g, 24.9 mmol) in dioxane:$H_2O$=3:1 (120.0 mL) was added $NaIO_4$ (8.8 g, 41.5 mmol), then the reaction mixture was stirred at r.t. for 2 h, LC-MS and TLC showed that the raw material was disappeared, then the reaction mixture was cooled to 0° C., and $NaBH_4$ (2.4 g, 41.5 mmol) was added into the mixture and stirred at 0° C. for 0.5 h, LC-MS and TLC showed that the raw material was disappeared, then $NH_4Cl$ was added into the mixture to adjust pH to be slightly alkaline, and concentrated to give the crude product, which was purified by silica gel column (PE:EA=5:1 to 1:1) to give 8 (8.0 g, 79.5% yield). ESI-LCMS: m/z=364.1 $[M+H]^+$; $^1H$ NMR (400 MHz, DMSO-$d_6$) δ 11.26 (s, 1H), 8.14 (d, J=7.5 Hz, 1H), 8.07-7.94 (m, 2H), 7.67-7.59 (m, 1H), 7.52 (t, J=7.6 Hz, 2H), 7.37 (s, 1H), 5.91 (d, J=6.0 Hz, 1H), 4.77 (t, J=5.6 Hz, 1H), 4.70 (t, J=5.1 Hz, 1H), 3.70 (ddd, J=11.5, 5.0, 2.5 Hz, 1H), 3.57-3.39 (m, 6H), 3.31 (s, 3H).

Preparation of 9: To a solution of 8 (4.0 g, 11.0 mmol) in pyridine (50.0 mL) was added DMTrCl (5.5 g, 16.5 mmol), then the reaction mixture was stirred at r.t. for 2 h, LC-MS showed that the raw material was 20.0% and The ratio of product to by-product was 3.5:1. then the solvent was concentrated to get residue which was purified by silica gel column to give the purified products and by-products was 5 g in total, then the product was purified by SFC to get 9 (3.0 g, 40.9% yield). ESI-LCMS: m/z=666.2 $[M+H]^+$; $^1H$ NMR (400 MHz, DMSO-$d_6$) δ 11.33 (s, 1H), 8.20 (d, J=7.4 Hz, 1H), 8.04 (d, J=7.7 Hz, 2H), 7.64 (t, J=7.4 Hz, 1H), 7.53 (t, J=7.6 Hz, 2H), 7.40 (d, J=7.8 Hz, 3H), 7.36-7.18 (m, 7H), 6.89 (d, J=8.4 Hz, 4H), 5.96 (d, J=5.7 Hz, 1H), 4.79 (t, J=5.7 Hz, 1H), 3.73 (s, 6H), 3.66-3.46 (m, 4H), 3.37 (s, 3H), 3.16 (ddd, J=10.1, 7.1, 3.0 Hz, 1H), 3.04 (dt, J=10.9, 3.4 Hz, 1H), 2.08 (s, 1H).

Preparation of 10: To a solution of 9 (2.8 g, 4.2 mmol) in DCM (30.0 mL) was added $CEP[N(iPr)_2]_2$ (1.3 g, 4.2 mmol) and DCI (601.2 mg, 5.1 mmol). The mixture was stirred at r.t. for 1 h. LC-MS showed 9 was consumed completely. The solution was washed with a solution of $NaHCO_3$ twice and washed with brine and dried over $Na_2SO_4$. Then concentrated to give a residue which was purified by Flash-Prep-HPLC with the following conditions (IntelFlash-1): Column, $C_{18}$ silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20.0 min, the eluted product was collected at $CH_3CN/H_2O$ (0.5% $NH_4HCO_3$)=90/10; Detector, UV 254 nm. This resulted in to give 10 (2.8 g, 76.8% yield). ESI-LCMS: m/z=866.2 $[M+H]^+$; $^1H$ NMR (400 MHz, DMSO-$d_6$) δ 11.34 (s, 1H), 8.22 (d, J=7.4 Hz, 1H), 8.09-7.98 (m, 2H), 7.64 (t, J=7.4 Hz, 1H), 7.53 (t, J=7.6 Hz, 2H), 7.45 (d, J=7.3 Hz, 1H), 7.39 (d, J=7.5 Hz, 2H), 7.31 (t, J=7.6 Hz, 2H), 7.24 (t, J=9.1 Hz, 5H), 6.89 (d, J=8.8 Hz, 4H), 5.96 (d, J=6.1 Hz, 1H), 4.02-3.86 (m, 1H), 3.84-3.63 (m, 11H), 3.56 (dtq, J=13.3, 6.6, 3.5, 3.1 Hz, 3H), 3.37 (s, 2H), 3.16 (ddd, J=10.0, 6.8, 3.3 Hz, 1H), 3.04 (ddd, J=10.7, 5.5, 3.0 Hz, 1H), 2.75 (td, J=5.9, 2.3 Hz, 2H), 1.18-1.07 (m, 12H); $^{31}P$ NMR (DMSO-$d_6$) δ 148.02 (d, J=12.0 Hz).

Example 7

Scheme-6

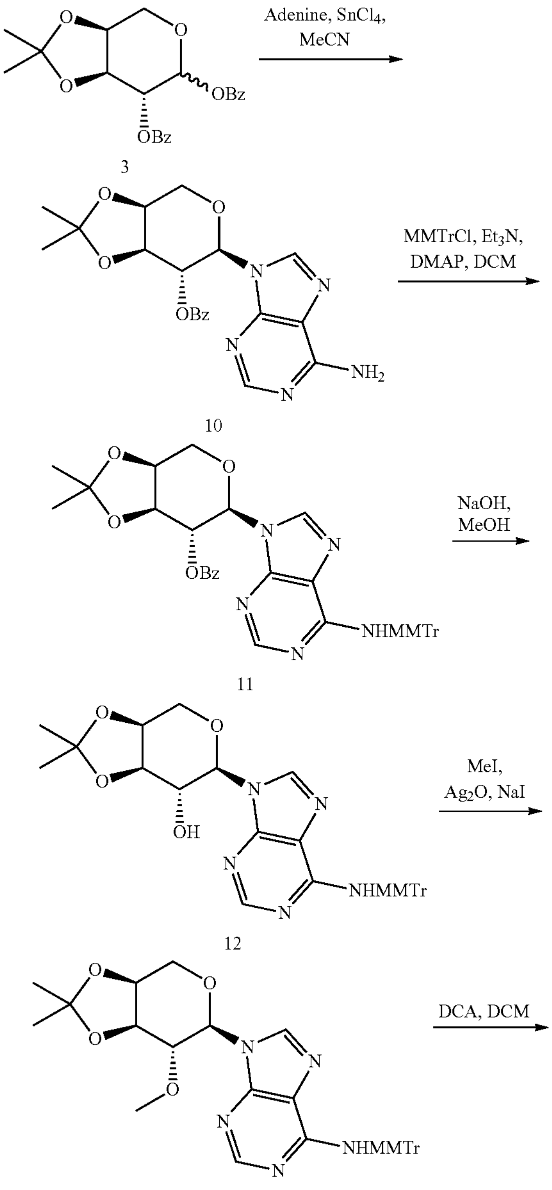

3

10

11

12

13

-continued

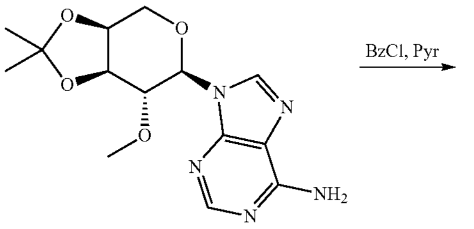

14

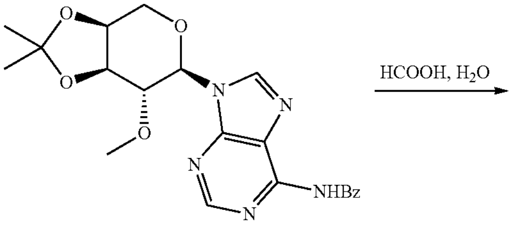

15

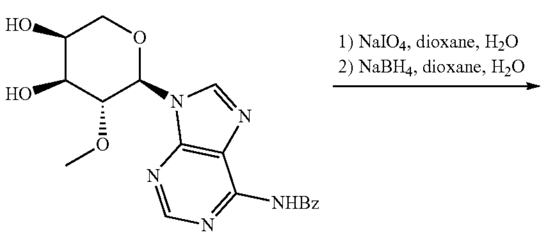

16

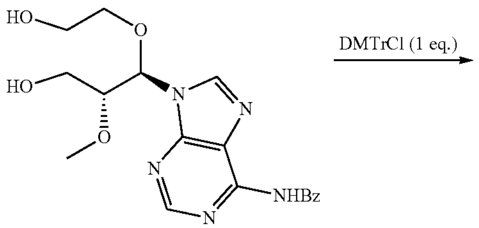

17

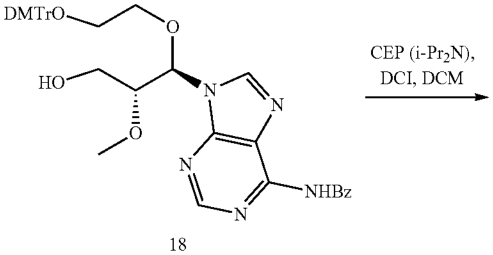

18

-continued

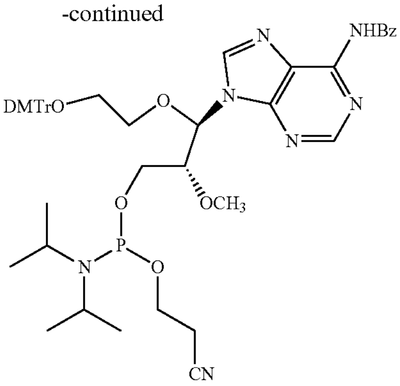

19

Example 7

Preparation of 10: To the solution of 3 (200.0 g, 0.5 mol) in ACN (2000.0 mL) was added a solution of $SnCl_4$ in DCM (1000.0 mL) at 0° C. under $N_2$, and the reaction mixture was stirred at 0° C. for 4 h under $N_2$ atmosphere. Then the reaction solution was poured into saturated sodium bicarbonate solution, the resulting product was extracted with EA (3*500.0 mL). The combined organic layer was washed with water and brine, dried over $Na_2SO_4$, and concentrated to give the crude, which was purified by silica gel column (PE:EA=5:1 to 0:1) to give 10 (65.0 g, 31.4% yield) as a white solid. ESI-LCMS: m/z=412.0 $[M+H]^+$; $^1$H NMR (400 MHz, DMSO-$d_6$) δ 8.27 (s, 1H), 8.09 (s, 1H), 7.74-7.60 (m, 2H), 7.59-7.57 (m, 1H), 7.44-7.40 (m, 2H), 7.24 (s, 2H), 5.90 (d, J=9.6 Hz, 1H), 5.73 (dd, J=7.4 Hz, 1H), 4.63 (t, 1H), 4.50-4.30 (m, 2H), 4.21 (dd, J=13.6 Hz, 1H), 1.61 (s, 3H), 1.35 (s, 3H).

Preparation of 11: To a solution of 10 (40.0 g, 97.3 mmol) in DCM (500.0 mL) was added $Et_3N$ (30.0 g, 297.0 mmol) and DMAP (1.2 g, 9.8 mmol) at r.t. The reaction mixture was replaced with $N_2$ over 3 times, then MMTrCl (45.0 g, 146.1 mmol) was added to the mixture. The reaction mixture was stirred at r.t. overnight. TLC and LC-MS showed that 10 was consumed, and the reaction mixture was added to an aqueous solution of $NaHCO_3$ in ice-water. Then extracted product with EA, washed the organic phase with brine, and dried the organic phase over $Na_2SO_4$, then concentrated to get 11 (66.5 g) as a crude, used next step directly.

Preparation of 12: To a solution of 11 (66.5 g, 97.3 mmol) in pyridine (600.0 mL) was added 2N NaOH ($H_2O$: MeOH=4:1) (200.0 mL) at r.t. Then the reaction mixture was stirred at 0° C. for 30 min, LC-MS and TLC showed that the raw material was disappeared, then the mixture was poured into a solution of $NH_4Cl$, EA was added for extraction, and the organic phase was washed with brine, dried over $Na_2SO_4$ and concentrated to give the crude product which was purified by silica gel column (EA:PE=1:5 to 1:1) to give 12 (50.0 g, 88.7% yield for two step). ESI-LCMS: m/z=580.4 $[M+H]^+$; $^1$H NMR (400 MHz, DMSO-$d_6$) δ 8.44 (s, 1H), 7.92 (s, 1H), 7.36-7.16 (m, 13H), 6.89-6.80 (m, 2H), 5.59 (d, J=6.0 Hz, 1H), 5.35 (d, J=9.6 Hz, 1H), 4.32-4.12 (m, 4H), 4.08-3.95 (m, 3H), 3.72 (s, 3H), 1.99 (s, 3H), 1.54 (s, 3H), 1.32 (s, 3H), 1.17 (t, J=7.1 Hz, 3H).

Preparation of 13: To a solution of 12 (46.0 g, 79.4 mmol) in $CH_3I$ (200.0 mL) was added $Ag_2O$ (36.6 g, 158.4 mmol) and NaI (6.0 g, 42.5 mmol), then the reaction mixture was stirred at r.t. for 4 h, then the reaction mixture was filtrated and concentrated the solvent to obtain the product 13 (46.0 g, 97.6% yield), used next step directly. ESI-LCMS: m/z=594.3 $[M+H]^+$.

Preparation of 14: To a stirred solution of DCA (22.5 mL) in DCM (750.0 mL) was added 13 (46.0 g, 77.5 mmol) and $Et_3Si$ (185.0 mL) at r.t. And the reaction mixture was stirred at r.t. for 12 h. The reaction solution was evaporated to dryness under reduced pressure to give a residue, which was slurry with a solution of $NaHCO_3$ (50.0 mL) to get 14 (19.0 g, 76% yield), which was used next step directly.

Preparation of 15: To a solution of 14 (16.0 g, 49.7 mmol) in pyridine (200.0 mL) was added BzCl (9.0 g, 64.7 mmol) at 0° C. Then the reaction mixture was stirred at r.t. for 2 h. LC-MS showed 6 was consumed completely, then the mixture was cooled to 0° C., and a solution of NaOH in MeOH and $H_2O$ (2 N, 50.0 mL) was added into the reaction mixture, and the mixture was stirred for 1 h at 0° C., then the mixture was poured into a solution of $NH_4Cl$. The product was extracted with EA (300.0 mL) and the organic layer was washed with brine and dried over $Na_2SO_4$. Then the organic layer was concentrated to give a residue, which was purified by slurry with PE:EA (8:1, 900.0 mL) to get 15 (20.0 g, 95.0% yield). ESI-LCMS: m/z=426.2 $[M+H]^+$; 1H NMR (400 MHz, DMSO-$d_6$) δ 11.21 (s, 1H), 8.77-8.69 (m, 2H), 8.06 (d, J=7.6 Hz, 2H), 7.65 (t, J=7.4 Hz, 1H), 7.56 (t, J=7.6 Hz, 2H), 7.34-7.23 (m, 4H), 7.23-7.12 (m, 5H), 6.89-6.80 (m, 4H), 5.90 (d, J=7.9 Hz, 1H), 4.36-4.29 (m, 1H), 4.06 (t, J=8.8 Hz, 1H), 3.92 (dd, J=25.0, 6.9 Hz, OH), 3.72 (d, J=1.0 Hz, 7H), 3.59 (dt, J=10.4, 6.6 Hz, 1H), 3.24 (s, 3H), 2.97 (d, J=7.7 Hz, 1H), 2.76 (q, J=5.5 Hz, 2H), 1.14 (dd, J=9.2, 5.7 Hz, 12H).

Preparation of 16: To a mixture solution of HCOOH (180.0 mL) and $H_2O$ (20.0 mL) was added 15 (19.0 g, 44.7 mmol). The reaction mixture was stirred at r.t. for 4 h. LC-MS showed 15 was consumed completely. Then the reaction mixture was concentrated to give a residue which was purified by slurry with MeOH (100.0 mL) to get 16 (16.0 g, 92.7% yield) as a white solid. ESI-LCMS: m/z=385.9 $[M+H]^+$; 1H NMR (400 MHz, DMSO-$d_6$) δ 11.21 (s, 1H), 8.77 (d, J=1.2 Hz, 2H), 8.09-8.02 (m, 2H), 7.70-7.61 (m, 1H), 7.56 (t, J=7.6 Hz, 2H), 5.56 (d, J=9.2 Hz, 1H), 5.21 (d, J=6.1 Hz, 1H), 4.94 (d, J=4.5 Hz, 1H), 4.18 (t, J=9.1 Hz, 1H), 4.09 (q, J=5.2 Hz, 1H), 3.88-3.71 (m, 4H), 3.21-3.14 (m, 6H).

Preparation of 17: To a solution of 16 (16.0 g, 41.4 mmol) in dioxane (200.0 mL) was added $H_2O$ (32.0 mL), and $NaIO_4$ (9.7 g, 45.5 mmol), then the reaction mixture was stirred at r.t. for 1 h, LC-MS and TLC showed that the raw material was disappeared, then the reaction mixture was cooled to 0° C., and $NaBH_4$ (1.7 g, 45.5 mmol) was added into the mixture and stirred at 0° C. for 0.5 h, LC-MS and TLC showed that the intermediate state was disappeared, then the $NH_4Cl$ was added into the mixture to adjust pH to be slightly alkaline, and concentrated at r.t. to give the crude product which was purified by silica gel column (DCM: MeOH=20:1 to 8:1) to give 17 (16.0 g, 99.5% yield). ESI-LCMS: m/z=388.0 $[M+H]^+$; $^1$H NMR (400 MHz, DMSO-$d_6$) δ 11.18 (s, 1H), 8.75 (s, 1H), 8.67 (s, 1H), 8.09-7.99 (m, 2H), 7.65 (t, J=7.4 Hz, 1H), 7.56 (t, J=7.6 Hz, 2H), 5.90 (d, J=7.6 Hz, 1H), 4.88 (t, J=5.7 Hz, 1H), 4.67 (t, J=5.5 Hz, 1H), 4.08-3.98 (m, 2H), 3.78 (ddd, J=12.1, 5.2, 3.1 Hz, 1H), 3.68-3.39 (m, 4H), 3.36 (s, OH), 3.20 (s, 3H), 1.99 (s, 1H), 1.17 (t, J=7.1 Hz, 1H).

Preparation of 18: To a solution of 17 (12.0 g, 31.0 mmol) in pyridine (50.0 mL) was added DMTrCl (11.5 g, 34.1 mmol), then the reaction mixture was stirred at r.t. for 2 h, LC-MS showed that the raw material was 15.0% remained and the ratio of product to by-product was 3.5:1. Then the reaction solution was poured into ice-water, and extracted with EA, wished with brine, dried over $Na_2SO_4$, filtered and concentrated to get residue which was purified by silica gel column to give the purified product and by-product were 13.0 g in total, then 4.0 g crude was purified by SFC to get 18 (3.3 g, 15.4% yield). ESI-LCMS: m/z=690.3 $[M+H]^+$; $^1$H NMR (400 MHz, DMSO-$d_6$) δ 11.21 (s, 1H), 8.75 (s, 1H), 8.69 (s, 1H), 8.10-8.03 (m, 2H), 7.70-7.61 (m, 1H), 7.56 (t, J=7.6 Hz, 2H), 7.35-7.12 (m, 9H), 6.90-6.80 (m, 4H), 5.94 (d, J=7.5 Hz, 1H), 4.88 (t, J=5.6 Hz, 1H), 4.36 (t, J=5.1 Hz, 1H), 4.11 (dt, J=7.4, 3.6 Hz, 1H), 3.82 (ddd, J=11.9, 5.1, 3.1 Hz, 1H), 3.72 (d, J=1.3 Hz, 7H), 3.64 (ddd, J=11.9, 6.2, 4.2 Hz, 1H), 3.45 (qd, J=7.0, 4.9 Hz, 2H), 3.24 (s, 3H), 3.09 (ddd, J=9.9, 6.4, 3.2 Hz, 1H), 2.97 (ddd, J=9.9, 5.7, 3.2 Hz, 1H), 1.23 (s, OH), 1.06 (t, J=7.0 Hz, 1H).

Preparation of 19: To a suspension of 18 (3.3 g, 4.8 mmol) in DCM (40.0 mL) was added DCI (0.5 g, 4.0 mmol) and $CEP[N(iPr)_2]_2$ (1.6 g, 5.3 mmol). The mixture was stirred at r.t. for 0.5 h. LC-MS showed 10 was consumed completely. The solution was washed with a solution of $NaHCO_3$ twice and washed with brine and dried over $Na_2SO_4$. Then concentrated to give a residue which was purified by Flash-Prep-HPLC with the following conditions (IntelFlash-1): Column, $C_{18}$ silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=1/0; Detector, UV 254 nm. This resulted in to give 19 (3.0 g, 3.9 mmol, 81.2% yield) as a white solid. ESI-LCMS: m/z=765.3 $[M+H]^+$; $^1$H NMR (400 MHz, DMSO-$d_6$) δ 11.22 (s, 1H), 8.80-8.71 (m, 2H), 8.11-8.04 (m, 2H), 7.65 (t, J=7.3 Hz, 1H), 7.56 (t, J=7.5 Hz, 2H), 7.36-7.24 (m, 4H), 7.24-7.15 (m, 5H), 6.89-6.82 (m, 4H), 5.92 (d, J=7.7 Hz, 1H), 4.34 (dt, J=7.5, 3.5 Hz, 1H), 4.08 (ddd, J=10.7, 7.3, 2.7 Hz, 1H), 4.03-3.89 (m, 1H), 3.80-3.72 (m, 10H), 3.67-3.53 (m, 2H), 3.47 (dp, J=10.5, 3.4 Hz, 1H), 3.26 (s, 3H) 3.11 (ddd, J=10.3, 6.2, 3.5 Hz, 1H), 3.00 (q, J=6.6, 5.2 Hz, 1H), 2.77 (q, J=5.6 Hz, 2H), 2.08 (s, 1H), 1.15 (t, J=7.0 Hz, 12H); $^{31}$P NMR (162 MHz, DMSO-$d_6$) δ 148.30, 147.99.

Example 8

Scheme-7

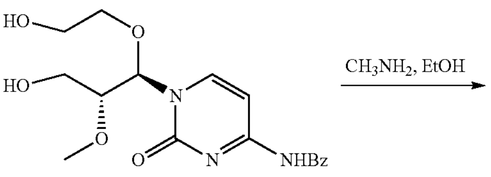

8

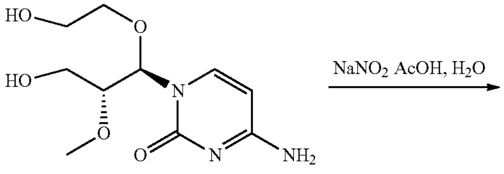

19

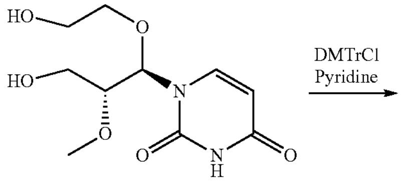

20

-continued

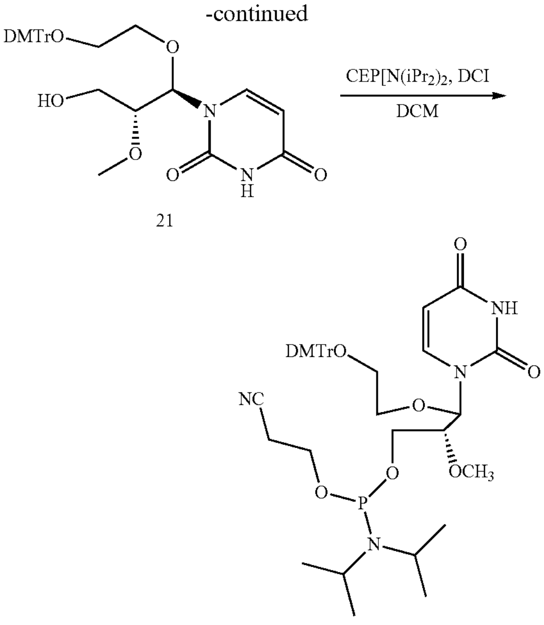

21

22

Preparation of 19: To a solution of 8 (8.0 g, 22.0 mmol) in EtOH (50.0 mL) was added a solution of $CH_3NH_2$ (50.0 mL), then the reaction mixture was stirred at r.t. for 4 h, after the reaction, the solvent was concentrated to give the crude, which was added into a mixture solvent of EA (20.0 mL) and PE (10.0 mL), then the mixture was stirred for 30 min and filtered to get 19 (5.5 g, 96.5% yield), which was used directly to next step.

Preparation of 20; (J. Chem. Soc., *Perkin Trans.* 1, 1992, 1943-1952) To a solution of 19 (5.0 g, 19.3 mmol) in $H_2O$ (50.0 mL) and AcOH (50.0 mL) was added $NaNO_2$ (65.0 g, 772.0 mmol), then the reaction mixture was stirred at r.t. for 2 h, after the reaction, the reaction mixture was concentrated to give the crude product which was purified by silica gel column (DCM:MeOH=20:1 to 6:1) and MPLC (ACN: $H_2O$=0:100 to 10:90) to give 20 (3.0 g, 59.6% yield). ESI-LCMS: m/z=261.2 $(M+H)^+$; $^1H$ NMR (400 MHz, DMSO-$d_6$) δ 11.29 (s, 1H), 7.66 (d, J=8.0 Hz, 1H), 5.67 (dd, J=17.5, 7.6 Hz, 2H), 4.74 (d, J=36.0 Hz, 2H), 3.86-3.63 (m, 1H), 3.58-3.40 (m, 6H).

Preparation of 21: To a solution of 20 (3.0 g, 11.5 mmol) in pyridine (30.0 mL) was added DMTrCl (3.9 g, 11.5 mmol), then the reaction mixture was stirred at r.t. for 2 h, LC-MS showed that the raw material was 20.0% and The ratio of product to by-product was 3:1, then the mixture was poured into a solution of $NaHCO_3$ (100.0 mL), and extracted with EA (100.0 mL), washed with brine and dried over $Na_2SO_4$, filtered and concentrated to get residue, which was purified by silica gel column to give The purified products and by-products were 5.0 g in total, then the product was purified by SFC to give 21 (1.8 g). ESI-LCMS: m/z=561.2 $[M+H]^+$; $^1H$ NMR (400 MHz, DMSO-$d_6$) δ 11.31 (s, 1H), 7.69 (d, J=8.1 Hz, 1H), 7.45-7.15 (m, 8H), 6.88 (d, J=8.5 Hz, 4H), 5.71 (d, J=6.8 Hz, 1H), 5.64 (d, J=8.0 Hz, 1H), 4.79 (t, J=5.5 Hz, 1H), 3.74 (s, 6H), 3.60 (s, 1H), 3.51 (d, J=5.5 Hz, 3H), 3.11 (d, J=6.7 Hz, 1H), 3.02 (d, J=7.0 Hz, 1H).

Preparation of 22: To a solution of 21 (1.8 g, 3.2 mmol) in DCM (20.0 mL) was added $CEP[N(iPr)_2]_2$ (1.0 g, 3.4 mmol) and DCI (321.0 mg, 2.7 mmol). The mixture was stirred at r.t. for 1 h. LC-MS showed 21 was consumed completely. The solution was washed with solution of $NaHCO_3$ twice and washed with brine and dried over $Na_2SO_4$. Then concentrated to give a residue, which was purified by Flash-Prep-HPLC with the following conditions (IntelFlash-1): Column, $C_{18}$ silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20.0 min, the eluted product was collected at $CH_3CN/H_2O$ (0.5% $NH_4HCO_3$)=90/10; Detector, UV 254 nm. This resulted in to give 22 (2.0 g, 82% yield). ESI-LCMS: m/z=761.2 $[M+H]^+$; $^1H$ NMR (400 MHz, DMSO-$d_6$) δ 11.35 (s, 1H), 7.73 (dd, J=8.0, 2.0 Hz, 1H), 7.39 (d, J=7.4 Hz, 2H), 7.35-7.18 (m, 7H), 6.94-6.82 (m, 4H), 5.81-5.74 (m, 1H), 5.67 (d, J=8.0 Hz, 1H), 4.11-3.85 (m, 1H), 3.82-3.67 (m, 11H), 3.67-3.50 (m, 5H), 3.17-3.09 (m, 1H), 3.09-3.01 (m, 1H), 2.74 (td, J=5.8, 2.9 Hz, 2H), 1.13 (dd, J=9.2, 6.7 Hz, 13H); $^{31}P$ NMR (DMSO-$d_6$) δ 148.09 (d, J=41.8 Hz).

Example 9

Scheme-8

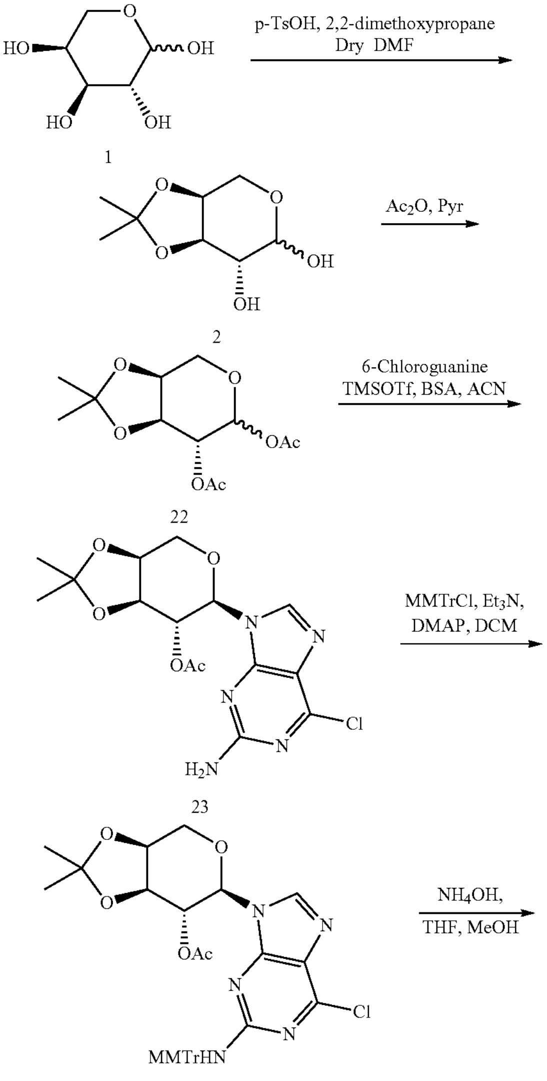

1

2

22

23

24

-continued

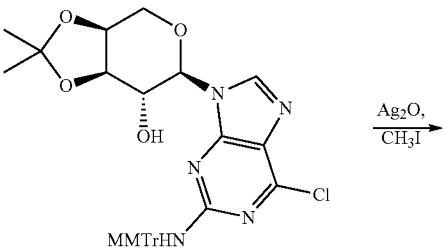

25

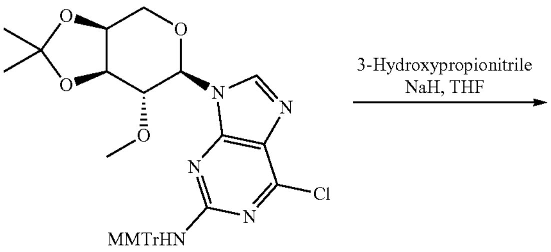

26

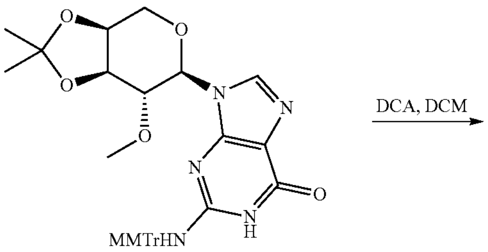

27

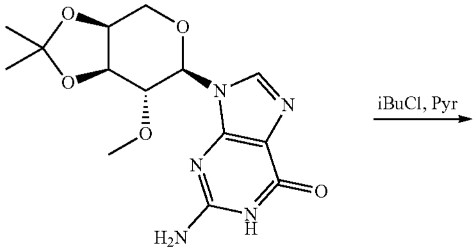

28

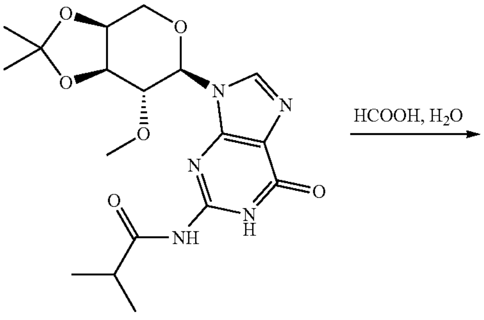

29

-continued

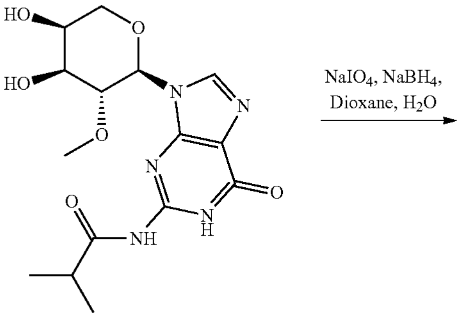

30

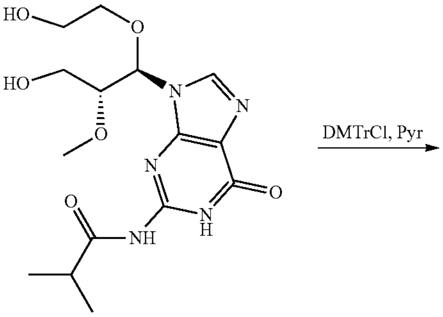

31

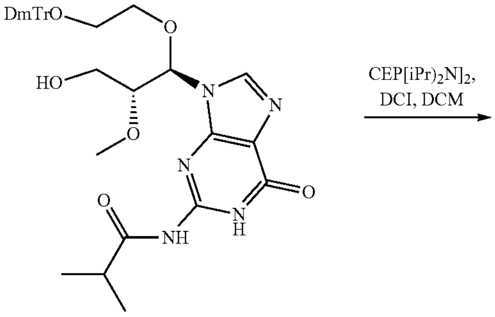

32

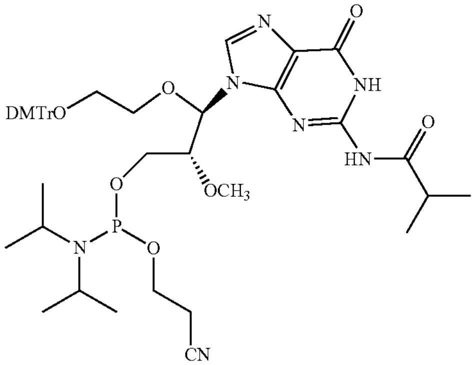

33

Preparation of 2 (*J. Chem. Soc., Perkin Trans.* 1, 1992, 1943-1952): To a solution of 1 (150.0 g, 999.1 mmol) in DMF (1000.0 mL) was added P-TsOH (1.7 g, 10.0 mmol), then 2,2-dimethoxy-propane (312.2 g, 3.0 mol) was added to the reaction mixture. The reaction mixture was stirred for 5 h at r.t. 90.0% 1 was consumed by TLC. Then $NaHCO_3$ (8.4 g, 99.9 mmol) was added to the reaction mixture, filtered out the solid after 30 min, and concentrated the organic phase by vacuum to obtain crude, which was purified by c.c. (PE:EA=1:1 to 0:1) to get compound 2 (115.0 g, 60.5% yield) as a white solid.

Preparation of 22 (Rajkamal; Pathak, Navendu P.; Halder, Tanmoy; Dhara, Shubhajit; Yadav, Somnath[*Chemistry-A European Journal,* 2017, vol. 23, #47, p. 11323-11329]): A solution of 2 (115.0 g, 604.6 mmol) in pyridine (600.0 mL) was cooled to 0° C., then $Ac_2O$ (185.2 g, 1.81 mol) was added drop wise to the reaction mixture. The reaction was stirred for 2 h at r.t., and the raw material was consumed by TLC. The reaction solution was added into water, extracted product with EA. The organic phase was washed with brine, and dried the organic phase with $Na_2SO_4$, and concentrated to get 22 (150.0 g, 90.4% yield), which was used for next step directly. $^1H$ NMR (400 MHz, Chloroform-d) δ 6.20 (d, J=3.4 Hz, 1H), 5.66 (d, J=6.8 Hz, 1H), 5.17 (t, J=6.9 Hz, 1H), 5.10 (dd, J=7.0, 3.4 Hz, 1H), 4.40-4.25 (m, 3H), 4.21 (dd, J=7.0, 6.1 Hz, 1H), 4.16-4.02 (m, 3H), 3.95 (dd, J=12.9, 4.4 Hz, 1H), 2.17 (s, 1H), 2.15-2.03 (m, 12H), 1.56 (d, J=4.0 Hz, 6H), 1.37 (d, J=3.1 Hz, 6H).

Preparation of 23: To a solution of 22 (150.0 g, 546.9 mmol) in ACN (2200.0 mL) was added 6-chloroguanine (139.1 g, 820.4 mmol) and BSA (333.7 g, 1.6 mol) at r.t., then the reaction mixture was replaced with $N_2$ over 3 times. The reaction was stirred for 30 min at 50° C. After that, the reaction mixture was cooled to 0° C. under $N_2$. Then TMSOTf (182.1 g, 820.4 mmol) was added into the mixture. After addition, the reaction was stirred for 1.5 h at 70° C. TLC and LC-MS showed the raw material was consumed. Concentrated the most organic solvent by vacuum, then the residual was added to an aqueous solution of $NaHCO_3$ in ice-water, extracted product with EA (4.0 L), dried the organic phase over $Na_2SO_4$, and filtered and concentrated to get crude, which was purified by c.c. (DCM to DCM:EA=5:1) to get compound 23 (82.0 g, 35.0% yield) as a white solid. ESI-LCMS: m/z=384.8 $[M+H]^+$; $^1H$ NMR (400 MHz, DMSO-$d_6$) δ 8.23 (s, 1H), 7.04 (d, J=22.3 Hz, 2H), 5.57 (d, J=9.6 Hz, 1H), 5.40 (dd, J=9.6, 7.3 Hz, 1H), 4.48 (dd, J=7.4, 5.4 Hz, 1H), 4.40-4.30 (m, 2H), 4.11 (dd, J=13.6, 2.4 Hz, 1H), 1.81 (s, 3H), 1.55 (s, 3H), 1.34 (s, 3H).

Preparation of 24: To a solution of 23 (82.0 g, 192.3 mmol) in DCM (1000.0 mL) was added $Et_3N$ (59.4 g, 576.9 mmol) and DMAP (2.4 g, 19.2 mmol) at r.t. The reaction mixture was replaced with $N_2$ over 3 times, then MMTrCl (90.9 g, 288.4 mmol) was added into the mixture. The reaction mixture was stirred at r.t. overnight. TLC and LC-MS showed that 92.0% raw material was consumed, and the reaction mixture was added to an aqueous solution of $NaHCO_3$ in ice-water, then extracted product with EA. Washed the organic phase with brine, and dried the organic phase over $Na_2SO_4$, then concentrated to get crude, which was purified by c.c. (DCM) to give compound 24 (110.0 g, 86.4% yield) as a white solid. ESI-LCMS: m/z=657.1 $[M+H]^+$; $^1H$ NMR (400 MHz, DMSO-$d_6$) δ 8.21 (s, 1H), 7.37-7.31 (m, 4H), 7.29-7.23 (m, 6H), 7.20-7.15 (m, 2H), 6.86-6.80 (m, 2H), 5.75 (s, 1H), 5.23 (dd, J=9.6, 7.2 Hz, 1H), 4.85 (s, 1H), 4.44-4.16 (m, 3H), 3.71 (s, 4H), 1.70 (s, 3H), 1.49 (s, 3H), 1.31 (s, 3H).

Preparation of 25: To a solution of 24 (110.0 g, 164.3 mmol) in a mixed solvent of THF (500.0 mL) and MeOH (160.0 mL) was added $NH_4OH$ (330.0 mL). The reaction mixture was stirred overnight at r.t., and the raw material was consumed by TLC and LC-MS. The reaction liquid was added into water, extracted product with EA. Washed the organic phase with brine, then dried the organic phase over $Na_2SO_4$, then concentrated to get the crude, which was purified by c.c. (PE:EA=10:1-1:2) to give compound 25 (98.0 g, 94.2% yield) as a white solid. ESI-LCMS: m/z=615.1 $[M+H]^+$; $^1H$ NMR (400 MHz, DMSO-$d_6$) δ 8.32 (s, 1H), 7.36 (dt, J=8.2, 1.4 Hz, 4H), 7.31-7.21 (m, 6H), 7.15 (t, J=7.2 Hz, 2H), 6.85-6.76 (m, 2H), 5.57 (d, J=4.6 Hz, 1H), 4.69 (s, 1H), 4.25 (dt, J=5.1, 2.4 Hz, 1H), 4.03 (q, J=7.1 Hz, 4H), 3.70 (s, 3H), 3.62-3.44 (m, 1H), 1.51 (s, 3H), 1.31 (s, 3H).

Preparation of 26 (Ref WO2011/95576, 2011, A1): To a solution of 25 (70.0 g, 114.0 mmol) in $CH_3I$ (350.0 mL) was added $Ag_2O$ (79.2 g, 342.0 mmol) at r.t. Then the reaction mixture was stirred for 4 h at r.t. TLC and LC-MS showed that the raw material was consumed. Filtered out the residue with diatomite, and concentrated the filtrate by vacuum to get crude, which was purified by c.c. (PE:EA=10:1-1:1) to get compound 26 (28.0 g, 31.3% yield) as a white solid. ESI-LCMS: m/z=629.1 $[M+H]^+$.

Preparation of 27: A solution of 3-hydroxy-propionitrile (15.6 g, 219.7 mmol) in THF (200.0 mL) was cooled to 0° C. The reaction mixture was replaced by $N_2$ over 3 times. Then NaH (12.4 g, 310.0 mmol, 60.0%) was added to the reaction mixture in turn. The reaction was stirred for 30 min at r.t., and then the reaction was cooled to 0° C. again. A solution of 26 (26.0 g, 33.0 mmol) in THF (150.0 mL) was added drop wise to the reaction mixture. Then the reaction mixture was stirred at r.t. overnight. TLC and LC-MS showed the raw material was consumed. The reaction liquid was added into water, extracted product with EA. The organic phase was washed with brine, and dried over $Na_2SO_4$, then concentrated to get the crude, which was purified by c.c. (DCM:MeOH=50:1-30:1) to get compound 27 (18.0 g, 88.0% yield) as white solid. ESI-LCMS: m/z=610.7 $[M+H]^+$; $^1H$ NMR (400 MHz, DMSO-$d_6$) δ 10.68 (s, 1H), 7.90 (s, 1H), 7.69 (s, 1H), 7.34-7.15 (m, 12H), 6.92-6.81 (m, 2H), 4.46 (d, J=9.5 Hz, 1H), 4.22 (dt, J=5.5, 2.5 Hz, 1H), 4.07 (t, J=6.4 Hz, 1H), 3.84 (dd, J=13.5, 2.1 Hz, 1H), 3.64-3.54 (m, 1H), 3.36 (dd, J=13.3, 2.8 Hz, 1H), 3.08 (s, 3H), 2.59 (t, J=6.0 Hz, 3H), 1.49 (s, 3H), 1.30 (s, 3H).

Preparation of 28 (Beigelman, Leonid; Deval, Jerome; Jin, Zhinan WO2014/209979, 2014, A1): To a solution of 27 (18.0 g, 29.5 mmol) in DCM (300.0 mL) was added triethylsilane (70.0 mL) and DCA (10.0 mL) at r.t. Then the reaction mixture was stirred for 6 h at r.t., TLC and LC-MS showed that the raw material was consumed. Concentrated the almost organic solvent by vacuum, then PE (600.0 mL) was added to the reaction mixture. Filtered of the organic phase to get the solid, which was purified by MPLC (MeCN:$H_2O$=40:60 to 50:50) to get compound 28 (7.5 g, 75.0% yield) as a white solid. ESI-LCMS: m/z=338.3 $[M+H]^+$; $^1H$ NMR (400 MHz, DMSO-$d_6$) δ 10.70 (s, 1H), 8.03 (s, 1H), 6.49 (s, 2H), 5.15 (d, J=9.6 Hz, 1H), 4.28 (d, J=5.1 Hz, 2H), 4.20 (d, J=13.6 Hz, 1H), 3.93 (ddd, J=13.3, 10.6, 3.7 Hz, 2H), 3.26 (s, 3H), 1.59 (s, 3H), 1.33 (s, 3H);

Preparation of 29: A solution of 28 (7.0 g, 20.6 mmol) in Pyr (150.0 mL) was cooled to 0° C. Then the reaction mixture was added i-BuCl (6.6 g, 61.8 mmol) drop wise. The reaction mixture was stirred for 30 min, TLC and LC-MS showed the raw material was consumed. The reaction liquid was added to ice-water, extracted product with EA. The organic phase was washed with brine, and dried over $Na_2SO_4$, and filtered and concentrated to get the crude, which was purified by c.c. (DCM:MeOH=100:1-30:1) to get compound 29 (5.8 g, 68.6% yield) as a white solid. ESI-LCMS: m/z=409.4 $[M+H]^+$; $^1H$ NMR (400 MHz, DMSO-$d_6$) δ 12.13 (s, 1H), 11.66 (s, 1H), 8.39 (s, 1H), 5.24 (d, J=9.6 Hz, 1H), 4.36-4.23 (m, 3H), 3.99-3.88 (m, 2H), 3.27 (s, 4H), 2.78 (hept, J=6.8 Hz, 1H), 1.61 (s, 3H), 1.35 (s, 3H), 1.12 (d, J=6.8 Hz, 6H).

Preparation of 30: A solution of 29 (5.8 g, 14.1 mmol) was added into a mixed solvent of HCOOH (54.0 mL) and $H_2O$ (6.0 mL) at r.t. Then reaction mixture was stirred for 1 h at r.t. TLC and LC-MS showed the raw material was consumed. Concentrated the reaction solution by vacuum at r.t. to get compound 30 (5.2 g, 14.0 mmol, 98.0% yield), which was used for next step directly. ESI-LCMS: m/z=368.4 $[M+H]^+$; $^1H$ NMR (400 MHz, DMSO-$d_6$) δ 12.13 (s, 1H), 11.72 (s, 1H), 8.30 (s, 1H), 8.14 (s, 2H), 5.19 (d, J=9.2 Hz, 1H), 3.93 (t, J=9.2 Hz, 1H), 3.85 (dd, J=12.4, 1.9 Hz, 1H), 3.77 (d, J=3.7 Hz, 1H), 3.69-3.62 (m, 2H), 3.20 (s, 3H), 2.79 (h, J=6.8 Hz, 1H), 1.13 (dd, J=6.9, 1.2 Hz, 6H).

Preparation of 31: To a solution of 30 (5.2 g, 14.0 mmol) in dioxane (90.0 mL) and $H_2O$ (30.0 mL) was added $NaIO_4$ (3.7 g, 15.4 mmol) at r.t. The reaction mixture was stirred for 3 h at r.t. LC-MS showed the raw material was consumed, and the reaction solution was cooled to 0° C. Then $NaBH_4$ (970.0 mg, 25.2 mmol) was added to the reaction mixture, and the raw material was consumed after 3 h by LC-MS. The reaction liquid was quenched with ammonium chloride, and adjusted the pH to 6-7 with 1N HCl, the mixture solution was concentrated to get the crude, which was purified by c.c. (DCM:MeOH=100:1-30:1) to get compound 31 (4.0 g, 68.6% yield) as a white solid. ESI-LCMS: m/z=370.4 $[M+H]^+$; $^1H$ NMR (400 MHz, DMSO-$d_6$) δ 11.91 (d, J=151.0 Hz, 2H), 8.62-8.51 (m, 1H), 8.18 (s, 1H), 7.44-7.33 (m, 1H), 5.62 (d, J=7.9 Hz, 1H), 4.84 (t, J=5.7 Hz, 1H), 4.65 (d, J=5.2 Hz, 1H), 3.84 (dd, J=7.7, 3.5 Hz, 1H), 3.76 (ddd, J=12.1, 4.7, 2.7 Hz, 1H), 3.60 (ddd, J=12.0, 5.8, 3.6 Hz, 1H), 3.46 (d, J=8.8 Hz, 2H), 3.16 (s, 3H), 2.77 (h, J=6.8 Hz, 1H), 1.12 (dd, J=6.8, 2.4 Hz, 6H);

Preparation of 32: A solution of 31 (4.0 g, 6.4 mmol) was dissolved in pyridine (100.0 mL), and the reaction mixture was replaced by $N_2$ over 3 times, and then DMTrCl (5.1 g, 8.9 mmol) was added to the reaction mixture at r.t. Then the reaction was stirred for 30 min, TLC and LC-MS showed raw material was consumed. The reaction liquid was added into ice-water, and extracted product with EA. The organic phase was washed with brine, and dried the organic phase over $Na_2SO_4$, and concentrated to get crude, which was purified by c.c. (DCM:MeOH=100:1-30:1) and SFC to get compound 32 (2.7 g, 37.1% yield) as a white solid. ESI-LCMS: m/z=672.7 $[M+H]^+$; $^1H$ NMR (400 MHz, DMSO-$d_6$) δ 11.50 (s, 2H), 8.22 (s, 1H), 7.32-7.24 (m, 4H), 7.22-7.12 (m, 5H), 6.84 (dd, J=9.0, 2.4 Hz, 4H), 5.63 (d, J=7.9 Hz, 1H), 4.85 (t, J=5.6 Hz, 1H), 3.95 (dt, J=7.4, 3.3 Hz, 1H), 3.85-3.77 (m, 1H), 3.73 (s, 7H), 3.65-3.57 (m, 1H), 3.43 (ddt, J=9.9, 6.9, 3.4 Hz, 1H), 3.05 (ddd, J=10.0, 6.2, 3.3 Hz, 1H), 2.96 (ddd, J=10.0, 5.6, 3.4 Hz, 1H), 2.78 (p, J=6.8 Hz, 1H), 1.11 (d, J=6.7 Hz, 6H).

Preparation of 33: To a solution of 32 (2.7 g, 2.4 mmol) in DCM (35.0 mL) was added DCI (390.0 mg, 2.0 mmol) at r.t. Then CEP $[N(iPr)_2]_2$ (1.2 g, 2.5 mmol) was added to the reaction mixture, then reaction mixture was stirred for 30 min at r.t. LC-MS showed raw material was consumed. The reaction liquid was added to an aqueous solution of $NaHCO_3$ into ice-water, and extracted product with DCM, washed the organic phase with brine, and dried the organic phase over $Na_2SO_4$, then filtered and concentrated to give a residue, which was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20.0 min, the eluted product was collected at $CH_3CN/H_2O$ (0.5% $NH_4HCO_3$)=100/0; Detector, UV 254 nm. This resulted in to give compound 33 (2.0 g, 56.4% yield) as a white solid. ESI-LCMS: m/z=872.3 $[M+H]^+$; 1H NMR (400 MHz, DMSO-$d_6$) δ 11.79 (s, 2H), 8.23 (d, J=1.7 Hz, 1H), 7.35-7.07 (m, 9H), 6.92-6.75 (m, 4H), 5.52 (d, J=8.0 Hz, 1H), 4.21 (s, 1H), 4.10-3.99 (m, 1H), 3.84-3.65 (m, 10H), 3.63-3.52 (m, 2H), 3.45 (ddd, J=10.2, 6.7, 3.6 Hz, 1H), 3.34 (s, 1H), 3.22 (s, 3H), 3.07 (ddd, J=10.2, 6.4, 3.4 Hz, 1H), 2.97 (ddd, J=10.0, 5.6, 3.5 Hz, 1H), 2.78 (dt, J=12.2, 6.4 Hz, 3H), 1.20-1.05 (m, 18H), $^{31}P$ NMR (162 MHz, DMSO-$d_6$) δ 148.20, 147.13.

Example 10

Scheme-9

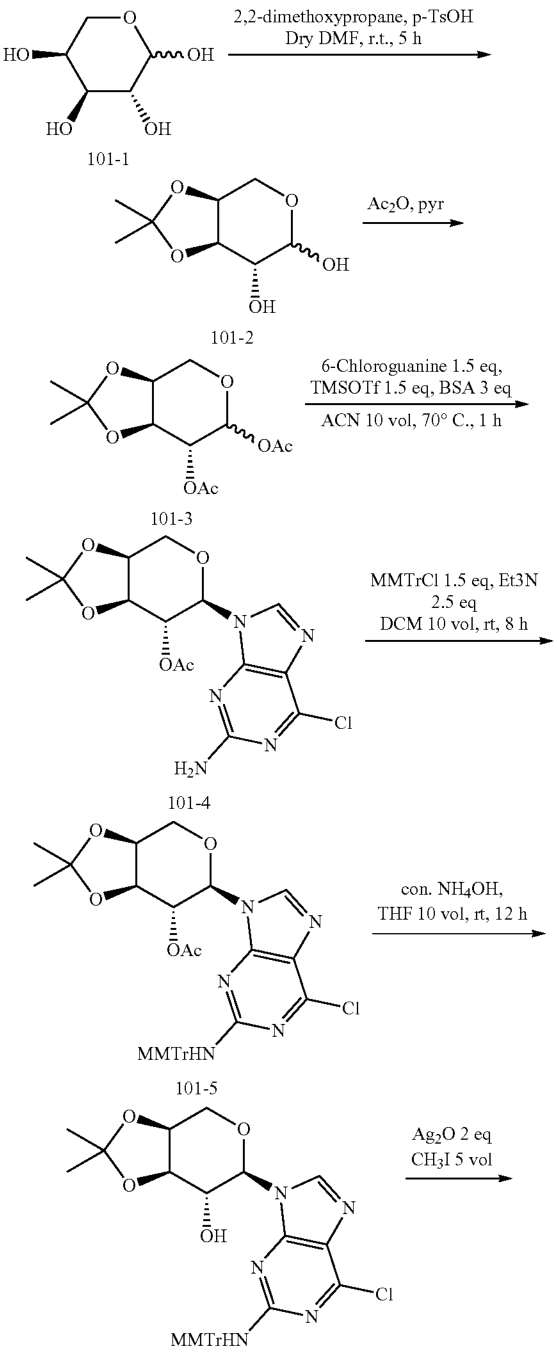

101-1

101-2

101-3

101-4

101-5

101-6

-continued
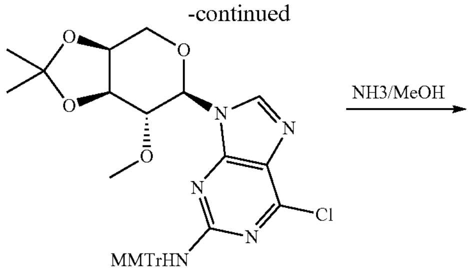
101-7
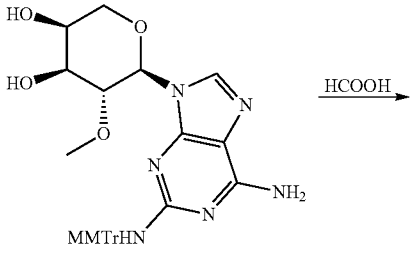
101-8
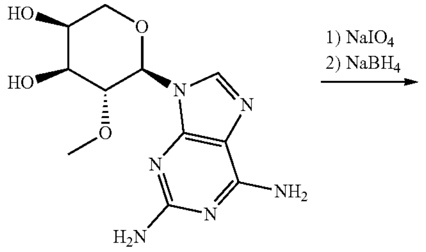
101-9
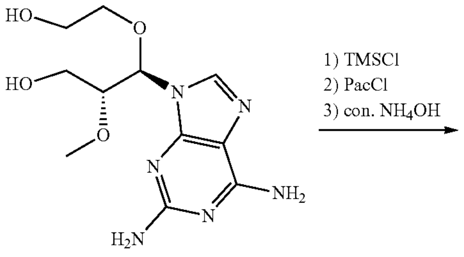
101-10
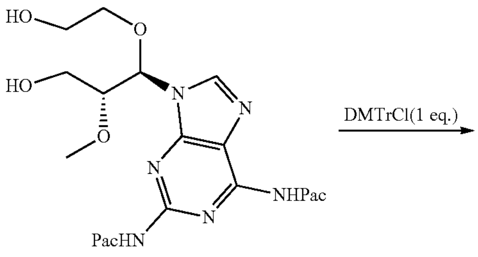
101-11
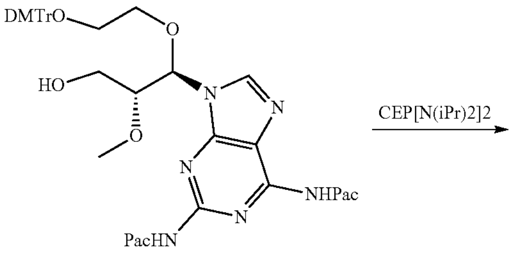
101-12
-continued
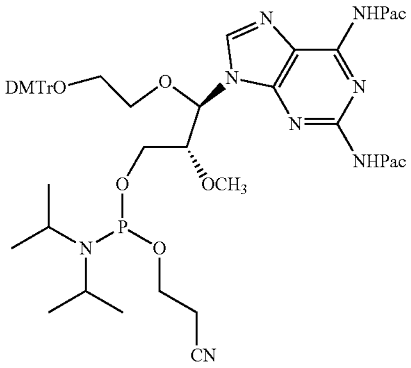
101
Example 11
Scheme-10
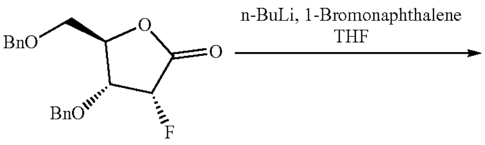
1
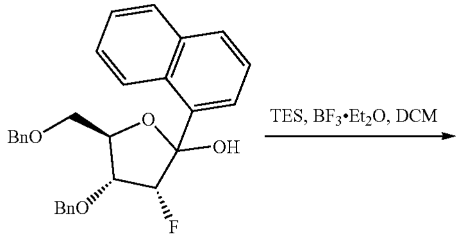
2
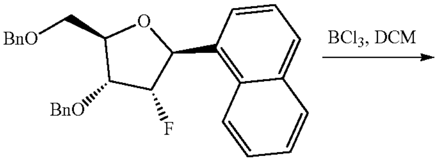
3
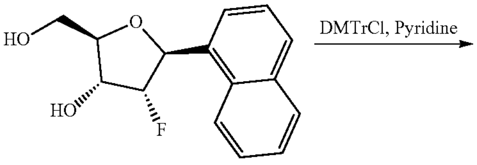
4
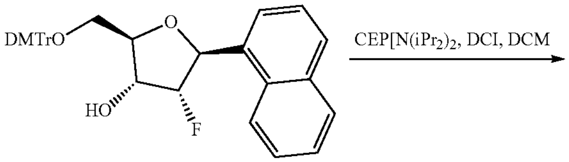
5

-continued

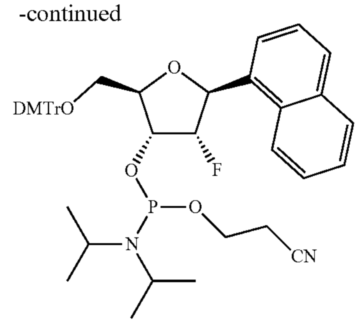

6

Preparation of 2: To a solution of 1-bromonaphthalene (5.2 g, 25.0 mmol) in dry THF (100.0 mL) was added n-BuLi (13.5 mL, 21.7 mmol, 1.6 M) drop wise at −78° C., then the mixture was stirred at −78° C. for 0.5 h, after that, a solution of 1 (5.5 g, 16.7 mmol) in THF (20.0 mL) was added into the mixture drop wise maintaining inner temperature below −70° C., then the reaction mixture was stirred for 1 h at −70° C. LC-MS showed 1 was consumed completely, the reaction was quenched with saturated ammonium chloride solution (80.0 mL) and extracted with EA, The organic layer was washed with brine, dried over $Na_2SO_4$, and concentrated under reduced pressure to give a residue, which was purified by Flash-Prep-HPLC with the following conditions (IntelFlash-1): Column, $C_{18}$ silica gel; mobile phase, $CH_3CN/H_2O$ (0.5% $NH_4HCO_3$)=2/3 increasing to $CH_3CN/H_2O$ (0.5% $NH_4HCO_3$)=4/1 within 25 min, the eluted product was collected at $CH_3CN/H_2O$ (0.5% $NH_4HCO_3$)=3/2; Detector, UV 254 nm. This resulted in to give 2 (5.8 g, 76.3% yield) as a white solid. ESI-LCMS: m/z 441 $[M-OH]^-$.

Preparation of 3: To the solution of 2 (5.8 g, 12.6 mmol) in DCM (100.0 mL) was added TES (1.7 g, 14.7 mmol) at −78° C., $BF_3$. $Et_2O$ (2.7 g, 18.9 mmol) was added into the mixture drop-wise at −78° C. The mixture was stirred at −40° C. for 1 h. LC-MS showed 2 was consumed completely, the solution was added into a saturated sodium bicarbonate solution (50.0 mL) and extracted with DCM. The organic layer was washed with brine, dried over $Na_2SO_4$, and concentrated under reduced pressure to give a residue, which was purified by Flash-Prep-HPLC with the following conditions (IntelFlash-1): Column, $C_{18}$ silica gel; mobile phase, $CH_3CN/H_2O$ (0.5% $NH_4HCO_3$)=2/3 increasing to $CH_3CN/H_2O$ (0.5% $NH_4HCO_3$)=4/1 within 25 min, the eluted product was collected at $CH_3CN/H_2O$ (0.5% $NH_4HCO_3$)=7/3; Detector, UV 254 nm. This resulted in to give 3 (2.7 g, 48.2%) as a white solid. ESI-LCMS: m/z 460 $[M+H_2O]$; $^1$H-NMR (600 MHz, $CDCl_3$): δ 8.01-8.00 (d, J=6.5 Hz, 1H), 7.88-7.87 (d, J=7.6 Hz, 2H), 7.77-7.76 (d, J=8.2 Hz, 1H), 7.56-7.49 (m, 2H), 7.38-7.23 (m, 11H), 6.98-5.94 (d, J=26.9 Hz, 1H), 5.09-4.99 (dd, J=61.1 Hz, 1H), 4.71-4.69 (d, J=11.6 Hz, 1H), 4.66-4.59 (m, 2H), 4.43-4.41 (d, J=11.6 Hz, 2H), 4.14-4.08 (m, 1H), 4.02-4.00 (dd, J=13.4 Hz, 1H), 3.81-3.78 (dd, J=14.8 Hz, 1H); $^{19}$F-NMR ($CDCl_3$): δ-193.24.

Preparation of 4: To a solution of 3 (2.7 g, 6.0 mmol) in dry DCM (40.0 mL) was added $BCl_3$ (36.0 mL, 36.0 mmol, 1 M) drop wise at −78° C., and the reaction mixture was stirred at −78° C. for 0.5 h. LC-MS showed 3 was consumed completely. After completion of reaction, the resulting mixture was quenched with MeOH (20.0 mL), then neutralized with sodium hydroxide solution (40.0 mL, 2 M). The mixture was extracted with DCM and concentrated to give a crude, the crude was dissolved in MeOH (30.0 mL) and added a sodium hydroxide solution (30.0 mL, 4 M), and the mixture was stirred at r.t. for 30 min. The mixture was extracted with EA, the organic layer was washed with brine, dried over $Na_2SO_4$, and concentrated under reduced pressure to give a residue, which was purified by silica gel column chromatography (DCM:MeOH=40:1-15:1) to give 4 (1.3 g, 81.2%) as a white solid. ESI-LCMS: m/z 261 $[M-H]^-$; $^1$H-NMR (DMSO-$d_6$): δ 7.98-7.97 (d, J=10.2 Hz, 2H), 7.89-7.87 (m, 2H), 7.63-7.49 (m, 3H), 5.80-5.76 (d, J=26.3 Hz, 1H), 5.43 (s, 1H), 5.00 (s, 1H), 4.85-4.76 (d, J=58.4 Hz, 1H), 4.03-3.85 (m, 3H), 3.68-3.66 (m, 1H), 3.65-3.53 (m, 1H); $^{19}$F-NMR (DMSO-$d_6$): δ-192.76.

Preparation of 5: To a solution of 4 (1.3 g, 5.0 mmol) in pyridine (20.0 mL) was added DMTrCl (6.1 g, 16.0 mmol) at r.t. The reaction mixture was stirred at r.t. for 1 h. The LC-MS showed 4 was consumed and water (100.0 mL) was added. The product was extracted with EA and the organic layer was washed with brine and dried over $Na_2SO_4$, concentrated to give the crude, which was further purified by silica gel (EA:PE=1:30-1:10) to give 5 (2.2 g, 78.5%) as a yellow solid. ESI-LCMS: m/z 563 $[M-H]^-$; $^1$H-NMR (600 MHz, DMSO-$d_6$): δ 8.03-7.99 (m, 2H), 7.91-7.86 (m, 2H), 7.64-7.57 (m, 2H), 7.49-7.48 (d, J=6.8 Hz, 2H), 7.40-7.24 (m, 8H), 6.89-6.88 (m, 4H), 5.92-5.88 (d, J=26.6 Hz, 1H), 5.50-5.49 (d, J=4.5 Hz, 1H), 4.96-4.87 (d, J=56.2 Hz, 1H), 4.18-4.14 (m, 2H), 3.74 (s, 6H), 3.42-3.40 (d, J=9.9 Hz, 1H), 3.33 (m, 2H); $^{19}$F-NMR (DMSO-$d_6$): δ-192.18.

Preparation of 6: To a suspension of 5 (2.2 g, 3.9 mmol) in DCM (20.0 mL) was added DCI (391.0 mg, 3.3 mmol) and $CEP[N(iPr)_2]_2$ (1.4 g, 4.7 mmol). The mixture was stirred at r.t. for 1 h. The LC-MS showed 5 was consumed completely. The solution was washed with a saturated sodium bicarbonate solution and brine successively, dried over $Na_2SO_4$, concentrated to give the crude, which was purified by Flash-Prep-HPLC with the following conditions (IntelFlash-1): Column, $C_{18}$ silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=1/0; Detector, UV 254 nm. This resulted in to give 6 (2.5 g, 83.8%) as a white solid. ESI-LCMS: m/z 765 $[M+H]^+$; $^1$H-NMR (400 MHz, DMSO-$d_6$): δ 8.07-7.86 (m, 4H), 7.64-7.56 (m, 2H), 7.49-7.45 (m, 2H), 7.41-7.21 (m, 8H), 6.89-6.84 (m, 4H), 6.02-5.93 (m, 1H), 5.19-4.98 (m, 1H), 4.61-4.34 (m, 1H), 4.26-4.24 (m, 1H), 3.74-3.73 (m, 6H), 3.70-3.61 (m, 1H), 3.57-3.42 (m, 4H), 3.29-3.24 (m, 1H), 2.67-2.64 (m, 1H), 2.56-2.52 (m, 1H), 1.09-1.04 (m, 1H), 0.98-0.97 (d, J=6.7 Hz, 3H), 0.89-0.87 (d, J=6.7 Hz, 3H); $^{19}$F-NMR (DMSO-$d_6$): δ-191.75,−191.76,−191.84,−191.85; $^{31}$P-NMR (DMSO-$d_6$): δ 149.51, 149.47, 149.16, 149.14.

Example 12

Scheme-11

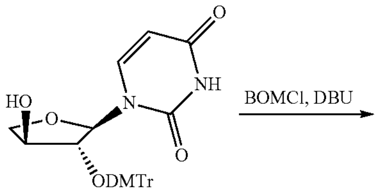

PH-ALIG-14-4-8

-continued

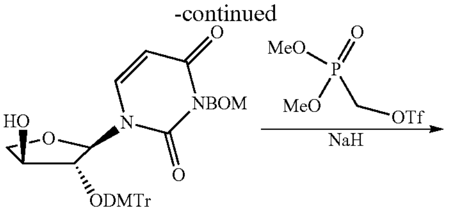

ALG-14-5-008B

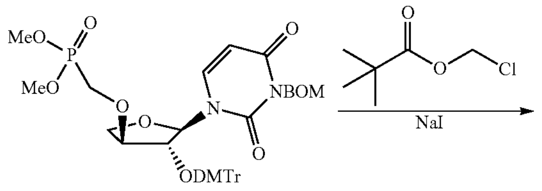

ALG-14-5-009A

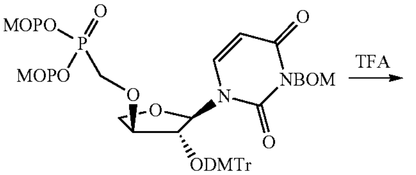

ALG-14-5-010A

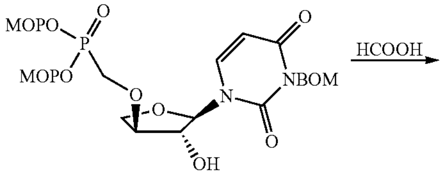

ALG-14-5-010C

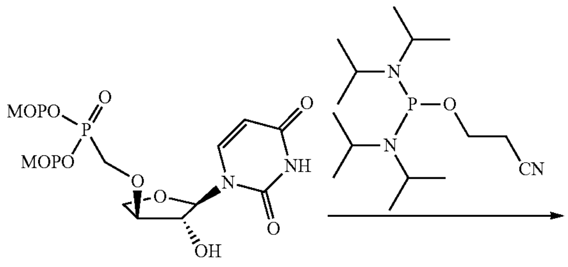

ALG-14-5-011A

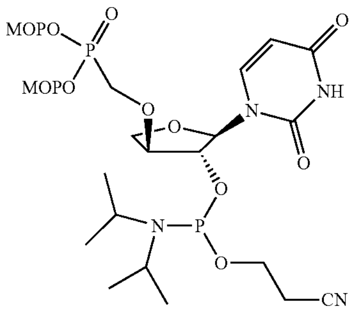

ALG-14-5

Preparation of ALG-14-5-008B

To a solution of PH-ALIG-14-4-8 (from Example 5) (6.6 g, 10.86 mmol, 85% purity, 1 eq) and DBU (3.31 g, 21.72 mmol, 3.27 mL, 2 eq) in DMF (70 mL) was added BOMCl (2.55 g, 16.29 mmol, 2.26 mL, 1.5 eq) at 0° C. The mixture was stirred at 20° C. for 12 h. The mixture was diluted with EtOAc (180 mL) and washed with $H_2O$ (80 mL*3), and brine (80 mL), dried over $Na_2SO_4$, filtered and concentrated under reduced pressure to give a residue. The residue was purified by flash silica gel chromatography (ISCO®; 80 g SepaFlash® Silica Flash Column, Eluent of 10-60%, EtOAc/PE gradient @ 60 mL/min) to give ALG-14-5-008B (5.2 g, 70% yield) as a white foam. LCMS (ESI): m/z 659.1; $^1$H NMR (400 MHz, DMSO-$d_6$) δ=7.63 (d, J=8.3 Hz, 1H), 7.40-7.15 (m, 14H), 6.85 (t, J=8.0 Hz, 4H), 5.97 (s, 1H), 5.75 (d, J=8.0 Hz, 1H), 5.39-5.26 (m, 2H), 5.24 (d, J=2.0 Hz, 1H), 4.61 (s, 2H), 3.97 (s, 1H), 3.94-3.83 (m, 2H), 3.68 (d, J=10.0 Hz, 6H), 3.38 (s, 1H)

Preparation of ALG-14-5-009 A

To a solution of ALG-14-5-008B (5.2 g, 8.17 mmol, 1 eq) and dimethoxyphosphorylmethyl trifluoromethanesulfonate (6.67 g, 24.50 mmol, 3 eq) in THF (50 mL) was added NaH (816.65 mg, 20.42 mmol, 60% purity, 2.5 eq) at −5° C. The mixture was stirred at 0° C. for 0.5 h. The reaction mixture was quenched by addition $H_2O$ (50 mL) and diluted with EtOAc (100 mL), then washed with $H_2O$ (50 mL), brine (50 mL), the organic layer was dried over $Na_2SO_4$, filtered and concentrated under reduced pressure. The residue was purified by flash silica gel chromatography (ISCO®; 80 g SepaFlash® Silica Flash Column, Eluent of 0-50%, EtOAc/DCM gradient @ 60 mL/min) to give ALG-14-5-009 A (4.2 g, 66.42% yield) as a white foam. LCMS (ESI): m/z 781.1 $[M+Na]^+$, $^1$H NMR (400 MHz, $CDCl_3$) δ=7.49-7.25 (m, 14H), 7.21-7.15 (m, 1H), 6.82 (d, J=8.8 Hz, 4H), 6.46 (s, 1H), 5.65 (d, J=8.2 Hz, 1H), 5.57-5.39 (m, 2H), 4.72 (s, 2H), 4.16-4.07 (m, 2H), 3.93 (dd, J=2.6, 10.8 Hz, 1H), 3.81-3.59 (m, 11H), 3.81-3.59 (m, 1H), 3.24 (dd, J=10.6, 13.5 Hz, 1H), 3.10 (dd, J=9.8, 13.3 Hz, 1H), 2.79 (d, J=2.2 Hz, 1H)$^{31}$P NMR ($CD_3CN$) δ=22.37 (s)

Preparation of ALG-14-5-010 A

To a solution of ALG-14-5-009 A (4.6 g, 6.06 mmol, 1 eq) and NaI (2.73 g, 18.19 mmol, 3 eq) in MeCN (15 mL) was added chloromethyl 2,2-dimethylpropanoate (3.65 g, 24.25 mmol, 3.51 mL, 4 eq). The mixture was stirred at 85° C. for 24 h. The reaction mixture was concentrated under reduced pressure to give a residue. The residue was purified by flash silica gel chromatography (ISCO®; 40 g SepaFlash® Silica Flash Column, Eluent of 0-50%, EtOAc/PE gradient @ 40 mL/min) to give ALG-14-5-010 A (2.7 g, 44.6% yield) as a pale yellow solid. LCMS (m/z): 981.1 $[M+Na]^+$.

Preparation of ALG-14-5-010C

To a solution of ALG-14-5-010 A (2.7 g, 2.82 mmol, 1 eq) in DCM (20 mL) was added $Et_3SiH$ (645.45 mg, 2.82 mmol, 5 mL, 1 eq), followed by addition of TFA (1.54 g, 13.51 mmol, 1 mL, 4.80 eq). The mixture was stirred at 20° C. for 0.5 h. The reaction mixture was concentrated under reduced pressure to give a residue. The residue was purified by flash silica gel chromatography (ISCO®; 24 g SepaFlash® Silica Flash Column, Eluent of 0-50%, EtOAc/DCM gradient @ 30 mL/min) to give ALG-14-5-010C (1.6 g, 84.82% yield) as a pale yellow solid. LCMS (ESI): m/z 679.1 $[M+Na]^+$; $^1$H NMR (400 MHz, $CDCl_3$) δ=7.44 (d, J=8.2 Hz, 1H), 7.38-7.26 (m, 5H), 5.76 (d, J=8.2 Hz, 1H), 5.69-5.62 (m, 4H), 5.51-5.43 (m, 1H), 5.51-5.43 (m, 1H), 4.70 (s, 2H), 4.30 (s, 1H), 4.26-4.06 (m, 4H), 3.90 (dd, J=4.9, 8.4 Hz, 2H), 3.22-3.06 (m, 1H), 1.22 (s, 18H)$^{31}$P NMR (162 MHz, $CD_3CN$) δ=20.25 (s, 1P).

Preparation of ALG-14-5-011 A

To a mixture of ALG-14-5-010C (1.4 g, 2.13 mmol, 1 eq) in isopropanol (20 ml) and $H_2O$ (2 mL) added Pd/C (1.4 g) and HCOOH (51.22 mg, 1.07 mmol, 2 mL) under $N_2$. The suspension was degassed under vacuum and purged with $H_2$ several times. The mixture was stirred under $H_2$ (15 PSI) at 15° C. for 5 h. The reaction mixture was filtered and the filtrate was concentrated to give a residue. The residue was purified by flash silica gel chromatography (ISCO®; 24 g SepaFlash® Silica Flash Column, Eluent of 0-50%, EtOAc/DCM gradient @ 30 mL/min) to give ALG-14-5-011 A (848 mg, 74.14% yield) as a white foam. LCMS (ESI): m/z 537.0 $[M+H]^+$; $^1H$ NMR (400 MHz, $CDCl_3$) δ=10.01 (s, 1H), 7.53 (d, J=8.0 Hz, 1H), 5.78-5.63 (m, 6H), 4.40 (s, 1H), 4.35-4.22 (m, 3H), 4.11 (d, J=1.5 Hz, 1H), 3.88 (d, J=8.5 Hz, 2H), 1.22 (s, 18H)$^{31}P$ NMR (162 MHz, $CD_3CN$) δ=20.17 (s, 1P.)

Preparation of ALG-14-5

To a solution of ALG-14-5-011 A (848 mg, 1.58 mmol, 1 eq) in DCM (10 mL) was added 3-bis(diisopropylamino) phosphanyloxypropanenitrile (571.73 mg, 1.90 mmol, 602.45 uL, 1.2 eq) at 0° C., followed by addtion of 1H-imidazole-4,5-dicarbonitrile (186.7 mg, 1.58 mmol, 1 eq). The mixture was stirred at 15° C. for 1 h. The reaction mixture was quenched by addition of sat. aq. $NaHCO_3$ (10 mL) and diluted with DCM (20 mL). Then the organic layer was washed with sat. aq. $NaHCO_3$ (10 mL*2), dried over $Na_2S04$, filtered and concentrated under reduced pressure. The residue was purified by flash silica gel chromatography (ISCO®; 12 g SepaFlash® Silica Flash Column, Eluent of 0-50%, phase A: PE with 0.5% TEA; phase B: EA with 10% EtOH, 30 mL/min) to give ALG-14-5 (720 mg, 61.21% yield) as a colorless oil. LCMS (ESI): m/z 737.1 $[M+H]^+$; $^1H$ NMR (400 MHz, $CD_3CN$) δ=9.17 (s, 1H), 7.49 (d, J=8.0 Hz, 1H), 5.91-5.77 (m, 1H), 5.65-5.54 (m, 5H), 4.49-4.26 (m, 2H), 4.23-4.07 (m, 2H), 3.92-3.55 (m, 6H), 2.71-2.61 (m, 2H), 1.24-1.16 (m, 30H); $^{31}P$ NMR (162 MHz, $CD_3CN$) δ=151.59.

Example 13: Synthesis of 102

Scheme-12

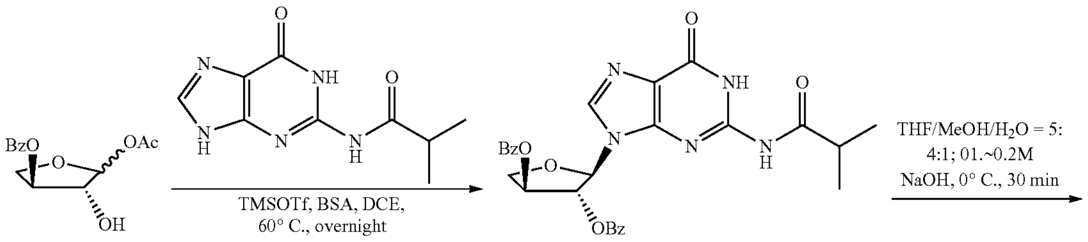

PH-ALIG-14-4-5

102-1

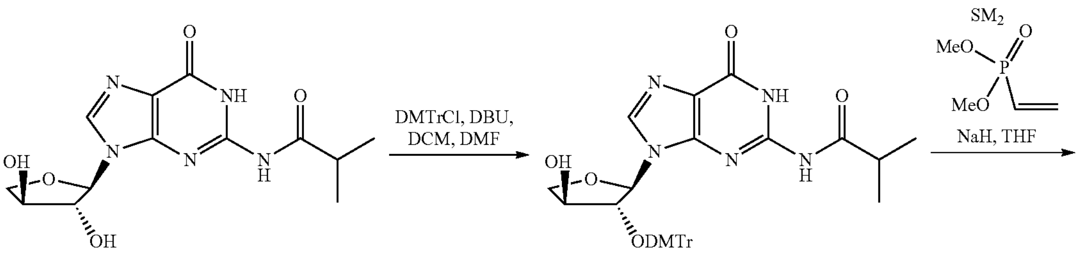

102-2

102-3

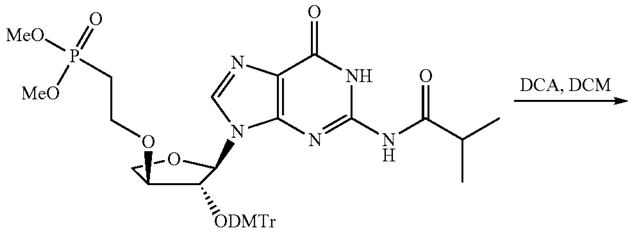

102-4

-continued
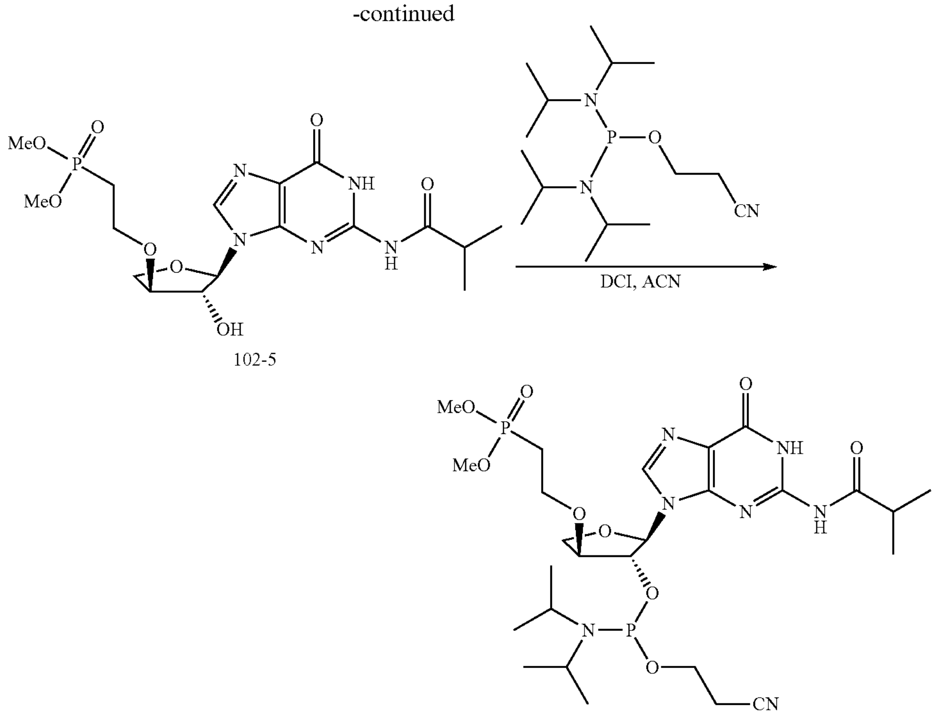
102-5
102
Example 14: Synthesis of 103
Scheme-13
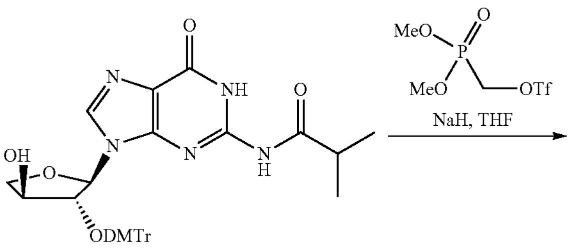
102-2
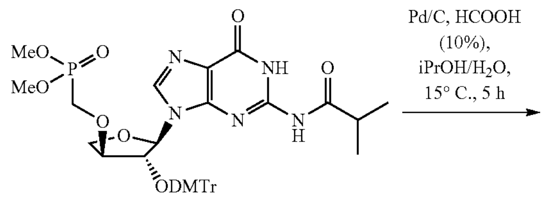
103-1
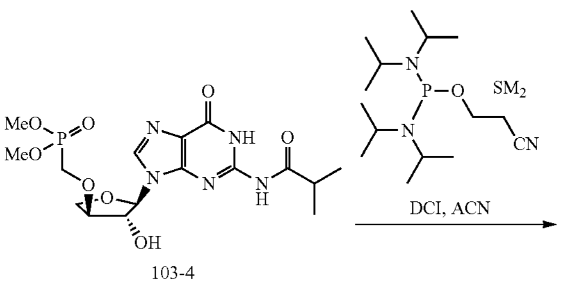
103-4
-continued
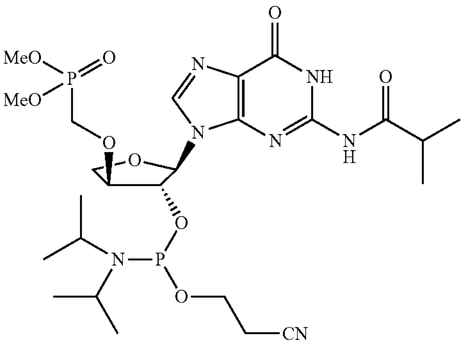
103
Example 15: Synthesis of 104
Scheme-14
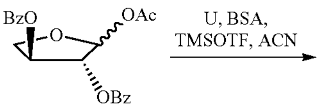
PH-ALIG-14-4-5

-continued
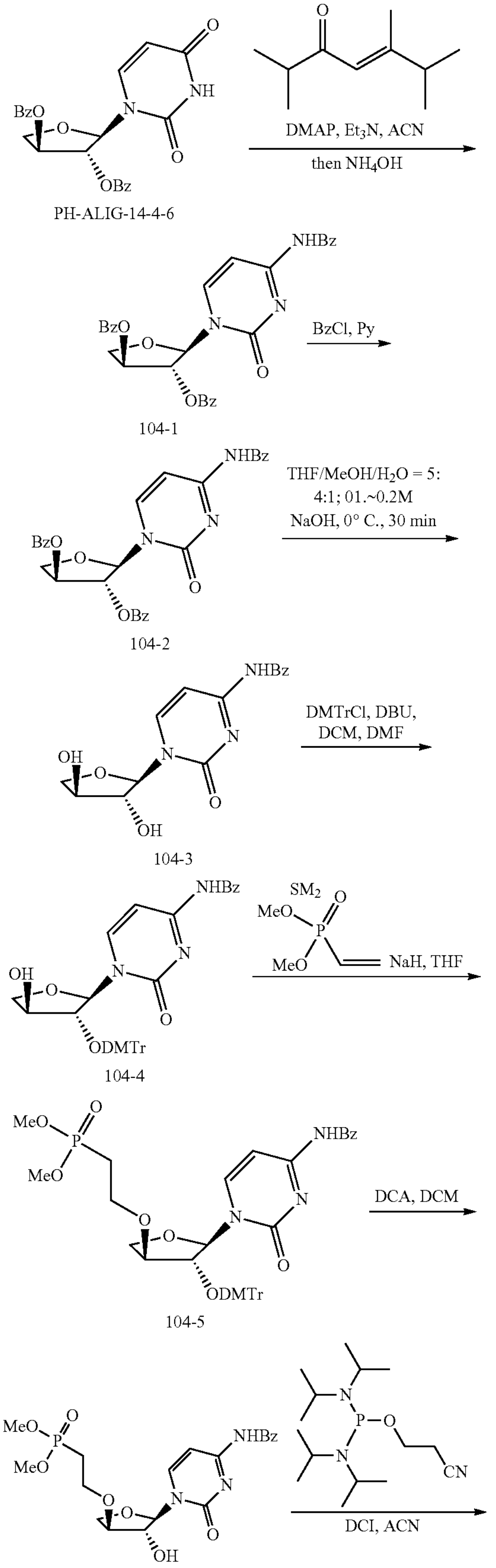
PH-ALIG-14-4-6
104-1
104-2
104-3
104-4
104-5
104-6
-continued
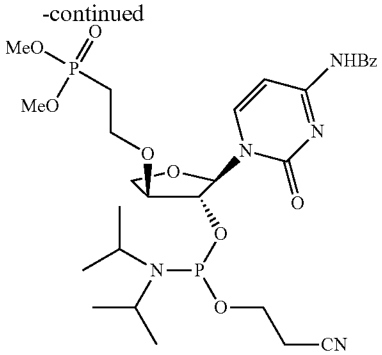
104
Example 16: Synthesis of 105
Scheme-15
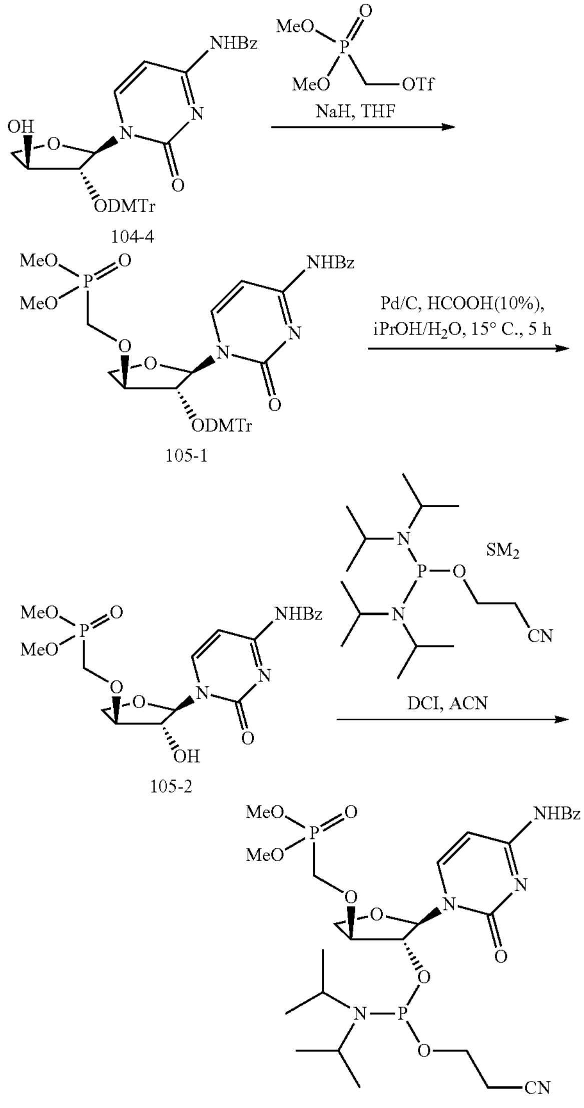
104-4
105-1
105-2
105

Example 17

Scheme-16

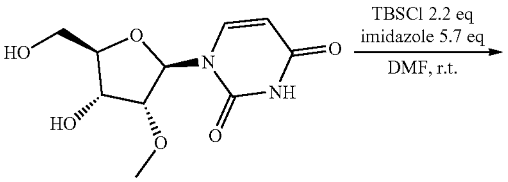

1

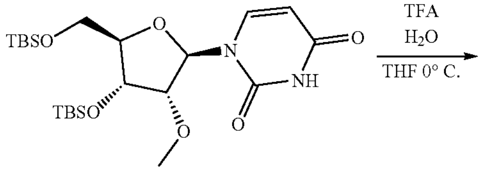

2

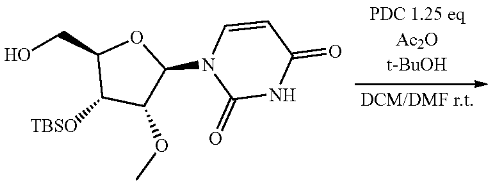

3

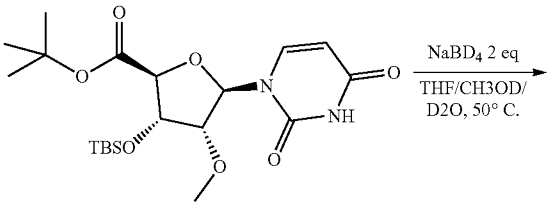

4

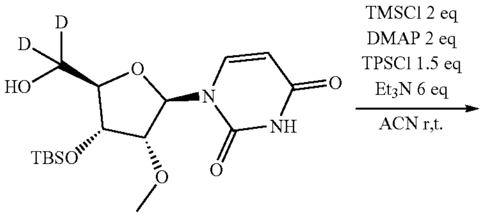

5

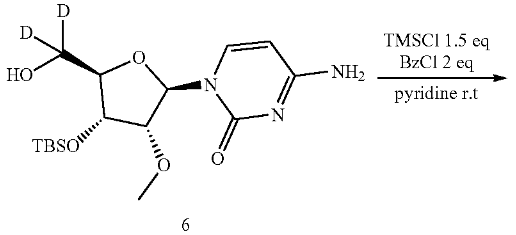

6

-continued

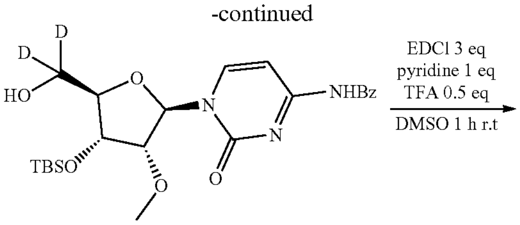

7

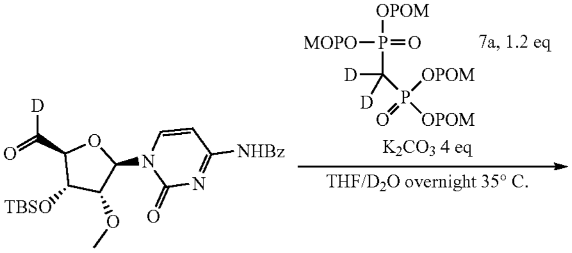

8

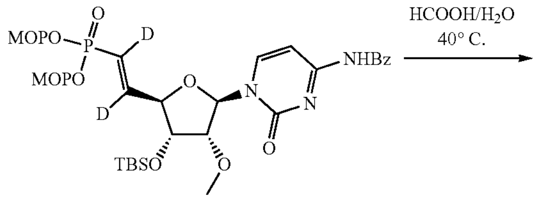

9

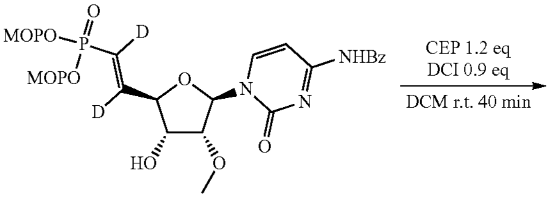

10

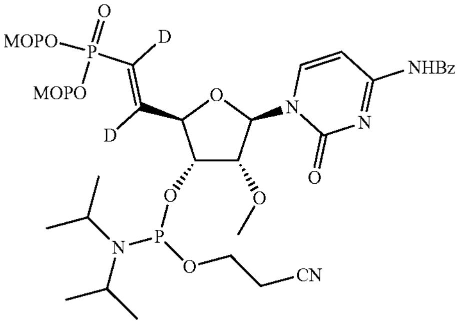

11

Preparation of 2: A 2 L three-necked round bottom flask equipped with magnetic stirrer and thermometer was charged with 1 (60.0 g, 228.8 mmol) in dry DMF (600.0 mL) at r.t., imidazole (95.2 g, 1.3 mol) was added into the mixture reaction, then the reaction mixture was cooled down to turn 5° C., TBSCl (76.8 g, 499.3 mmol) was added into the mixture reaction, the reaction mixture was allowed to stir for 12 h at r.t. 1 was consumed by LCMS, then the reaction mixture was added in the saturated sodium bicarbonate solution (1.0 L), after quenching the reaction, the aqueous layer was extracted with EA (400.0 mL*2), the combined organic layer was washed with saturated brine and dried over anhydrous sodium sulfate, the organic layer was concentrated to get crude 2 (110.2 g, 212.8 mmol, 93.1% yield)

as a white solid, the crude product was used directly for the next step without purification. ESI-LCMS: m/z=487.3 $[M+H]^+$.

Preparation of 3: A 3 L three-necked round bottom flask equipped with magnetic stirrer and thermometer was charged with 2 (117.0 g, 225.9 mmol) in THF (550.0 mL) at r.t., water (275.0 mL) was added into the mixture reaction, then the reaction mixture was cooled down to turn 0° C. and add TFA (275.0 mL) by constant pressure funnel after 4 h, the reaction mixture was allowed to stir for 2 h at 0° C. 2 was consumed by TLC. Then, reaction mixture was added in a mixture solvent of ammonium hydroxide (250.0 mL) and water (800.0 mL) at 0° C., after quenching the reaction, the aqueous layer was extracted with EA (500.0 mL*2), the combined organic layer was washed with saturated brine and dried over anhydrous sodium sulfate, the organic layer was concentrated to get crude which was purified by silica gel column chromatography (PE:EA=10:1 to 0:1) to give compound 3 (51.1 g, 59.3% yield) as a white solid. $^1$H-NMR (600 MHz, DMSO-$d_6$): δ=11.35 (s, 1H), 7.919 (d, J=6 Hz, 1H), 5.82 (s, 1H), 5.65 (d, J=6 Hz, 1H), 5.18 (s, 1H), 4.29 (s, 1H), 3.83 (s, 2H), 3.65 (d, J=12 Hz, 1H), 3.53 (d, J=6 Hz, 1H), 3.32 (d, J=6 Hz, 1H), 0.87 (s, 9H), 0.08 (s, 6H). ESI-LCMS: m/z=373.1 $[M+H]^+$.

Preparation of 4: A 3 L three-necked round bottom flask equipped with magnetic stirrer and thermometer was charged with 3 (50.0 g, 131.5 mmol) in a mixture solvent of DCM (250.0 mL) and DMF (70.0 mL) at r.t., the mixture solution was cooled down to turn 5° C., PDC (63.1 g, 164.4 mmol) and t-BuOH (200.0 mL) were added into the mixture reaction, keep the reaction at 5° C. and add $Ac_2O$ (130.0 mL) by constant pressure funnel after 0.5 h, the reaction mixture was allowed to stir for 4 h at r.t. 3 was consumed by 1c-ms, then the reaction mixture was added in the saturated sodium bicarbonate (400.0 mL), after quenching the reaction, the aqueous layer was extracted with DCM (500.0 mL*2), the combined organic layer was washed with saturated brine and dried over anhydrous sodium sulfate, the organic layer was concentrated to get crude which was purified by silica gel column chromatography (PE:EA=10:1 to 2:1) to give compound 4 (29.8 g, 50.6% yield) as a white solid. $^1$H-NMR (DMSO $d_6$): δ=11.42 (s, 1H), 8.04 (d, J=6 Hz, 1H), 5.82 (s, 1H), 5.78 (d, J=6 Hz, 1H), 4.44 (s, 1H), 4.25 (s, 1H), 3.84 (s, 1H), 3.32 (s, 3H), 1.46 (s, 9H), 0.89 (s, 9H), 0.12 (s, 6H). ESI-LCMS: m/z=443.1 $[M+H]^+$.

Preparation of 5: To a solution of 4 (33.0 g, 74.7 mmol) in dry THF (330.0 mL) was added $CH_3OD$ (66.0 mL) and $D_2O$ (33.0 mL) at r.t. Then the reaction mixture was added $NaBD_4$ (9.4 g, 224.0 mmol) three times per an hour at 50° C. The solution was stirred at 50° C. for 3 h. LCMS showed 4 was consumed. Water (300.0 mL) was added. The product was extracted with EA (2*300.0 mL). The organic layer was washed with brine and dry over by $Na_2SO_4$. Then the solution was concentrated under reduced pressure, crude was purified by by silica gel column chromatography (PE: EA=10:1 to 3:1) to give 5 (19.1 g, 68.5% yield) as a white solid. $^1$H-NMR (600 MHz, DMSO $d_6$): δ=11.35 (s, 1H), 7.92-7.91 (d, J=6 Hz, 1H), 5.83-5.82 (d, J=6 Hz, 1H), 5.66-5.65 (d, J=6 Hz, 1H), 5.14 (s, 1H), 4.30-4.28 (m, 1H), 3.84-3.82 (m, 2H), 3.34 (s, 3H), 0.88 (s, 9H), 0.09 (s, 6H). ESI-LCMS: m/z 375 $[M+H]^+$.

Preparation of 6: To a solution of 5 (19.1 g, 51.1 mmol) in dry ACN (190.0 mL) was added $Et_3N$ (20.7 g, 204.6 mmol) at r.t. and TMSCl (11.1 g, 102.1 mmol) at 0° C. Then the reaction mixture was stirred at r.t. for 40 min. LCMS showed 5 was consumed and an intermediate was formed. Then the solution was added DMAP (12.5 g, 102.3 mmol), $Et_3N$ (10.3 g, 102.1 mmol) and TPSCl (23.2 g, 76.6 mmol). The reaction mixture was stirred at r.t. for 15 h. LCMS showed the intermediate was consumed and conformed another intermediate. Then was added $NH_4OH$ (200.0 mL) and stirred at r.t. for 24 h to give the mixture of product. The product was extracted with EA (2*200.0 mL). The organic layer was washed with brine and dry over by $Na_2SO_4$. Then the solution was concentrated under reduced pressure, crude was purified by Flash-Prep-HPLC with the following conditions (IntelFlash-1): Column, C18 silica gel; mobile phase, $CH_3CN/H_2O$=1/2 increasing to $CH_3CN/H_2O$=1/0 within 20 min, the eluted product was collected at $CH_3CN/H_2O$=1/0; Detector, UV 254 nm. This resulted in to give 6 (14.0 g, 73.7% yield). $^1$H-NMR (DMSO-$d_6$): δ=7.89-7.88 (d, J=6 Hz, 1H), 7.20-7.18 (d, J=12 Hz, 2H), 5.85-5.84 (d, J=6 Hz, 1H), 5.73-5.72 (d, J=6 Hz, 1H), 5.09 (s, 1H), 4.24-4.23 (m, 1H), 3.81-3.80 (d, J=6 Hz, 1H), 3.69-3.68 (m, 1H), 3.36 (s, 3H), 0.87 (s, 9H), 0.07 (s, 6H). ESI-LCMS: m/z 374 $[M+H]^+$.

Preparation of 7: To a solution of 6 (14.0 g, 37.5 mmol) in pyridine (140.0 mL) was added TMSCl (6.3 g, 58.0 mmol) at 0° C. and the mixture was stirred at r.t. for 1.5 h. LCMS showed 6 was consumed and an intermediate(a) was formed. Then was added BzCl (10.8 g, 76.8 mmol) at 0° C. and the mixture was stirred at r.t. for 1.5 h. LCMS showed the intermediate was consumed and another intermediate was formed. Then the mixture was added $NH_4OH$ (30.0 mL) and was stirred at r.t. for 15 h. LCMS showed the intermediate was consumed. Water (300.0 mL) was added. The solution was extracted with EA (2*200.0 mL). The organic layer was washed with brine and dry over by $Na_2SO_4$. Then the solution was concentrated under reduced pressure, crude was purified by Flash-Prep-HPLC with the following conditions (IntelFlash-1): Column, C18 silica gel; mobile phase, $CH_3CN/H_2O$=1/1 increasing to $CH_3CN/H_2O$=1/0 within 20 min, the eluted product was collected at $CH_3CN/H_2O$=1/0; Detector, UV 254 nm. This resulted in to give 7 (10.5 g, 58.6% yield). $^1$H-NMR (600 MHz, DMSO $d_6$): δ=11.29 (s, 1H), 8.53-8.52 (d, J=6 Hz, 1H), 8.01-8.00 (d, J=6 Hz, 2H), 7.63-7.61 (m, 1H), 7.52-7.50 (m, 2H), 7.36 (s, 1H), 5.88 (s, 1H), 5.24 (s, 1H), 4.28-4.26 (m, 1H), 3.91 (s, 1H), 3.81-3.79 (m, 1H), 3.46 (s, 3H), 0.87 (s, 9H), 0.08 (s, 6H). ESI-LCMS: m/z 478 $[M+H]^+$.

Preparation of 8: To a solution of 7 (10.5 g, 22.0 mmol) in DMSO (105.0 mL) was added EDCI (12.7 g, 66.0 mmol), dry pyridine (1.7 g, 22.0 mmol) at r.t. and TFA (1.3 g, 11.0 mmol) at 0° C. Then the reaction mixture was stirred for 1 h. LCMS showed 7 was consumed. Water (100.0 mL) was added. The solution was extracted with EA (2*200.0 mL). The organic layer was washed with brine and dry over by $Na_2SO_4$. Then the solution was concentrated under reduced pressure to give the crude product 8 which was used in next step directly. ESI-LCMS: m/z 475 $[M+H]^+$.

Preparation of 9: To a solution of 8 in dry THF (120.0 mL) and $D_2O$ (40.0 mL) was added $K_2CO_3$ (12.2 g, 88.1 mmol) and 7a (16.8 g, 26.5 mmol) then the reaction mixture was stirred for 15 h at 35° C. under the $N_2$ atmosphere. LCMS showed 95% 7 was consumed. Water (60.0 mL) was added. The solution was extracted with EA (2*150.0 mL). The organic layer was washed with brine and dry over by $Na_2SO_4$. Then the solution was concentrated under reduced pressure, crude was purified by Flash-Prep-HPLC with the following conditions (IntelFlash-1): Column, C18 silica gel; mobile phase, $CH_3CN/H_2O$=1/1 increasing to $CH_3CN/H_2O$=1/0 within 20 min, the eluted product was collected at $CH_3CN/H_2O$=4/1; Detector, UV 254 nm. This resulted in to give 9 (9.3 g, 54.1% yield). $^1$H-NMR (DMSO-$d_6$) δ=11.33

(s, 1H), 8.17-8.15 (d, J=12, 1H), 8.02-8.00 (d, J=12, 1H), 7.64-7.62 (m, 1H), 7.53-7.50 (m, 2H), 7.44-7.42 (d, J=12, 1H), 4.46-4.44 (d, J=12, 1H), 4.24-4.23 (d, J=6, 1H), 3.93-3.91 (d, J=12, 1H), 1.16 (s, 18H), 0.86 (s, 9H)), 0.08-0.06 (d, J=12, 6H). ESI-LCMS: m/z 782 $[M+H]^+$. $^{31}$P-NMR (DMSO-$d_6$) δ=16.77, 16.00.

Preparation of 10: 9 (9.3 g, 11.9 mmol) in the mixture solution of HOAc (140.0 mL) and $H_2O$ (140.0 mL) was stirred at 30° C. for 15 h. LCMS showed 9 was consumed. The solution was added in the ice water and extracted with EA (2*300.0 mL). The organic layer was quenched to pH=6-7 and then washed with brine and dry over $Na_2SO_4$. Then the solution was concentrated under reduced, crude was purified by pressure Flash-Prep-HPLC with the following conditions (IntelFlash-1): Column, C18 silica gel; mobile phase, $CH_3CN/H_2O$=1/1 increasing to $CH_3CN/H_2O$=1/0 within 20 min, the eluted product was collected at $CH_3CN/H_2O$=2.5/1; Detector, UV 254 nm. This resulted in to give 10 (5.1 g, 64.6% yield). $^1$H-NMR (DMSO-$d_6$) δ=9.09 (s, 1H), 7.92-7.85 (m, 3H), 7.60-7.48 (m, 4H), 6.02 (s, 1H), 5.71-5.64 (m, 4H), 4.53-4.51 (m, 1H), 3.94-3.70 (m, 5H), 3.31 (s, 1H), 1.21 (s, 18H). $^{31}$P-NMR (DMSO-$d_6$) δ=16.45. ESI-LCMS: m/z 668 $[M+H]^+$.

Preparation of 11: To a suspension of 10 (4.6 g, 6.9 mmol) in DCM (45.0 mL) added $CEOP[N(ipr)_2]_2$ (2.5 g, 8.3 mmol), DCI (730.4 mg, 6.2 mmol). The mixture was stirred at r.t. for 1 h. LCMS showed 10 was consumed completely. The solution was quenched by water (40.0 mL), washed with brine (2*20.0 mL) and dry over by $Na_2SO_4$. Then the solution was concentrated under reduced pressure and the residue was purified by Flash-Prep-HPLC with the following conditions (IntelFlash-1): Column, C18 silica gel; mobile phase, $CH_3CN/H_2O$=1/1 increasing to $CH_3CN/H_2O$=1/0 within 20 min, the eluted product was collected at $CH_3CN/H_2O$=4/1; Detector, UV 254 nm. This resulted in to give 11 (4.7 g, 5.4 mmol, 78.3% yield) as a white solid. $^1$H-NMR (600 MHz, DMSO-$d_6$) δ=11.34 (s, 1H), 8.18-8.16 (m, 1H), 8.02-8.01 (d, J=6, 2H), 7.65-7.42 (m, 4H), 5.95-5.93 (m, 1H), 5.66-5.61 (m, 4H), 4.64-4.57 (m, 1H), 4.32-4.31 (d, J=6, 1H), 4.12-4.10 (m, 1H), 3.81-3.45 (m, 7H), 2.81-2.79 (m, 2H), 1.16-1.13 (m, 30H). $^{31}$P-NMR ($CDCl_3$-$d_6$) δ=150.65, 150.20, 16.64, 15.41. ESI-LCMS: m/z 868 $[M+H]^+$;

Example 18

Scheme-17

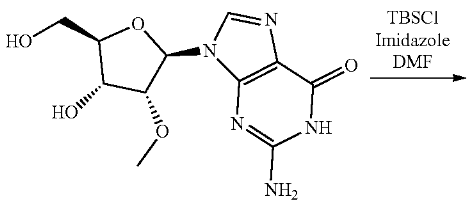

1

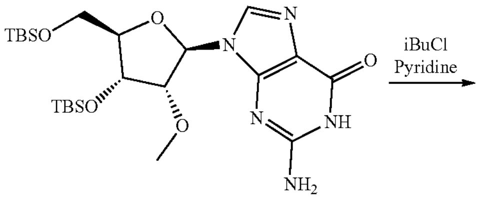

2

-continued

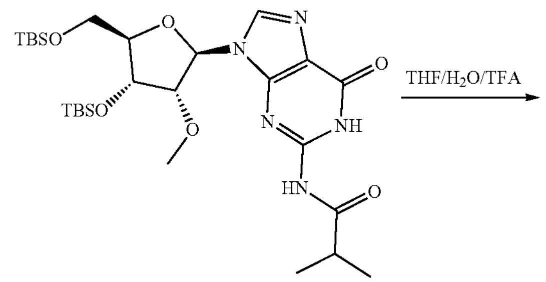

3

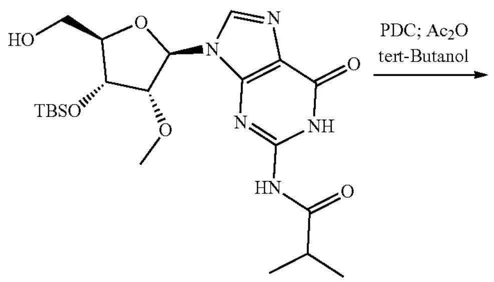

4

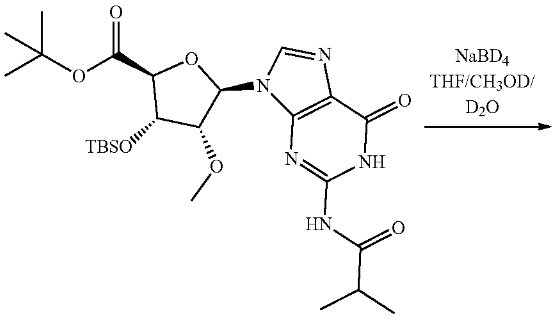

5

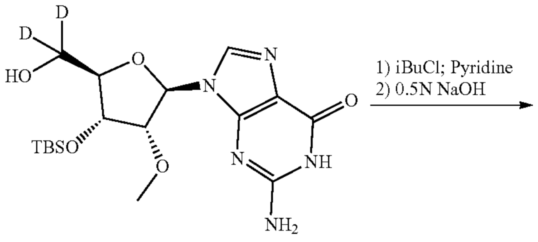

6

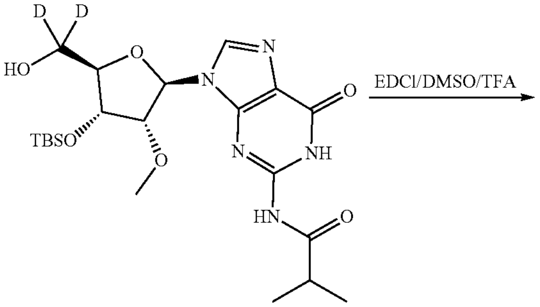

7

-continued

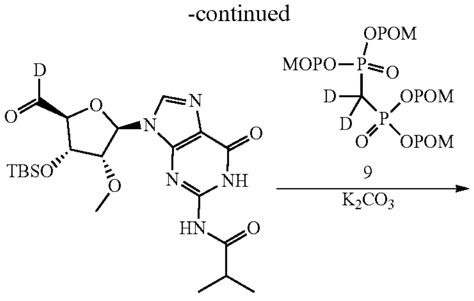

8

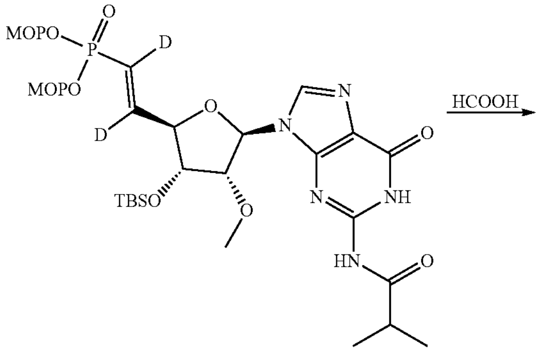

10

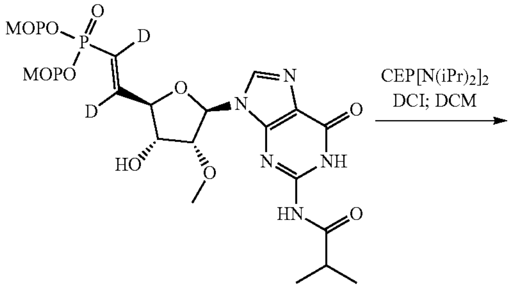

11

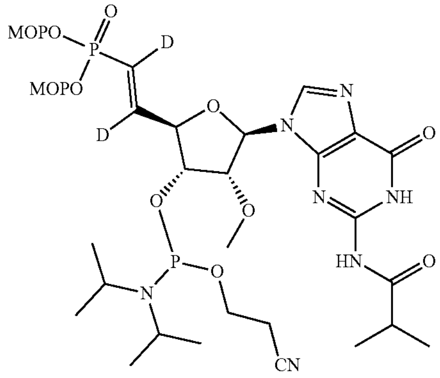

12

Preparation of 2: 1 (94.5 g, 317.9 mmol) was dissolved in dry DMF (1000 mL) under $N_2$ atmosphere. To the solution TBSCl (119.3 g, 794.7 mmol) and imidazole (75.8 g, 1.1 mol) was added at 25° C. and stirred for 17 hr. LCMS showed all of 1 consumed. The reaction mixture was washed with $H_2O$ (3000*2 mL), EA (2000*2 mL) and brine (1500 mL). Dried over $Na_2SO_4$ and concentrated to give crude which goes to the next step. The reaction mixture was concentrated to give crude 2 (200 g, crude). ESI-LCMS: m/z 526 $[M+H]^+$.

Preparation of 3: 2 (175.1 g, 333.0 mmol) was evaporated with pyridine and dried in vacuo for two times. The residue was dissolved in pyridine (1500 mL) under $N_2$. To the solution, i-BuCl (88.7 g, 832.6 mmol) was added at 5° C. under $N_2$ atmosphere and stirred for 3 hr. LCMS showed all of 2 consumed. The reaction mixture was washed with $H_2O$ (3000*2 mL), EA (2000*2 mL) and brine (1500 mL). Dried over $Na_2SO_4$ and concentrated to give crude which goes to the next step. The reaction mixture was concentrated to give crude 3 (228 g, crude). ESI-LCMS: m/z 596 $[M+H]^+$.

Preparation of 4: A solution of 3 (225 g, 377.6 mmol) was in THF (2000 mL) was added $H_2O$ (500 mL) and TFA (500 mL) was added at 5° C. Then the reaction mixture was stirred at 5° C. for 1 hr. LCMS showed all of 3 consumed. Con $NH_4OH$ (aq) was added to mixture to quench the reaction until the pH=7-8, then washed with $H_2O$ (2000*2 mL), EA (2000*2 mL) and brine (1500 mL). Dried over $Na_2SO_4$ and concentrated to give crude which was purified by cc. The reaction mixture was concentrated to give 4 (155.6 g, 83.9% yield). ESI-LCMS: m/z 482 $[M+H]^+$.

Preparation of 5: 4 (100 g, 207.6 mmol) was dissolved in dry DMF (1000 mL) under $N_2$. To the solution, t-BuOH (307.8 g, 4.2 mol), PDC (156.1 g, 0.4 mol) and $Ac_2O$ (212.0 g, 2.1 mol) was added at 25° C. under $N_2$ atmosphere and stirred at 25° C. for 2 hr. LCMS and TLC showed all of 4 consumed. $NaHCO_3$ (aq) was added to mixture to quench the reaction until the pH=7-8, then washed with $H_2O$ (500*2 mL), EA (500*2 mL) and brine (500 mL). Dried over $Na_2SO_4$ and concentrated to give crude which was purified by cc. and MPLC. The reaction mixture was concentrated to give 5 (77.3 g, 61.6% yield). ESI-LCMS: m/z 552 $[M-H]^+$.

Preparation of 6: 5 (40.0 g, 72.6 mmol) was dissolved in dry THF (400 mL) under $N_2$. To the solution, MeOD (80 mL) and D20 (40 mL) was added at 25° C. under $N_2$ atmosphere, then $NaBD_4$ (9.1 g, 217.4 mmol) was added for three times and stirred for 15 hr. LCMS and TLC showed all of 5 consumed. The mixture was concentrated to give crude which goes to the next step. The reaction mixture was concentrated to give crude 6 (30 g, crude). ESI-LCMS: m/z 414 $[M+H]^+$ Preparation of 7: 6 (30 g, crude) was evaporated with pyridine and dried in vacuo for two times. The residue was dissolved in dry pyridine (300 mL) under $N_2$. Then iBuCl (15.5 g, 145.3 mmol) was slowly added to the reaction mixture at 0° C. under $N_2$ atmosphere and stirred at 25° C. for 1 hr. LCMS and TLC showed all of 6 consumed. $NaHCO_3$ (aq) was added to mixture to quench the reaction until the pH=7.5, then washed with $H_2O$ (1500 mL), EA (1000*2 mL) and brine (1500 mL). Dried over $Na_2SO_4$ and concentrated to give crude residue R1. NaOH (8 g, 0.2 mol), MeOH (80 mL) and $H_2O$ (20 mL) made up NaOH (aq). The residue R1 (40 g, 3.63 mmol) was dissolved in pyridine (20 mL). To the solution, 2N NaOH (aq) (100 ml) was added to the solution and stirred the reaction 15 min at 5° C. TLC showed all of R1 consumed. The mixture was added $NH_4Cl$ to pH=7-8 at 5° C., and concentrated to give crude which was purified by cc. The product was concentrated to give 7 (15.5 g, 33.00% yield over two steps). ESI-LCMS: m/z 484$[M+H]^+$.

Preparation of 8: To a stirred solution of 7 (15.5 g, 32.1 mmol) in DMSO (150 mL) were added EDCI (18.5 g, 96.3 mmol), pyridine (2.5 g, 32.1 mmol), TFA (1.8 g, 16.0 mmol) at room temperature under $N_2$ atmosphere. The reaction mixture was stirred for 1 h at room temperature. The reaction was quenched with water, extracted with EA (300.0 mL), washed with brine, dried over $Na_2SO_4$ and evaporated under reduced pressure give a crude 8 (17.3 g, crude) which was used directly to next step. ESI-LCMS: m/z=481 $[M+H]^+$.

Preparation of 10: A solution of 8 (17.3 g, crude), 9 (21.4 g, 33.7 mmol) and $K_2CO_3$ (13.3 g, 96.3 mmol) in dry THF (204 mL) and D20 (34 mL) was stirred 5 h at 40° C. The mixture was quenched with water, extracted with EA (600.0 mL), washed with brine, dried over $Na_2SO_4$ and evaporated under reduced pressure. The residue was purified by silica gel (PE:EA=5:1~ 1:1) to give 10 (9.3 g, 36.6% yield over 2 steps) as a white solid. ESI-LCMS m/z=787$[M+H]^+$.

$^1$H-NMR (DMSO-$d_6$): δ 11.24 (s, 1H, exchanged with D20), 8.74 (d, J=2.7 Hz, 2H), 8.05-8.04 (d, J=7.4 Hz, 2H), 7.65 (t, 1H), 7.57-7.54 (t, 2H), 6.20 (d, J=5.0 Hz, 1H), 5.64-5.58 (m, 4H), 4.77 (t, 1H), 4.70 (t, 1H), 4.57-4.56 (t, 1H), 3.35 (s, 3H), 1.09 (d, J=6.5 Hz, 18H), 0.93 (s, 9H), 0.15 (d, J=1.8 Hz, 6H); $^{31}$P NMR (DMSO-$d_6$): δ 17.05;

Preparation of 11: To a round-bottom flask was added 10 (9.3 g, 11.5 mmol) in a mixture of $H_2O$ (93 mL) and HCOOH (93 mL). The reaction mixture was stirred for 5 h at 50° C. and 15 h at 35° C. The mixture was extracted with EA (500.0 mL), washed with water, $NaHCO_3$ solution and brine successively, dried over $Na_2SO_4$ and evaporated under reduced pressure. The residue was purified by Flash-Prep-HPLC with the following conditions (IntelFlash-1): Column, C18 silica gel; mobile phase, $CH_3CN/H_2O$ (0.5% $NH_4HCO_3$)=1/2 increasing to $CH_3CN/H_2O$ (0.5% $NH_4HCO_3$)=1/0 within 20 min, the eluted product was collected at $CH_3CN/H_2O$ (0.5% $NH_4HCO_3$)=3/2; Detector, UV 254 nm. To give product 11 (6.3 g, 78% yield). $^1$H-NMR (600 MHz, DMSO-$d_6$): δ 12.17 (s, 1H, exchanged with D20), 11.51 (s, 1H), 8.28 (s, 1H), 6.02-6.03 (d, J=4.2 Hz, 1H), 5.63-5.72 (m, 5H), 4.60 (s, 1H), 4.43-4.45 (m, 2H), 3.40 (s, 1H), 3.38 (s, 1H), 2.83-2.88 (m, 1H), 1.15-1.23 (m, 24H); $^{31}$P NMR (DMSO-$d_6$) δ=17.69. ESI-LCMS m/z=674 $[M+H]^+$.

Preparation of 12: To a solution of 11 (5.6 g, 8.3 mmol) in DCM (55.0 mL) was added the DCI (835 mg, 7.1 mmol), then CEP$[N(ipr)_2]_2$ (3.3 g, 10.8 mmol) was added. The mixture was stirred at r.t. for 1 h. The reaction mixture was washed with $H_2O$ (50.0 mL) and brine (50.0 mL), dried over $Na_2SO_4$ and evaporated under pressure. The residue was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=9/1; Detector, UV 254 nm. The product was concentrated to give 12 (6.3 g, 87% yield) as a white solid. $^1$H-NMR (DMSO-$d_6$): δ 12.14 (s, 1H, exchanged with D20), 11.38 (s, 1H), 8.27-8.28 (d, J=6 Hz, 1H), 5.92-5.98 (m, 1H), 5.59-5.65 (m, 4H), 4.57-4.68 (m, 3H), 3.61-3.85 (m, 4H), 3.37 (s, 1H), 3.32 (s, 1H), 2.81-2.85 (m, 3H), 1.09-1.20 (m, 36H); $^{31}$P NMR (DMSO-$d_6$): δ 150.60, 149.97, 17.59, 17.16; ESI-LCMS m/z=874 $[M+H]^+$.

Example 19: ds-siNA Activity

This example investigates the activity of the ds-siNAs synthesized in Example 1.

*Homo sapiens* HepG2.2.15 cells were cultured in Dulbecco's Modified Eagle's Medium (DMEM) (ATCC 30-2002) supplemented to also contain 10% fetal calf serum (FCS). Cells were incubated at 37° C. in an atmosphere with 5% CO2 in a humidified incubator. For transfection of HepG2.2.15 cells with HBV targeting siRNAs, cells were seeded at a density of 15000 cells/well in 96-well regular tissue culture plates. Transfection of cells was carried out using RNAiMAX (Invitrogen/Life Technologies) according to the manufacturer's instructions. Dose-response experiments were done with oligo concentrations of 40, 20, 10, 5, 2.5, 1.25, 0.625, 0.3125, 0.15625 and 0.07813 nM. For each HBV targeting siRNA treatment (e.g., ds-siRNA, as identified by the ds-siNA ID in Table 6), four wells were transfected in parallel, and individual data points were collected from each well. After 24 h of incubation with siRNA, media was removed, and cells were lysed and analyzed with a QuantiGene2.0 branched DNA (bDNA) probe set specific for HBV genotype D (also called Hepatitis B virus subtype ayw, complete genome of 3182 base-pairs) as present in cell line HepG2.2.15.

For each well, the HBV on-target mRNA levels were normalized to the GAPDH mRNA level. As shown in Tables 6-10, the activity of the HBV targeting ds-siRNAs was expressed as EC50, 50% reduction of normalized HBV RNA level from no drug control. As shown in Tables 6-10, the cytotoxicity of the HBV targeting ds-siRNAs was expressed by CC50 of 50% reduction of GAPDH mRNA from no drug control.

Example 20: Use of Ds-siNAs to Treat Hepatitis B Virus Infection

In this example, the ds-siNAs synthesized in Example 1 are used to treat a hepatitis B virus infection in a subject. Generally, a composition comprising a ds-siNA from Tables 1-5 (as identified by the ds-siNA ID) and a pharmaceutically acceptable carrier is administered to the subject suffering from hepatitis B virus. The ds-siNA from Tables 1-5 are conjugated to N-acetylgalactosamine. The ds-siNA is administered at a dose of 0.3 to 5 mg/kg every three weeks by subcutaneous injection or intravenous infusion.

Example 21: siNA Activity Assays

This example provides exemplary methods for testing the activity of the siNAs disclosed herein.

In Vitro Assay:

HepG2.2.15 cells were cultured in Dulbecco's Modified Eagle's Medium (DMEM) (ATCC 30-2002) supplemented to also contain 10% fetal calf serum (FCS). Cells were incubated at 37° C. in an atmosphere with 5% $CO_2$ in a humidified incubator. For transfection of HepG2.2.15 cells with HBV targeting siRNAs, cells were seeded at a density of 15000 cells/well in 96-well regular tissue culture plates. Transfection of cells was carried out using RNAiMAX (Invitrogen/Life Technologies) according to the manufacturer's instructions. Dose-response experiments were done with oligo concentrations of 40, 20, 10, 5, 2.5, 1.25, 0.625, 0.3125, 0.15625 and 0.07813 nM. For each HBIV targeting siRNA treatment (e.g., ds-siRNA, as identified by the ds-siNA ID in Tables 6-10), four wells were transfected in parallel, and individual data points were collected from each well. After 24 h of incubation with siRNA, media was removed, and cells were lysed and analyzed with a QuantiGene2.0 branched DNA (bDNA) probe set specific for HBV genotype D (also called Hepatitis B virus subtype ayw, complete genome of 3182 base-pairs) as present in cell line HepG2.2.15.

For each well, the HBV on-target mRNA levels were normalized to the GAPDH mRNA level. As shown in Tables 6-10, the activity of the HBV targeting ds-siRNAs was expressed as $EC_{50}$, 5000 reduction of normalized HBV RNA level from no drug control. As shown in Tables 6 and 10, the cytotoxicity of the HBV targeting ds-siRNAs was expressed by $CC_{50}$ of 50% reduction of GAPDH mRNA from no drug control.

TABLE 6 siNA Comprising 2'-Fluoro Nucleotides

| Name | SS/AS 5' to 3' | $EC_{50}$ | Emax (%) | $CC_{50}$ (nM) |
| --- | --- | --- | --- | --- |
| ds-siNA-001 | mGpsmUpsmGmGfUmGfGfAfCmUmUmCmUmCmUmCmAmAmU<br>(SEQ ID NO: 1)<br>mApsf**2P**psmUmGmAfGmAmGmAmAmGmUmCfCmAfCmCmAmCpsmGpsmA<br>(SEQ ID NO: 2) | A | 71 | >45 |
| ds-siNA-002 | mGpsmUpsmGmGfUmGfGfAfCmUmUmCmUmCmUmCmAmAmU<br>(SEQ ID NO: 3)<br>mApsfUpsmUmGmAfGmAmGmAmAmGmUmC**f4P**mAfCmCmAmCpsmGpsmA<br>(SEQ ID NO: 4) | B | 59 | >45 |
| ds-siNA-003 | mGpsmUpsmGmGfUmGfGfAfCmUmUmCmUmCmUmCmAmAmU<br>(SEQ ID NO: 5)<br>mApsfUpsmUmGmAfGmAmGmAmAmGmUmCfCmA**f2P**mCmAmCpsmGpsmA<br>(SEQ ID NO: 6) | A | 68 | >45 |
| ds-siNA-004 | mGpsmUpsmGmGfUmGfGfAfCmUmUmCmUmCmUmCmAmAmU<br>(SEQ ID NO: 7)<br>mApsfUpsmUmGmAfGmAmGmAmAmGmUmC**f2P**mA**f2P**mCmAmCpsmGpsmA<br>(SEQ ID NO: 8) | B | 61 | >45 |
| ds-siNA-005 | mGpsmUpsmGmGfUmGfGfAfCmUmUmCmUmCmUmCmAmAmU<br>(SEQ ID NO: 9)<br>mAps**fB**psmUmGmAfGmAmGmAmAmGmUmCfCmAfCmCmAmCpsmGpsmA<br>(SEQ ID NO: 10) | B | 71 | >45 |
| ds-siNA-006 | mGpsmUpsmGmGfUmGfGfAfCmUmUmCmUmCmUmCmAmAmU<br>(SEQ ID NO: 11)<br>mApsfUpsmUmGmAfGmAmGmAmAmGmUmC**fB**mAfCmCmAmCpsmGpsmA<br>(SEQ ID NO: 12) | B | 70 | >45 |
| ds-siNA-007 | mGpsmUpsmGmGfUmGfGfAfCmUmUmCmUmCmUmCmAmAmU<br>(SEQ ID NO: 13)<br>mApsfUpsmUmGmAfGmAmGmAmAmGmUmC**fB**mA**fB**mCmAmCpsmGpsmA<br>(SEQ ID NO: 14) | D | — | >45 |
| ds-siNA-008 | mGpsmUpsmGmGfUmGfGfAfCmUmUmCmUmCmUmCmAmAmU<br>(SEQ ID NO: 15)<br>mApsfUpsmUmGmAfGmAmGmAmAmGmUmC**f2P**mAfCmCmAmCpsmGpsmA<br>(SEQ ID NO: 16) | A | 67 | >45 |
| CONTROL 1 | mGpsmUpsmGmGfUmGfGfAfCmUmUmCmUmCmUmCmAmAmU<br>(SEQ ID NO: 41)<br>mApsfUpsmUmGmAfGmAmGmAmAmGmUmCf<br>CmAfCmCmAmCpsmGpsmA<br>(SEQ ID NO: 42) | A | 61 | >45 |

For $EC_{50}$, A = $EC_{50} \leq 0.1$ nM;
B = 0.1 nM $\leq EC_{50} < 1$ nM;
C = 1 nM $< EC_{50} < 10$;
D = $EC_{50} \geq 10$ nM.
mX = 2'-O-methyl nucleotide;
fX = 2'-fluoro nucleotide;
5dcd3X = nucleotide of Formula 17;
5dfX = nucleotide of Formula 16;
vX= 5' vinyl phosphonate nucleotide;
d2vX = deuterated 5'
vinyl phosphonate nucleotide;
vmX = 5' vinyl phosphonate, 2'-methyl nucleotide;
f4P =

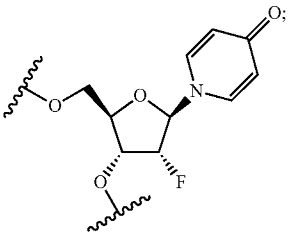 [SMILES: *OC[C@H]1O[C@@H](n2ccc(=O)cc2)[C@H](F)[C@@H]1O*]

f2P =

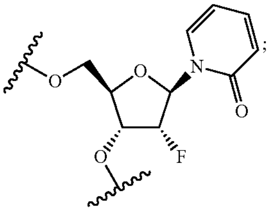 [SMILES: *OC[C@H]1O[C@@H](n2ccccc2=O)[C@H](F)[C@@H]1O*]

TABLE 6-continued siNA Comprising 2'-Fluoro Nucleotides

| Name | SS/AS 5' to 3' | $EC_{50}$ | Emax (%) | $CC_{50}$ (nM) |
|---|---|---|---|---|

fB =

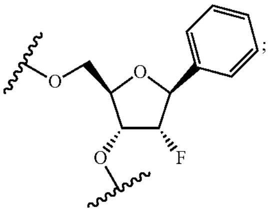 [SMILES: *OC[C@H]1O[C@@H](c2ccccc2)[C@H](F)[C@@H]1O*]

;

ps = phosphorothioate linkage;
X is a nucleobase (e.g. A, G, C, U or T)

TABLE 7 siNA Comprising Nucleotide Phosphate Mimics

| Name | SS/AS 5' to 3' | $EC_{50}$ |
|---|---|---|
| CONTROL 2 | mCpsmCpsmGmUfGmUfGfCfAmCmUmUmCmGmC mUmUmCmA-**p-ps2-GalNAc4** (SEQ ID NO: 43) mUpsfGpsmAmAfGmCmGfAmAmGmUmGmCfAmC mAfCmGmGpsmUpsmC (SEQ ID NO: 44) | A |
| ds-siNA-009 | mCpsmCpsmGmUfGmUfGfCfAmCmUmUmCmGmC mUmUmCmAp-**ps2-GalNAc4** (SEQ ID NO: 17) **omeco-d3U**psfGpsmAmAfGmCmGfAmAmGmUmGmCfAm CmAfCmGmGpsmUpsmC (SEQ ID NO: 18) | A |
| ds-siNA-010 | mCpsmCpsmGmUfGmUfGfCfAmCmUmUmCmGmC mUmUmCmAp-**ps2-GalNAc4** (SEQ ID NO: 19) **4hU**psfGpsmAmAfGmCmGfAmAmGmUmGmCfAm CmAfCmGmGpsmUpsmC (SEQ ID NO: 20) | A |
| ds-siNA-011 | mCpsmCpsmGmUfGmUfGfCfAmCmUmUmCmGmC mUmUmCmAp-**ps2-GalNAc4** (SEQ ID NO: 21) **d2vd3U**psfGpsmAmAfGmCmGfAmAmGmUmGmCf AmCmAfCmGmGpsmUpsmC (SEQ ID NO: 22) | A |
| ds-siNA-012 | mCpsmCpsmGmUfGmUfGfCfAmCmUmUmCmGmC mUmUmCmA-**p-ps2-GalNAc4** (SEQ ID NO: 23) **v-munU**psfGpsmAmAfGmCmGfAmAmGmUmGmCfA mCmAfCmGmGpsmUpsmC (SEQ ID NO: 24) | A |
| ds-siNA-013 | mCpsmCpsmGmUfGmUfGfCfAmCmUmUmCmGmC mUmUmCmA-**p-ps2-GalNAc4** (SEQ ID NO: 25) c2o-**4hU**psfGpsmAmAfGmCmGfAmAmGmUmGmCfAm CmAfCmGmGpsmUpsmC (SEQ ID NO: 26) | A |
| ds-siNA-014 | mCpsmCpsmGmUfGmUfGfCfAmCmUmUmCmGmC mUmUmCmA-**p-ps2-GalNAc4** (SEQ ID NO: 27) **omeco-munU**psfGpsmAmAfGmCmGfAmAmGmUmGmCfA mCmAfCmGmGpsmUpsmC (SEQ ID NO: 28) | B |
| ds-siNA-015 | mCpsmCpsmGmUfGmUfGfCfAmCmUmUmCmGmC mUmUmCmA-**p-ps2-GalNAc4** (SEQ ID NO: 29) **omeco-munU**psfGpsmAmAfGmCmGfAmAmGmUmGmCfA mCmAfCmGmGpsmUpsmC (SEQ ID NO: 30) | A |

TABLE 7-continued siNA Comprising Nucleotide Phosphate Mimics

| Name | SS/AS 5' to 3' | $EC_{50}$ |
|---|---|---|
| ds-siNA-016 | mGpsmUpsmGmGfUmGfGfAfCmUmUmCmUmCmU<br>mCmAmAmU-**p-ps2-GalNAc4**<br>(SEQ ID NO: 33)<br>d2vmApsfUpsmUmGmAfGmAmGmAmAmGmUmCf<br>CmAf2PmCmAmCpsmGpsmA<br>(SEQ ID NO: 34) | A |
| ds-siNA-023 | 5'-<br>mCpsmCpsmGmUfGmUfGf**(4nh)Q**fAmCmUmUmCm<br>GmCmUmUmCmA-p-(ps)2-GalNAc4<br>(SEQ ID NO: 63)<br>3'-<br>mCpsmUpsmGmGfCmAmCfAmCmGmUmGmAfAm<br>GmCfGmAmApsfGps**d2vd3U**-5'<br>(SEQ ID NO: 64) | A |
| ds-siNA-024 | 5'-<br>mCpsmCpsmGmUfGmUfGfCfAmCmUmUmCmGmC<br>mUmUmCmA-**p-(ps)2-GalNAc4**<br>(SEQ ID NO: 65)<br>3'-<br>mCpsmUpsmGmGfCmAmCfAmCmGmUmGmAfAm<br>Gf**(4nh)Q**fGmAmApsfGps**d2vd3U**-5'<br>(SEQ ID NO: 66) | A |
| ds-siNA-025 | 5'-<br>mCpsmCpsmGmUfGmUfGfCfAmCmUmUmCmGmC<br>mUmUmCmA-**p-(ps)2GalNAc4**<br>(SEQ ID NO: 67)<br>3'-<br>mCpsmUpsmGmGf**(4nh)Q**mAmCfAmCmGmUmGm<br>AfAmGmCfGmAmApsfGps**d2vd3U**-5'<br>(SEQ ID NO: 68) | A |
| ds-siNA-050* | mCpsmCpsmGmUfGmUfGfCfAmCmUmUmCmGmC<br>mUmUmCmA-p-(ps)2-GalNAc4<br>(SEQ ID NO: 93)<br>**coc-**<br>**4hU**psfGpsmAmAfGmCmGfAmAmGmUmGmCfAm<br>CmAfCmGmGpsm UpsmC<br>(SEQ ID NO: 114) | C |

For EC50, A = EC50 ≤ 0.1 nM; B = 0.1 nM < EC50 ≤ 1 nM; C = 1 nM < EC50 < 10; D = EC50 ≥ 10 nM.

*ds-siNA-050 was also assessed for CC50 and the CC50 for ds-siNA-050 is >1 nm.

mX = 2'-O-methyl nucleotide; fX = 2'-fluoro nucleotide; 5dcd3X = nucleotide of Formula 17; 5dfX = nucleotide of Formula 16; vX = 5' vinyl phosphonate nucleotide; d2vX = deuterated 5' vinyl phosphonate nucleotide; vmX = 5' vinyl phosphonate, 2'-O-methyl nucleotide;

omeco-d3U =

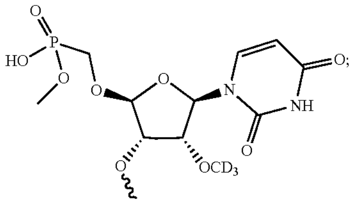

4hU =

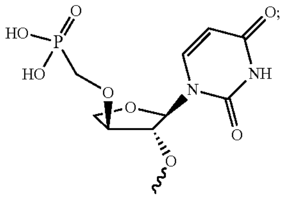

d2vd3U =

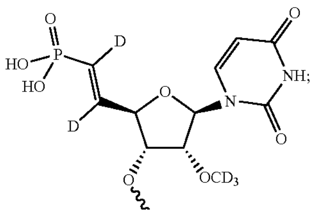

TABLE 7-continued

| siNA Comprising Nucleotide Phosphate Mimics | | |
|---|---|---|
| Name | SS/AS 5' to 3' | $EC_{50}$ |

v-munU =

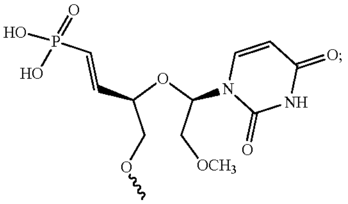

c2o-4hU =

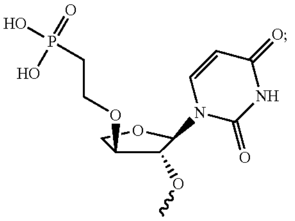

coc-4hU =

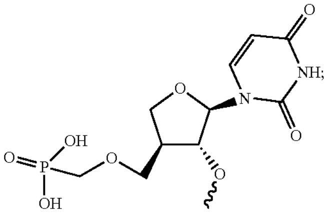

omeco-munU =

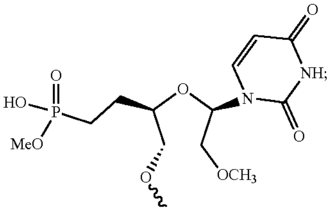

ps = phosphorothioate linkage; X is a nucleobase (e.g. A, G, C, U or T)

TABLE 8

| siNA Comprising Modified Unlocked Nucleotides | | | |
|---|---|---|---|
| Name | SS/AS (5' to 3') | Position of mod. | $EC_{50}$ |
| CONTROL 3 | mCpsmCpsmGmUfGmUfGfCfAmCmUmUmCmGmCmUmUmCmA (SEQ ID NO: 45)<br>mUpsfGpsmAmAfG**unC**mGfAmAmGmUmGmCfAmCmAfCmGmGpsmUpsmC (SEQ ID NO: 46) | 6 | A |
| CONTROL 4 | mCpsmCpsmGmUfGmUfGfCfAmCmUmUmCmGmCmUmUmCmA (SEQ ID NO: 47)<br>mUpsfGpsmAmAfGmC**unG**fAmAmGmUmGmCfAmCmAfCmGmGpsmUpsmC (SEQ ID NO: 48) | 7 | A |
| CONTROL 5 | mCpsmCpsmGmUfGmUfGfCfAmCmUmUmCmGmCmUmUmCmA (SEQ ID NO: 49)<br>mUpsfGpsmAmAfGmCmGfAmAmGmUmGmCfAmCmAfCmGmGpsmUpsmC (SEQ ID NO: 50) | — | A |
| ds-siNA-017 | mCpsmCpsmGmUfGmUfGfCfAmCmUmUmCmGmCmUmUmCmA (SEQ ID NO: 35)<br>mUpsfGpsmAmAfG**mun34C**mGfAmAmGmUmGmCfAmCmAfCmGmGpsmUpsmC (SEQ ID NO: 36) | 6 | B |
| ds-siNA-018 | mCpsmCpsmGmUfGmUfGfCfAmCmUmUmCmGmCmUmUmCmA (SEQ ID NO: 37)<br>mUpsfGpsmAmAfGmC**mun34G**fAmAmGmUmGmCfAmCmAfCmGmGpsmUpsmC (SEQ ID NO: 38) | 7 | A |
| ds-siNA-019 | mCpsmCpsmGmUfGmUfGfCfAmCmUmUmCmGmCmUmUmCmA-**p-ps2-GalNAc4** (SEQ ID NO: 39) | 7 | A |

TABLE 8-continued

| siNA Comprising Modified Unlocked Nucleotides | | | |
|---|---|---|---|
| Name | SS/AS (5' to 3') | Position of mod. | $EC_{50}$ |
| | **d2vd3U**psfGpsmAmAfGmC**mun34G**fAmAmGmUmGmCfAmCmAfCmGmGpsmUpsmC (SEQ ID NO: 40) | | |
| ds-siNA-034 | mCpsmCps**mun34**GmUfGmUfGfCfAmCmUmUmCmGmCmUmUmCmA (SEQ ID NO: 93) psmUpsfGmAmAfGmCmGfAmAmGmUmGmCfAmCmAfCmGpsmGpsmUmC (SEQ ID NO: 94) | 3 | A |
| ds-siNA-035 | mCpsmCpsmG**mun34U**fGmUfGfCfAmCmUmUmCmGmCmUmUmCmA (SEQ ID NO: 95) psmUpsfGmAmAfGmCmGfAmAmGmUmGmCfAmCmAfCmGpsmGpsmUmC (SEQ ID NO: 94) | 4 | A |
| ds-siNA-036 | mCpsmCpsmGmUfG**mun34U**fGfCfAmCmUmUmCmGmCmUmUmCmA (SEQ ID NO: 96) psmUpsfGmAmAfGmCmGfAmAmGmUmGmCfAmCmAfCmGpsmGpsmUmC (SEQ ID NO: 94) | 6 | A |
| ds-siNA-037 | mCpsmCpsmGmUfGmUfGfCfA**mun34C**mUmUmCmGmCmUmUmCmA (SEQ ID NO: 97) psmUpsfGmAmAfGmCmGfAmAmGmUmGmCfAmCmAfCmGpsmGpsmUmC (SEQ ID NO: 94) | 10 | B |
| ds-siNA-038 | mCpsmCpsmGmUfGmUfGfCfAmC**mun34U**mUmCmGmCmUmUmCmA (SEQ ID NO: 98) psmUpsfGmAmAfGmCmGfAmAmGmUmGmCfAmCmAfCmGpsmGpsmUmC (SEQ ID NO: 94) | 11 | A |
| ds-siNA-039 | mCpsmCpsmGmUfGmUfGfCfAmCmU**mun34U**mCmGmCmUmUmCmA (SEQ ID NO: 99) psmUpsfGmAmAfGmCmGfAmAmGmUmGmCfAmCmAfCmGpsmGpsmUmC (SEQ ID NO: 94) | 12 | A |
| ds-siNA-040 | mCpsmCpsmGmUfGmUfGfCfAmCmUmU**mun34C**mGmCmUmUmCmA (SEQ ID NO: 100) psmUpsfGmAmAfGmCmGfAmAmGmUmGmCfAmCmAfCmGpsmGpsmUmC (SEQ ID NO: 94) | 13 | A |
| ds-siNA-041 | mCpsmCpsmGmUfGmUfGfCfAmCmUmUmC**mun34G**mCmUmUmCmA (SEQ ID NO: 101) psmUpsfGmAmAfGmCmGfAmAmGmUmGmCfAmCmAfCmGpsmGpsmUmC (SEQ ID NO: 94) | 14 | A |
| ds-siNA-042 | mCpsmCpsmGmUfGmUfGfCfAmCmUmUmCmG**mun34C**mUmUmCmA (SEQ ID NO: 102) psmUpsfGmAmAfGmCmGfAmAmGmUmGmCfAmCmAfCmGpsmGpsmUmC (SEQ ID NO: 94) | 15 | A |
| ds-siNA-043 | mCpsmCpsmGmUfGmUfGfCfAmCmUmUmCmGmC**mun34U**mUmCmA (SEQ ID NO: 103) psmUpsfGmAmAfGmCmGfAmAmGmUmGmCfAmCmAfCmGpsmGpsmUmC (SEQ ID NO: 94) | 16 | A |
| ds-siNA-044 | mCpsmCpsmGmUfGmUfGfCfAmCmUmUmCmGmCmU**mun34U**mCmA (SEQ ID NO: 104) psmUpsfGmAmAfGmCmGfAmAmGmUmGmCfAmCmAfCmGpsmGpsmUmC (SEQ ID NO: 94) | 17 | A |
| ds-siNA-045 | mCpsmCpsmGmUfGmUfGfCfAmCmUmUmCmGmCmUmU**mun34C**mA (SEQ ID NO: 105) psmUpsfGmAmAfGmCmGfAmAmGmUmGmCfAmCmAfCmGpsmGpsmUmC (SEQ ID NO: 94) | 18 | A |

For EC50,
A = EC50 ≤ 0.1 nM;
B = 0.1 nM < EC50 ≤ 1 nM;
C = 1 nM < ECso < 10;
D = $EC_{50}$ ≥ 10 nM.
mX = 2'--methyl nucleotide;
fX = 2'-fluoro nucleotide;
5dcd3X = nucleotide of Formula 17;
5dfX = nucleotide of Formula 16;
vX= 5' vinyl phosphonate nucleotide;
d2vX = deuterated 5' vinyl phosphonate nucleotide;
vmX = 5' vinyl phosphonate, 2'-O-methyl nucleotide;
d2vd3U = 6;

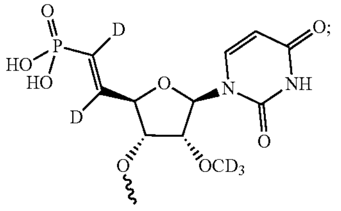

TABLE 8-continued

| siNA Comprising Modified Unlocked Nucleotides | | | |
|---|---|---|---|
| Name | SS/AS (5' to 3') | Position of mod. | $EC_{50}$ |

mun34C = 3;

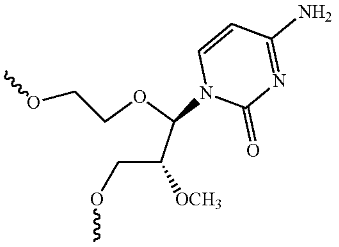

mun34G =

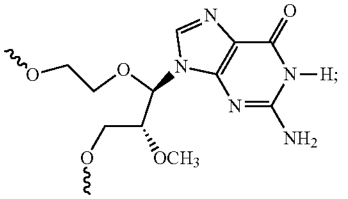

unC =

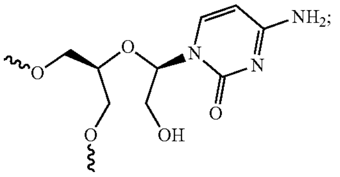

unG =

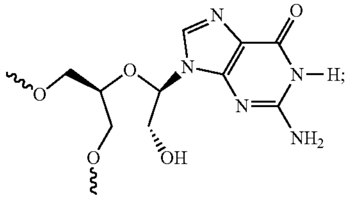

ps = phosphorothioate linkage;
X is a nucleobase (e.g. A, G, C, U or T)

TABLE 9

| siNA Comprising Mesyl Phosphoroamidate Internucleoside Linkages | | |
|---|---|---|
| Name | SS/AS (5' to 3') | $EC_{50}$ |
| ds-siNA-020 | 5'-mGpsmUpsmGmGfUmGfGfAfCmUmUmCmUmCmUmCmAmAmU-**p-(ps)2-GalNAc4** (SEQ ID NO: 69) 3'-mApsmGpsmCmAmCfCmAfCmCmUmGmAmAmGmAfGmAmGmU**yp**fU**yp**m A-5' (SEQ ID NO: 70) | A |
| ds-siNA-021 | 5'-mGpsmUpsmGmGfUmGfGfAfCmUmUmCmUmCmUmCmAmAmU-**p-(ps)2-GalNAc4** (SEQ ID NO: 71) 3'-m**Ayp**m**Gyp**mCmAmCfCmAfCmCmUmGmAmAmGmAfGmAmGmUpsfUpsm A-5' (SEQ ID NO: 72) | C |
| ds-siNA-O22 | 5'-mGpsmUpsmGmGfUmGfGfAfCmUmUmCmUmCmUmCmAmAmU-**p-(ps)2-GalNAc4** (SEQ ID NO: 73) 3'-m**Ayp**m**Gyp**mCmAmCfCmAfCmCmUmGmAmAmGmAfGmAmGmU**yp**fU**yp**mA-5' (SEQ ID NO: 74) | C |

TABLE 9-continued siNA Comprising Mesyl Phosphoroamidate Internucleoside Linkages

| Name | SS/AS (5' to 3') | $EC_{50}$ |
|---|---|---|
| CONTROL 8 | 5'-mGpsmUpsmGmGfUmGfGfAfCmUmUmCmUmCmUmCmAmAmU-**p-(ps)2-GalNAc4**<br>(SEQ ID NO: 75)<br>3'-mApsmGpsmCmAmCfCmAfCmCmUmGmAmAmGmAfGmAmGmUpsfUpsm A-5'<br>(SEQ ID NO: 76) | A |

For $EC_{50}$,
A = EC50 ≤ 0.1 nM;
B = 0.1 nM < $EC_{50}$ ≤ 1 nM;
C = 1 nM < $EC_{50}$ < 10;
D = $EC_{50}$ ≥ 10 nM.
mX = 2'-O-methyl nucleotide;
fX = 2'-fluoro nucleotide;
ps = phosphorothioate linkage;
X is a nucleobase (e.g. A, G, C, U or T);
yp =

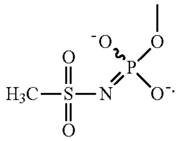

TABLE 10 siNA Comprising Modified apU Nucleotides

| Name | SS/AS (5' to 3') | $EC_{50}$ | $CC_{50}$ |
|---|---|---|---|
| ds-siNA-026 | mCpsmCpsmG**aU**fGmUfGfCfAmCmUmUmCmGmCmUmUmCmA-**p-(ps)2-GalNAc4**<br>(SEQ ID NO: 77)<br>**d2vd3U**psfGpsmAmAfGmCmGfAmAmGmUmGmCfAmCmAfCmGmGpsmUpsmC<br>(SEQ ID NO: 78) | A | >1 |
| ds-siNA-027 | mCpsmCpsmGmUfG**aU**fGfCfAmCmUmUmCmGmCmUmUmCmA-**p-(ps)2-GalNAc4**<br>(SEQ ID NO: 79)<br>**d2vd3U**psfGpsmAmAfGmCmGfAmAmGmUmGmCfAmCmAfCmGmGpsmUpsmC<br>(SEQ ID NO: 80) | A | >1 |
| ds-siNA-028 | mCpsmCpsmGmUfGmUfGfCfAmCmU**aU**mCmGmCmUmUmCmA-**p-(ps)2-GalNAc4**<br>(SEQ ID NO: 81)<br>**d2vd3U**psfGpsmAmAfGmCmGfAmAmGmUmGmCfAmCmAfCmGmGpsmUpsmC<br>(SEQ ID NO: 82) | A | >1 |
| ds-siNA-o29 | mCpsmCpsmGmUfGmUfGfCfAmCmUmUmCmGmC**aU**mUmCmA-**p-(ps)2-GalNAc4**<br>(SEQ ID NO: 83)<br>**d2vd3U**psfGpsmAmAfGmCmGfAmAmGmUmGmCfAmCmAfCmGmGpsmUpsmC<br>(SEQ ID NO: 84) | A | >1 |
| ds-siNA-030 | mCpsmCpsmGmUfGmUfGfCfAmCmUmUmCmGmCmU**aU**mCmA-**p-(ps)2-GalNAc4**<br>(SEQ ID NO: 85)<br>**d2vd3U**psfGpsmAmAfGmCmGfAmAmGmUmGmCfAmCmAfCmGmGpsmUpsmC<br>(SEQ ID NO: 86) | A | >1 |
| ds-siNA-031 | mCpsmCpsmGmUfGmUfGfCfAmCmUmUmCmGmCmUmUmCmA-**p-(ps)2-GalNAc4**<br>(SEQ ID NO: 87)<br>**d2vd3U**psfGpsmAmAfGmCmGfAmAmG**aU**mGmCfAmCmAfCmGmGpsmUpsmC<br>(SEQ ID NO: 88) | A | >1 |
| ds-siNA-032 | mCpsmCpsmGmUfGmUfGfCfAmCmUmUmCmGmCmUmUmCmA-**p-(ps)2-GalNAc4**<br>(SEQ ID NO: 89)<br>**d2vd3U**psfGpsmAmAfGmCmGfAmAmGmUmGmCfAmCmAfCmGmGps**aU**psmC<br>(SEQ ID NO: 90) | A | >1 |
| ds-siNA-033 | mCpsmCpsmGmUfGmUfGfCfAmCmUmUmCmGmCmUmUmCmA-p-(ps)2-GalNAc4<br>(SEQ ID NO: 91)<br>**aU**psfGpsmAmAfGmCmGfAmAmGmUmGmCfAmCmAfCmGmGpsmUpsmC<br>(SEQ ID NO: 92) | A | >1 |

For $EC_{50}$,
A = $EC_{50}$ ≤ 0.1 nM;
B = 0.1 nM < $EC_{50}$ ≤ 1 nM;
C = 1 nM < $EC_{50}$ < 10;
D = $EC_{50}$ ≥ 10 nM.
mX = 2'-methyl nucleotide;
fX = 2'-fluoro nucleotide;
5dcd3X = nucleotide of Formula 17;
5dfX = nucleotide of Formula 16;
vX = 5' vinyl phosphonate nucleotide;

TABLE 10-continued

| siNA Comprising Modified apU Nucleotides | | |
|---|---|---|
| Name | SS/AS (5' to 3') | $EC_{50}$ $CC_{50}$ |

d2vX = deuterated 5'
vinyl phosphonate nucleotide;
vmX = 5' vinyl phosphonate, 2'-O-methyl nucleotide;
d2vd3U =

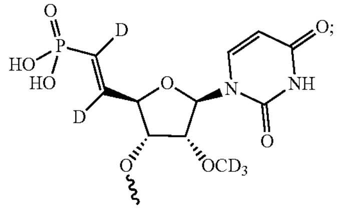

aU =

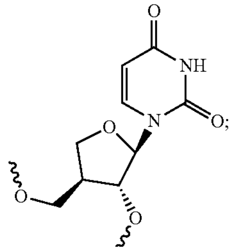

ps = phosphorothioate linkage;
X is a nucleobase (e.g. A, G, C, U or T)

In Vivo Assay:

AAV/HBV is a recombinant AAV carrying replicable HBV genome. Taking advantage of the highly hepatotropic feature of genotype 8 AAV, the HBV genome can be efficiently delivered to the mouse liver cells. Infection of immune competent mouse with AAV/HBV can result in long term HBV viremia, which mimics chronic HBV infection in patients. The AAV/HBV model can be used to evaluate the in vivo activity of various types of anti-HBV agents. Mice were infected with AAV-HBV on day−28 of the study. The test articles or negative control (PBS) were dosed subcutaneously (unless specified otherwise) as single dose on days 0 at 5 mg/kg. Serial blood collections were usually taken every 5 days on day 0, 5, 10 and 15 etc. until the termination of studies. Serum HBV S antigen (HBsAg) was assayed through ELISA.

Figure 4:
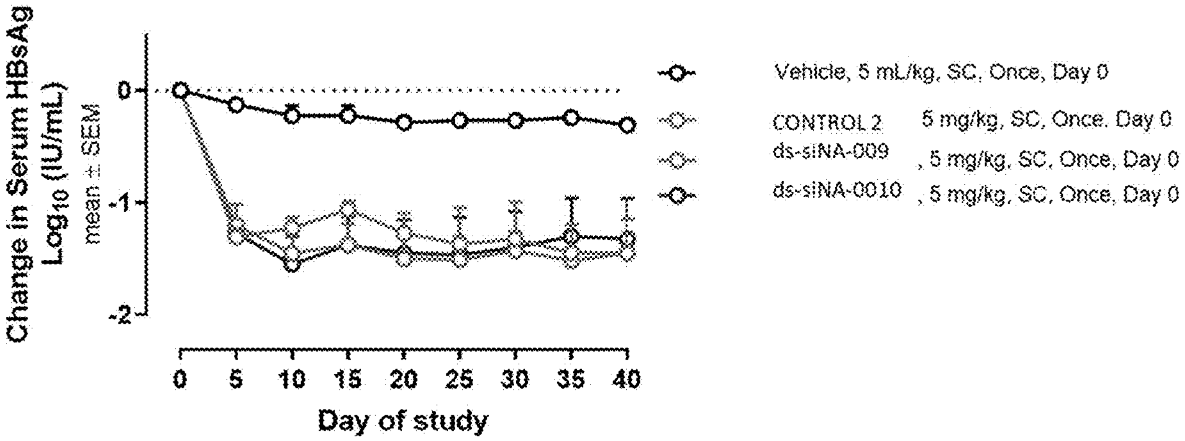
FIG. 4 shows a graph of the change in serum HBsAg from AAV-HBV mice treated with vehicle (G01), CONTROL 2, ds-siNA-009, or ds-siNA-010.

Table 11 shows the siNA that were assessed to determine the impact of some of the exemplary nucleotide phosphate mimics. The results of this assessment are shown in FIG. 4, which provides a graph of the change in serum HBsAg from AAV-HBV mice treated with vehicle (G01), CONTROL 2, ds-siNA-009, or ds-siNA-010.

TABLE 11

| Name | SS/AS 5' to 3' |
|---|---|
| CONTROL 2 | mCpsmCpsmGmUfGmUfGfCfAmCmUmUmCmGmCmUmUm CmAp-**ps2-GalNAc4** (SEQ ID NO: 43) |
| | mUpsfGpsmAmAfGmCmGfAmAmGmUmGmCfAmCmAfCm GmGpsmUpsmC (SEQ ID NO: 44) |
| ds-siNA-009 | mCpsmCpsmGmUfGmUfGfCfAmCmUmUmCmGmCmUmUm CmAp-**ps2-GalNAc4** (SEQ ID NO: 17) |

TABLE 11-continued

| Name | SS/AS 5' to 3' |
|---|---|
| | **omeco-d3U**psfGpsmAmAfGmCmGfAmAmGmUmGmCfAmCmAf CmGmGpsmUpsmC (SEQ ID NO: 18) |
| ds-siNA-010 | mCpsmCpsmGmUfGmUfGfCfAmCmUmUmCmGmCmUmUm CmAp-**ps2-GalNAc4** (SEQ ID NO: 19) |
| | **4hU**psfGpsmAmAfGmCmGfAmAmGmUmGmCfAmCmAf CmGmGpsmUpsmC (SEQ ID NO: 20) |

Figure 5A:
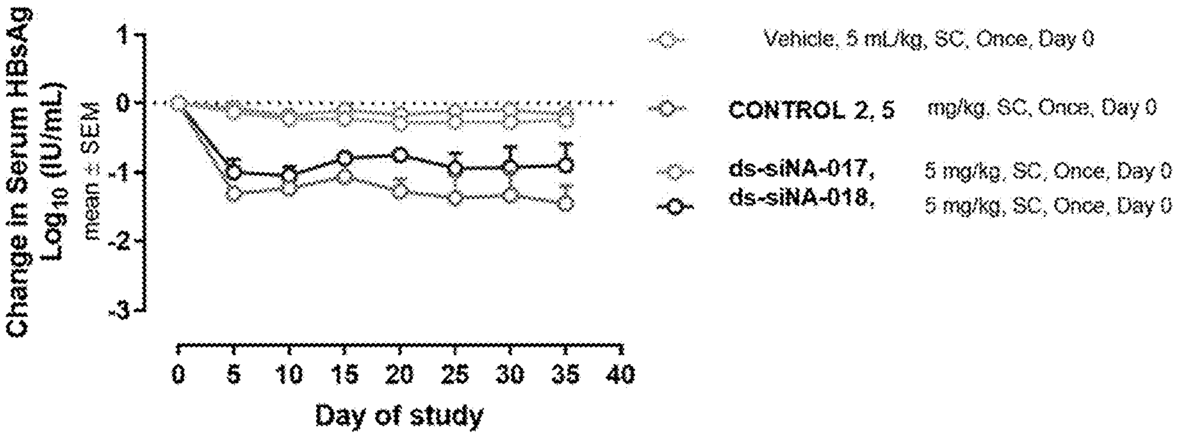
FIG. 5A shows a graph of the change in serum HBsAg from AAV-HBV mice treated with vehicle (G01), CONTROL 2, ds-siNA-017 (with the addition of a GalNAc), or ds-siNA-018 (with the addition of a GalNAc).

Table 12 shows the siNA that were assessed to determine the impact of some of the exemplary nucleotide phosphate mimics. The results of this assessment are shown in FIG. 5A, which provides a graph of the change in serum HBsAg from AAV-HBV mice treated with vehicle (G011), CONTROL 2, ds-siNA-017 (with the addition of a GalNAc), or ds-siNA-018 (with the addition of a GalNAc).

TABLE 12

| Name | SS/AS 5' to 3' |
|---|---|
| ds-siNA-0017 | mCpsmCpsmGmUfGmUfGfCfAmCmUmUmCmGmCmUmUm CmA-**p-ps2-GalNac4** (SEQ ID NO: 35) |
| | mUpsfGpsmAmAf**Gmun34**CmGfAmAmGmUmGmCfAmCm AfCmGmGpsmUpsmC (SEQ ID NO: 36) |

TABLE 12-continued

| Name | SS/AS 5' to 3' |
|---|---|
| ds-siNA-0018 | mCpsmCpsmGmUfGmUfGfCfAmCmUmUmCmGmCmUmUmCmA-**p-ps2-GalNac4** (SEQ ID NO: 37) |
| | mUpsfGpsmAmAfGmC**mun34G**fAmAmGmUmGmCfAmCmAfCmGmGpsmUpsmC (SEQ ID NO: 38) |
| CONTROL 2 | mCpsmCpsmGmUfGmUfGfCfAmCmUmUmCmGmCmUmUmCmAp-**ps2-GalNAc4** (SEQ ID NO: 43) |
| | mUpsfGpsmAmAfGmCmGfAmAmGmUmGmCfAmCmAfCmGmGpsmUpsmC (SEQ ID NO: 44) |

Figure 5B:
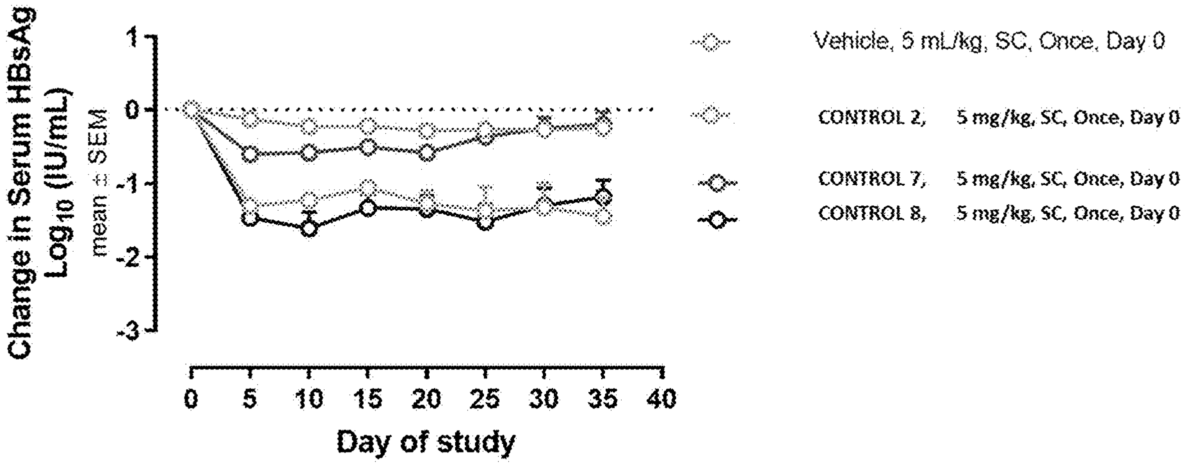
FIG. 5B shows a graph of the change in serum HBsAg from AAV-HBV mice treated with vehicle (G01), CONTROL 2, CONTROL 7, or CONTROL 8.

Table 13 shows siAN comprising traditional UNA that were also assessed. These siNA can be considered controls of the novel 3',4' seco modified nucleotides disclosed herein. FIG. 5B provides a graph of the change in serum HBsAg from AAV-HBV mice treated with vehicle (G01), CONTROL 2, CONTROL 7, or CONTROL 8.

TABLE 13

| Name | SS/AS |
|---|---|
| CONTROL 7 | mCpsmCpsmGmUfGmUfGfCfAmCmUmUmCmGmCmUmUmCmA-**p-ps2-GalNAc4** (SEQ ID NO: 51) |
| | mUpsfGpsmAmAf**GunC**mGfAmAmGmUmGmCfAmCmAfCmGmGpsmUpsmC (SEQ ID NO: 52) |
| CONTROL 8 | mCpsmCpsmGmUfGmUfGfCfAmCmUmUmCmGmCmUmUmCmA-**p-ps2-GalNac4** (SEQ ID NO: 53) |
| | mUpsfGpsmAmAfGmC**unG**fAmAmGmUmGmCfAmCmAfCmGmGpsmUpsmC (SEQ ID NO: 54) |

Figure 6:
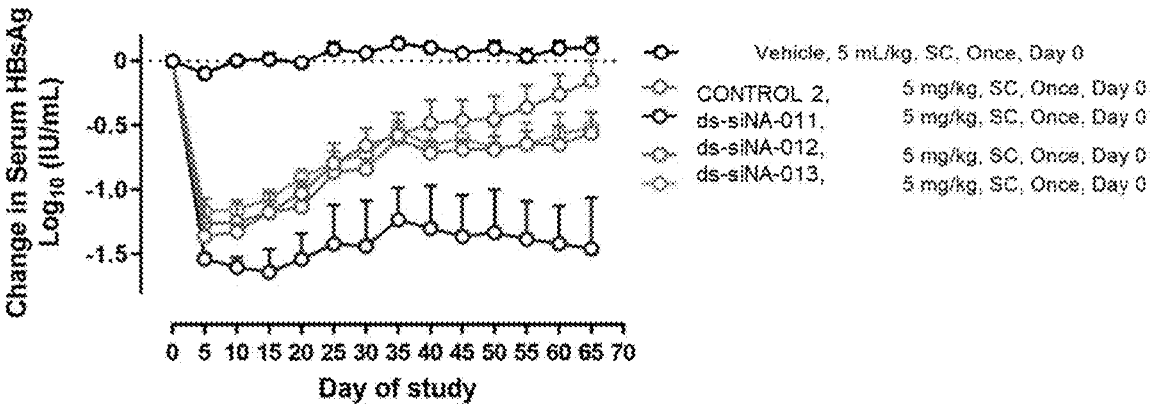
FIG. 6 shows a graph of the change in serum HBsAg from AAV-HBV mice treated with vehicle (G01), CONTROL 2, ds-siNA-011, ds-siNA-012, or ds-siNA-013.

Table 14 shows the siNA that were assessed to determine the impact of some of the exemplary nucleotide phosphate mimics. The results of this assessment are shown in FIG. 6, which provides a graph of the change in serum HBsAg from AAV-HBV mice treated with vehicle (G01), CONTROL 2, ds-siNA-011, ds-siNA-012, or ds-siNA-013.

TABLE 14

| Name | SS/AS 5' to 3' |
|---|---|
| CONTROL 2 | mCpsmCpsmGmUfGmUfGfCfAmCmUmUmCmGmCmUmUmCmAp-**ps2-GalNAc4** (SEQ ID NO: 43) |
| | mUpsfGpsmAmAfGmCmGfAmAmGmUmGmCfAmCmAfCmGmGpsmUpsmC (SEQ ID NO: 44) |
| ds-siNA-011 | mCpsmCpsmGmUfGmUfGfCfAmCmUmUmCmGmCmUmUmCmAp-**ps2-GalNAc4** (SEQ ID NO: 21) |
| | **d2vd3**UpsfGpsmAmAfGmCmGfAmAmGmUmGmCfAmCmAfCmGmGpsmUpsmC (SEQ ID NO: 22) |

TABLE 14-continued

| Name | SS/AS 5' to 3' |
|---|---|
| ds-siNA-012 | mCpsmCpsmGmUfGmUfGfCfAmCmUmUmCmGmCmUmUmCmA-**p-ps2-GalNAc4** (SEQ ID NO: 23) |
| | **v-munU**psfGpsmAmAfGmCmGfAmAmGmUmGmCfAmCmAfCmGmGpsmUpsmC (SEQ ID NO: 24) |
| ds-siNA-013 | mCpsmCpsmGmUfGmUfGfCfAmCmUmUmCmGmCmUmUmCmA-**p-ps2-GalNAc4** (SEQ ID NO: 25) |
| | **c2o-4hU**psfGpsmAmAfGmCmGfAmAmGmUmGmCfAmCmAfCmGmGpsmUpsmC (SEQ ID NO: 26) |

Figure 7:
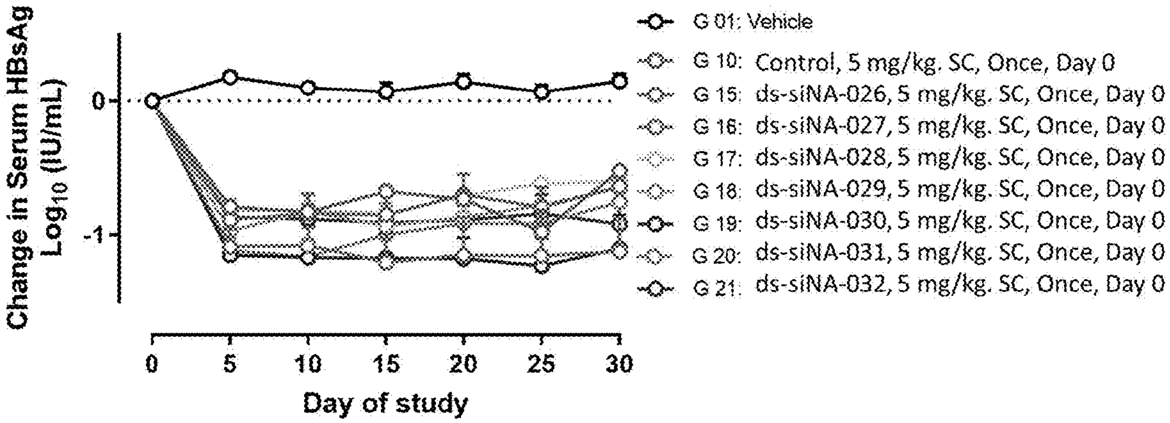
FIG. 7 shows shows a graph of the change in serum HBsAg from AAV-HBV mice treated with vehicle (G01), CONTROL 2, ds-siNA-026, ds-siNA-027, ds-siNA-028, ds-siNA-029, ds-siNA-030, ds-siNA-031, or ds-siNA-032.

Table 15 shows the siNA that were assessed to determine the impact of incorporation of an apU nucleotide. The results of this assessment are shown in FIG. 7, which provides a graph of the change in serum HBsAg from AAV-HBV mice treated with vehicle (G01), CONTROL 2, ds-siNA-026, ds-siNA-027, ds-siNA-028, ds-siNA-029, ds-siNA-030, ds-siNA-031, or ds-siNA-032.

TABLE 15

| Name | SS/AS 5' to 3' |
|---|---|
| CONTROL 2 | mCpsmCpsmGmUfGmUfGfCfAmCmUmUmCmGmCmUmUmCmAp-**ps2-GalNAc4** (SEQ ID NO: 43) |
| | mUpsfGpsmAmAfGmCmGfAmAmGmUmGmCfAmCmAfCmGmGpsmUpsmC (SEQ ID NO: 44) |
| ds-siNA-026 | mCpsmCpsmG**aU**fGmUfGfCfAmCmUmUmCmGmCmUmUmCmA-**p-(ps)2-GalNAc4** (SEQ ID NO: 77) |
| | **d2vd3U**psfGpsmAmAfGmCmGfAmAmGmUmGmCfAmCmAfCmGmGpsmUpsmC (SEQ ID NO: 78) |
| ds-siNA-027 | mCpsmCpsmGmUfG**aU**fGfCfAmCmUmUmCmGmCmUmUmCmA-**p-(ps)2-GalNAc4** (SEQ ID NO: 79) |
| | **d2vd3U**psfGpsmAmAfGmCmGfAmAmGmUmGmCfAmCmAfCmGmGpsmUpsmC (SEQ ID NO: 80) |
| ds-siNA-028 | mCpsmCpsmGmUfGmUfGfCfAmCmU**aU**mCmGmCmUmUmCmA-**p-(ps)2-GalNAc4** (SEQ ID NO: 81) |
| | **d2vd3U**psfGpsmAmAfGmCmGfAmAmGmUmGmCfAmCmAfCmGmGpsmUpsmC (SEQ ID NO: 82) |
| ds-siNA-029 | mCpsmCpsmGmUfGmUfGfCfAmCmUmUmCmGmC**aU**mUmCmA-**p-(ps)2-GalNAc4** (SEQ ID NO: 83) |
| | **d2vd3U**psfGpsmAmAfGmCmGfAmAmGmUmGmCfAmCmAfCmGmGpsmUpsmC (SEQ ID NO: 84) |

TABLE 15-continued

| Name | SS/AS 5' to 3' |
|---|---|
| ds-siNA-030 | mCpsmCpsmGmUfGmUfGfCfAmCmUmUmCmGmCmU**aU**m CmA-**p**-(**ps**)**2**-**GalNAc4** (SEQ ID NO: 85) |
| | **d2vd3U**psfGpsmAmAfGmCmGfAmAmGmUmGmCfAmCm AfCmGmGpsmUpsmC (SEQ ID NO: 86) |
| ds-siNA-031 | mCpsmCpsmGmUfGmUfGfCfAmCmUmUmCmGmCmUmUm CmA-**p**-(**ps**)**2**-**GalNAc4** (SEQ ID NO: 87) |
| | **d2vd3U**psfGpsmAmAfGmCmGfAmAmG**aU**mGmCfAmCm AfCmGmGpsmUpsmC (SEQ ID NO: 88) |
| ds-siNA-032 | mCpsmCpsmGmUfGmUfGfCfAmCmUmUmCmGmCmUmUm CmA-**p**-(**ps**)**2**-**GalNAc4** (SEQ ID NO: 89) |
| | **d2vd3U**psfGpsmAmAfGmCmGfAmAmGmUmGmCfAmCm AfCmGmGps**aU**psmC (SEQ ID NO: 90) |

Figure 8:
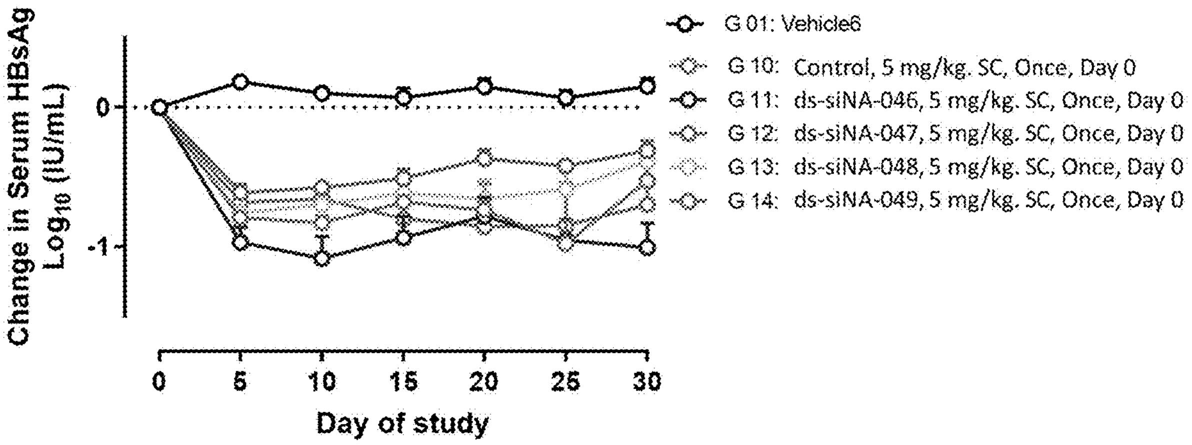
FIG. 8 shows shows a graph of the change in serum HBsAg from AAV-HBV mice treated with vehicle (G01), CONTROL 2, ds-siNA-046, ds-siNA-047, ds-siNA-048, or ds-siNA-049.

Additionally, the most active compounds from the in vitro screening of ds-siNA-034 to ds-siNA-045 were further modified to attach a GalNAc to the 3' end of the sense strand and incorporated a deuterated vinyl phosphonate into the antisense strand. The most active compounds among ds-siNA-034 to ds-siNA-045 were ds-siNA-034 (mun34 at position 3 of sense strand), ds-siNA-043 (mun34 at position 16 of sense strand), ds-siNA-044 (mun34 at position 17 of sense strand), and ds-siNA-045 (mun34 at position 18 of sense strand). The GalNAc-conjugated/deuterated versions of these compounds were assigned ds-siNA-046 to ds-siNA-049 (shown in Table 16) and FIG. 8 provides a graph of the change in serum HBsAg from AAV-HBV mice treated with vehicle (G01), CONTROL 2, ds-siNA-046, ds-siNA-047, ds-siNA-048, or ds-siNA-049.

TABLE 16

| Name | SS/AS 5' to 3' |
|---|---|
| CONTROL 2 | mCpsmCpsmGmUfGmUfGfCfAmCmUmUmCmGmCmUmUm CmAp-ps2-GalNAc4 (SEQ ID NO: 43 ) |
| | mUpsfGpsmAmAfGmCmGfAmAmGmUmGmCfAmCmAfCm GmGpsmUpsmC (SEQ ID NO: 44) |
| ds-si-NA-046 | mCpsmCps**mun34G**mUfGmUfGfCfAmCmUmUmCmGmCmUm UmCmA-p-(ps)2-GalNAc (SEQ ID NO: 106) |
| | psd2vd3UpsfGmAmAfGmCmGfAmAmGmUmGmCfAmCmAf CmGpsmGpsmUmC (SEQ ID NO: 107) |
| ds-si-NA-047 | mCpsmCpsmGmUfGmUfGfCfAmCmUmUmCmGmCmun**34Um** UmCmA-p-(ps)2-GalNAc (SEQ ID NO: 108) |
| | psd2vd3UpsfGmAmAfGmCmGfAmAmGmUmGmCfAmCmAf CmGpsmGpsmUmC (SEQ ID NO: 107) |
| ds-si-NA-048 | mCpsmCpsmGmUfGmUfGfCfAmCmUmUmCmGmCmU**mun34** **U**mCmA-p-(ps)2-GalNAc (SEQ ID NO: 109) |
| | psd2vd3UpsfGmAmAfGmCmGfAmAmGmUmGmCfAmCmAf CmGpsmGpsmUmC (SEQ ID NO: 107) |
| ds-si-NA-049 | mCpsmCpsmGmUfGmUfGfCfAmCmUmUmCmGmCmUmU**mun** **34C**mA-p-(ps)2-GalNAc (SEQ ID NO: 110) |
| | psd2vd3UpsfGmAmAfGmCmGfAmAmGmUmGmCfAmCmAf CmGpsmGpsmUmC (SEQ ID NO: 107) |

Example 22: Preparation of Compound 40-9 (GalNAc4 Amidite)

Compound 40-9 can be conjugated to any siNA disclosed herein as a targeting moiety. This compound, pictured below, can be prepared according to the following brief description.

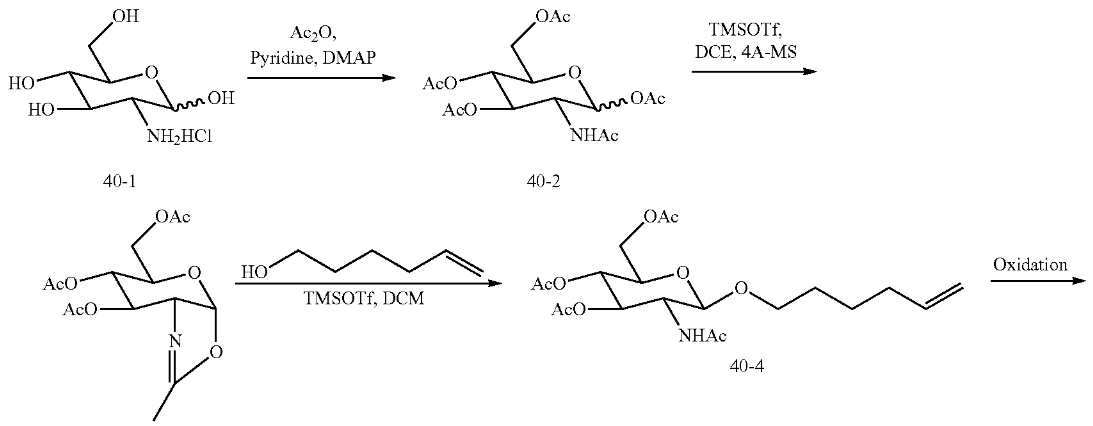

40-1 40-2 40-3 40-4

-continued

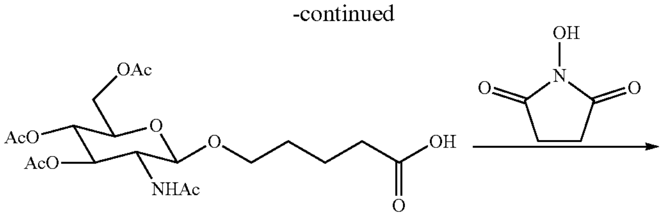

40-5

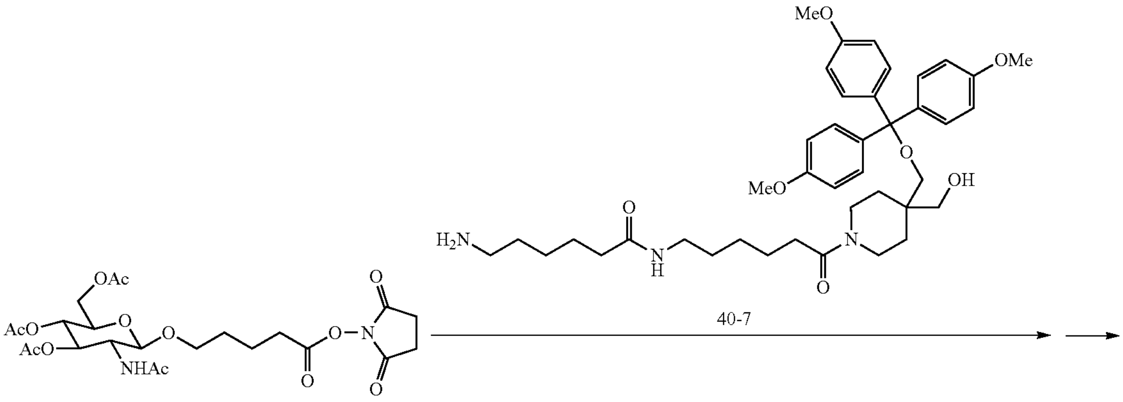

40-6

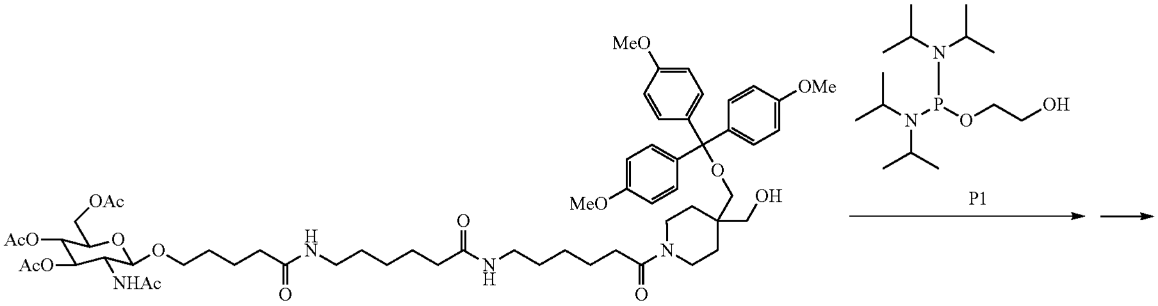

40-8

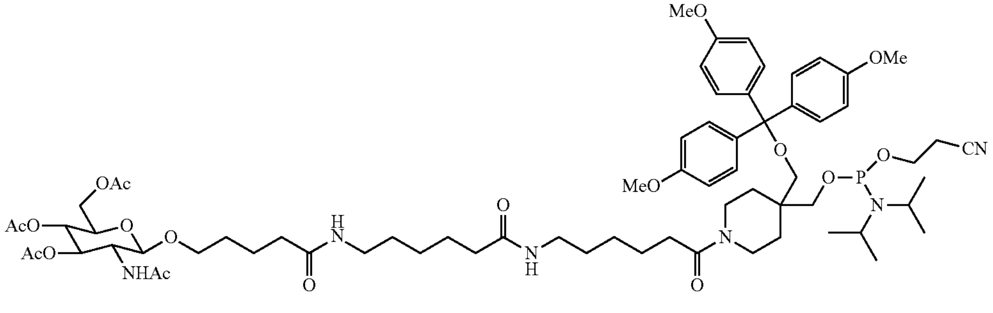

40-9

The building block compound 40-9 is useful for making embodiments of modified phosphorothioated oligonucleotides. The compound 40-9 was prepared as follows:

Preparation of compound 40-2: To a solution of commercially available glucosamine hydrochloride 40-1 (60 g, 278.25 mmol, 1 eq) in DCM (300 mL) at 0° C. was added $Ac_2O$ (323.83 g, 3.17 mol, 297.09 mL, 11.4 eq) dropwise, followed by pyridine (300 mL) and DMAP (3.40 g, 27.83 mmol, 0.1 eq). The mixture was allowed to gradually warm to 20° C. and stirred at 20° C. for 24 hours. Upon completion as monitored by LCMS, the mixture was concentrated under reduced pressure, diluted with DCM (900 mL), and extracted with $NaHCO_3$(sat., aqueous 300 mL*3). The combined organic layers were washed with brine (300 mL), dried over $Na_2SO_4$, filtered and concentrated under reduced pressure to give compound 40-2 (89.5 g, crude) as a yellow solid. $^1H$ NMR (400 MHz, $CDCl_3$) δ=6.16 (d, J=3.8 Hz, 1H), 5.62 (d, J=9.0 Hz, 1H), 5.27-5.16 (m, 2H), 4.54-4.43 (m, 1H), 4.24 (dd, J=4.0, 12.5 Hz, 1H), 4.10-3.94 (m, 2H), 2.18 (s, 3H), 2.08 (s, 3H), 2.04 (d, J=4.0 Hz, 6H), 1.93 (s, 3H; LCMS (ESI): m/z calcd. for $C_{16}H_{23}NaNO_{10}$ 412.34 $[M+Na]^+$, found 412.0).

Preparation of compound 40-3: To a solution of compound 40-2 (40 g, 102.73 mmol, 1 eq) in DCE (320 mL) at 25° C. was added dropwise TMSOTf (23.98 g, 107.87 mmol, 19.49 mL, 1.05 eq), and the mixture was stirred at 60°

C. for 4 hours. Upon completion as monitored by LCMS, the mixture was quenched by addition of TEA (60 mL) at 20° C., stirred for 15 min, diluted with DCM (500 mL), and washed with $NaHCO_3$(sat., aqueous 300 mL*2). The organic layer was washed with brine (300 mL), dried over $Na_2SO_4$, filtered, and concentrated under reduced pressure to give compound 40-3 (32.5 g, crude) as a yellow oil. $^1$H NMR (400 MHz, $CDCl_3$) δ=5.96 (d, J=7.3 Hz, 1H), 5.25 (t, J=2.4 Hz, 1H), 4.95-4.88 (m, 1H), 4.19-4.08 (m, 3H), 3.59 (m, 1H), 2.13-2.05 (m, 12H).

Preparation of compound 40-4: To a mixture of compound 40-3 (32.5 g, 98.69 mmol, 1 eq) in DCM (250 mL) was added hex-5-en-1-ol (11.86 g, 118.43 mmol, 13.96 mL, 1.2 eq) and 4 A MS (32.5 g). The mixture was stirred at 30° C. for 0.5 h, followed by dropwise addition of TMSOTf (13.16 g, 59.22 mmol, 10.70 mL, 0.6 eq). The mixture was stirred at 30° C. for 16 hours. Upon completion as monitored by LCMS, the reaction mixture was filtered, and the filtrate was diluted with DCM (300 mL) and washed with $NaHCO_3$(sat., aqueous 150 mL*2). The organic layer was washed with brine (150 mL), dried over $Na_2SO_4$, filtered and concentrated under reduced pressure. The residue was purified by flash silica gel chromatography (ISCO®; 220 g SepaFlash® Silica Flash Column, Eluent of 0~70% PE/EA gradient at 100 mL/min) to give compound 40-4 (12.3 g, 28.64 mmol, 29.02% yield) as a white solid. $^1$H NMR (400 MHz, $CDCl_3$) δ=5.78 (m, 1H), 5.45 (d, J=8.8 Hz, 1H), 5.31 (dd, J=9.4, 10.7 Hz, 1H), 5.06 (t, J=9.5 Hz, 1H), 5.02-4.92 (m, 2H), 4.68 (d, J=8.3 Hz, 1H), 4.30-4.23 (m, 1H), 4.16-4.10 (m, 1H), 3.91-3.76 (m, 2H), 3.73-3.66 (m, 1H), 3.48 (td, J=6.7, 9.5 Hz, 1H), 2.09-2.01 (m, 11H), 1.94 (s, 3H), 1.60-1.36 (m, 4H); LCMS (ESI): m/z calcd. for $C_{20}H_{32}NO_9$, 430.47 $[M+H]^+$, found 430.1.

Preparation of compound 40-5: To a solution of compound 40-4 (12.3 g, 28.64 mmol, 1 eq) in a mixed solvent of DCM (60 mL) and MeCN (60 mL) was added $NaIO_4$ (2.5 M, 57.28 mL, 5 eq), and the mixture was stirred at 20° C. for 0.5 hours. $RuCl_3$ (123.00 mg, 592.97 umol, 0.02 eq) was added, and the mixture was stirred at 20° C. for 2 hours. Upon completion as monitored by LCMS, saturated aqueous $NaHCO_3$ was added to the mixture to adjust pH>7. The mixture was diluted with DCM (300 mL) and subjected to extraction. The aqueous layer was adjusted to pH<7 by citric acid, and the aqueous layer was extracted with DCM (300 mL*3). The combined organic layers were washed with brine (300 mL), dried over $Na_2SO_4$, filtered, and concentrated under reduced pressure to give compound 40-5 (8.9 g, 69.31% yield, as a brown solid. $^1$H NMR (400 MHz, $CDCl_3$) δ=6.14 (d, J=8.8 Hz, 1H), 5.34-5.20 (m, 1H), 5.08-5.01 (m, 1H), 4.67 (d, J=8.3 Hz, 1H), 4.24 (dd, J=4.8, 12.3 Hz, 1H), 4.17-4.05 (m, 1H), 3.90-3.83 (m, 2H), 3.75-3.62 (m, 2H), 3.50 (d, J=5.9, 9.9 Hz, 1H), 2.44-2.27 (m, 2H), 2.09-1.93 (m, 12H), 1.75-1.53 (m, 4H); LCMS (ESI): m/z calcd. for $C_{19}H_{30}NO_{11}$, 448.44 $[M+H]^+$, found 448.1.

Preparation of compound 40-6: To a solution of compound 40-5 (10 g, 22.35 mmol, 1 eq) and 1-hydroxypyrrolidine-2,5-dione (2.83 g, 24.58 mmol, 1.1 eq) in DCM (100 mL) was added EDCI HCl (5.57 g, 29.05 mmol, 1.3 eq), and the mixture was stirred at 20° C. for 2 hour. Upon completion as monitored by LCMS, the reaction mixture was diluted with DCM (200 mL) and washed with $H_2O$ (100 mL). The organic layer was washed with $NaHCO_3$(sat. aqueous) (100 mL*2) and brine (100 mL), dried over $Na_2SO_4$, filtered, and concentrated under reduced pressure to give compound 40-6 (10.1 g, 82.66%) as a white solid. $^1$H NMR (400 MHz, $CDCl_3$) δ=5.85 (d, J=8.8 Hz, 1H), 5.31-5.26 (m, 1H), 5.06 (t, J=9.7 Hz, 1H), 4.69 (d, J=8.3 Hz, 1H), 4.25 (dd, J=4.7, 12.2 Hz, 1H), 4.12 (dd, J=2.3, 12.2 Hz, 1H), 3.94-3.79 (m, 2H), 3.75-3.65 (m, 1H), 3.63-3.53 (m, 1H), 2.87 (br d, J=4.3 Hz, 4H), 2.76-2.56 (m, 2H), 2.08 (s, 3H), 2.02 (d, J=1.8 Hz, 6H), 1.92 (s, 3H), 1.86-1.66 (m, 4H); LCMS (ESI): m/z calcd. for $C_{23}H_{33}N_2O_{13}$, 545.51 $[M+H]^+$, found 545.1.

Preparation of compound 40-8: To a solution of compound 40-7 (40-7 prepared by following the general procedure described in WO 2018013999 A1) (9.8 g, 13.92 mmol, 1 eq) in DCM (100 mL) was added DIEA (3.60 g, 27.84 mmol, 4.85 mL, 2 eq), followed by addition of (2,5-dioxopyrrolidin-1-yl) 5-[3-acetamido-4,5-diacetoxy-6-(acetoxymethyl)tetrahydropyran-2-yl]oxypentanoate (compound 40-6) (9.86 g, 18.10 mmol, 1.3 eq), and the mixture was stirred at 20° C. for 2 hours. Upon completion as monitored by LCMS, the reaction mixture was diluted with water (100 mL), and then extracted with DCM (100 mL*2). The combined organic layers were washed brine (100 mL), dried over anhydrous $Na_2SO_4$, filtered and the filtrate was concentrated under reduced pressure to give a residue. The residue was purified by flash silica gel chromatography (ISCO®; 120 g SepaFlash® Silica Flash Column, Eluent of 0~6% MeOH/DCM gradient at 80 mL/min) to give compound 40-8 (13.1 g, 80.95% yield) as a white solid. $^1$H NMR (400 MHz, DMSO-$d_6$) δ=8.06 (d, J=9.3 Hz, 1H), 7.81 (q, J=5.4 Hz, 2H), 7.21 (d, J=8.8 Hz, 6H), 6.84 (d, J=9.0 Hz, 6H), 5.04 (t, J=10.0 Hz, 1H), 4.78 (t, J=9.7 Hz, 1H), 4.55 (d, J=8.5 Hz, 1H), 4.17 (dd, J=4.5, 12.3 Hz, 1H), 3.97 (d, J=10.0 Hz, 1H), 3.77 (dd, J=2.6, 9.9 Hz, 1H), 3.72-3.64 (m, 11H), 3.46-3.25 (m, 5H), 3.05-2.84 (m, 8H), 2.18 (t, J=7.2 Hz, 2H), 2.05-1.95 (m, 7H), 1.93 (s, 3H), 1.88 (s, 3H), 1.74 (s, 3H), 1.47-1.13 (m, 20H); LCMS (ESI): RT=2.017 min, m/z calcd. for $C_{60}H_{84}NaN_4O_{17}$, 1156.32$[M+Na]^+$, 1155.5.

Preparation of compound 40-9: To a mixture of compound 40-8 (5 g, 4.41 mmol, 1 eq) and 4 A MS (5 g) in DCM (50 mL) was added 3-bis(diisopropylamino)phosphanyloxypropanenitrile (1.73 g, 5.74 mmol, 1.82 mL, 1.3 eq) at −10° C., followed by addition of 1H-imidazole-4,5-dicarbonitrile (573.12 mg, 4.85 mmol, 1.1 eq), and the mixture was stirred at 0° C. for 2 hours. Upon completion as monitored by LCMS, the reaction mixture was diluted with DCM (100 mL), washed with $NaHCO_3$(sat., aqueous, 50 mL*2), dried over $Na_2SO_4$, and concentrated under reduced pressure to give a pale yellow foam. The residue was purified by flash silica gel chromatography (ISCO®; 40 g SepaFlash® Silica Flash Column, 0% to 10% i-PrOH in DCM contain 2% TEA) to give compound 40-9 (3.35 g, 56.60% yield) as a white solid. $^1$H NMR (400 MHz, $CD_3CN$) δ=7.35-7.25 (m, 6H), 6.88-6.82 (m, 6H), 6.79 (d, J=9.3 Hz, 1H), 6.63-6.46 (m, 2H), 5.17-5.08 (m, 1H), 4.93 (t, J=9.7 Hz, 1H), 4.59 (d, J=8.6 Hz, 1H), 4.22 (dd, J=4.9, 12.2 Hz, 1H), 4.04 (dd, J=2.4, 12.2 Hz, 1H), 3.85-3.32 (m, 22H), 3.15-3.00 (m, 8H), 2.59 (t, J=5.8 Hz, 2H), 2.23 (br t, J=6.6 Hz, 3H), 2.12-2.04 (m, 4H), 2.00 (s, 3H), 1.96 (s, 3H), 1.93 (s, 3H), 1.82 (s, 3H), 1.66-1.45 (m, 12H), 1.42-1.21 (m, 6H), 1.19-1.07 (m, 12H); LCMS (ESI) m/z calcd. for $C_{69}H_{101}NaN_6O_{18}P$ 1355.68 $[M+Na]^+$, found 1355.7; $^{31}$P NMR ($CD_3CN$) δ=147.00.

Example 23: Preparation of GalNAc4 CPG

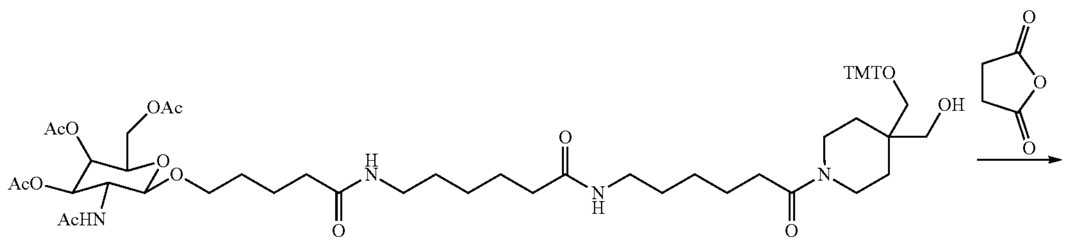

1

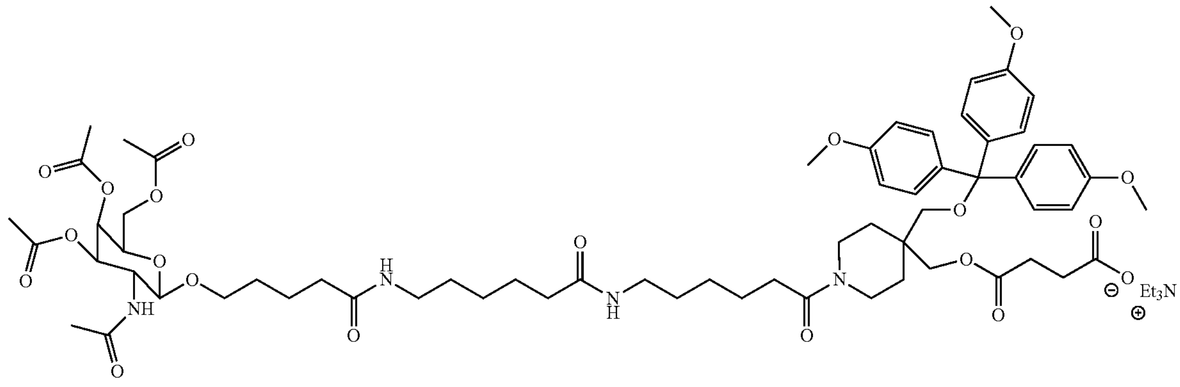

AGS-6-5

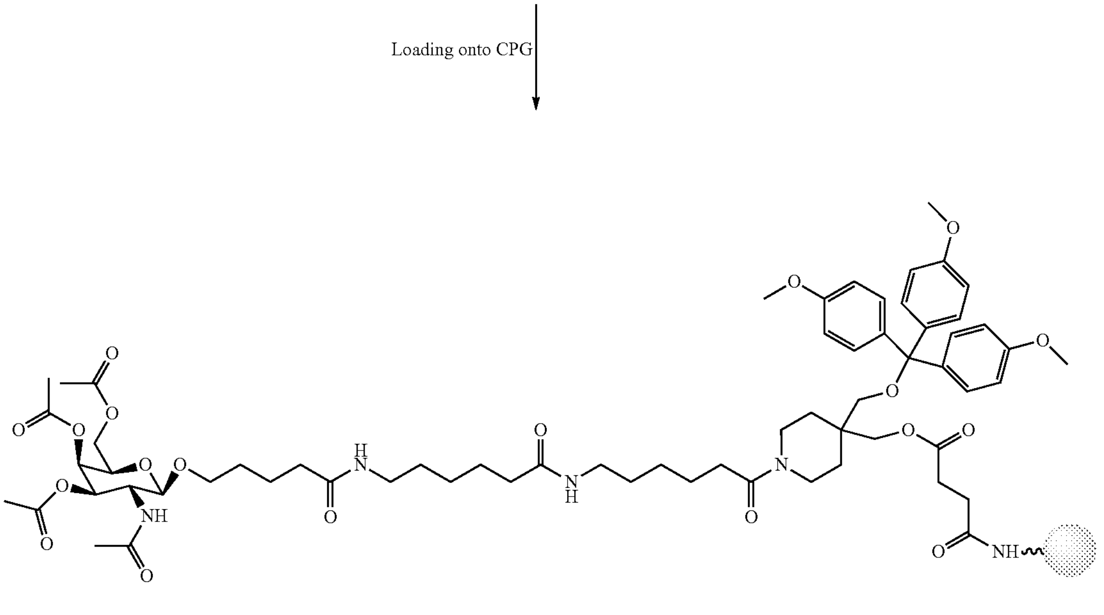

To a solution of 40-8 (21 g, 18.53 mmol, 1 eq) and succinic anhydride (9.27 g, 92.65 mmol, 5 eq) in DCM (160 mL) were added TEA (18.75 g, 185.30 mmol, 25.79 mL, 10 eq) and DMAP (2.26 g, 18.53 mmol, 1 eq) at 15° C. The mixture was stirred at 15° C. for 16 h. TLC (DCM: MeOH=10: 1) showed the reaction was complete. The reaction mixture was diluted with water (200 mL), and then extracted with DCM (300 mL*2). The combined organic layers were washed with brine (300 mL*3), dried over anhydrous $Na_2SO_4$, concentrated under reduced pressure. The residue was purified by flash silica gel chromatography (ISCO®; 220 g SepaFlash® Silica Flash Column, Eluent of 0~10% MeOH/DCM/TEA DCM was added 0.5 @ 100 mL/min) to give AGS-6-5 (12.8 g, 56% yield) LCMS: (ESI): m/z 1233.6 $[M+H]^+$. Further Succinate AGS-6-5 was loaded onto LCAA (CNA) 500 Å CPG by following the general procedure to give GalNAc 4 CPG.

Example 24: Synthesis of Monomer

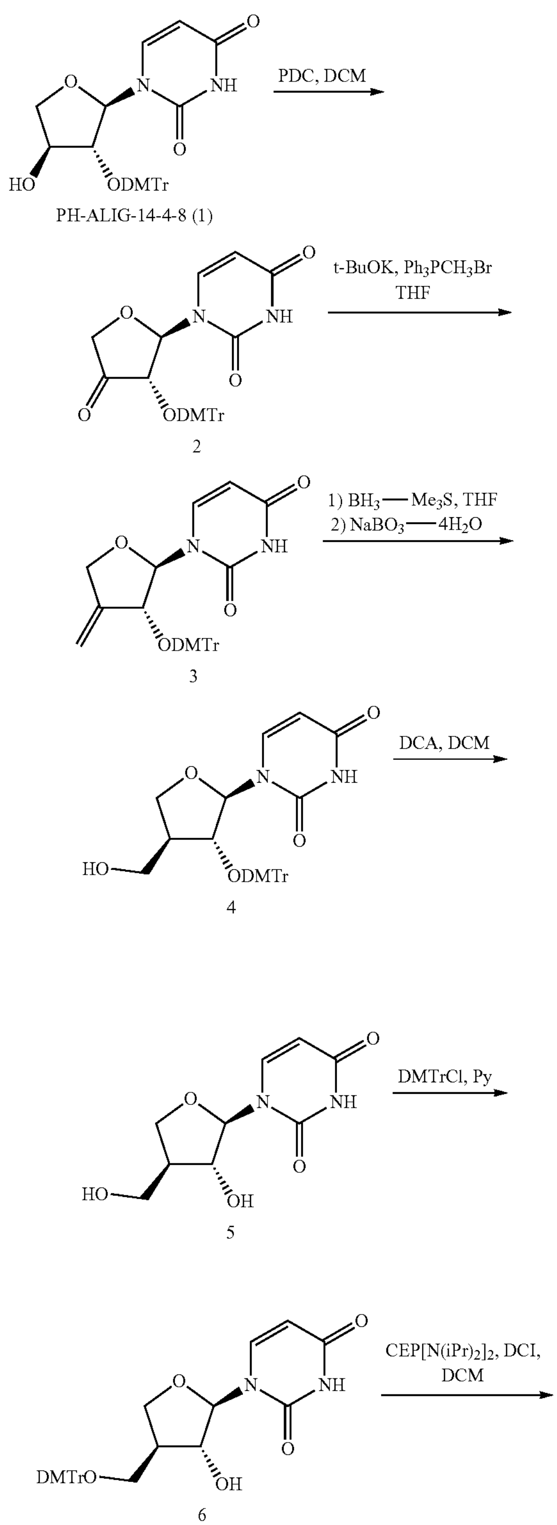

PH-ALIG-14-4-8 (1)

2

3

4

5

6

-continued

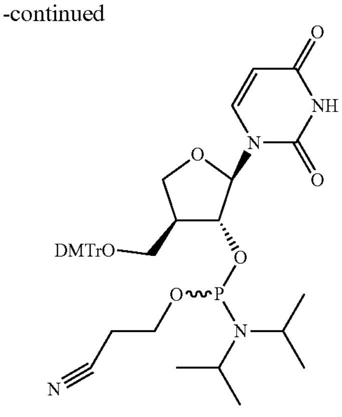

7

Example 24 Monomer

Preparation of (2): Into a 1000 mL round-bottom flask were added PDC (8.48 g, 22.53 mmol, 1.2 equiv) and 4 A-MS (18 g) and DCM (300 mL) and PH-ALG-14-4-8 (from example 5) (9.7 g, 18.8 mmol) at room temperature. The resulting mixture was stirred for 5 h at room temperature under argon atmosphere. The resulting mixture was diluted with ethyl acetate (30 mL). The resulting mixture was filtered, the filter cake was washed with ethyl acetate (4x30 mL). The filtrate was concentrated under reduced pressure. This resulted 2 (9 g, crude) as a yellow solid. LC-MS: m/z 513.2 $[M-H]^-$ Preparation of (3): Into a 1000 mL 3-necked round-bottom flask were added methyl triphenyl-phosphonium bromide (15.62 g, 43.73 mmol) and THF (180 mL) and t-BuOK (43.7 mL, 2M in TIHF) at 0° C. The resulting mixture was stirred for 30 min at 0° C. under argon atmosphere. To a stirred mixture, 3'-ketone 2 (9 g, 17.49 mmol) in THF was added dropwise at 0° C. under argon atmosphere. The resulting mixture was stirred for 2 h at room temperature under argon atmosphere. The reaction was quenched by the addition of water (1 mL) at room temperature. The resulting mixture was filtered, the filter cake was washed with ethyl acetate (4x20 mL). The filtrate was washed with water (3x20 mL), dried over anhydrous $Na_2SO_4$. After filtration, the filtrate was concentrated under reduced pressure. The residue was purified by reverse flash chromatography with the following conditions: column, C18; mobile phase, ACN in water, 45% to 70% gradient in 30 min; detector, UV 254 to afford 3 (5.6 g, 56% yield in two steps) as a white solid. LC-MS: m/z 511.15 $[M-H]^-$; $^1$H-NMR (400 MHz, DMSO-$d_6$) δ 11.26 (s, 1H), 7.38 (d, J=7.3 Hz, 2H), 7.33-7.18 (m, 8H), 6.90-6.78 (m, 4H), 5.71 (d, J=3.7 Hz, 1H), 5.42 (dd, J=8.1, 1.9 Hz, 1H), 4.96 (d, J=2.1 Hz, 1H), 4.88 (d, J=3.6 Hz, 1H), 4.47 (d, J=15.1 Hz, 3H), 3.72 (d, J=3.8 Hz, 6H).

Preparation of (4): Into a 500 mL round-bottom flask were added intermediate 3 (5.5 g, 10.73 mmol) and THF (140 mL) and $BH_3$-$Me_2S$ (24.14 mL, 48.28 mmol) at 0° C. The resulting mixture was stirred for 5 days at 0° C. under argon atmosphere. To a stirred mixture, MeOH (56 mL) was added dropwise at 0° C. under argon atmosphere. The resulting mixture was stirred for 20 min at 0° C. under argon atmosphere. To a stirred mixture, $H_2O$ (84 mL) were added dropwise at 0° C. under argon atmosphere. Further $NaBO_3.4H_2O$ (29.7 g, 193.14 mmol) were added in several batches at 0° C. under argon atmosphere. The resulting mixture was stirred for 1 day at room temperature under argon atmosphere. The resulting mixture was diluted with ethyl acetate (200 mL). The resulting mixture was extracted with EtOAc (3×200 mL). The combined organic layers were washed with brine (2×100 mL), dried over anhydrous $Na_2SO_4$. After filtration, the filtrate was concentrated under reduced pressure. The residue was purified by reverse flash chromatography with the following conditions: column, C18; mobile phase, ACN in water, 35% to 70% gradient in 30 min; detector, UV 254 nm. to give compound 4 (1.4 g, 24% yield) as a white solid. LC-MS: m/z 529.15 $[M-H]^-$; $^1$H-NMR: (400 MHz, DMSO-$d_6$) δ 11.19 (s, 1H), 7.41 (d, J=7.3 Hz, 2H), 7.35-7.16 (m, 8H), 6.92-6.77 (m, 4H), 5.61 (d, J=3.6 Hz, 1H), 5.41 (d, J=8.0 Hz, 1H), 4.79 (s, 1H), 4.29 (t, J=3.7 Hz, 1H), 4.02 (dd, J=9.0, 7.4 Hz, 1H), 3.84 (m, 1H), 3.71 (d, J=5.6 Hz, 6H), 3.17 (m, 2H), 2.85-2.67 (m, 1H), 2.45 (m, 1H).

Preparation of (5): A solution of compound 4 (980 mg, 1.85 mmol) in 2,2-dichloroacetic acid (20 mL, 3% in DCM) was stirred for 30 min at 0° C. under argon atmosphere. The resulting mixture was diluted with pyridine (2 mL). The resulting mixture was concentrated under reduced pressure, and resulted crude 5, which was used without purification.

Preparation of (6): A solution compound 5 and DMTrCl (1.47 g, 4.34 mmol) in pyridine (20 mL) was stirred for 2 h at room temperature under argon atmosphere. Reaction was quenched with water at room temperature. The resulting mixture was extracted with EtOAc (3×20 mL). The combined organic layers were washed with brine (2×30 mL), dried over anhydrous $Na_2SO_4$. After filtration, the filtrate was concentrated under reduced pressure. The residue was purified by reverse flash chromatography with the following conditions: column, C18; mobile phase, ACN in water, 10% to 90% gradient in 30 min; detector, UV 254 nm to give 6 (780 mg) as white solid.

Preparation of (7): A mixture of 1H-imidazole-4,5-dicarbonitrile (257.53 mg, 2.18 mmol) and $CEP[N(iPr)_2]_2$ (606.7 mg, 2.01 mmol) in DCM (8 mL) was stirred for 10 min at room temperature under argon atmosphere followed by the addition of compound 6 (890 mg, 1.68 mmol) dropwise/in portions at room temperature. The resulting mixture was stirred for 1 h at room temperature under argon atmosphere. The reaction was quenched with $NaHCO_3$ (aqueous). The resulting mixture was extracted with $CH_2C_2$ (3×10 mL). The combined organic layers were washed with brine (2×5 mL), dried over anhydrous $Na_2SO_4$. After filtration, the filtrate was concentrated under reduced pressure. The residue was purified by silica gel column chromatography, eluted with PE/EA with 0.5% TEA (1:1) to afford 7 (example 24 monomer) (950 mg, 75.56%) as a white solid. ESI-LCMS: m/z 731 $[M+H]^+$; $^1$HNMR: (300 MHz, DMSO-$d_6$) δ 11.34 (d, J=8.4 Hz, 1H), 7.63 (t, J=7.9 Hz, 1H), 7.40-7.26 (m, 4H), 7.29-7.15 (m, 5H), 6.92-6.82 (m, 4H), 5.70 (d, J=5.0 Hz, 1H), 5.53 (d, J=8.1 Hz, 1H), 4.42 (s, 1H), 4.26 (q, J=8.2 Hz, 1H), 4.10-3.92 (m, 1H), 3.72 (d, J=1.6 Hz, 6H), 3.69-3.56 (m, 1H), 3.54-3.35 (m, 3H), 3.20-3.02 (m, 2H), 2.67 (q, J=7.3, 6.0 Hz, 2H), 1.04 (dd, J=6.7, 3.8 Hz, 6H), 0.92 (dd, J=18.1, 6.7 Hz, 6H); $^{31}$P NMR: (DMSO-$d_6$) δ 149.57, 149.07

Example 25: Synthesis of Monomer

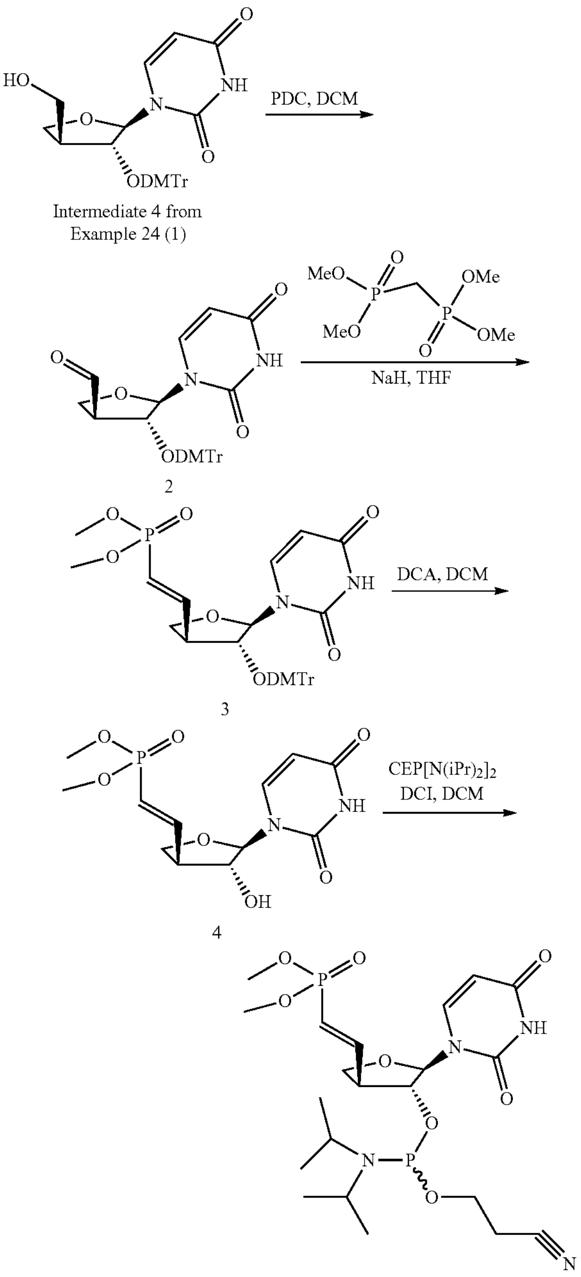

Intermediate 4 from Example 24 (1)

2

3

4

5
Example 25 monomer

Preparation of (2): Into a 100 mL round-bottom flask were added compound 1 (intermediate 4, example 24) (1 g, 1.83 mmol), molecular sieve (1.7 g) and PDC (0.83 g, 2.2 mmol) at room temperature. To the above mixture was added DCM (30.00 mL). The resulting mixture was stirred for 2 h at room temperature under argon atmosphere. The precipitated solids were collected by filtration and washed with EtOAc (3×20 mL). The resulting mixture was concentrated under reduced pressure. This resulted in compound 2 (1.2 g, 124.10%) as a brown solid. The crude product 2 was used in the next step directly without further purification.

Preparation of (3): To a solution of dimethyl (dimethoxyphosphoryl)methylphosphonate (0.79 g, 3.4 mmol) in 18 mL THF was added sodium hydride (60%, 0.27 g) at −50° C. The mixture was stirred for 30 min. Compound 2 (1.2 g, 2.27 mmol) in 18 mL THF was added and the mixture was allowed to warm to room temperature and stirred for 1 h. The reaction was quenched with sat. $NH_4Cl$ (aq.) at room temperature. The resulting mixture was extracted with EtOAc (3×30 mL). The combined organic layers were washed with brine (3×10 mL), dried over anhydrous $Na_2SO_4$. After filtration, the filtrate was concentrated under reduced pressure. The residue was purified by reverse flash chromatography with the following conditions: column, C18 silica gel; mobile phase, MeCN in water, 5% to 95% gradient in 30 min; detector, UV 254 nm. This resulted in 3 (680 mg, 47.20%) as a white solid. ESI-LCMS: m/z 633 $[M+H]^+$; $^1$H-NMR (400 MHz, Acetonitrile-$d_3$) δ 8.80 (s, 1H), 7.45-7.30 (m, 2H), 7.26-7.07 (m, 7H), 6.81-6.67 (m, 4H), 6.57 (d, J=8.0 Hz, 1H), 6.45 (ddd, J=21.7, 17.2, 8.5 Hz, 1H), 5.70 (dd, J=20.1, 17.3 Hz, 1H), 5.23 (d, J=8.0 Hz, 1H), 5.10 (d, J=3.1 Hz, 1H), 4.65 (dd, J=4.6, 3.1 Hz, 1H), 4.05 (t, J=8.4 Hz, 1H), 3.65 (d, J=5.4 Hz, 6H), 3.51 (dd, J=11.0, 6.1 Hz, 6H), 3.40-3.26 (m, 1H).

Preparation of (4): To a stirred solution of compound 3 (680 mg, 1.07 mmol) in DCM (20 mL) was added dichloroacetic acid (0.6 mL) dropwise at 0° C. under air atmosphere. The resulting mixture was stirred for 30 min at 0° C. under air atmosphere. The reaction was quenched with sat. $NaHCO_3$ (aq.) at 0° C. The mixture was extracted with water (2×20 mL). The resulting mixture was concentrated to 25 mL under reduced pressure. The residue was purified by reverse flash chromatography with the following conditions: column, C18 silica gel; mobile phase, MeCN in water, 5% to 95% gradient in 115 min; detector, UV 254 nm. This resulted compound 4 (299 mg, 84%) as a white solid. ESI-LCMS: m/z 333 $[M-H]^-$; $^1$H NMR (400 MHz, Deuterium Oxide) δ 7.60 (d, J=8.1 Hz, 1H), 6.64 (ddd, J=22.6, 17.4, 7.2 Hz, 1H), 5.98-5.87 (m, 1H), 5.77 (d, J=8.1 Hz, 1H), 5.66 (d, J=4.7 Hz, 1H), 4.45 (dd, J=6.8, 4.7 Hz, 1H), 4.27 (dd, J=9.1, 7.8 Hz, 1H), 4.15 (dd, J=9.1, 8.0 Hz, 1H), 3.63 (d, J=11.2 Hz, 6H), 3.22 (qdd, J=7.0, 2.6, 1.3 Hz, 1H).

Preparation of (5): A solution of $CEP[N(iPr)_2]_2$ (272.16 mg, 0.9 mmol) in DCM (12 mL) was treated with molecular sieve under argon atmosphere followed by the addition of 1H-imidazole-4,5-dicarbonitrile (106.6 mg, 0.9 mmol). To the resulted solution, compound 4 (200 mg, 0.6 mmol) in 10 mL DCM was added dropwise slowly at room temperature. The resulting mixture was stirred for 1 h at room temperature under argon atmosphere. The resulting mixture was diluted with 0.5% TEA in DCM (20 mL). The reaction was quenched with Water at room temperature. The resulting mixture was extracted with 0.5% TEA in $CH_2Cl_2$ (3×15 mL). The combined organic layers were washed with brine (2×10 mL), dried over anhydrous $MgSO_4$. After filtration, the filtrate was concentrated under reduced pressure. The residue was purified by Prep-TLC (0.5% TEA in $CH_2Cl_2$/MeOH 12:1) to afford final monomer 5 (example 25) (170 mg, 50.60%) as off-white semi-solid. ESI-LCMS: m/z 533 $[M+H]^+$; $^1$H NMR (400 MHz, Acetonitrile-$d_3$) δ 8.95 (s, 1H), 7.38 (dd, J=8.1, 6.1 Hz, 1H), 6.61 (dddd, J=21.5, 17.1, 11.1, 8.0 Hz, 1H), 5.92-5.64 (m, 2H), 5.56 (d, J=8.1 Hz, 1H), 4.64-4.44 (m, 1H), 4.11 (td, J=8.5, 4.5 Hz, 1H), 4.02 (td, J=8.9, 6.4 Hz, 1H), 3.82-3.36 (m, 10H), 3.24 (tq, J=16.6, 8.0 Hz, 1H), 2.59 (t, J=6.0 Hz, 1H), 2.54-2.45 (m, 1H), 1.09-0.97 (m, 12H); $^{31}$P NMR: δ 149.67, 149.32, 19.25, 19.13.

Additional Tables

TABLE 17

| SEQ ID NO: | Description | Sequence$^+$ |
|---|---|---|
| 55 | Hepatitis B virus (Genbank Accession No. U95551.1) | aattccacaacctttcaccaaactctgcaagatcccagagtgagaggcctgtatttccctg<br>ctggtggctccagttcaggagcagtaaaccctgttccgactactgcctctcccttatcgtca<br>atcttctcgaggattggggaccctgcgctgaacatggagaacatcacatcaggattccta<br>ggacccettctcgtgttacaggcggggtttttcttgttgacaagaatcctcacaataccgca<br>gagtctagactcgtggtggacttctctcaattttctagggggaactaccgtgtgtcttggcc<br>aaaattcgcagtccccaacctccaatcactcaccaacctcctgtcctccaacttgtcctggt<br>tatcgctggatgtgtctgcggcgttttatcatcttcctcttcatcctgctgctatgcctcatcttc<br>ttgttggttcttctggactatcaaggtatgttgcccgtttgtcctctaattccaggatcctcaac<br>caccagcacgggaccatgccgaacctgcatgactactgctcaaggaacctctatgtatcc<br>ctcctgttgctgtaccaaaccttcggacggaaattgcacctgtattcccatcccatcatcct<br>gggctttcggaaaattcctatgggagtgggcctcagcccgtttctcctggctcagtttacta<br>gtgccatttgttcagtggttcgtagggctttcccccactgtttggctttcagttatatggatgat<br>gtggtattgggggccaagtctgtacagcatcttgagtccctttttaccgctgttaccaattttc<br>ttttgtctttgggtatacatttaaaccctaacaaaacaaagagatggggttactctctgaatttt<br>atgggttatgtcattggaagttatgggtccttgccacaagaacacatcatacaaaaaatca<br>aagaatgttttagaaaacttcctattaacaggcctattgattggaaagtatgtcaacgaattg<br>tgggtcttttgggttttgctgccccatttacacaatgtggttatcctgcgttaatgcccttgtat<br>gcatgtattcaatctaagcaggctttcactttctcgccaacttacaaggcctttctgtgtaaac<br>aatacctgaacctttaccccgttgcccggcaacggccaggtctgtgccaagtgtttgctga<br>cgcaacccccactggctggggcttggtcatgggccatcagcgcgtgcgtggaacctttt<br>cggctcctctgccgatccatactgcggaactcctagccgcttgttttgctcgcagcaggtc<br>tggagcaaacattatcgggactgataactctgttgtcctctcccgcaaatatacatcgtatc<br>catggctgctaggctgtgctgccaactggatcctgcgcgggacgtcctttgtttacgtccc<br>gtcggcgctgaatcctgcggacgacccttctcggggtcgcttgggactctctcgtcccctt<br>ctccgtctgccgttccgaccgaccacggggcgcacctctctttacgcggactccccgtct<br>gtgccttctcatctgccggaccgtgtgcacttcgcttcacctctgcacgtcgcatggagac<br>caccgtgaacgcccaccgaatgttgcccaaggtcttacataagaggactcttggactctct<br>gcaatgtcaacgaccgaccttgaggcatacttcaaagactgtttgtttaaagactgggagg<br>agttgggggaggagattagattaaaggtctttgtactaggaggctgtaggcataaattggt<br>ctgcgcaccagcaccatgcaactttttcacctctgcctaatcatctcttgttcatgtcctactg<br>ttcaagcctccaagctgtgccttgggtggctttggggcatggacatcgacccttataaaga<br>atttggagctactgtggagttactctcgtttttgccttctgacttctttccttcagtacgagatct<br>tctagataccgcctcagctctgtatcgggaagccttagagtctcctgagcattgttcacctc<br>accatactgcactcaggcaagcaattctttgctgggggaactaatgactctagctacctg<br>ggtgggtgttaatttggaagatccagcatctagagacctagtagtcagttatgtcaacacta |

TABLE 17-continued

| SEQ ID NO: | Description | Sequence⁺ |
|---|---|---|
| | | atatgggcctaaagttcaggcaactcttgtggtttcacatttcttgtctcacttttggaagaga<br>aaccgttatagagtatttggtgtctttcggagtgtggattcgcactcctccagcttatagacc<br>accaaatgcccctatcctatcaacacttccggaaactactgttgttagacgacgaggcag<br>gtcccctagaagaagaactccctcgcctcgcagacgaaggtctcaatcgccgcgtcgca<br>gaagatctcaatctcgggaacctcaatgttagtattccttggactcataaggtggggaactt<br>tactggtctttattcttctactgtacctgtctttaatcctcattggaaaacaccatcttttcctaat<br>atacatttacaccaagacattatcaaaaaatgtgaacagtttgtaggcccacttacagttaat<br>gagaaaagaagattgcaattgattatgcctgctaggttttatccaaaggttaccaaatattta<br>ccattggataagggtattaaaccttattatccagaacatctagttaatcattacttccaaacta<br>gacactatttacacactctatggaaggcgggtatattatataagagagaaacaacacatag<br>cgcctcattttgtgggtcaccatattcttgggaacaagatctacagcatggggcagaatctt<br>tccaccagcaatcctctgggattctttcccgaccaccagttggatccagccttcagagcaa<br>acacagcaaatccagattgggacttcaatcccaacaaggacacctggccagacgccaa<br>caaggtaggagctggagcattcgggctgggtttcaccccaccgcacggaggccttttgg<br>ggtggagccctcaggctcagggcatactacaaactttgccagcaaatccgcctcctgcct<br>ccaccaatcgccagacaggaaggcagcctaccccgctgtctccacctttgagaaacact<br>catcctcaggccatgcagtgg |
| 56 | MCJ mRNA (GenBank Accession No. NM_013238.3) | agtcactgccgcggcgccttgagtctccgggccgccttgccatggctgcccgtggtgtcatc<br>gctccagttggcgagagtttgcgctacgctgagtacttgcagccctcggccaaacggccag<br>acgccgacgtcgaccagcagagactggtaagaagtttgatagctgtaggactgggtgttgc<br>agctcttgcatttgcaggtcgctacgcatttcggatctggaaacctctagaacaagttatcaca<br>gaaactgcaaagaagatttcaactcctagcttttcatcctactataaaggaggatttgaacaga<br>aaatgagtaggcgagaagctggtcttattttaggtgtaagcccatctgctggcaaggctaaga<br>ttagaacagctcataggagagtcatgattttgaatcacccagataaaggtggatctccttacgt<br>agcagccaaaataaatgaagcaaaagacttgctagaaacaaccaccaaacattgatgcttaa<br>ggaccacactgaaggaaaaaaaaagaggggacttcgaaaaaaaaaaaagccctgcaaaa<br>tattctaaaacatggtcttcttaattttctatatggattgaccacagtcttatcttccaccattaagct<br>gtataacaataaaatgttaatagtcttgctttttattatcttttaaagatctccttaaattctataactg<br>atctttttttcttattttgtttgtgacattcatacatttttaagatttttgttatgttctgaattcccccctac<br>acacacacacacacacacacacacacacacgtgcaaaaaatatgatcaagaatgcaattgg<br>gatttgtgagcaatgagtagacctcttattgtttatatttgtaccctcattgtcaatttttttttaggg<br>aatttgggactctgcctatataaggtgttttaaatgtcttgagaacaagcactggctgatacctc<br>ttggagatatgatctgaaatgtaatggaatttattaaatggtgtttagtaaagtaggggttaagg<br>acttgttaaagaaccccactatctctgagaccctatagccaaagcatgaggacttggagagct<br>actaaaatgattcaggtttacaaaatgagccctgtgaggaaaggttgagagaagtctgagga<br>gtttgtatttaattatagtcttccagtactgtatattcattcattactcattctacaaatatttattgacc<br>ccttttgatgtgcaaggcactatcgtgcgtcccctgagagttgcaagtatgaagcagtcatgg<br>atcatgaaccaaaggaacttatatgtagaggaaggataaatcacaaatagtgaatactgttag<br>atacagatgatatattttaaaagttcaaaggaagaaaagaatgtgttaaacactgcatgagag<br>gaggaataagtggcatagagctaggctttagaaaagaaaaatattccgataccatatgattgg<br>tgaggtaagtgttattctgagatgagaattagcagaaatagatatatcaatcggagtgattaga<br>gtgcagggtttctggaaagcaaggtttggacagagtggtcatcaaaggccagccctgtgact<br>tacactgcattaaattaatttcttagaacatagtccctgatcattatcactttactattccaaaggt<br>gagagaacagattcagatagagtgccagcattgtttcccagtattcctttacaaatcttgggttc<br>attccaggtaaactgaactactgcattgtttctatcttaaaatactttttagatatcctagatgcatc<br>tttcaacttctaacattctgtagtttaggagttctcaaccttggcattattgacatgttaggccaaa<br>taatttttttttgtgggaggtctcttgtgcgttttagatgattagcaataatccctgacctgttatcta<br>ctaaagactagtcgtttctcatcagttgtgacaacaaaaatggttccagatattgccaaatgcc<br>ctttagaggacagtaatcgcccccagttgagaaccatttcagtaaaactttaattactatttttttct<br>tttggtttataaaataatgatcctgaattaaattgatggaaccttgaagtcgataaaatatatttctt<br>gctttaaagtccccatacgtgtcctactaattttctcatgctttagtgttttcacttttctcctgttatc<br>cttgtacctaagaatgccatcccaatccccagatgtccacctgcccaaagtctaggcatagct<br>gaaggccaagctaaaatgtatccctctttttctggtacatgcagcaaaagtaatatgaattatca<br>gctttctgagagcaggcattgtatctgtcttgtttggtgttacattggcacccaataaatatttgtt<br>gagtgaatgaataaattcccatagcactttattcttcacatggtacataactataggggctatag<br>cttggtaccttgtgaagcaactcttggtgtaacataccttatttctcatactaaaatgcaagaacc<br>tttagagcaaggatcttgccattcatctttgtaacctctttactctggagcacttgcatttagcag<br>gcatcataaagttttacgtaccaagaaaatgttgctgttttctgaatactatgcatcaaaaaatgt<br>taccactaatttttaaagctctgctaaggaatattggggcaccctcagatgcaccttttaattgat<br>gtcatattttcctaatccatactttattcatgagaatttgagtcaccccagcattagcttggaatttc<br>cttatttcccatttgctttgcaggtgccttggagtcagatctggttttgaatactatcttcctgttat<br>gtgatcttgggcagttacttaattttctagtcaataacccgtatctataaaatagagaaaataatc<br>ctacacaccggggcctgttgtggggcggggagagggggggagggatcgcatttggagatat<br>actaatgtaaatgacaagttaattggtgcagcacaccaacatggctcatgtctacatatgtaac<br>aaacctgcacgttgtgcacatgtgccctagaacttaaagtataataaaaagaaattttaaaaaa<br>tcctgtcaaataaggttatagtagagaataaggatgtgtaaagcatttagtcacgtaaatgctta<br>aaaaaatgtaatttttacttctttcactgcctcatttaattagttttatctttaataataccttggattca<br>gggtaaagtttcagttatgtcccagtaatcatttattttaccctcgaatctgcaatttggatagaa<br>catggtggggacagctcgtctctattccttgcagcattaacaggctggaggcaccacttctct<br>ggccagcaagttgggcctggttgttggctgagagcctcagttcctttctgcacaggttcctctt<br>tacataggcttctcaacagggctactagagcatcgtcaccatagcagctgtcttataacagag<br>agtggtcggtctgagagacaaaaaatggaagctgccaaattgttctgggtctggaaactgtc<br>agggcatcacttgtgccatattcagttggcctaagaattacagagcctgcctcgattcaaagg<br>gagaggatagagaggactgaaggaatcagtgctcatctttaatatgcagcaggacaggtttg<br>ggatttttttttccccccttgagtctgtgaaggcattacttaagaacaaagtcaggcatgtataattg<br>aactacagttacttgaaatataagcccagaaagtttcagataataaatacaactatttttctgctg |

TABLE 17-continued

| SEQ ID NO: | Description | Sequence+ |
|---|---|---|
| | | ttacccttgtacctaaagatgccatcctaatccccagatctccacaactatacctacatagtaga<br>aggttaaaatgtatccctctttttctggtgcatccagcaaaagtaatatcatgaattatgagctct<br>ctgagagcaaggatcatatcagtcttgtttattgttgcagtgaacaagtacagttgcagatattc<br>aggagtaattatctaaatggcagtaggcttataaaactgaattttcaccagccacaccctcccc<br>ccaactccttatctgtaaaaagcttatttgagtggttacctgtcttcagtaaagattgcgcttgca<br>tatttgctgtcattgcatattctgcttaattaagctctgttgatattgcagtttctgtgcatacttacat<br>cttagatgcaatctgagggcctaggaaggccttttaaaaataaaacaattccgattgcagaga<br>aagtgtaagtcaaggacagttaattcaaggggaacatagaaagctatttagattttagttgatg<br>gtgccagtcttcagcgtaaagtcaaaagtggagggaagtttagtaaggaaaaaatgttgggc<br>ttggaatacattgtttagtcttcaaagcactttactttttatgaaatatattttagacattcagcaaat<br>attgaatacttactatatcaggcagtaaagatataaattcattcttaaaatgtgcaacatgttcaa<br>actgaaaaaaatacattcttaaacaggaaactttttccttcatactttttaattaacaagacatata<br>agagttgcattaatgggcgtgcttatgattgatcacccagcagcatcattagaaataatatatttt<br>attcatgtgcagaaatcttttggttgtcctggggaaccttgaacacagaaaagagcttttattga<br>taaggtaattgaacacacttgacaattagcttaatatggtttaataccatttgtgggagaagatg<br>aatcagccaggctctttacgtcaagaatatgaagtttctcttgagtcaaccaacttaagatgag<br>ctacggagactgcagtgaaaagttaaatatccaagtacaccagccaatttcacacagtggaa<br>ccatgctgtcctcgggcaccctgcacctcgcccaacagtcatcaactagatggaggctcctg<br>gctgcaaggaggatttgatgggaatgagtaaatgtgtcagcatagtccgtcccttctaatgga<br>aaagcaacccaaagagcaaatcctattaatggctggatcagtatcatctacttgtcaaaaaca<br>ttccatgaattatgagtcaaaattttatttatggtggcattacacacattaagagatgaggacttc<br>tgttagcataatttattagctggaaaagttgagaaggttctctggactcatttttataggtggaac<br>ctaagtgatctggataattgcccaccagcaaaattgctgggcatggtggacaaagaaaatgtt<br>ccttctaatgatttttatgagctgagtagctattgttcccagctgagtgctcttttcctctttttattg<br>ttgctgagcaaaagaatttataaaaagctctttcttttgtattaaaaaccctgctcaattgaaatg<br>caagttcattaagtaatcttcatttctcttcctgccataataaccctttccctctctgttcgattcaa<br>cagtatctagcagcactgctccaaattttaagtctgaacagactatattacatagatgtagaga<br>aatactcaatcttcagcattaagagggagcttaatttcacacgggtggaatatgatcactcagg<br>ctagatgttggccataaatttcaaattagtatctcaacttagcaggggggatcaacagtggca<br>aacttcaattatgacaggataaaaatcacatagagatattggttcaatatggacatctaaactat<br>aatgctaaaagccaataattagaataagttcattttaagaaaagcattaataatattagctaacg<br>tttagtacctgtgccaaacattctacctatgttaccttgattttcatagccagcctaagaggtact<br>attatgtatccccattttacaggttaagaaacaggctcagaggagtttaggatcttttccaagatt<br>acatagccagtaagtggtggcactaggaaccaaattcagactctgaatcgcatgctgtttatat<br>tatattgcactcattctaaatatgtgggaatcagaatgaaggggcttgtatgacttttggctcatt<br>ttttgatgcatgtgacctgggattataaatgtgaaattaggtttacgaaaggatccagtgtcatt<br>gtgcatcatgggcaaggagtacctaatctctttaattcttccctggaagcttacgatgtccatcc<br>aagtgcacatagcaaaagttctgttgtaaagtttagcagagtgactttctttgactcagagtgat<br>gacggaggaagctttgataagattttatctgaaatgttcatggacaagagctttcaaggagaa<br>catccagagcaaggttctgaagacagctcatgaaggtgaagcagcagacctggcacaaga<br>aatgaagagagagctcagtgtattaaagatgaaaacaagaaaaccgaatatattgaaagga<br>gcagagaggcaatgaaaacaagacaactgaaatgaggtaacttgcagcaattgaaaggga<br>atttcagtacttttatagaattcttaaaaattgtttcctgctgtttattttcaattttgaacagggttatt<br>tgtccatgccatactttttttgccaaattccaaaattgtgtatagttctatagttgtctggtggagtc<br>aatggaactttagttaccagtctaagaatgtgtctttgagattgtccagttaattctctatttccagt<br>agctgtaataaatggtgaaaaggtttctgactcctggagaaagtttctaactccttatgactaat<br>attcataacagacttgtgagttccttgaacatggatacacctatatgcaagagtgtattccaaag<br>ctaactcagtgatctttccatttatctattcttggattagtggtgcctttgctctttccttctgtaaatg<br>tgaatagttaagagttgactgcagaagtgtttacactttggcttccatgcctctggaatgtttgtg<br>ctttggtggtgagatgtgagactatatttgtatagtctgcatctctcaggctgccccagaatgtt<br>gtacagtgcagtgctgaagaaagcagcaggtacacacagaaatgcagcctttcctggttaa<br>ccctgcttggatctgagttacactttgtttcctgacttcttgggacttaggtaatcagtttgccttct<br>actctatctcattttgtactcgcttacatactacattcttgtttgggctttcgtttcttcttgtaagcag<br>agatttttaaaatccaatatgtgaaaatacggatgcactacaattaaataaataaaatgctgttg<br>tgtttgttttgctttaaaattgtaaaggataaacaataagatagttttatctatgtggttttcccgatg<br>cagttaaaataaaacctaatctgctaaaattgaa |
| 57 | TAZ (GenBank Accession No. NM_000116.5) | gctttccggcggttgcaccgggccggggtgccagcgcccgccttcccgtttcctcccgttcc<br>gcagcgcgcccacggcctgtgaccccggcgaccgctccccagtgacgagagagcgggg<br>ccgggcgctgctccggcctgacctgcgaagggacctcggtccagtcccctgttgcgccgc<br>gcccccgtccgtccgtgcgcgggccagtcaggggccagtgtctcgagcggtcgaggtcg<br>cagacctagaggcgccccacaggccggcccggggcgctgggagcgccggccgcgggc<br>cgggtggggatgcctctgcacgtgaagtggccgttccccgcggtgccgccgctcacctgg<br>accctggccagcagcgtcgtcatgggcttggtgggcacctacagctgcttctggaccaagt<br>acatgaaccacctgaccgtgcacaacagggaggtgctgtacgagctcatcgagaagcgag<br>gcccggccacgcccctcatcaccgtgtccaatcaccagtcctgcatggacgaccctcatctc<br>tggggggatcctgaaactccgccacatctggaacctgaagttgatgcgttggacccctgcagc<br>tgcagacatctgcttcaccaaggagctacactcccacttcttcagcttgggcaagtgtgtgcct<br>gtgtgccgaggagcagaatttttccaagcagagaatgaggggaaaggtgttctagacacag<br>gcaggcacatgccaggtgctggaaaaagaagagagaaaggagatggcgtctaccagaag<br>gggatggacttcattttggagaagctcaaccatggggactgggtgcatatcttcccagaagg<br>gaaagtgaacatgagttccgaattcctgcgtttcaagtggggaatcgggcgcctgattgctg<br>agtgtcatctcaaccccatcatcctgcccctgtggcatgtcggaatgaatgacgtccttcctaa<br>cagtccgccctacttcccccgctttggacagaaaatcactgtgctgatcgggaagcccttca<br>gtgccctgcctgtactcgagcggctccgggcggagaacaagtcggctgtggagatgcgga<br>aagccctgacggacttcattcaagaggaattccagcatctgaagactcaggcagagcagct<br>ccacaaccacctccagcctgggagataggccttgcttgctgccttctggattcttggcccgca |

TABLE 17-continued

| SEQ ID NO: | Description | Sequence+ |
|---|---|---|
| | | cagagctggggctgagggatggactgatgcttttagctcaaacgtggcttttagacagatttg ttcatagaccctctcaagtgccctctccgagctggtaggcattccagctcctccgtgcttcctc agttacacaaaggacctcagctgcttctcccacttggccaagcagggaggaagaagcttag gcagggctctctttccttcttgccttcagatgttctctcccaggggctggcttcaggagggagc atagaaggcaggtgagcaaccagttggctaggggagcaggggggcccaccagagctgtg gagaggggaccctaagactcctcggcctggctcctacccaccgcccttgccgaaccagga gctgctcactacctcctcagggatggccgttggccacgtcttccttctgcctgagcttcccccc caccacaggccctttcctcaggcaaggtctggcctcaggtgggccgcaggcgggaaaag cagcccttggccagaagtcaagcccagccacgtggagcctagagtgagggcctgaggtct ggctgcttgcccccatgctggcgccaacaacttctccatcctttctgcctctcaacatcacttg aatcctagggcctgggttttcatgtttttgaaacagaaccataaagcatatgtgttggcttgttgt aaaa |
| 58 | ANGPTL3 (GenBank Accession No. NM_014495.4) | agaagaaaacagttccacgttgcttgaaattgaaaatcaagataaaaatgttcacaattaagct ccttctttttattgttcctctagttatttcctccagaattgatcaagacaattcatcatttgattctctat ctccagagccaaaatcaagatttgctatgttagacgatgtaaaaattttagccaatggcctcctt cagttgggacatggtcttaaagactttgtccataagacgaagggccaaattaatgacatatttc aaaaactcaacatatttgatcagtctttttatgatctatcgctgcaaaccagtgaaatcaaagaa gaagaaaaggaactgagaagaactacatataaactacaagtcaaaaatgaagaggtaaag aatatgtcacttgaactcaactcaaaacttgaaagcctcctagaagaaaaaattctacttcaac aaaaagtgaaatatttagaagagcaactaactaacttaattcaaaatcaacctgaaactccag aacacccagaagtaacttcacttaaaacttttgtagaaaaacaagataatagcatcaaagacc ttctccagaccgtggaagaccaatataaacaattaaaccaacagcatagtcaaataaaagaa atagaaaatcagctcagaaggactagtattcaagaacccacagaaatttctctatcttccaag ccaagagcaccaagaactactccctttcttcagttgaatgaaataagaaatgtaaaacatgat ggcattcctgctgaatgtaccaccatttataacagaggtgaacatacaagtggcatgtatgcc atcagacccagcaactctcaagtttttcatgtctactgtgatgttatatcaggtagtccatggac attaattcaacatcgaatagatggatcacaaaacttcaatgaaacgtgggagaactacaaata tggttttgggaggcttgatggagaattttggttgggcctagagaagatatactccatagtgaag caatctaattatgttttacgaattgagttggaagactggaaagacaacaaacattatattgaata ttctttttacttgggaaatcacgaaaccaactatacgctacatctagttgcgattactggcaatgt ccccaatgcaatcccggaaaacaaagatttggtgttttctacttgggatcacaaagcaaaagg acacttcaactgtccagagggttattcaggaggctggtggtggcatgatgagtgtggagaaa acaacctaaatggtaaatataacaaaccaagagcaaaatctaagccagagaggagaagag gattatcttggaagtctcaaaatggaaggttatactctataaaatcaaccaaaatgttgatccat ccaacagattcagaaagctttgaatgaactgaggcaaatttaaaaggcaataatttaaacatta acctcattccaagttaatgtggtctaataatctggtattaaatccttaagagaaagcttgagaaa tagattttttttatcttaaagtcactgtctatttaagattaaacatacaatcacataaccttaaagaa taccgtttacatttctcaatcaaaattcttataatactatttgttttaaattttgtgatgtgggaatcaa ttttagatggtcacaatctagattataatcaataggtgaacttattaaataacttttctaaataaaa aatttagagacttttattttaaaaggcatcatatgagctaatatcacaactttcccagtttaaaaaa ctagtactcttgttaaaactctaaacttgactaaatacagaggactggtaattgtacagttcttaa atgttgtagtattaatttcaaaactaaaaatcgtcagcacagagtatgtgtaaaaatctgtaatac aaatttttaaactgatgcttcattttgctacaaaataatttggagtaaatgtttgatatgatttatttat gaaacctaatgaagcagaattaaatactgtattaaaataagttcgctgtctttaaacaaatgga gatgactactaagtcacattgactttaacatgaggtatcactataccttatttgttaaaatatatac tgtatacattttatatattttaacacttaatactatgaaaacaaataattgtaaaggaatcttgtcag attacagtaagaatgaacatatttgtggcatcgagttaaagtttatatttcccctaaatatgctgt gattctaatacattcgtgtaggttttcaagtagaaataaacctcgtaacaagttactgaacgttta aacagcctgacaagcatgtatatatgtttaaaattcaataaacaaagacccagtccctaaatta tagaaatttaaattattcttgcatgtttatcgacatcacaacagatccctaaatccctaaatcccta aagattagatacaaattttttaccacagtatcacttgtcagaatttatttttaaatatgatttttttaaa actgccagtaagaaattttaaattaaacccatttgttaaaggatatagtgcccaagttatatggt gacctacctttgtcaatacttagcattatgtatttcaaattatccaatatacatgtcatatatattttta tatgtcacatatataaaagatatgtatgatctatgtgaatcctaagtaaatattttgttccagaaaa gtacaaaataataaaggtaaaaataatctataattttcaggaccacagactaagctgtcgaaat taacgctgatttttttagggccagaataccaaaatggctcctctcttcccccaaaattggacaat ttcaaatgcaaaataattcattatttaatatatgagttgcttcctctatttggtttcc |
| 59 | DGAT2 (GenBank Accession No. NM_001253891.1) | tgccccgttgtgaggtgataaagtgttgcgctccgggacgccagcgccgcggctgccgcct ctgctggggtctaggctgtttctctcgcgccaccactggccgccggccgcagctccaggtgt cctagccgcccagcctcgacgccgtcccgggacccctgtgctctgcgcgaagccctggcc ccgggggccggggcatgggccaggggcgcggggtgaagcggcttcccgcggggccgt gactgggcgggcttcagccatgaagaccctcatagccgcctactccggggtcctgcgcgg cgagcgtcaggccgaggctgaccggagccagcgctctcacggaggacctgcgctgtcgc gcgaggggtctgggagatggggagtggcctgcagtgccatcctcatgtacatattctgcact gattgctggctcatcgctgtgctctacttcacttggctggtgtttgactggaacacacccaaga aaggtggcaggaggtcacagtgggtccgaaactgggctgtgtggcgctactttcgagacta ctttcccatccagctggtgaagacacacaacctgctgaccaccaggaactatatctttggata ccacccccatggtatcatgggcctgggtgccttctgcaacttcagcacagaggccacagaa gtgagcaagaagttcccaggcatacggccttacctggctacactggcaggcaacttccgaa tgcctgtgttgagggagtacctgatgtctggaggtatctgccctgtcagccgggacaccata gactatttgctttcaaagaatgggagtggcaatgctatcatcatcgtggtcgggggtgcggct gagtctctgagctccatgcctggcaagaatgcagtcaccctgcggaaccgcaagggctttgt gaaactggccctgcgtcatggagctgacctggttcccatctactcctttggagagaatgaagt gtacaagcaggtgatcttcgaggagggctcctggggccgatgggtccagaagaagttcca gaaatacattggtttcgccccatgcatcttccatggtcgaggcctcttctcctccgacacctgg |

TABLE 17-continued

| SEQ ID NO: | Description | Sequence+ |
|---|---|---|
| | | gggctggtgccctactccaagcccatcaccactgttgtgggagagcccatcaccatcccca<br>agctggagcacccaacccagcaagacatcgacctgtaccacaccatgtacatggaggccc<br>tggtgaagctcttcgacaagcacaagaccaagttcggcctcccggagactgaggtcctgga<br>ggtgaactgagccagccttcggggccaattccctggaggaaccagctgcaaatcactttttt<br>gctctgtaaatttggaagtgtcatgggtgtctgtgggttatttaaaagaaattataacaattttgct<br>aaaccattacaatgttaggtcttttttaagaaggaaaaagtcagtatttcaagttctttcacttcca<br>gcttgccctgttctaggtggtggctaaatctgggcctaatctgggtggctcagctaacctctctt<br>cttcccttcctgaagtgacaaaggaaactcagtcttcttggggaagaaggattgccattagtg<br>acttggaccagttagatgattcactttttgcccctagggatgagaggcgaaagccacttctcat<br>acaagcccctttattgccactaccccacgctcgtctagtcctgaaactgcaggaccagtttctc<br>tgccaaggggaggagttggagagcacagttgccccgttgtgtgagggcagtagtaggcat<br>ctggaatgctccagtttgatctcccttctgccacccctacctcacccctagtcactcatatcgga<br>gcctggactggcctccaggatgaggatgggggtggcaatgacaccctgcaggggaaagg<br>actgccccccatgcaccattgcagggaggatgccgccaccatgagctaggtggagtaact<br>ggtttttcttgggtggctgatgacatggatgcagcacagactcagccttggcctggagcacat<br>gcttactggtggcctcagtttaccttccccagatcctagattctggatgtgaggaagagatccc<br>tcttcagaaggggcctggccttctgagcagcagattagttccaaagcaggtggcccccgaa<br>cccaagcctcacttttctgtgccttcctgaggggggttgggccggggaggaaacccaaccctc<br>tcctgtgtgttctgttatctcttgatgagatcattgcaccatgtcagacttttgtatatgccttgaaa<br>ataaatgaaagtgagaatcctctaaaaaaaaaaaa |
| 60 | HBV Genbank Accession No. KC315400.1 | ctccaccactttccaccaaactcttcaagatcccagagtcagggccctgtactttcctgctggt<br>ggctcaagttccggaacagtaaaccctgctccgactactgcctctcccatatcgtcaatcttct<br>cgaggactggggaccctgtaccgaatatggagagcaccacatcaggattcctaggacccct<br>gctcgtgttacaggcggggtttttcttgttgacaagaatcctcacaataccacagagtctagac<br>tcgtggtggacttctctcaattttctagggggagcacccacgtgtcctggccaaaatttgcagt<br>ccccaacctccaatcactcaccaacctcttgtcctccaatttgtcctggttatcgctggatgtgt<br>ctgcggcgttttatcatcttcctcttcatcctgctgctatgcctcatcttcttgttggttcttctggac<br>taccaaggtatgttgcccgtttgtcctctacttccaggaacatcaactaccagcaccggaccat<br>gcaaaacctgcacaactactgctcaagggacctctatgtttccctcatgttgctgtacaaaacc<br>tacggacggaaactgcacctgtattcccatcccatcatcttgggctttcgcaaaatacctatgg<br>gagtgggcctcagtccgtttctcttggctcagtttactagtgccatttgttcagtggttcgtagg<br>gctttcccccactgtctggctttcagttatatggatgatgtggttttgggggccaagtctgtaca<br>acatcttgagtccctttataccgctgttaccaattttcttttatctttgggtatacatttaaaccctca<br>caaaacaaaaagatggggatattcccttaacttcatgggatatgtaattgggagttggggcac<br>tttgcctcaggaacatattgtacaaaaaatcaagcaatgttttaggaaacttcctgtaaacagg<br>cctattgattggaaagtatgtcaacraattgtgggtcttttggggtttgccgcccctttcacgca<br>atgtggatatcctgctttaatgcctttatatgcatgtatacaagctaagcaggcttttactttctcg<br>ccaacttacaaggcctttctgtgtaaacaatatctgaacctttaccccgttgctcggcaacggt<br>caggtctttgccaagtgtttgctgacgcaacccccactggttggggcttggccataggccatc<br>agcgcatgcgtggaacctttgtggctcctctgccgatccatactgcggaactcctagcagctt<br>gttttgctcgcagccggtctggagcaaaacttatcggcaccgacaactctgttgtcctctctcg<br>gaaatacacctcctttccatggctgctaggatgtgctgccaactggatcctgcgcgggacgt<br>cctttgtctacgtcccgtcggcgctgaatcccgcggacgacccatctcggggccgtttggga<br>ctctaccgtccccttctgcgtctgccgttccgcccgaccacggggcgcacctctctttacgcg<br>gtctccccgtctgtgccttctcatctgccggaccgtgtgcacttcgcttcacctctgcacgtcg<br>catggagaccaccgtgaacgcccacgggaacctgcccaaggtcttgcataagaggactctt<br>ggactttcagcaatgtcaacgaccgaccttgaggcatacttcaaagactgtgtgtttactgagt<br>gggaggagttgggggaggaggttaggttaaaggtctttgtactaggaggctgtaggcataa<br>attggtgtgttcaccagcaccatgcaactttttcacctctgcctaatcatctcatgttcatgtccta<br>ctgttcaagcctccaagctgtgccttgggtggctttggggcatggacattgacccgtataaag<br>aatttggagcttctgtggagttactctcttttttgccttctgacttctttccttctattcgagatctcct<br>cgacaccgcctctgctctgtatcgggaggccttagagtctccggaacattgttcacctcacca<br>tacggcactcaggcaagcaattctgtgttggggtgagttaatgaatctagccacctgggtgg<br>gaagtaatttggaagatccagcatccagggaattagtagtcagctatgtcaacgttaatatgg<br>gcctaaaaatcagacaactattgtggtttcacatttcctgtcttacttttgggagagaaactgttc<br>ttgaatatttggtgtcttttggagtgtggattcgcactcctcctgcatatagaccacaaaatgcc<br>cctatcttatcaacacttccggaaactactgttgttagacgaagaggcaggtcccctagaaga<br>agaactccctcgcctcgcagacgaaggtctcaatcgccgcgtcgcagaagatctcaatctc<br>gggaatctcaatgttagtattccttggacacataaggtgggaaactttacggggctttattcttct<br>acggtaccttgctttaatcctaaatggcaaactccttcttttcctgacattcatttgcaggaggac<br>attgttgatagatgtaagcaatttgtggggccccttacagtaaatgaaaacaggagacttaaat<br>taattatgcctgctaggttttatcccaatgttactaaatatttgcccttagataaagggatcaaac<br>cgtattatccagagtatgtagttaatcattacttccagacgcgacattatttacacactctttgga<br>aggcggggatcttatataaaagagagtccacacgtagcgcctcattttgcgggtcaccatatt<br>cttgggaacaagatctacagcatgggaggttggtcttccaaacctcgaaaaggcatgggga<br>caaatctttctgtccccaatcccctgggattcttccccgatcatcagttggaccctgcattcaaa<br>gccaactcagaaaatccagattgggacctcaacccacacaaggacaactggccggacgcc<br>aacaaggtgggagtgggagcattcgggccagggttcacccctcctcatgggggactgttg<br>gggtggagccctcaggctcagggcatattcacaacagtgccagcagctcctcctcctgcct<br>ccaccaatcggcagtcaggaaggcagcctactcccttctctccacctctaagagacactcat<br>cctcaggccatgcagtggaa |
| 61 | ASO 1 | GalNAc4-ps-GalNAc4-ps-GalNAc4-po-mA-po-<br>lnGpslnApslnTpslnApslnApsApsAps(5OH)CpsGps(5m)Cps(5m)<br>CpsGps(5m)CpslnApslnGpslnApscp(5m)C |

TABLE 17-continued

| SEQ ID NO: | Description | Sequence+ |
|---|---|---|
| 62 | ASO 2 | mA-po-<br>lnGpslnApslnTpslnApslnApsApsAps(5OH)CpsGps(5m)Cps(5m)<br>CpsGps(5m)CpslnApslnGpslnApscp(5m)C |
| 113 | SARS-CoV-2 genome (Genbank Accession No. NC_045512.2) | attaaaggtttataccttcccaggtaacaaaccaaccaactttcgatctcttgtagatctgttctct<br>aaacgaactttaaaatctgtgtggctgtcactcggctgcatgcttagtgcactcacgcagtata<br>attaataactaattactgtcgttgacaggacacgagtaactcgtctatcttctgcaggctgctta<br>cggtttcgtccgtgttgcagccgatcatcagcacatctaggtttcgtccgggtgtgaccgaaa<br>ggtaagatggagagccttgtccctggtttcaacgagaaaacacacgtccaactcagtttgcct<br>gttttacaggttcgcgacgtgctcgtacgtggctttggagactccgtggaggaggtcttatca<br>gaggcacgtcaacatcttaaagatggcacttgtggcttagtagaagttgaaaaaggcgttttg<br>cctcaacttgaacagccctatgtgttcatcaaacgttcggatgctcgaactgcacctcatggtc<br>atgttatggttgagctggtagcagaactcgaaggcattcagtacggtcgtagtggtgagaca<br>cttggtgtccttgtccctcatgtgggcgaaataccagtggcttaccgcaaggttcttcttcgtaa<br>gaacggtaataaaggagctggtggccatagttacggcgccgatctaaagtcatttgacttag<br>gcgacgagcttggcactgatccttatgaagattttcaagaaaactggaacactaaacatagca<br>gtggtgttacccgtgaactcatgcgtgagcttaacggaggggcatacactcgctatgtcgata<br>acaacttctgtggccctgatggctaccctcttgagtgcattaaagaccttctagcacgtgctgg<br>taaagcttcatgcactttgtccgaacaactggactttattgacactaagaggggtgtatactgct<br>gccgtgaacatgagcatgaaattgcttggtacacggaacgttctgaaaagagctatgaattg<br>cagacaccttttgaaattaaattggcaaagaaatttgacaccttcaatggggaatgtccaaattt<br>tgtatttcccttaaattccataatcaagactattcaaccaagggttgaaaagaaaaagcttgatg<br>gctttatgggtagaattcgatctgtctatccagttgcgtcaccaaatgaatgcaaccaaatgtg<br>cctttcaactctcatgaagtgtgatcattgtggtgaaacttcatggcagacgggcgattttgtta<br>aagccacttgcgaattttgtggcactgagaatttgactaaagaaggtgccactacttgtggtta<br>cttaccccaaaatgctgttgttaaaatttattgtccagcatgtcacaattcagaagtaggacctg<br>agcatagtcttgccgaataccataatgaatctggcttgaaaaccattcttcgtaagggtggtcg<br>cactattgcctttggaggctgtgtgttctcttatgttggttgccataacaagtgtgcctattgggtt<br>ccacgtgctagcgctaacataggttgtaaccatacaggtgttgttggagaaggttccgaaggt<br>cttaatgacaaccttcttgaaatactccaaaaagagaaagtcaacatcaatattgttggtgactt<br>taaacttaatgaagagatcgccattattttggcatctttttctgcttccacaagtgcttttgtggaa<br>actgtgaaaggtttggattataaagcattcaaacaaattgttgaatcctgtggtaattttaaagtt<br>acaaaaggaaaagctaaaaaaggtgcctggaatattggtgaacagaaatcaatactgagtc<br>ctctttatgcatttgcatcagaggctgctcgtgttgtacgatcaattttctcccgcactcttgaaa<br>ctgctcaaaattctgtgcgtgttttacagaaggccgctataacaatactagatggaatttcaca<br>gtattcactgagactcattgatgctatgatgttcacatctgatttggctactaacaatctagttgta<br>atggcctacattacaggtggtgttgttcagttgacttcgcagtggctaactaacatctttggcac<br>tgtttatgaaaaactcaaacccgtccttgattggcttgaagagaagtttaaggaaggtgtagag<br>tttcttagagacggttgggaaattgttaaatttatctcaacctgtgcttgtgaaattgtcggtgga<br>caaattgtcacctgtgcaaaggaaattaaggagagtgttcagacattctttaagcttgtaaata<br>aatttttggctttgtgtgctgactctatcattattggtggagctaaacttaaagccttgaatttaggt<br>gaaacatttgtcacgcactcaaagggattgtacagaaagtgtgttaaatccagagaagaaac<br>tggcctactcatgcctctaaaagccccaaaagaaattatcttcttagagggagaaacacttcc<br>cacagaagtgttaacagaggaagttgtcttgaaaactggtgatttacaaccattagaacaacc<br>tactagtgaagctgttgaagctccattggttggtacaccagtttgtattaacgggcttatgttgct<br>cgaaatcaaagacacagaaaagtactgtgcccttgcacctaatatgatggtaacaaacaata<br>ccttcacactcaaaggcggtgcaccaacaaaggttacttttggtgatgacactgtgatagaag<br>tgcaaggttacaagagtgtgaatatcacttttgaacttgatgaaaggattgataaagtacttaat<br>gagaagtgctctgcctatacagttgaactcggtacagaagtaaatgagttcgcctgtgttgtg<br>gcagatgctgtcataaaaactttgcaaccagtatctgaattacttacaccactgggcattgattt<br>agatgagtggagtatggctacatactacttatttgatgagtctggtgagtttaaattggcttcac<br>atatgtattgttctttctaccctccagatgaggatgaagaagaaggtgattgtgaagaagaaga<br>gtttgagccatcaactcaatatgagtatggtactgaagatgattaccaaggtaaacctttggaa<br>tttggtgccacttctgctgctcttcaacctgaagaagagcaagaagaagattggttagatgatg<br>atagtcaacaaactgttggtcaacaagacggcagtgaggacaatcagacaactactattcaa<br>acaattgttgaggttcaacctcaattagagatggaacttacaccagttgttcagactattgaagt<br>gaatagttttagtggttatttaaaacttactgacaatgtatacattaaaaatgcagacattgtgga<br>agaagctaaaaaggtaaaaccaacagtggttgttaatgcagccaatgtttaccttaaacatgg<br>aggaggtgttgcaggagccttaaataaggctactaacaatgccatgcaagttgaatctgatg<br>attacatagctactaatggaccacttaaagtgggtggtagttgtgttttaagcggacacaatctt<br>gctaaacactgtcttcatgttgtcggcccaaatgttaacaaaggtgaagacattcaacttcttaa<br>gagtgcttatgaaaattttaatcagcacgaagttctacttgcaccattattatcagctggtattttt<br>ggtgctgaccctatacattctttaagagtttgtgtagatactgttcgcacaaatgtctacttagct<br>gtctttgataaaaatctctatgacaaacttgtttcaagctttttggaaatgaagagtgaaaagca<br>agttgaacaaaagatcgctgagattcctaaagaggaagttaagccatttataactgaaagtaa<br>accttcagttgaacagagaaaacaagatgataagaaaatcaaagcttgtgttgaagaagttac<br>aacaactctggaagaaactaagttcctcacagaaaacttgttactttatattgacattaatggca<br>atcttcatccagattctgccactcttgttagtgacattgacatcactttcttaaagaaagatgctc<br>catatatagtgggtgatgttgttcaagagggtgttttaactgctgtggttatacctactaaaaag<br>gctggtggcactactgaaatgctagcgaaagctttgagaaaagtgccaacagacaattatat<br>aaccacttacccgggtcagggtttaaatggttacactgtagaggaggcaaagacagtgctta<br>aaaagtgtaaaagtgccttttacattctaccatctattatctctaatgagaagcaagaaattcttg<br>gaactgtttcttggaatttgcgagaaatgcttgcacatgcagaagaaacacgcaaattaatgc<br>ctgtctgtgtggaaactaaagccatagtttcaactatacagcgtaaatataagggtattaaaata<br>caagagggtgtggttgattatggtgctagattttacttttacaccagtaaaacaactgtagcgtc<br>acttatcaacacacttaacgatctaaatgaaactcttgttacaatgccacttggctatgtaacac<br>atggcttaaatttggaagaagctgctcggtatatgagatctctcaaagtgccagctacagtttct |

TABLE 17-continued

| SEQ ID NO: | Description | Sequence+ |
|---|---|---|
| | | gtttcttcacctgatgctgttacagcgtataatggttatcttacttcttcttctaaaacacctgaag |
| | | aacattttattgaaaccatctcacttgctggttcctataaagattggtcctattctggacaatctac |
| | | acaactaggtatagaatttcttaagagaggtgataaaagtgtatattacactagtaatcctacca |
| | | cattccacctagatggtgaagttatcacctttgacaatcttaagacacttctttctttgagagaag |
| | | tgaggactattaaggtgtttacaacagtagacaacattaacctccacacgcaagttgtggaca |
| | | tgtcaatgacatatggacaacagtttggtccaacttatttggatggagctgatgttactaaaata |
| | | aaacctcataattcacatgaaggtaaaacattttatgttttacctaatgatgacactctacgtgtt |
| | | gaggcttttgagtactaccacacaactgatcctagttttctgggtaggtacatgtcagcattaaa |
| | | tcacactaaaaagtggaaatacccacaagttaatggtttaacttctattaaatgggcagataac |
| | | aactgttatcttgccactgcattgttaacactccaacaaatagagttgaagtttaatccacctgct |
| | | ctacaagatgcttattacagagcaagggctggtgaagctgctaacttttgtgcacttatcttagc |
| | | ctactgtaataagacagtaggtgagttaggtgatgttagagaaacaatgagttacttgtttcaa |
| | | catgccaatttagattcttgcaaaagagtcttgaacgtggtgtgtaaaacttgtggacaacagc |
| | | agacaacccttaagggtgtagaagctgttatgtacatgggcacactttcttatgaacaatttaa |
| | | gaaaggtgttcagataccttgtacgtgtggtaaacaagctacaaaatatctagtacaacagga |
| | | gtcaccttttgttatgatgtcagcaccacctgctcagtatgaacttaagcatggtacatttacttg |
| | | tgctagtgagtacactggtaattaccagtgtggtcactataaacatataacttctaaagaaactt |
| | | tgtattgcatagacggtgctttacttacaaagtcctcagaatacaaaggtcctattacggatgttt |
| | | tctacaaagaaaacagttacacaacaaccataaaaccagttacttataaattggatggtgttgtt |
| | | tgtacagaaattgaccctaagttggacaattattataagaaagacaattcttatttcacagagca |
| | | accaattgatcttgtaccaaaccaaccatatccaaacgcaagcttcgataattttaagtttgtat |
| | | gtgataatatcaaatttgctgatgatttaaaccagttaactggttataagaaacctgcttcaaga |
| | | gagcttaaagttacatttttccctgacttaaatggtgatgtggtggctattgattataaacactac |
| | | acaccctcttttaagaaaggagctaaattgttacataaacctattgtttggcatgttaacaatgca |
| | | actaataaagccacgtataaaccaaatacctggtgtatacgttgtctttggagcacaaaacca |
| | | gttgaaacatcaaattcgtttgatgtactgaagtcagaggacgcgcagggaatggataatctt |
| | | gcctgcgaagatctaaaaccagtctctgaagaagtagtggaaaatcctaccatacagaaag |
| | | acgttcttgagtgtaatgtgaaaactaccgaagttgtaggagacattatacttaaaccagcaaa |
| | | taatagtttaaaaattacagaagaggttggccacacagatctaatggctgcttatgtagacaat |
| | | tctagtcttactattaagaaacctaatgaattatctagagtattaggtttgaaaacccttgctactc |
| | | atggtttagctgctgttaatagtgtcccttgggatactatagctaattatgctaagccttttcttaa |
| | | caaagttgttagtacaactactaacatagttacacggtgtttaaaccgtgtttgtactaattatatg |
| | | ccttatttctttactttattgctacaattgtgtacttttactagaagtacaaattctagaattaaagca |
| | | tctatgccgactactatagcaaagaatactgttaagagtgtcggtaaattttgtctagaggcttc |
| | | atttaattatttgaagtcacctaatttttctaaactgataaatattataatttggtttttactattaagtg |
| | | tttgcctaggttctttaatctactcaaccgctgctttaggtgttttaatgtctaatttaggcatgcctt |
| | | cttactgtactggttacagagaaggctatttgaactctactaatgtcactattgcaacctactgta |
| | | ctggttctataccttgtagtgtttgtcttagtggtttagattctttagacacctatccttctttagaaa |
| | | ctatacaaattaccatttcatcttttaaatgggatttaactgcttttggcttagttgcagagtggtttt |
| | | tggcatatattcttttcactaggtttttctatgtacttggattggctgcaatcatgcaattgtttttca |
| | | gctattttgcagtacattttattagtaattcttggcttatgtggttaataattaatcttgtacaaatgg |
| | | ccccgatttcagctatggttagaatgtacatcttctttgcatcattttattatgtatggaaaagttat |
| | | gtgcatgttgtagacggttgtaattcatcaacttgtatgatgtgttacaaacgtaatagagcaac |
| | | aagagtcgaatgtacaactattgttaatggtgttagaaggtccttttatgtctatgctaatggag |
| | | gtaaaggcttttgcaaactacacaattggaattgtgttaattgtgatacattctgtgctggtagta |
| | | catttattagtgatgaagttgcgagagacttgtcactacagtttaaaagaccaataaatcctact |
| | | gaccagtcttcttacatcgttgatagtgttacagtgaagaatggttccatccatctttactttgata |
| | | aagctggtcaaaagacttatgaaagacattctctctctcattttgttaacttagacaacctgaga |
| | | gctaataacactaaaggttcattgcctattaatgttatagtttttgatggtaaatcaaaatgtgaa |
| | | gaatcatctgcaaaatcagcgtctgtttactacagtcagcttatgtgtcaacctatactgttacta |
| | | gatcaggcattagtgtctgatgttggtgatagtgcggaagttgcagttaaaatgtttgatgctta |
| | | cgttaatacgttttcatcaacttttaacgtaccaatggaaaaactcaaaacactagttgcaactg |
| | | cagaagctgaacttgcaaagaatgtgtccttagacaatgtcttatctacttttatttcagcagctc |
| | | ggcaagggtttgttgattcagatgtagaaactaaagatgttgttgaatgtcttaaattgtcacatc |
| | | aatctgacatagaagttactggcgatagttgtaataactatatgctcacctataacaaagttgaa |
| | | aacatgacaccccgtgaccttggtgcttgtattgactgtagtgcgcgtcatattaatgcgcagg |
| | | tagcaaaaagtcacaacattgctttgatatggaacgttaaagatttcatgtcattgtctgaacaa |
| | | ctacgaaaacaaatacgtagtgctgctaaaaagaataacttaccttttaagttgacatgtgcaa |
| | | ctactagacaagttgttaatgttgtaacaacaaagatagcacttaagggtggtaaaattgttaat |
| | | aattggttgaagcagttaattaaagttacacttgtgttccttttgttgctgctattttctatttaataa |
| | | cacctgttcatgtcatgtctaaacatactgacttttcaagtgaaatcataggatacaaggctatt |
| | | gatggtggtgtcactcgtgacatagcatctacagatacttgttttgctaacaaacatgctgatttt |
| | | gacacatggtttagccagcgtggtggtagttatactaatgacaaagcttgcccattgattgctg |
| | | cagtcataacaagagaagtgggttttgtcgtgcctggtttgcctggcacgatattacgcacaa |
| | | ctaatggtgactttttgcatttcttacctagagtttttagtgcagttggtaacatctgttacacacca |
| | | tcaaaacttatagagtacactgactttgcaacatcagcttgtgttttggctgctgaatgtacaatt |
| | | tttaaagatgcttctggtaagccagtaccatattgttatgataccaatgtactagaaggttctgtt |
| | | gcttatgaaagtttacgccctgacacacgttatgtgctcatggatggctctattattcaatttcct |
| | | aacacctaccttgaaggttctgttagagtggtaacaacttttgattctgagtactgtaggcacg |
| | | gcacttgtgaaagatcagaagctggtgtttgtgtatctactagtggtagatgggtacttaacaat |
| | | gattattacagatctttaccaggagttttctgtggtgtagatgctgtaaatttacttactaatatgttt |
| | | acaccactaattcaacctattggtgctttggacatatcagcatctatagtagctggtggtattgta |
| | | gctatcgtagtaacatgccttgcctactattttatgaggtttagaagagcttttggtgaatacagt |
| | | catgtagttgcctttaatactttactattccttatgtcattcactgtactctgtttaacaccagtttact |
| | | cattcttacctggtgtttattctgttatttacttgtacttgacattttatcttactaatgatgtttcttttt |
| | | agcacatattcagtggatggttatgttcacacctttagtacctttctggataacaattgcttatatc |
| | | atttgtatttccacaaagcatttctattggttctttagtaattacctaaagagacgtgtagtctttaat |

TABLE 17-continued

| SEQ ID NO: | Description | Sequence+ |
|---|---|---|
| | | ggtgtttcctttagtacttttgaagaagctgcgctgtgcaccttttttgttaaataaagaaatgtatc |
| | | taaagttgcgtagtgatgtgctattacctcttacgcaatataatagatacttagctctttataataa |
| | | gtacaagtattttagtggagcaatggatacaactagctacagagaagctgcttgttgtcatctc |
| | | gcaaaggctctcaatgacttcagtaactcaggttctgatgttctttaccaaccaccacaaacct |
| | | ctatcacctcagctgttttgcagagtggttttagaaaaatggcattcccatctggtaaagttgag |
| | | ggttgtatggtacaagtaacttgtggtacaactacacttaacggtctttggcttgatgacgtagt |
| | | ttactgtccaagacatgtgatctgcacctctgaagacatgcttaaccctaattatgaagatttact |
| | | cattcgtaagtctaatcataatttcttggtacaggctggtaatgttcaactcagggttattggaca |
| | | ttctatgcaaaattgtgtacttaagcttaaggttgatacagccaatcctaagacacctaagtata |
| | | agtttgttcgcattcaaccaggacagactttttcagtgttagcttgttacaatggttcaccatctg |
| | | gtgtttaccaatgtgctatgaggcccaatttcactattaagggttcattccttaatggttcatgtg |
| | | gtagtgttggttttaacatagattatgactgtgtctctttttgttacatgcaccatatggaattacca |
| | | actggagttcatgctggcacagacttagaaggtaacttttatggaccttttgttgacaggcaaa |
| | | cagcacaagcagctggtacggacacaactattacagttaatgttttagcttggttgtacgctgc |
| | | tgttataaatggagacaggtggtttctcaatcgatttaccacaactcttaatgactttaaccttgt |
| | | ggctatgaagtacaattatgaacctctaacacaagaccatgttgacatactaggacctctttct |
| | | gctcaaactggaattgccgttttagatatgtgtgcttcattaaaagaattactgcaaaatggtat |
| | | gaatggacgtaccatattgggtagtgctttattagaagatgaatttacaccttttgatgttgttag |
| | | acaatgctcaggtgttactttccaaagtgcagtgaaaagaacaatcaagggtacacaccact |
| | | ggttgttactcacaattttgacttcacttttagttttagtccagagtactcaatggtctttgttcttttt |
| | | ttgtatgaaaatgcctttttaccttttgctatgggtattattgctatgtctgcttttgcaatgatgtttg |
| | | tcaaacataagcatgcatttctctgtttgtttttgttaccttctcttgccactgtagcttattttaatat |
| | | ggtctatatgcctgctagttgggtgatgcgtattatgacatggttggatatggttgatactagttt |
| | | gtctggttttaagctaaaagactgtgttatgtatgcatcagctgtagtgttactaatccttatgaca |
| | | gcaagaactgtgtatgatgatggtgctaggagagtgtggacacttatgaatgtcttgacactc |
| | | gtttataaagtttattatggtaatgctttagatcaagccatttccatgtgggctcttataatctctgtt |
| | | acttctaactactcaggtgtagttacaactgtcatgtttttggccagaggtattgtttttatgtgtgt |
| | | tgagtattgccctattttcttcataactggtaatacacttcagtgtataatgctagtttattgtttctta |
| | | ggctatttttgtacttgttactttggcctcttttgtttactcaaccgctactttagactgactcttggt |
| | | gtttatgattacttagtttctacacaggagtttagatatatgaattcacagggactactcccaccc |
| | | aagaatagcatagatgccttcaaactcaacattaaattgttgggtgttggtggcaaaccttgtat |
| | | caaagtagccactgtacagtctaaaatgtcagatgtaaagtgcacatcagtagtcttactctca |
| | | gttttgcaacaactcagagtagaatcatcatctaaattgtgggctcaatgtgtccagttacacaa |
| | | tgacattctcttagctaaagatactactgaagcctttgaaaaaatggtttcactactttctgttttg |
| | | ctttccatgcagggtgctgtagacataaacaagctttgtgaagaaatgctggacaacagggc |
| | | aaccttacaagctatagcctcagagtttagttcccttccatcatatgcagcttttgctactgctca |
| | | agaagcttatgagcaggctgttgctaatggtgattctgaagttgttcttaaaaagttgaagaagt |
| | | ctttgaatgtggctaaatctgaatttgaccgtgatgcagccatgcaacgtaagttggaaaagat |
| | | ggctgatcaagctatgacccaaatgtataaacaggctagatctgaggacaagagggcaaaa |
| | | gttactagtgctatgcagacaatgcttttcactatgcttagaaagttggataatgatgcactcaa |
| | | caacattatcaacaatgcaagagatggttgtgttcccttgaacataatacctcttacaacagca |
| | | gccaaactaatggttgtcataccagactataacacatataaaaatacgtgtgatggtacaacat |
| | | ttacttatgcatcagcattgtgggaaatccaacaggttgtagatgcagatagtaaaattgttcaa |
| | | cttagtgaaattagtatggacaattcacctaatttagcatggcctcttattgtaacagctttaagg |
| | | gccaattctgctgtcaaattacagaataatgagcttagtcctgttgcactacgacagatgtcttg |
| | | tgctgccggtactacacaaactgcttgcactgatgacaatgcgttagcttactacaacacaac |
| | | aaagggaggtaggtttgtacttgcactgttatccgatttacaggatttgaaatgggctagattcc |
| | | ctaagagtgatggaactggtactatctatacagaactggaaccaccttgtaggtttgttacaga |
| | | cacacctaaaggtcctaaagtgaagtatttatactttattaaaggattaaacaacctaaatagag |
| | | gtatggtacttggtagtttagctgccacagtacgtctacaagctggtaatgcaacagaagtgc |
| | | ctgccaattcaactgtattatctttctgtgcttttgctgtagatgctgctaaagcttacaaagattat |
| | | ctagctagtgggggacaaccaatcactaattgtgttaagatgttgtgtacacacactggtactg |
| | | gtcaggcaataacagttacaccggaagccaatatggatcaagaatcctttggtggtgcatcgt |
| | | gttgtctgtactgccgttgccacatagatcatccaaatcctaaaggattttgtgacttaaaaggt |
| | | aagtatgtacaaatacctacaacttgtgctaatgaccctgtgggttttacacttaaaaacacagt |
| | | ctgtaccgtctgcggtatgtggaaaggttatggctgtagttgtgatcaactccgcgaacccat |
| | | gcttcagtcagctgatgcacaatcgtttttaaacgggtttgcggtgtaagtgcagcccgtctta |
| | | caccgtgcggcacaggcactagtactgatgtcgtatacagggcttttgacatctacaatgata |
| | | aagtagctggttttgctaaattcctaaaaactaattgttgtcgcttccaagaaaaggacgaaga |
| | | tgacaatttaattgattcttactttgtagttaagagacacactttctctaactaccaacatgaagaa |
| | | acaatttataatttacttaaggattgtccagctgttgctaaacatgacttctttaagtttagaatag |
| | | acggtgacatggtaccacatatatcacgtcaacgtcttactaaatacacaatggcagacctcg |
| | | tctatgctttaaggcattttgatgaaggtaattgtgacacattaaaagaaatacttgtcacataca |
| | | attgttgtgatgatgattatttcaataaaaaggactggtatgattttgtagaaaacccagatatatt |
| | | acgcgtatacgccaacttaggtgaacgtgtacgccaagctttgttaaaaacagtacaattctgt |
| | | gatgccatgcgaaatgctggtattgttggtgtactgacattagataatcaagatctcaatggta |
| | | actggtatgatttcggtgatttcatacaaaccacgccaggtagtggagttcctgttgtagattctt |
| | | attattcattgttaatgcctatattaaccttgaccagggctttaactgcagagtcacatgttgaca |
| | | ctgacttaacaaagccttacattaagtgggatttgttaaaatatgacttcacggaagagaggtt |
| | | aaaactctttgaccgttattttaaatattgggatcagacataccacccaaattgtgttaactgtttg |
| | | gatgacagatgcattctgcattgtgcaaactttaatgttttattctctacagtgttcccacctacaa |
| | | gttttggaccactagtgagaaaaatatttgttgatggtgttccatttgtagtttcaactggatacc |
| | | acttcagagagctaggtgttgtacataatcaggatgtaaacttacatagctctagacttagtttta |
| | | aggaattacttgtgtatgctgctgaccctgctatgcacgctgcttctggtaatctattactagata |
| | | aacgcactacgtgcttttcagtagctgcacttactaacaatgttgcttttcaaactgtcaaaccc |
| | | ggtaattttaacaaagacttctatgactttgctgtgtctaagggtttctttaaggaaggaagttct |
| | | gttgaattaaaacacttcttctttgctcaggatggtaatgctgctatcagcgattatgactactat |

TABLE 17-continued

| SEQ ID NO: | Description | Sequence+ |
|---|---|---|
| | | cgttataatctaccaacaatgtgtgatatcagacaactactatttgtagttgaagttgttgataag |
| | | tactttgattgttacgatggtggctgtattaatgctaaccaagtcatcgtcaacaacctagacaa |
| | | atcagctggttttccatttaataaatggggtaaggctagactttattatgattcaatgagttatga |
| | | ggatcaagatgcacttttcgcatatacaaaacgtaatgtcatccctactataactcaaatgaatc |
| | | ttaagtatgccattagtgcaaagaatagagctcgcaccgtagctggtgtctctatctgtagtact |
| | | atgaccaatagacagtttcatcaaaaattattgaaatcaatagccgccactagaggagctact |
| | | gtagtaattggaacaagcaaattctatggtggttggcacaacatgttaaaaactgtttatagtga |
| | | tgtagaaaaccctcaccttatgggttgggattatcctaaatgtgatagagccatgcctaacatg |
| | | cttagaattatggcctcacttgttcttgctcgcaaacatacaacgtgttgtagcttgtcacaccgt |
| | | ttctatagattagctaatgagtgtgctcaagtattgagtgaaatggtcatgtgtggcggttcact |
| | | atatgttaaaccaggtggaacctcatcaggagatgccacaactgcttatgctaatagtgtttttta |
| | | acatttgtcaagctgtcacggccaatgttaatgcacttttatctactgatggtaacaaaattgcc |
| | | gataagtatgtccgcaatttacaacacagactttatgagtgtctctatagaaatagagatgttga |
| | | cacagactttgtgaatgagttttacgcatatttgcgtaaacatttctcaatgatgatactctctgac |
| | | gatgctgttgtgtgtttcaatagcacttatgcatctcaaggtctagtggctagcataaagaacttt |
| | | aagtcagttctttattatcaaaacaatgtttttatgtctgaagcaaaatgttggactgagactgac |
| | | cttactaaaggacctcatgaattttgctctcaacatacaatgctagttaaacagggtgatgatta |
| | | tgtgtaccttccttacccagatccatcaagaatcctaggggccggctgttttgtagatgatatcg |
| | | taaaaacagatggtacacttatgattgaacggttcgtgtctttagctatagatgcttacccactta |
| | | ctaaacatcctaatcaggagtatgctgatgtctttcatttgtacttacaatacataagaaagctac |
| | | atgatgagttaacaggacacatgttagacatgtattctgttatgcttactaatgataacacttcaa |
| | | ggtattgggaacctgagttttatgaggctatgtacacaccgcatacagtcttacaggctgttgg |
| | | ggcttgtgttctttgcaattcacagacttcattaagatgtggtgcttgcatacgtagaccattctta |
| | | tgttgtaaatgctgttacgaccatgtcatatcaacatcacataaattagtcttgtctgttaatccgt |
| | | atgtttgcaatgctccaggttgtgatgtcacagatgtgactcaactttacttaggaggtatgagc |
| | | tattattgtaaatcacataaaccacccattagttttccattgtgtgctaatggacaagtttttggttt |
| | | atataaaaatacatgtgttggtagcgataatgttactgactttaatgcaattgcaacatgtgactg |
| | | gacaaatgctggtgattacattttagctaacacctgtactgaaagactcaagctttttgcagca |
| | | gaaacgctcaaagctactgaggagacatttaaactgtcttatggtattgctactgtacgtgaag |
| | | tgctgtctgacagagaattacatctttcatgggaagttggtaaacctagaccaccacttaaccg |
| | | aaattatgtctttactggttatcgtgtaactaaaaacagtaaagtacaaataggagagtacacct |
| | | ttgaaaaaggtgactatggtgatgctgttgtttaccgaggtacaacaacttacaaattaaatgtt |
| | | ggtgattattttgtgctgacatcacatacagtaatgccattaagtgcacctacactagtgccaca |
| | | agagcactatgttagaattactggcttatacccaacactcaatatctcagatgagttttctagca |
| | | atgttgcaaattatcaaaaggttggtatgcaaaagtattctacactccagggaccacctggtac |
| | | tggtaagagtcattttgctattggcctagctctctactacccttctgctcgcatagtgtatacagc |
| | | ttgctctcatgccgctgttgatgcactatgtgagaaggcattaaaatatttgcctatagataaat |
| | | gtagtagaattatacctgcacgtgctcgtgtagagtgttttgataaattcaaagtgaattcaaca |
| | | ttagaacagtatgtcttttgtactgtaaatgcattgcctgagacgacagcagatatagttgtcttt |
| | | gatgaaatttcaatggccacaaattatgatttgagtgttgtcaatgccagattacgtgctaagca |
| | | ctatgtgtacattggcgaccctgctcaattacctgcaccacgcacattgctaactaagggcac |
| | | actagaaccagaatatttcaattcagtgtgtagacttatgaaaactataggtccagacatgttcc |
| | | tcggaacttgtcggcgttgtcctgctgaaattgttgacactgtgagtgctttggtttatgataata |
| | | agcttaaagcacataaagacaaatcagctcaatgctttaaaatgttttataagggtgttatcacg |
| | | catgatgtttcatctgcaattaacaggccacaaataggcgtggtaagagaattccttacacgta |
| | | accctgcttggagaaaagctgtctttatttcaccttataattcacagaatgctgtagcctcaaag |
| | | attttgggactaccaactcaaactgttgattcatcacagggctcagaatatgactatgtcatatt |
| | | cactcaaaccactgaaacagctcactcttgtaatgtaaacagatttaatgttgctattaccagag |
| | | caaaagtaggcatactttgcataatgtctgatagagacctttatgacaagttgcaatttacaagt |
| | | cttgaaattccacgtaggaatgtggcaactttacaagctgaaaatgtaacaggactctttaaag |
| | | attgtagtaaggtaatcactgggttacatcctacacaggcacctacacacctcagtgttgaca |
| | | ctaaattcaaaactgaaggtttatgtgttgacatacctggcatacctaaggacatgacctatag |
| | | aagactcatctctatgatgggttttaaaatgaattatcaagttaatggttaccctaacatgtttatc |
| | | acccgcgaagaagctataagacatgtacgtgcatggattggcttcgatgtcgaggggtgtca |
| | | tgctactagagaagctgttggtaccaatttacctttacagctaggtttttctacaggtgttaacct |
| | | agttgctgtacctacaggttatgttgatacacctaataatacagatttttccagagttagtgctaa |
| | | accaccgcctggagatcaatttaaacacctcataccacttatgtacaaaggacttccttggaat |
| | | gtagtgcgtataaagattgtacaaatgttaagtgacacacttaaaaatctctctgacagagtcg |
| | | tatttgtcttatgggcacatggctttgagttgacatctatgaagtattttgtgaaaataggacctg |
| | | agcgcacctgttgtctatgtgatagacgtgccacatgcttttccactgcttcagacacttatgcc |
| | | tgttggcatcattctattggatttgattacgtctataatccgtttatgattgatgttcaacaatgggg |
| | | ttttacaggtaacctacaaagcaaccatgatctgtattgtcaagtccatggtaatgcacatgtag |
| | | ctagttgtgatgcaatcatgactaggtgtctagctgtccacgagtgctttgttaagcgtgttgac |
| | | tggactattgaatatcctataattggtgatgaactgaagattaatgcggcttgtagaaaggttca |
| | | acacatggttgttaaagctgcattattagcagacaaattcccagttcttcacgacattggtaacc |
| | | ctaaagctattaagtgtgtacctcaagctgatgtagaatggaagttctatgatgcacagccttgt |
| | | agtgacaaagcttataaaatagaagaattattctattcttatgccacacattctgacaaattcaca |
| | | gatggtgtatgcctattttggaattgcaatgtcgatagatatcctgctaattccattgtttgtagatt |
| | | tgacactagagtgctatctaaccttaacttgcctggttgtgatggtggcagtttgtatgtaaataa |
| | | acatgcattccacacaccagcttttgataaaagtgcttttgttaatttaaaacaattaccatttttct |
| | | attactctgacagtccatgtgagtctcatggaaaacaagtagtgtcagatatagattatgtacc |
| | | actaaagtctgctacgtgtataacacgttgcaatttaggtggtgctgtctgtagacatcatgcta |
| | | atgagtacagattgtatctcgatgcttataacatgatgatctcagctggctttagcttgtgggttt |
| | | acaaacaatttgatacttataacctctggaacacttttacaagacttcagagtttagaaaatgtg |
| | | gcttttaatgttgtaaataagggacactttgatggacaacagggtgaagtaccagtttctatcat |
| | | taataacactgtttacacaaaagttgatggtgttgatgtagaattgtttgaaaataaaacaacatt |
| | | acctgttaatgtagcatttgagctttgggctaagcgcaacattaaaccagtaccagaggtgaa |

TABLE 17-continued

| SEQ ID NO: | Description | Sequence+ |
|---|---|---|
| | | aatactcaataatttgggtgtggacattgctgctaatactgtgatctgggactacaaaagagat<br>gctccagcacatatatctactattggtgtttgttctatgactgacatagccaagaaaccaactga<br>aacgatttgtgcaccactcactgtctttttttgatggtagagttgatggtcaagtagacttatttag<br>aaatgcccgtaatggtgttcttattacagaaggtagtgttaaaggtttacaaccatctgtaggtc<br>ccaaacaagctagtcttaatggagtcacattaattggagaagccgtaaaaacacagttcaatt<br>attataagaaagttgatggtgttgtccaacaattacctgaaacttactttactcagagtagaaatt<br>tacaagaatttaaacccaggagtcaaatggaaattgatttcttagaattagctatggatgaattc<br>attgaacggtataaattagaaggctatgccttcgaacatatcgtttatggagattttagtcatagt<br>cagttaggtggtttacatctactgattggactagctaaacgttttaaggaatcaccttttgaatta<br>gaagattttattcctatggacagtacagttaaaaactatttcataacagatgcgcaaacaggttc<br>atctaagtgtgtgtgttctgttattgatttattacttgatgattttgttgaaataataaaatcccaaga<br>tttatctgtagtttctaaggttgtcaaagtgactattgactatacagaaatttcatttatgctttggtg<br>taaagatggccatgtagaaacattttacccaaaattacaatctagtcaagcgtggcaaccggg<br>tgttgctatgcctaatctttacaaaatgcaaagaatgctattagaaaagtgtgaccttcaaaatta<br>tggtgatagtgcaacattacctaaaggcataatgatgaatgtcgcaaaatatactcaactgtgt<br>caatatttaaacacattaacattagctgtaccctataatatgagagttatacattttggtgctggtt<br>ctgataaaggagttgcaccaggtacagctgttttaagacagtggttgcctacgggtacgctgc<br>ttgtcgattcagatcttaatgactttgtctctgatgcagattcaactttgattggtgattgtgcaact<br>gtacatacagctaataaatgggatctcattattagtgatatgtacgaccctaagactaaaaatgt<br>tacaaaagaaaatgactctaaagagggtttttttcacttacatttgtgggtttatacaacaaaagc<br>tagctcttggaggttccgtggctataaagataacagaacattcttggaatgctgatctttataag<br>ctcatgggacacttcgcatggtggacagcctttgttactaatgtgaatgcgtcatcatctgaag<br>catttttaattggatgtaattatcttggcaaaccacgcgaacaaatagatggttatgtcatgcatg<br>caaattacatattttggaggaatacaaatccaattcagttgtcttcctattctttatttgacatgagt<br>aaatttccccttaaattaaggggtactgctgttatgtctttaaaagaaggtcaaatcaatgatatg<br>attttatctcttcttagtaaaggtagacttataattagagaaaacaacagagttgttatttctagtg<br>atgttcttgttaacaactaaacgaacaatgtttgtttttcttgttttattgccactagtctctagtcag<br>tgtgttaatcttacaaccagaactcaattacccccctgcatacactaattctttcacacgtggtgttt<br>attaccctgacaaagttttcagatcctcagttttacattcaactcaggacttgttcttacctttctttt<br>ccaatgttacttggttccatgctatacatgtctctgggaccaatggtactaagaggtttgataac<br>cctgtcctaccatttaatgatggtgtttattttgcttccactgagaagtctaacataataagaggc<br>tggatttttggtactactttagattcgaagacccagtccctacttattgttaataacgctactaatg<br>ttgttattaaagtctgtgaatttcaattttgtaatgatccatttttgggtgtttattaccacaaaaaca<br>acaaaagttggatggaaagtgagttcagagtttattctagtgcgaataattgcacttttgaatat<br>gtctctcagccttttcttatggaccttgaaggaaaacagggtaatttcaaaaatcttagggaattt<br>gtgtttaagaatattgatggttattttaaaatatattctaagcacacgcctattaatttagtgcgtga<br>tctccctcagggtttttcggctttagaaccattggtagatttgccaataggtattaacatcactag<br>gtttcaaactttacttgctttacatagaagttatttgactcctggtgattcttcttcaggttggacag<br>ctggtgctgcagcttattatgtgggttatcttcaacctaggacttttctattaaaatataatgaaaa<br>tggaaccattacagatgctgtagactgtgcacttgaccctctctcagaaacaaagtgtacgttg<br>aaatccttcactgtagaaaaaggaatctatcaaacttctaactttagagtccaaccaacagaat<br>ctattgttagatttcctaatattacaaacttgtgcccttttggtgaagtttttaacgccaccagattt<br>gcatctgtttatgcttggaacaggaagagaatcagcaactgtgttgctgattattctgtcctatat<br>aattccgcatcattttccacttttaagtgttatggagtgtctcctactaaattaaatgatctctgcttt<br>actaatgtctatgcagattcatttgtaattagaggtgatgaagtcagacaaatcgctccagggc<br>aaactggaaagattgctgattataattataaattaccagatgattttacaggctgcgttatagctt<br>ggaattctaacaatcttgattctaaggttggtggtaattataattacctgtatagattgtttaggaa<br>gtctaatctcaaaccttttgagagagatatttcaactgaaatctatcaggccggtagcacacctt<br>gtaatggtgttgaaggttttaattgttactttcctttacaatcatatggtttccaacccactaatggt<br>gttggttaccaaccatacagagtagtagtactttcttttgaacttctacatgcaccagcaactgtt<br>tgtggacctaaaaagtctactaatttggttaaaaacaaatgtgtcaatttcaacttcaatggttta<br>acaggcacaggtgttcttactgagtctaacaaaaagtttctgcctttccaacaatttggcagag<br>acattgctgacactactgatgctgtccgtgatccacagacacttgagattcttgacattacacc<br>atgttcttttggtggtgtcagtgttataacaccaggaacaaatacttctaaccaggttgctgttctt<br>tatcaggatgttaactgcacagaagtccctgttgctattcatgcagatcaacttactcctacttg<br>gcgtgtttattctacaggttctaatgtttttcaaacacgtgcaggctgtttaataggggctgaaca<br>tgtcaacaactcatatgagtgtgacatacccattggtgcaggtatatgcgctagttatcagact<br>cagactaattctcctcggcgggcacgtagtgtagctagtcaatccatcattgcctacactatgt<br>cacttggtgcagaaaattcagttgcttactctaataactctattgccatacccacaaattttactat<br>tagtgttaccacagaaattctaccagtgtctatgaccaagacatcagtagattgtacaatgtac<br>atttgtggtgattcaactgaatgcagcaatcttttgttgcaatatggcagtttttgtacacaattaa<br>accgtgctttaactggaatagctgttgaacaagacaaaaacacccaagaagtttttgcacaag<br>tcaaacaaatttacaaaacaccaccaattaaagattttggtggttttaatttttcacaaatattacc<br>agatccatcaaaaccaagcaagaggtcatttattgaagatctacttttcaacaaagtgacactt<br>gcagatgctggcttcatcaaacaatatggtgattgccttggtgatattgctgctagagacctca<br>tttgtgcacaaaagtttaacggccttactgttttgccacctttgctcacagatgaaatgattgctc<br>aatacacttctgcactgttagcgggtacaatcacttctggttggacctttggtgcaggtgctgc<br>attacaaataccatttgctatgcaaatggcttataggtttaatggtattggagttacacagaatgt<br>tctctatgagaaccaaaaattgattgccaaccaatttaatagtgctattggcaaaattcaagact<br>cactttcttccacagcaagtgcacttggaaaacttcaagatgtggtcaaccaaaatgcacaag<br>ctttaaacacgcttgttaaacaacttagctccaattttggtgcaatttcaagtgttttaaatgatatc<br>ctttcacgtcttgacaaagttgaggctgaagtgcaaattgataggttgatcacaggcagacttc<br>aaagtttgcagacatatgtgactcaacaattaattagagctgcagaaatcagagcttctgctaa<br>tcttgctgctactaaaatgtcagagtgtgtacttggacaatcaaaaagagttgattttgtggaa<br>agggctatcatcttatgtccttccctcagtcagcacctcatggtgtagtcttcttgcatgtgactt<br>atgtccctgcacaagaaaagaacttcacaactgctcctgccatttgtcatgatggaaaagcac<br>actttcctcgtgaaggtgtctttgtttcaaatggcacacactggtttgtaacacaaaggaatttt |

TABLE 17-continued

| SEQ ID NO: | Description | Sequence+ |
| --- | --- | --- |
| | | atgaaccacaaatcattactacagacaacacatttgtgtctggtaactgtgatgttgtaatagga<br>attgtcaacaacacagtttatgatcctttgcaacctgaattagactcattcaaggaggagttaga<br>taaatattttaagaatcatacatcaccagatgttgatttaggtgacatctctggcattaatgcttca<br>gttgtaaacattcaaaaagaaattgaccgcctcaatgaggttgccaagaatttaaatgaatctc<br>tcatcgatctccaagaacttggaaagtatgagcagtatataaaatggccatggtacatttggct<br>aggttttatagctggcttgattgccatagtaatggtgacaattatgctttgctgtatgaccagttg<br>ctgtagttgtctcaagggctgttgttcttgtggatcctgctgcaaatttgatgaagacgactctg<br>agccagtgctcaaaggagtcaaattacattacacataaacgaacttatggatttgtttatgaga<br>atcttcacaattggaactgtaactttgaagcaaggtgaaatcaaggatgctactccttcagattt<br>tgttcgcgctactgcaacgataccgatacaagcctcactccctttcggatggcttattgttggc<br>gttgcacttcttgctgtttttcagagcgcttccaaaatcataaccctcaaaaagagatggcaact<br>agcactctccaagggtgttcactttgtttgcaacttgctgttgtttgtaacagtttactcacac<br>cttttgctcgttgctgctggccttgaagccccttttctctatctttatgctttagtctacttcttgcag<br>agtataaactttgtaagaataataatgaggctttggctttgctggaaatgccgttccaaaaacc<br>cattactttatgatgccaactattttctttgctggcatactaattgttacgactattgtataccttaca<br>atagtgtaacttcttcaattgtcattacttcaggtgatggcacaacaagtcctatttctgaacatg<br>actaccagattggtggttatactgaaaaatgggaatctggagtaaaagactgtgttgtattaca<br>cagttacttcacttcagactattaccagctgtactcaactcaattgagtacagacactggtgttg<br>aacatgttaccttcttcatctacaataaaattgttgatgagcctgaagaacatgtccaaattcac<br>acaatcgacggttcatccggagttgttaatccagtaatggaaccaatttatgatgaaccgacg<br>acgactactagcgtgcctttgtaagcacaagctgatgagtacgaacttatgtactcattcgtttc<br>ggaagagacaggtacgttaatagttaatagcgtacttctttttcttgctttcgtggtattcttgcta<br>gttacactagccatccttactgcgcttcgattgtgtgcgtactgctgcaatattgttaacgtgagt<br>cttgtaaaaccttctttttacgtttactctcgtgttaaaaatctgaattcttctagagttcctgatcttc<br>tggtctaaacgaactaaatattatattagtttttctgtttggaactttaattttagccatggcagatt<br>ccaacggtactattaccgttgaagagcttaaaaagctccttgaacaatggaacctagtaatag<br>gtttcctattccttacatggatttgtcttctacaatttgcctatgccaacaggaataggtttttgtat<br>ataattaagttaattttcctctggctgttatggccagtaactttagcttgttttgtgcttgctgctgttt<br>acagaataaattggatcaccggtggaattgctatcgcaatggcttgtcttgtaggcttgatgtg<br>gctcagctacttcattgcttctttcagactgtttgcgcgtacgcgttccatgtggtcattcaatcc<br>agaaactaacattcttctcaacgtgccactccatggcactattctgaccagaccgcttctagaa<br>agtgaactcgtaatcggagctgtgatccttcgtggacatcttcgtattgctggacaccatctag<br>gacgctgtgacatcaaggacctgcctaaagaaatcactgttgctacatcacgaacgctttctt<br>attacaaattgggagcttcgcagcgtgtagcaggtgactcaggttttgctgcatacagtcgct<br>acaggattggcaactataaattaaacacagaccattccagtagcagtgacaatattgctttgct<br>tgtacagtaagtgacaacagatgtttcatctcgttgactttcaggttactatagcagagatattac<br>taattattatgaggacttttaaagtttccatttggaatcttgattacatcataaacctcataattaaa<br>aatttatctaagtcactaactgagaataaatattctcaattagatgaagagcaaccaatggaga<br>ttgattaaacgaacatgaaaattattcttttcttggcactgataacactcgctacttgtgagcttta<br>tcactaccaagagtgtgttagaggtacaacagtacttttaaaagaaccttgctcttctggaacat<br>acgagggcaattcaccatttcatcctctagctgataacaaatttgcactgacttgctttagcact<br>caatttgcttttgcttgtcctgacggcgtaaaacacgtctatcagttacgtgccagatcagtttca<br>cctaaactgttcatcagacaagaggaagttcaagaactttactctccaatttttcttattgttgcg<br>gcaatagtgtttataacactttgcttcacactcaaaagaaagacagaatgattgaactttcatta<br>attgacttctatttgtgctttttagcctttctgctattccttgttttaattatgcttattatcttttggttctc<br>acttgaactgcaagatcataatgaaacttgtcacgcctaaacgaacatgaaatttcttgttttctt<br>aggaatcatcacaactgtagctgcatttcaccaagaatgtagtttacagtcatgtactcaacat<br>caaccatatgtagttgatgacccgtgtcctattcacttctattctaaatggtatattagagtagga<br>gctagaaaatcagcacctttaattgaattgtgcgtggatgaggctggttctaaatcacccattc<br>agtacatcgatatcggtaattatacagtttcctgtttaccttttacaattaattgccaggaacctaa<br>attgggtagtcttgtagtgcgttgttcgttctatgaagactttttagagtatcatgacgttcgtgtt<br>gttttagatttcatctaaacgaacaaactaaaatgtctgataatggaccccaaaatcagcgaaa<br>tgcaccccgcattacgtttggtggaccctcagattcaactggcagtaaccagaatggagaac<br>gcagtggggcgcgatcaaaacaacgtcggccccaaggtttacccaataatactgcgtcttg<br>gttcaccgctctcactcaacatggcaaggaagaccttaaattccctcgaggacaaggcgttc<br>caattaacaccaatagcagtccagatgaccaaattggctactaccgaagagctaccagacg<br>aattcgtggtggtgacggtaaaatgaaagatctcagtccaagatggtatttctactacctagga<br>actgggccagaagctggacttccctatggtgctaacaaagacggcatcatatgggttgcaac<br>tgagggagccttgaatacaccaaaagatcacattggcacccgcaatcctgctaacaatgctg<br>caatcgtgctacaacttcctcaaggaacaacattgccaaaaggcttctacgcagaagggag<br>cagaggcggcagtcaagcctcttctcgttcctcatcacgtagtcgcaacagttcaagaaattc<br>aactccaggcagcagtaggggaacttctcctgctagaatggctggcaatggcggtgatgct<br>gctcttgctttgctgctgcttgacagattgaaccagcttgagagcaaaatgtctggtaaaggcc<br>aacaacaacaaggccaaactgtcactaagaaatctgctgctgaggcttctaagaagcctcg<br>gcaaaaacgtactgccactaaagcatacaatgtaacacaagctttcggcagacgtggtcca<br>gaacaaacccaaggaaattttggggaccaggaactaatcagacaaggaactgattacaaac<br>attggccgcaaattgcacaatttgcccccagcgcttcagcgttcttcggaatgtcgcgcattg<br>gcatggaagtcacaccttcgggaacgtggttgacctacacaggtgccatcaaattggatgac<br>aaagatccaaatttcaaagatcaagtcattttgctgaataagcatattgacgcatacaaaacatt<br>cccaccaacagagcctaaaaaggacaaaaagaagaaggctgatgaaactcaagccttacc<br>gcagagacagaagaaacagcaaactgtgactcttcttcctgctgcagatttggatgatttctcc<br>aaacaattgcaacaatccatgagcagtgctgactcaactcaggcctaaactcatgcagacca |

TABLE 17-continued

| SEQ ID NO: | Description | Sequence+ |
|---|---|---|
| | | cacaaggcagatgggctatataaacgttttcgcttttccgtttacgatatatagtctactcttgtg cagaatgaattctcgtaactacatagcacaagtagatgtagttaactttaatctcacatagcaat ctttaatcagtgtgtaacattagggaggacttgaaagagccaccacattttcaccgaggccac gcggagtacgatcgagtgtacagtgaacaatgctagggagagctgcctatatggaagagc cctaatgtgtaaaattaattttagtagtgctatccccatgtgattttaatagcttcttaggagaatg acaaaaaaaaaaaaaaaaaaaaaaaaaaaaaaaa |

+ln = Locked nucleic acid (LNA) =

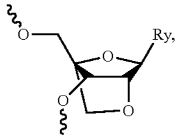

wherein Ry is a nucleobase;
lnA = Locked nucleic acid (LNA) A;
ln(5m)C = ln(5m)C = Locked nucleic acid (LNA)-5 methyl C;
lnG = Locked nucleic acid (LNA) G;
lnT = Locked nucleic acid (LNA) T;
(5m)C = 5 methyl C;
scp = = spirocyclopropyl;
scp(5m)C = cyclopropyl-5 methyl C;
(5OH)C =

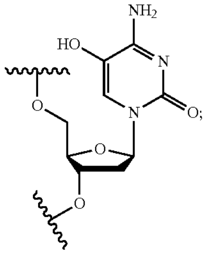

po = phosphodiester linkage;
ps = phosphorothioate linkage

What is claimed is:

1. A nucleotide comprising a structure of:

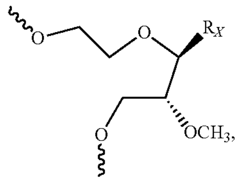

wherein Rx is a nucleobase, aryl, heteroaryl, or H, and wherein represents a phosphodiester linkage.

2. A nucleotide of claim 1 comprising a structure of:

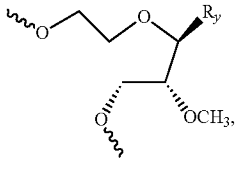

wherein $R_y$ is a nucleobase, and wherein represents a phosphodiester linkage.

3. A nucleotide comprising a structure of:

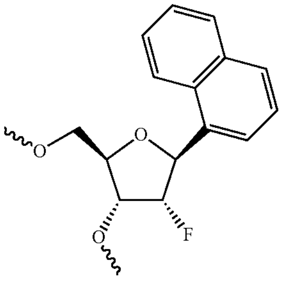

(fN)

wherein $R_y$ is a nucleobase, and wherein represents a phosphodiester linkage.

4. A short interfering nucleic acid (siNA) molecule comprising a sense strand and an antisense strand, and comprising at least one modified nucleotide selected from

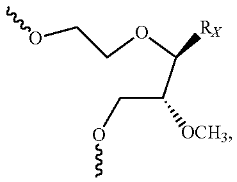

wherein Rx is a nucleobase, aryl, heteroaryl, or H;

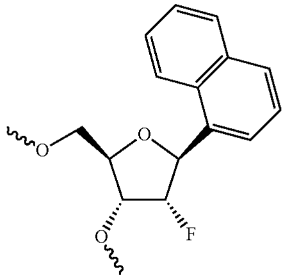

or (fN)

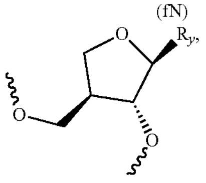

(apN)

wherein $R_y$ is a nucleobase, and any combination thereof; Wherein the modified nucleotide is not a 3' or 5' end cap of the sense strand or antisense strand.

5. A short interfering nucleic acid (siNA) molecule comprising:

(a) a sense strand comprising a first nucleotide sequence that is at least about 90% identical to an RNA corresponding to a target gene, wherein the first nucleotide sequence:

(i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 3, 5, 7, 8, 9, 10, 11, 12, 14, 17, and/or 19 from the 5' end of the first nucleotide sequence is a 2'-fluoro nucleotide or wherein at least one modified nucleotide is a 2'-O-methyl nucleotide and at least one modified nucleotide is a 2'-fluoro nucleotide; and an antisense strand comprising a second nucleotide sequence that is at least about 90% complementary to the RNA corresponding to the target gene, wherein the second nucleotide sequence:

iii) is 15 to 30 nucleotides in length; and (iv) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; or (b) a sense strand comprising a first nucleotide sequence that is at least about 60%, identical to an RNA corresponding to a target gene, wherein the first nucleotide sequence:

(i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence:

(iii) is 15 to 30 nucleotides in length; and (iv) comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 2, 5, 6, 8, 10, 14, 16, 17, and/or 18 from the 5' end of the second nucleotide sequence is a 2'-fluoro nucleotide;

wherein the sense strand and/or the antisense strand comprise at least one modified nucleotide according to claim 1;

wherein the modified nucleotide is not a 5' end cap of the sense strand or antisense strand.

6. The siNA molecule of claim 4, wherein the antisense strand comprises a 5'-stabilized end cap selected from:

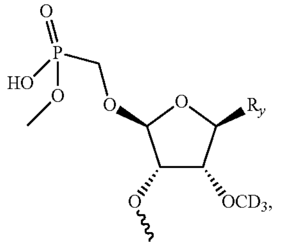

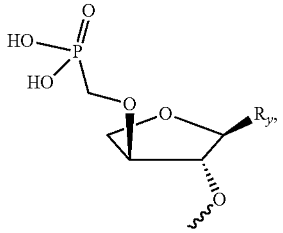

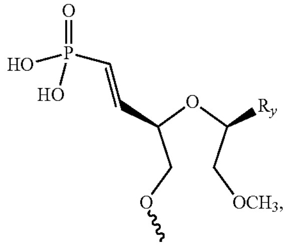

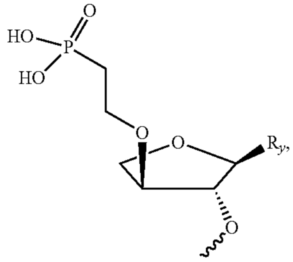

-continued

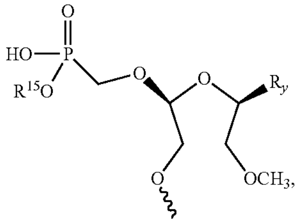

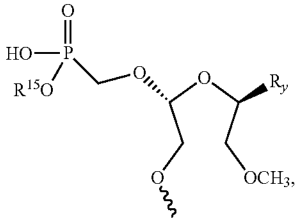

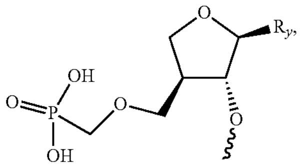

or

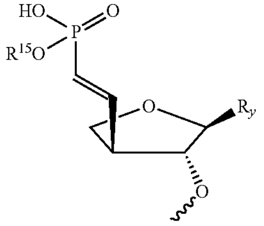

wherein $R_y$ is a nucleobase and $R^{15}$ is H or $CH_3$.

7. The siNA molecule according to claim 4, wherein the antisense strand comprises a 5'-stabilized end cap selected from the group consisting of Formula (1) to Formula (16), Formula (9X) to Formula (12X), Formula (16X), Formula (9Y) to Formula (12Y), Formula (16Y), Formula (21) to Formula (36), Formula 36X, Formula (41) to (56), Formula (49X) to (52X), Formula (49Y) to (52Y), Formula 56X, Formula 56Y, Formula (61), Formula (62), and Formula (63):

Formula (1)

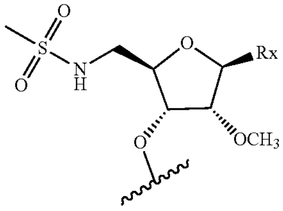

Formula (2)

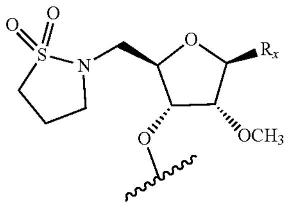

-continued

Formula (3)

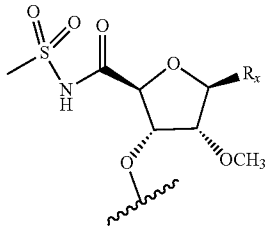

Formula (4)

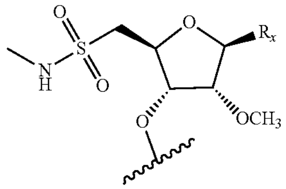

Formula (5)

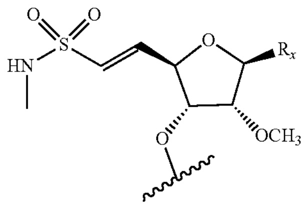

Formula (6)

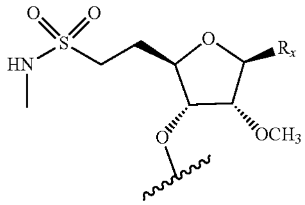

Formula (7)

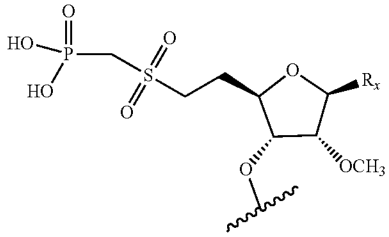

Formula (8)

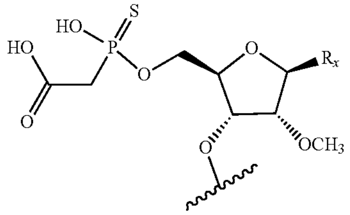

Formula (9)

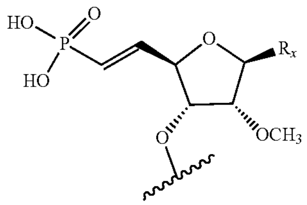

-continued
Formula (9X)
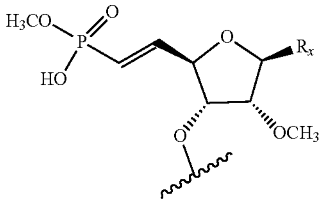
Formula (9Y)
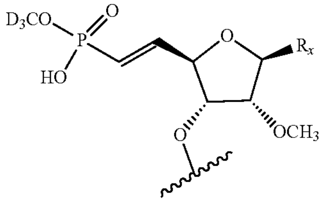
Formula (10)
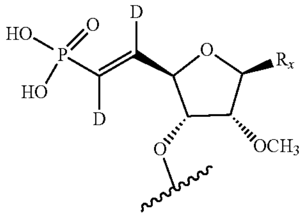
Formula (10X)
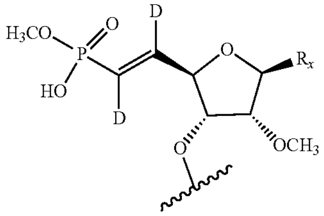
Formula (10Y)
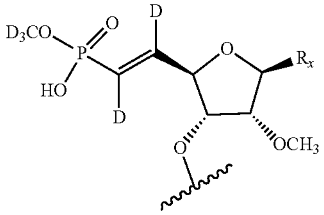
Formula (11)
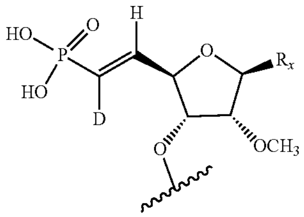
Formula (11X)
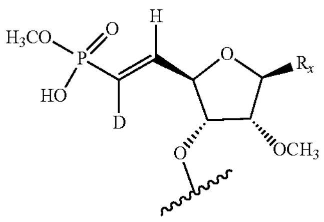
-continued
Formula (11Y)
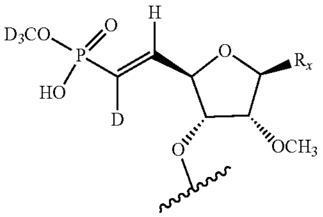
Formula (12)
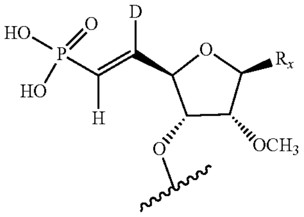
Formula (12X)
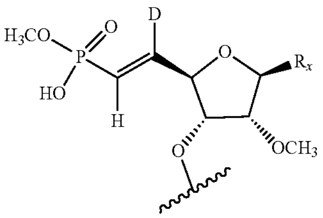
Formula (12Y)
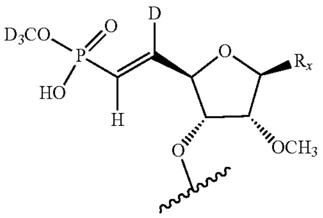
Formula (13)
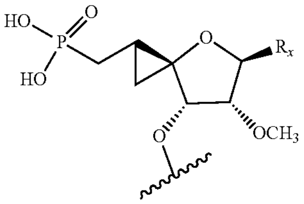
Formula (14)
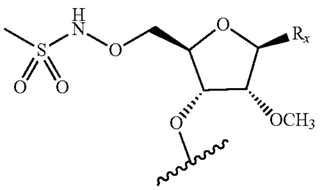
Formula (15)
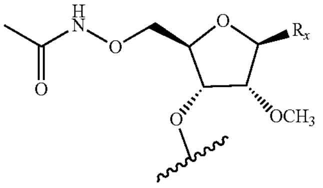

-continued
Formula (16)
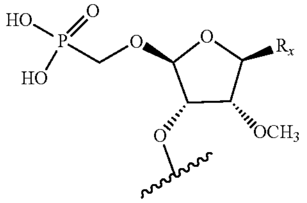
Formula (16X)
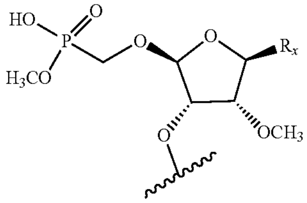
Formula (16Y)
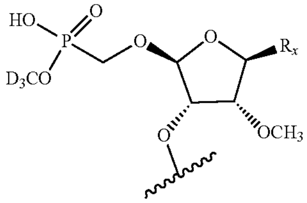
Formula (21)
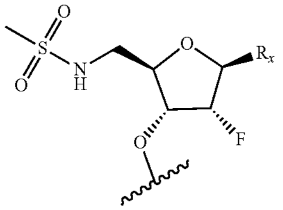
Formula (22)
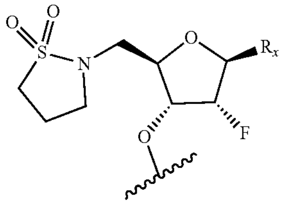
Formula (23)
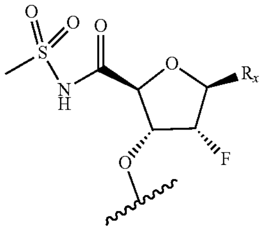
Formula (24)
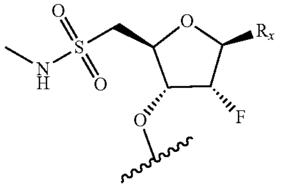
-continued
Formula (25)
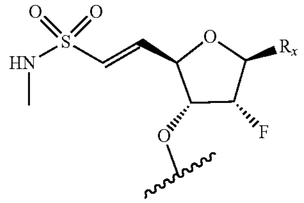
Formula (26)
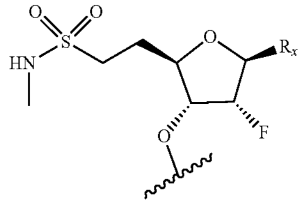
Formula (27)
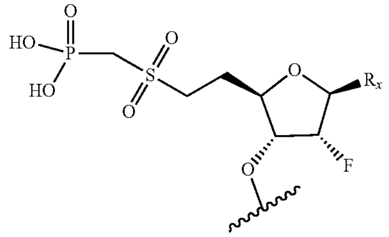
Formula (28)
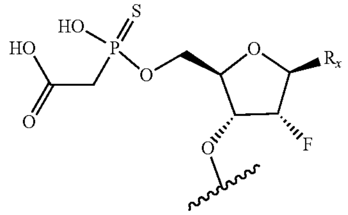
Formula (29)
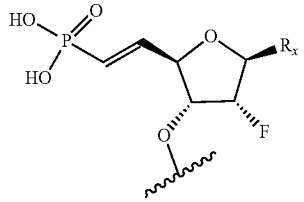
Formula (30)
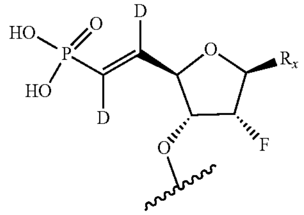
Formula (31)
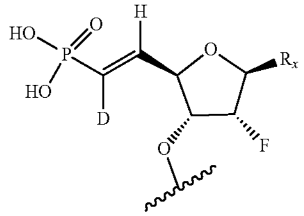

-continued
Formula (32)
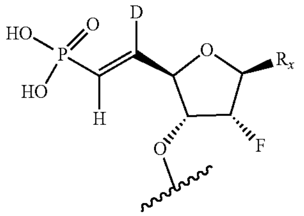
Formula (33)
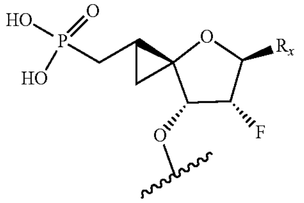
Formula (34)
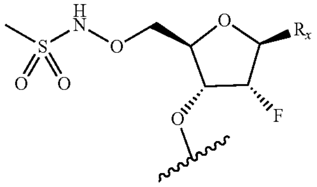
Formula (35)
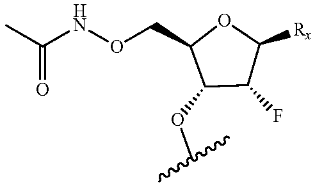
Formula (36)
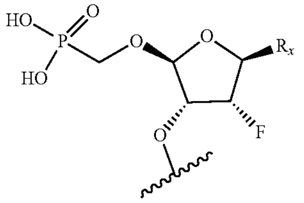
Formula (36X)
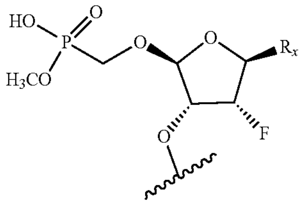
Formula (41)
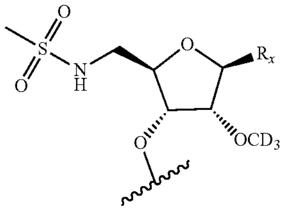
-continued
Formula (42)
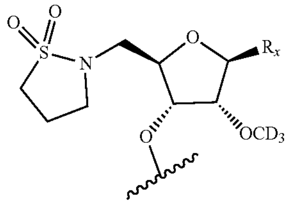
Formula (43)
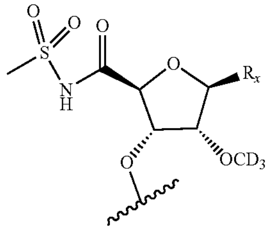
Formula (44)
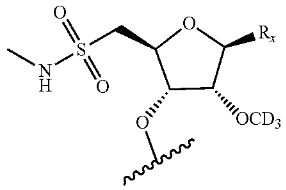
Formula (45)
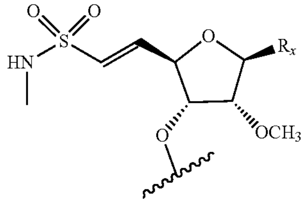
Formula (46)
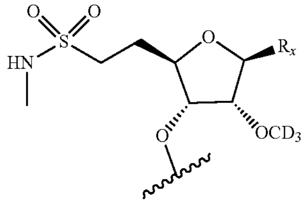
Formula (47)
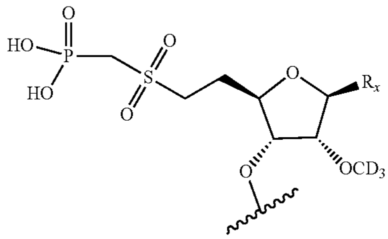
Formula (48)
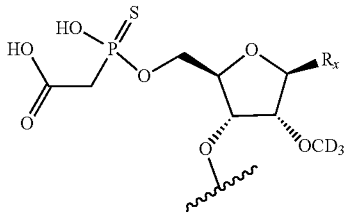

-continued
Formula (49)
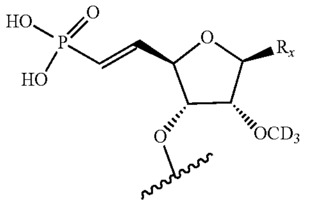
Formula (49X)
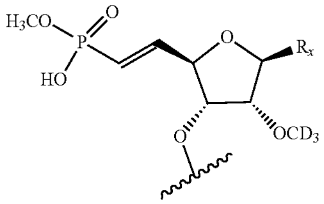
Formula (49Y)
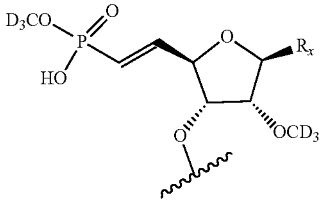
Formula (50)
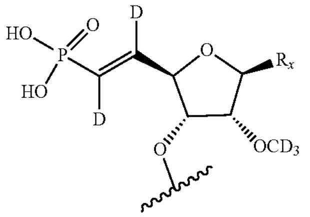
Formula (50X)
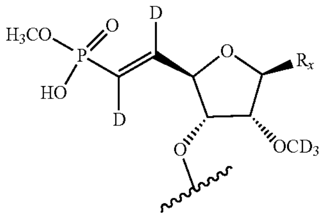
Formula (50Y)
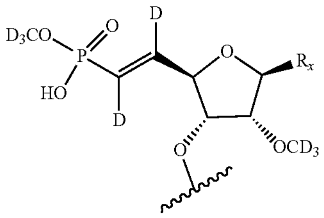
Formula (51)
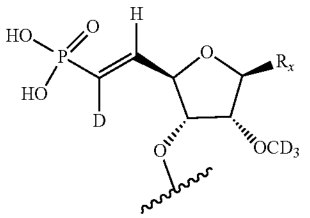
-continued
Formula (51X)
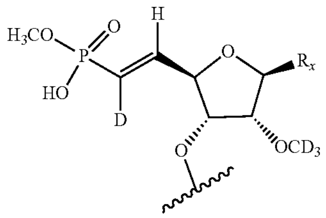
Formula (51Y)
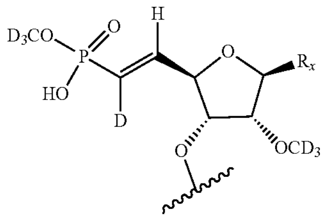
Formula (52)
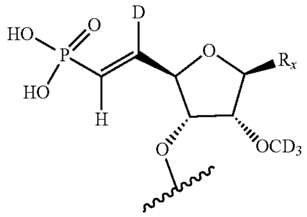
Formula (52X)
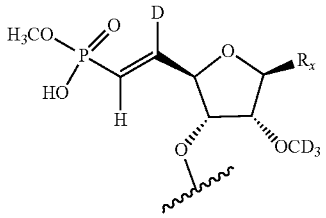
Formula (52Y)
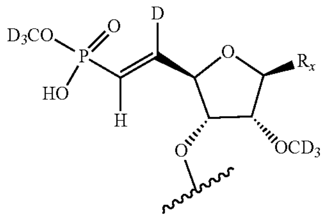
Formula (53)
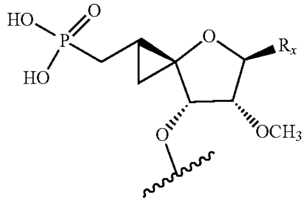
Formula (54)
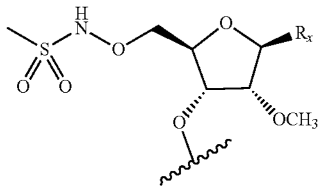

-continued

Formula (55)

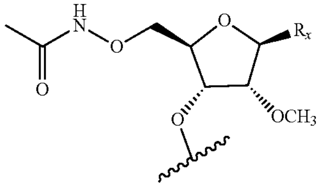

Formula (56)

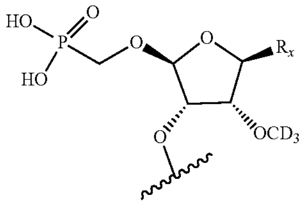

Formula (56X)

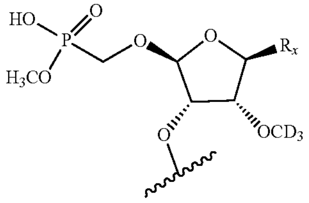

Formula (56Y)

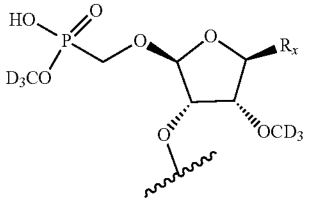

Formula (61)

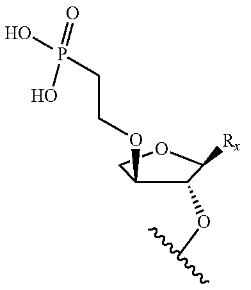

Formula (62)

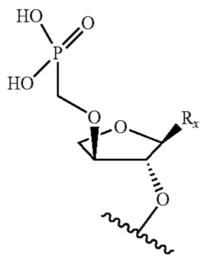

-continued

Formula (63)

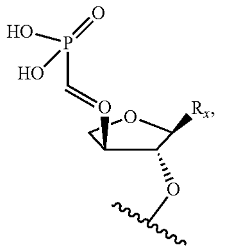

wherein $R_x$ is a nucleobase, aryl, heteroaryl, or H.

8. The siNA molecule according to claim 4, wherein the antisense strand comprises a 5'-stabilized end cap selected from the group consisting of Formula (71) to Formula (86), Formula (79X) to Formula (82X), Formula (79Y) to (82Y), Formula 86X, Formula 86X', Formula 86Y, and Formula 86Y':

Formula (71)

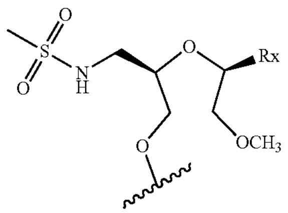

Formula (72)

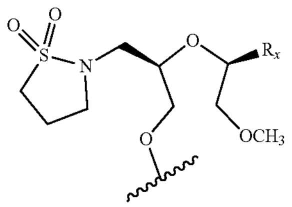

Formula (73)

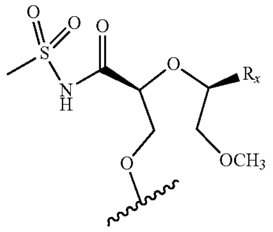

Formula (74)

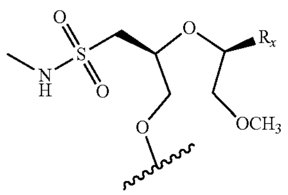

Formula (75)

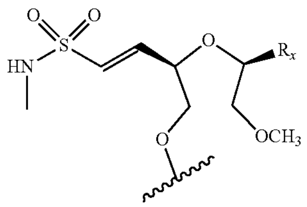

-continued
Formula (76)
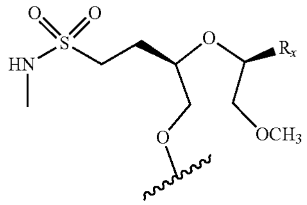
Formula (77)
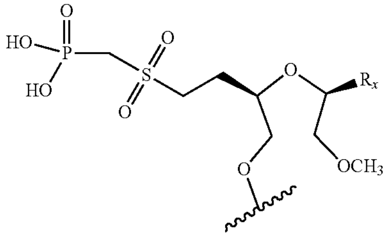
Formula (78)
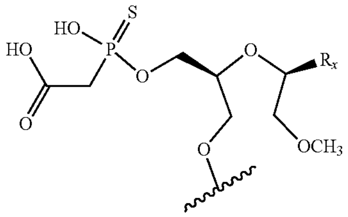
Formula (79)
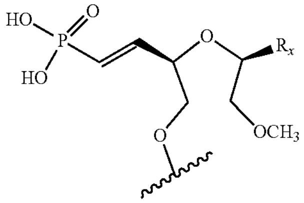
Formula (79X)
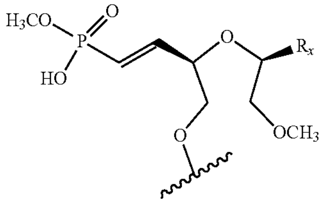
Formula (79Y)
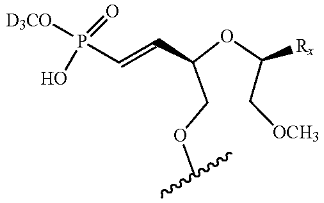
Formula (80)
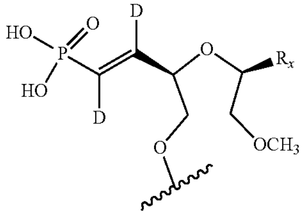
-continued
Formula (80X)
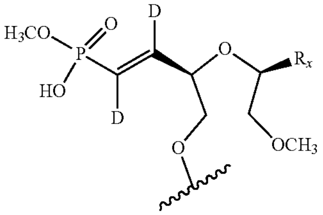
Formula (80Y)
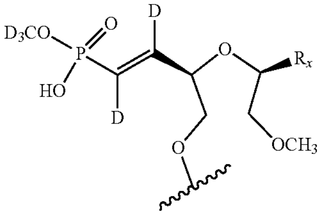
Formula (81)
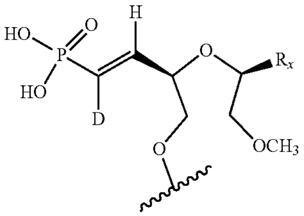
Formula (81X)
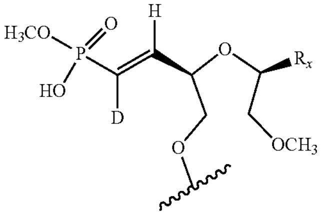
Formula (81Y)
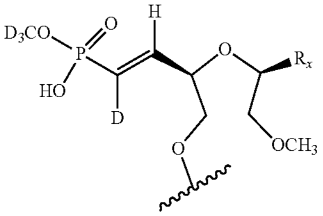
Formula (82)
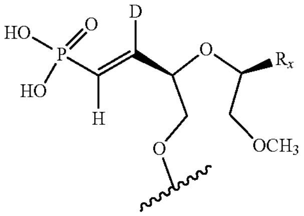
Formula (82X)
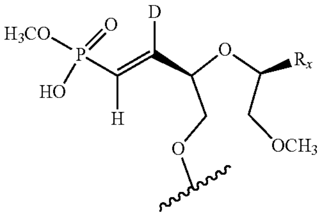

-continued

Formula (82Y)

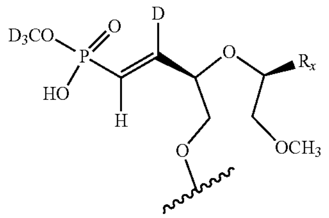

Formula (83)

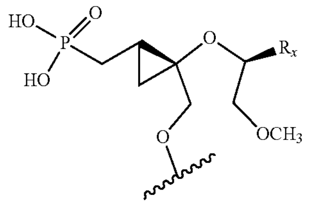

Formula (84)

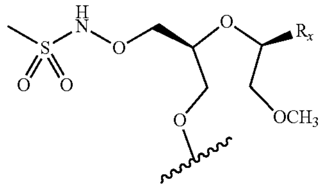

Formula (85)

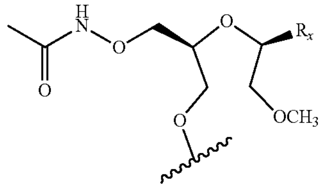

Formula (86)

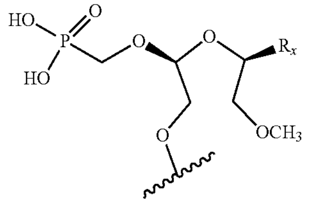

Formula (86X)

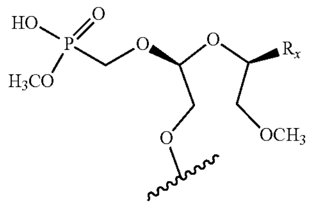

Formula (86X′)

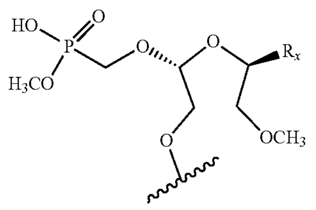

-continued

Formula (86Y)

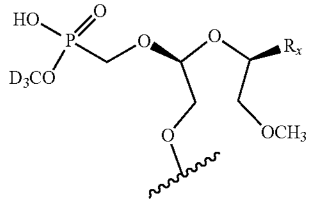

Formula (86Y′)

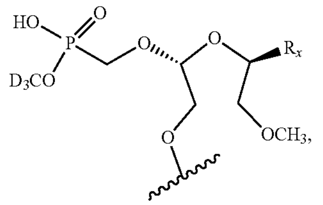

wherein $R_x$ is a nucleobase, aryl, heteroaryl, or H.

9. The siNA molecule according to claim 4, wherein the antisense strand comprises a 5'-stabilized end cap selected from the group consisting of Formulas (1A)-(15A), Formulas (1A-1)-(7A-1), Formulas (1A-2)-(7A-2), Formulas (1A-3)-(7A-3), Formulas (1A-4)-(7A-4), Formulas (9B)-(12B), Formulas (9AX)-(12AX), Formulas (9AY)-(12AY), Formulas (9BX)-(12BX), and Formulas (9BY)-(12BY):

Formula (1A)

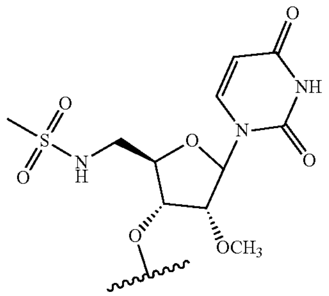

Formula (2A)

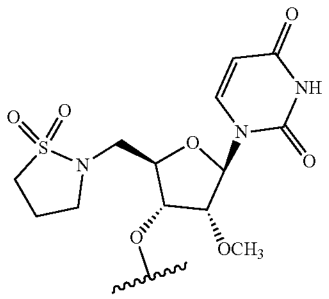

Formula (3A)

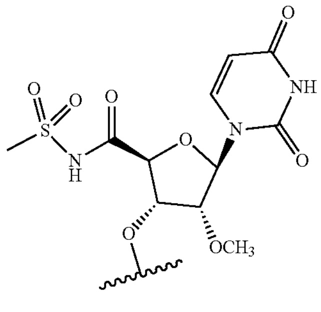

-continued
Formula (4A)
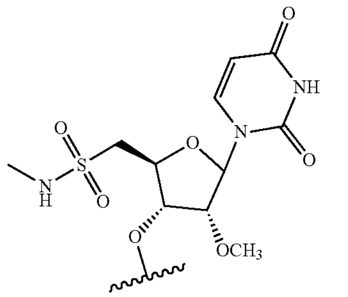
Formula (1A-1)
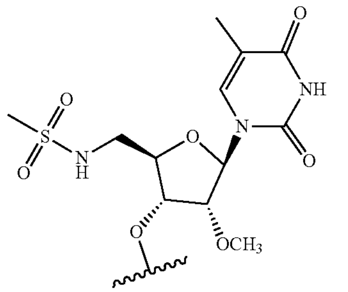
Formula (2A-1)
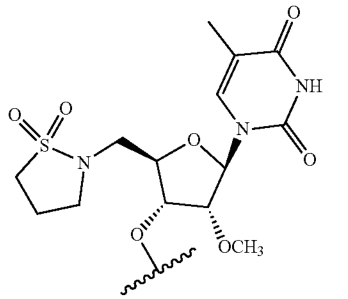
Formula (3A-1)
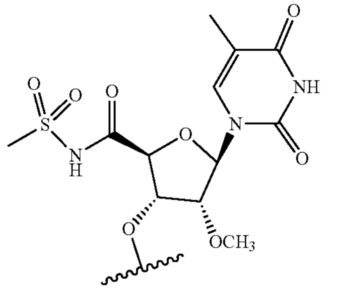
Formula (4A-1)
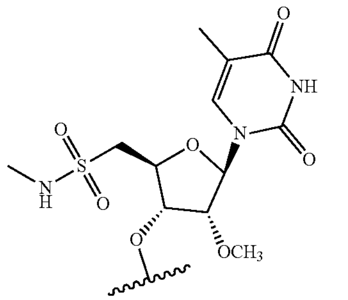
-continued
Formula (1A-2)
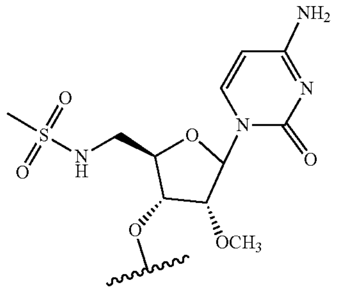
Formula (2A-2)
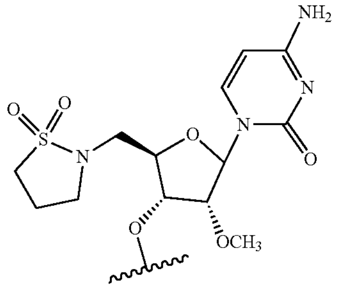
Formula (3A-2)
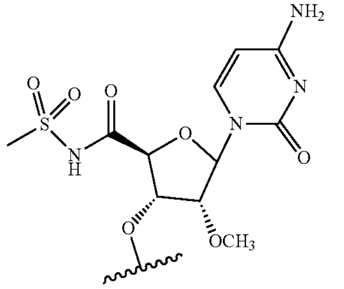
Formula (4A-2)
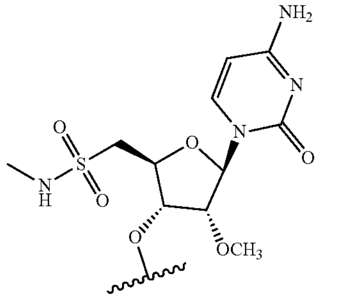
Formula (1A-3)
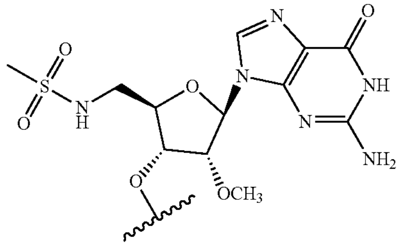

-continued
Formula (2A-3)
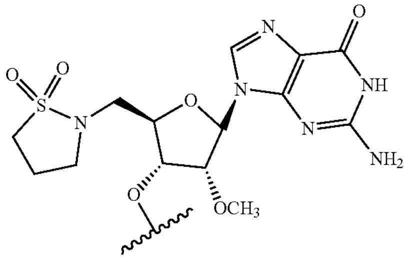
Formula (3A-3)
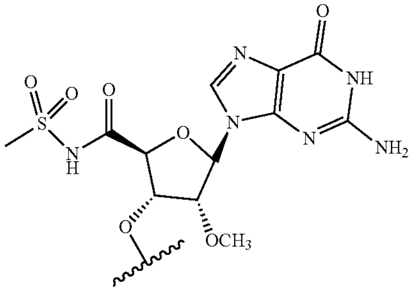
Formula (4A-3)
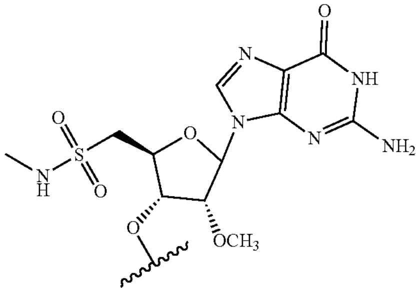
Formula (1A-4)
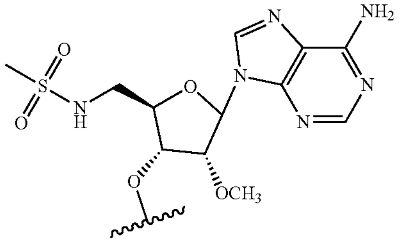
Formula (2A-4)
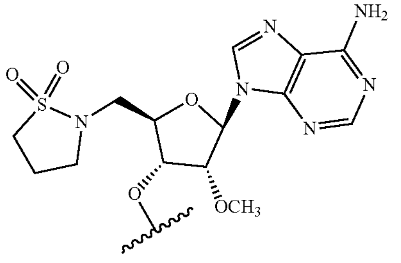
-continued
Formula (3A-4)
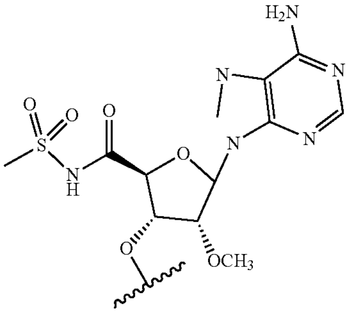
Formula (4A-4)
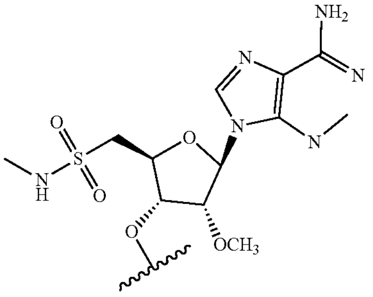
Formula (5A)
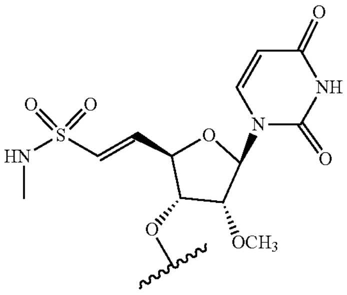
Formula (5A-1)
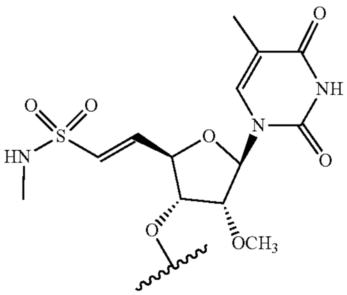
Formula (5A-2)
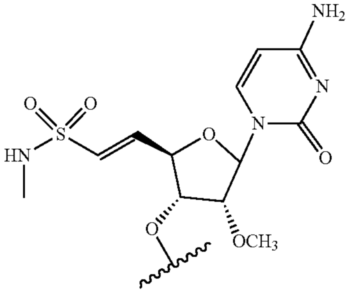

-continued
Formula (5A-3)
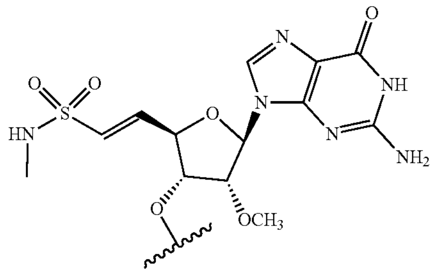
Formula (5A-4)
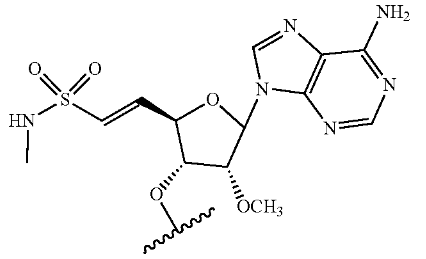
Formula (6A)
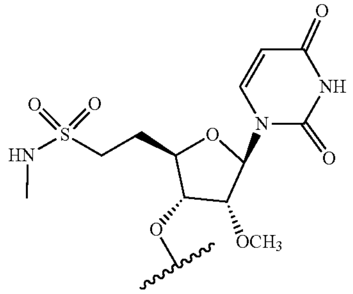
Formula (6A-1)
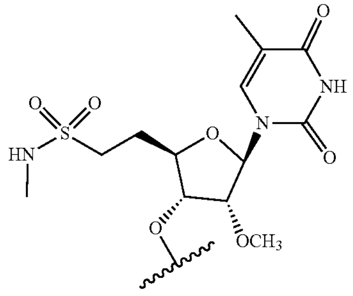
Formula (6A-2)
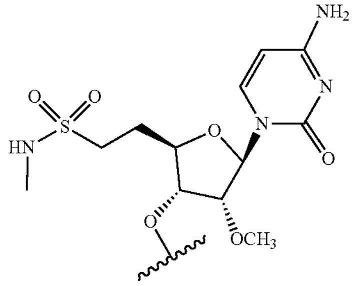
-continued
Formula (6A-3)
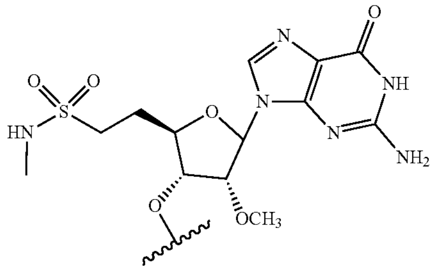
Formula (6A-4)
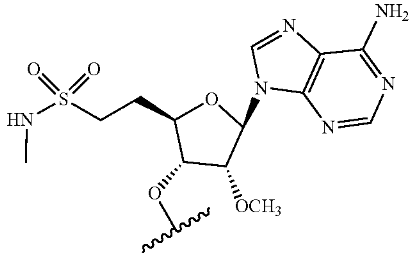
Formula (7A)
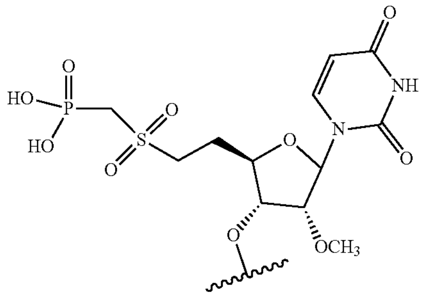
Formula (7A-1)
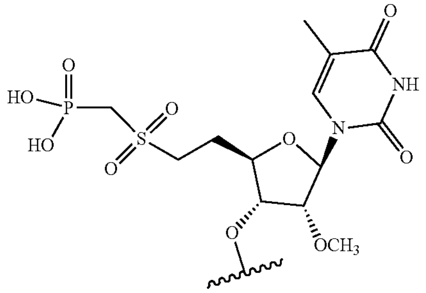
Formula (7A-2)
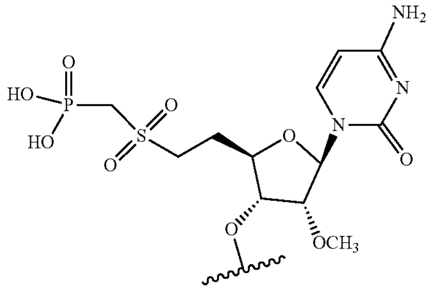

-continued
Formula (7A-3)
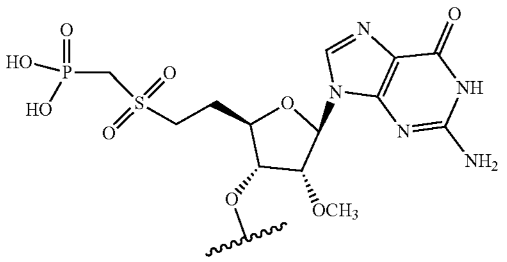
Formula (7A-4)
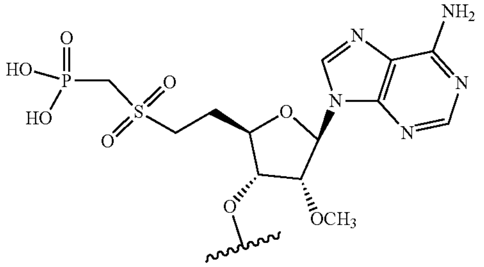
Formula (8A)
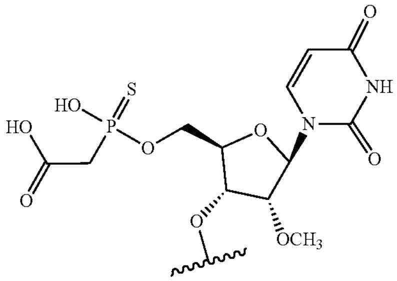
Formula (9A)
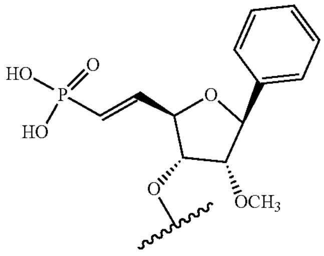
Formula (9AX)
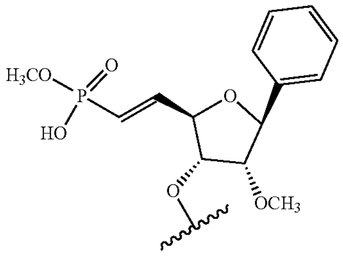
Formula (9AY)
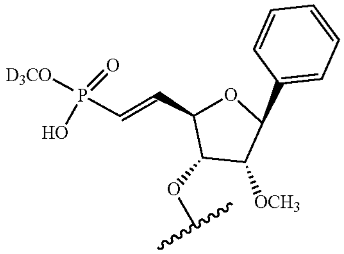
-continued
Formula (9B)
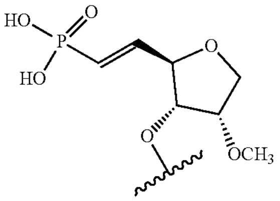
Formula (9BX)
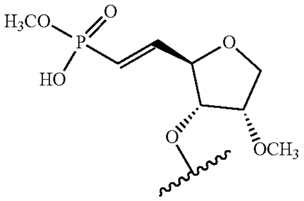
Formula (9BY)
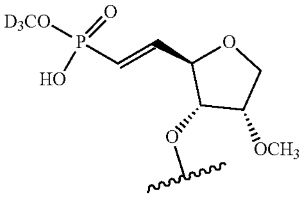
Formula (10A)
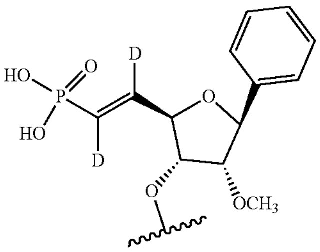
Formula (10AX)
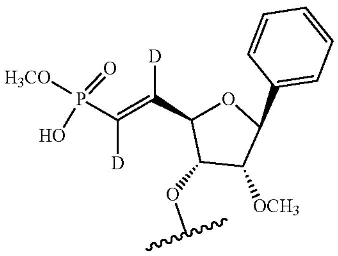
Formula (10AY)
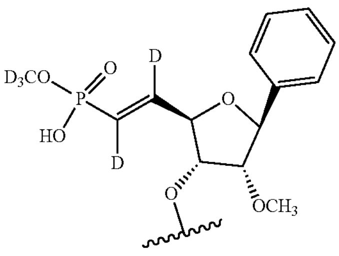
Formula (10B)
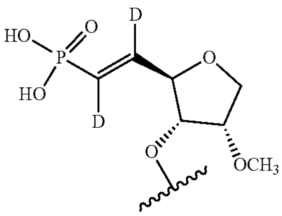

-continued
Formula (10BX)
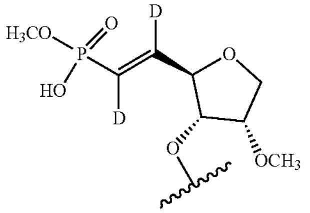
Formula (10BY)
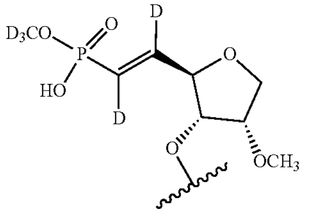
Formula (11A)
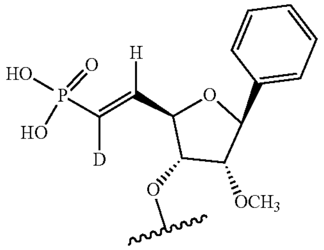
Formula (11AX)
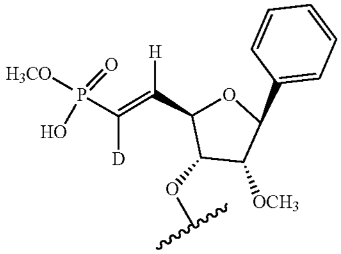
Formula (11AY)
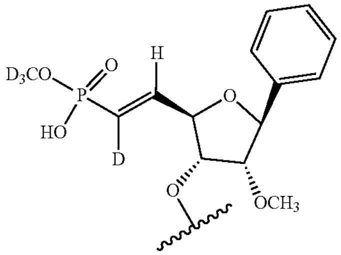
Formula (11B)
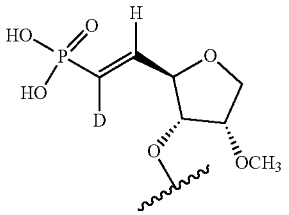
-continued
Formula (11BX)
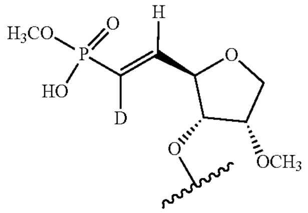
Formula (11BY)
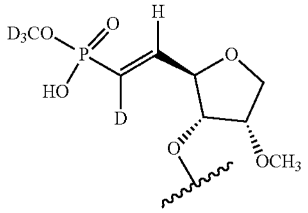
Formula (12A)
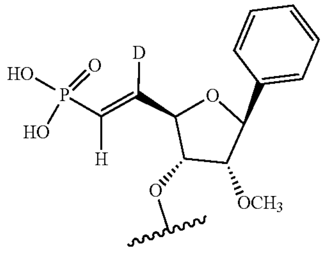
Formula (12AX)
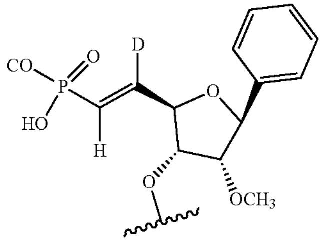
Formula (12AY)
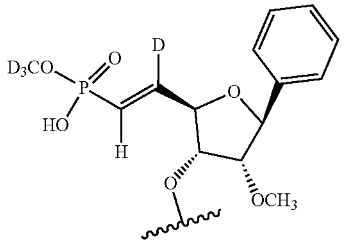
Formula (12B)
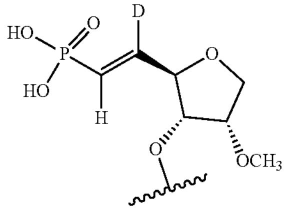
Formula (12BX)
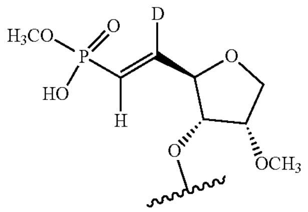

-continued
Formula (12BY)
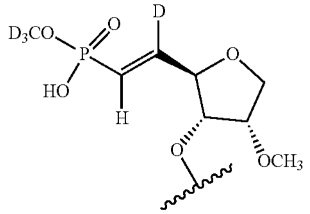
Formula (13A)
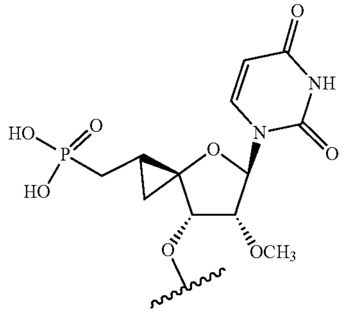
Formula (14A)
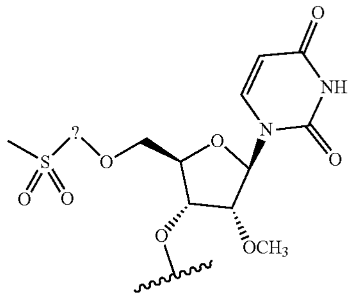
Formula (15A)
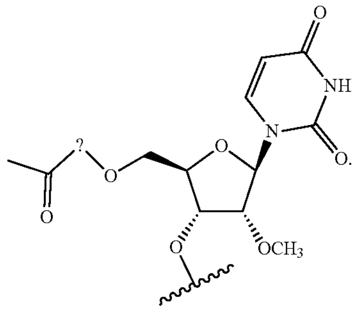
10. The siNA molecule according to claim 4, wherein the antisense strand comprises a 5'-stabilized end cap selected from the group consisting of Formulas (21A)-(35A), Formulas (29B)-(32B), Formulas (29AX)-(32AX), Formulas (29AY)-(32AY), Formulas (29BX)-(32BX), and Formulas (29BY)-(32BY):
Formula (21A)
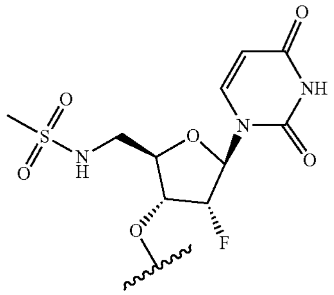
Formula (22A)
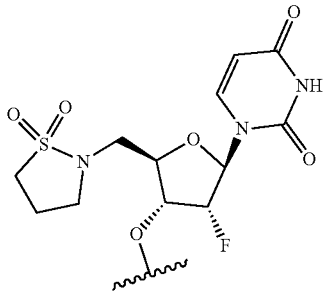
Formula (23A)
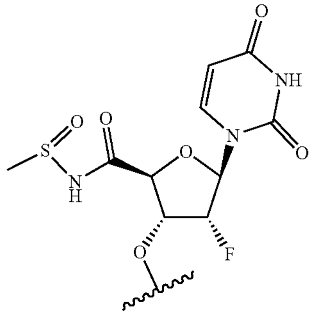
Formula (24A)
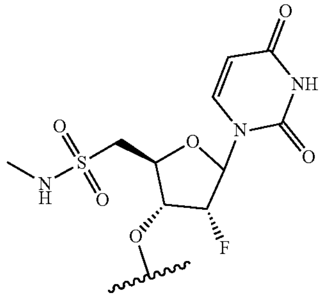
Formula (25A)
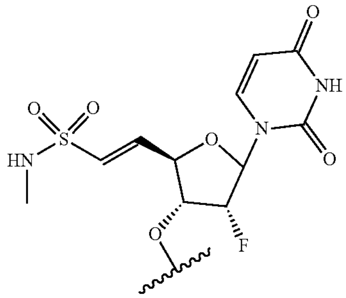

-continued
Formula (26A)
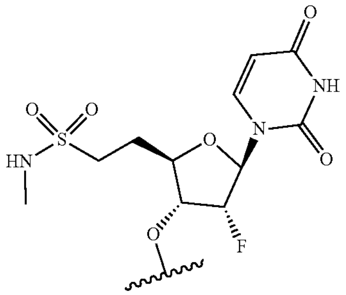
Formula (27A)
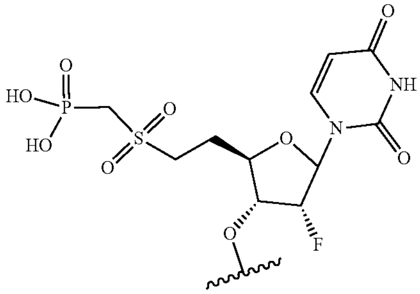
Formula (28A)
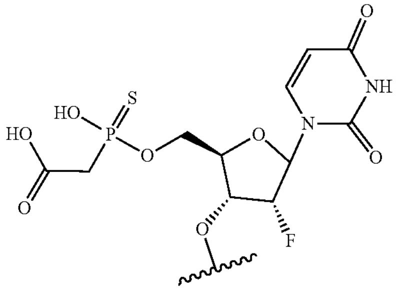
Formula (29A)
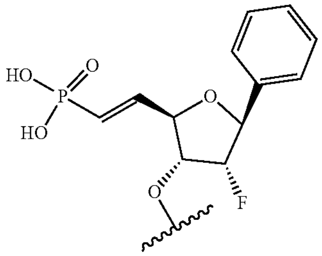
Formula (29AX)
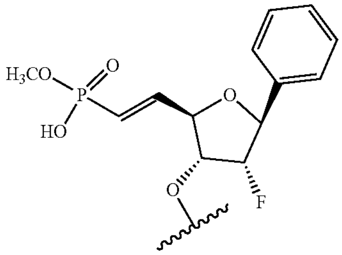
-continued
Formula (29AY)
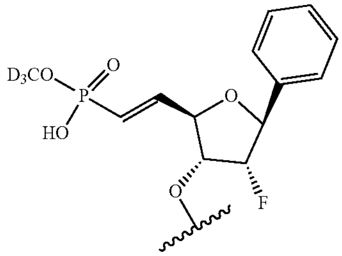
Formula (29B)
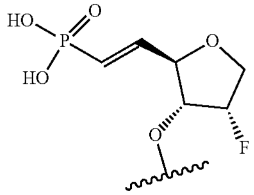
Formula (29BX)
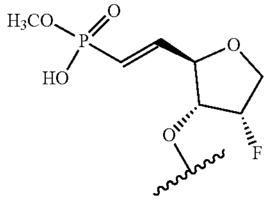
Formula (29BY)
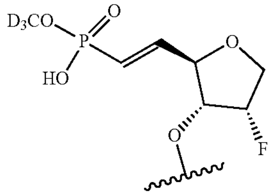
Formula (30A)
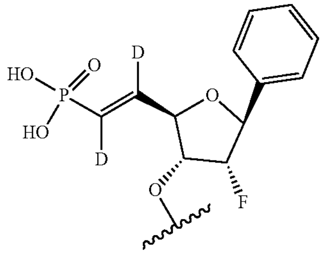
Formula (30AX)
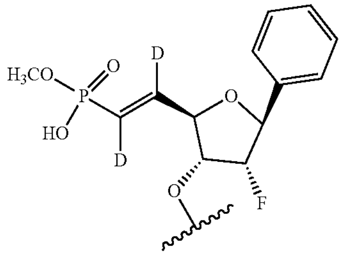

-continued
Formula (30AY)
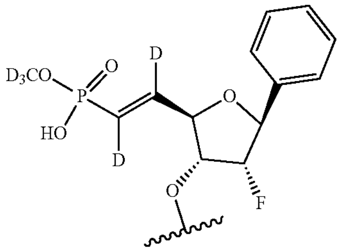
Formula (30B)
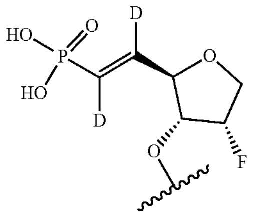
Formula (30BX)
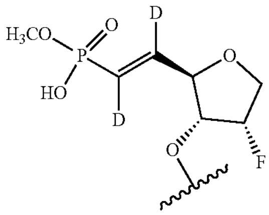
Formula (30BY)
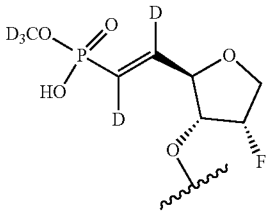
Formula (31A)
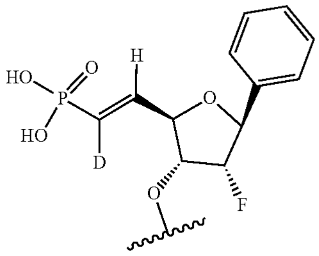
Formula (31AX)
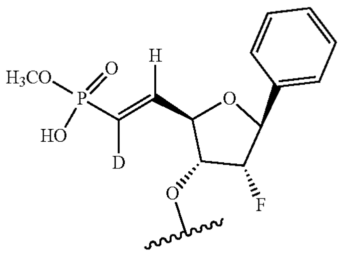
-continued
Formula (31AY)
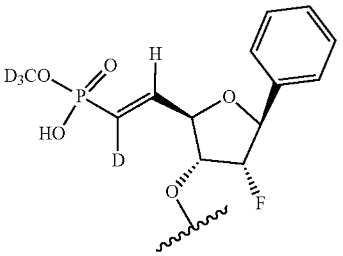
Formula (31B)
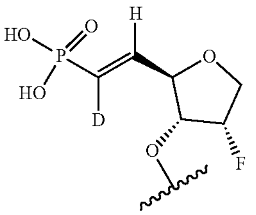
Formula (31BX)
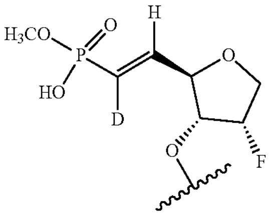
Formula (31BY)
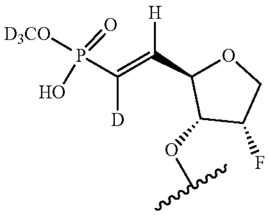
Formula (32A)
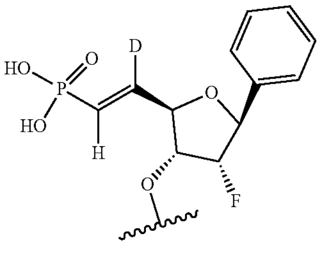
Formula (32AX)
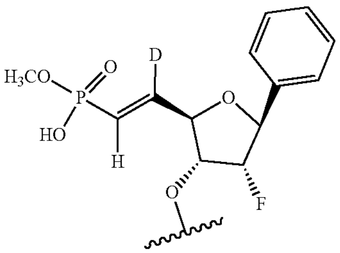

-continued
Formula (32AY)
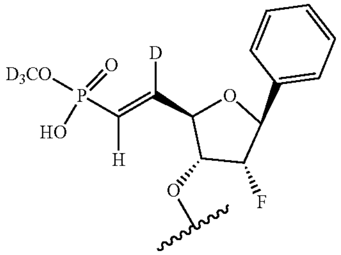
Formula (32B)
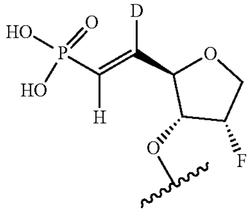
Formula (32BX)
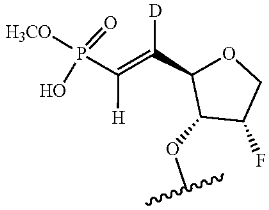
Formula (32BY)
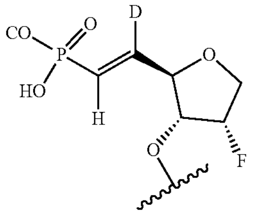
Formula (33A)
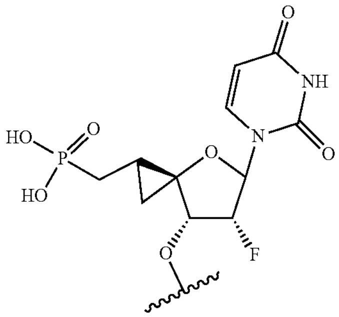
Formula (34A)
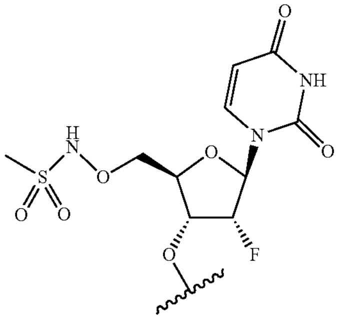
-continued
Formula (35A)
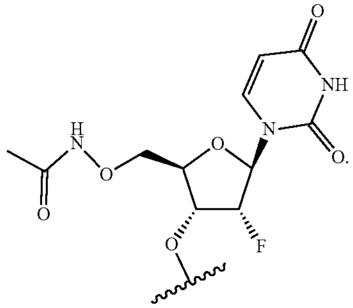
11. The siNA molecule according to claim 4, wherein the antisense strand comprises a 5'-stabilized end cap selected from the group consisting of Formulas (71A)-(86A), Formulas (79XA)-(82XA), Formulas (79YA)-(82YA); Formula (86XA), Formula (86X'A), Formula (86Y), and Formula (86Y'):
Formula (71A)
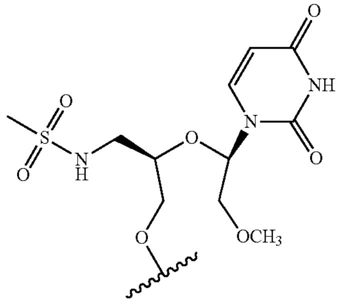
Formula (72A)
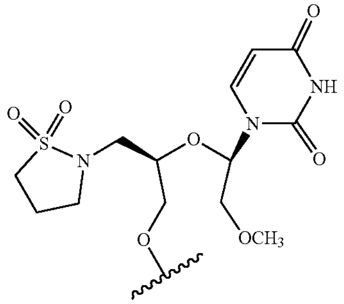
Formula (73A)
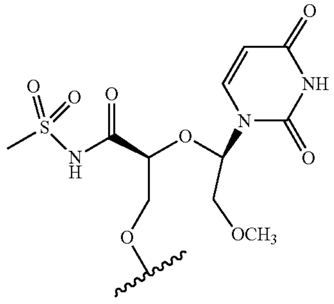

-continued
Formula (74A)
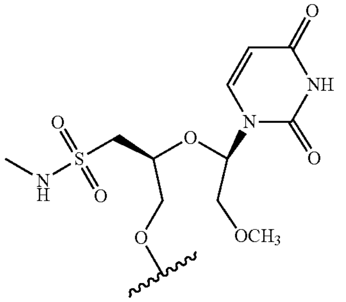
Formula (75A)
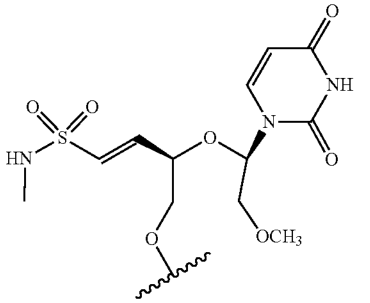
Formula (76A)
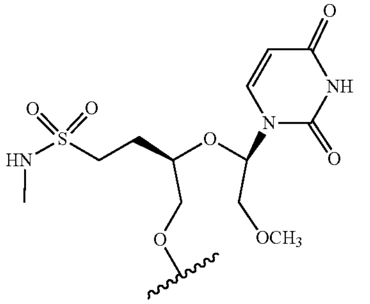
Formula (77A)
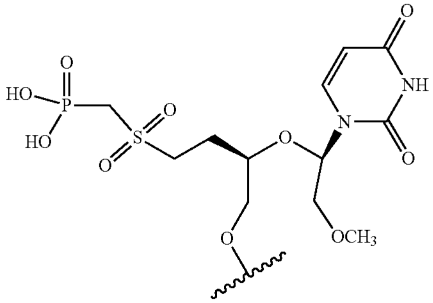
Formula (78A)
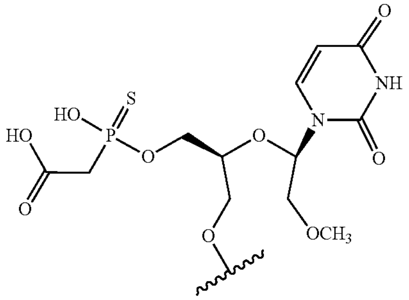
-continued
Formula (79A)
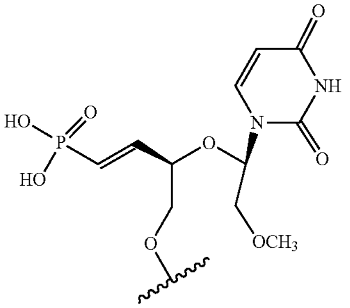
Formula (79XA)
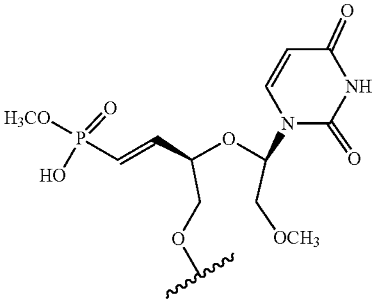
Formula (79YA)
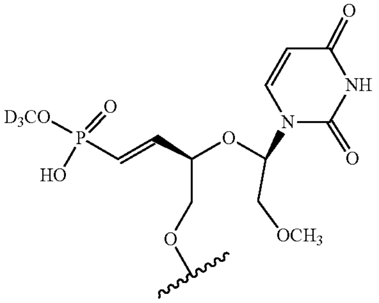
Formula (80A)
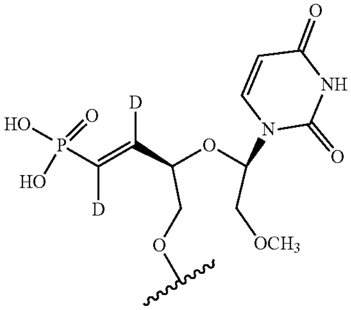
Formula (80XA)
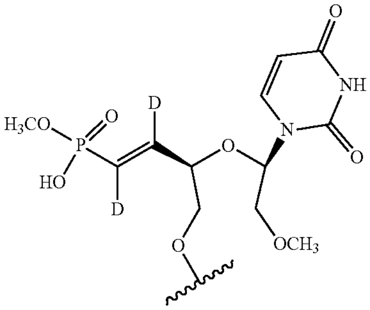

-continued
Formula (80YA)
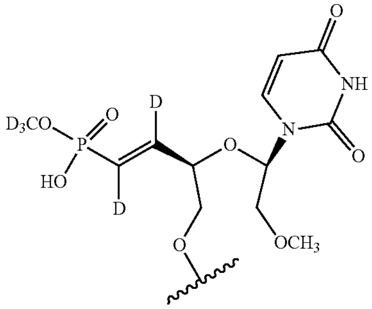
Formula (81A)
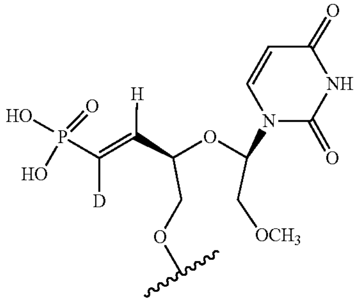
Formula (81XA)
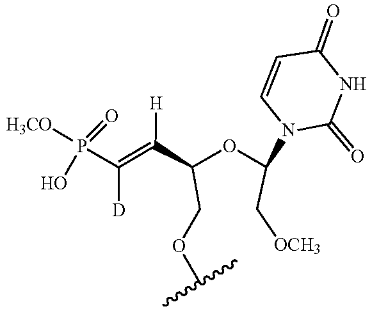
Formula (81YA)
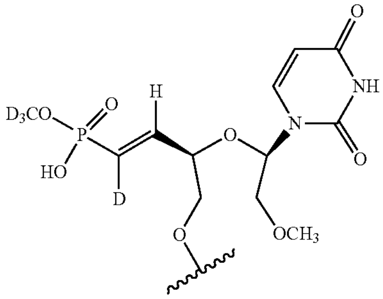
Formula (82A)
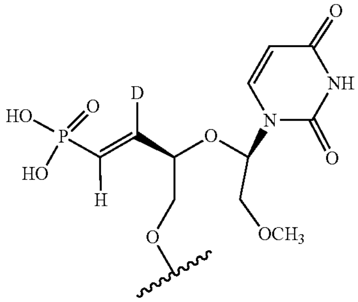
-continued
Formula (82XA)
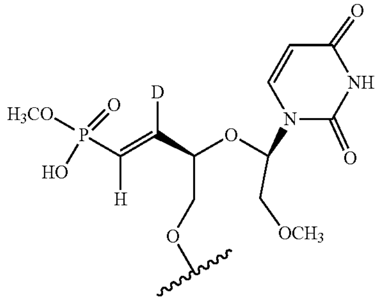
Formula (82YA)
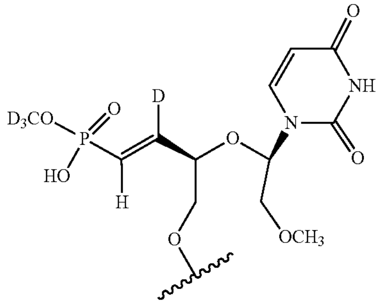
Formula (83A)
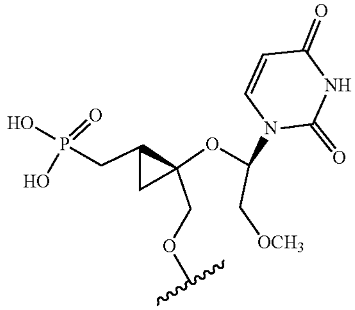
Formula (84A)
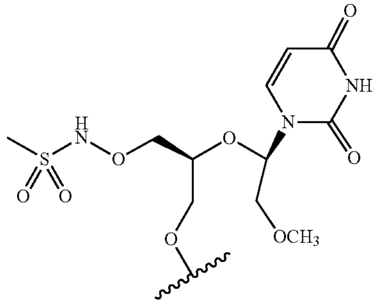
Formula (85A)
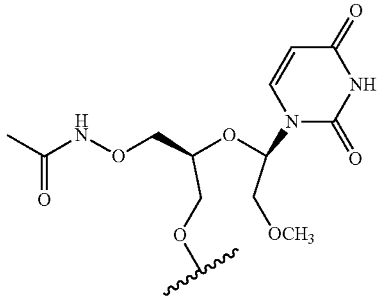

-continued

Formula (86A)

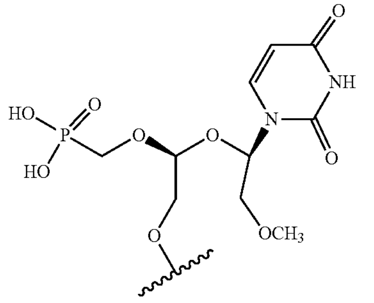

Formula (86XA)

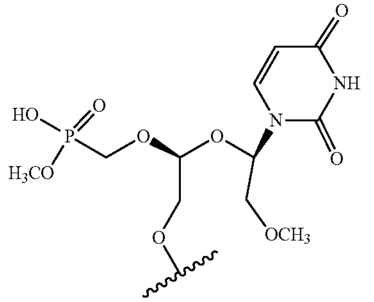

Formula (86X'A)

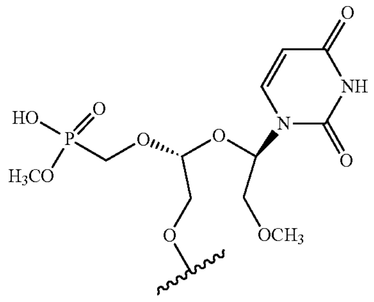

Formula (86Y)

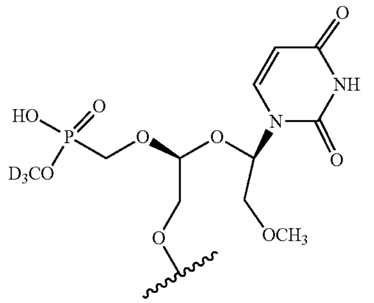

Formula (86Y')

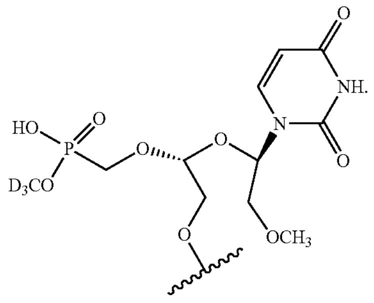

12. The siNA molecule of claim 4, wherein the sense strand and/or the antisense strand independently comprise 1 or more phosphorothioate internucleoside linkages, 1 or more mesyl phosphoroamidate internucleoside linkages, or a combination thereof.

13. The siNA molecule of claim 4, wherein the siNA further comprises a phosphorylation blocker.

14. The siNA molecule of claim 12, wherein:

(i) at least one phosphorothioate internucleoside linkage in the sense strand is between the nucleotides at positions 1 and 2 from the 5' end of the first nucleotide sequence; (ii) at least one phosphorothioate internucleoside linkage is between the nucleotides at positions 2 and 3 from the 5' end of the first nucleotide sequence;

(ii) at least one phosphorothioate internucleoside linkage in the antisense strand is between the nucleotides at positions 1 and 2 from the 5' end of the second nucleotide sequence;

(iii) at least one phosphorothioate internucleoside linkage in the antisense strand is between the nucleotides at positions 2 and 3 from the 5' end of the second nucleotide sequence;

(iv) at least one phosphorothioate internucleoside linkage in the antisense strand is between the nucleotides at positions 1 and 2 from the 3' end of the second nucleotide sequence; and/or (iv) at least one phosphorothioate internucleoside linkage is between the nucleotides at positions 2 and 3 from the 3' end of the second nucleotide sequence.

15. The siNA molecule of claim 12, wherein:

(i) at least one mesyl phosphoroamidate internucleoside linkage in the sense strand is between the nucleotides at positions 1 and 2 from the 5' end of the first nucleotide sequence; (ii) at least one mesyl phosphoroamidate internucleoside linkage is between the nucleotides at positions 2 and 3 from the 5' end of the first nucleotide sequence;

(ii) at least one mesyl phosphoroamidate internucleoside linkage in the antisense strand is between the nucleotides at positions 1 and 2 from the 5' end of the second nucleotide sequence;

(iii) at least one mesyl phosphoroamidate internucleoside linkage in the antisense strand is between the nucleotides at positions 2 and 3 from the 5' end of the second nucleotide sequence;

(iv) at least one mesyl phosphoroamidate internucleoside linkage in the antisense strand is between the nucleotides at positions 1 and 2 from the 3' end of the second nucleotide sequence; and/or (iv) at least one mesyl phosphoroamidate internucleoside linkage is between the nucleotides at positions 2 and 3 from the 3' end of the second nucleotide sequence.

16. The siNA molecule according to claim 4, wherein the siNA further comprises a galactosamine.

17. The siNA according to claim 16, wherein the galactosamine is N-acetylgalactosamine (GalNAc) of Formula (VI):

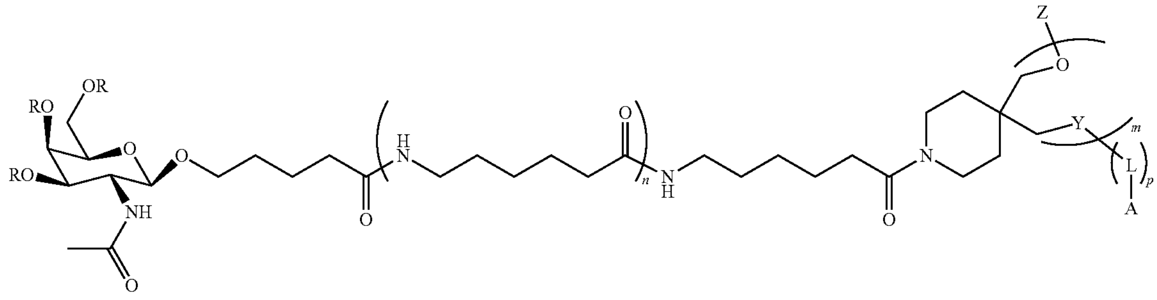

wherein m is 1, 2, 3, 4, or 5;

each n is independently 1 or 2; p is 0 or 1;

each R is independently H;

each Y is independently selected from —O—P(═O)(SH)—, —O—P(═O)(O)—, —O—P(═O)(OH)—, and —O—P(S)S—;

Z is H or a second protecting group;

either L is a linker or L and Y in combination are a linker; and

A is H, OH, a third protecting group, an activated group, or an oligonucleotide.

18. The siNA according to claim 16, wherein the galactosamine is N-acetylgalactosamine (GalNAc) of Formula (VII):

19. The siNA molecule according to claim 4, wherein:

at least one end of the siNA comprises an overhang, wherein the overhang comprises at least one nucleotide.

20. The siNA molecule according to claim 4, wherein;

the target gene is a viral gene.

21. A siNA comprising a nucleotide sequence of any one of SEQ ID Nos: 36, 38, 40, 77, 79, 81, 83, 85, 88, 90, 93, and 95-106.

22. A composition comprising the siNA according to claim 4; and a pharmaceutically acceptable excipient.

23. The composition of claim 22 further comprising 2, or more siNAs comprising a sense strand and an antisense strand, and comprising at least one nucleotide selected from

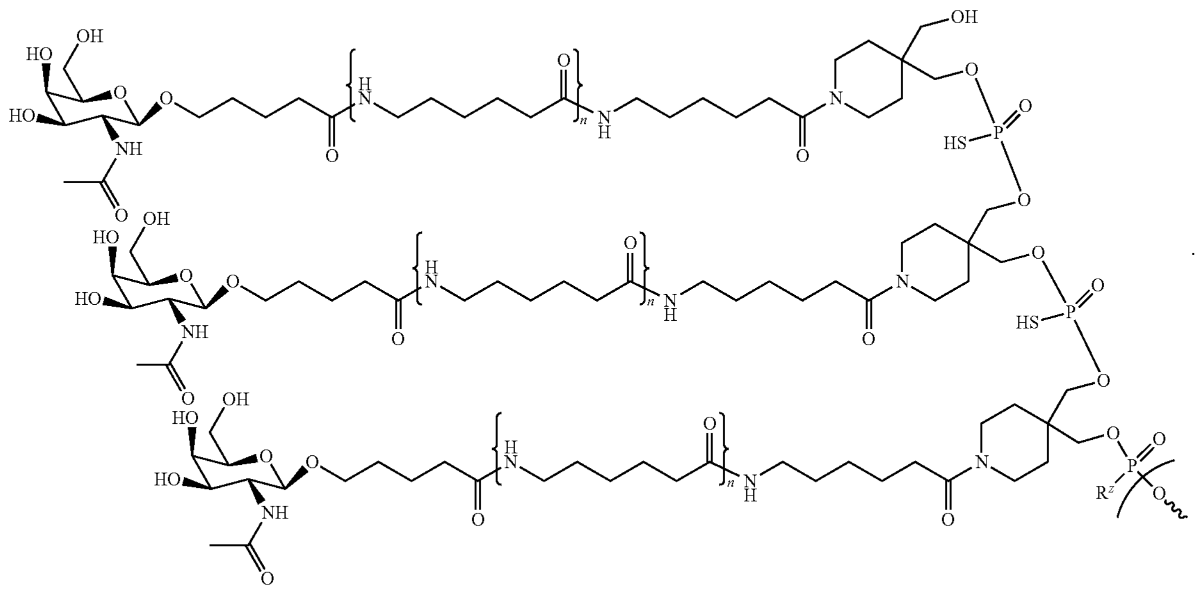

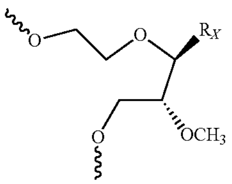

wherein Rx is a nucleobase, aryl, heteroaryl, or H;

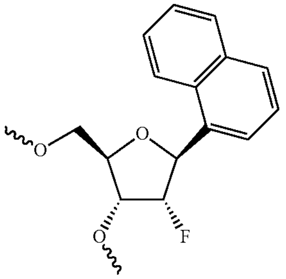

;

(fN)

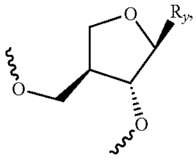

(apN)

wherein $R_y$ is a nucleobase; and any combination thereof.

24. The composition according to claim 22 further comprising an additional treatment agent.

25. The composition of claim 24, wherein the additional treatment agent is selected from a nucleotide analog, nucleoside analog, a capsid assembly modulator (CAM), a recombinant interferon, an entry inhibitor, a small molecule immunomodulatory, and oligonucleotide therapy.

26. The composition of claim 25, wherein the oligonucleotide therapy is an additional siNA, an antisense oligonucleotide (ASO), NAPs, or STOPS™.

27. The siNA molecule according to claim 4, wherein the at least one modified nucleotide is:

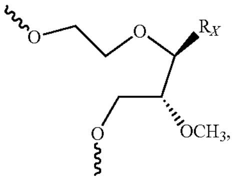

wherein $R_x$ is a nucleobase, aryl, heteroaryl, or H.

28. The siNA molecule according to claim 4, wherein the at least one modified nucleotide is:

(fN)

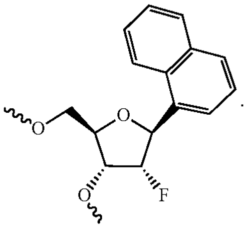

29. The siNA molecule according to claim 4, wherein the at least one modified nucleotide is:

(apN)

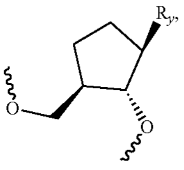

wherein $R_y$ is a nucleobase.

* * * * *

SEQUENCE LISTING

```
Sequence total quantity: 114
SEQ ID NO: 1            moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 1
gtggtggact tctctcaat                                          19

SEQ ID NO: 2            moltype = RNA  length = 21
FEATURE                 Location/Qualifiers
source                  1..21
                        mol_type = other RNA
                        organism = synthetic construct
modified_base           order(1,3..5,7..13,15,17..21)
                        mod_base = OTHER
                        note = 2-prime-O-methyl RNA nucleotides
modified_base           order(2,6,14,16)
                        mod_base = OTHER
                        note = 2-prime-fluoro RNA nucleotides
modified_base           1^2
```

-continued

```
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 2
antgagagaa gtccaccacg a                                         21

SEQ ID NO: 3            moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 3
gtggtggact tctctcaat                                            19

SEQ ID NO: 4            moltype = RNA  length = 21
FEATURE                 Location/Qualifiers
source                  1..21
                        mol_type = other RNA
                        organism = synthetic construct
modified_base           order(1,3..5,7..13,15,17..21)
                        mod_base = OTHER
                        note = 2-prime-O-methyl RNA nucleotides
modified_base           order(2,6,14,16)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 4
attgagagaa gtcnaccacg a                                         21

SEQ ID NO: 5            moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 5
gtggtggact tctctcaat                                            19
```

```
SEQ ID NO: 6            moltype = RNA  length = 21
FEATURE                 Location/Qualifiers
source                  1..21
                        mol_type = other RNA
                        organism = synthetic construct
modified_base           order(1,3..5,7..13,15,17..21)
                        mod_base = OTHER
                        note = 2-prime-O-methyl RNA nucleotides
modified_base           order(2,6,14,16)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 6
attgagagaa gtccancacg a                                                21

SEQ ID NO: 7            moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 7
gtggtggact tctctcaat                                                   19

SEQ ID NO: 8            moltype = RNA  length = 21
FEATURE                 Location/Qualifiers
source                  1..21
                        mol_type = other RNA
                        organism = synthetic construct
modified_base           order(1,3..5,7..13,15,17..21)
                        mod_base = OTHER
                        note = 2-prime-O-methyl RNA nucleotides
modified_base           order(2,6,14,16)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 8
attgagagaa gtcnancacg a                                                21

SEQ ID NO: 9            moltype = RNA  length = 19
FEATURE                 Location/Qualifiers
source                  1..19
                        mol_type = other RNA
                        organism = synthetic construct
modified_base           order(1..4,6,10..19)
```

```
                       mod_base = OTHER
                       note = 2-prime-O-methyl RNA nucleotides
modified_base          order(5,7..9)
                       mod_base = OTHER
                       note = 2-prime-fluoro RNA nucleotides
modified_base          1^2
                       mod_base = OTHER
                       note = phosphorothioate
modified_base          2^3
                       mod_base = OTHER
                       note = phosphorothioate
SEQUENCE: 9
gtggtggact tctctcaat                                              19

SEQ ID NO: 10          moltype = RNA  length = 21
FEATURE                Location/Qualifiers
source                 1..21
                       mol_type = other RNA
                       organism = synthetic construct
modified_base          order(1,3..5,7..13,15,17..21)
                       mod_base = OTHER
                       note = 2-prime-O-methyl RNA nucleotides
modified_base          order(2,6,14,16)
                       mod_base = OTHER
                       note = 2-prime-fluoro RNA nucleotides
modified_base          1^2
                       mod_base = OTHER
                       note = phosphorothioate
modified_base          2^3
                       mod_base = OTHER
                       note = phosphorothioate
modified_base          19^20
                       mod_base = OTHER
                       note = phosphorothioate
modified_base          20^21
                       mod_base = OTHER
                       note = phosphorothioate
SEQUENCE: 10
abtgagagaa gtccaccacg a                                           21

SEQ ID NO: 11          moltype = RNA  length = 19
FEATURE                Location/Qualifiers
source                 1..19
                       mol_type = other RNA
                       organism = synthetic construct
modified_base          order(1..4,6,10..19)
                       mod_base = OTHER
                       note = 2-prime-O-methyl RNA nucleotides
modified_base          order(5,7..9)
                       mod_base = OTHER
                       note = 2-prime-fluoro RNA nucleotides
modified_base          1^2
                       mod_base = OTHER
                       note = phosphorothioate
modified_base          2^3
                       mod_base = OTHER
                       note = phosphorothioate
SEQUENCE: 11
gtggtggact tctctcaat                                              19

SEQ ID NO: 12          moltype = RNA  length = 21
FEATURE                Location/Qualifiers
source                 1..21
                       mol_type = other RNA
                       organism = synthetic construct
modified_base          order(1,3..5,7..13,15,17..21)
                       mod_base = OTHER
                       note = 2-prime-O-methyl RNA nucleotides
modified_base          order(2,6,14,16)
                       mod_base = OTHER
                       note = 2-prime-fluoro RNA nucleotides
modified_base          1^2
                       mod_base = OTHER
                       note = phosphorothioate
modified_base          2^3
                       mod_base = OTHER
                       note = phosphorothioate
modified_base          19^20
                       mod_base = OTHER
```

```
                        note = phosphorothioate
modified_base           20^21
                        mod_base = OTHER
                        note = phosphorothioate
SEQUENCE: 12
attgagagaa gtcbaccacg a                                       21

SEQ ID NO: 13           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 13
gtggtggact tctctcaat                                          19

SEQ ID NO: 14           moltype = RNA  length = 21
FEATURE                 Location/Qualifiers
source                  1..21
                        mol_type = other RNA
                        organism = synthetic construct
modified_base           order(1,3..5,7..13,15,17..21)
                        mod_base = OTHER
                        note = 2-prime-O-methyl RNA nucleotides
modified_base           order(2,6,14,16)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 14
attgagagaa gtcbabcacg a                                       21

SEQ ID NO: 15           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 15
gtggtggact tctctcaat                                          19

SEQ ID NO: 16           moltype = RNA  length = 21
FEATURE                 Location/Qualifiers
source                  1..21
                        mol_type = other RNA
                        organism = synthetic construct
modified_base           order(1,3..5,7..13,15,17..21)
```

```
                          mod_base = OTHER
                          note = 2-prime-O-methyl RNA nucleotides
modified_base             order(2,6,14,16)
                          mod_base = OTHER
                          note = 2-prime-fluoro RNA nucleotides
modified_base             1^2
                          mod_base = OTHER
                          note = phosphorothioate
modified_base             2^3
                          mod_base = OTHER
                          note = phosphorothioate
modified_base             19^20
                          mod_base = OTHER
                          note = phosphorothioate
modified_base             20^21
                          mod_base = OTHER
                          note = phosphorothioate
SEQUENCE: 16
attgagagaa gtcnaccacg a                                        21

SEQ ID NO: 17             moltype = RNA  length = 19
FEATURE                   Location/Qualifiers
source                    1..19
                          mol_type = other RNA
                          organism = synthetic construct
modified_base             order(1..4,6,10..19)
                          mod_base = OTHER
                          note = 2-prime-O-methyl RNA nucleotides
modified_base             order(5,7..9)
                          mod_base = OTHER
                          note = 2-prime-fluoro RNA nucleotides
modified_base             1^2
                          mod_base = OTHER
                          note = phosphorothioate
modified_base             2^3
                          mod_base = OTHER
                          note = phosphorothioate
SEQUENCE: 17
ccgtgtgcac ttcgcttca                                           19

SEQ ID NO: 18             moltype = RNA  length = 21
FEATURE                   Location/Qualifiers
source                    1..21
                          mol_type = other RNA
                          organism = synthetic construct
modified_base             order(1,3,4,6,7,9..13,15,16,18..21)
                          mod_base = OTHER
                          note = 2-prime-O-methyl RNA nucleotides
modified_base             order(2,5,8,14,17)
                          mod_base = OTHER
                          note = 2-prime-fluoro RNA nucleotides
modified_base             1^2
                          mod_base = OTHER
                          note = phosphorothioate
modified_base             2^3
                          mod_base = OTHER
                          note = phosphorothioate
modified_base             19^20
                          mod_base = OTHER
                          note = phosphorothioate
modified_base             20^21
                          mod_base = OTHER
                          note = phosphorothioate
SEQUENCE: 18
tgaagcgaag tgcacacggt c                                        21

SEQ ID NO: 19             moltype = RNA  length = 19
FEATURE                   Location/Qualifiers
source                    1..19
                          mol_type = other RNA
                          organism = synthetic construct
modified_base             order(1..4,6,10..19)
                          mod_base = OTHER
                          note = 2-prime-O-methyl RNA nucleotides
modified_base             order(5,7..9)
                          mod_base = OTHER
                          note = 2-prime-fluoro RNA nucleotides
modified_base             1^2
                          mod_base = OTHER
```

```
                        note = phosphorothioate
modified_base           2^3
                        mod_base = OTHER
                        note = phosphorothioate
SEQUENCE: 19
ccgtgtgcac ttcgcttca                                          19

SEQ ID NO: 20           moltype = RNA  length = 21
FEATURE                 Location/Qualifiers
source                  1..21
                        mol_type = other RNA
                        organism = synthetic construct
modified_base           order(1,3,4,6,7,9..13,15,16,18..21)
                        mod_base = OTHER
                        note = 2-prime-O-methyl RNA nucleotides
modified_base           order(2,5,8,14,17)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 20
tgaagcgaag tgcacacggt c                                       21

SEQ ID NO: 21           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 21
ccgtgtgcac ttcgcttca                                          19

SEQ ID NO: 22           moltype = RNA  length = 21
FEATURE                 Location/Qualifiers
source                  1..21
                        mol_type = other RNA
                        organism = synthetic construct
modified_base           order(1,3,4,6,7,9..13,15,16,18..21)
                        mod_base = OTHER
                        note = 2-prime-O-methyl RNA nucleotides
modified_base           order(2,5,8,14,17)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 22
tgaagcgaag tgcacacggt c                                       21
```

```
SEQ ID NO: 23           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 23
ccgtgtgcac ttcgcttca                                                19

SEQ ID NO: 24           moltype = RNA  length = 21
FEATURE                 Location/Qualifiers
source                  1..21
                        mol_type = other RNA
                        organism = synthetic construct
modified_base           order(1,3,4,6,7,9..13,15,16,18..21)
                        mod_base = OTHER
                        note = 2-prime-O-methyl RNA nucleotides
modified_base           order(2,5,8,14,17)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 24
tgaagcgaag tgcacacggt c                                             21

SEQ ID NO: 25           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 25
ccgtgtgcac ttcgcttca                                                19

SEQ ID NO: 26           moltype = RNA  length = 21
FEATURE                 Location/Qualifiers
source                  1..21
                        mol_type = other RNA
                        organism = synthetic construct
modified_base           order(1,3,4,6,7,9..13,15,16,18..21)
                        mod_base = OTHER
                        note = 2-prime-O-methyl RNA nucleotides
modified_base           order(2,5,8,14,17)
                        mod_base = OTHER
                        note = 2-prime-fluoro RNA nucleotides
modified_base           1^2
                        mod_base = OTHER
```

```
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 26
tgaagcgaag tgcacacggt c                                                 21

SEQ ID NO: 27           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 27
ccgtgtgcac ttcgcttca                                                    19

SEQ ID NO: 28           moltype = RNA  length = 21
FEATURE                 Location/Qualifiers
source                  1..21
                        mol_type = other RNA
                        organism = synthetic construct
modified_base           order(1,3,4,6,7,9..13,15,16,18..21)
                        mod_base = OTHER
                        note = 2-prime-O-methyl RNA nucleotides
modified_base           order(2,5,8,14,17)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 28
tgaagcgaag tgcacacggt c                                                 21

SEQ ID NO: 29           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 29
ccgtgtgcac ttcgcttca                                                    19
```

```
SEQ ID NO: 30           moltype = RNA  length = 21
FEATURE                 Location/Qualifiers
source                  1..21
                        mol_type = other RNA
                        organism = synthetic construct
modified_base           order(1,3,4,6,7,9..13,15,16,18..21)
                        mod_base = OTHER
                        note = 2-prime-O-methyl RNA nucleotides
modified_base           order(2,5,8,14,17)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 30
tgaagcgaag tgcacacggt c                                     21

SEQ ID NO: 31           moltype =   length =
SEQUENCE: 31
000

SEQ ID NO: 32           moltype =   length =
SEQUENCE: 32
000

SEQ ID NO: 33           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 33
gtggtggact tctctcaat                                        19

SEQ ID NO: 34           moltype = RNA  length = 21
FEATURE                 Location/Qualifiers
source                  1..21
                        mol_type = other RNA
                        organism = synthetic construct
modified_base           order(1,3..5,7..13,15,17..21)
                        mod_base = OTHER
                        note = 2-prime-O-methyl RNA nucleotides
modified_base           order(2,6,14,16)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 34
attgagagaa gtccancacg a                                     21
```

```
SEQ ID NO: 35           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 35
ccgtgtgcac ttcgcttca                                               19

SEQ ID NO: 36           moltype = RNA  length = 21
FEATURE                 Location/Qualifiers
source                  1..21
                        mol_type = other RNA
                        organism = synthetic construct
modified_base           order(1,3,4,7,9..13,15,16,18..21)
                        mod_base = OTHER
                        note = 2-prime-O-methyl RNA nucleotides
modified_base           order(2,5,8,14,17)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
modified_base           6
                        mod_base = OTHER
                        note = 3-prime,4-prime seco modified nucleotide
SEQUENCE: 36
tgaagcgaag tgcacacggt c                                            21

SEQ ID NO: 37           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 37
ccgtgtgcac ttcgcttca                                               19

SEQ ID NO: 38           moltype = RNA  length = 21
FEATURE                 Location/Qualifiers
source                  1..21
                        mol_type = other RNA
                        organism = synthetic construct
modified_base           order(1,3,4,6,9..13,15,16,18..21)
                        mod_base = OTHER
                        note = 2-prime-O-methyl RNA nucleotides
modified_base           order(2,5,8,14,17)
```

```
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
modified_base           7
                        mod_base = OTHER
                        note = 3-prime,4-prime seco modified nucleotide
SEQUENCE: 38
tgaagcgaag tgcacacggt c                                          21

SEQ ID NO: 39           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 39
ccgtgtgcac ttcgcttca                                             19

SEQ ID NO: 40           moltype = RNA  length = 21
FEATURE                 Location/Qualifiers
source                  1..21
                        mol_type = other RNA
                        organism = synthetic construct
modified_base           order(1,3,4,6,9..13,15,16,18..21)
                        mod_base = OTHER
                        note = 2-prime-O-methyl RNA nucleotides
modified_base           order(2,5,8,14,17)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
modified_base           7
                        mod_base = OTHER
                        note = 3-prime,4-prime seco modified nucleotide
SEQUENCE: 40
tgaagcgaag tgcacacggt c                                          21

SEQ ID NO: 41           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
```

```
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 41
gtggtggact tctctcaat                                             19

SEQ ID NO: 42           moltype = RNA  length = 21
FEATURE                 Location/Qualifiers
source                  1..21
                        mol_type = other RNA
                        organism = synthetic construct
modified_base           order(1,3..5,7..13,15,17..21)
                        mod_base = OTHER
                        note = 2-prime-O-methyl RNA nucleotides
modified_base           order(2,6,14,16)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 42
attgagagaa gtccaccacg a                                          21

SEQ ID NO: 43           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 43
ccgtgtgcac ttcgcttca                                             19

SEQ ID NO: 44           moltype = RNA  length = 21
FEATURE                 Location/Qualifiers
source                  1..21
                        mol_type = other RNA
                        organism = synthetic construct
modified_base           order(1,3,4,6,7,9..13,15,16,18..21)
                        mod_base = OTHER
                        note = 2-prime-O-methyl RNA nucleotides
modified_base           order(2,5,8,14,17)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
```

```
SEQUENCE: 44
tgaagcgaag tgcacacggt c                                              21

SEQ ID NO: 45          moltype = RNA  length = 19
FEATURE                Location/Qualifiers
source                 1..19
                       mol_type = other RNA
                       organism = synthetic construct
modified_base          order(1..4,6,10..19)
                       mod_base = OTHER
                       note = 2-prime-O-methyl RNA nucleotides
modified_base          order(5,7..9)
                       mod_base = OTHER
                       note = 2-prime-fluoro RNA nucleotides
modified_base          1^2
                       mod_base = OTHER
                       note = phosphorothioate
modified_base          2^3
                       mod_base = OTHER
                       note = phosphorothioate
SEQUENCE: 45
ccgtgtgcac ttcgcttca                                                 19

SEQ ID NO: 46          moltype = RNA  length = 21
FEATURE                Location/Qualifiers
source                 1..21
                       mol_type = other RNA
                       organism = synthetic construct
modified_base          order(1,3,4,6,7,9..13,15,16,18..21)
                       mod_base = OTHER
                       note = 2-prime-O-methyl RNA nucleotides
modified_base          order(2,5,8,14,17)
                       mod_base = OTHER
                       note = 2-prime-fluoro RNA nucleotides
modified_base          1^2
                       mod_base = OTHER
                       note = phosphorothioate
modified_base          2^3
                       mod_base = OTHER
                       note = phosphorothioate
modified_base          19^20
                       mod_base = OTHER
                       note = phosphorothioate
modified_base          20^21
                       mod_base = OTHER
                       note = phosphorothioate
SEQUENCE: 46
tgaagcgaag tgcacacggt c                                              21

SEQ ID NO: 47          moltype = RNA  length = 19
FEATURE                Location/Qualifiers
source                 1..19
                       mol_type = other RNA
                       organism = synthetic construct
modified_base          order(1..4,6,10..19)
                       mod_base = OTHER
                       note = 2-prime-O-methyl RNA nucleotides
modified_base          order(5,7..9)
                       mod_base = OTHER
                       note = 2-prime-fluoro RNA nucleotides
modified_base          1^2
                       mod_base = OTHER
                       note = phosphorothioate
modified_base          2^3
                       mod_base = OTHER
                       note = phosphorothioate
SEQUENCE: 47
ccgtgtgcac ttcgcttca                                                 19

SEQ ID NO: 48          moltype = RNA  length = 21
FEATURE                Location/Qualifiers
source                 1..21
                       mol_type = other RNA
                       organism = synthetic construct
modified_base          order(1,3,4,6,7,9..13,15,16,18..21)
                       mod_base = OTHER
                       note = 2-prime-O-methyl RNA nucleotides
modified_base          order(2,5,8,14,17)
                       mod_base = OTHER
```

```
                         note = 2-prime-fluoro RNA nucleotides
modified_base            1^2
                         mod_base = OTHER
                         note = phosphorothioate
modified_base            2^3
                         mod_base = OTHER
                         note = phosphorothioate
modified_base            19^20
                         mod_base = OTHER
                         note = phosphorothioate
modified_base            20^21
                         mod_base = OTHER
                         note = phosphorothioate
SEQUENCE: 48
tgaagcgaag tgcacacggt c                                        21

SEQ ID NO: 49            moltype = RNA  length = 19
FEATURE                  Location/Qualifiers
source                   1..19
                         mol_type = other RNA
                         organism = synthetic construct
modified_base            order(1..4,6,10..19)
                         mod_base = OTHER
                         note = 2-prime-O-methyl RNA nucleotides
modified_base            order(5,7..9)
                         mod_base = OTHER
                         note = 2-prime-fluoro RNA nucleotides
modified_base            1^2
                         mod_base = OTHER
                         note = phosphorothioate
modified_base            2^3
                         mod_base = OTHER
                         note = phosphorothioate
SEQUENCE: 49
ccgtgtgcac ttcgcttca                                           19

SEQ ID NO: 50            moltype = RNA  length = 21
FEATURE                  Location/Qualifiers
source                   1..21
                         mol_type = other RNA
                         organism = synthetic construct
modified_base            order(1,3,4,6,7,9..13,15,16,18..21)
                         mod_base = OTHER
                         note = 2-prime-O-methyl RNA nucleotides
modified_base            order(2,5,8,14,17)
                         mod_base = OTHER
                         note = 2-prime-fluoro RNA nucleotides
modified_base            1^2
                         mod_base = OTHER
                         note = phosphorothioate
modified_base            2^3
                         mod_base = OTHER
                         note = phosphorothioate
modified_base            19^20
                         mod_base = OTHER
                         note = phosphorothioate
modified_base            20^21
                         mod_base = OTHER
                         note = phosphorothioate
SEQUENCE: 50
tgaagcgaag tgcacacggt c                                        21

SEQ ID NO: 51            moltype = RNA  length = 19
FEATURE                  Location/Qualifiers
source                   1..19
                         mol_type = other RNA
                         organism = synthetic construct
modified_base            order(1..4,6,10..19)
                         mod_base = OTHER
                         note = 2-prime-O-methyl RNA nucleotides
modified_base            order(5,7..9)
                         mod_base = OTHER
                         note = 2-prime-fluoro RNA nucleotides
modified_base            1^2
                         mod_base = OTHER
                         note = phosphorothioate
modified_base            2^3
                         mod_base = OTHER
                         note = phosphorothioate
```

-continued

```
SEQUENCE: 51
ccgtgtgcac ttcgcttca                                             19

SEQ ID NO: 52          moltype = RNA  length = 21
FEATURE                Location/Qualifiers
source                 1..21
                       mol_type = other RNA
                       organism = synthetic construct
modified_base          order(1,3,4,6,7,9..13,15,16,18..21)
                       mod_base = OTHER
                       note = 2-prime-O-methyl RNA nucleotides
modified_base          order(2,5,8,14,17)
                       mod_base = OTHER
                       note = 2-prime-fluoro RNA nucleotides
modified_base          1^2
                       mod_base = OTHER
                       note = phosphorothioate
modified_base          2^3
                       mod_base = OTHER
                       note = phosphorothioate
modified_base          19^20
                       mod_base = OTHER
                       note = phosphorothioate
modified_base          20^21
                       mod_base = OTHER
                       note = phosphorothioate
SEQUENCE: 52
tgaagcgaag tgcacacggt c                                          21

SEQ ID NO: 53          moltype = RNA  length = 19
FEATURE                Location/Qualifiers
source                 1..19
                       mol_type = other RNA
                       organism = synthetic construct
modified_base          order(1..4,6,10..19)
                       mod_base = OTHER
                       note = 2-prime-O-methyl RNA nucleotides
modified_base          order(5,7..9)
                       mod_base = OTHER
                       note = 2-prime-fluoro RNA nucleotides
modified_base          1^2
                       mod_base = OTHER
                       note = phosphorothioate
modified_base          2^3
                       mod_base = OTHER
                       note = phosphorothioate
SEQUENCE: 53
ccgtgtgcac ttcgcttca                                             19

SEQ ID NO: 54          moltype = RNA  length = 21
FEATURE                Location/Qualifiers
source                 1..21
                       mol_type = other RNA
                       organism = synthetic construct
modified_base          order(1,3,4,6,7,9..13,15,16,18..21)
                       mod_base = OTHER
                       note = 2-prime-O-methyl RNA nucleotides
modified_base          order(2,5,8,14,17)
                       mod_base = OTHER
                       note = 2-prime-fluoro RNA nucleotides
modified_base          1^2
                       mod_base = OTHER
                       note = phosphorothioate
modified_base          2^3
                       mod_base = OTHER
                       note = phosphorothioate
modified_base          19^20
                       mod_base = OTHER
                       note = phosphorothioate
modified_base          20^21
                       mod_base = OTHER
                       note = phosphorothioate
SEQUENCE: 54
tgaagcgaag tgcacacggt c                                          21

SEQ ID NO: 55          moltype = DNA  length = 3182
FEATURE                Location/Qualifiers
source                 1..3182
                       mol_type = other DNA
```

organism = Hepatitis B virus
SEQUENCE: 55
aattccacaa cctttcacca aactctgcaa gatcccagag tgagaggcct gtatttccct 60
gctggtggct ccagttcagg agcagtaaac cctgttccga ctactgcctc tcccttatcg 120
tcaatcttct cgaggattgg ggaccctgcg ctgaacatgg agaacatcac atcaggattc 180
ctaggacccc ttctcgtgtt acaggcgggg tttttcttgt tgacaagaat cctcacaata 240
ccgcagagtc tagactcgtg gtggacttct ctcaattttc taggggggac taccgtgtgt 300
cttggccaaa attcgcagtc cccaacctcc aatcactcac caacctcctg tcctccaact 360
tgtcctggtt atcgctggat gtgtctgcgg cgttttatca tcttcctctt catcctgctg 420
ctatgcctca tcttcttgtt ggttcttctg gactatcaag gtatgttgcc cgtttgtcct 480
ctaattccag gatcctcaac caccagcacg ggaccatgcc gaacctgcat gactactgct 540
caaggaacct ctatgtatcc ctcctgttgc tgtaccaaac cttcggacgg aaattgcacc 600
tgtattccca tcccatcatc ctgggctttc ggaaaattcc tatgggagtg ggcctcagcc 660
cgtttctcct ggctcagttt actagtgcca tttgttcagt ggttcgtagg gctttccccc 720
actgtttggc tttcagttat atggatgatg tggtattggg ggccaagtct gtacagcatc 780
ttgagtccct ttttaccgct gttaccaatt ttcttttgtc tttgggtata catttaaacc 840
ctaacaaaac aaagagatgg ggttactctc tgaattttat gggttatgtc attggaagtt 900
atgggtcctt gccacaagaa cacatcatac aaaaaatcaa agaatgtttt agaaaacttc 960
ctattaacag gcctattgat tggaaagtat gtcaacgaat tgtgggtctt ttgggttttg 1020
ctgccccatt tacacaatgt ggttatcctg cgttaatgcc cttgtatgca tgtattcaat 1080
ctaagcaggc tttcactttc tcgccaactt acaaggcctt tctgtgtaaa caatacctga 1140
acctttaccc cgttgcccgg caacggccag gtctgtgcca agtgtttgct gacgcaaccc 1200
ccactggctg gggcttggtc atgggccatc agcgcgtgcg tggaaccttt tcggctcctc 1260
tgccgatcca tactgcggaa ctcctagccg cttgttttgc tcgcagcagg tctggagcaa 1320
acattatcgg gactgataac tctgttgtcc tctcccgcaa atatacatcg tatccatggc 1380
tgctaggctg tgctgccaac tggatcctgc gcgggacgtc ctttgtttac gtcccgtcgg 1440
cgctgaatcc tgcggacgac ccttctcggg gtcgcttggg actctctcgt ccccttctcc 1500
gtctgccgtt ccgaccgacc acggggcgca cctctcttta cgcggactcc ccgtctgtgc 1560
cttctcatct gccggaccgt gtgcacttcg cttcacctct gcacgtcgca tggagaccac 1620
cgtgaacgcc caccgaatgt tgcccaaggt cttacataag aggactcttg gactctctgc 1680
aatgtcaacg accgaccttg aggcatactt caaagactgt ttgtttaaag actgggagga 1740
gttgggggag gagattagat taaaggtctt tgtactagga ggctgtaggc ataaattggt 1800
ctgcgcacca gcaccatgca actttttcac ctctgcctaa tcatctcttg ttcatgtcct 1860
actgttcaag cctccaagct gtgccttggg tggctttggg gcatggacat cgacccttat 1920
aaagaatttg gagctactgt ggagttactc tcgtttttgc cttctgactt ctttccttca 1980
gtacgagatc ttctagatac cgcctcagct ctgtatcggg aagccttaga gtctcctgag 2040
cattgttcac ctcaccatac tgcactcagg caagcaattc tttgctgggg ggaactaatg 2100
actctagcta cctgggtggg tgttaatttg gaagatccag catctagaga cctagtagtc 2160
agttatgtca acactaatat gggcctaaag ttcaggcaac tcttgtggtt tcacatttct 2220
tgtctcactt ttggaagaga aaccgttata gagtatttgg tgtctttcgg agtgtggatt 2280
cgcactcctc cagcttatag accaccaaat gcccctatcc tatcaacact tccggaaact 2340
actgttgtta gacgacgagg caggtcccct agaagaagaa ctccctcgcc tcgcagacga 2400
aggtctcaat cgccgcgtcg cagaagatct caatctcggg aacctcaatg ttagtattcc 2460
ttggactcat aaggtgggga actttactgg tctttattct tctactgtac ctgtctttaa 2520
tcctcattgg aaaacaccat cttttcctaa tatacattta caccaagaca ttatcaaaaa 2580
atgtgaacag tttgtaggcc cacttacagt taatgagaaa agaagattgc aattgattat 2640
gcctgctagg ttttatccaa aggttaccaa atatttacca ttggataagg gtattaaacc 2700
ttattatcca gaacatctag ttaatcatta cttccaaact agacactatt tacacactct 2760
atggaaggcg ggtatattat ataagagaga aacaacacat agcgcctcat tttgtgggtc 2820
accatattct tgggaacaag atctacagca tggggcagaa tctttccacc agcaatcctc 2880
tgggattctt tcccgaccac cagttggatc cagccttcag agcaaacaca gcaaatccag 2940
attgggactt caatcccaac aaggacacct ggccagacgc caacaaggta ggagctggag 3000
cattcgggct gggtttcacc ccaccgcacg gaggcctttt ggggtggagc cctcaggctc 3060
agggcatact acaaactttg ccagcaaatc cgcctcctgc ctccaccaat cgccagacag 3120
gaaggcagcc taccccgctg tctccacctt tgagaaacac tcatcctcag gccatgcagt 3180
gg 3182

SEQ ID NO: 56 moltype = DNA length = 7459
FEATURE Location/Qualifiers
source 1..7459
mol_type = other DNA
organism = synthetic construct
SEQUENCE: 56
agtcactgcc gcggcgcctt gagtctccgg gccgccttgc catggctgcc cgtggtgtca 60
tcgctccagt tggcgagagt ttgcgctacg ctgagtactt gcagccctcg gccaaacggc 120
cagacgccga cgtcgaccag cagagactgg taagaagttt gatagctgta ggactgggtg 180
ttgcagctct tgcatttgca ggtcgctacg catttcggat ctggaaacct ctagaacaag 240
ttatcacaga aactgcaaag aagatttcaa ctcctagctt ttcatcctac tataaaggag 300
gatttgaaca gaaaatgagt aggcgagaag ctggtcttat tttaggtgta agcccatctg 360
ctggcaaggc taagattaga acagctcata ggagagtcat gattttgaat cacccagata 420
aaggtggatc tccttacgta gcagccaaaa taaatgaagc aaaagacttg ctagaaacaa 480
ccaccaaaca ttgatgctta aggaccacac tgaaggaaaa aaaaagaggg gacttcgaaa 540
aaaaaaaaag ccctgcaaaa tattctaaaa catggtcttc ttaattttct atatggattg 600
accacagtct tatcttccac cattaagctg tataacaata aaatgttaat agtcttgctt 660
tttattatct tttaaagatc tccttaaatt ctataactga tcttttttct tattttgttt 720
gtgacattca tacattttta agatttttgt tatgttctga attcccccct acacacacac 780
acacacacac acacacacac acgtgcaaaa aatatgatca agaatgcaat tgggatttgt 840
gagcaatgag tagacctctt attgtttata tttgtaccct cattgtcaat tttttttag 900
ggaatttggg actctgccta tataaggtgt tttaaatgtc ttgagaacaa gcactggctg 960

-continued

```
atacctcttg gagatatgat ctgaaatgta atggaattta ttaaatggtg tttagtaaag  1020
taggggttaa ggacttgtta aagaacccca ctatctctga gaccctatag ccaaagcatg  1080
aggacttgga gagctactaa aatgattcag gtttacaaaa tgagccctgt gaggaaaggt  1140
tgagagaagt ctgaggagtt tgtatttaat tatagtcttc cagtactgta tattcattca  1200
ttactcattc tacaaatatt tattgacccc ttttgatgtg caaggcacta tcgtgcgtcc  1260
cctgagagtt gcaagtatga agcagtcatg gatcatgaac caaaggaact tatatgtaga  1320
ggaaggataa atcacaaata gtgaatactg ttagatacag atgatatatt ttaaaagttc  1380
aaaggaagaa aagaatgtgt taaacactgc atgagaggag gaataagtgg catagagcta  1440
ggctttagaa aagaaaaata ttccgatacc atatgattgg tgaggtaagt gttattctga  1500
gatgagaatt agcagaaata gatatatcaa tcggagtgat tagagtgcag ggtttctgga  1560
aagcaaggtt tggacagagt ggtcatcaaa ggccagccct gtgacttaca ctgcattaaa  1620
ttaatttctt agaacatagt ccctgatcat tatcacttta ctattccaaa ggtgagagaa  1680
cagattcaga tagagtgcca gcattgtttc ccagtattcc tttacaaatc ttgggttcat  1740
tccaggtaaa ctgaactact gcattgtttc tatcttaaaa tactttttag atatcctaga  1800
tgcatctttc aacttctaac attctgtagt ttaggagttc tcaaccttgg cattattgac  1860
atgttaggcc aaataatttt ttttgtggga ggtctcttgt gcgttttaga tgattagcaa  1920
taatccctga cctgttatct actaaagact agtcgtttct catcagttgt gacaacaaaa  1980
atggttccag atattgccaa atgcccttta gaggacagta atcgccccca gttgagaacc  2040
atttcagtaa aactttaatt actatttttt cttttggttt ataaaataat gatcctgaat  2100
taaattgatg gaaccttgaa gtcgataaaa tatatttctt gctttaaagt ccccatacgt  2160
gtcctactaa ttttctcatg ctttagtgtt ttcacttttc tcctgttatc cttgtaccta  2220
agaatgccat cccaatcccc agatgtccac ctgcccaaag tctaggcata gctgaaggcc  2280
aagctaaaat gtatccctct ttttctggta catgcagcaa aagtaatatg aattatcagc  2340
tttctgagag caggcattgt atctgtcttg tttggtgtta cattggcacc caataaatat  2400
ttgttgagtg aatgaataaa ttcccatagc actttattct tcacatggta cataactata  2460
ggggctatag cttggtacct tgtgaagcaa ctcttggtgt aacatacctt atttctcata  2520
ctaaaatgca agaaccttta gagcaaggat cttgccattc atctttgtaa cctctttact  2580
ctggagcact tgcatttagc aggcatcata aagttttacg taccaagaaa atgttgctgt  2640
tttctgaata ctatgcatca aaaaatgtta ccactaattt ttaaagctct gctaaggaat  2700
attggggcac cctcagatgc accttttaat tgatgtcata ttttcctaat ccatacttta  2760
ttcatgagaa tttgagtcac cccagcatta gcttggaatt tccttatttc ccatttgctt  2820
tgcaggtgcc ttggagtcag atctggtttt gaatactatc ttcctgttat gtgatcttgg  2880
gcagttactt aattttctag tcaataaccc gtatctataa aatagagaaa ataatcctac  2940
acaccggggc ctgttgtggg gcggggagag gggggaggga tcgcatttgg agatatacta  3000
atgtaaatga caagttaatt ggtgcagcac accaacatgg ctcatgtcta catatgtaac  3060
aaacctgcac gttgtgcaca tgtgccctag aacttaaagt ataataaaaa gaaattttaa  3120
aaaatcctgt caaataaggt tatagtagag aataaggatg tgtaaagcat ttagtcacgt  3180
aaatgcttaa aaaaatgtaa tttttacttc tttcactgcc tcatttaatt agttttatct  3240
ttaataatac cttggattca gggtaaagtt tcagttatgt cccagtaatc atttatttta  3300
ccctcgaatc tgcaatttgg atagaacatg gtggggacag ctcgtctcta ttccttgcag  3360
cattaacagg ctggaggcac cacttctctg gccagcaagt tgggcctggt tgttggctga  3420
gagcctcagt tcctttctgc acaggttcct ctttacatag gcttctcaac agggctacta  3480
gagcatcgtc accatagcag ctgtcttata acagagagtg gtcggtctga gagacaaaaa  3540
atggaagctg ccaaattgtt ctgggtctgg aaactgtcag ggcatcactt gtgccatatt  3600
cagttggcct aagaattaca gagcctgcct cgattcaaag ggagaggata gagaggactg  3660
aaggaatcag tgctcatctt taatatgcag caggacaggt ttgggatttt ttttccccct  3720
tgagtctgtg aaggcattac ttaagaacaa agtcaggcat gtataattga actacagtta  3780
cttgaaatat aagcccagaa agtttcagat aataaataca actatttttc tgctgttacc  3840
cttgtaccta aagatgccat cctaatcccc agatctccac aactatacct acatagtaga  3900
aggttaaaat gtatccctct ttttctggtg catccagcaa aagtaatatc atgaattatg  3960
agctctctga gagcaaggat catatcagtc ttgtttattg ttgcagtgaa caagtacagt  4020
tgcagatatt caggagtaat tatctaaatg gcagtaggct tataaaactg aattttcacc  4080
agccacaccc tccccccaac tccttatctg taaaaagctt atttgagtgg ttacctgtct  4140
tcagtaaaga ttgcgcttgc atatttgctg tcattgcata ttctgcttaa ttaagctctg  4200
ttgatattgc agtttctgtg catacttaca tcttagatgc aatctgaggg cctaggaagg  4260
ccttttaaaa ataaaacaat tccgattgca gagaaagtgt aagtcaagga cagttaattc  4320
aaggggaaca tagaaagcta tttagatttt agttgatggt gccagtcttc agcgtaaagt  4380
caaaagtgga gggaagttta gtaaggaaaa aatgttgggc ttggaataca ttgtttagtc  4440
ttcaaagcac tttacttttt atgaaatata ttttagacat tcagcaaata ttgaatactt  4500
actatatcag gcagtaaaga tataaattca ttcttaaaat gtgcaacatg ttcaaactga  4560
aaaaaataca ttcttaaaca ggaaactttt tccttcatac tttttaatta acaagacata  4620
taagagttgc attaatgggc gtgcttatga ttgatcaccc agcagcatca ttagaaataa  4680
tatattttat tcatgtgcag aaatcttttg gttgtcctgg ggaaccttga acacagaaaa  4740
gagcttttat tgataaggta attgaacaca cttgacaatt agcttaatat ggtttaatac  4800
catttgtggg agaagatgaa tcagccaggc tctttacgtc aagaatatga agtttctctt  4860
gagtcaacca acttaagatg agctacggag actgcagtga aaagttaaat atccaagtac  4920
accagccaat ttcacacagt ggaaccatgc tgtcctcggg caccctgcac ctcgcccaac  4980
agtcatcaac tagatggagg ctcctggctg caaggaggat ttgatgggaa tgagtaaatg  5040
tgtcagcata gtccgtccct tctaatggaa aagcaaccca aagagcaaat cctattaatg  5100
gctggatcag tatcatctac ttgtcaaaaa cattccatga attatgagtc aaaattttat  5160
ttatggtggc attacacaca ttaagagatg aggacttctg ttagcataat ttattagctg  5220
gaaaagttga gaaggttctc tggactcatt tttataggtg gaacctaagt gatctggata  5280
attgcccacc agcaaaattg ctgggcatgg tggacaaaga aaatgttcct tctaatgatt  5340
ttttatgagc tgagtagcta ttgttcccag ctgagtgctc ttttcctctt tttattgttg  5400
ctgagcaaaa gaatttataa aaagctcttt cttttgtatt aaaaaccctg ctcaattgaa  5460
atgcaagttc attaagtaat cttcatttct cttcctgcca taataaccct ttccctctct  5520
gttcgattca acagtatcta gcagcactgc tccaaatttt aagtctgaac agactatatt  5580
acatagatgt agagaaatac tcaatcttca gcattaagag ggagcttaat ttcacacggg  5640
tggaatatga tcactcaggc tagatgttgg ccataaattt caaattagta tctcaactta  5700
```

-continued

```
gcagggggga tcaacagtgg caaacttcaa ttatgacagg ataaaaatca catagagata  5760
ttggttcaat atggacatct aaactataat gctaaaagcc aataattaga ataagttcat  5820
tttaagaaaa gcattaataa tattagctaa cgtttagtac ctgtgccaaa cattctacct  5880
atgttacctt gattttcata gccagcctaa gaggtactat tatgtatccc cattttacag  5940
gttaagaaac aggctcagag gagtttagga tcttttccaa gattacatag ccagtaagtg  6000
gtggcactag gaaccaaatt cagactctga atcgcatgct gtttatatta tattgcactc  6060
attctaaata tgtgggaatc agaatgaagg ggcttgtatg acttttggct catttttttga  6120
tgcatgtgac ctgggattat aaatgtgaaa ttaggtttac gaaaggatcc agtgtcattg  6180
tgcatcatgg gcaaggagta cctaatctct ttaattcttc cctggaagct tacgatgtcc  6240
atccaagtgc acatagcaaa agttctgttg taaagtttag cagagtgact ttctttgact  6300
cagagtgatg acggaggaag ctttgataag attttatctg aaatgttcat ggacaagagc  6360
tttcaaggag aacatccaga gcaaggttct gaagacagct catgaaggtg aagcagcaga  6420
cctggcacaa gaaatgaaga gagagctcag tgtattaaag atgaaaacaa gaaaaccgaa  6480
tatattgaaa ggagcagaga ggcaatgaaa acaagacaac tgaaatgagg taacttgcag  6540
caattgaaag ggaatttcag tacttttata gaattcttaa aaattgtttc ctgctgttta  6600
ttttcaattt tgaacagggt tatttgtcca tgccatactt tttttgccaa attccaaaat  6660
tgtgtatagt tctatagttg tctggtggag tcaatggaac tttagttacc agtctaagaa  6720
tgtgtctttg agattgtcca gttaattctc tatttccagt agctgtaata aatggtgaaa  6780
aggtttctga ctcctggaga aagtttctaa ctccttatga ctaatattca taacagactt  6840
gtgagttcct tgaacatgga tacacctata tgcaagagtg tattccaaag ctaactcagt  6900
gatctttcca tttatctatt cttggattag tggtgccttt gctctttcct tctgtaaatg  6960
tgaatagtta agagttgact gcagaagtgt ttacactttg gcttccatgc ctctggaatg  7020
tttgtgcttt ggtggtgaga tgtgagacta tatttgtata gtctgcatct ctcaggctgc  7080
cccagaatgt tgtacagtgc agtgctgaag aaagcagcag gtacacacag aaatgcagcc  7140
tttcctggtt aaccctgctt ggatctgagt tacactttgt ttcctgactt cttgggactt  7200
aggtaatcag tttgccttct actctatctc attttgtact cgcttacata ctacattctt  7260
gtttgggctt tcgtttcttc ttgtaagcag agatttttta aaatccaata tgtgaaaata  7320
cggatgcact acaattaaat aaataaaatg ctgttgtgtt tgttttgctt taaaattgta  7380
aaggataaac aataagatag ttttatctat gtggttttcc cgatgcagtt aaaataaaac  7440
ctaatctgct aaaattgaa                                               7459

SEQ ID NO: 57          moltype = DNA  length = 1906
FEATURE                Location/Qualifiers
source                 1..1906
                       mol_type = other DNA
                       organism = synthetic construct
SEQUENCE: 57
gctttccggc ggttgcaccg ggccggggtg ccagcgcccg ccttcccgtt tcctcccgtt  60
ccgcagcgcg cccacggcct gtgaccccgg cgaccgctcc ccagtgacga gagagcgggg  120
ccgggcgctg ctccggcctg acctgcgaag ggacctcggt ccagtcccct gttgcgccgc  180
gcccccgtcc gtccgtgcgc gggccagtca ggggccagtg tctcgagcgg tcgaggtcgc  240
agacctagag gcgccccaca ggccggcccg gggcgctggg agcgccggcc gcgggccggg  300
tggggatgcc tctgcacgtg aagtggccgt tccccgcggt gccgccgctc acctggaccc  360
tggccagcag cgtcgtcatg ggcttggtgg gcacctacag ctgcttctgg accaagtaca  420
tgaaccacct gaccgtgcac aacagggagg tgctgtacga gctcatcgag aagcgaggcc  480
cggccacgcc cctcatcacc gtgtccaatc accagtcctg catggacgac cctcatctct  540
gggggatcct gaaactccgc cacatctgga acctgaagtt gatgcgttgg accccctgcag  600
ctgcagacat ctgcttcacc aaggagctac actcccactt cttcagcttg ggcaagtgtg  660
tgcctgtgtg ccgaggagca gaattttttcc aagcagagaa tgaggggaaa ggtgttctag  720
acacaggcag gcacatgcca ggtgctggaa aaagaagaga gaaaggagat ggcgtctacc  780
agaaggggat ggacttcatt ttggagaagc tcaaccatgg ggactgggtg catatcttcc  840
cagaagggaa agtgaacatg agttccgaat tcctgcgttt caagtgggga atcgggcgcc  900
tgattgctga gtgtcatctc aaccccatca tcctgcccct gtggcatgtc ggaatgaatg  960
acgtccttcc taacagtccg ccctacttcc cccgctttgg acagaaaatc actgtgctga  1020
tcgggaagcc cttcagtgcc ctgcctgtac tcgagcggct ccgggcggag aacaagtcgg  1080
ctgtggagat gcggaaagcc ctgacggact tcattcaaga ggaattccag catctgaaga  1140
ctcaggcaga gcagctccac aaccacctcc agcctgggag ataggccttg cttgctgcct  1200
tctggattct tggcccgcac agagctgggg ctgagggatg gactgatgct tttagctcaa  1260
acgtggcttt tagacagatt tgttcataga ccctctcaag tgccctctcc gagctggtag  1320
gcattccagc tcctccgtgc ttcctcagtt acacaaagga cctcagctgc ttctcccact  1380
tggccaagca gggaggaaga agcttaggca gggctctctt tccttcttgc cttcagatgt  1440
tctctcccag gggctggctt caggagggag catagaaggc aggtgagcaa ccagttggct  1500
aggggagcag ggggcccacc agagctgtgg agaggggacc ctaagactcc tcggcctggc  1560
tcctacccac cgcccttgcc gaaccaggag ctgctcacta cctcctcagg gatggccgtt  1620
ggccacgtct tccttctgcc tgagcttccc ccccaccaca ggccctttcc tcaggcaagg  1680
tctggcctca ggtgggccgc aggcgggaaa agcagccctt ggccagaagt caagcccagc  1740
cacgtggagc ctagagtgag ggcctgaggt ctggctgctt gcccccatgc tggcgccaac  1800
aacttctcca tcctttctgc ctctcaacat cacttgaatc ctagggcctg ggttttcatg  1860
tttttgaaac agaaccataa agcatatgtg ttggcttgtt gtaaaa                 1906

SEQ ID NO: 58          moltype = DNA  length = 2926
FEATURE                Location/Qualifiers
source                 1..2926
                       mol_type = other DNA
                       organism = synthetic construct
SEQUENCE: 58
agaagaaaac agttccacgt tgcttgaaat tgaaaatcaa gataaaaatg ttcacaatta  60
agctccttct ttttattgtt cctctagtta tttcctccag aattgatcaa gacaattcat  120
catttgattc tctatctcca gagccaaaat caagatttgc tatgttagac gatgtaaaaa  180
```

```
ttttagccaa tggcctcctt cagttgggac atggtcttaa agactttgtc cataagacga  240
agggccaaat taatgacata tttcaaaaac tcaacatatt tgatcagtct ttttatgatc  300
tatcgctgca aaccagtgaa atcaaagaag aagaaaagga actgagaaga actacatata  360
aactacaagt caaaaatgaa gaggtaaaga atatgtcact tgaactcaac tcaaaacttg  420
aaagcctcct agaagaaaaa attctacttc aacaaaaagt gaaatattta gaagagcaac  480
taactaactt aattcaaaat caacctgaaa ctccagaaca cccagaagta acttcactta  540
aaactttttgt agaaaaacaa gataatagca tcaaagacct tctccagacc gtggaagacc  600
aatataaaca attaaaccaa cagcatagtc aaataaaaga aatagaaaat cagctcagaa  660
ggactagtat tcaagaaccc acagaaattt ctctatcttc caagccaaga gcaccaagaa  720
ctactccctt tcttcagttg aatgaaataa gaaatgtaaa acatgatggc attcctgctg  780
aatgtaccac catttataac agaggtgaac atacaagtgg catgtatgcc atcagaccca  840
gcaactctca agtttttcat gtctactgtg atgttatatc aggtagtcca tggacattaa  900
ttcaacatcg aatagatgga tcacaaaact tcaatgaaac gtgggagaac tacaaatatg  960
gttttgggag gcttgatgga gaattttggt tgggcctaga gaagatatac tccatagtga  1020
agcaatctaa ttatgtttta cgaattgagt tggaagactg gaaagacaac aaacattata  1080
ttgaatattc tttttacttg ggaaatcacg aaaccaacta tacgctacat ctagttgcga  1140
ttactggcaa tgtccccaat gcaatcccgg aaaacaaaga tttggtgttt tctacttggg  1200
atcacaaagc aaaaggacac ttcaactgtc cagagggtta ttcaggaggc tggtggtggc  1260
atgatgagtg tggagaaaac aacctaaatg gtaaatataa caaaccaaga gcaaaatcta  1320
agccagagag gagaagagga ttatcttgga agtctcaaaa tggaaggtta tactctataa  1380
aatcaaccaa aatgttgatc catccaacag attcagaaag ctttgaatga actgaggcaa  1440
atttaaaagg caataattta aacattaacc tcattccaag ttaatgtggt ctaataatct  1500
ggtattaaat ccttaagaga aagcttgaga aatagatttt ttttatctta aagtcactgt  1560
ctatttaaga ttaaacatac aatcacataa ccttaaagaa taccgtttac atttctcaat  1620
caaaattctt ataatactat ttgttttaaa ttttgtgatg tgggaatcaa ttttagatgg  1680
tcacaatcta gattataatc aataggtgaa cttattaaat aacttttcta aataaaaaat  1740
ttagagactt ttattttaaa aggcatcata tgagctaata tcacaacttt cccagtttaa  1800
aaaactagta ctcttgttaa aactctaaac ttgactaaat acagaggact ggtaattgta  1860
cagttcttaa atgttgtagt attaatttca aaactaaaaa tcgtcagcac agagtatgtg  1920
taaaaatctg taatacaaat ttttaaactg atgcttcatt ttgctacaaa ataatttgga  1980
gtaaatgttt gatatgattt atttatgaaa cctaatgaag cagaattaaa tactgtatta  2040
aaataagttc gctgtcttta aacaaatgga gatgactact aagtcacatt gactttaaca  2100
tgaggtatca ctatacctta tttgttaaaa tatatactgt atacatttta tatattttaa  2160
cacttaatac tatgaaaaca aataattgta aaggaatctt gtcagattac agtaagaatg  2220
aacatatttg tggcatcgag ttaaagttta tatttcccct aaatatgctg tgattctaat  2280
acattcgtgt aggttttcaa gtagaaataa acctcgtaac aagttactga acgtttaaac  2340
agcctgacaa gcatgtatat atgtttaaaa ttcaataaac aaagacccag tccctaaatt  2400
atagaaattt aaattattct tgcatgttta tcgacatcac aacagatccc taaatcccta  2460
aatccctaaa gattagatac aaatttttta ccacagtatc acttgtcaga atttattttt  2520
aaatatgatt ttttaaaact gccagtaaga aattttaaat taaacccatt tgttaaagga  2580
tatagtgccc aagttatatg gtgacctacc tttgtcaata cttagcatta tgtatttcaa  2640
attatccaat atacatgtca tatatatttt tatatgtcac atatataaaa gatatgtatg  2700
atctatgtga atcctaagta aatattttgt tccagaaaag tacaaaataa taaaggtaaa  2760
aataatctat aattttcagg accacagact aagctgtcga aattaacgct gattttttta  2820
gggccagaat accaaaatgg ctcctctctt cccccaaaat tggacaattt caaatgcaaa  2880
ataattcatt atttaatata tgagttgctt cctctatttg gtttcc                 2926

SEQ ID NO: 59          moltype = DNA  length = 2336
FEATURE                Location/Qualifiers
source                 1..2336
                       mol_type = other DNA
                       organism = synthetic construct
SEQUENCE: 59
tgccccgttg tgaggtgata aagtgttgcg ctccgggacg ccagcgccgc ggctgccgcc  60
tctgctgggg tctaggctgt ttctctcgcg ccaccactgg ccgccggccg cagctccagg  120
tgtcctagcc gcccagcctc gacgccgtcc cgggacccct gtgctctgcg cgaagccctg  180
gccccggggg ccggggcatg ggccagggc gcggggtgaa gcggcttccc gcggggccgt  240
gactgggcgg gcttcagcca tgaagaccct catagccgcc tactccgggg tcctgcgcgg  300
cgagcgtcag gccgaggctg accggagcca gcgctctcac ggaggacctg cgctgtcgcg  360
cgaggggtct gggagatggg gagtggcctg cagtgccatc ctcatgtaca tattctgcac  420
tgattgctgg ctcatcgctg tgctctactt cacttggctg gtgtttgact ggaacacacc  480
caagaaaggt ggcaggaggt cacagtgggt ccgaaactgg gctgtgtggc gctactttcg  540
agactacttt cccatccagc tggtgaagac acacaacctg ctgaccacca ggaactatat  600
ctttggatac cacccccatg gtatcatggg cctgggtgcc ttctgcaact tcagcacaga  660
ggccacagaa gtgagcaaga agttcccagg catacggcct tacctggcta cactggcagg  720
caacttccga atgcctgtgt tgagggagta cctgatgtct ggaggtatct gccctgtcag  780
ccgggacacc atagactatt tgctttcaaa gaatgggagt ggcaatgcta tcatcatcgt  840
ggtcgggggt gcggctgagt ctctgagctc catgcctggc aagaatgcag tcaccctgcg  900
gaaccgcaag ggctttgtga aactggccct gcgtcatgga gctgacctgg ttcccatcta  960
ctcctttgga gagaatgaag tgtacaagca ggtgatcttc gaggagggct cctggggccg  1020
atgggtccag aagaagttcc agaaatacat tggtttcgcc ccatgcatct tccatggtcg  1080
aggcctcttc tcctccgaca cctgggggct ggtgccctac tccaagccca tcaccactgt  1140
tgtgggagag cccatcacca tccccaagct ggagcaccca acccagcaag acatcgacct  1200
gtaccacacc atgtacatgg aggccctggt gaagctcttc gacaagcaca agaccaagtt  1260
cggcctcccg gagactgagg tcctggaggt gaactgagcc agccttcggg gccaattccc  1320
tggaggaacc agctgcaaat cacttttttg ctctgtaaat ttggaagtgt catgggtgtc  1380
tgtgggttat ttaaaagaaa ttataacaat tttgctaaac cattacaatg ttaggtcttt  1440
tttaagaagg aaaaagtcag tatttcaagt tctttcactt ccagcttgcc ctgttctagg  1500
tggtggctaa atctgggcct aatctgggtg gctcagctaa cctctcttct tcccttcctg  1560
```

-continued

```
aagtgacaaa ggaaactcag tcttcttggg gaagaaggat tgccattagt gacttggacc  1620
agttagatga ttcacttttt gcccctaggg atgagaggcg aaagccactt ctcatacaag  1680
cccctttatt gccactaccc cacgctcgtc tagtcctgaa actgcaggac cagtttctct  1740
gccaagggga ggagttggag agcacagttg ccccgttgtg tgagggcagt agtaggcatc  1800
tggaatgctc cagtttgatc tcccttctgc cacccctacc tcacccctag tcactcatat  1860
cggagcctgg actggcctcc aggatgagga tgggggtggc aatgacaccc tgcaggggaa  1920
aggactgccc cccatgcacc attgcaggga ggatgccgcc accatgagct aggtggagta  1980
actggttttt cttgggtggc tgatgacatg gatgcagcac agactcagcc ttggcctgga  2040
gcacatgctt actggtggcc tcagtttacc ttccccagat cctagattct ggatgtgagg  2100
aagagatccc tcttcagaag gggcctggcc ttctgagcag cagattagtt ccaaagcagg  2160
tggcccccga acccaagcct cacttttctg tgccttcctg agggggttgg gccggggagg  2220
aaacccaacc ctctcctgtg tgttctgtta tctcttgatg agatcattgc accatgtcag  2280
acttttgtat atgccttgaa aataaatgaa agtgagaatc ctctaaaaaa aaaaaa      2336
```

```
SEQ ID NO: 60           moltype = DNA  length = 3215
FEATURE                 Location/Qualifiers
source                  1..3215
                        mol_type = other DNA
                        organism = synthetic construct
SEQUENCE: 60
ctccaccact ttccaccaaa ctcttcaaga tcccagagtc agggccctgt actttcctgc  60
tggtggctca agttccggaa cagtaaaccc tgctccgact actgcctctc ccatatcgtc  120
aatcttctcg aggactgggg accctgtacc gaatatggag agcaccacat caggattcct  180
aggacccctg ctcgtgttac aggcggggtt tttcttgttg acaagaatcc tcacaatacc  240
acagagtcta gactcgtggt ggacttctct caattttcta gggggagcac ccacgtgtcc  300
tggccaaaat ttgcagtccc caacctccaa tcactcacca acctcttgtc ctccaatttg  360
tcctggttat cgctggatgt gtctgcggcg ttttatcatc ttcctcttca tcctgctgct  420
atgcctcatc ttcttgttgg ttcttctgga ctaccaaggt atgttgcccg tttgtcctct  480
acttccagga acatcaacta ccagcaccgg accatgcaaa acctgcacaa ctactgctca  540
agggacctct atgtttccct catgttgctg tacaaaacct acggacggaa actgcacctg  600
tattcccatc ccatcatctt gggctttcgc aaaataccta tgggagtggg cctcagtccg  660
tttctcttgg ctcagtttac tagtgccatt tgttcagtgg ttcgtagggc tttcccccac  720
tgtctggctt tcagttatat ggatgatgtg gttttggggg ccaagtctgt acaacatctt  780
gagtcccttt ataccgctgt taccaatttt cttttatctt tgggtataca tttaaaccct  840
cacaaaacaa aaagatgggg atattccctt aacttcatgg gatatgtaat tgggagttgg  900
ggcactttgc ctcaggaaca tattgtacaa aaaatcaagc aatgttttag gaaacttcct  960
gtaaacaggc ctattgattg gaaagtatgt caacraattg tgggtctttt ggggtttgcc  1020
gccccttca cgcaatgtgg atatcctgct ttaatgcctt tatatgcatg tatacaagct  1080
aagcaggctt ttactttctc gccaacttac aaggcctttc tgtgtaaaca atatctgaac  1140
ctttaccccg ttgctcggca acggtcaggt ctttgccaag tgtttgctga cgcaaccccc  1200
actggttggg gcttggccat aggccatcag cgcatgcgtg gaacctttgt ggctcctctg  1260
ccgatccata ctgcggaact cctagcagct tgttttgctc gcagccggtc tggagcaaaa  1320
cttatcggca ccgacaactc tgttgtcctc tctcggaaat acacctcctt tccatggctg  1380
ctaggatgtg ctgccaactg gatcctgcgc gggacgtcct ttgtctacgt cccgtcggcg  1440
ctgaatcccg cggacgaccc atctcggggc cgtttgggac tctaccgtcc ccttctgcgt  1500
ctgccgttcc gcccgaccac ggggcgcacc tctctttacg cggtctcccc gtctgtgcct  1560
tctcatctgc cggaccgtgt gcacttcgct tcacctctgc acgtcgcatg gagaccaccg  1620
tgaacgccca cgggaacctg cccaaggtct tgcataagag gactcttgga ctttcagcaa  1680
tgtcaacgac cgaccttgag gcatacttca aagactgtgt gtttactgag tgggaggagt  1740
tgggggagga ggttaggtta aaggtctttg tactaggagg ctgtaggcat aaattggtgt  1800
gttcaccagc accatgcaac tttttcacct ctgcctaatc atctcatgtt catgtcctac  1860
tgttcaagcc tccaagctgt gccttgggtg gctttggggc atggacattg acccgtataa  1920
agaatttgga gcttctgtgg agttactctc tttttttgcct tctgacttct ttccttctat  1980
tcgagatctc ctcgacaccg cctctgctct gtatcgggag gccttagagt ctccggaaca  2040
ttgttcacct caccatacgg cactcaggca agcaattctg tgttggggtg agttaatgaa  2100
tctagccacc tgggtgggaa gtaatttgga agatccagca tccagggaat tagtagtcag  2160
ctatgtcaac gttaatatgg gcctaaaaat cagacaacta ttgtggtttc acatttcctg  2220
tcttactttt gggagagaaa ctgttcttga atatttggtg tcttttggag tgtggattcg  2280
cactcctcct gcatatagac cacaaaatgc ccctatctta tcaacacttc cggaaactac  2340
tgttgttaga cgaagaggca ggtcccctag aagaagaact ccctcgcctc gcagacgaag  2400
gtctcaatcg ccgcgtcgca gaagatctca atctcgggaa tctcaatgtt agtattcctt  2460
ggacacataa ggtgggaaac tttacggggc tttattcttc tacggtacct tgctttaatc  2520
ctaaatggca aactccttct tttcctgaca ttcatttgca ggaggacatt gttgatagat  2580
gtaagcaatt tgtggggccc cttacagtaa atgaaaacag gagacttaaa ttaattatgc  2640
ctgctaggtt ttatcccaat gttactaaat atttgccctt agataaaggg atcaaaccgt  2700
attatccaga gtatgtagtt aatcattact tccagacgcg acattattta cacactcttt  2760
ggaaggcggg gatcttatat aaaagagagt ccacacgtag cgcctcattt tgcgggtcac  2820
catattcttg ggaacaagat ctacagcatg ggaggttggt cttccaaacc tcgaaaaggc  2880
atggggacaa atctttctgt ccccaatccc ctgggattct tccccgatca tcagttggac  2940
cctgcattca aagccaactc agaaaatcca gattgggacc tcaacccaca caaggacaac  3000
tggccggacg ccaacaaggt gggagtggga gcattcgggc cagggttcac ccctcctcat  3060
gggggactgt tggggtggag ccctcaggct cagggcatat tcacaacagt gccagcagct  3120
cctcctcctg cctccaccaa tcggcagtca ggaaggcagc ctactccctt ctctccacct  3180
ctaagagaca ctcatcctca ggccatgcag tggaa                            3215
```

```
SEQ ID NO: 61           moltype = DNA  length = 18
FEATURE                 Location/Qualifiers
misc_feature            4
                        note = DNA
```

-continued

```
misc_feature            order(1..3,5..18)
                        note = RNA
source                  1..18
                        mol_type = other DNA
                        organism = synthetic construct
modified_base           1
                        mod_base = OTHER
                        note = 2-prime-O-methyl RNA nucleotide
modified_base           order(2..6,15..17)
                        mod_base = OTHER
                        note = Locked nucleic acids
modified_base           9
                        mod_base = OTHER
                        note = (5OH)C
modified_base           order(11,12,14)
                        mod_base = OTHER
                        note = 5 methyl cytosine nucleotides
modified_base           18
                        mod_base = OTHER
                        note = Cyclopropyl-5 methyl Cytosine nucleotide
modified_base           1^2
                        mod_base = OTHER
                        note = phosphodiester
modified_base           2^3
                        mod_base = OTHER
                        note = phosphorothioate
modified_base           3^4
                        mod_base = OTHER
                        note = phosphorothioate
modified_base           4^5
                        mod_base = OTHER
                        note = phosphorothioate
modified_base           5^6
                        mod_base = OTHER
                        note = phosphorothioate
modified_base           6^7
                        mod_base = OTHER
                        note = phosphorothioate
modified_base           7^8
                        mod_base = OTHER
                        note = phosphorothioate
modified_base           8^9
                        mod_base = OTHER
                        note = phosphorothioate
modified_base           9^10
                        mod_base = OTHER
                        note = phosphorothioate
modified_base           10^11
                        mod_base = OTHER
                        note = phosphorothioate
modified_base           11^12
                        mod_base = OTHER
                        note = phosphorothioate
modified_base           12^13
                        mod_base = OTHER
                        note = phosphorothioate
modified_base           13^14
                        mod_base = OTHER
                        note = phosphorothioate
modified_base           15^16
                        mod_base = OTHER
                        note = phosphorothioate
modified_base           14^15
                        mod_base = OTHER
                        note = phosphorothioate
modified_base           16^17
                        mod_base = OTHER
                        note = phosphorothioate
modified_base           17^18
                        mod_base = OTHER
                        note = phosphorothioate
SEQUENCE: 61
agataaaacg ccgcagac                                                18

SEQ ID NO: 62           moltype = DNA  length = 18
FEATURE                 Location/Qualifiers
misc_feature            4
                        note = DNA
misc_feature            order(1..3,5..18)
```

```
                        note = RNA
source                  1..18
                        mol_type = other DNA
                        organism = synthetic construct
modified_base           1
                        mod_base = OTHER
                        note = 2-prime-O-methyl RNA nucleotide
modified_base           order(2..6,15..17)
                        mod_base = OTHER
                        note = Locked nucleic acids
modified_base           9
                        mod_base = OTHER
                        note = (5OH)C
modified_base           order(11,12,14)
                        mod_base = OTHER
                        note = 5 methyl cytosine nucleotides
modified_base           18
                        mod_base = OTHER
                        note = Cyclopropyl-5 methyl Cytosine nucleotide
modified_base           1^2
                        mod_base = OTHER
                        note = phosphodiester
modified_base           2^3
                        mod_base = OTHER
                        note = phosphorothioate
modified_base           3^4
                        mod_base = OTHER
                        note = phosphorothioate
modified_base           4^5
                        mod_base = OTHER
                        note = phosphorothioate
modified_base           5^6
                        mod_base = OTHER
                        note = phosphorothioate
modified_base           6^7
                        mod_base = OTHER
                        note = phosphorothioate
modified_base           7^8
                        mod_base = OTHER
                        note = phosphorothioate
modified_base           8^9
                        mod_base = OTHER
                        note = phosphorothioate
modified_base           9^10
                        mod_base = OTHER
                        note = phosphorothioate
modified_base           10^11
                        mod_base = OTHER
                        note = phosphorothioate
modified_base           11^12
                        mod_base = OTHER
                        note = phosphorothioate
modified_base           12^13
                        mod_base = OTHER
                        note = phosphorothioate
modified_base           13^14
                        mod_base = OTHER
                        note = phosphorothioate
modified_base           15^16
                        mod_base = OTHER
                        note = phosphorothioate
modified_base           14^15
                        mod_base = OTHER
                        note = phosphorothioate
modified_base           16^17
                        mod_base = OTHER
                        note = phosphorothioate
modified_base           17^18
                        mod_base = OTHER
                        note = phosphorothioate
SEQUENCE: 62
agataaaacg ccgcagac                                              18

SEQ ID NO: 63           moltype = RNA  length = 19
FEATURE                 Location/Qualifiers
source                  1..19
                        mol_type = other RNA
                        organism = synthetic construct
modified_base           order(1..4,6,10..19)
```

```
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 63
ccgtgtgnac ttcgcttca                                               19

SEQ ID NO: 64           moltype = RNA  length = 21
FEATURE                 Location/Qualifiers
source                  1..21
                        mol_type = other RNA
                        organism = synthetic construct
modified_base           order(1,3,4,6,7,9..13,15,16,18..21)
                        mod_base = OTHER
                        note = 2-prime-O-methyl RNA nucleotides
modified_base           order(2,5,8,14,17)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 64
tgaagcgaag tgcacacggt c                                            21

SEQ ID NO: 65           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 65
ccgtgtgcac ttcgcttca                                               19

SEQ ID NO: 66           moltype = RNA  length = 21
FEATURE                 Location/Qualifiers
source                  1..21
                        mol_type = other RNA
                        organism = synthetic construct
modified_base           order(1,3,4,7,9..13,15,16,18..21)
                        mod_base = OTHER
                        note = 2-prime-O-methyl RNA nucleotides
modified_base           order(2,5,6,8,14,17)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
```

```
                        note = phosphorothioate
modified_base           20^21
                        mod_base = OTHER
                        note = phosphorothioate
SEQUENCE: 66
tgaagngaag tgcacacggt c                                            21

SEQ ID NO: 67           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 67
ccgtgtgcac ttcgcttca                                               19

SEQ ID NO: 68           moltype = RNA  length = 21
FEATURE                 Location/Qualifiers
source                  1..21
                        mol_type = other RNA
                        organism = synthetic construct
modified_base           order(1,3,4,6,7,9..13,15,16,18..21)
                        mod_base = OTHER
                        note = 2-prime-O-methyl RNA nucleotides
modified_base           order(2,5,8,14,17)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 68
tgaagcgaag tgcacanggt c                                            21

SEQ ID NO: 69           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 69
gtggtggact tctctcaat                                               19

SEQ ID NO: 70           moltype = RNA  length = 21
FEATURE                 Location/Qualifiers
source                  1..21
                        mol_type = other RNA
                        organism = synthetic construct
modified_base           order(1,3..5,7..13,15,17..21)
```

```
                          mod_base = OTHER
                          note = 2-prime-O-methyl RNA nucleotides
modified_base             order(2,6,14,16)
                          mod_base = OTHER
                          note = 2-prime-fluoro RNA nucleotides
modified_base             1^2
                          mod_base = OTHER
                          note = mesyl phosphoramidate
modified_base             2^3
                          mod_base = OTHER
                          note = mesyl phosphoramidate
modified_base             19^20
                          mod_base = OTHER
                          note = phosphorothioate
modified_base             20^21
                          mod_base = OTHER
                          note = phosphorothioate
SEQUENCE: 70
attgagagaa gtccaccacg a                                         21

SEQ ID NO: 71             moltype = RNA  length = 19
FEATURE                   Location/Qualifiers
source                    1..19
                          mol_type = other RNA
                          organism = synthetic construct
modified_base             order(1..4,6,10..19)
                          mod_base = OTHER
                          note = 2-prime-O-methyl RNA nucleotides
modified_base             order(5,7..9)
                          mod_base = OTHER
                          note = 2-prime-fluoro RNA nucleotides
modified_base             1^2
                          mod_base = OTHER
                          note = phosphorothioate
modified_base             2^3
                          mod_base = OTHER
                          note = phosphorothioate
SEQUENCE: 71
gtggtggact tctctcaat                                            19

SEQ ID NO: 72             moltype = RNA  length = 21
FEATURE                   Location/Qualifiers
source                    1..21
                          mol_type = other RNA
                          organism = synthetic construct
modified_base             order(1,3..5,7..13,15,17..21)
                          mod_base = OTHER
                          note = 2-prime-O-methyl RNA nucleotides
modified_base             order(2,6,14,16)
                          mod_base = OTHER
                          note = 2-prime-fluoro RNA nucleotides
modified_base             1^2
                          mod_base = OTHER
                          note = phosphorothioate
modified_base             2^3
                          mod_base = OTHER
                          note = phosphorothioate
modified_base             19^20
                          mod_base = OTHER
                          note = mesyl phosphoramidate
modified_base             20^21
                          mod_base = OTHER
                          note = mesyl phosphoramidate
SEQUENCE: 72
attgagagaa gtccaccacg a                                         21

SEQ ID NO: 73             moltype = RNA  length = 19
FEATURE                   Location/Qualifiers
source                    1..19
                          mol_type = other RNA
                          organism = synthetic construct
modified_base             order(1..4,6,10..19)
                          mod_base = OTHER
                          note = 2-prime-O-methyl RNA nucleotides
modified_base             order(5,7..9)
                          mod_base = OTHER
                          note = 2-prime-fluoro RNA nucleotides
modified_base             1^2
                          mod_base = OTHER
```

```
                        note = phosphorothioate
modified_base           2^3
                        mod_base = OTHER
                        note = phosphorothioate
SEQUENCE: 73
gtggtggact tctctcaat                                            19

SEQ ID NO: 74           moltype = RNA  length = 21
FEATURE                 Location/Qualifiers
source                  1..21
                        mol_type = other RNA
                        organism = synthetic construct
modified_base           order(1,3..5,7..13,15,17..21)
                        mod_base = OTHER
                        note = 2-prime-O-methyl RNA nucleotides
modified_base           order(2,6,14,16)
                        mod_base = OTHER
                        note = 2-prime-fluoro RNA nucleotides
modified_base           1^2
                        mod_base = OTHER
                        note = mesyl phosphoramidate
modified_base           2^3
                        mod_base = OTHER
                        note = mesyl phosphoramidate
modified_base           19^20
                        mod_base = OTHER
                        note = mesyl phosphoramidate
modified_base           20^21
                        mod_base = OTHER
                        note = mesyl phosphoramidate
SEQUENCE: 74
agcaccacct gaagagagtt a                                         21

SEQ ID NO: 75           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 75
gtggtggact tctctcaat                                            19

SEQ ID NO: 76           moltype = RNA  length = 21
FEATURE                 Location/Qualifiers
source                  1..21
                        mol_type = other RNA
                        organism = synthetic construct
modified_base           order(1,3..5,7..13,15,17..21)
                        mod_base = OTHER
                        note = 2-prime-O-methyl RNA nucleotides
modified_base           order(2,6,14,16)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 76
agcaccacct gaagagagtt a                                         21
```

-continued

```
SEQ ID NO: 77           moltype = RNA  length = 19
FEATURE                 Location/Qualifiers
source                  1..19
                        mol_type = other RNA
                        organism = synthetic construct
modified_base           order(1..3,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           4
                        mod_base = OTHER
                        note = apU nucleotide
SEQUENCE: 77
ccgtgtgcac ttcgcttca                                              19

SEQ ID NO: 78           moltype = RNA  length = 21
FEATURE                 Location/Qualifiers
source                  1..21
                        mol_type = other RNA
                        organism = synthetic construct
modified_base           order(1,3,4,6,7,9..13,15,16,18..21)
                        mod_base = OTHER
                        note = 2-prime-O-methyl RNA nucleotides
modified_base           order(2,5,8,14,17)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 78
tgaagcgaag tgcacacggt c                                           21

SEQ ID NO: 79           moltype = RNA  length = 19
FEATURE                 Location/Qualifiers
source                  1..19
                        mol_type = other RNA
                        organism = synthetic construct
modified_base           order(1..4,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           6
                        mod_base = OTHER
                        note = apU nucleotide
SEQUENCE: 79
ccgtgtgcac ttcgcttca                                              19

SEQ ID NO: 80           moltype = RNA  length = 21
FEATURE                 Location/Qualifiers
source                  1..21
                        mol_type = other RNA
                        organism = synthetic construct
modified_base           order(1,3,4,6,7,9..13,15,16,18..21)
                        mod_base = OTHER
```

```
                        note = 2-prime-O-methyl RNA nucleotides
modified_base           order(2,5,8,14,17)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 80
tgaagcgaag tgcacacggt c                                               21

SEQ ID NO: 81           moltype = RNA  length = 19
FEATURE                 Location/Qualifiers
source                  1..19
                        mol_type = other RNA
                        organism = synthetic construct
modified_base           order(1..4,6,10,11,13..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           12
                        mod_base = OTHER
                        note = apU nucleotide
modified_base           1^2
                        mod_base = OTHER
                        note = phosphorothioate
modified_base           2^3
                        mod_base = OTHER
                        note = phosphorothioate
SEQUENCE: 81
ccgtgtgcac ttcgcttca                                                  19

SEQ ID NO: 82           moltype = RNA  length = 21
FEATURE                 Location/Qualifiers
source                  1..21
                        mol_type = other RNA
                        organism = synthetic construct
modified_base           order(1,3,4,6,7,9..13,15,16,18..21)
                        mod_base = OTHER
                        note = 2-prime-O-methyl RNA nucleotides
modified_base           order(2,5,8,14,17)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 82
tgaagcgaag tgcacacggt c                                               21

SEQ ID NO: 83           moltype = RNA  length = 19
FEATURE                 Location/Qualifiers
source                  1..19
                        mol_type = other RNA
                        organism = synthetic construct
modified_base           order(1..4,6,10..15,17..19)
                        mod_base = OTHER
                        note = 2-prime-O-methyl RNA nucleotides
modified_base           order(5,7..9)
                        mod_base = OTHER
                        note = 2-prime-fluoro RNA nucleotides
```

```
modified_base          16
                       mod_base = OTHER
                       note = apU nucleotide
modified_base          1^2
                       mod_base = OTHER
                       note = phosphorothioate
modified_base          2^3
                       mod_base = OTHER
                       note = phosphorothioate
SEQUENCE: 83
ccgtgtgcac ttcgcttca                                                19

SEQ ID NO: 84          moltype = RNA  length = 21
FEATURE                Location/Qualifiers
source                 1..21
                       mol_type = other RNA
                       organism = synthetic construct
modified_base          order(1,3,4,6,7,9..13,15,16,18..21)
                       mod_base = OTHER
                       note = 2-prime-O-methyl RNA nucleotides
modified_base          order(2,5,8,14,17)
                       mod_base = OTHER
                       note = 2-prime-fluoro RNA nucleotides
modified_base          1^2
                       mod_base = OTHER
                       note = phosphorothioate
modified_base          2^3
                       mod_base = OTHER
                       note = phosphorothioate
modified_base          19^20
                       mod_base = OTHER
                       note = phosphorothioate
modified_base          20^21
                       mod_base = OTHER
                       note = phosphorothioate
SEQUENCE: 84
tgaagcgaag tgcacacggt c                                             21

SEQ ID NO: 85          moltype = RNA  length = 19
FEATURE                Location/Qualifiers
source                 1..19
                       mol_type = other RNA
                       organism = synthetic construct
modified_base          order(1..4,6,10..16,18,19)
                       mod_base = OTHER
                       note = 2-prime-O-methyl RNA nucleotides
modified_base          order(5,7..9)
                       mod_base = OTHER
                       note = 2-prime-fluoro RNA nucleotides
modified_base          17
                       mod_base = OTHER
                       note = apU nucleotide
modified_base          1^2
                       mod_base = OTHER
                       note = phosphorothioate
modified_base          2^3
                       mod_base = OTHER
                       note = phosphorothioate
SEQUENCE: 85
ccgtgtgcac ttcgcttca                                                19

SEQ ID NO: 86          moltype = RNA  length = 21
FEATURE                Location/Qualifiers
source                 1..21
                       mol_type = other RNA
                       organism = synthetic construct
modified_base          order(1,3,4,6,7,9..13,15,16,18..21)
                       mod_base = OTHER
                       note = 2-prime-O-methyl RNA nucleotides
modified_base          order(2,5,8,14,17)
                       mod_base = OTHER
                       note = 2-prime-fluoro RNA nucleotides
modified_base          1^2
                       mod_base = OTHER
                       note = phosphorothioate
modified_base          2^3
                       mod_base = OTHER
                       note = phosphorothioate
modified_base          19^20
```

```
                        mod_base = OTHER
                        note = phosphorothioate
modified_base           20^21
                        mod_base = OTHER
                        note = phosphorothioate
SEQUENCE: 86
tgaagcgaag tgcacacggt c                                           21

SEQ ID NO: 87           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 87
ccgtgtgcac ttcgcttca                                              19

SEQ ID NO: 88           moltype = RNA  length = 21
FEATURE                 Location/Qualifiers
source                  1..21
                        mol_type = other RNA
                        organism = synthetic construct
modified_base           11
                        mod_base = OTHER
                        note = apU nucleotide
modified_base           order(1,3,4,6,7,9,10,12,13,15,16,18..21)
                        mod_base = OTHER
                        note = 2-prime-O-methyl RNA nucleotides
modified_base           order(2,5,8,14,17)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 88
tgaagcgaag tgcacacggt c                                           21

SEQ ID NO: 89           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 89
ccgtgtgcac ttcgcttca                                              19

SEQ ID NO: 90           moltype = RNA  length = 21
FEATURE                 Location/Qualifiers
```

```
source                  1..21
                        mol_type = other RNA
                        organism = synthetic construct
modified_base           order(1,3,4,6,7,9..13,15,16,18,19,21)
                        mod_base = OTHER
                        note = 2-prime-O-methyl RNA nucleotides
modified_base           order(2,5,8,14,17)
                        mod_base = OTHER
                        note = 2-prime-fluoro RNA nucleotides
modified_base           20
                        mod_base = OTHER
                        note = apU nucleotide
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 90
tgaagcgaag tgcacacggt c                                              21

SEQ ID NO: 91           moltype = RNA  length = 19
FEATURE                 Location/Qualifiers
source                  1..19
                        mol_type = other RNA
                        organism = synthetic construct
modified_base           order(1..4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           1^2
                        mod_base = OTHER
                        note = phosphorothioate
modified_base           2^3
                        mod_base = OTHER
                        note = phosphorothioate
SEQUENCE: 91
ccgtgtgcac ttcgcttca                                                 19

SEQ ID NO: 92           moltype = RNA  length = 21
FEATURE                 Location/Qualifiers
source                  1..21
                        mol_type = other RNA
                        organism = synthetic construct
modified_base           order(3,4,6,7,9..13,15,16,18..21)
                        mod_base = OTHER
                        note = 2-prime-O-methyl RNA nucleotides
modified_base           order(2,5,8,14,17)
                        mod_base = OTHER
                        note = 2-prime-fluoro RNA nucleotides
modified_base           1
                        mod_base = OTHER
                        note = apU nucleotide
modified_base           1^2
                        mod_base = OTHER
                        note = phosphorothioate
modified_base           2^3
                        mod_base = OTHER
                        note = phosphorothioate
modified_base           19^20
                        mod_base = OTHER
                        note = phosphorothioate
modified_base           20^21
                        mod_base = OTHER
                        note = phosphorothioate
SEQUENCE: 92
tgaagcgaag tgcacacggt c                                              21

SEQ ID NO: 93           moltype = RNA  length = 19
FEATURE                 Location/Qualifiers
source                  1..19
```

```
                          mol_type = other RNA
                          organism = synthetic construct
modified_base             order(1,2,4,6,10..19)
                          mod_base = OTHER
                          note = 2-prime-O-methyl RNA nucleotides
modified_base             order(5,7..9)
                          mod_base = OTHER
                          note = 2-prime-fluoro RNA nucleotides
modified_base             1^2
                          mod_base = OTHER
                          note = phosphorothioate
modified_base             2^3
                          mod_base = OTHER
                          note = phosphorothioate
modified_base             3
                          mod_base = OTHER
                          note = 3-prime,4-prime seco modified nucleotide
SEQUENCE: 93
ccgtgtgcac ttcgcttca                                                19

SEQ ID NO: 94             moltype = RNA  length = 22
FEATURE                   Location/Qualifiers
source                    1..22
                          mol_type = other RNA
                          organism = synthetic construct
modified_base             order(3,4,6,7,9..13,15,16,18..21)
                          mod_base = OTHER
                          note = 2-prime-O-methyl RNA nucleotides
modified_base             1
                          mod_base = OTHER
                          note = Nucleotide Phosphate mimic
modified_base             order(2,5,8,14,17)
                          mod_base = OTHER
                          note = 2-prime-fluoro RNA nucleotides
modified_base             1^2
                          mod_base = OTHER
                          note = phosphorothioate
modified_base             2^3
                          mod_base = OTHER
                          note = phosphorothioate
modified_base             19^20
                          mod_base = OTHER
                          note = phosphorothioate
modified_base             20^21
                          mod_base = OTHER
                          note = phosphorothioate
SEQUENCE: 94
ttgaagcgaa gtgcacacgg tc                                            22

SEQ ID NO: 95             moltype = RNA  length = 19
FEATURE                   Location/Qualifiers
source                    1..19
                          mol_type = other RNA
                          organism = synthetic construct
modified_base             order(1..3,6,10..19)
                          mod_base = OTHER
                          note = 2-prime-O-methyl RNA nucleotides
modified_base             order(5,7..9)
                          mod_base = OTHER
                          note = 2-prime-fluoro RNA nucleotides
modified_base             4
                          mod_base = OTHER
                          note = 3-prime,4-prime seco modified nucleotide
modified_base             1^2
                          mod_base = OTHER
                          note = phosphorothioate
modified_base             2^3
                          mod_base = OTHER
                          note = phosphorothioate
SEQUENCE: 95
ccgtgtgcac ttcgcttca                                                19

SEQ ID NO: 96             moltype = RNA  length = 19
FEATURE                   Location/Qualifiers
source                    1..19
                          mol_type = other RNA
                          organism = synthetic construct
modified_base             order(1..4,10..19)
                          mod_base = OTHER
```

```
                      note = 2-prime-O-methyl RNA nucleotides
modified_base         order(5,7..9)
                      mod_base = OTHER
                      note = 2-prime-fluoro RNA nucleotides
modified_base         6
                      mod_base = OTHER
                      note = 3-prime,4-prime seco modified nucleotide
modified_base         1^2
                      mod_base = OTHER
                      note = phosphorothioate
modified_base         2^3
                      mod_base = OTHER
                      note = phosphorothioate
SEQUENCE: 96
ccgtgtgcac ttcgcttca                                            19

SEQ ID NO: 97         moltype = RNA  length = 19
FEATURE               Location/Qualifiers
source                1..19
                      mol_type = other RNA
                      organism = synthetic construct
modified_base         order(1..4,6,11..19)
                      mod_base = OTHER
                      note = 2-prime-O-methyl RNA nucleotides
modified_base         order(5,7..9)
                      mod_base = OTHER
                      note = 2-prime-fluoro RNA nucleotides
modified_base         10
                      mod_base = OTHER
                      note = 3-prime,4-prime seco modified nucleotide
modified_base         1^2
                      mod_base = OTHER
                      note = phosphorothioate
modified_base         2^3
                      mod_base = OTHER
                      note = phosphorothioate
SEQUENCE: 97
ccgtgtgcac ttcgcttca                                            19

SEQ ID NO: 98         moltype = RNA  length = 19
FEATURE               Location/Qualifiers
source                1..19
                      mol_type = other RNA
                      organism = synthetic construct
modified_base         order(1..4,6,10,12..19)
                      mod_base = OTHER
                      note = 2-prime-O-methyl RNA nucleotides
modified_base         order(5,7..9)
                      mod_base = OTHER
                      note = 2-prime-fluoro RNA nucleotides
modified_base         11
                      mod_base = OTHER
                      note = 3-prime,4-prime seco modified nucleotide
modified_base         1^2
                      mod_base = OTHER
                      note = phosphorothioate
modified_base         2^3
                      mod_base = OTHER
                      note = phosphorothioate
SEQUENCE: 98
ccgtgtgcac ttcgcttca                                            19

SEQ ID NO: 99         moltype = RNA  length = 19
FEATURE               Location/Qualifiers
source                1..19
                      mol_type = other RNA
                      organism = synthetic construct
modified_base         order(1..4,6,10,11,13..19)
                      mod_base = OTHER
                      note = 2-prime-O-methyl RNA nucleotides
modified_base         order(5,7..9)
                      mod_base = OTHER
                      note = 2-prime-fluoro RNA nucleotides
modified_base         12
                      mod_base = OTHER
                      note = 3-prime,4-prime seco modified nucleotide
modified_base         1^2
                      mod_base = OTHER
                      note = phosphorothioate
```

-continued

```
modified_base          2^3
                       mod_base = OTHER
                       note = phosphorothioate
SEQUENCE: 99
ccgtgtgcac ttcgcttca                                              19

SEQ ID NO: 100         moltype = RNA  length = 19
FEATURE                Location/Qualifiers
source                 1..19
                       mol_type = other RNA
                       organism = synthetic construct
modified_base          order(1..4,6,10..12,14..19)
                       mod_base = OTHER
                       note = 2-prime-O-methyl RNA nucleotides
modified_base          order(5,7..9)
                       mod_base = OTHER
                       note = 2-prime-fluoro RNA nucleotides
modified_base          13
                       mod_base = OTHER
                       note = 3-prime,4-prime seco modified nucleotide
modified_base          1^2
                       mod_base = OTHER
                       note = phosphorothioate
modified_base          2^3
                       mod_base = OTHER
                       note = phosphorothioate
SEQUENCE: 100
ccgtgtgcac ttcgcttca                                              19

SEQ ID NO: 101         moltype = RNA  length = 19
FEATURE                Location/Qualifiers
source                 1..19
                       mol_type = other RNA
                       organism = synthetic construct
modified_base          order(1..4,6,10..13,15..19)
                       mod_base = OTHER
                       note = 2-prime-O-methyl RNA nucleotides
modified_base          order(5,7..9)
                       mod_base = OTHER
                       note = 2-prime-fluoro RNA nucleotides
modified_base          14
                       mod_base = OTHER
                       note = 3-prime,4-prime seco modified nucleotide
modified_base          1^2
                       mod_base = OTHER
                       note = phosphorothioate
modified_base          2^3
                       mod_base = OTHER
                       note = phosphorothioate
SEQUENCE: 101
ccgtgtgcac ttcgcttca                                              19

SEQ ID NO: 102         moltype = RNA  length = 19
FEATURE                Location/Qualifiers
source                 1..19
                       mol_type = other RNA
                       organism = synthetic construct
modified_base          order(1..4,6,10..14,16..19)
                       mod_base = OTHER
                       note = 2-prime-O-methyl RNA nucleotides
modified_base          order(5,7..9)
                       mod_base = OTHER
                       note = 2-prime-fluoro RNA nucleotides
modified_base          15
                       mod_base = OTHER
                       note = 3-prime,4-prime seco modified nucleotide
modified_base          1^2
                       mod_base = OTHER
                       note = phosphorothioate
modified_base          2^3
                       mod_base = OTHER
                       note = phosphorothioate
SEQUENCE: 102
ccgtgtgcac ttcgcttca                                              19

SEQ ID NO: 103         moltype = RNA  length = 19
FEATURE                Location/Qualifiers
source                 1..19
                       mol_type = other RNA
```

```
                        organism = synthetic construct
modified_base           order(1..4,6,10..15,17..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           16
                        mod_base = OTHER
                        note = 3-prime,4-prime seco modified nucleotide
modified_base           1^2
                        mod_base = OTHER
                        note = phosphorothioate
modified_base           2^3
                        mod_base = OTHER
                        note = phosphorothioate
SEQUENCE: 103
ccgtgtgcac ttcgcttca                                                19

SEQ ID NO: 104          moltype = RNA  length = 19
FEATURE                 Location/Qualifiers
source                  1..19
                        mol_type = other RNA
                        organism = synthetic construct
modified_base           order(1..4,6,10..16,18,19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           17
                        mod_base = OTHER
                        note = 3-prime,4-prime seco modified nucleotide
modified_base           1^2
                        mod_base = OTHER
                        note = phosphorothioate
modified_base           2^3
                        mod_base = OTHER
                        note = phosphorothioate
SEQUENCE: 104
ccgtgtgcac ttcgcttca                                                19

SEQ ID NO: 105          moltype = RNA  length = 19
FEATURE                 Location/Qualifiers
source                  1..19
                        mol_type = other RNA
                        organism = synthetic construct
modified_base           order(1..4,6,10..17,19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           18
                        mod_base = OTHER
                        note = 3-prime,4-prime seco modified nucleotide
modified_base           1^2
                        mod_base = OTHER
                        note = phosphorothioate
modified_base           2^3
                        mod_base = OTHER
                        note = phosphorothioate
SEQUENCE: 105
ccgtgtgcac ttcgcttca                                                19

SEQ ID NO: 106          moltype = RNA  length = 19
FEATURE                 Location/Qualifiers
source                  1..19
                        mol_type = other RNA
                        organism = synthetic construct
modified_base           order(1,2,4,6,10..19)
                        mod_base = OTHER
                        note = 2-prime-O-methyl RNA nucleotides
modified_base           order(5,7..9)
                        mod_base = OTHER
                        note = 2-prime-fluoro RNA nucleotides
modified_base           3
                        mod_base = OTHER
                        note = 3-prime,4-prime seco modified nucleotide
```

```
modified_base          1^2
                       mod_base = OTHER
                       note = phosphorothioate
modified_base          2^3
                       mod_base = OTHER
                       note = phosphorothioate
SEQUENCE: 106
ccgtgtgcac ttcgcttca                                               19

SEQ ID NO: 107         moltype = RNA  length = 21
FEATURE                Location/Qualifiers
source                 1..21
                       mol_type = other RNA
                       organism = synthetic construct
modified_base          order(1,3,4,6,7,9..13,15,16,18..21)
                       mod_base = OTHER
                       note = 2-prime-O-methyl RNA nucleotides
modified_base          order(2,5,8,14,17)
                       mod_base = OTHER
                       note = 2-prime-fluoro RNA nucleotides
modified_base          1^2
                       mod_base = OTHER
                       note = phosphorothioate
modified_base          18^19
                       mod_base = OTHER
                       note = phosphorothioate
modified_base          19^20
                       mod_base = OTHER
                       note = phosphorothioate
SEQUENCE: 107
tgaagcgaag tgcacacggt c                                            21

SEQ ID NO: 108         moltype = RNA  length = 19
FEATURE                Location/Qualifiers
source                 1..19
                       mol_type = other RNA
                       organism = synthetic construct
modified_base          order(1..4,6,10..15,17..19)
                       mod_base = OTHER
                       note = 2-prime-O-methyl RNA nucleotides
modified_base          order(5,7..9)
                       mod_base = OTHER
                       note = 2-prime-fluoro RNA nucleotides
modified_base          16
                       mod_base = OTHER
                       note = 3-prime,4-prime seco modified nucleotide
modified_base          1^2
                       mod_base = OTHER
                       note = phosphorothioate
modified_base          2^3
                       mod_base = OTHER
                       note = phosphorothioate
SEQUENCE: 108
ccgtgtgcac ttcgcttca                                               19

SEQ ID NO: 109         moltype = RNA  length = 19
FEATURE                Location/Qualifiers
source                 1..19
                       mol_type = other RNA
                       organism = synthetic construct
modified_base          order(1..4,6,10..16,18,19)
                       mod_base = OTHER
                       note = 2-prime-O-methyl RNA nucleotides
modified_base          order(5,7..9)
                       mod_base = OTHER
                       note = 2-prime-fluoro RNA nucleotides
modified_base          17
                       mod_base = OTHER
                       note = 3-prime,4-prime seco modified nucleotide
modified_base          1^2
                       mod_base = OTHER
                       note = phosphorothioate
modified_base          2^3
                       mod_base = OTHER
                       note = phosphorothioate
SEQUENCE: 109
ccgtgtgcac ttcgcttca                                               19

SEQ ID NO: 110         moltype = RNA  length = 19
```

-continued

```
FEATURE                Location/Qualifiers
source                 1..19
                       mol_type = other RNA
                       organism = synthetic construct
modified_base          order(1..4,6,10..17,19)
                       mod_base = OTHER
                       note = 2-prime-O-methyl RNA nucleotides
modified_base          order(5,7..9)
                       mod_base = OTHER
                       note = 2-prime-fluoro RNA nucleotides
modified_base          18
                       mod_base = OTHER
                       note = 3-prime,4-prime seco modified nucleotide
modified_base          1^2
                       mod_base = OTHER
                       note = phosphorothioate
modified_base          2^3
                       mod_base = OTHER
                       note = phosphorothioate
SEQUENCE: 110
ccgtgtgcac ttcgcttca                                            19

SEQ ID NO: 111         moltype = RNA  length = 19
FEATURE                Location/Qualifiers
source                 1..19
                       mol_type = other RNA
                       organism = synthetic construct
modified_base          order(1..4,6,10..19)
                       mod_base = OTHER
                       note = 2-prime-O-methyl RNA nucleotides
modified_base          order(5,7..9)
                       mod_base = OTHER
                       note = 2-prime-fluoro RNA nucleotides
modified_base          1^2
                       mod_base = OTHER
                       note = phosphorothioate
modified_base          2^3
                       mod_base = OTHER
                       note = phosphorothioate
SEQUENCE: 111
ccgtgtgcac ttcgcttca                                            19

SEQ ID NO: 112         moltype = RNA  length = 21
FEATURE                Location/Qualifiers
source                 1..21
                       mol_type = other RNA
                       organism = synthetic construct
modified_base          1
                       mod_base = OTHER
                       note = Nucleotide Phosphate mimic
modified_base          order(3,4,6,7,9..13,15,16,18..21)
                       mod_base = OTHER
                       note = 2-prime-O-methyl RNA nucleotides
modified_base          order(2,5,8,14,17)
                       mod_base = OTHER
                       note = 2-prime-fluoro RNA nucleotides
modified_base          1^2
                       mod_base = OTHER
                       note = phosphorothioate
modified_base          2^3
                       mod_base = OTHER
                       note = phosphorothioate
modified_base          19^20
                       mod_base = OTHER
                       note = phosphorothioate
modified_base          20^21
                       mod_base = OTHER
                       note = phosphorothioate
SEQUENCE: 112
tgaagcgaag tgcacacggt c                                         21

SEQ ID NO: 113         moltype = DNA  length = 29903
FEATURE                Location/Qualifiers
source                 1..29903
                       mol_type = other DNA
                       organism = synthetic construct
SEQUENCE: 113
attaaaggtt tataccttcc caggtaacaa accaaccaac tttcgatctc ttgtagatct  60
gttctctaaa cgaactttaa aatctgtgtg gctgtcactc ggctgcatgc ttagtgcact  120
```

-continued

```
cacgcagtat aattaataac taattactgt cgttgacagg acacgagtaa ctcgtctatc  180
ttctgcaggc tgcttacggt ttcgtccgtg ttgcagccga tcatcagcac atctaggttt  240
cgtccgggtg tgaccgaaag gtaagatgga gagccttgtc cctggtttca acgagaaaac  300
acacgtccaa ctcagtttgc ctgttttaca ggttcgcgac gtgctcgtac gtggctttgg  360
agactccgtg gaggaggtct tatcagaggc acgtcaacat cttaaagatg gcacttgtgg  420
cttagtagaa gttgaaaaag gcgttttgcc tcaacttgaa cagccctatg tgttcatcaa  480
acgttcggat gctcgaactg cacctcatgg tcatgttatg gttgagctgg tagcagaact  540
cgaaggcatt cagtacggtc gtagtggtga gacacttggt gtccttgtcc ctcatgtggg  600
cgaaatacca gtggcttacc gcaaggttct tcttcgtaag aacggtaata aaggagctgg  660
tggccatagt tacggcgccg atctaaagtc atttgactta ggcgacgagc ttggcactga  720
tccttatgaa gattttcaag aaaactggaa cactaaacat agcagtggtg ttacccgtga  780
actcatgcgt gagcttaacg gaggggcata cactcgctat gtcgataaca acttctgtgg  840
ccctgatggc taccctcttg agtgcattaa agaccttcta gcacgtgctg gtaaagcttc  900
atgcactttg tccgaacaac tggactttat tgacactaag aggggtgtat actgctgccg  960
tgaacatgag catgaaattg cttggtacac ggaacgttct gaaaagagct atgaattgca  1020
gacacctttt gaaattaaat tggcaaagaa atttgacacc ttcaatgggg aatgtccaaa  1080
ttttgtattt cccttaaatt ccataatcaa gactattcaa ccaagggttg aaaagaaaaa  1140
gcttgatggc tttatgggta gaattcgatc tgtctatcca gttgcgtcac caaatgaatg  1200
caaccaaatg tgcctttcaa ctctcatgaa gtgtgatcat tgtggtgaaa cttcatggca  1260
gacgggcgat tttgttaaag ccacttgcga attttgtggc actgagaatt tgactaaaga  1320
aggtgccact acttgtggtt acttacccca aaatgctgtt gttaaaattt attgtccagc  1380
atgtcacaat tcagaagtag gacctgagca tagtcttgcc gaataccata atgaatctgg  1440
cttgaaaacc attcttcgta agggtggtcg cactattgcc tttggaggct gtgtgttctc  1500
ttatgttggt tgccataaca agtgtgccta ttgggttcca cgtgctagcg ctaacatagg  1560
ttgtaaccat acaggtgttg ttggagaagg ttccgaaggt cttaatgaca accttcttga  1620
aatactccaa aaagagaaag tcaacatcaa tattgttggt gactttaaac ttaatgaaga  1680
gatcgccatt attttggcat ctttttctgc ttccacaagt gcttttgtgg aaactgtgaa  1740
aggtttggat tataaagcat tcaaacaaat tgttgaatcc tgtggtaatt ttaaagttac  1800
aaaaggaaaa gctaaaaaag gtgcctggaa tattggtgaa cagaaatcaa tactgagtcc  1860
tctttatgca tttgcatcag aggctgctcg tgttgtacga tcaattttct cccgcactct  1920
tgaaactgct caaaattctg tgcgtgtttt acagaaggcc gctataacaa tactagatgg  1980
aatttcacag tattcactga gactcattga tgctatgatg ttcacatctg atttggctac  2040
taacaatcta gttgtaatgg cctacattac aggtggtgtt gttcagttga cttcgcagtg  2100
gctaactaac atctttggca ctgtttatga aaaactcaaa cccgtccttg attggcttga  2160
agagaagttt aaggaaggtg tagagtttct tagagacggt tgggaaattg ttaaatttat  2220
ctcaacctgt gcttgtgaaa ttgtcggtgg acaaattgtc acctgtgcaa aggaaattaa  2280
ggagagtgtt cagacattct ttaagcttgt aaataaattt ttggctttgt gtgctgactc  2340
tatcattatt ggtggagcta aacttaaagc cttgaattta ggtgaaacat ttgtcacgca  2400
ctcaaaggga ttgtacagaa agtgtgttaa atccagagaa gaaactggcc tactcatgcc  2460
tctaaaagcc ccaaaagaaa ttatcttctt agagggagaa acacttccca cagaagtgtt  2520
aacagaggaa gttgtcttga aaactggtga tttacaacca ttagaacaac ctactagtga  2580
agctgttgaa gctccattgg ttggtacacc agtttgtatt aacgggctta tgttgctcga  2640
aatcaaagac acagaaaagt actgtgccct tgcacctaat atgatggtaa caaacaatac  2700
cttcacactc aaaggcggtg caccaacaaa ggttactttt ggtgatgaca ctgtgataga  2760
agtgcaaggt tacaagagtg tgaatatcac ttttgaactt gatgaaagga ttgataaagt  2820
acttaatgag aagtgctctg cctatacagt tgaactcggt acagaagtaa atgagttcgc  2880
ctgtgttgtg gcagatgctg tcataaaaac tttgcaacca gtatctgaat tacttacacc  2940
actgggcatt gatttagatg agtggagtat ggctacatac tacttatttg atgagtctgg  3000
tgagtttaaa ttggcttcac atatgtattg ttctttctac cctccagatg aggatgaaga  3060
agaaggtgat tgtgaagaag aagagtttga gccatcaact caatatgagt atggtactga  3120
agatgattac caaggtaaac ctttggaatt tggtgccact tctgctgctc ttcaacctga  3180
agaagagcaa gaagaagatt ggttagatga tgatagtcaa caaactgttg gtcaacaaga  3240
cggcagtgag gacaatcaga caactactat tcaaacaatt gttgaggttc aacctcaatt  3300
agagatggaa cttacaccag ttgttcagac tattgaagtg aatagtttta gtggttattt  3360
aaaacttact gacaatgtat acattaaaaa tgcagacatt gtggaagaag ctaaaaaggt  3420
aaaaccaaca gtggttgtta atgcagccaa tgtttacctt aaacatggag gaggtgttgc  3480
aggagcctta aataaggcta ctaacaatgc catgcaagtt gaatctgatg attacatagc  3540
tactaatgga ccacttaaag tgggtggtag ttgtgtttta agcggacaca atcttgctaa  3600
acactgtctt catgttgtcg gcccaaatgt taacaaaggt gaagacattc aacttcttaa  3660
gagtgcttat gaaaatttta atcagcacga agttctactt gcaccattat tatcagctgg  3720
tatttttggt gctgacccta tacattcttt aagagtttgt gtagatactg ttcgcacaaa  3780
tgtctactta gctgtctttg ataaaaatct ctatgacaaa cttgtttcaa gctttttgga  3840
aatgaagagt gaaaagcaag ttgaacaaaa gatcgctgag attcctaaag aggaagttaa  3900
gccatttata actgaaagta aaccttcagt tgaacagaga aaacaagatg ataagaaaat  3960
caaagcttgt gttgaagaag ttacaacaac tctggaagaa actaagttcc tcacagaaaa  4020
cttgttactt tatattgaca ttaatggcaa tcttcatcca gattctgcca ctcttgttag  4080
tgacattgac atcactttct taaagaaaga tgctccatat atagtgggtg atgttgttca  4140
agagggtgtt ttaactgctg tggttatacc tactaaaaag gctggtggca ctactgaaat  4200
gctagcgaaa gctttgagaa aagtgccaac agacaattat ataaccactt acccgggtca  4260
gggtttaaat ggttacactg tagaggaggc aaagacagtg cttaaaaagt gtaaaagtgc  4320
cttttacatt ctaccatcta ttatctctaa tgagaagcaa gaaattcttg gaactgtttc  4380
ttggaatttg cgagaaatgc ttgcacatgc agaagaaaca cgcaaattaa tgcctgtctg  4440
tgtggaaact aaagccatag tttcaactat acagcgtaaa tataagggta ttaaaataca  4500
agagggtgtg gttgattatg gtgctagatt ttacttttac accagtaaaa caactgtagc  4560
gtcacttatc aacacactta acgatctaaa tgaaactctt gttacaatgc cacttggcta  4620
tgtaacacat ggcttaaatt tggaagaagc tgctcggtat atgagatctc tcaaagtgcc  4680
agctacagtt tctgtttctt cacctgatgc tgttacagcg tataatggtt atcttacttc  4740
ttcttctaaa acacctgaag aacattttat tgaaaccatc tcacttgctg gttcctataa  4800
agattggtcc tattctggac aatctacaca actaggtata gaatttctta agagaggtga  4860
```

-continued

```
taaaagtgta tattacacta gtaatcctac cacattccac ctagatggtg aagttatcac  4920
ctttgacaat cttaagacac ttctttcttt gagagaagtg aggactatta aggtgtttac  4980
aacagtagac aacattaacc tccacacgca agttgtggac atgtcaatga catatggaca  5040
acagtttggt ccaacttatt tggatggagc tgatgttact aaaataaaac ctcataattc  5100
acatgaaggt aaaacatttt atgttttacc taatgatgac actctacgtg ttgaggcttt  5160
tgagtactac cacacaactg atcctagttt tctgggtagg tacatgtcag cattaaatca  5220
cactaaaaag tggaaatacc cacaagttaa tggtttaact tctattaaat gggcagataa  5280
caactgttat cttgccactg cattgttaac actccaacaa atagagttga agtttaatcc  5340
acctgctcta caagatgctt attacagagc aagggctggt gaagctgcta acttttgtgc  5400
acttatctta gcctactgta ataagacagt aggtgagtta ggtgatgtta gagaaacaat  5460
gagttacttg tttcaacatg ccaatttaga ttcttgcaaa agagtcttga acgtggtgtg  5520
taaaacttgt ggacaacagc agacaaccct taagggtgta gaagctgtta tgtacatggg  5580
cacactttct tatgaacaat ttaagaaagg tgttcagata ccttgtacgt gtggtaaaca  5640
agctacaaaa tatctagtac aacaggagtc acctttttgtt atgatgtcag caccacctgc  5700
tcagtatgaa cttaagcatg gtacatttac ttgtgctagt gagtacactg gtaattacca  5760
gtgtggtcac tataaacata taacttctaa agaaactttg tattgcatag acggtgcttt  5820
acttacaaag tcctcagaat acaaaggtcc tattacggat gttttctaca aagaaaacag  5880
ttacacaaca accataaaac cagttactta taaattggat ggtgttgttt gtacagaaat  5940
tgaccctaag ttggacaatt attataagaa agacaattct tatttcacag agcaaccaat  6000
tgatcttgta ccaaaccaac catatccaaa cgcaagcttc gataatttta agtttgtatg  6060
tgataatatc aaatttgctg atgatttaaa ccagttaact ggttataaga aacctgcttc  6120
aagagagctt aaagttacat ttttccctga cttaaatggt gatgtggtgg ctattgatta  6180
taaacactac acaccctctt ttaagaaagg agctaaattg ttacataaac ctattgtttg  6240
gcatgttaac aatgcaacta ataaagccac gtataaacca aatacctggt gtatacgttg  6300
tctttggagc acaaaaccag ttgaaacatc aaattcgttt gatgtactga agtcagagga  6360
cgcgcaggga atggataatc ttgcctgcga agatctaaaa ccagtctctg aagaagtagt  6420
ggaaaatcct accatacaga aagacgttct tgagtgtaat gtgaaaacta ccgaagttgt  6480
aggagacatt atacttaaac cagcaaataa tagtttaaaa attacagaag aggttggcca  6540
cacagatcta atggctgctt atgtagacaa ttctagtctt actattaaga aacctaatga  6600
attatctaga gtattaggtt tgaaaaccct tgctactcat ggtttagctg ctgttaatag  6660
tgtcccttgg gatactatag ctaattatgc taagcctttt cttaacaaag ttgttagtac  6720
aactactaac atagttacac ggtgtttaaa ccgtgtttgt actaattata tgccttattt  6780
ctttacttta ttgctacaat tgtgtacttt tactagaagt acaaattcta gaattaaagc  6840
atctatgccg actactatag caaagaatac tgttaagagt gtcggtaaat tttgtctaga  6900
ggcttcattt aattatttga agtcacctaa tttttctaaa ctgataaata ttataatttg  6960
gtttttacta ttaagtgttt gcctaggttc tttaatctac tcaaccgctg ctttaggtgt  7020
tttaatgtct aatttaggca tgccttctta ctgtactggt tacagagaag gctatttgaa  7080
ctctactaat gtcactattg caacctactg tactggttct ataccttgta gtgtttgtct  7140
tagtggttta gattctttag acacctatcc ttctttagaa actatacaaa ttaccatttc  7200
atcttttaaa tgggatttaa ctgcttttgg cttagttgca gagtggtttt tggcatatat  7260
tcttttcact aggtttttct atgtacttgg attggctgca atcatgcaat tgtttttcag  7320
ctattttgca gtacatttta ttagtaattc ttggcttatg tggttaataa ttaatcttgt  7380
acaaatggcc ccgatttcag ctatggttag aatgtacatc ttctttgcat cattttatta  7440
tgtatggaaa agttatgtgc atgttgtaga cggttgtaat tcatcaactt gtatgatgtg  7500
ttacaaacgt aatagagcaa caagagtcga atgtacaact attgttaatg gtgttagaag  7560
gtccttttat gtctatgcta atggaggtaa aggcttttgc aaactacaca attggaattg  7620
tgttaattgt gatacattct gtgctggtag tacatttatt agtgatgaag ttgcgagaga  7680
cttgtcacta cagtttaaaa gaccaataaa tcctactgac cagtcttctt acatcgttga  7740
tagtgttaca gtgaagaatg gttccatcca tctttacttt gataaagctg gtcaaaagac  7800
ttatgaaaga cattctctct ctcattttgt taacttagac aacctgagag ctaataacac  7860
taaaggttca ttgcctatta atgttatagt ttttgatggt aaatcaaaat gtgaagaatc  7920
atctgcaaaa tcagcgtctg tttactacag tcagcttatg tgtcaaccta tactgttact  7980
agatcaggca ttagtgtctg atgttggtga tagtgcggaa gttgcagtta aaatgtttga  8040
tgcttacgtt aatacgtttt catcaacttt taacgtacca atggaaaaac tcaaaacact  8100
agttgcaact gcagaagctg aacttgcaaa gaatgtgtcc ttagacaatg tcttatctac  8160
ttttatttca gcagctcggc aagggtttgt tgattcagat gtagaaacta aagatgttgt  8220
tgaatgtctt aaattgtcac atcaatctga catagaagtt actggcgata gttgtaataa  8280
ctatatgctc acctataaca aagttgaaaa catgacaccc cgtgaccttg gtgcttgtat  8340
tgactgtagt gcgcgtcata ttaatgcgca ggtagcaaaa agtcacaaca ttgctttgat  8400
atggaacgtt aaagatttca tgtcattgtc tgaacaacta cgaaaacaaa tacgtagtgc  8460
tgctaaaaag aataacttac cttttaagtt gacatgtgca actactagac aagttgttaa  8520
tgttgtaaca acaaagatag cacttaaggg tggtaaaatt gttaataatt ggttgaagca  8580
gttaattaaa gttacacttg tgttcctttt tgttgctgct attttctatt taataacacc  8640
tgttcatgtc atgtctaaac atactgactt ttcaagtgaa atcataggat acaaggctat  8700
tgatggtggt gtcactcgtg acatagcatc tacagatact tgttttgcta acaaacatgc  8760
tgattttgac acatggttta gccagcgtgg tggtagttat actaatgaca aagcttgccc  8820
attgattgct gcagtcataa caagagaagt gggttttgtc gtgcctggtt tgcctggcac  8880
gatattacgc acaactaatg gtgacttttt gcatttctta cctagagttt ttagtgcagt  8940
tggtaacatc tgttacacac catcaaaact tatagagtac actgactttg caacatcagc  9000
ttgtgttttg gctgctgaat gtacaatttt taaagatgct tctggtaagc cagtaccata  9060
ttgttatgat accaatgtac tagaaggttc tgttgcttat gaaagtttac gccctgacac  9120
acgttatgtg ctcatggatg gctctattat tcaatttcct aacacctacc ttgaaggttc  9180
tgttagagtg gtaacaactt ttgattctga gtactgtagg cacggcactt gtgaaagatc  9240
agaagctggt gtttgtgtat ctactagtgg tagatgggta cttaacaatg attattacag  9300
atctttacca ggagttttct gtggtgtaga tgctgtaaat ttacttacta atatgtttac  9360
accactaatt caacctattg gtgctttgga catatcagca tctatagtag ctggtggtat  9420
tgtagctatc gtagtaacat gccttgccta ctattttatg aggtttagaa gagcttttgg  9480
tgaatacagt catgtagttg cctttaatac tttactattc cttatgtcat tcactgtact  9540
ctgtttaaca ccagtttact cattcttacc tggtgtttat tctgttattt acttgtactt  9600
```

-continued

```
gacattttat cttactaatg atgtttcttt tttagcacat attcagtgga tggttatgtt  9660
cacaccttta gtacctttct ggataacaat tgcttatatc atttgtattt ccacaaagca  9720
tttctattgg ttctttagta attacctaaa gagacgtgta gtctttaatg gtgtttcctt  9780
tagtactttt gaagaagctg cgctgtgcac ctttttgtta aataaagaaa tgtatctaaa  9840
gttgcgtagt gatgtgctat tacctcttac gcaatataat agatacttag ctctttataa  9900
taagtacaag tattttagtg gagcaatgga tacaactagc tacagagaag ctgcttgttg  9960
tcatctcgca aaggctctca atgacttcag taactcaggt tctgatgttc tttaccaacc  10020
accacaaacc tctatcacct cagctgtttt gcagagtggt tttagaaaaa tggcattccc  10080
atctggtaaa gttgagggtt gtatggtaca agtaacttgt ggtacaacta cacttaacgg  10140
tctttggctt gatgacgtag tttactgtcc aagacatgtg atctgcacct ctgaagacat  10200
gcttaaccct aattatgaag atttactcat tcgtaagtct aatcataatt tcttggtaca  10260
ggctggtaat gttcaactca gggttattgg acattctatg caaaattgtg tacttaagct  10320
taaggttgat acagccaatc ctaagacacc taagtataag tttgttcgca ttcaaccagg  10380
acagactttt tcagtgttag cttgttacaa tggttcacca tctggtgttt accaatgtgc  10440
tatgaggccc aatttcacta ttaagggttc attccttaat ggttcatgtg gtagtgttgg  10500
ttttaacata gattatgact gtgtctcttt ttgttacatg caccatatgg aattaccaac  10560
tggagttcat gctggcacag acttagaagg taacttttat ggaccttttg ttgacaggca  10620
aacagcacaa gcagctggta cggacacaac tattacagtt aatgttttag cttggttgta  10680
cgctgctgtt ataaatggag acaggtggtt tctcaatcga tttaccacaa ctcttaatga  10740
ctttaacctt gtggctatga agtacaatta tgaacctcta acacaagacc atgttgacat  10800
actaggacct ctttctgctc aaactggaat tgccgtttta gatatgtgtg cttcattaaa  10860
agaattactg caaaatggta tgaatggacg taccatattg ggtagtgctt tattagaaga  10920
tgaatttaca ccttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgccttttt  11100
accttttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
gaatgtcttg acactcgttt ataaagttta ttatggtaat gctttagatc aagccatttc  11460
catgtgggct cttataatct ctgttacttc taactactca ggtgtagtta caactgtcat  11520
gtttttggcc agaggtattg tttttatgtg tgttgagtat tgccctattt tcttcataac  11580
tggtaataca cttcagtgta taatgctagt ttattgtttc ttaggctatt tttgtacttg  11640
ttactttggc ctcttttgtt tactcaaccg ctactttaga ctgactcttg gtgtttatga  11700
ttacttagtt tctacacagg agtttagata tatgaattca cagggactac tcccacccaa  11760
gaatagcata gatgccttca aactcaacat taaattgttg ggtgttggtg gcaaaccttg  11820
tatcaaagta gccactgtac agtctaaaat gtcagatgta aagtgcacat cagtagtctt  11880
actctcagtt ttgcaacaac tcagagtaga atcatcatct aaattgtggg ctcaatgtgt  11940
ccagttacac aatgacattc tcttagctaa agatactact gaagcctttg aaaaaatggt  12000
ttcactactt tctgttttgc tttccatgca gggtgctgta gacataaaca agctttgtga  12060
agaaatgctg gacaacaggg caaccttaca agctatagcc tcagagttta gttcccttcc  12120
atcatatgca gcttttgcta ctgctcaaga agcttatgag caggctgttg ctaatggtga  12180
ttctgaagtt gttcttaaaa agttgaagaa gtctttgaat gtggctaaat ctgaatttga  12240
ccgtgatgca gccatgcaac gtaagttgga aaagatggct gatcaagcta tgacccaaat  12300
gtataaacag gctagatctg aggacaagag ggcaaaagtt actagtgcta tgcagacaat  12360
gcttttcact atgcttagaa agttggataa tgatgcactc aacaacatta tcaacaatgc  12420
aagagatggt tgtgttccct tgaacataat acctcttaca acagcagcca aactaatggt  12480
tgtcatacca gactataaca catataaaaa tacgtgtgat ggtacaacat ttacttatgc  12540
atcagcattg tgggaaatcc aacaggttgt agatgcagat agtaaaattg ttcaacttag  12600
tgaaattagt atggacaatt cacctaattt agcatggcct cttattgtaa cagctttaag  12660
ggccaattct gctgtcaaat tacagaataa tgagcttagt cctgttgcac tacgacagat  12720
gtcttgtgct gccggtacta cacaaactgc ttgcactgat gacaatgcgt tagcttacta  12780
caacacaaca aagggaggta ggtttgtact tgcactgtta tccgatttac aggatttgaa  12840
atgggctaga ttccctaaga gtgatggaac tggtactatc tatacagaac tggaaccacc  12900
ttgtaggttt gttacagaca cacctaaagg tcctaaagtg aagtatttat actttattaa  12960
aggattaaac aacctaaata gaggtatggt acttggtagt ttagctgcca cagtacgtct  13020
acaagctggt aatgcaacag aagtgcctgc caattcaact gtattatctt tctgtgcttt  13080
tgctgtagat gctgctaaag cttacaaaga ttatctagct agtgggggac aaccaatcac  13140
taattgtgtt aagatgttgt gtacacacac tggtactggt caggcaataa cagttacacc  13200
ggaagccaat atggatcaag aatcctttgg tggtgcatcg tgttgtctgt actgccgttg  13260
ccacatagat catccaaatc ctaaaggatt ttgtgactta aaaggtaagt atgtacaaat  13320
acctacaact tgtgctaatg accctgtggg ttttacactt aaaaacacag tctgtaccgt  13380
ctgcggtatg tggaaaggtt atggctgtag ttgtgatcaa ctccgcgaac ccatgcttca  13440
gtcagctgat gcacaatcgt ttttaaacgg gtttgcggtg taagtgcagc ccgtcttaca  13500
ccgtgcggca caggcactag tactgatgtc gtatacaggg cttttgacat ctacaatgat  13560
aaagtagctg gttttgctaa attcctaaaa actaattgtt gtcgcttcca agaaaaggac  13620
gaagatgaca atttaattga ttcttacttt gtagttaaga gacacacttt ctctaactac  13680
caacatgaag aaacaattta taatttactt aaggattgtc cagctgttgc taaacatgac  13740
ttctttaagt ttagaataga cggtgacatg gtaccacata tatcacgtca acgtcttact  13800
aaatacacaa tggcagacct cgtctatgct ttaaggcatt ttgatgaagg taattgtgac  13860
acattaaaag aaatacttgt cacatacaat tgttgtgatg atgattattt caataaaaag  13920
gactggtatg attttgtaga aaacccagat atattacgcg tatacgccaa cttaggtgaa  13980
cgtgtacgcc aagctttgtt aaaaacagta caattctgtg atgccatgcg aaatgctggt  14040
attgttggtg tactgacatt agataatcaa gatctcaatg gtaactggta tgatttcggt  14100
gatttcatac aaaccacgcc aggtagtgga gttcctgttg tagattctta ttattcattg  14160
ttaatgccta tattaacctt gaccagggct ttaactgcag agtcacatgt tgacactgac  14220
ttaacaaagc cttacattaa gtgggatttg ttaaaatatg acttcacgga agagaggtta  14280
aaactctttg accgttattt taaatattgg gatcagacat accacccaaa ttgtgttaac  14340
```

-continued

```
tgtttggatg acagatgcat tctgcattgt gcaaacttta atgttttatt ctctacagtg  14400
ttcccaccta caagttttgg accactagtg agaaaaatat ttgttgatgg tgttccattt  14460
gtagtttcaa ctggatacca cttcagagag ctaggtgttg tacataatca ggatgtaaac  14520
ttacatagct ctagacttag ttttaaggaa ttacttgtgt atgctgctga ccctgctatg  14580
cacgctgctt ctggtaatct attactagat aaacgcacta cgtgcttttc agtagctgca  14640
cttactaaca atgttgcttt tcaaactgtc aaacccggta attttaacaa agacttctat  14700
gactttgctg tgtctaaggg tttctttaag gaaggaagtt ctgttgaatt aaaacacttc  14760
ttctttgctc aggatggtaa tgctgctatc agcgattatg actactatcg ttataatcta  14820
ccaacaatgt gtgatatcag acaactacta tttgtagttg aagttgttga taagtacttt  14880
gattgttacg atggtggctg tattaatgct aaccaagtca tcgtcaacaa cctagacaaa  14940
tcagctggtt ttccatttaa taaatggggt aaggctagac tttattatga ttcaatgagt  15000
tatgaggatc aagatgcact tttcgcatat acaaaacgta atgtcatccc tactataact  15060
caaatgaatc ttaagtatgc cattagtgca aagaatagag ctcgcaccgt agctggtgtc  15120
tctatctgta gtactatgac caatagacag tttcatcaaa aattattgaa atcaatagcc  15180
gccactagag gagctactgt agtaattgga acaagcaaat tctatggtgg ttggcacaac  15240
atgttaaaaa ctgtttatag tgatgtagaa aaccctcacc ttatgggttg ggattatcct  15300
aaatgtgata gagccatgcc taacatgctt agaattatgg cctcacttgt tcttgctcgc  15360
aaacatacaa cgtgttgtag cttgtcacac cgtttctata gattagctaa tgagtgtgct  15420
caagtattga gtgaaatggt catgtgtggc ggttcactat atgttaaacc aggtggaacc  15480
tcatcaggag atgccacaac tgcttatgct aatagtgttt ttaacatttg tcaagctgtc  15540
acggccaatg ttaatgcact tttatctact gatggtaaca aaattgccga taagtatgtc  15600
cgcaatttac aacacagact ttatgagtgt ctctatagaa atagagatgt tgacacagac  15660
tttgtgaatg agttttacgc atatttgcgt aaacatttct caatgatgat actctctgac  15720
gatgctgttg tgtgtttcaa tagcacttat gcatctcaag gtctagtggc tagcataaag  15780
aactttaagt cagttcttta ttatcaaaac aatgttttta tgtctgaagc aaaatgttgg  15840
actgagactg accttactaa aggacctcat gaattttgct ctcaacatac aatgctagtt  15900
aaacagggtg atgattatgt gtaccttcct tacccagatc catcaagaat cctaggggcc  15960
ggctgttttg tagatgatat cgtaaaaaca gatggtacac ttatgattga acggttcgtg  16020
tctttagcta tagatgctta cccacttact aaacatccta atcaggagta tgctgatgtc  16080
tttcatttgt acttacaata cataagaaag ctacatgatg agttaacagg acacatgtta  16140
gacatgtatt ctgttatgct tactaatgat aacacttcaa ggtattggga acctgagttt  16200
tatgaggcta tgtacacacc gcatacagtc ttacaggctg ttggggcttg tgttctttgc  16260
aattcacaga cttcattaag atgtggtgct tgcatacgta gaccattctt atgttgtaaa  16320
tgctgttacg accatgtcat atcaacatca cataaattag tcttgtctgt taatccgtat  16380
gtttgcaatg ctccaggttg tgatgtcaca gatgtgactc aactttactt aggaggtatg  16440
agctattatt gtaaatcaca taaaccaccc attagtttc cattgtgtgc taatggacaa  16500
gtttttggtt tatataaaaa tacatgtgtt ggtagcgata atgttactga ctttaatgca  16560
attgcaacat gtgactggac aaatgctggt gattacattt tagctaacac ctgtactgaa  16620
agactcaagc tttttgcagc agaaacgctc aaagctactg aggagacatt taaactgtct  16680
tatggtattg ctactgtacg tgaagtgctg tctgacagag aattacatct ttcatgggaa  16740
gttggtaaac ctagaccacc acttaaccga aattatgtct ttactggtta tcgtgtaact  16800
aaaaacagta aagtacaaat aggagagtac acctttgaaa aaggtgacta tggtgatgct  16860
gttgtttacc gaggtacaac aacttacaaa ttaaatgttg gtgattattt tgtgctgaca  16920
tcacatacag taatgccatt aagtgcacct acactagtgc cacaagagca ctatgttaga  16980
attactggct tatacccaac actcaatatc tcagatgagt tttctagcaa tgttgcaaat  17040
tatcaaaagg ttggtatgca aaagtattct acactccagg gaccacctgg tactggtaag  17100
agtcattttg ctattggcct agctctctac taccttctg ctcgcatagt gtatacagct  17160
tgctctcatg ccgctgttga tgcactatgt gagaaggcat taaaatattt gcctatagat  17220
aaatgtagta gaattatacc tgcacgtgct cgtgtagagt gttttgataa attcaaagtg  17280
aattcaacat tagaacagta tgtcttttgt actgtaaatg cattgcctga gacgacagca  17340
gatatagttg tctttgatga aatttcaatg gccacaaatt atgatttgag tgttgtcaat  17400
gccagattac gtgctaagca ctatgtgtac attggcgacc ctgctcaatt acctgcacca  17460
cgcacattgc taactaaggg cacactagaa ccagaatatt tcaattcagt gtgtagactt  17520
atgaaaacta taggtccaga catgttcctc ggaacttgtc ggcgttgtcc tgctgaaatt  17580
gttgacactg tgagtgcttt ggtttatgat aataagctta aagcacataa agacaaatca  17640
gctcaatgct ttaaaatgtt ttataagggt gttatcacgc atgatgtttc atctgcaatt  17700
aacaggccac aaataggcgt ggtaagagaa ttccttacac gtaaccctgc ttggagaaaa  17760
gctgtcttta tttcacctta taattcacag aatgctgtag cctcaaagat tttgggacta  17820
ccaactcaaa ctgttgattc atcacagggc tcagaatatg actatgtcat attcactcaa  17880
accactgaaa cagctcactc ttgtaatgta aacagattta atgttgctat taccagagca  17940
aaagtaggca tactttgcat aatgtctgat agagaccttt atgacaagtt gcaatttaca  18000
agtcttgaaa ttccacgtag gaatgtggca actttacaag ctgaaaatgt aacaggactc  18060
tttaaagatt gtagtaaggt aatcactggg ttacatccta cacaggcacc tacacacctc  18120
agtgttgaca ctaaattcaa aactgaaggt ttatgtgttg acatacctgg catacctaag  18180
gacatgacct atagaagact catctctatg atgggtttta aaatgaatta tcaagttaat  18240
ggttacccta acatgtttat cacccgcgaa gaagctataa gacatgtacg tgcatggatt  18300
ggcttcgatg tcgagggggtg tcatgctact agagaagctg ttggtaccaa tttaccttta  18360
cagctaggtt tttctacagg tgttaaccta gttgctgtac ctacaggtta tgttgataca  18420
cctaataata cagattttc cagagttagt gctaaaccac cgcctggaga tcaatttaaa  18480
cacctcatac cacttatgta caaaggactt ccttggaatg tagtgcgtat aaagattgta  18540
caaatgttaa gtgacacact taaaaatctc tctgacagag tcgtatttgt cttatgggca  18600
catggctttg agttgacatc tatgaagtat tttgtgaaaa taggacctga gcgcacctgt  18660
tgtctatgtg atagacgtgc cacatgcttt tccactgctt cagacactta tgcctgttgg  18720
catcattcta ttggatttga ttacgtctat aatccgttta tgattgatgt tcaacaatgg  18780
ggttttacag gtaacctaca aagcaaccat gatctgtatt gtcaagtcca tggtaatgca  18840
catgtagcta gttgtgatgc aatcatgact aggtgtctag ctgtccacga gtgctttgtt  18900
aagcgtgttg actggactat tgaatatcct ataattggtg atgaactgaa gattaatgcg  18960
gcttgtagaa aggttcaaca catggttgtt aaagctgcat tattagcaga caaattccca  19020
gttcttcacg acattggtaa ccctaaagct attaagtgtg tacctcaagc tgatgtagaa  19080
```

-continued

```
tggaagttct atgatgcaca gccttgtagt gacaaagctt ataaaataga agaattattc  19140
tattcttatg ccacacattc tgacaaattc acagatggtg tatgcctatt ttggaattgc  19200
aatgtcgata gatatcctgc taattccatt gtttgtagat ttgacactag agtgctatct  19260
aaccttaact tgcctggttg tgatggtggc agtttgtatg taaataaaca tgcattccac  19320
acaccagctt ttgataaaag tgcttttgtt aatttaaaac aattaccatt tttctattac  19380
tctgacagtc catgtgagtc tcatggaaaa caagtagtgt cagatataga ttatgtacca  19440
ctaaagtctg ctacgtgtat aacacgttgc aatttaggtg gtgctgtctg tagacatcat  19500
gctaatgagt acagattgta tctcgatgct tataacatga tgatctcagc tggctttagc  19560
ttgtgggttt acaaacaatt tgatacttat aacctctgga acacttttac aagacttcag  19620
agtttagaaa atgtggcttt taatgttgta aataagggac actttgatgg acaacagggt  19680
gaagtaccag tttctatcat taataacact gtttacacaa aagttgatgg tgttgatgta  19740
gaattgtttg aaaataaaac aacattacct gttaatgtag catttgagct ttgggctaag  19800
cgcaacatta aaccagtacc agaggtgaaa atactcaata atttgggtgt ggacattgct  19860
gctaatactg tgatctggga ctacaaaaga gatgctccag cacatatatc tactattggt  19920
gtttgttcta tgactgacat agccaagaaa ccaactgaaa cgatttgtgc accactcact  19980
gtcttttttg atggtagagt tgatggtcaa gtagacttat ttagaaatgc ccgtaatggt  20040
gttcttatta cagaaggtag tgttaaaggt ttacaaccat ctgtaggtcc caaacaagct  20100
agtcttaatg gagtcacatt aattggagaa gccgtaaaaa cacagttcaa ttattataag  20160
aaagttgatg gtgttgtcca acaattacct gaaacttact ttactcagag tagaaattta  20220
caagaattta aacccaggag tcaaatggaa attgatttct tagaattagc tatggatgaa  20280
ttcattgaac ggtataaatt agaaggctat gccttcgaac atatcgttta tggagatttt  20340
agtcatagtc agttaggtgg tttacatcta ctgattggac tagctaaacg ttttaaggaa  20400
tcacttttg aattagaaga ttttattcct atggacagta cagttaaaaa ctatttcata  20460
acagatgcgc aaacaggttc atctaagtgt gtgtgttctg ttattgattt attacttgat  20520
gattttgttg aaataataaa atcccaagat ttatctgtag tttctaaggt tgtcaaagtg  20580
actattgact atacagaaat ttcatttatg ctttggtgta aagatggcca tgtagaaaca  20640
ttttacccaa aattacaatc tagtcaagcg tggcaaccgg gtgttgctat gcctaatctt  20700
tacaaaatgc aaagaatgct attagaaaag tgtgaccttc aaaattatgg tgatagtgca  20760
acattaccta aaggcataat gatgaatgtc gcaaaatata ctcaactgtg tcaatattta  20820
aacacattaa cattagctgt accctataat atgagagtta tacattttgg tgctggttct  20880
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
aagactaaaa atgttacaaa agaaaatgac tctaaagagg gtttttcac ttacatttgt  21120
gggtttatac aacaaaagct agctcttgga ggttccgtgg ctataaagat aacagaacat  21180
tcttggaatg ctgatcttta taagctcatg ggacacttcg catggtggac agcctttgtt  21240
actaatgtga atgcgtcatc atctgaagca tttttaattg gatgtaatta tcttggcaaa  21300
ccacgcgaac aaatagatgg ttatgtcatg catgcaaatt acatattttg gaggaataca  21360
aatccaattc agttgtcttc ctattcttta tttgacatga gtaaatttcc ccttaaatta  21420
aggggtactg ctgttatgtc tttaaaagaa ggtcaaatca atgatatgat tttatctctt  21480
cttagtaaag gtagacttat aattagagaa aacaacagag ttgttatttc tagtgatgtt  21540
cttgttaaca actaaacgaa caatgtttgt ttttcttgtt ttattgccac tagtctctag  21600
tcagtgtgtt aatcttacaa ccagaactca attaccccct gcatacacta attctttcac  21660
acgtggtgtt tattaccctg acaaagtttt cagatcctca gttttacatt caactcagga  21720
cttgttctta cctttctttt ccaatgttac ttggttccat gctatacatg tctctgggac  21780
caatggtact aagaggtttg ataaccctgt cctaccattt aatgatggtg tttattttgc  21840
ttccactgag aagtctaaca taataagagg ctggattttt ggtactactt tagattcgaa  21900
gacccagtcc ctacttattg ttaataacgc tactaatgtt gttattaaag tctgtgaatt  21960
tcaattttgt aatgatccat ttttgggtgt ttattaccac aaaaacaaca aaagttggat  22020
ggaaagtgag ttcagagttt attctagtgc gaataattgc acttttgaat atgtctctca  22080
gccttttctt atggaccttg aaggaaaaca gggtaatttc aaaaatctta gggaatttgt  22140
gtttaagaat attgatggtt attttaaaat atattctaag cacacgccta ttaatttagt  22200
gcgtgatctc cctcagggtt tttcggcttt agaaccattg gtagatttgc caataggtat  22260
taacatcact aggtttcaaa ctttacttgc tttacataga agttatttga ctcctggtga  22320
ttcttcttca ggttggacag ctggtgctgc agcttattat gtgggttatc ttcaacctag  22380
gacttttcta ttaaaatata atgaaaatgg aaccattaca gatgctgtag actgtgcact  22440
tgaccctctc tcagaaacaa agtgtacgtt gaaatccttc actgtagaaa aaggaatcta  22500
tcaaacttct aactttagag tccaaccaac agaatctatt gttagatttc ctaatattac  22560
aaacttgtgc ccttttggtg aagtttttaa cgccaccaga tttgcatctg tttatgcttg  22620
gaacaggaag agaatcagca actgtgttgc tgattattct gtcctatata attccgcatc  22680
atttttccact tttaagtgtt atggagtgtc tcctactaaa ttaaatgatc tctgctttac  22740
taatgtctat gcagattcat ttgtaattag aggtgatgaa gtcagacaaa tcgctccagg  22800
gcaaactgga aagattgctg attataatta taaattacca gatgatttta caggctgcgt  22860
tatagcttgg aattctaaca atcttgattc taaggttggt ggtaattata attacctgta  22920
tagattgttt aggaagtcta atctcaaacc ttttgagaga gatatttcaa ctgaaatcta  22980
tcaggccggt agcacacctt gtaatggtgt tgaaggtttt aattgttact ttcctttaca  23040
atcatatggt ttccaaccca ctaatggtgt tggttaccaa ccatacagag tagtagtact  23100
ttcttttgaa cttctacatg caccagcaac tgtttgtgga cctaaaaagt ctactaattt  23160
ggttaaaaac aaatgtgtca atttcaactt caatggttta acaggcacag gtgttcttac  23220
tgagtctaac aaaaagtttc tgcctttcca acaatttggc agagacattg ctgacactac  23280
tgatgctgtc cgtgatccac agacacttga gattcttgac attacaccat gttcttttgg  23340
tggtgtcagt gttataacac caggaacaaa tacttctaac caggttgctg ttctttatca  23400
ggatgttaac tgcacagaag tccctgttgc tattcatgca gatcaactta ctcctacttg  23460
gcgtgtttat tctacaggtt ctaatgtttt tcaaacacgt gcaggctgtt taataggggc  23520
tgaacatgtc aacaactcat atgagtgtga catacccatt ggtgcaggta tatgcgctag  23580
ttatcagact cagactaatt ctcctcggcg ggcacgtagt gtagctagtc aatccatcat  23640
tgcctacact atgtcacttg gtgcagaaaa ttcagttgct tactctaata actctattgc  23700
catacccaca aattttacta ttagtgttac cacagaaatt ctaccagtgt ctatgaccaa  23760
gacatcagta gattgtacaa tgtacatttg tggtgattca actgaatgca gcaatctttt  23820
```

-continued

```
gttgcaatat ggcagttttt gtacacaatt aaaccgtgct ttaactggaa tagctgttga  23880
acaagacaaa aacacccaag aagtttttgc acaagtcaaa caaatttaca aaacaccacc  23940
aattaaagat tttggtggtt ttaatttttc acaaatatta ccagatccat caaaaccaag  24000
caagaggtca tttattgaag atctactttt caacaaagtg acacttgcag atgctggctt  24060
catcaaacaa tatggtgatt gccttggtga tattgctgct agagacctca tttgtgcaca  24120
aaagtttaac ggccttactg ttttgccacc tttgctcaca gatgaaatga ttgctcaata  24180
cacttctgca ctgttagcgg gtacaatcac ttctggttgg acctttggtg caggtgctgc  24240
attacaaata ccatttgcta tgcaaatggc ttataggttt aatggtattg gagttacaca  24300
gaatgttctc tatgagaacc aaaaattgat tgccaaccaa tttaatagtg ctattggcaa  24360
aattcaagac tcactttctt ccacagcaag tgcacttgga aaacttcaag atgtggtcaa  24420
ccaaaatgca caagctttaa acacgcttgt taaacaactt agctccaatt ttggtgcaat  24480
ttcaagtgtt ttaaatgata tcctttcacg tcttgacaaa gttgaggctg aagtgcaaat  24540
tgataggttg atcacaggca gacttcaaag tttgcagaca tatgtgactc aacaattaat  24600
tagagctgca gaaatcagag cttctgctaa tcttgctgct actaaaatgt cagagtgtgt  24660
acttggacaa tcaaaaagag ttgatttttg tggaaagggc tatcatctta tgtccttccc  24720
tcagtcagca cctcatggtg tagtcttctt gcatgtgact tatgtccctg cacaagaaaa  24780
gaacttcaca actgctcctg ccatttgtca tgatggaaaa gcacactttc ctcgtgaagg  24840
tgtctttgtt tcaaatggca cacactggtt tgtaacacaa aggaattttt atgaaccaca  24900
aatcattact acagacaaca catttgtgtc tggtaactgt gatgttgtaa taggaattgt  24960
caacaacaca gtttatgatc ctttgcaacc tgaattagac tcattcaagg aggagttaga  25020
taaatatttt aagaatcata catcaccaga tgttgattta ggtgacatct ctggcattaa  25080
tgcttcagtt gtaaacattc aaaaagaaat tgaccgcctc aatgaggttg ccaagaattt  25140
aaatgaatct ctcatcgatc tccaagaact tggaaagtat gagcagtata taaaatggcc  25200
atggtacatt tggctaggtt ttatagctgg cttgattgcc atagtaatgg tgacaattat  25260
gctttgctgt atgaccagtt gctgtagttg tctcaagggc tgttgttctt gtggatcctg  25320
ctgcaaattt gatgaagacg actctgagcc agtgctcaaa ggagtcaaat tacattacac  25380
ataaacgaac ttatggattt gtttatgaga atcttcacaa ttggaactgt aactttgaag  25440
caaggtgaaa tcaaggatgc tactccttca gattttgttc gcgctactgc aacgataccg  25500
atacaagcct cactcccttt cggatggctt attgttggcg ttgcacttct tgctgttttt  25560
cagagcgctt ccaaaatcat aaccctcaaa aagagatggc aactagcact ctccaagggt  25620
gttcactttg tttgcaactt gctgttgttg tttgtaacag tttactcaca ccttttgctc  25680
gttgctgctg gccttgaagc ccctttttctc tatctttatg ctttagtcta cttcttgcag  25740
agtataaact ttgtaagaat aataatgagg ctttggcttt gctggaaatg ccgttccaaa  25800
aacccattac tttatgatgc caactatttt ctttgctggc atactaattg ttacgactat  25860
tgtatacctt acaatagtgt aacttcttca attgtcatta cttcaggtga tggcacaaca  25920
agtcctattt ctgaacatga ctaccagatt ggtggttata ctgaaaaatg ggaatctgga  25980
gtaaaagact gtgttgtatt acacagttac ttcacttcag actattacca gctgtactca  26040
actcaattga gtacagacac tggtgttgaa catgttacct tcttcatcta caataaaatt  26100
gttgatgagc ctgaagaaca tgtccaaatt cacacaatcg acggttcatc cggagttgtt  26160
aatccagtaa tggaaccaat ttatgatgaa ccgacgacga ctactagcgt gcctttgtaa  26220
gcacaagctg atgagtacga acttatgtac tcattcgttt cggaagagac aggtacgtta  26280
atagttaata gcgtacttct ttttcttgct ttcgtggtat tcttgctagt tacactagcc  26340
atccttactg cgcttcgatt gtgtgcgtac tgctgcaata ttgttaacgt gagtcttgta  26400
aaaccttctt tttacgttta ctctcgtgtt aaaaatctga attcttctag agttcctgat  26460
cttctggtct aaacgaacta aatattatat tagtttttct gtttggaact ttaattttag  26520
ccatggcaga ttccaacggt actattaccg ttgaagagct taaaaagctc cttgaacaat  26580
ggaacctagt aataggtttc ctattcctta catggatttg tcttctacaa tttgcctatg  26640
ccaacaggaa taggtttttg tatataatta agttaatttt cctctggctg ttatggccag  26700
taactttagc ttgttttgtg cttgctgctg tttacagaat aaattggatc accggtggaa  26760
ttgctatcgc aatggcttgt cttgtaggct tgatgtggct cagctacttc attgcttctt  26820
tcagactgtt tgcgcgtacg cgttccatgt ggtcattcaa tccagaaact aacattcttc  26880
tcaacgtgcc actccatggc actattctga ccagaccgct tctagaaagt gaactcgtaa  26940
tcggagctgt gatccttcgt ggacatcttc gtattgctgg acaccatcta ggacgctgtg  27000
acatcaagga cctgcctaaa gaaatcactg ttgctacatc acgaacgctt tcttattaca  27060
aattgggagc ttcgcagcgt gtagcaggtg actcaggttt tgctgcatac agtcgctaca  27120
ggattggcaa ctataaatta aacacagacc attccagtag cagtgacaat attgctttgc  27180
ttgtacagta agtgacaaca gatgtttcat ctcgttgact ttcaggttac tatagcagag  27240
atattactaa ttattatgag gacttttaaa gtttccattt ggaatcttga ttacatcata  27300
aacctcataa ttaaaaattt atctaagtca ctaactgaga ataaatattc tcaattagat  27360
gaagagcaac caatggagat tgattaaacg aacatgaaaa ttattctttt cttggcactg  27420
ataacactcg ctacttgtga gctttatcac taccaagagt gtgttagagg tacaacagta  27480
cttttaaaag aaccttgctc ttctggaaca tacgagggca attcaccatt tcatcctcta  27540
gctgataaca aatttgcact gacttgcttt agcactcaat ttgcttttgc ttgtcctgac  27600
ggcgtaaaac acgtctatca gttacgtgcc agatcagttt cacctaaact gttcatcaga  27660
caagaggaag ttcaagaact ttactctcca atttttctta ttgttgcggc aatagtgttt  27720
ataacacttt gcttcacact caaaagaaag acagaatgat tgaactttca ttaattgact  27780
tctatttgtg ctttttagcc tttctgctat tccttgtttt aattatgctt attatctttt  27840
ggttctcact tgaactgcaa gatcataatg aaacttgtca cgcctaaacg aacatgaaat  27900
ttcttgtttt cttaggaatc atcacaactg tagctgcatt tcaccaagaa tgtagtttac  27960
agtcatgtac tcaacatcaa ccatatgtag ttgatgaccc gtgtcctatt cacttctatt  28020
ctaaatggta tattagagta ggagctagaa aatcagcacc tttaattgaa ttgtgcgtgg  28080
atgaggctgg ttctaaatca cccattcagt acatcgatat cggtaattat acagtttcct  28140
gtttaccttt tacaattaat tgccaggaac ctaaattggg tagtcttgta gtgcgttgtt  28200
cgttctatga agacttttta gagtatcatg acgttcgtgt tgttttagat ttcatctaaa  28260
cgaacaaact aaaatgtctg ataatggacc ccaaaatcag cgaaatgcac cccgcattac  28320
gtttggtgga ccctcagatt caactggcag taaccagaat ggagaacgca gtggggcgcg  28380
atcaaaacaa cgtcggcccc aaggtttacc caataatact gcgtcttggt tcaccgctct  28440
cactcaacat ggcaaggaag accttaaatt ccctcgagga caaggcgttc caattaacac  28500
caatagcagt ccagatgacc aaattggcta ctaccgaaga gctaccagac gaattcgtgg  28560
```

-continued

```
tggtgacggt aaaatgaaag atctcagtcc aagatggtat ttctactacc taggaactgg  28620
gccagaagct ggacttccct atggtgctaa caaagacggc atcatatggg ttgcaactga  28680
gggagccttg aatacaccaa aagatcacat tggcacccgc aatcctgcta acaatgctgc  28740
aatcgtgcta caacttcctc aaggaacaac attgccaaaa ggcttctacg cagaagggag  28800
cagaggcggc agtcaagcct cttctcgttc ctcatcacgt agtcgcaaca gttcaagaaa  28860
ttcaactcca ggcagcagta ggggaacttc tcctgctaga atggctggca atggcggtga  28920
tgctgctctt gctttgctgc tgcttgacag attgaaccag cttgagagca aaatgtctgg  28980
taaaggccaa caacaacaag gccaaactgt cactaagaaa tctgctgctg aggcttctaa  29040
gaagcctcgg caaaaacgta ctgccactaa agcatacaat gtaacacaag ctttcggcag  29100
acgtggtcca gaacaaaccc aaggaaattt tggggaccag gaactaatca gacaaggaac  29160
tgattacaaa cattggccgc aaattgcaca atttgccccc agcgcttcag cgttcttcgg  29220
aatgtcgcgc attggcatgg aagtcacacc ttcgggaacg tggttgacct acacaggtgc  29280
catcaaattg gatgacaaag atccaaattt caaagatcaa gtcattttgc tgaataagca  29340
tattgacgca tacaaaacat tcccaccaac agagcctaaa aaggacaaaa agaagaaggc  29400
tgatgaaact caagccttac cgcagagaca gaagaaacag caaactgtga ctcttcttcc  29460
tgctgcagat ttggatgatt tctccaaaca attgcaacaa tccatgagca gtgctgactc  29520
aactcaggcc taaactcatg cagaccacac aaggcagatg ggctatataa acgttttcgc  29580
ttttccgttt acgatatata gtctactctt gtgcagaatg aattctcgta actacatagc  29640
acaagtagat gtagttaact ttaatctcac atagcaatct ttaatcagtg tgtaacatta  29700
gggaggactt gaaagagcca ccacattttc accgaggcca cgcggagtac gatcgagtgt  29760
acagtgaaca atgctaggga gagctgccta tatggaagag ccctaatgtg taaaattaat  29820
tttagtagtg ctatccccat gtgattttaa tagcttctta ggagaatgac aaaaaaaaaa  29880
aaaaaaaaaa aaaaaaaaaa aaa                                          29903

SEQ ID NO: 114          moltype = RNA  length = 21
FEATURE                 Location/Qualifiers
source                  1..21
                        mol_type = other RNA
                        organism = synthetic construct
modified_base           order(1,3,4,6,7,9..13,15,16,18..21)
                        mod_base = OTHER
                        note = 2-prime-O-methyl RNA nucleotides
modified_base           order(2,5,8,14,17)
                        mod_base = OTHER
                        note = 2-prime-fluoro RNA nucleotides
modified_base           1^2
                        mod_base = OTHER
                        note = phosphorothioate
modified_base           18^19
                        mod_base = OTHER
                        note = phosphorothioate
modified_base           19^20
                        mod_base = OTHER
                        note = phosphorothioate
SEQUENCE: 114
tgaagcgaag tgcacacggt c                                            21
```